US012550610B2

(12) United States Patent
Takahashi et al.

(10) Patent No.: US 12,550,610 B2
(45) **Date of Patent: *Feb. 10, 2026**

(54) ORGANIC ELECTROLUMINESCENCE DEVICE AND ELECTRONIC APPARATUS USING THE SAME

(71) Applicant: IDEMITSU KOSAN CO.,LTD., Tokyo (JP)

(72) Inventors: Ryota Takahashi, Sodegaura (JP); Yuki Nakano, Sodegaura (JP); Kazuma Mase, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 1106 days.

This patent is subject to a terminal disclaimer.

(21) Appl. No.: 17/615,683

(22) PCT Filed: Jun. 11, 2020

(86) PCT No.: PCT/JP2020/022967

§ 371 (c)(1),
(2) Date: Dec. 1, 2021

(87) PCT Pub. No.: WO2020/250961

PCT Pub. Date: Dec. 17, 2020

(65) Prior Publication Data

US 2022/0255018 A1 Aug. 11, 2022

(30) Foreign Application Priority Data

Jun. 14, 2019 (JP) ................................ 2019-110912

(51) Int. Cl.
*C07F 15/00* (2006.01)
*C07D 307/91* (2006.01)
(Continued)

(52) U.S. Cl.
CPC ....... *H10K 85/6572* (2023.02); *C07D 307/91* (2013.01); *C07D 487/22* (2013.01);
(Continued)

(58) Field of Classification Search
CPC ............. H10K 85/6572; H10K 85/615; H10K 85/626; C09K 11/06
See application file for complete search history.

(56) References Cited

U.S. PATENT DOCUMENTS 10,249,832 B1 4/2019 Takahashi et al.
10,593,889 B1 * 3/2020 Takahashi ............ H10K 85/626
(Continued)

FOREIGN PATENT DOCUMENTS

CN 1480012 A 3/2004
JP 2004-515506 A 5/2004
(Continued)

OTHER PUBLICATIONS

Taniguchi et al. Chemistry Letters, vol. 48, Issue 9, Sep. 2019, pp. 1160-1163, https://doi.org/10.1246/cl.190494. Published Jul. 17, 2019. (Year: 2019).*

(Continued)

*Primary Examiner* — Michael M Dollinger
(74) *Attorney, Agent, or Firm* — Foley & Lardner LLP

(57) ABSTRACT

A compound represented by the following formula (A1) (wherein one or more among $R_1$ to $R_7$, $R_{10}$ to $R_{16}$, $R_{21}$, and
(Continued)

$R_{22}$ are deuterium atoms or groups which possess deuterium atoms):

(A1)

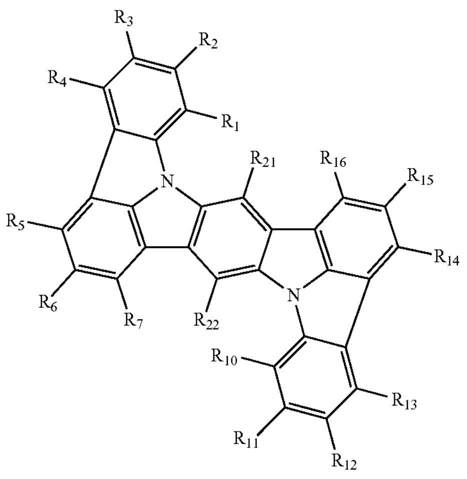

20 Claims, 1 Drawing Sheet

(51) Int. Cl.

| | |
|---|---|
| ***C07D 487/22*** | (2006.01) |
| ***C09K 11/06*** | (2006.01) |
| ***H10K 85/60*** | (2023.01) |
| *H10K 50/11* | (2023.01) |

(52) U.S. Cl.

CPC ............ *C09K 11/06* (2013.01); *H10K 85/615* (2023.02); *H10K 85/626* (2023.02); *H10K 85/636* (2023.02); *H10K 85/6574* (2023.02); *C09K 2211/1011* (2013.01); *H10K 50/11* (2023.02)

(56) References Cited

U.S. PATENT DOCUMENTS

| | | | | |
|---|---|---|---|---|
| 10,658,594 | B2 * | 5/2020 | Takahashi | H10K 85/6572 |
| 10,672,989 | B2 * | 6/2020 | Takahashi | H10K 85/6572 |
| 10,680,181 | B2 * | 6/2020 | Takahashi | C09K 11/06 |
| 11,557,730 | B2 * | 1/2023 | Takahashi | C07D 491/22 |
| 11,569,449 | B2 * | 1/2023 | Takahashi | H10K 85/626 |
| 12,108,666 | B2 * | 10/2024 | Takahashi | H10K 85/654 |
| 12,262,634 | B2 * | 3/2025 | Takahashi | H10K 50/11 |
| 2002/0076576 | A1 | 6/2002 | Li et al. | |
| 2003/0129439 | A1 | 7/2003 | Li et al. | |
| 2003/0134140 | A1 | 7/2003 | Li et al. | |
| 2003/0138657 | A1 | 7/2003 | Li et al. | |
| 2013/0026422 | A1 * | 1/2013 | Parham | C07D 498/06 544/31 |
| 2017/0324045 | A1 | 11/2017 | Takahashi et al. | |
| 2018/0198076 | A1 | 7/2018 | Takahashi et al. | |
| 2019/0097142 | A1 | 3/2019 | Takahashi et al. | |
| 2020/0052225 | A1 | 2/2020 | Takahashi et al. | |

FOREIGN PATENT DOCUMENTS

| | | | |
|---|---|---|---|
| WO | WO-2017/175690 | A1 | 10/2017 |
| WO | WO-2018/151065 | A1 | 8/2018 |
| WO | WO-2019/111971 | A1 | 6/2019 |

OTHER PUBLICATIONS

Office Action issued in corresponding Chinese Patent Application No. 202080043516.8 dated Dec. 21, 2023 (15 pages).

Wang et al., "Synthesis of all-deuterated tris(2-phenylpyridine) iridium for highly stable electrophosphorescence: the deuterium effect", Journal of Materials Chemistry C, vol. 1, Jul. 2, 2013, pp. 4821-4825.

International Preliminary Report on Patentability (including the Written Opinion) from PCT/JP2020/022967 dated Dec. 23, 2021 (5 pages).

International Search Report and Written Opinion from PCT/JP2020/022967 dated Sep. 1, 2020 (12 pages).

Kawanishi, et al., "Deuterium compound for electronic devices", Organic Square, No. 36, 2011, (20 pages).

Yoko, et al., "Synthesis and Evaluation of Deuterated OLED Material", Taiyo Nippon Sanso Technical Report, No. 32, pp. 5-8, 2013.

* cited by examiner

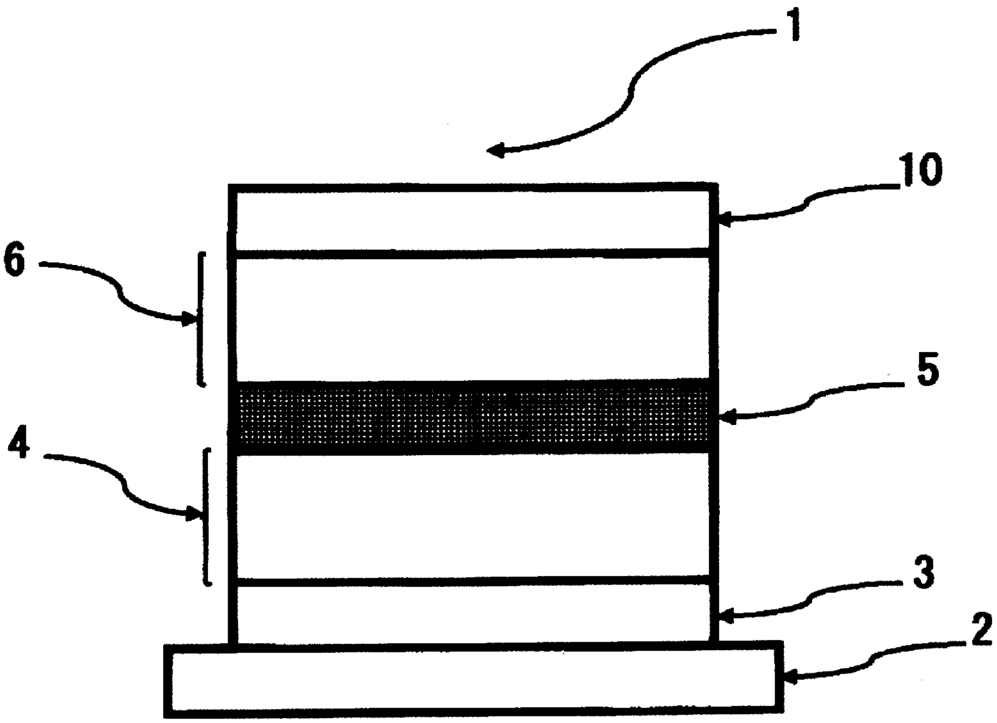
1
10
6
5
4
3
2

ORGANIC ELECTROLUMINESCENCE DEVICE AND ELECTRONIC APPARATUS USING THE SAME

CROSS-REFERENCE TO RELATED APPLICATIONS

The present application claims priority under 37 U.S.C. § 371 to International Patent Application No. PCT/JP2020/022967, filed Jun. 11, 2020, which claims priority to and the benefit of Japanese Patent Application No. 2019-110912, filed on Jun. 14, 2019. The contents of these applications are hereby incorporated by reference in their entireties.

TECHNICAL FIELD

The invention relates to an organic electroluminescence device and an electronic apparatus using the same.

BACKGROUND ART

When voltage is applied to an organic electroluminescence device (hereinafter, referred to as an organic EL device in several cases), holes and electrons are injected into an emitting layer from an anode and a cathode, respectively. Then, thus injected holes and electrons are recombined in the emitting layer, and excitons are formed therein.

Patent Documents 1 to 3 disclose the use of a compound having a specific fused-ring structure as a material for an emitting layer of an organic EL device.

RELATED ART DOCUMENTS

Patent Documents

[Patent Document 1] WO 2018/151065 A1
[Patent Document 2] WO 2017/175690 A1
[Patent Document 3] U.S. Ser. No. 10/249,832 B1

SUMMARY OF THE INVENTION

It is an object of the invention to provide a novel compound useful as a material of an organic EL device, an organic EL device having a long lifetime, and an electronic apparatus using the organic EL device.

According to the invention, the following compound, organic EL device, and electronic apparatus are provided.

1. A compound represented by the following formula (A1):

(A1)

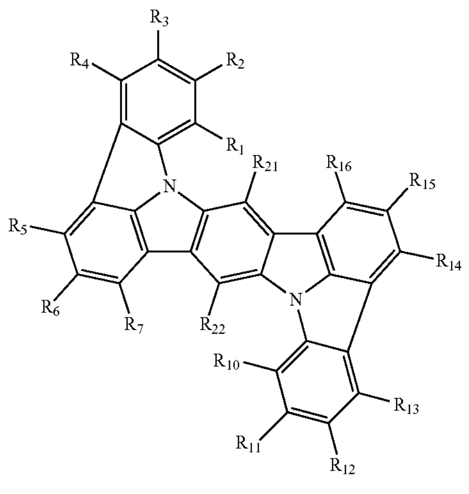

wherein in the formula (A1), one or more sets of adjacent two or more among $R_1$ to $R_7$ and $R_{10}$ to $R_{16}$ form a substituted or unsubstituted, saturated or unsaturated ring by bonding with each other, or do not form a substituted or unsubstituted, saturated or unsaturated ring;

$R_{21}$ and $R_{22}$, $R_1$ to $R_7$ that do not form the substituted or unsubstituted, saturated or unsaturated ring, and $R_{10}$ to $R_{16}$ that do not form the substituted or unsubstituted, saturated or unsaturated ring are independently a hydrogen atom, or a substituent R;

the substituent R is a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms;

when two or more of the substituent R's are present, the two or more of the substituent R's may be the same as or different from each other;

$R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms;

when two or more of each or $R_{901}$ to $R_{907}$ are present, the two or more of each of $R_{901}$ to $R_{907}$ may be the same as or different from each other; and one or more hydrogen atoms selected from the group consisting of the followings are deuterium atoms:

hydrogen atoms possessed by the formed substituted or unsubstituted, saturated or unsaturated ring, hydrogen atoms possessed by a substituent that substitutes on the formed substituted or unsubstituted, saturated or unsaturated ring, hydrogen atoms when each of $R_{21}$ and $R_{22}$ is a hydrogen atom, hydrogen atoms when each of $R_1$ to $R_7$ and $R_{10}$ to $R_{16}$ is a hydrogen atom, and hydrogen atoms possessed by $R_{21}$, $R_{22}$, $R_1$ to $R_7$, and $R_{10}$ to $R_{16}$ when each of $R_{21}$, $R_{22}$, $R_1$ to $R_7$, and $R_{10}$ to $R_{16}$ is the substituent R.

2. A material for an organic electroluminescence device, comprising the compound represented by the formula (A1).

3. An organic electroluminescence device comprising:

a cathode;

an anode; and at least one organic layer disposed between the cathode and the anode; wherein at least one layer of the at least one organic layer comprises the compound represented by formula (A1).

4. An organic electroluminescence device comprising:

a cathode;

an anode; and at least one organic layer disposed between the cathode and the anode; wherein the at least one organic layer comprises an emitting layer, and the emitting layer comprises the compound represented by the formula (A1), and a compound represented by the following formula (10):

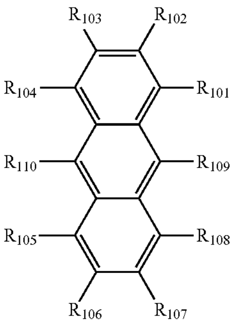

(10)

wherein in the formula (10), one or more sets of adjacent two or more among $R_{101}$ to $R_{110}$ form a substituted or unsubstituted, saturated or unsaturated ring, or do not form a substituted or unsubstituted, saturated or unsaturated ring;

$R_{101}$ to $R_{110}$ that do not form the substituted or unsubstituted, saturated or unsaturated ring are independently a hydrogen atom, a substituent R, or a group represented by the following formula (11):

$$-L_{101}-Ar_{101} \quad (11)$$

wherein in the formula (11), $L_{101}$ is a single bond, a substituted or unsubstituted arylene group including 6 to 50 ring carbon atoms, or a substituted or unsubstituted divalent heterocyclic group including 5 to 50 ring atoms;

$Ar_{101}$ is a substituted or unsubstituted aryl group including 6 to 50 ring carbon atoms, or a substituted or unsubstituted monovalent heterocyclic group including 5 to 50 ring atoms; the substituent R is a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, $-Si(R_{901})(R_{902})(R_{903})$, $-O-(R_{904})$, $-S-(R_{905})$, $-N(R_{906})(R_{907})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms;

when two or more of the substituent R's are present, the two or more of the substituent R's may be the same as or different from each other;

$R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms;

when two or more of each of $R_{901}$ to $R_{907}$ are present, the two or more of each of $R_{901}$ to $R_{906}$ may be the same as or different from each other;

provided that at least one $R_{101}$ to $R_{110}$ which does not form the substituted or unsubstituted, saturated or unsaturated ring is a group represented by the formula (11);

when two or more groups represented by the formula (11) are present, the two or more of each of the groups represented by the formula (11) may be the same as or different from each other.

5. An electronic apparatus, equipped with the organic electroluminescence device according to 3 or 4.

According to the invention, a novel compound useful as a material of an organic EL device, an organic EL device having a long lifetime, and an electronic apparatus using the organic EL device can be provided.

BRIEF DESCRIPTION OF THE DRAWINGS

The FIGURE is a diagram showing a schematic configuration of an organic EL device according to one aspect of the invention.

MODE FOR CARRYING OUT THE INVENTION

Definition

In this specification, a hydrogen atom includes its isotopes different in the number of neutrons, namely, a protium, a deuterium and a tritium.

In this specification, at a bondable position in a chemical formula where a symbol such as "R", or "D" representing a deuterium atom is not indicated, a hydrogen atom, that is, a protium atom, a deuterium atom or a tritium atom is bonded.

In this specification, the number of ring carbon atoms represents the number of carbon atoms forming a subject ring itself among the carbon atoms of a compound having a structure in which atoms are bonded in a ring form (for example, a monocyclic compound, a fused ring compound, a cross-linked compound, a carbocyclic compound, or a heterocyclic compound). When the subject ring is substituted by a substituent, the carbon contained in the substituent is not included in the number of ring carbon atoms. The same shall apply to "the number of ring carbon atoms" described below, unless otherwise specified. For example, a benzene ring has 6 ring carbon atoms, a naphthalene ring includes 10 ring carbon atoms, a pyridine ring includes 5 ring carbon atoms, and a furan ring includes 4 ring carbon atoms. Further, for example, a 9,9-diphenylfluorenyl group includes 13 ring carbon atoms, and a 9,9'-spirobifluorenyl group includes 25 ring carbon atoms.

When a benzene ring is substituted by, for example, an alkyl group as a substituent, the number of carbon atoms of the alkyl group is not included in the number of ring carbon atoms of the benzene ring. Therefore, the number of ring carbon atoms of the benzene ring substituted by the alkyl group is 6. When a naphthalene ring is substituted by, for example, an alkyl group as a substituent, the number of carbon atoms of the alkyl group is not included in the number of ring carbon atoms of the naphthalene ring. Therefore, the number of ring carbon atoms of the naphthalene ring substituted by the alkyl group is 10.

In this specification, the number of ring atoms represents the number of atoms forming a subject ring itself among the atoms of a compound having a structure in which atoms are bonded in a ring form (for example, the structure includes a monocyclic ring, a fused ring and a ring assembly) (for example, a monocyclic compound, a fused ring compound, a cross-linked compound, a carbocyclic compound and a heterocyclic compound). The number of ring atoms does not include atoms that do not form the ring (for example, a hydrogen atom which terminates a bond of the atoms forming the ring), or atoms contained in a substituent when the ring is substituted by the substituent. The same shall apply to "the number of ring atoms" described below, unless otherwise specified. For example, the number of atoms of a pyridine ring is 6, the number of atoms of a quinazoline ring is 10, and the number of a furan ring is 5. For example, hydrogen atoms bonded to a pyridine ring and atoms constituting a substituent substituted on the pyridine ring are not included in the number of ring atoms of the pyridine ring. Therefore, the number of ring atoms of a pyridine ring with which a hydrogen atom or a substituent is bonded is 6. For example, hydrogen atoms and atoms constituting a substituent which are bonded with a quinazoline ring is not included in the number of ring atoms of the quinazoline ring. Therefore, the number of ring atoms of a quinazoline ring with which a hydrogen atom or a substituent is bonded is 10.

In this specification, "XX to YY carbon atoms" in the expression "a substituted or unsubstituted ZZ group including XX to YY carbon atoms" represents the number of carbon atoms in the case where the ZZ group is unsubstituted by a substituent, and does not include the number of carbon atoms of a substituent in the case where the ZZ group is substituted by the substituent. Here, "YY" is larger than "XX", and "XX" means an integer of 1 or more and "YY" means an integer of 2 or more.

In this specification, "XX to YY atoms" in the expression "a substituted or unsubstituted ZZ group including XX to YY atoms" represents the number of atoms in the case where the ZZ group is unsubstituted by a substituent, and does not include the number of atoms of a substituent in the case where the ZZ group is substituted by the substituent. Here, "YY" is larger than "XX", and "XX" means an integer of 1 or more and "YY" means an integer of 2 or more.

In this specification, the unsubstituted ZZ group represents the case where the "substituted or unsubstituted ZZ group" is a "ZZ group unsubstituted by a substituent", and the substituted ZZ group represents the case where the "substituted or unsubstituted ZZ group" is a "ZZ group substituted by a substituent".

In this specification, a term "unsubstituted" in the case of "a substituted or unsubstituted ZZ group" means that hydrogen atoms in the ZZ group are not substituted by a substituent. Hydrogen atoms in a term "unsubstituted ZZ group" are a protium atom, a deuterium atom, or a tritium atom.

In this specification, a term "substituted" in the case of "a substituted or unsubstituted ZZ group" means that one or more hydrogen atoms in the ZZ group are substituted by a substituent. Similarly, a term "substituted" in the case of "a BB group substituted by an AA group" means that one or more hydrogen atoms in the BB group are substituted by the AA group.

"Substituent as Described in this Specification"

Hereinafter, the substituent described in this specification will be explained.

The number of ring carbon atoms of the "unsubstituted aryl group" described in this specification is 6 to 50, preferably 6 to 30, and more preferably 6 to 18, unless otherwise specified.

The number of ring atoms of the "unsubstituted heterocyclic group" described in this specification is 5 to 50, preferably 5 to 30, and more preferably 5 to 18, unless otherwise specified.

The number of carbon atoms of the "unsubstituted alkyl group" described in this specification is 1 to 50, preferably 1 to 20, and more preferably 1 to 6, unless otherwise specified.

The number of carbon atoms of the "unsubstituted alkenyl group" described in this specification is 2 to 50, preferably 2 to 20, and more preferably 2 to 6, unless otherwise specified.

The number of carbon atoms of the "unsubstituted alkynyl group" described in this specification is 2 to 50, preferably 2 to 20, and more preferably 2 to 6, unless otherwise specified.

The number of ring carbon atoms of the "unsubstituted cycloalkyl group" described in this specification is 3 to 50, preferably 3 to 20, and more preferably 3 to 6, unless otherwise specified.

The number of ring carbon atoms of the "unsubstituted arylene group" described in this specification is 6 to 50, preferably 6 to 30, and more preferably 6 to 18, unless otherwise specified.

The number of ring atoms of the "unsubstituted divalent heterocyclic group" described in this specification is 5 to 50, preferably 5 to 30, and more preferably 5 to 18, unless otherwise specified.

The number of carbon atoms of the "unsubstituted alkylene group" described in this specification is 1 to 50, preferably 1 to 20, and more preferably 1 to 6, unless otherwise specified.

"Substituted or Unsubstituted Aryl Group"

Specific examples of the "substituted or unsubstituted aryl group" described in this specification (specific example group G1) include the following unsubstituted aryl groups (specific example group G1A), substituted aryl groups (specific example group G1B), and the like. (Here, the unsubstituted aryl group refers to the case where the "substituted or unsubstituted aryl group" is an "aryl group unsubstituted by a substituent", and the substituted aryl group refers to the case where the "substituted or unsubstituted aryl group" is an "aryl group substituted by a substituent"). In this specification, in the case where simply referred as an "aryl group", it includes both a "unsubstituted aryl group" and a "substituted aryl group."

The "substituted aryl group" means a group in which one or more hydrogen atoms of the "unsubstituted aryl group" are substituted by a substituent. Specific examples of the "substituted aryl group" include, for example, groups in which one or more hydrogen atoms of the "unsubstituted aryl group" of the following specific example group G1A are substituted by a substituent, the substituted aryl groups of the following specific example group G1B, and the like. It should be noted that the examples of the "unsubstituted aryl group" and the examples of the "substituted aryl group" enumerated in this specification are mere examples, and the "substituted aryl group" described in this specification also includes a group in which a hydrogen atom bonded with a carbon atom of the aryl group itself in the "substituted aryl group" of the following specific group G1B is further substituted by a substituent, and a group in which a hydrogen atom of a substituent in the "substituted aryl group" of the following specific group G1B is further substituted by a substituent.

Unsubstituted Aryl Group (Specific Example Group G1A):

a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group,
a perylenyl group, and
a monovalent aryl group derived by removing one hydrogen atom from the ring structures represented by any of the following general formulas (TEMP-1) to (TEMP-15).

(TEMP-1)

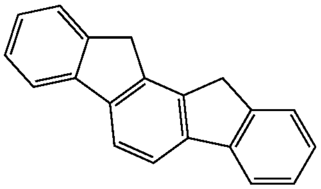

(TEMP-2)

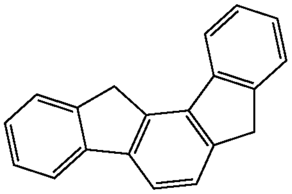

-continued (TEMP-3)

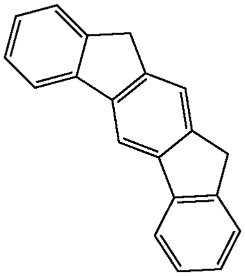

(TEMP-4)

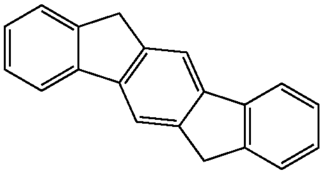

(TEMP-5)

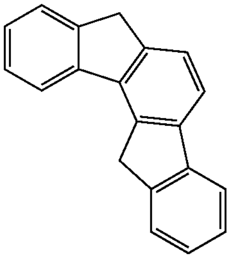

(TEMP-6)

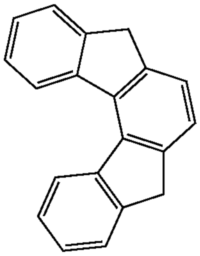

(TEMP-7)

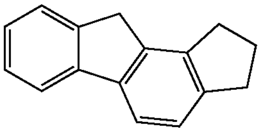

(TEMP-8)

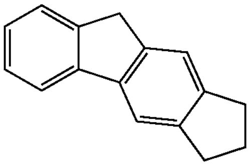

(TEMP-9)

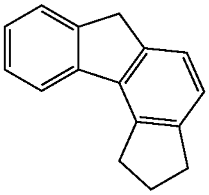

-continued (TEMP-10)

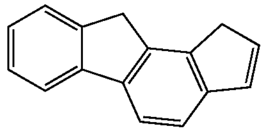

(TEMP-11)

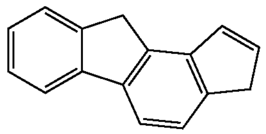

(TEMP-12)

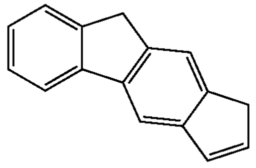

(TEMP-13)

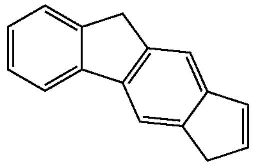

(TEMP-14)

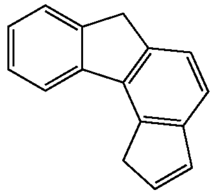

(TEMP-15)

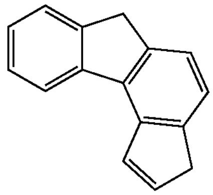

Substituted Aryl Group (Specific Example Group G1B):
- an o-tolyl group,
- a m-tolyl group,
- a p-tolyl group,
- a p-xylyl group,
- a m-xylyl group,
- an o-xylyl group,
- a p-isopropylphenyl group,
- a m-isopropylphenyl group,
- an o-isopropylphenyl group,
- a p-t-butylphenyl group,
- a m-t-butylphenyl group,
- an o-t-butylphenyl group,
- a 3,4,5-trimethylphenyl group,
- a 9,9-dimethylfluorenyl group,
- a 9,9-diphenylfluorenyl group,
- a 9,9-bis(4-methylphenyl)fluorenyl group,
- a 9,9-bis(4-isopropylphenyl)fluorenyl group,
- a 9,9-bis(4-t-butylphenyl)fluorenyl group,
- a cyanophenyl group,
- a triphenylsilylphenyl group,
- a trimethylsilylphenyl group,
- a phenylnaphthyl group,
- a naphthylphenyl group, and
- a group in which one or more hydrogen atoms of a monovalent group derived from the ring structures represented by any of the general formulas (TEMP-1) to (TEMP-15) are substituted by a substituent.

"Substituted or Unsubstituted Heterocyclic Group"

The "heterocyclic group" described in this specification is a ring group having at least one hetero atom in the ring atom. Specific examples of the hetero atom include a nitrogen atom, an oxygen atom, a sulfur atom, a silicon atom, a phosphorus atom, and a boron atom.

The "heterocyclic group" in this specification is a monocyclic group or a fused ring group.

The "heterocyclic group" in this specification is an aromatic heterocyclic group or a non-aromatic heterocyclic group.

Specific examples of the "substituted or unsubstituted heterocyclic group" (specific example group G2) described in this specification include the following unsubstituted heterocyclic group (specific example group G2A), the following substituted heterocyclic group (specific example group G2B), and the like. (Here, the unsubstituted heterocyclic group refers to the case where the "substituted or unsubstituted heterocyclic group" is a "heterocyclic group unsubstituted by a substituent", and the substituted heterocyclic group refers to the case where the "substituted or unsubstituted heterocyclic group" is a "heterocyclic group substituted by a substituent"). In this specification, in the case where simply referred as a "heterocyclic group", it includes both the "unsubstituted heterocyclic group" and the "substituted heterocyclic group."

The "substituted heterocyclic group" means a group in which one or more hydrogen atom of the "unsubstituted heterocyclic group" are substituted by a substituent. Specific examples of the "substituted heterocyclic group" include a group in which a hydrogen atom of "unsubstituted heterocyclic group" of the following specific example group G2A is substituted by a substituent, the substituted heterocyclic groups of the following specific example group G2B, and the like. It should be noted that the examples of the "unsubstituted heterocyclic group" and the examples of the "substituted heterocyclic group" enumerated in this specification are mere examples, and the "substituted heterocyclic group" described in this specification includes groups in which hydrogen atom bonded with a ring atom of the heterocyclic group itself in the "substituted heterocyclic group" of the specific example group G2B is further substituted by a substituent, and a group in which hydrogen atom of a substituent in the "substituted heterocyclic group" of the specific example group G2B is further substituted by a substituent.

Specific example group G2A includes, for example, the following unsubstituted heterocyclic group containing a nitrogen atom (specific example group G2A1), the following unsubstituted heterocyclic group containing an oxygen atom (specific example group G2A2), the following unsubstituted heterocyclic group containing a sulfur atom (specific example group G2A3), and the monovalent heterocyclic group derived by removing one hydrogen atom from the ring structures represented by any of the following general formulas (TEMP-16) to (TEMP-33) (specific example group G2A4).

Specific example group G2B includes, for example, the following substituted heterocyclic group containing a nitrogen atom (specific example group G2B1), the following substituted heterocyclic group containing an oxygen atom (specific example group G2B2), the following substituted heterocyclic group containing a sulfur atom (specific example group G2B3), and the following group in which one or more hydrogen atoms of the monovalent heterocyclic group derived from the ring structures represented by any of the following general formulas (TEMP-16) to (TEMP-33) are substituted by a substituent (specific example group G2B4).

Unsubstituted Heterocyclic Group Containing a Nitrogen Atom (Specific Example Group G2A1):

a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolyl group,
a phthalazinyl group,
a quinazolinyl group,
a quinoxalinyl group,
a benzimidazolyl group,
an indazolyl group,
a phenanthrolinyl group,
a phenanthridinyl group,
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

Unsubstituted Heterocyclic Group Containing an Oxygen Atom (Specific Example Group G2A2):

a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

Unsubstituted Heterocyclic Group Containing a Sulfur Atom (Specific Example Group G2A3):

a thienyl group,
a thiazolyl group,
an isothiazolyl group,
a thiadiazolyl group,
a benzothiophenyl group (benzothienyl group),
an isobenzothiophenyl group (isobenzothienyl group),
a dibenzothiophenyl group (dibenzothienyl group),
a naphthobenzothiophenyl group (naphthobenzothienyl group),
a benzothiazolyl group,
a benzisothiazolyl group,
a phenothiazinyl group,
a dinaphthothiophenyl group (dinaphthothienyl group),
an azadibenzothiophenyl group (azadibenzothienyl group),
a diazadibenzothiophenyl group (diazadibenzothienyl group),
an azanaphthobenzothiophenyl group (azanaphthobenzothienyl group), and
a diazanaphthobenzothiophenyl group (diazanaphthobenzothienyl group).

Monovalent Heterocyclic Group Derived by Removing One Hydrogen Atom from the Ring Structures Represented by any of the Following General Formulas (TEMP-16) to (TEMP-33) (Specific Example Group G2A4):

(TEMP-16)

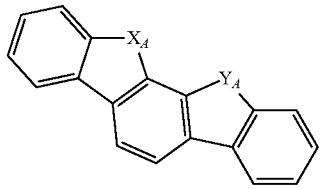

(TEMP-17)

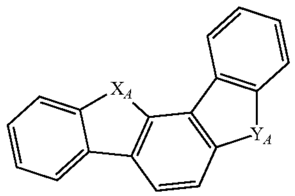

(TEMP-18)

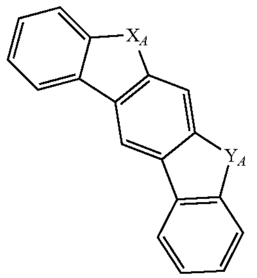

(TEMP-19)

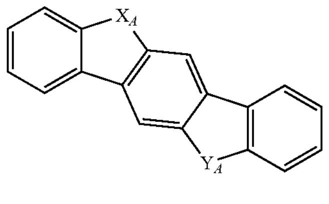

-continued (TEMP-20)

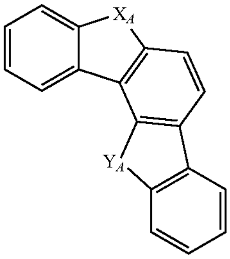

(TEMP-21)

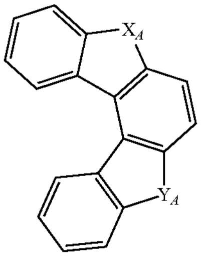

(TEMP-22)

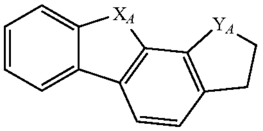

(TEMP-23)

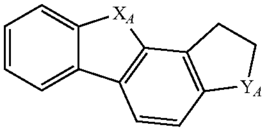

(TEMP-24)

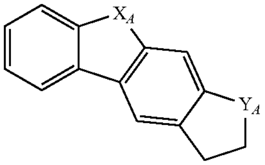

(TEMP-25)

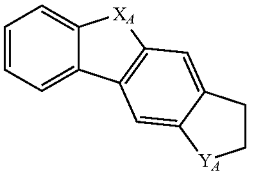

(TEMP-26)

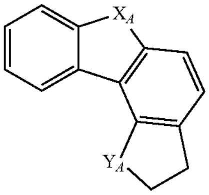

(TEMP-27)

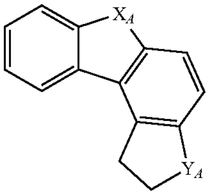

-continued (TEMP-28)

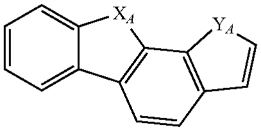

(TEMP-29)

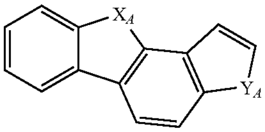

(TEMP-30)

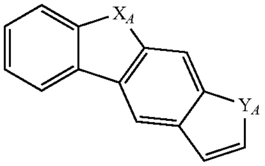

(TEMP-31)

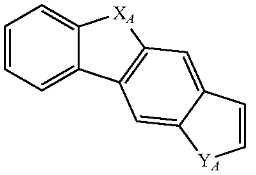

(TEMP-32)

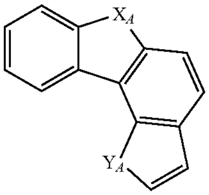

(TEMP-33)

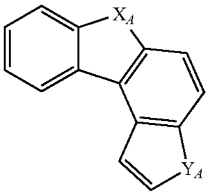

In the general formulas (TEMP-16) to (TEMP-33), $X_A$ and $Y_A$ are independently an oxygen atom, a sulfur atom, NH, or $CH_2$. Provided that at least one of $X_A$ and $Y_A$ is an oxygen atom, a sulfur atom, or NH.

In the general formulas (TEMP-16) to (TEMP-33), when at least one of $X_A$ and $Y_A$ is NH or $CH_2$, the monovalent heterocyclic group derived from the ring structures represented by any of the general formulas (TEMP-16) to (TEMP-33) includes a monovalent group derived by removing one hydrogen atom from these NH or $CH_2$.

Substituted Heterocyclic Group Containing a Nitrogen Atom (Specific Example Group G2B1):

a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenylyltriazinyl group, a diphenyltriazinyl group,
a phenylquinazolinyl group, and
a biphenylylquinazolinyl group.

Substituted Heterocyclic Group Containing an Oxygen Atom (Specific Example Group G2B2):

a phenyldibenzofuranyl group,
a methyldibenzofuranyl group,
a t-butyldibenzofuranyl group, and
a monovalent residue of spiro[9H-xanthene-9,9'-[9H] fluorene].

Substituted Heterocyclic Group Containing a Sulfur Atom (Specific Example Group G2B3):

a phenyldibenzothiophenyl group,
a methyldibenzothiophenyl group,
a t-butyldibenzothiophenyl group, and
a monovalent residue of spiro[9H-thioxanthene-9,9'-[9H] fluorene].

Group in which One or More Hydrogen Atoms of the Monovalent Heterocyclic Group Derived from the Ring Structures Represented by any of the Following General Formulas (TEMP-16) to (TEMP-33) are Substituted by a Substituent (Specific Example Group G2B4):

The "one or more hydrogen atoms of the monovalent heterocyclic group" means one or more hydrogen atoms selected from hydrogen atoms bonded with ring carbon atoms of the monovalent heterocyclic group, a hydrogen atom bonded with a nitrogen atom when at least one of $X_A$ and $Y_A$ is NH, and hydrogen atoms of a methylene group when one of $X_A$ and $Y_A$ is $CH_2$.

"Substituted or Unsubstituted Alkyl Group"

Specific examples of the "substituted or unsubstituted alkyl group" (specific example group G3) described in this specification include the following unsubstituted alkyl groups (specific example group G3A) and the following substituted alkyl groups (specific example group G3B). (Here, the unsubstituted alkyl group refers to the case where the "substituted or unsubstituted alkyl group" is an "alkyl group unsubstituted by a substituent", and the substituted alkyl group refers to the case where the "substituted or unsubstituted alkyl group" is an "alkyl group substituted by a substituent"). In this specification, in the case where simply referred as an "alkyl group" includes both the "unsubstituted alkyl group" and the "substituted alkyl group."

The "substituted alkyl group" means a group in which one or more hydrogen atoms in the "unsubstituted alkyl group" are substituted by a substituent. Specific examples of the "substituted alkyl group" include groups in which one or more hydrogen atoms in the following "unsubstituted alkyl group" (specific example group G3A) are substituted by a substituent, the following substituted alkyl group (specific example group G3B), and the like. In this specification, the alkyl group in the "unsubstituted alkyl group" means a linear alkyl group. Thus, the "unsubstituted alkyl group" includes a straight-chain "unsubstituted alkyl group" and a branched-chain "unsubstituted alkyl group". It should be noted that the examples of the "unsubstituted alkyl group" and the examples of the "substituted alkyl group" enumerated in this specification are mere examples, and the "substituted alkyl group" described in this specification includes a group in which hydrogen atom of the alkyl group itself in the "substituted alkyl group" of the specific example group G3B is further substituted by a substituent, and a group in which hydrogen atom of a substituent in the "substituted alkyl group" of the specific example group G3B is further substituted by a substituent.

Unsubstituted Alkyl Group (Specific Example Group G3A):

a methyl group,
an ethyl group,
a n-propyl group,
an isopropyl group,
a n-butyl group,
an isobutyl group,
a s-butyl group, and
a t-butyl group.

Substituted Alkyl Group (Specific Example Group G3B):

a heptafluoropropyl group (including isomers),
a pentafluoroethyl group,
a 2,2,2-trifluoroethyl group, and
a trifluoromethyl group.

"Substituted or Unsubstituted Alkenyl Group"

Specific examples of the "substituted or unsubstituted alkenyl group" described in this specification (specific example group G4) include the following unsubstituted alkenyl group (specific example group G4A), the following substituted alkenyl group (specific example group G4B), and the like. (Here, the unsubstituted alkenyl group refers to the case where the "substituted or unsubstituted alkenyl group" is a "alkenyl group unsubstituted by a substituent", and the "substituted alkenyl group" refers to the case where the "substituted or unsubstituted alkenyl group" is a "alkenyl group substituted by a substituent."). In this specification, in the case where simply referred as an "alkenyl group" includes both the "unsubstituted alkenyl group" and the "substituted alkenyl group."

The "substituted alkenyl group" means a group in which one or more hydrogen atoms in the "unsubstituted alkenyl group" are substituted by a substituent. Specific examples of the "substituted alkenyl group" include a group in which the following "unsubstituted alkenyl group" (specific example group G4A) has a substituent, the following substituted alkenyl group (specific example group G4B), and the like. It should be noted that the examples of the "unsubstituted alkenyl group" and the examples of the "substituted alkenyl group" enumerated in this specification are mere examples, and the "substituted alkenyl group" described in this specification includes a group in which a hydrogen atom of the alkenyl group itself in the "substituted alkenyl group" of the specific example group G4B is further substituted by a substituent, and a group in which a hydrogen atom of a substituent in the "substituted alkenyl group" of the specific example group G4B is further substituted by a substituent.

Unsubstituted Alkenyl Group (Specific Example Group G4A):

a vinyl group,
an allyl group,
a 1-butenyl group,
a 2-butenyl group, and
a 3-butenyl group.

Substituted Alkenyl Group (Specific Example Group G4B):

a 1,3-butanedienyl group,
a 1-methylvinyl group,
a 1-methylallyl group,
a 1,1-dimethylallyl group,
a 2-methylally group, and
a 1,2-dimethylallyl group.

"Substituted or Unsubstituted Alkynyl Group"

Specific examples of the "substituted or unsubstituted alkynyl group" described in this specification (specific example group G5) include the following unsubstituted alkynyl group (specific example group G5A) and the like. (Here, the unsubstituted alkynyl group refers to the case where the "substituted or unsubstituted alkynyl group" is an "alkynyl group unsubstituted by a substituent"). In this specification, in the case where simply referred as an "alkynyl group" includes both the "unsubstituted alkynyl group" and the "substituted alkynyl group."

The "substituted alkynyl group" means a group in which one or more hydrogen atoms in the "unsubstituted alkynyl group" are substituted by a substituent. Specific examples of the "substituted alkynyl group" include a group in which one or more hydrogen atoms in the following "unsubstituted alkynyl group" (specific example group G5A) are substituted by a substituent, and the like.

Unsubstituted Alkynyl Group (Specific Example Group G5A):

an ethynyl group.

"Substituted or Unsubstituted Cycloalkyl Group"

Specific examples of the "substituted or unsubstituted cycloalkyl group" described in this specification (specific example group G6) include the following unsubstituted cycloalkyl group (specific example group G6A), the following substituted cycloalkyl group (specific example group G6B), and the like. (Here, the unsubstituted cycloalkyl group refers to the case where the "substituted or unsubstituted cycloalkyl group" is a "cycloalkyl group unsubstituted by a substituent", and the substituted cycloalkyl group refers to the case where the "substituted or unsubstituted cycloalkyl group" is a "cycloalkyl group substituted by a substituent"). In this specification, in the case where simply referred as a "cycloalkyl group" includes both the "unsubstituted cycloalkyl group" and the "substituted cycloalkyl group."

The "substituted cycloalkyl group" means a group in which one or more hydrogen atoms in the "unsubstituted cycloalkyl group" are substituted by a substituent. Specific examples of the "substituted cycloalkyl group" include a group in which one or more hydrogen atoms in the following "unsubstituted cycloalkyl group" (specific example group G6A) are substituted by a substituent, and examples of the following substituted cycloalkyl group (specific example group G6B), and the like. It should be noted that the examples of the "unsubstituted cycloalkyl group" and the examples of the "substituted cycloalkyl group" enumerated in this specification are mere examples, and the "substituted cycloalkyl group" in this specification includes a group in which one or more hydrogen atoms bonded with the carbon atom of the cycloalkyl group itself in the "substituted cycloalkyl group" of the specific example group G6B are substituted by a substituent, and a group in which a hydrogen atom of a substituent in the "substituted cycloalkyl group" of specific example group G6B is further substituted by a substituent.

Unsubstituted Cycloalkyl Group (Specific Example Group G6A):

a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

Substituted Cycloalkyl Group (Specific Example Group G6B):

a 4-methylcyclohexyl group.

"Group Represented by —Si($R_{901}$)($R_{902}$)($R_{903}$)"

Specific examples of the group represented by —Si($R_{901}$)($R_{902}$)($R_{903}$) described in this specification (specific example group G7) include:

—Si(G1)(G1)(G1),
—Si(G1)(G2)(G2),
—Si(G1)(G1)(G2),
—Si(G2)(G2)(G2),
—Si(G3)(G3)(G3), and
—Si(G6)(G6)(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

A plurality of G1's in —Si(G1)(G1)(G1) are the same as or different from each other.

A plurality of G2's in —Si(G1)(G2)(G2) are the same as or different from each other.

A plurality of G1's in —Si(G1)(G1)(G2) are the same as or different from each other.

A plurality of G2's in —Si(G2)(G2)(G2) are be the same as or different from each other.

A plurality of G3's in —Si(G3)(G3)(G3) are the same as or different from each other.

A plurality of G6's in —Si(G6)(G6)(G6) are be the same as or different from each other.

"Group Represented by —O—($R_{904}$)"

Specific examples of the group represented by —O—($R_{904}$) in this specification (specific example group G8) include:

—O(G1),
—O(G2),
—O(G3), and
—O(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

"Group Represented by —S—($R_{905}$)"

Specific examples of the group represented by —S—($R_{905}$) in this specification (specific example group G9) include:

—S(G1),
—S(G2),
—S(G3), and
—S(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

"Group Represented by —N($R_{906}$)($R_{907}$)"

Specific examples of the group represented by —N($R_{906}$)($R_{907}$) in this specification (specific example group G10) include:

—N(G1)(G1),
—N(G2)(G2),
—N(G1)(G2),
—N(G3)(G3), and
—N(G6)(G6).

G1 is the "substituted or unsubstituted aryl group" described in the specific example group G1.

G2 is the "substituted or unsubstituted heterocylic group" described in the specific example group G2.

G3 is the "substituted or unsubstituted alkyl group" described in the specific example group G3.

G6 is the "substituted or unsubstituted cycloalkyl group" described in the specific example group G6.

A plurality of G1's in —N(G1)(G1) are the same as or different from each other.

A plurality of G2's in —N(G2)(G2) are the same as or different from each other.

A plurality of G3's in —N(G3)(G3) are the same as or different from each other.

A plurality of G6's in —N(G6)(G6) are the same as or different from each other.

"Halogen Atom"

Specific examples of the "halogen atom" described in this specification (specific example group G11) include a fluorine atom, a chlorine atom, a bromine atom, an iodine atom, and the like.

"Substituted or Unsubstituted Fluoroalkyl Group"

The "substituted or unsubstituted fluoroalkyl group" described in this specification is a group in which at least one hydrogen atom bonded with a carbon atom constituting the alkyl group in the "substituted or unsubstituted alkyl group" is substituted by a fluorine atom, and includes a group in which all hydrogen atoms bonded with a carbon atom constituting the alkyl group in the "substituted or unsubstituted alkyl group" are substituted by a fluorine atom (a perfluoro group). The number of carbon atoms of the "unsubstituted fluoroalkyl group" is 1 to 50, preferably 1 to 30, more preferably 1 to 18, unless otherwise specified in this specification. The "substituted fluoroalkyl group" means a group in which one or more hydrogen atoms of the "fluoroalkyl group" are substituted by a substituent. The "substituted fluoroalkyl group" described in this specification also includes a group in which one or more hydrogen atoms bonded with a carbon atom of the alkyl chains in the "substituted fluoroalkyl group" are further substituted by a substituent, and a group in which one or more hydrogen atom of a substituent in the "substituted fluoroalkyl group" are further substituted by a substituent. Specific examples of the "unsubstituted fluoroalkyl group" include a group in which one or more hydrogen atoms in the "alkyl group" (specific group G3) are substituted by a fluorine atom, and the like.

"Substituted or Unsubstituted Haloalkyl Group"

The "substituted or unsubstituted haloalkyl group" described in this specification is a group in which at least one hydrogen atom bonded with a carbon atom constituting the alkyl group in the "substituted or unsubstituted alkyl group" is substituted by a halogen atom, and also includes a group in which all hydrogen atoms bonded with a carbon atom constituting the alkyl group in the "substituted or unsubstituted alkyl group" are substituted by a halogen atom. The number of carbon atoms of the "unsubstituted haloalkyl group" is 1 to 50, preferably 1 to 30, more preferably 1 to 18, unless otherwise specified in this specification. The "substituted haloalkyl group" means a group in which one or more hydrogen atoms of the "haloalkyl group" are substituted by a substituent. The "substituted haloalkyl group" described in this specification also includes a group in which one or more hydrogen atoms bonded with a carbon atom of the alkyl chain in the "substituted haloalkyl group" are further substituted by a substituent, and a group in which one or more hydrogen atoms of a substituent in the "substituted haloalkyl group" are further substituted by a substituent. Specific examples of the "unsubstituted haloalkyl group" include a group in which one or more hydrogen atoms in the "alkyl group" (specific example group G3) are substituted by a halogen atom, and the like. A haloalkyl group is sometimes referred to as an alkyl halide group.

"Substituted or Unsubstituted Alkoxy Group"

Specific examples of the "substituted or unsubstituted alkoxy group" described in this specification include a group represented by —O(G3), wherein G3 is the "substituted or unsubstituted alkyl group" described in the specific example group G3. The number of carbon atoms of the "unsubstituted alkoxy group" is 1 to 50, preferably 1 to 30, more preferably 1 to 18, unless otherwise specified in this specification.

"Substituted or Unsubstituted Alkylthio Group"

Specific examples of the "substituted or unsubstituted alkylthio group" described in this specification include a group represented by —S(G3), wherein G3 is the "substituted or unsubstituted alkyl group" described in the specific example group G3. The number of carbon atoms of the "unsubstituted alkylthio group" is 1 to 50, preferably 1 to 30, more preferably 1 to 18, unless otherwise specified in this specification.

"Substituted or Unsubstituted Aryloxy Group"

Specific examples of the "substituted or unsubstituted aryloxy group" described in this specification include a group represented by —O(G1), wherein G1 is the "substituted or unsubstituted aryl group" described in the specific example group G1. The number of ring carbon atoms of the "unsubstituted aryloxy group" is 6 to 50, preferably 6 to 30, more preferably 6 to 18, unless otherwise specified in this specification.

"Substituted or Unsubstituted Arylthio Group"

Specific examples of the "substituted or unsubstituted arylthio group" described in this specification include a group represented by —S(G1), wherein G1 is a "substituted or unsubstituted aryl group" described in the specific example group G1. The number of ring carbon atoms of the "unsubstituted arylthio group" is 6 to 50, preferably 6 to 30, more preferably 6 to 18, unless otherwise specified in this specification.

"Substituted or Unsubstituted Trialkylsilyl Group"

Specific examples of the "trialkylsilyl group" described in this specification include a group represented by —Si(G3)(G3)(G3), where G3 is the "substituted or unsubstituted alkyl group" described in the specific example group G3. A plurality of G3's in —Si(G3)(G3)(G3) are the same as or different from each other. The number of carbon atoms in each alkyl group of the "trialkylsilyl group" is 1 to 50, preferably 1 to 20, more preferably 1 to 6, unless otherwise specified in this specification.

"Substituted or Unsubstituted Aralkyl Group"

Specific examples of the "substituted or unsubstituted aralkyl group" described in this specification is a group represented by -(G3)-(G1), wherein G3 is the "substituted or unsubstituted alkyl group" described in the specific example group G3, and G1 is the "substituted or unsubstituted aryl group" described in the specific example group G1. Therefore, the "aralkyl group" is a group in which a hydrogen atom of the "alkyl group" is substituted by an "aryl group" as a substituent, and is one form of the "substituted alkyl group." The "unsubstituted aralkyl group" is the "unsubstituted alkyl group" substituted by the "unsubstituted aryl group", and the number of carbon atoms of the "unsubstituted aralkyl group" is 7 to 50, preferably 7 to 30, more preferably 7 to 18, unless otherwise specified in this specification.

Specific examples of the "substituted or unsubstituted aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, and the like.

Unless otherwise specified in this specification, examples of the substituted or unsubstituted aryl group described in this specification preferably include a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, 9,9-dimethylfluorenyl group, 9,9-diphenylfluorenyl group, and the like.

Unless otherwise specified in this specification, examples of the substituted or unsubstituted heterocyclic groups described in this specification preferably include a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, a phenyldibenzothiophenyl group, and the like.

In this specification, the carbazolyl group is specifically any of the following groups, unless otherwise specified in this specification.

(TEMP-Cz1)

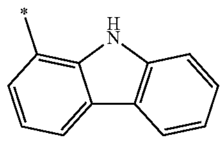

-continued (TEMP-Cz2)

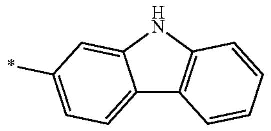

(TEMP-Cz3)

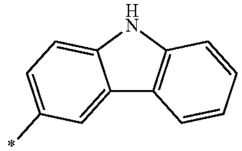

(TEMP-Cz4)

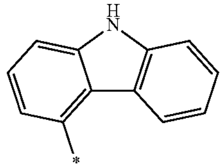

(TEMP-Cz5)

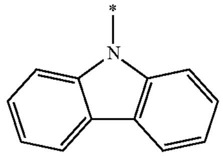

In this specification, the (9-phenyl)carbazolyl group is specifically any of the following groups, unless otherwise specified in this specification.

(TEMP-Cz6)

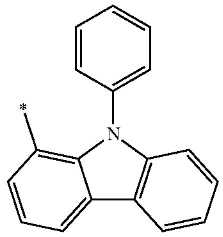

(TEMP-Cz7)

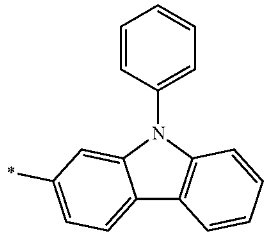

(TEMP-Cz8)

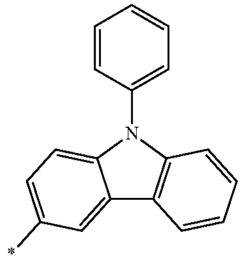

-continued (TEMP-Cz9)

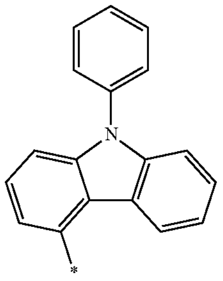

In the general formulas (TEMP-Cz1) to (TEMP-Cz9), * represents a bonding position.

In this specification, the dibenzofuranyl group and the dibenzothiophenyl group are specifically any of the following groups, unless otherwise specified in this specification.

(TEMP-34)

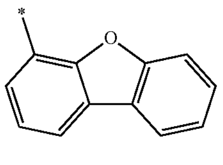

(TEMP-35)

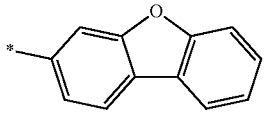

(TEMP-36)

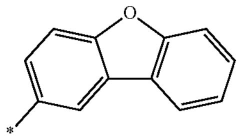

(TEMP-37)

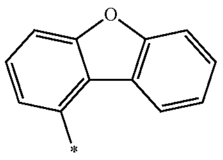

(TEMP-38)

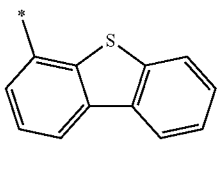

(TEMP-39)

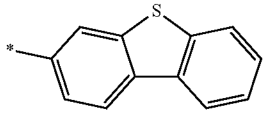

(TEMP-40)

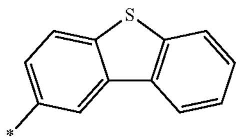

-continued (TEMP-41)

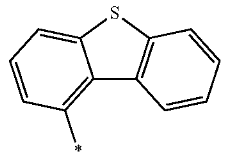

In the general formulas (TEMP-34) to (TEMP-41), * represents a bonding position.

The substituted or unsubstituted alkyl group described in this specification is preferably a methyl group, an ethyl group, a propyl group, an isopropyl group, a n-butyl group, an isobutyl group, a t-butyl group, or the like, unless otherwise specified in this specification.

"Substituted or Unsubstituted Arylene Group"

The "substituted or unsubstituted arylene group" described in this specification is a divalent group derived by removing one hydrogen atom on the aryl ring of the "substituted or unsubstituted aryl group", unless otherwise specified. Specific examples of the "substituted or unsubstituted arylene group" (specific example group G12) include a divalent group derived by removing one hydrogen atom on the aryl ring of the "substituted or unsubstituted aryl group" described in the specific example group G1, and the like.

"Substituted or Unsubstituted Divalent Heterocyclic Group"

The "substituted or unsubstituted divalent heterocyclic group" described in this specification is a divalent group derived by removing one hydrogen atom on the heterocycle of the "substituted or unsubstituted heterocyclic group", unless otherwise specified. Specific examples of the "substituted or unsubstituted divalent heterocyclic group" (specific example group G13) include a divalent group derived by removing one hydrogen atom on the heterocycle of the "substituted or unsubstituted heterocyclic group" described in the specific example group G2, and the like.

"Substituted or Unsubstituted Alkylene Group"

The "substituted or unsubstituted alkylene group" described in this specification is a divalent group derived by removing one hydrogen atom on the alkyl chain of the "substituted or unsubstituted alkyl group", unless otherwise specified. Specific examples of the "substituted or unsubstituted alkylene group" (specific example group G14) include a divalent group derived by removing one hydrogen atom on the alkyl chain of the "substituted or unsubstituted alkyl group" described in the specific example group G3, and the like.

The substituted or unsubstituted arylene group described in this specification is preferably any group of the following general formulas (TEMP-42) to (TEMP-68), unless otherwise specified in this specification.

(TEMP 42)

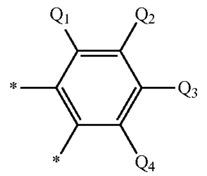

-continued
(TEMP-43)
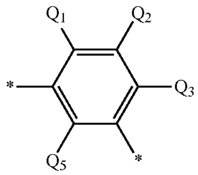
(TEMP-44)
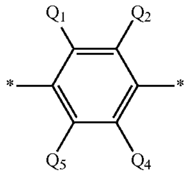
(TEMP-45)
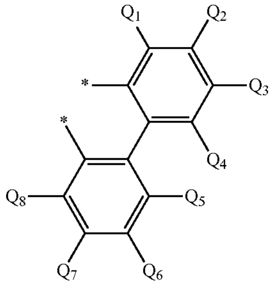
(TEMP-46)
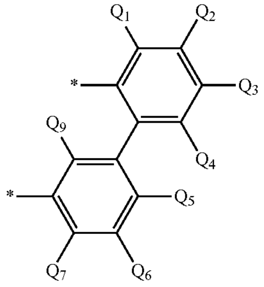
(TEMP-47)
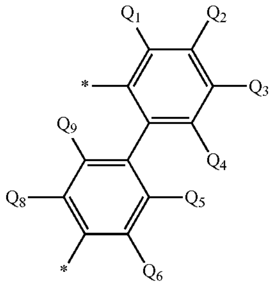
(TEMP-48)
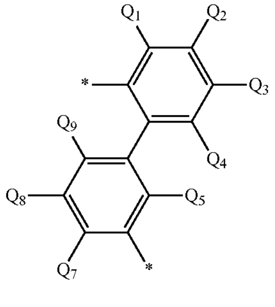
-continued
(TEMP-49)
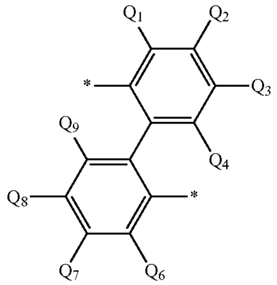
(TEMP-50)
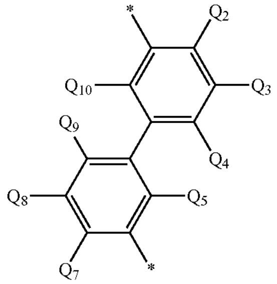
(TEMP-51)
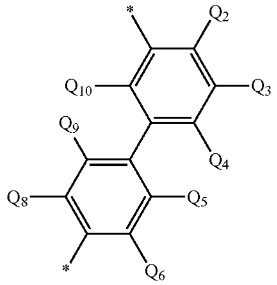
(TEMP-52)
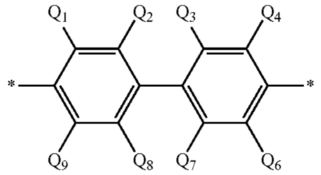
In the general formulas (TEMP-42) to (TEMP-52), $Q_1$ to $Q_{10}$ are independently a hydrogen atom or a substituent.
In the general formulas (TEMP-42) to (TEMP-52), * represents a bonding position.
(TEMP-53)
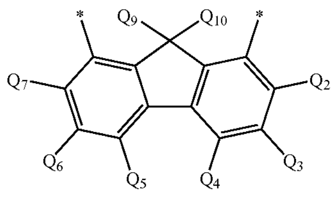
(TEMP-54)
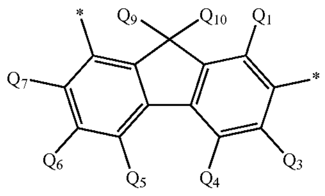

-continued (TEMP-55)

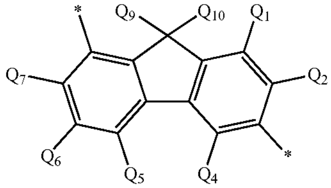

(TEMP-56)

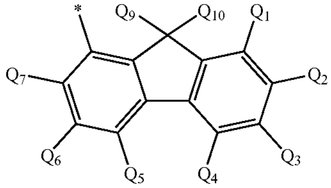

(TEMP-57)

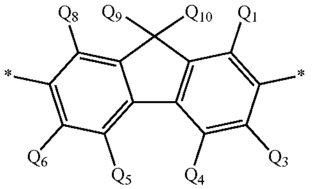

(TEMP-58)

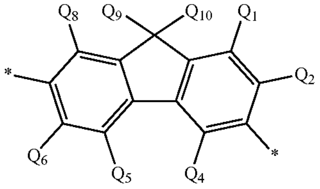

(TEMP-59)

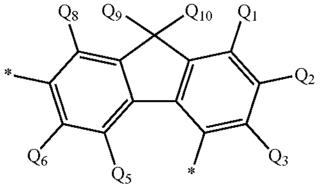

(TEMP-60)

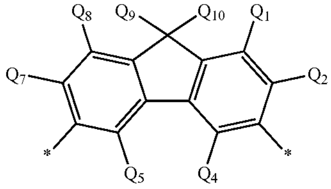

(TEMP-61)

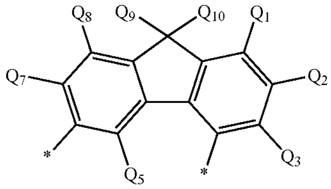

(TEMP-62)

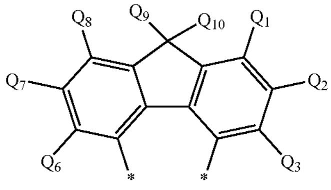

In the general formulas (TEMP-53) to (TEMP-62), $Q_1$ to $Q_{10}$ are independently a hydrogen atom or a substituent.

$Q_9$ and $Q_{10}$ may be bonded with each other via a single bond to form a ring.

In the general formulas (TEMP-53) to (TEMP-62), * represents a bonding position.

(TEMP-63)

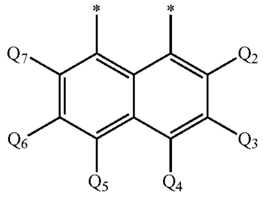

(TEMP-64)

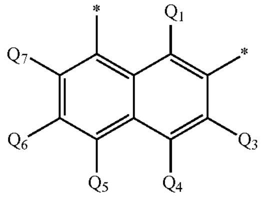

(TEMP-65)

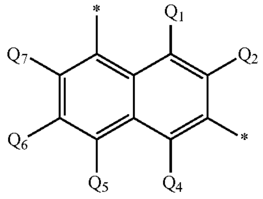

(TEMP-66)

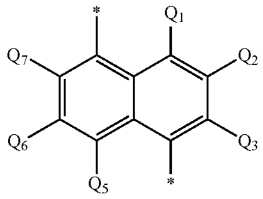

(TEMP-67)

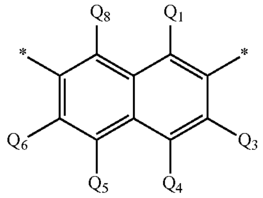

(TEMP-68)

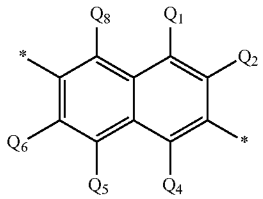

In the general formulas (TEMP-63) to (TEMP-68), $Q_1$ to $Q_8$ are independently a hydrogen atom or a substituent.

In the general formulas (TEMP-63) to (TEMP-68), * represents a bonding position.

The substituted or unsubstituted divalent heterocyclic group described in this specification is preferably any group of the following general formulas (TEMP-69) to (TEMP-102), unless otherwise specified in this specification.

-continued
(TEMP-69)
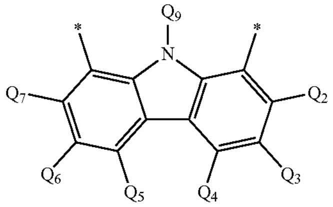
(TEMP-70)
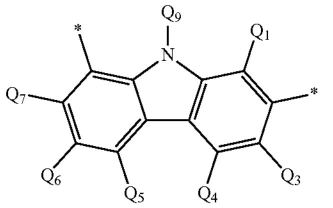
(TEMP-71)
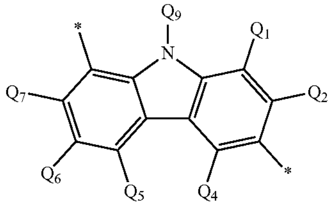
(TEMP-72)
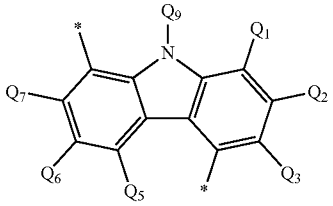
(TEMP-73)
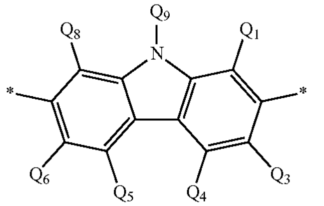
(TEMP-74)
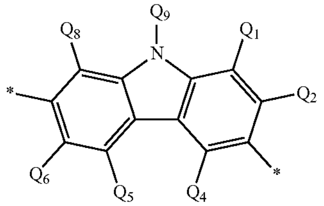
(TEMP-75)
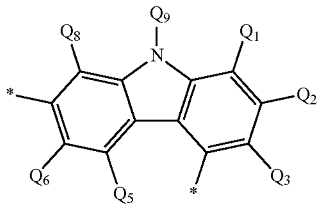
(TEMP-76)
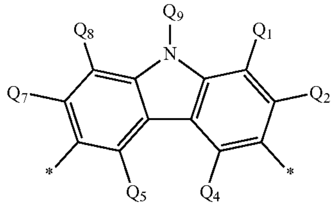
(TEMP-77)
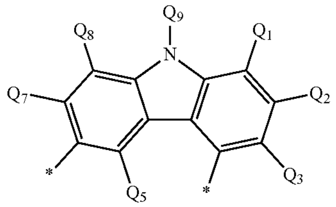
(TEMP-78)
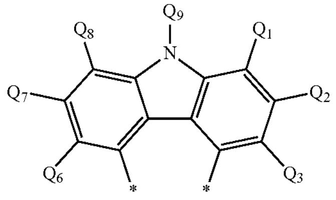
(TEMP-79)
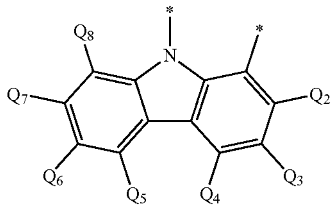
(TEMP-80)
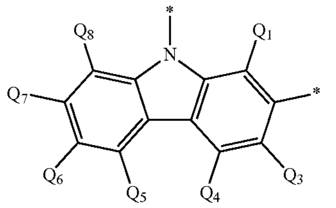
(TEMP-81)
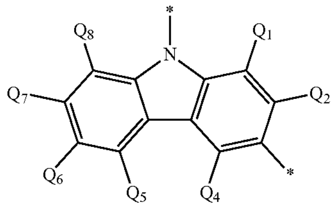
(TEMP-82)
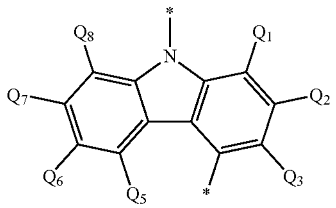

In the general formulas (TEMP-69) to (TEMP-82), $Q_1$ to $Q_9$ are independently a hydrogen atom or a substituent.
(TEMP-83)
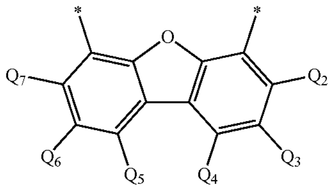
(TEMP-84)
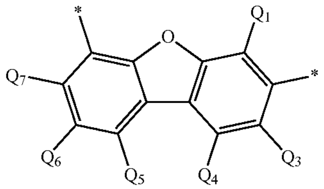
(TEMP-85)
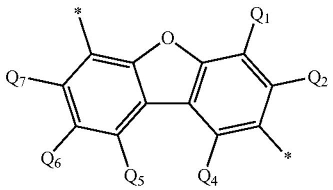
(TEMP-86)
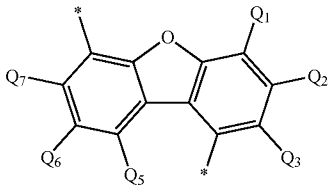
(TEMP-87)
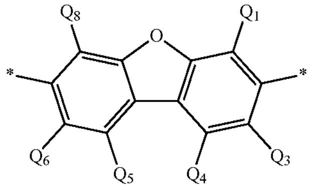
(TEMP-88)
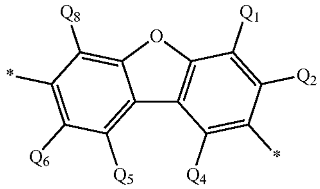
(TEMP-89)
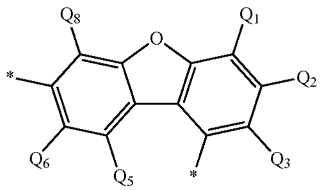
-continued
(TEMP-90)
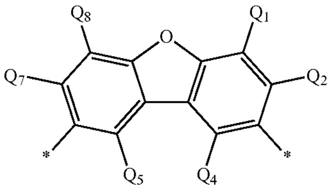
(TEMP-91)
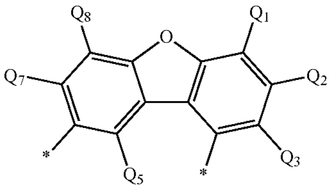
(TEMP-92)
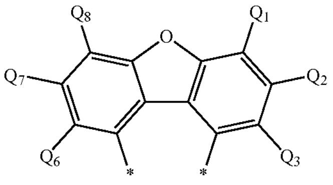
(TEMP-93)
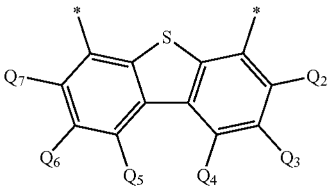
(TEMP-94)
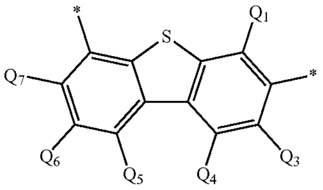
(TEMP-95)
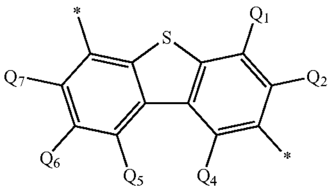
(TEMP-96)
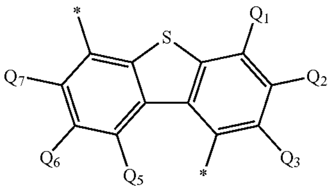
(TEMP-97)
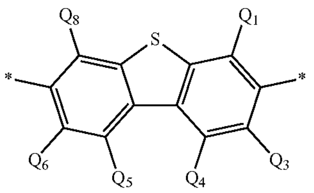

-continued (TEMP-98)

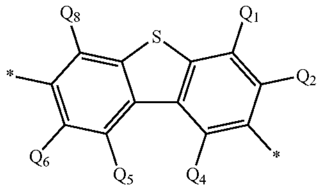

(TEMP-99)

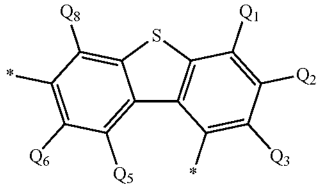

(TEMP-100)

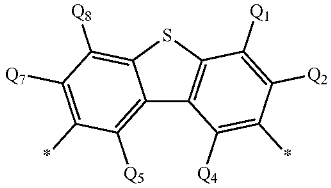

(TEMP-101)

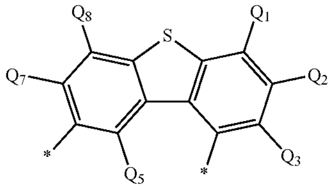

(TEMP-102)

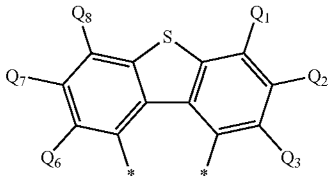

In the general formulas (TEMP-83) to (TEMP-102), $Q_1$ to $Q_8$ are independently a hydrogen atom or a substituent.

The above is the explanation of the "Substituent described in this specification."

"The Case where Bonded with Each Other to Form a Ring"

In this specification, the case where "one or more sets of adjacent two or more form a substituted or unsubstituted monocycle by bonding with each other, form a substituted or unsubstituted fused ring by bonding with each other, or do not bond with each other" means the case where "one or more sets of adjacent two or more form a substituted or unsubstituted monocycle by bonding with each other"; the case where "one or more sets of adjacent two or more form a substituted or unsubstituted fused ring by bonding with each other"; and the case where "one or more sets of adjacent two or more do not bond with each other."

The case where "one or more sets of adjacent two or more form a substituted or unsubstituted monocycle by bonding with each other" and the case where "one or more sets of adjacent two or more form a substituted or unsubstituted fused ring by bonding with each other" in this specification (these cases may be collectively referred to as "the case where forming a ring by bonding with each other") will be described below. The case of an anthracene compound represented by the following general formula (TEMP-103) in which the mother skeleton is an anthracene ring will be described as an example.

(TEMP-103)

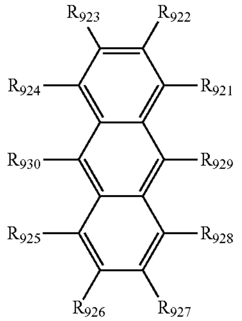

For example, in the case where "one or more sets of adjacent two or more among $R_{921}$ to $R_{930}$ form a ring by bonding with each other", the one set of adjacent two includes a pair of $R_{921}$ and $R_{922}$, a pair of $R_{922}$ and $R_{923}$, a pair of $R_{923}$ and $R_{924}$, a pair of $R_{924}$ and $R_{930}$, a pair of $R_{930}$ and $R_{925}$, a pair of $R_{925}$ and $R_{926}$, a pair of $R_{926}$ and $R_{927}$, a pair of $R_{927}$ and $R_{928}$, a pair of $R_{928}$ and $R_{929}$, and a pair of $R_{929}$ and $R_{921}$.

The "one or more sets" means that two or more sets of the adjacent two or more sets may form a ring at the same time. For example, $R_{921}$ and $R_{922}$ forma ring $Q_A$ by bonding with each other, and at the same, time $R_{925}$ and $R_{926}$ form a ring $Q_B$ by bonding with each other, the anthracene compound represented by the general formula (TEMP-103) is represented by the following general formula (TEMP-104).

(TEMP-104)

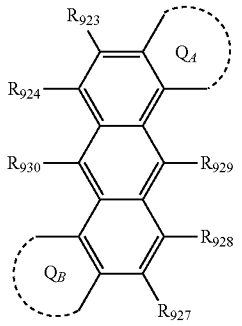

The case where the "set of adjacent two or more" form a ring includes not only the case where the set (pair) of adjacent "two" is bonded with as in the above-mentioned examples, but also the case where the set of adjacent "three or more" are bonded with each other. For example, it means the case where $R_{921}$ and $R_{922}$ form a ring $Q_A$ by bonding with each other, and $R_{922}$ and $R_{923}$ form a ring $Q_C$ by bonding with each other, and adjacent three ($R_{921}$, $R_{922}$ and $R_{923}$) form rings by bonding with each other and together fused to the anthracene mother skeleton. In this case, the anthracene compound represented by the general formula (TEMP-103) is represented by the following general formula (TEMP-105). In the following general formula (TEMP-105), the ring $Q_A$ and the ring $Q_C$ share $R_{922}$.

(TEMP-105)

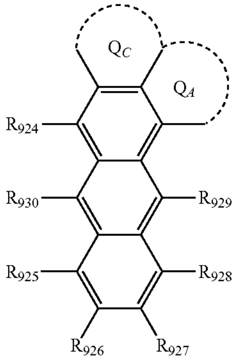

The “monocycle” or “fused ring” formed may be a saturated ring or an unsaturated ring, as a structure of the formed ring alone. Even when the “one pair of adjacent two” forms a “monocycle” or a “fused ring”, the “monocycle” or the “fused ring” may forma saturated ring or an unsaturated ring. For example, the ring $Q_A$ and the ring $Q_B$ formed in the general formula (TEMP-104) are independently a “monocycle” or a “fused ring.” The ring $Q_A$ and the ring $Q_C$ formed in the general formula (TEMP-105) are “fused ring.” The ring $Q_A$ and ring $Q_C$ of the general formula (TEMP-105) are fused ring by fusing the ring $Q_A$ and the ring $Q_C$ together. When the ring $Q_A$ of the general formula (TMEP-104) is a benzene ring, the ring $Q_A$ is a monocycle. When the ring $Q_A$ of the general formula (TMEP-104) is a naphthalene ring, the ring $Q_A$ is a fused ring.

The “unsaturated ring” means an aromatic hydrocarbon ring or an aromatic heterocycle. The “saturated ring” means an aliphatic hydrocarbon ring, or a non-aromatic heterocycle.

Specific examples of the aromatic hydrocarbon ring include a structure in which the group listed as a specific example in the specific example group G1 is terminated by a hydrogen atom.

Specific examples of the aromatic heterocycle include a structure in which the aromatic heterocyclic group listed as a specific example in the example group G2 is terminated by a hydrogen atom.

Specific examples of the aliphatic hydrocarbon ring include a structure in which the group listed as a specific example in the specific example group G6 is terminated by a hydrogen atom.

The term “to form a ring” means forming a ring only with a plurality of atoms of the mother skeleton, or with a plurality of atoms of the mother skeleton and one or more arbitrary elements in addition. For example, the ring $Q_A$ shown in the general formula (TEMP-104), which is formed by bonding $R_{921}$ and $R_{922}$ with each other, is a ring formed from the carbon atom of the anthracene skeleton with which $R_{921}$ is bonded, the carbon atom of the anthracene skeleton with which $R_{922}$ is bonded, and one or more arbitrary elements. For example, in the case where the ring $Q_A$ is formed with $R_{921}$ and $R_{922}$, when a monocyclic unsaturated ring is formed with the carbon atom of the anthracene skeleton with which $R_{921}$ is bonded, the carbon atom of the anthracene skeleton with which $R_{922}$ is bonded, and four carbon atoms, the ring formed with $R_{921}$ and $R_{922}$ is a benzene ring.

Here, the “arbitrary element” is preferably at least one element selected from the group consisting of a carbon element, a nitrogen element, an oxygen element, and a sulfur element, unless otherwise specified in this specification. In the arbitrary element (for example, a carbon element or a nitrogen element), a bond which does not form a ring may be terminated with a hydrogen atom or the like, or may be substituted with “arbitrary substituent” described below. When an arbitrary element other than a carbon element is contained, the ring formed is a heterocycle.

The number of “one or more arbitrary element(s)” constituting a monocycle or a fused ring is preferably 2 or more and 15 or less, more preferably 3 or more and 12 or less, and still more preferably 3 or more and 5 or less, unless otherwise specified in this specification.

The “monocycle” is preferable among the “monocycle” and the “fused ring”, unless otherwise specified in this specification.

The “unsaturated ring” is preferable among the “saturated ring” and the “unsaturated ring”, unless otherwise specified in this specification.

Unless otherwise specified in this specification, the “monocycle” is preferably a benzene ring.

Unless otherwise specified in this specification, the “unsaturated ring” is preferably a benzene ring.

Unless otherwise specified in this specification, when “one or more sets of adjacent two or more” are “bonded with each other to form a substituted or unsubstituted monocycle” or “bonded with each other to form a substituted or unsubstituted fused ring”, this specification, one or more sets of adjacent two or more are preferably bonded with each other to form a substituted or unsubstituted “unsaturated ring” from a plurality of atoms of the mother skeleton and one or more and 15 or less elements which is at least one kind selected from a carbon elements, a nitrogen element, an oxygen element, and a sulfur element.

The substituent in the case where the above-mentioned “monocycle” or “fused ring” has a substituent is, for example, an “arbitrary substituent” described below. Specific examples of the substituent which the above-mentioned “monocycle” or “fused ring” has include the substituent described above in the “Substituent described in this specification” section.

The substituent in the case where the above-mentioned “saturated ring” or “unsaturated ring” has a substituent is, for example, an “arbitrary substituent” described below. Specific examples of the substituent which the above-mentioned “monocycle” or “fused ring” has include the substituent described above in the “Substituent described in this specification” section.

The foregoing describes the case where “one or more sets of adjacent two or more form a substituted or unsubstituted monocycle by bonding with each other” and the case where “one or more sets of adjacent two or more form a substituted or unsubstituted fused ring by bonding with each other” (the case where “forming a ring by bonding with each other”).

Substituent in the Case of “Substituted or Unsubstituted”

In one embodiment in this specification, the substituent (in this specification, sometimes referred to as an “arbitrary substituent”) in the case of “substituted or unsubstituted” is, for example, a group selected from the group consisting of:

an unsubstituted alkyl group including 1 to 50 carbon atoms, an unsubstituted alkenyl group including 2 to 50 carbon atoms, an unsubstituted alkynyl group including 2 to 50 carbon atoms, an unsubstituted cycloalkyl group including 3 to 50 ring carbon atoms, —Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
an unsubstituted aryl group including 6 to 50 ring carbon atoms, and
an unsubstituted heterocyclic group including 5 to 50 ring atoms,
wherein, $R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted heterocyclic group including 5 to 50 ring atoms.

When two or more $R_{901}$'s are present, the two or more $R_{901}$'s may be the same as or different from each other.

When two or more $R_{902}$'s are present, the two or more $R_{902}$'s may be the same as or different from each other.

When two or more $R_{903}$'s are present, the two or more $R_{903}$'s may be the same as or different from each other.

When two or more $R_{904}$'s are present, the two or more $R_{904}$'s may be the same as or different from each other.

When two or more $R_{905}$'s are present, the two or more $R_{905}$'s may be the same as or different from each other.

When two or more $R_{906}$'s are present, the two or more $R_{906}$'s may be the same as or different from each other.

When two or more $R_{907}$'s are present, the two or more $R_{907}$'s may be the same as or different from each other.

In one embodiment, the substituent in the case of "substituted or unsubstituted" is a group selected from the group consisting of:
an alkyl group including 1 to 50 carbon atoms,
an aryl group including 6 to 50 ring carbon atoms, and
a heterocyclic group including 5 to 50 ring atoms.

In one embodiment, the substituent in the case of "substituted or unsubstituted" is a group selected from the group consisting of:
an alkyl group including 1 to 18 carbon atoms,
an aryl group including 6 to 18 ring carbon atoms, and
a heterocyclic group including 5 to 18 ring atoms.

Specific examples of each of the arbitrary substituents include specific examples of substituent described in the section "Substituent described in this specification" above.

Unless otherwise specified in this specification, adjacent arbitrary substituents may form a "saturated ring" or an "unsaturated ring", preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, more preferably form a benzene ring.

Unless otherwise specified in this specification, the arbitrary substituent may further have a substituent. The substituent which the arbitrary substituent further has is the same as that of the above-mentioned arbitrary substituent.

In this specification, the numerical range represented by "AA to BB" means the range including the numerical value AA described on the front side of "AA to BB" as the lower limit and the numerical value BB described on the rear side of "AA to BB" as the upper limit.

[Compound Represented by Formula (A1)]

The compound of one aspect of the invention is a compound represented by the following formula (A1).

(A1)

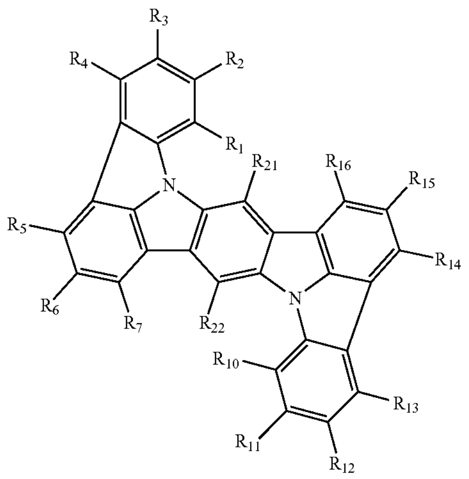

In the formula (A1),
one or more sets of adjacent two or more among $R_1$ to $R_7$ and $R_{10}$ to $R_{16}$ form a substituted or unsubstituted, saturated or unsaturated ring by bonding with each other, or do not form a substituted or unsubstituted, saturated or unsaturated ring;
$R_{21}$ and $R_{22}$, $R_1$ to $R_7$ that do not form the substituted or unsubstituted, saturated or unsaturated ring, and $R_{10}$ to $R_{16}$ that do not form the substituted or unsubstituted, saturated or unsaturated ring are independently
a hydrogen atom, or
a substituent R;
the substituent R is
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
when two or more of the substituent R's are present, the two or more of the substituent R's may be the same as or different from each other;
$R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or a substituted or unsubstituted monovalent heterocyclic group including 5 to 50 ring atoms;

when two or more of each of $R_{901}$ to $R_{907}$ are present, the two or more of each of $R_{901}$ to $R_{907}$ may be the same as or different from each other;

one or more hydrogen atoms selected from the group consisting of the followings are deuterium atoms:

hydrogen atoms possessed by the formed substituted or unsubstituted, saturated or unsaturated ring, hydrogen atoms possessed by a substituent that substitutes on the formed substituted or unsubstituted, saturated or unsaturated ring, hydrogen atoms when each of $R_{21}$ and $R_{22}$ is a hydrogen atom, hydrogen atoms when each of $R_1$ to $R_7$ and $R_{10}$ to $R_{16}$ is a hydrogen atom, and hydrogen atoms possessed by $R_{21}$, $R_{22}$, $R_1$ to $R_7$, and $R_{10}$ to $R_{16}$ when each of $R_{21}$, $R_{22}$, $R_1$ to $R_7$, and $R_{10}$ to $R_{16}$ is the substituent R.

When the substituent R described above has a substituent, a hydrogen atom possessed by the substituent may be a deuterium atom. In other words, the compound represented by the formula (A1) includes a compound in which a hydrogen atom possessed by a substituent that substitutes on the substituent R is a deuterium atom.

By using the compound represented by the formula (A1), an effect to make the lifetime of the organic EL device prolong is obtained.

An organic EL device described later has an effect to have an increased lifetime by the use of a compound represented by the formula (A1).

The compound represented by the formula (A1) has at least one deuterium atom.

The presence of deuterium atoms in a compound is confirmed by mass spectrometry or $^1$H-NMR spectrometry. The position where a deuterium atom is bonded to the compound is determined by $^1$H-NMR analysis. Specifically, the following method can be used.

A compound to be measured is subjected to mass spectrometry. If the molecular weight is increased by 1 compared to that of the corresponding compound in which all hydrogen atoms are protium atoms, it can be confirmed that the compound contains one deuterium atom. In addition, the number of deuterium atoms in the molecule can be confirmed by the integral value obtained by $^1$H-NMR analysis of the compound to be measured, since a deuterium atom gives no signal in $^1$H-NMR analysis. In addition, the position in the compound where the deuterium atom is bonded can be identified by carrying out $^1$H-NMR analysis of the compound to be measured, and assigning the obtained signals.

In one embodiment, at least one of $R_{21}$ and $R_{22}$, $R_1$ to $R_7$ that do not form the substituted or unsubstituted, saturated or unsaturated ring, and $R_{10}$ to $R_{16}$ that do not form the substituted or unsubstituted, saturated or unsaturated ring is the substituent Rand the rest are hydrogen atoms. The hydrogen atoms may be a protium atom or a deuterium atom. Further, hydrogen atoms possessed by the substituent R may also be a protium atom or a deuterium atom.

In one embodiment, the substituent R is

—N($R_{906}$)($R_{907}$), wherein $R_{906}$ and $R_{907}$ are as defined in the formula (A1), a substituted or unsubstituted aryl group including 6 to 50 ring carbon atoms, or a substituted or unsubstituted monovalent heterocyclic group including 5 to 50 ring atoms.

In one embodiment, at least one of $R_1$ to $R_7$ and $R_{10}$ to $R_{16}$ in the formula (A1) is —N($R_{906}$)($R_{907}$).

In one embodiment, at least two of $R_1$ to $R_7$ and $R_{10}$ to $R_{16}$ in the formula (A1) are —N($R_{906}$)($R_{907}$).

In one embodiment, the compound represented by the formula (A1) is a compound represented by the following formula (A10).

(A10)

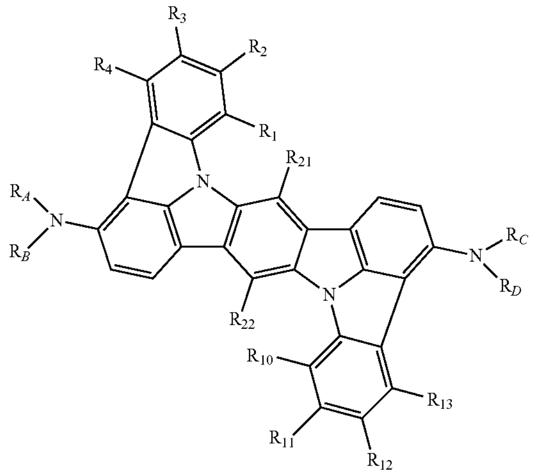

In the formula (A10), $R_1$ to $R_4$, $R_{10}$ to $R_{13}$, $R_{21}$, and $R_{22}$ are as defined in the formula (A1);

$R_A$, $R_B$, $R_C$, and $R_D$ are independently a substituted or unsubstituted aryl group including 6 to 18 ring carbon atoms, or a substituted or unsubstituted monovalent heterocyclic group including 5 to 18 ring atoms.

In one embodiment, the compound represented by the formula (A10) is a compound represented by the following formula (A11).

(A11)

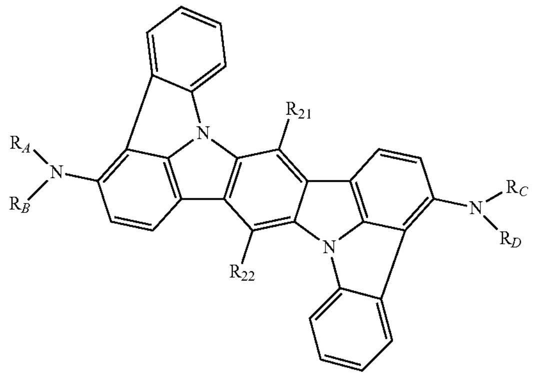

In the formula (A11), $R_{21}$, $R_{22}$, $R_A$, $R_B$, $R_C$, and $R_D$ are as defined in the formula (A10).

In one embodiment, in the formulas (A10) and (A11), $R_A$, $R_B$, $R_C$, and $R_D$ are independently a substituted or unsubstituted aryl group including 6 to 18 ring carbon atoms.

In one embodiment, in the formulas (A10) and (A11), $R_A$, $R_B$, $R_C$, and $R_D$ are independently a substituted or unsubstituted phenyl group.

In one embodiment, in the formula (A1), $R_{21}$ and $R_{22}$ are independently a protium atom, a deuterium atom, or a substituted or unsubstituted phenyl group.

In one embodiment, the compound represented by the formula (A1) is a compound represented by the following formula (A13).

(A13)

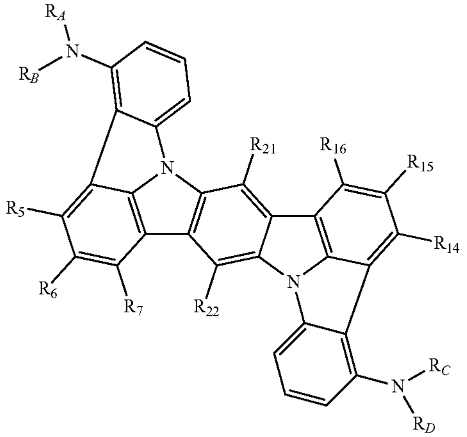

In the formula (A13), $R_5$ to $R_7$, $R_{14}$ to $R_{16}$, $R_{21}$, $R_{22}$, $R_A$, $R_B$, $R_C$, and $R_D$ are as defined in any of the formulas (A1) and (A10).

In one embodiment, the compound represented by the formula (A13) is a compound represented by the following formula (A14).

(A14)

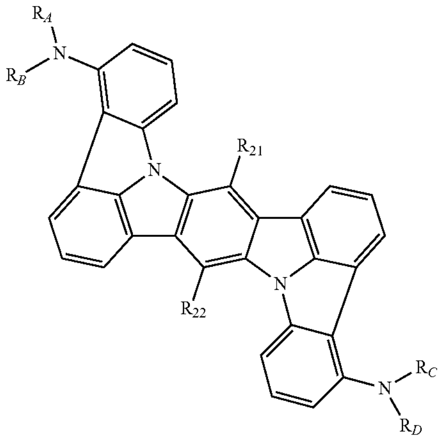

In the formula (A14), $R_{21}$, $R_{22}$, $R_A$, $R_B$, $R_C$, and $R_0$ are as defined in any of the formulas (A1) and (A10).

In one embodiment, the compound represented by the formula (A1) is a compound represented by the following formula (A15).

(A15)

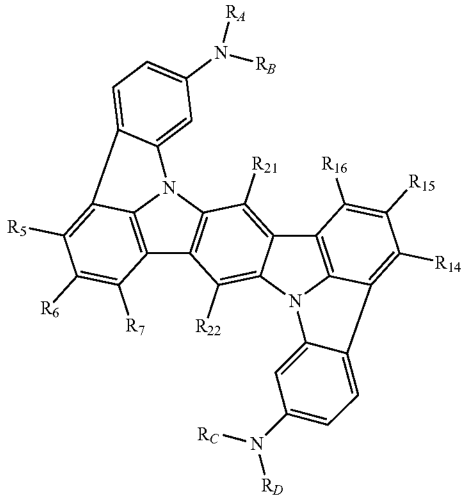

In the formula (A15), $R_1$ to $R_7$, $R_4$ to $R_{16}$, $R_{21}$, $R_{22}$, $R_A$, $R_B$, $R_C$, and $R_D$ are as defined in any of the formulas (A1) and (A15).

In one embodiment, the compound represented by the formula (A15) is a compound represented by the following formula (A16).

(A16)

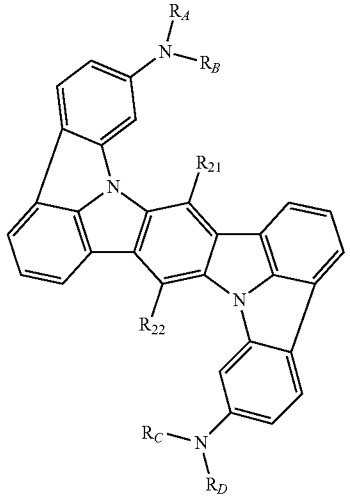

In the formula (A16), $R_{21}$, $R_{22}$, $R_A$, $R_B$, $R_C$, and $R_D$ are as defined in any of the formulas (A1) and (A10).

In one embodiment, the compound represented by the formula (A10) is a compound represented by the following formula (A17).

(A17)

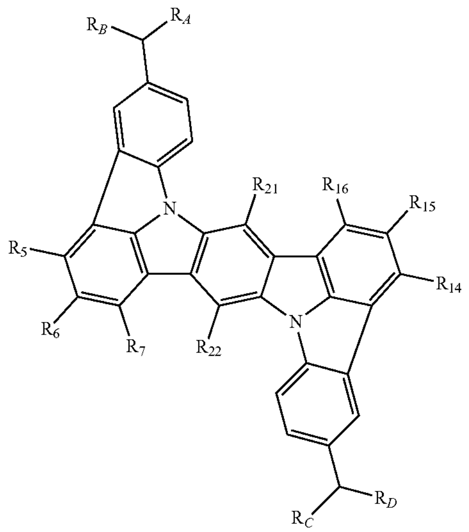

In the formula (A17), $R_5$ to $R_7$, $R_{14}$ to $R_{16}$, $R_{21}$, $R_{22}$, $R_A$, $R_B$, $R_C$, and $R_D$ are as defined in any of the formulas (A1) and (A10).

In one embodiment, the compound represented by the formula (A17) is a compound represented by the following formula (A18).

(A18)

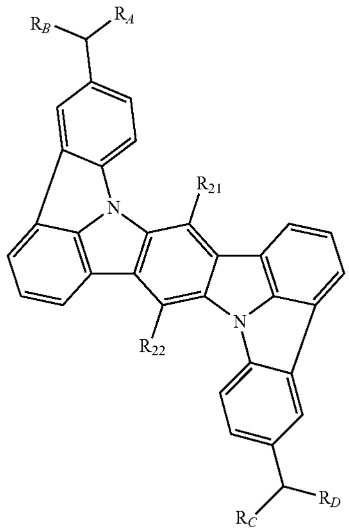

In the formula (A18), $R_{21}$, $R_{22}$, $R_A$, $R_B$, $R_C$, and $R_D$ are as defined in any of the formulas (A1) and (A10).

In one embodiment, $R_{21}$ and $R_{22}$ in the formula (A1) are hydrogen atoms. Here, the hydrogen atom may be a protium atom or a deuterium atom.

The details of each substituent in each of the above formulas and the substituent in the case of "substituted or unsubstituted" are as described in the column of [Definition] in this specification.

The compound represented by the formula (A1) can be synthesized in accordance with Synthesis Examples described later by using known alternative reactions or raw materials tailored to the target compound.

Specific examples of the compound represented by the formula (A1) include the following compounds. In the following specific examples, "Me" represents a methyl group, and "D" represents a deuterium atom.

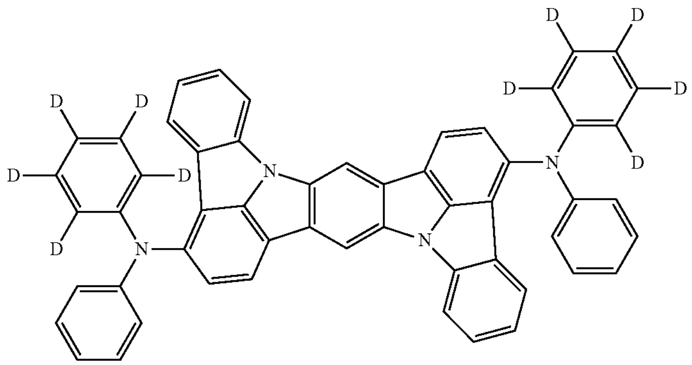

-continued
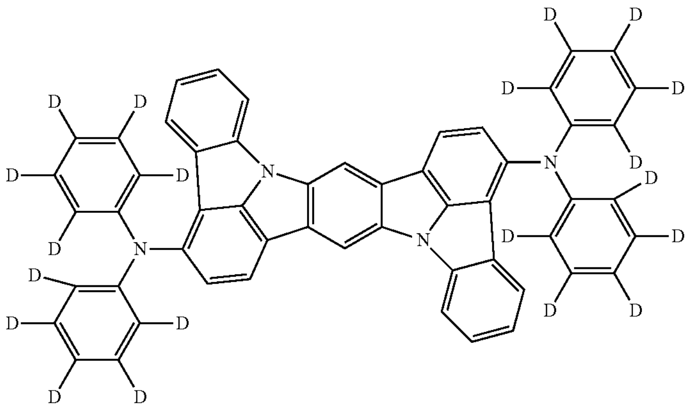
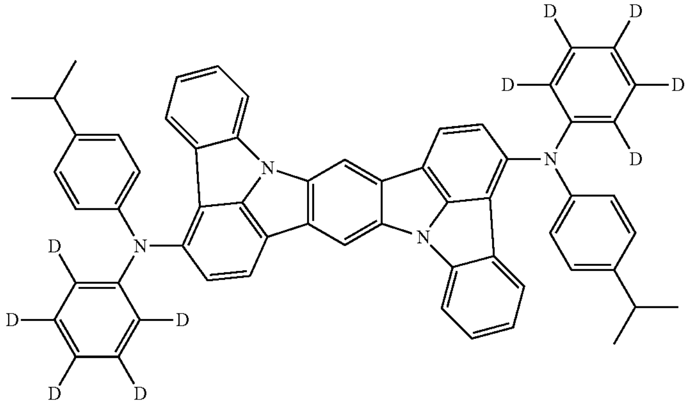
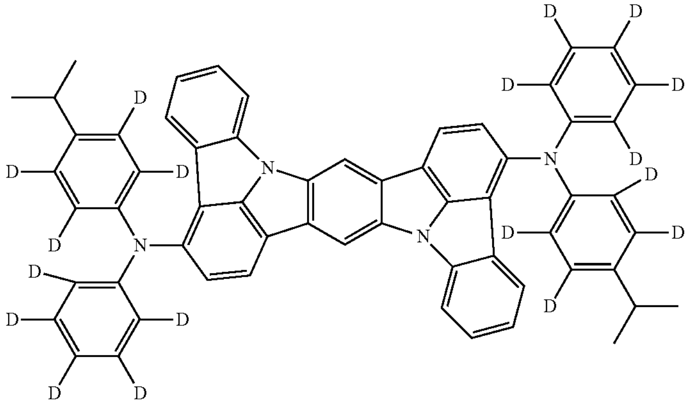
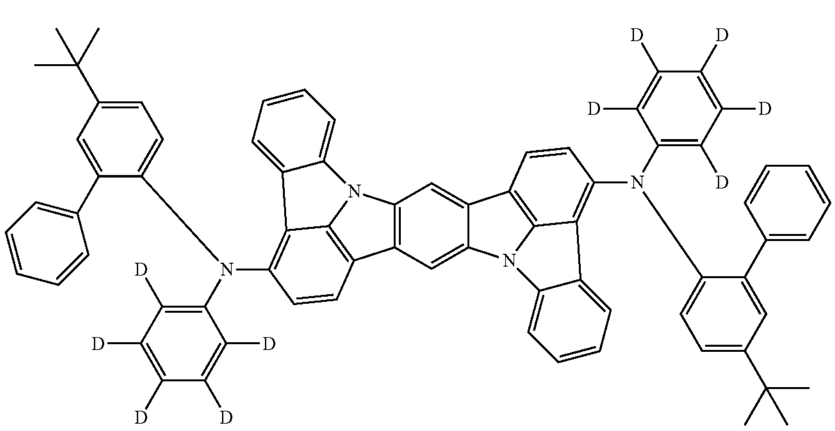

-continued
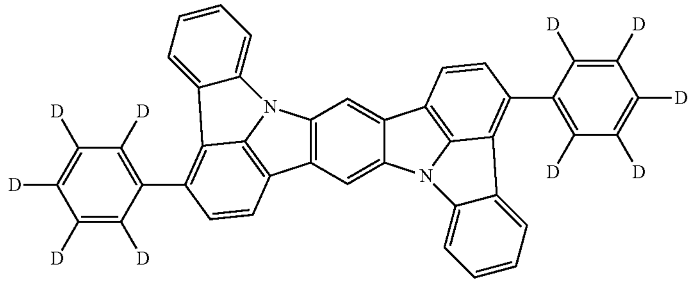
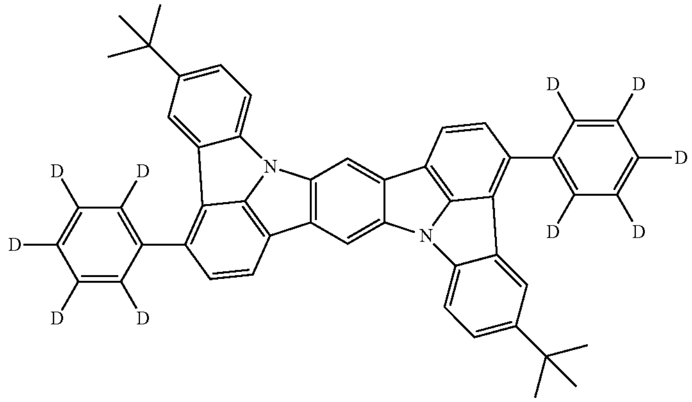
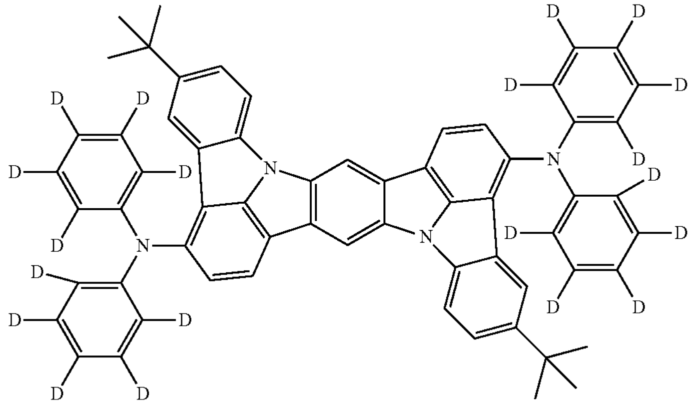
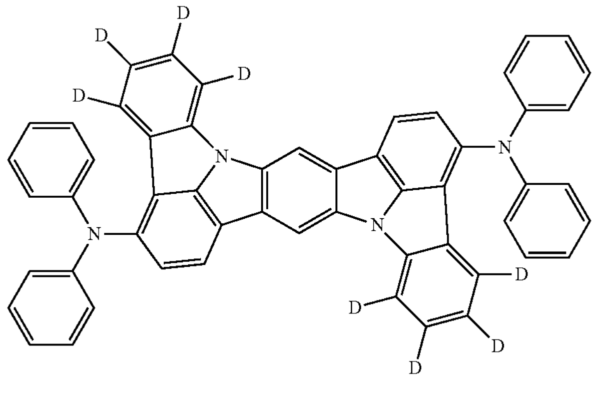

-continued
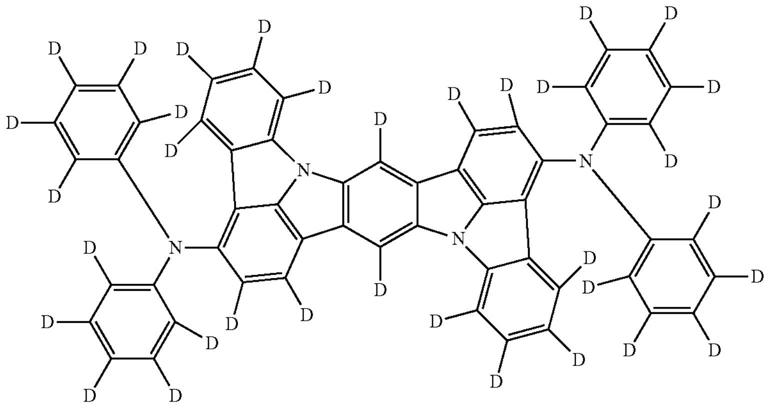
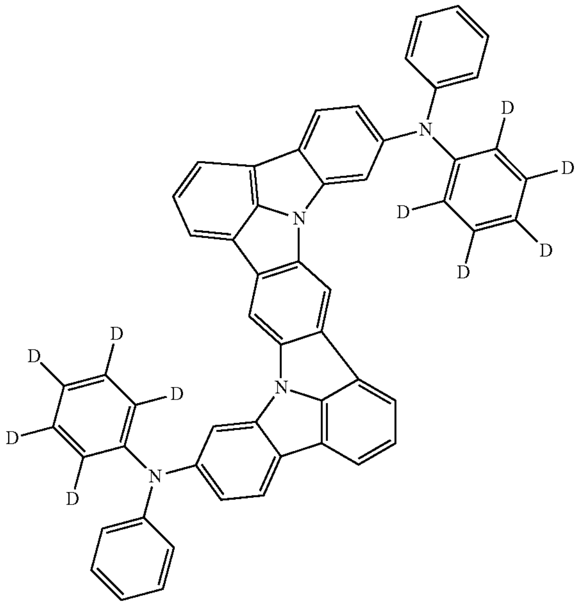
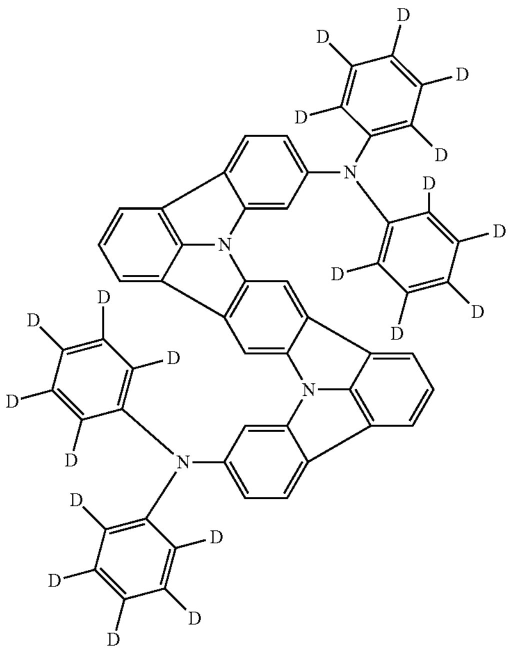
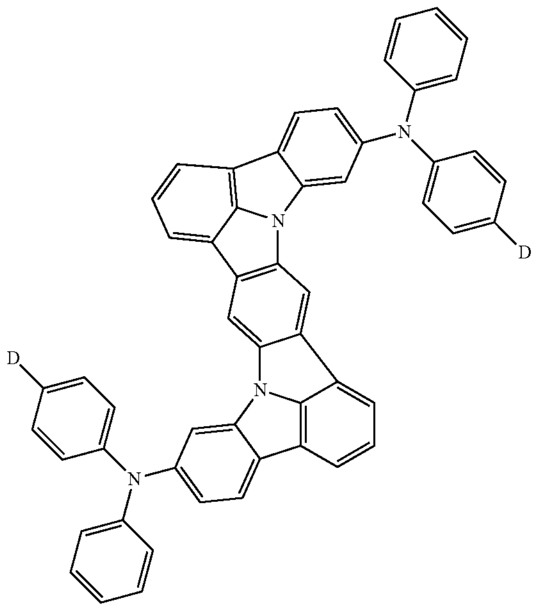

-continued
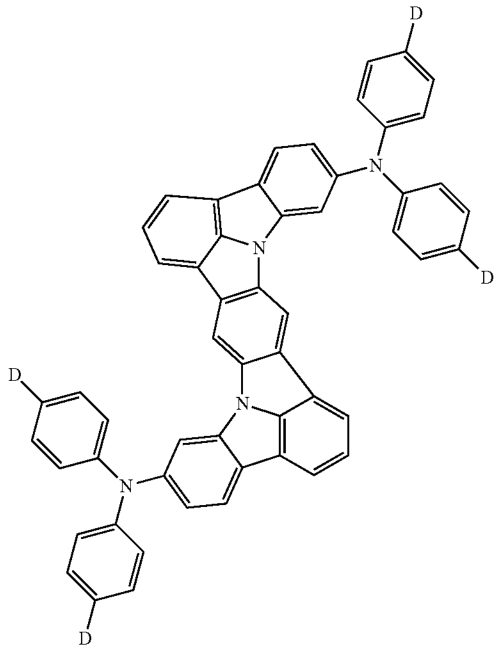
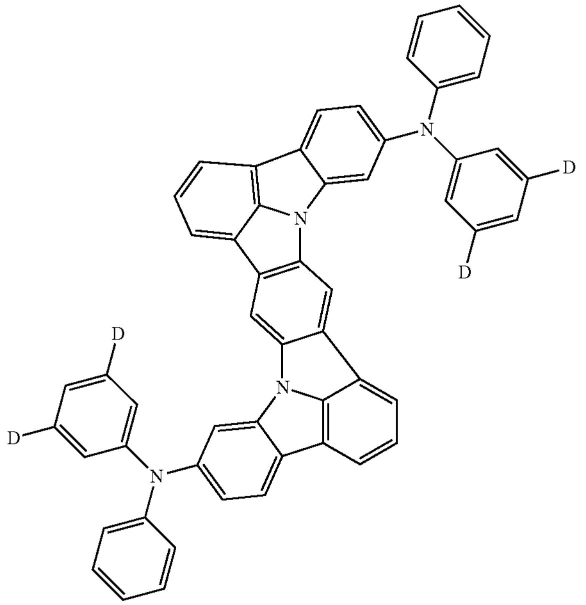
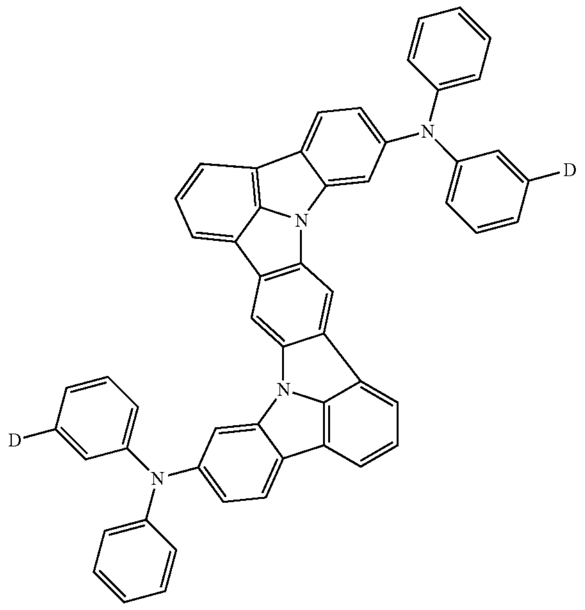
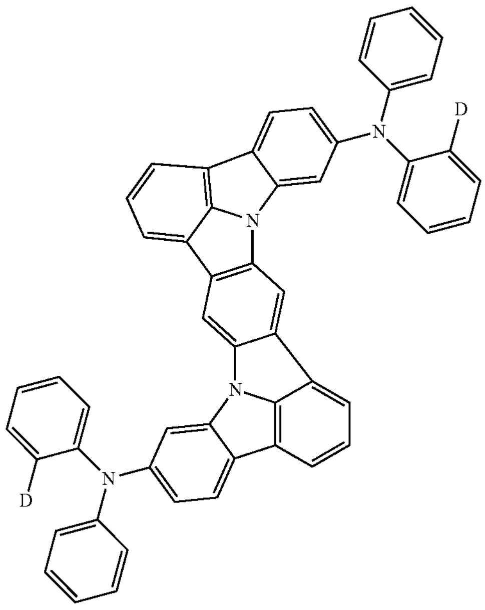

-continued
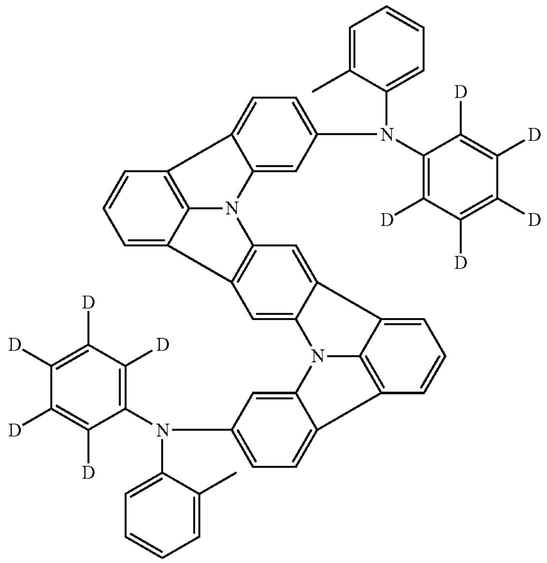
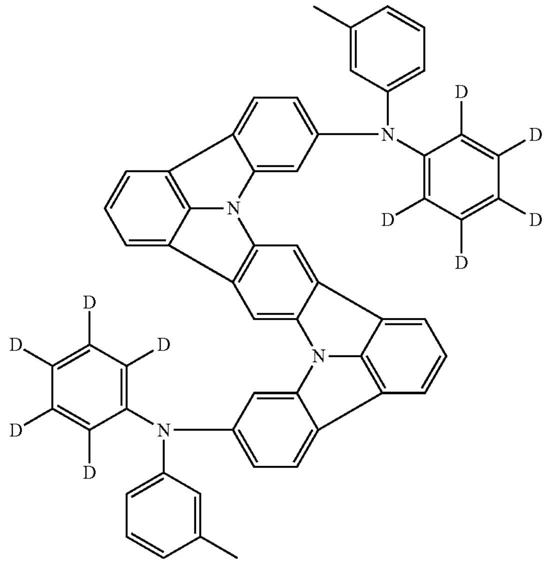
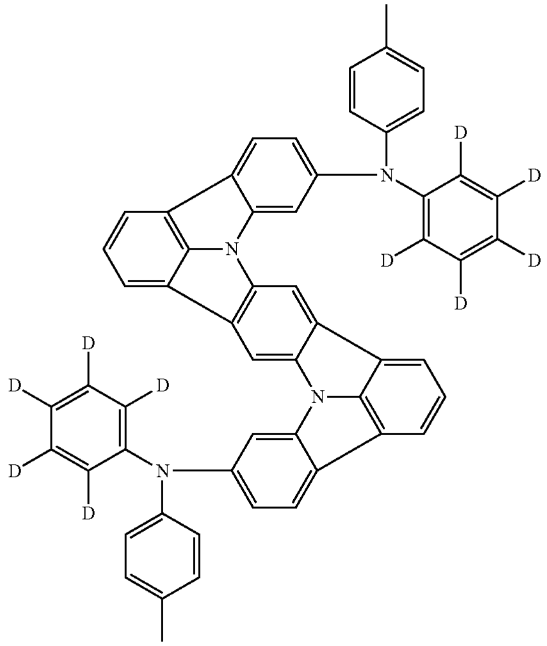
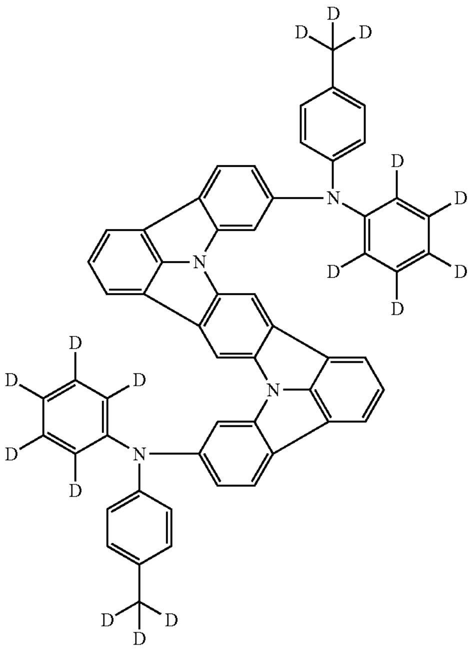

-continued
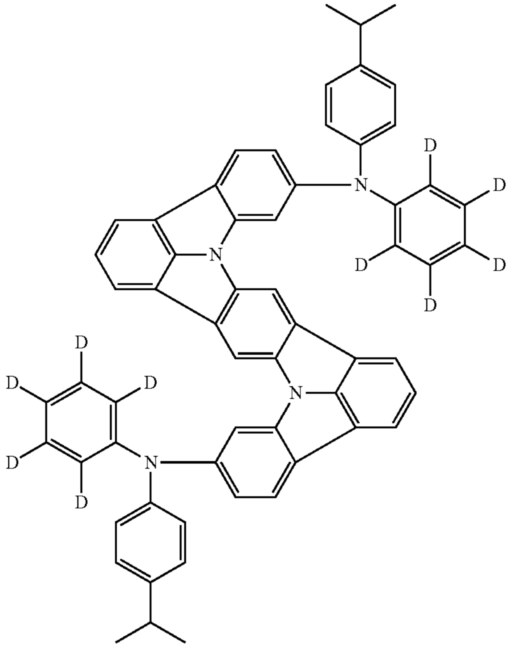
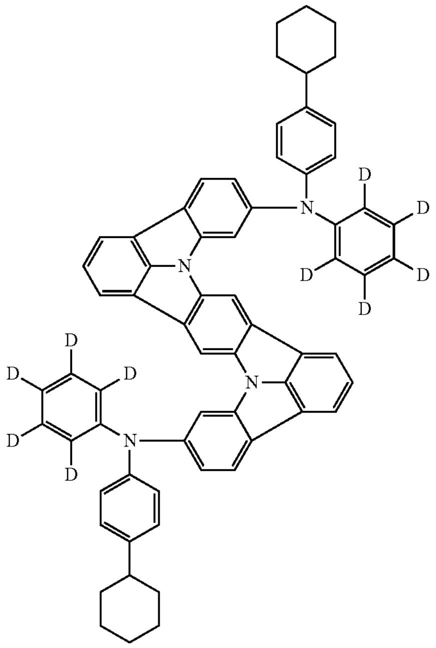
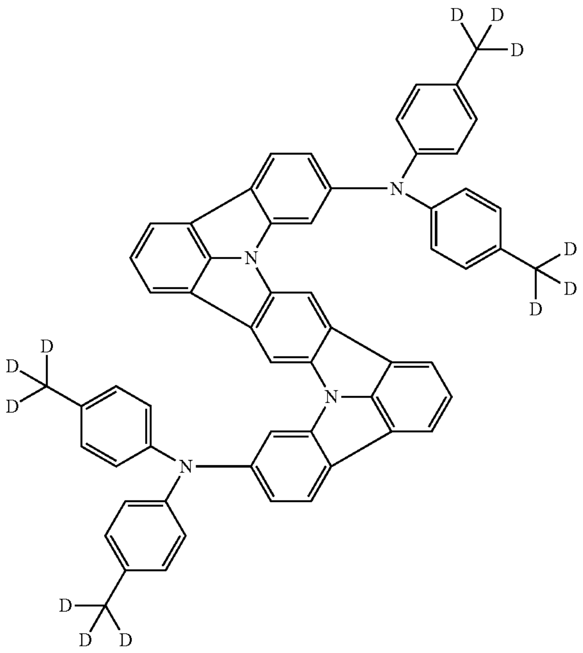

-continued
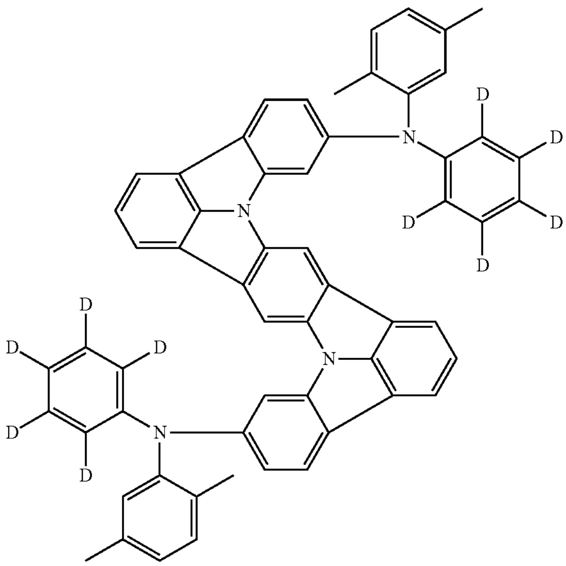
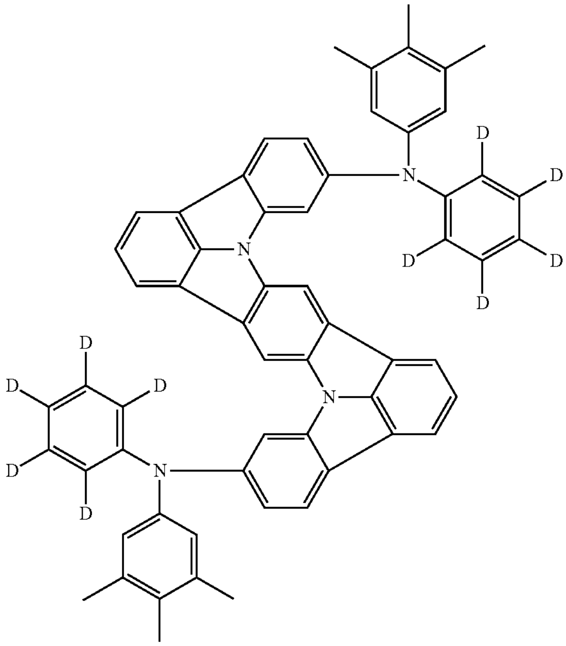
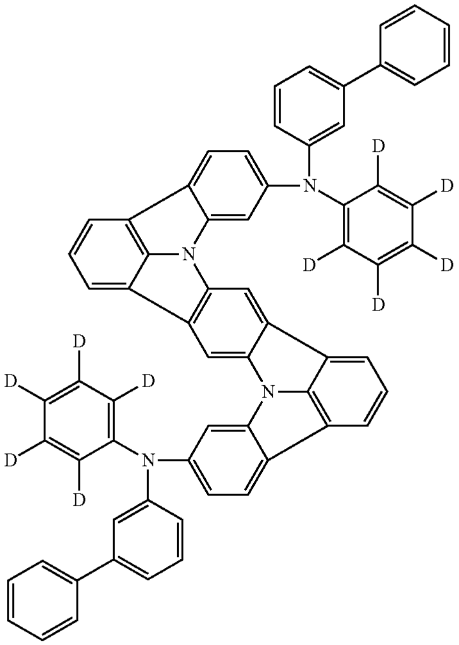

-continued
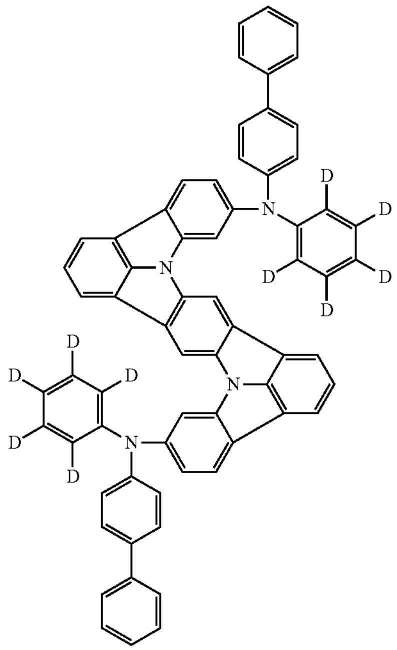
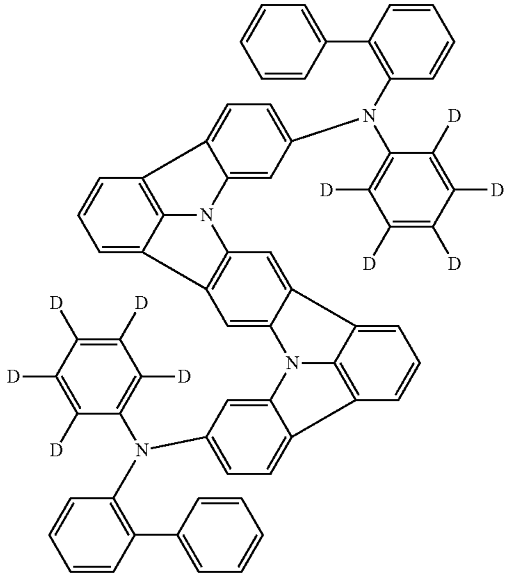
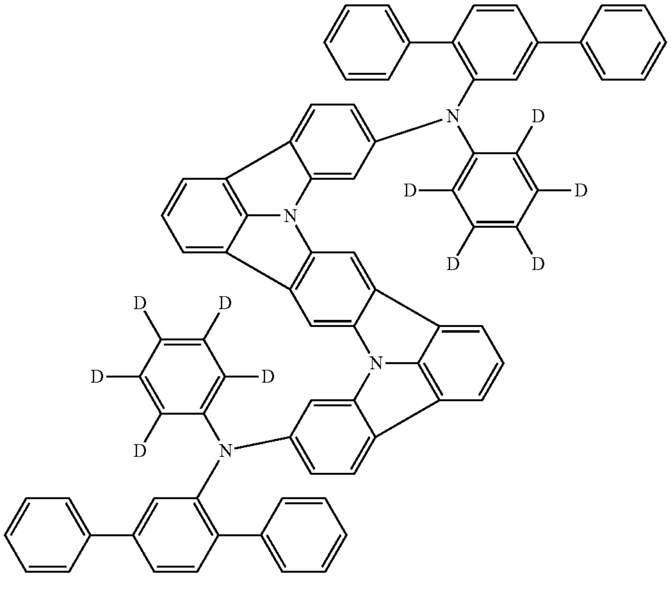

-continued
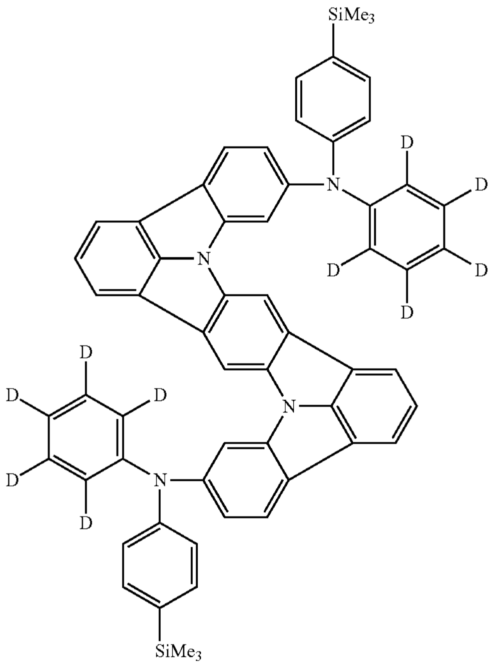
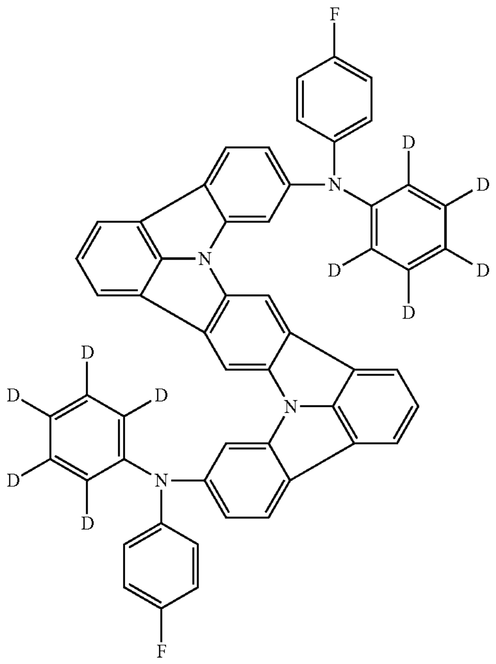
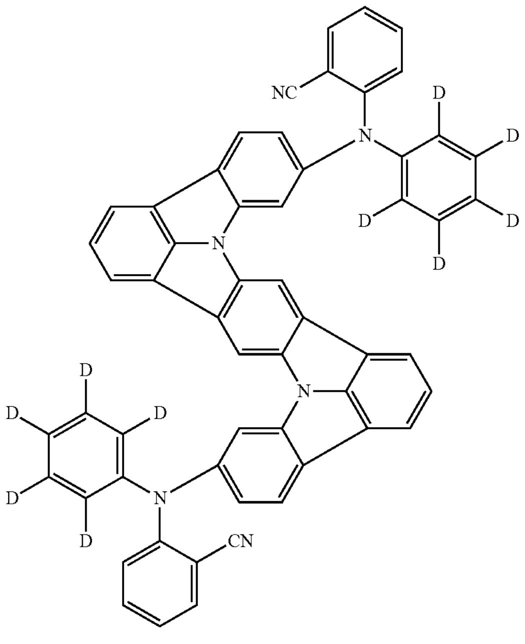
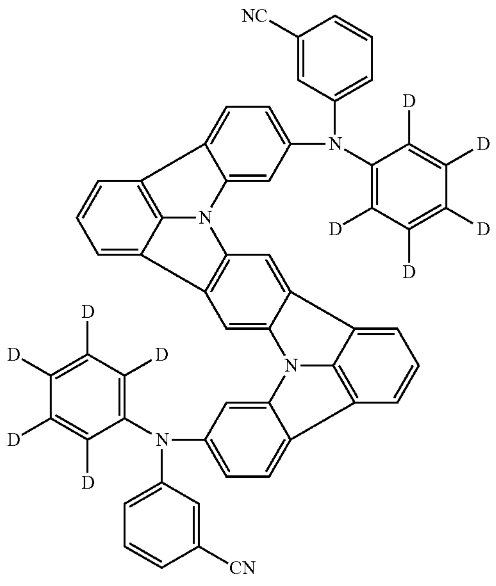

-continued
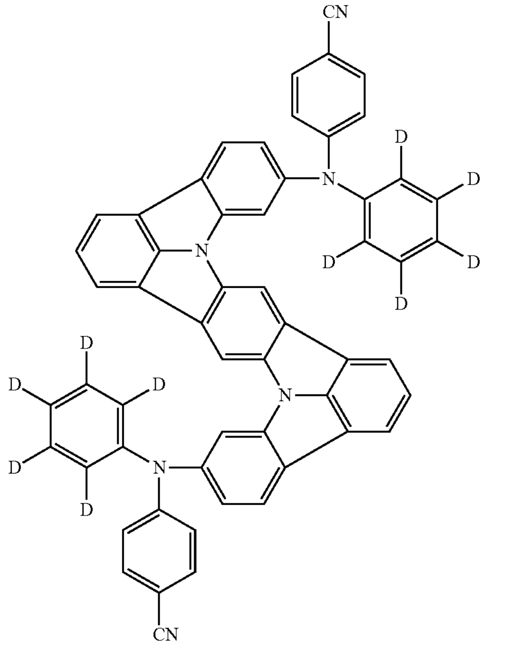
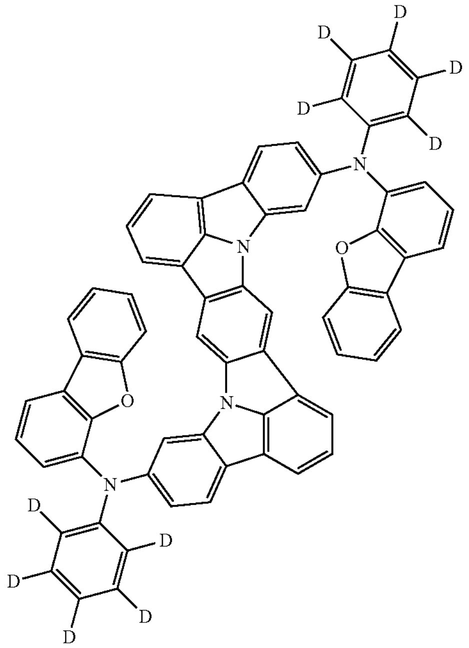
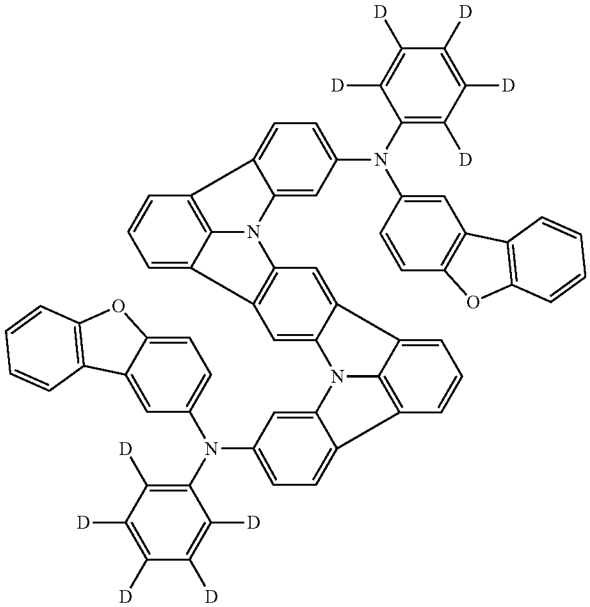

-continued
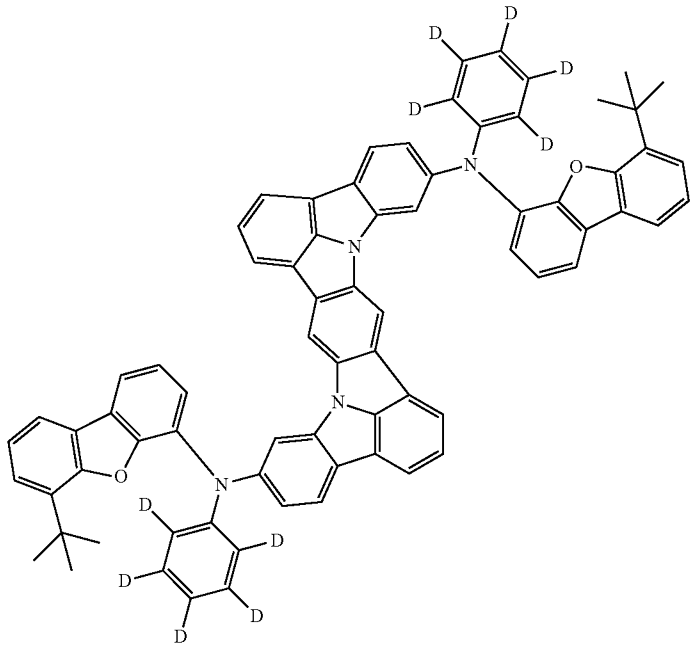
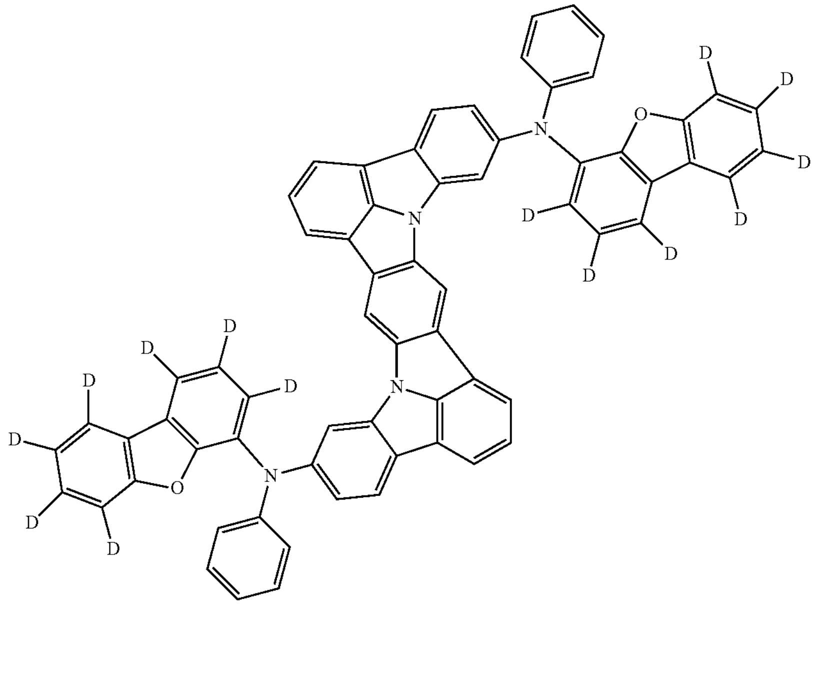

-continued
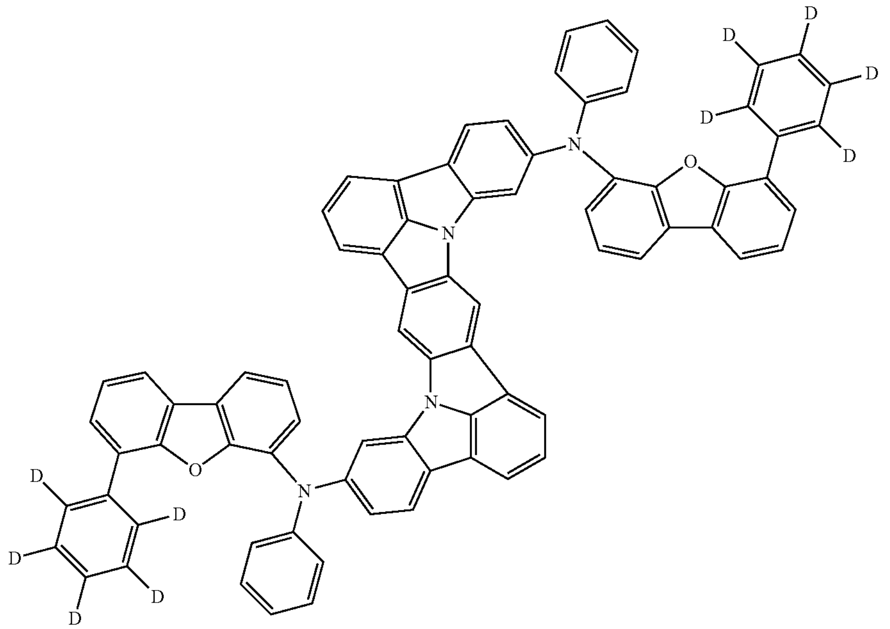
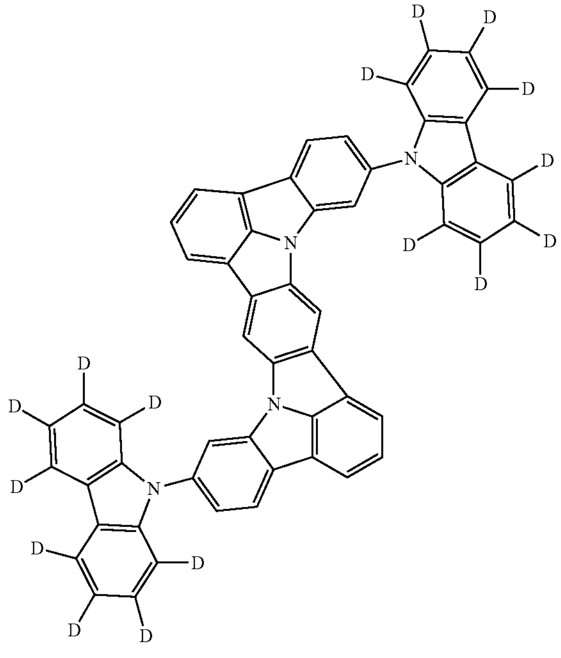
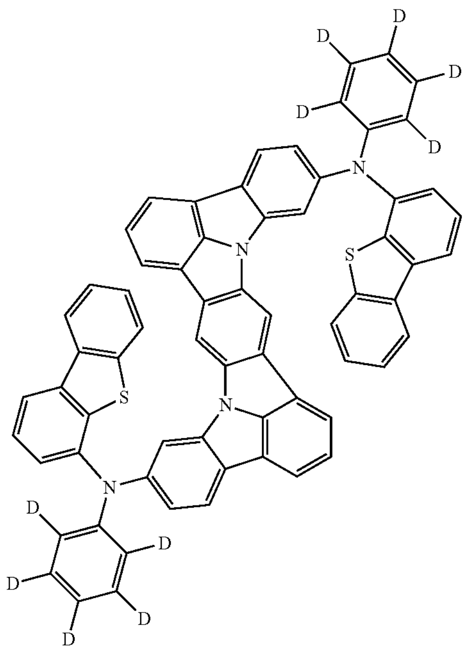

-continued
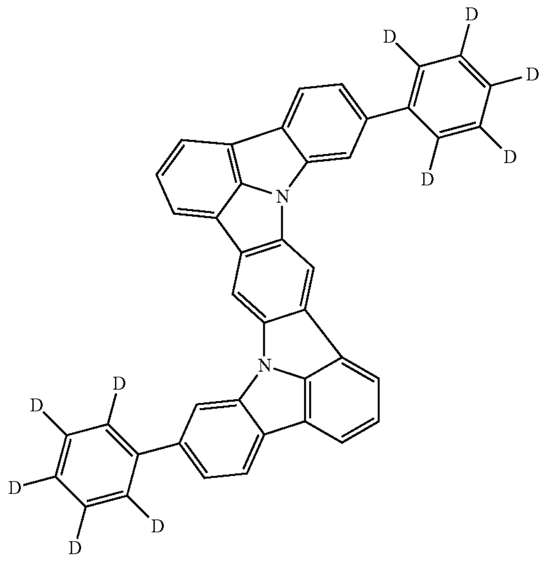
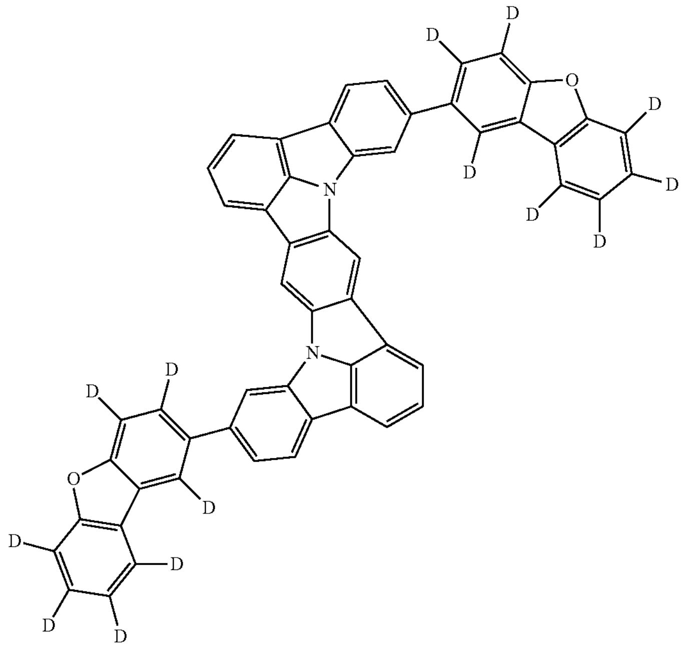
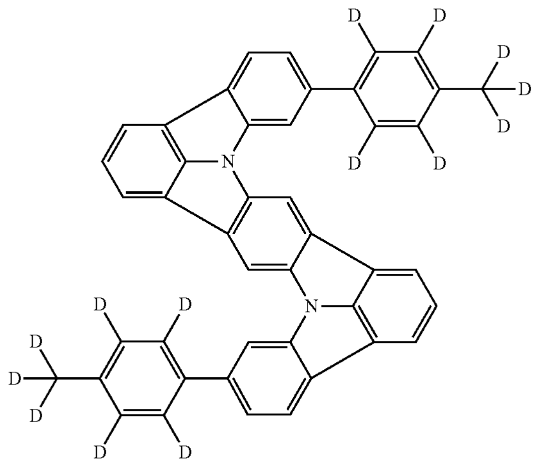

-continued
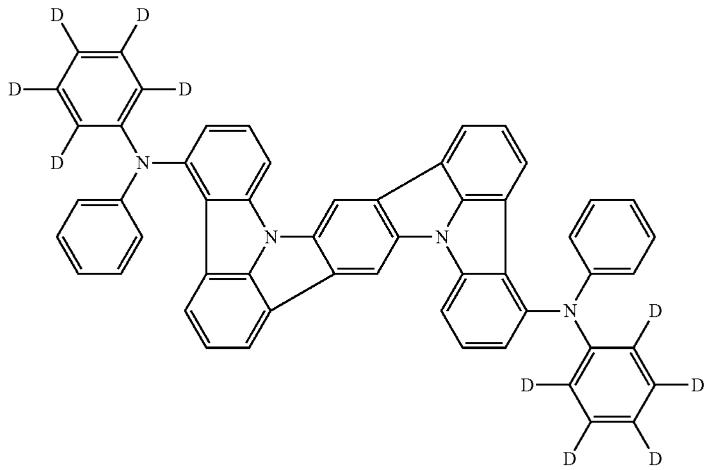
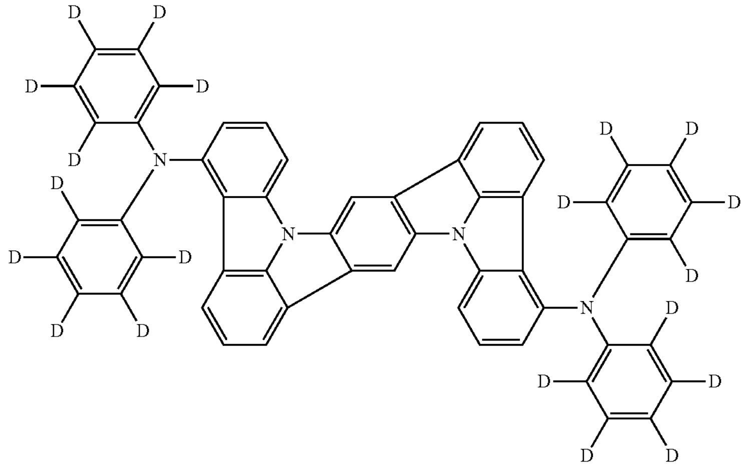
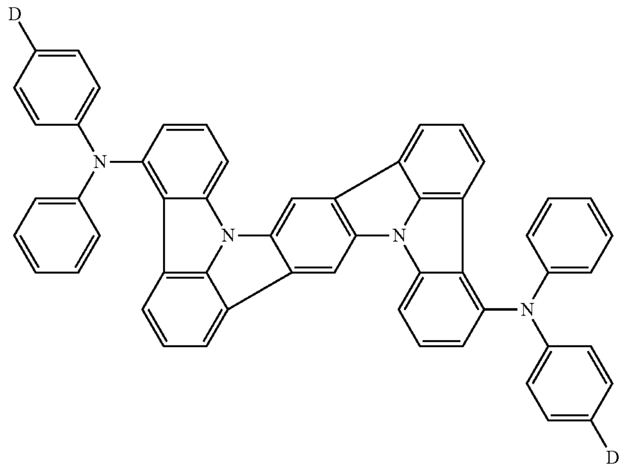

-continued
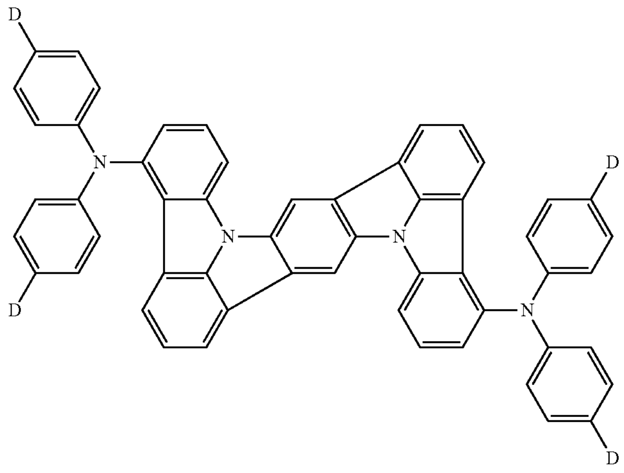
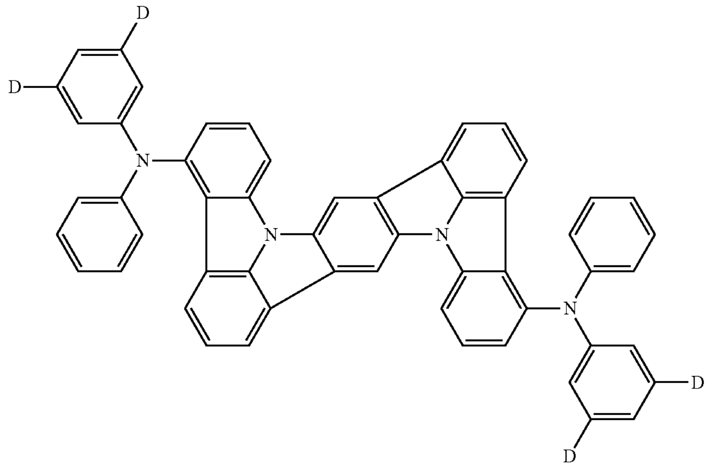
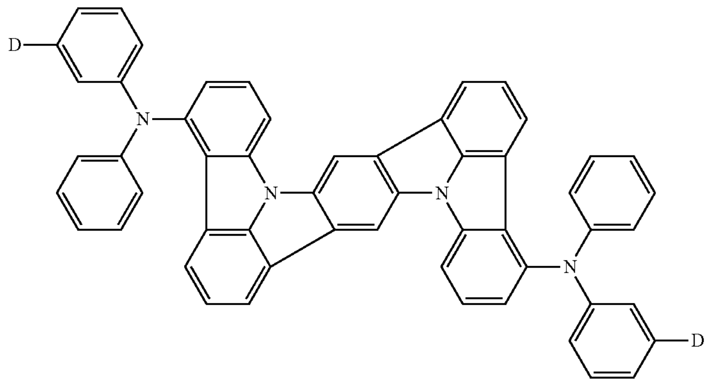
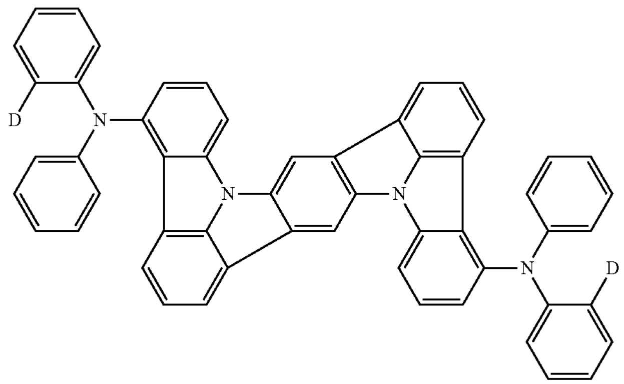

-continued
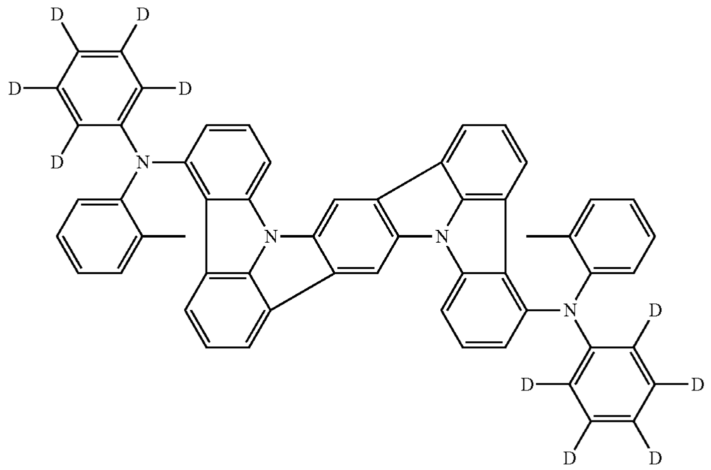
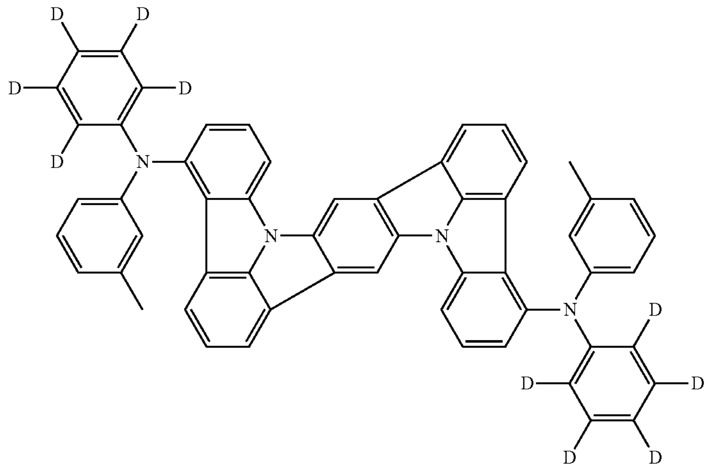
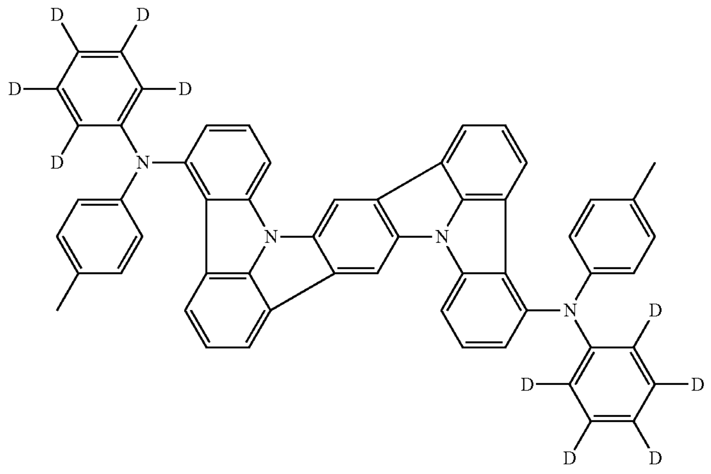

-continued
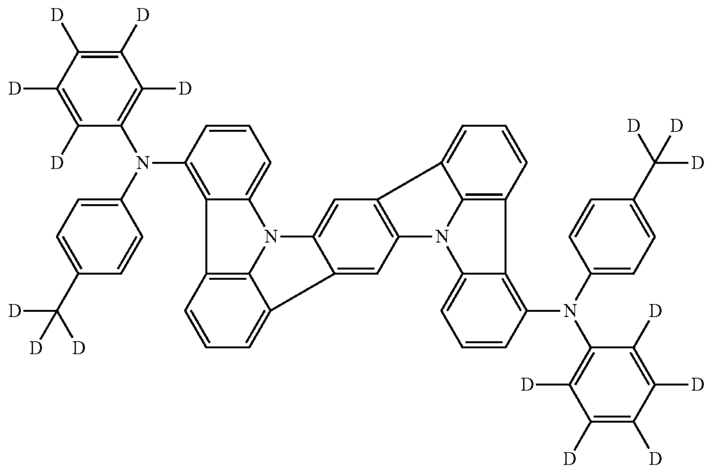
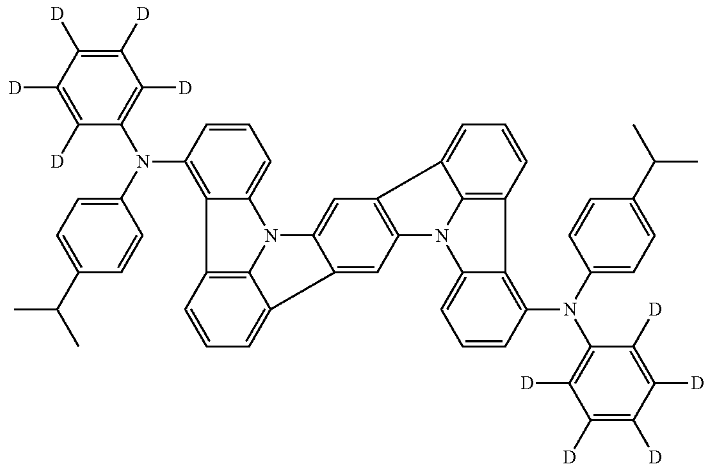
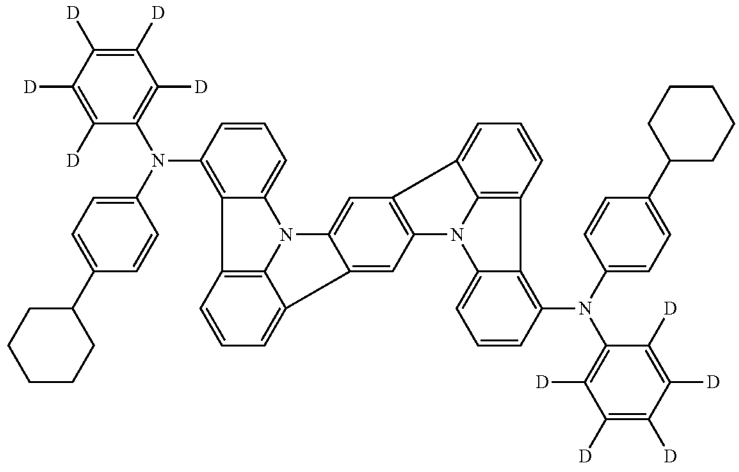

-continued
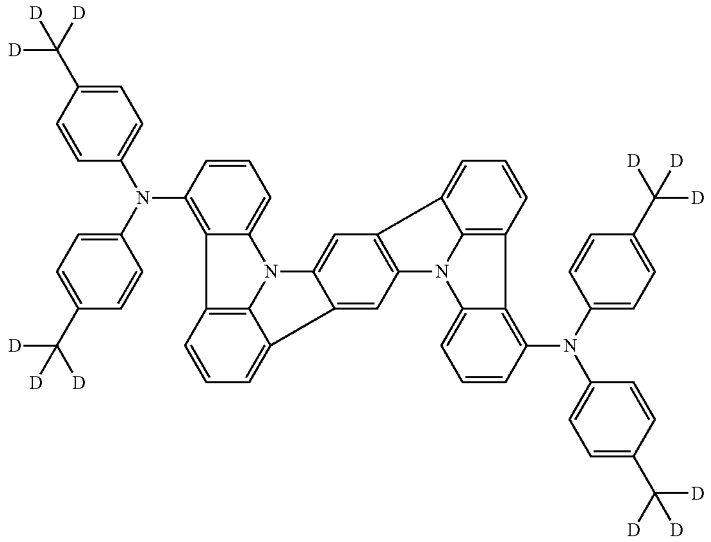
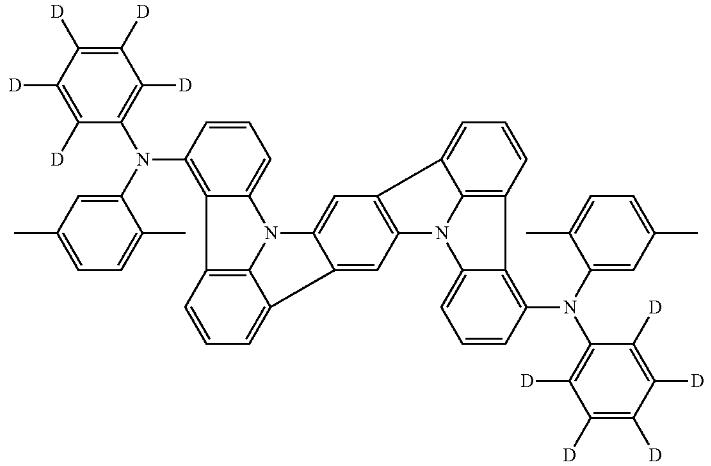
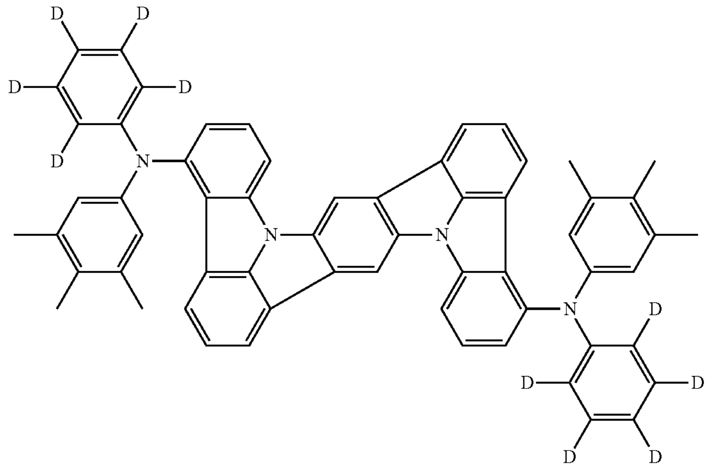

-continued
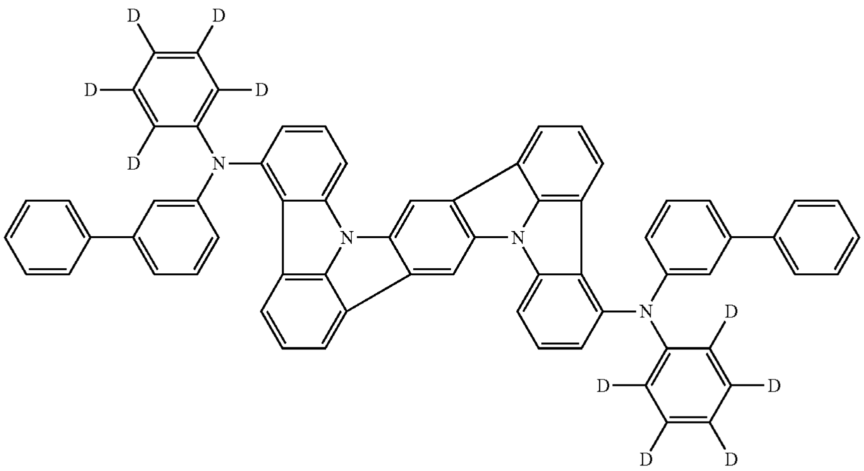
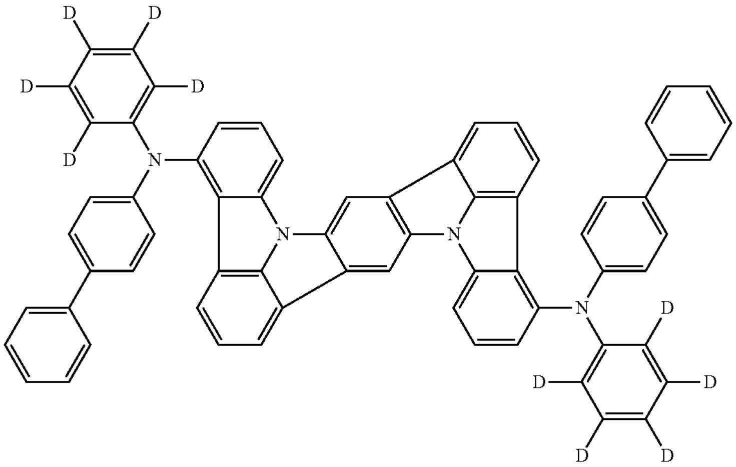
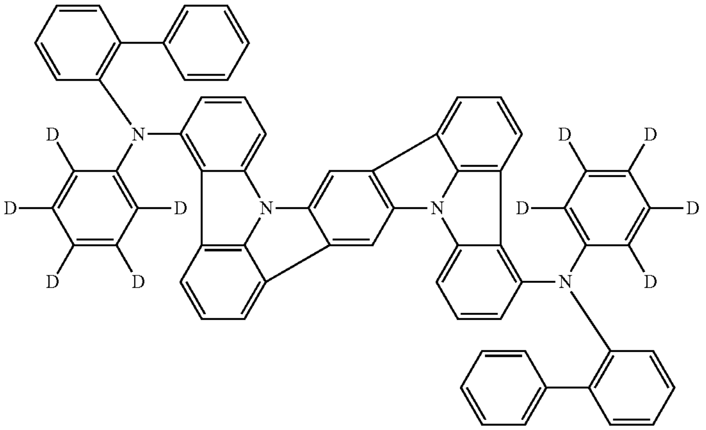

-continued
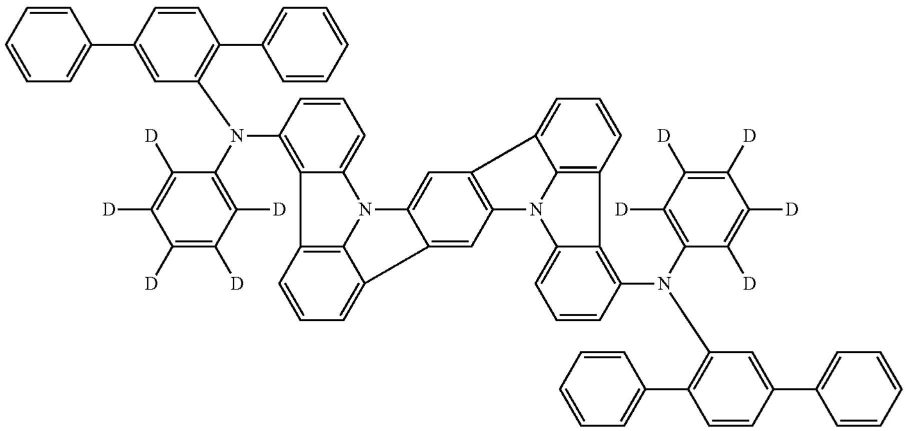
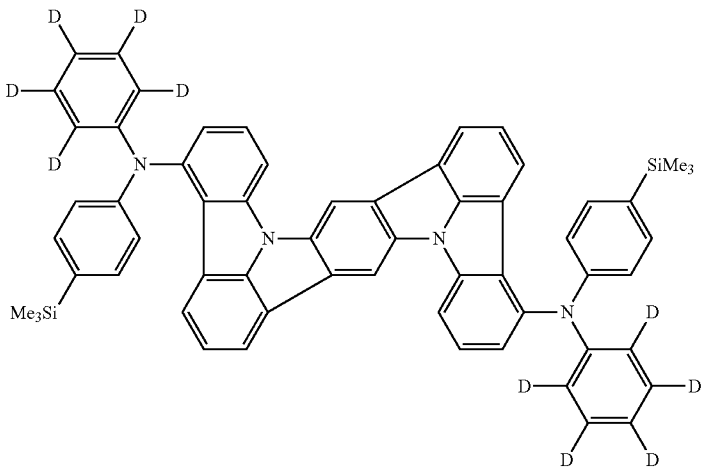
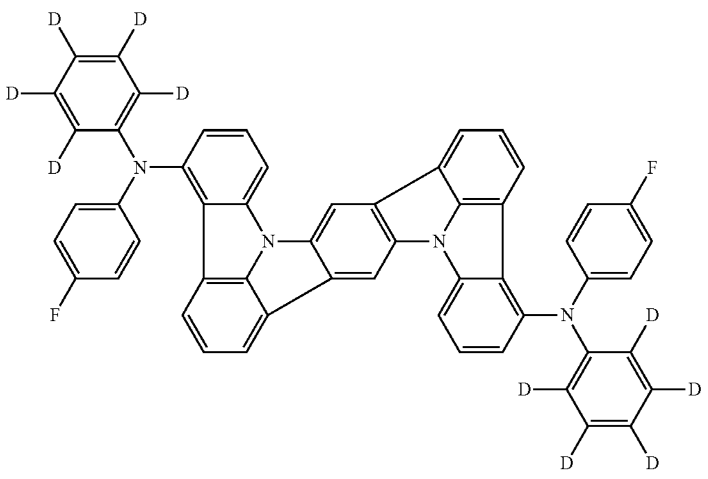

-continued
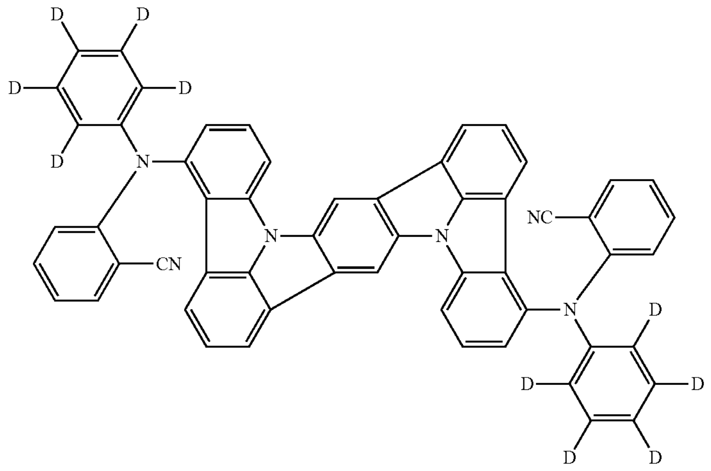
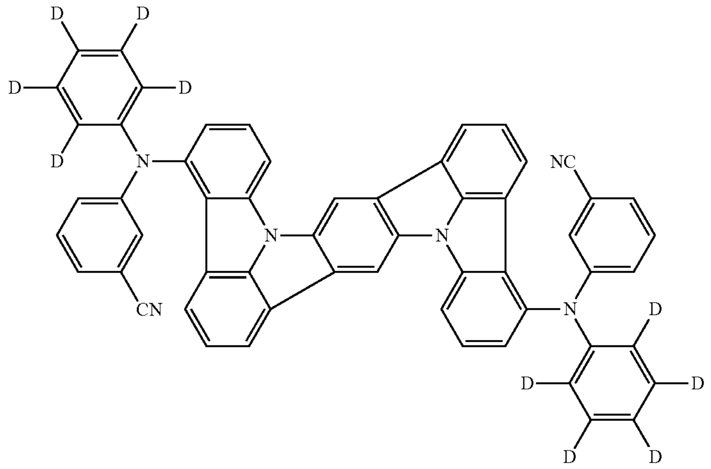
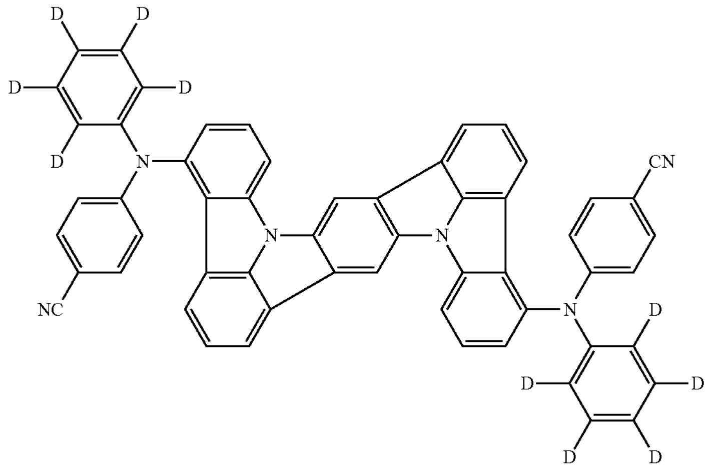

-continued
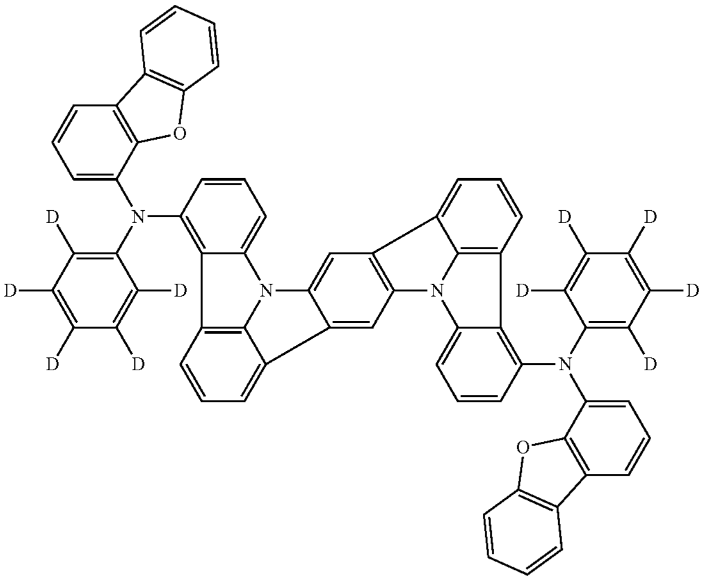
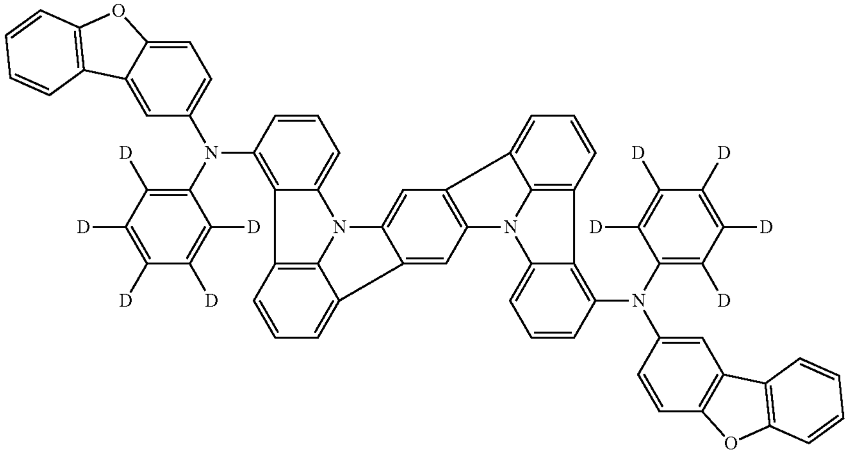
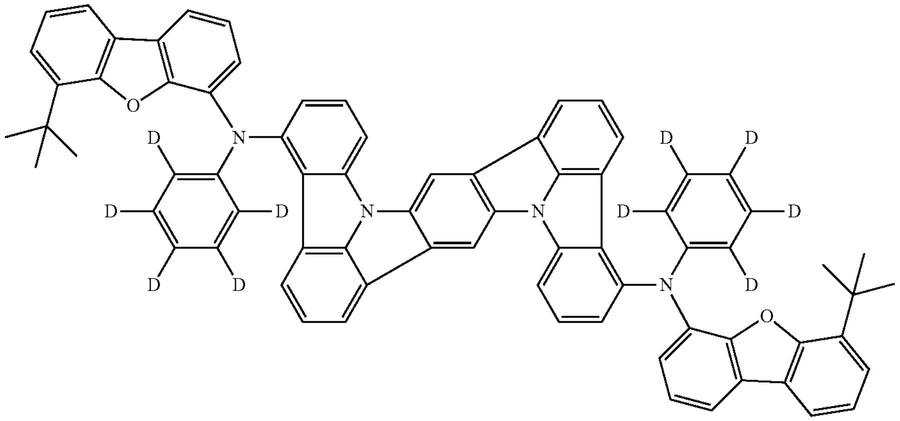

-continued
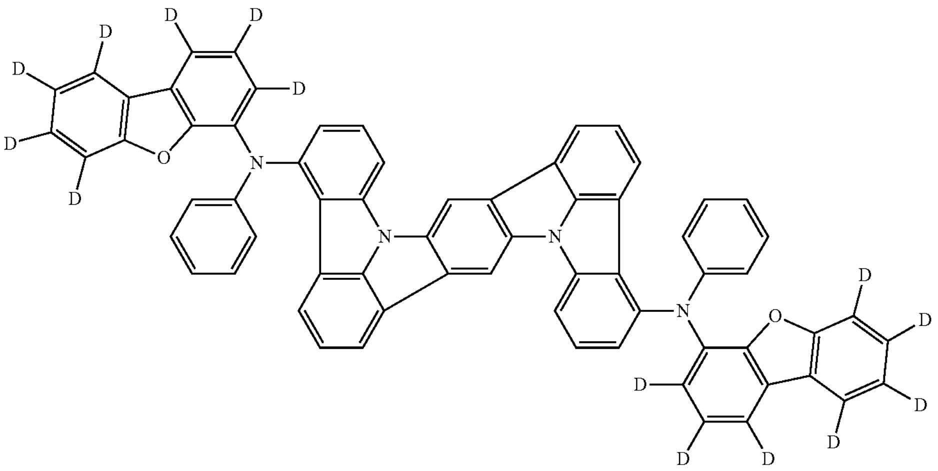
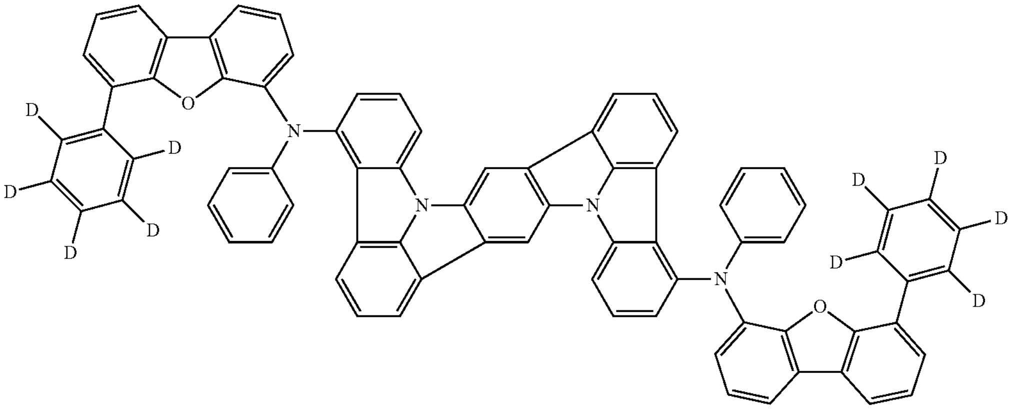
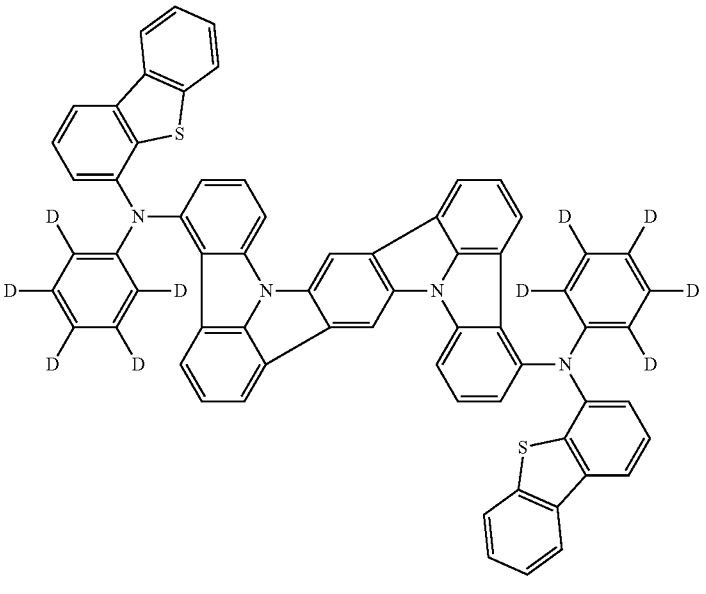

-continued
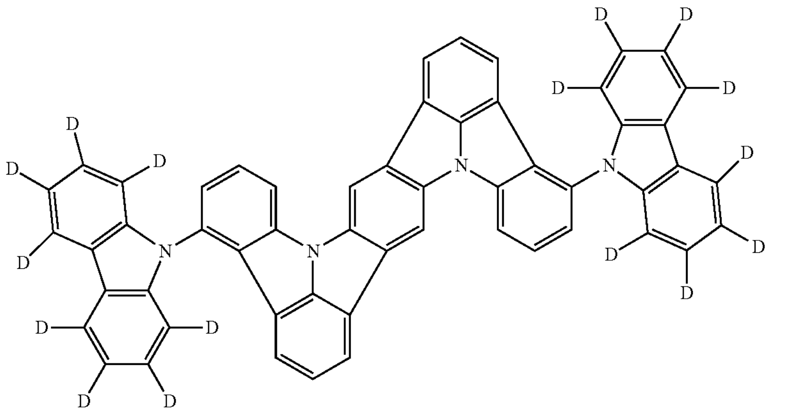
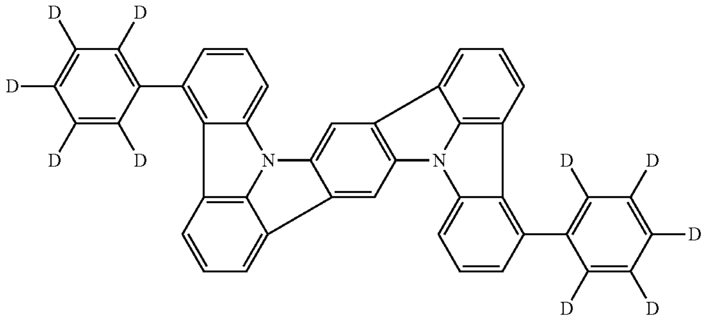
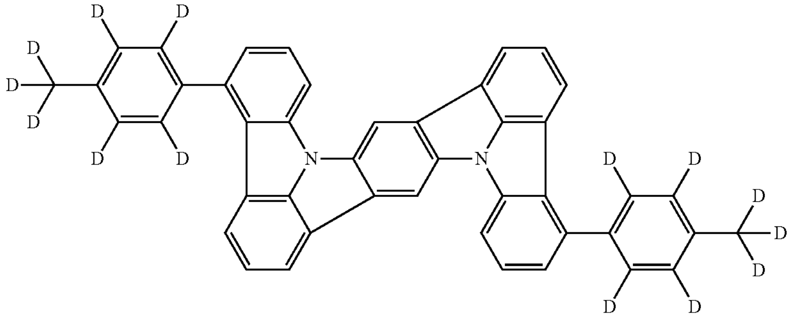
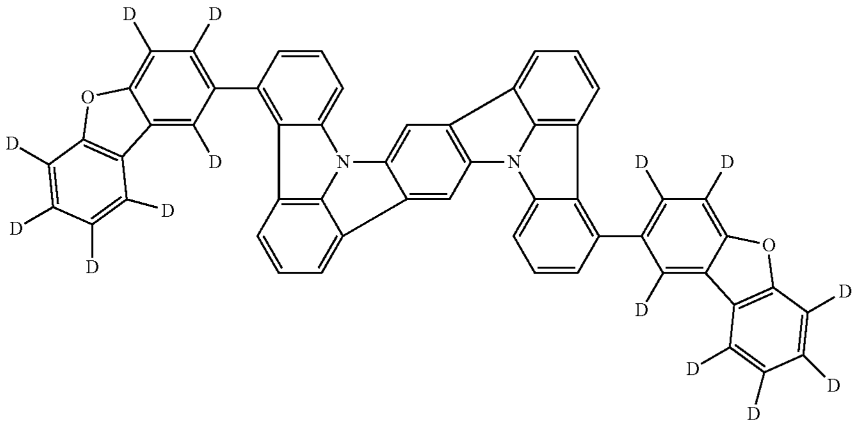

-continued
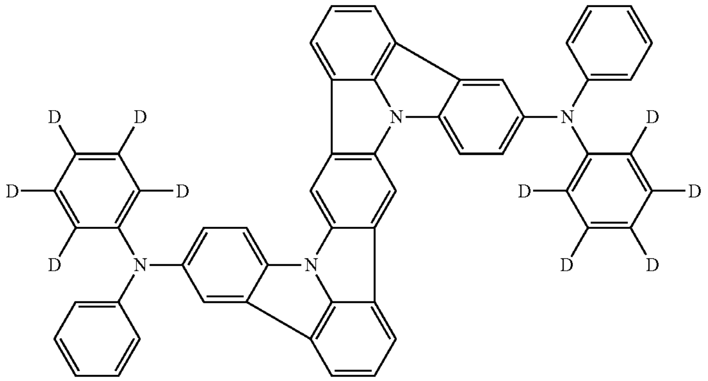
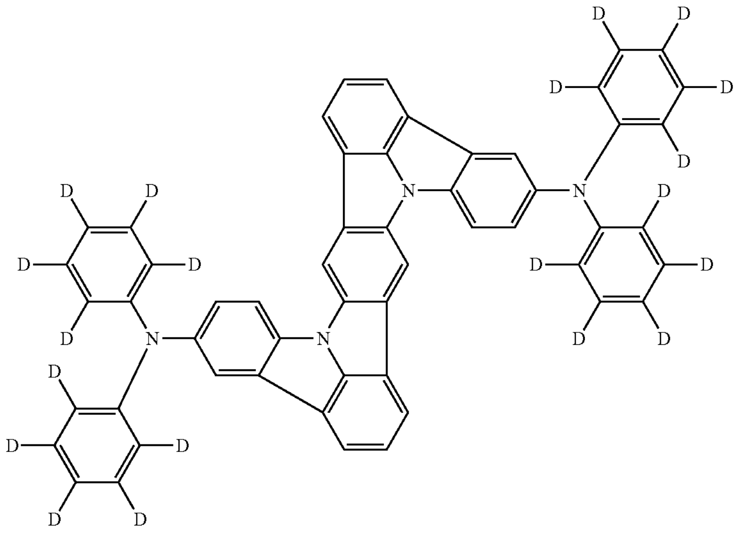
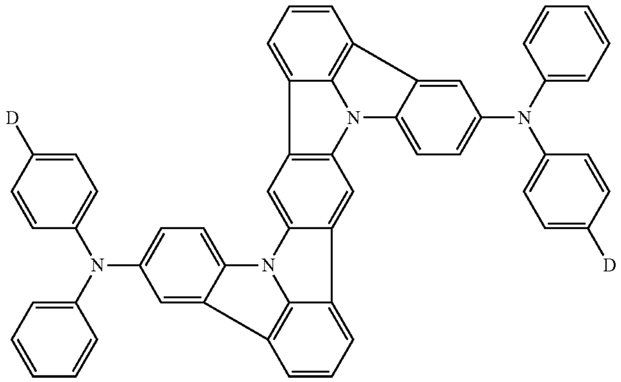

-continued
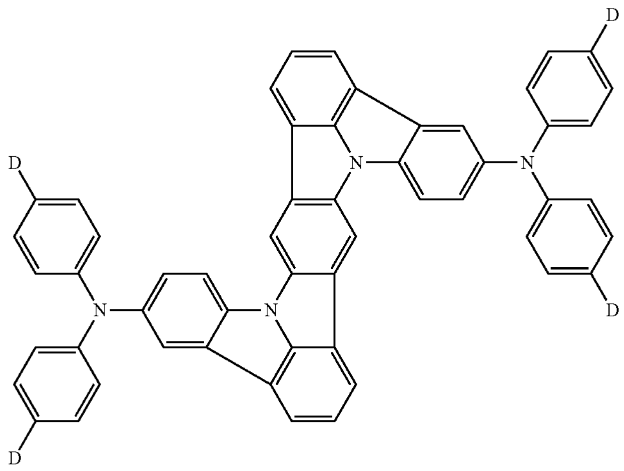
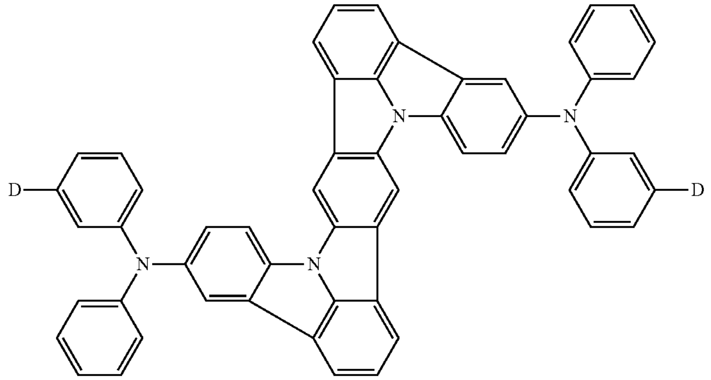
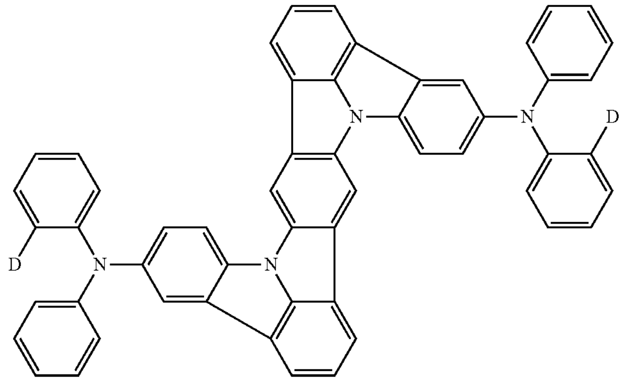
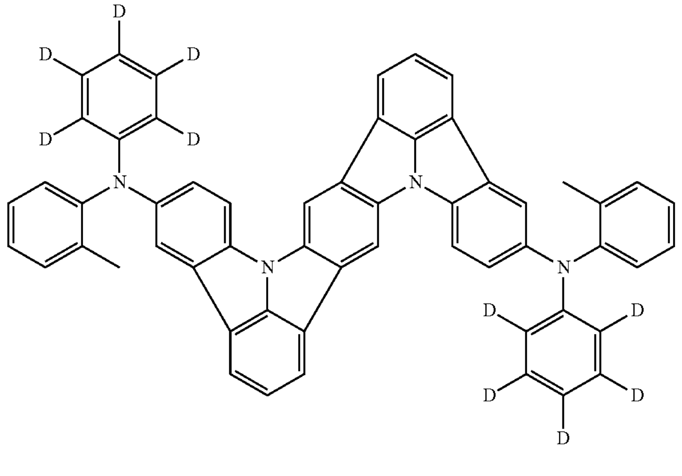

-continued
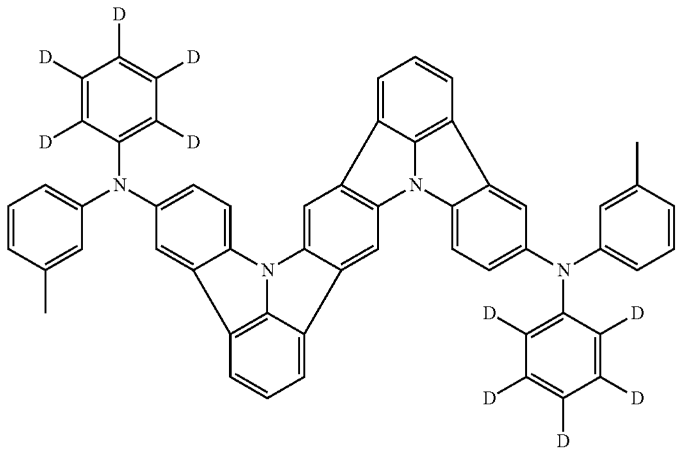
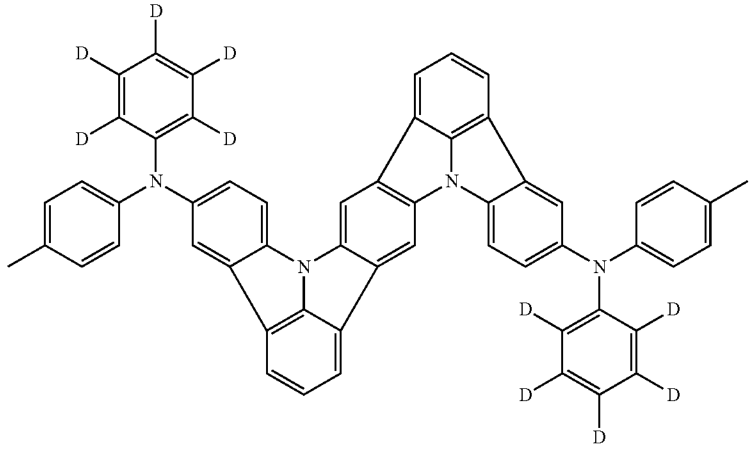
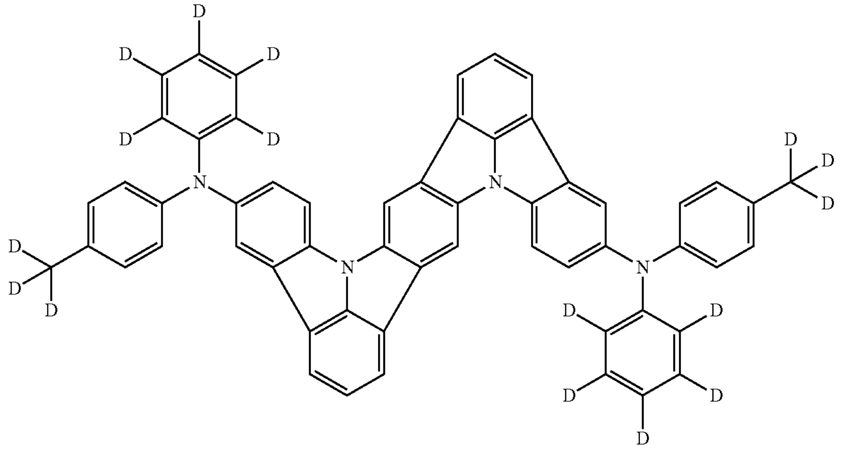

-continued
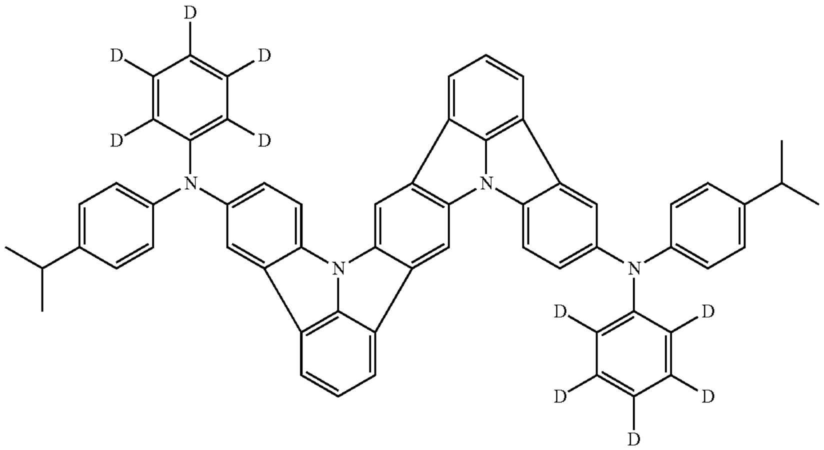
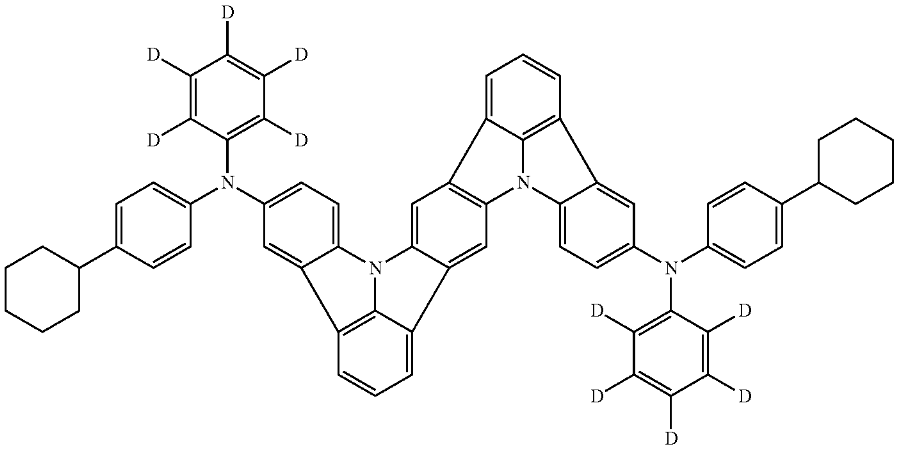
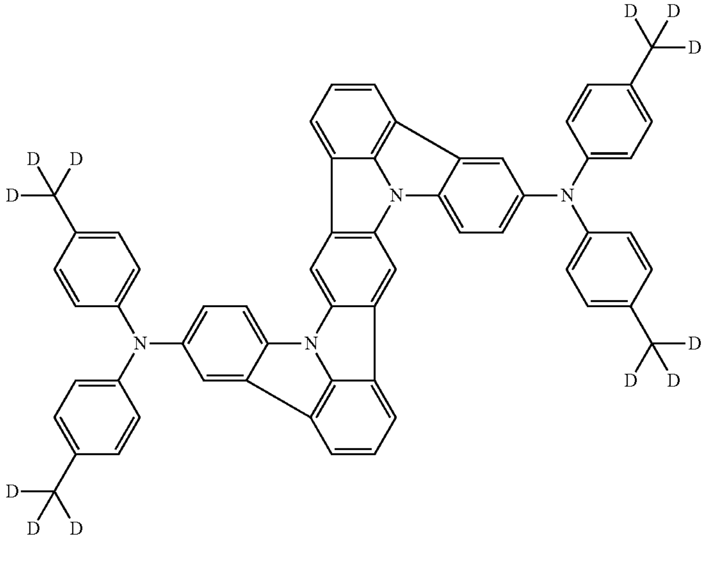

-continued
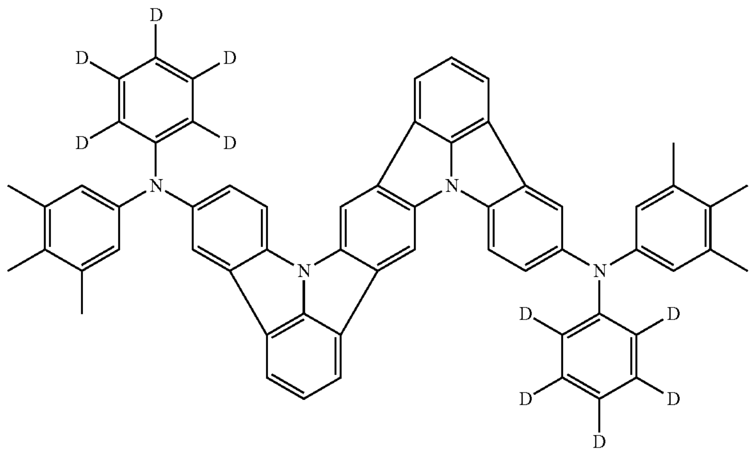
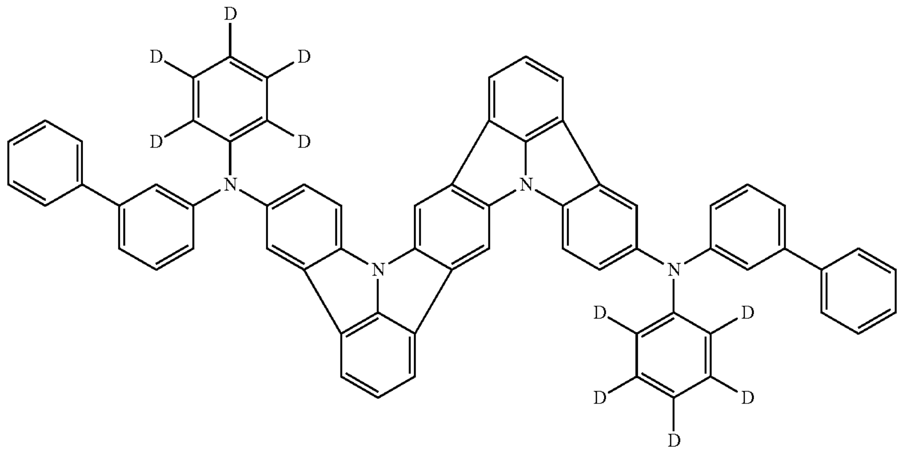
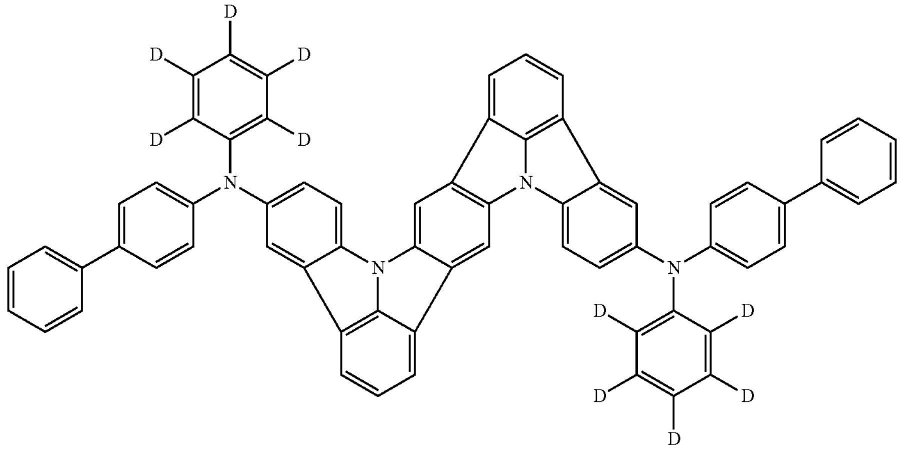

-continued
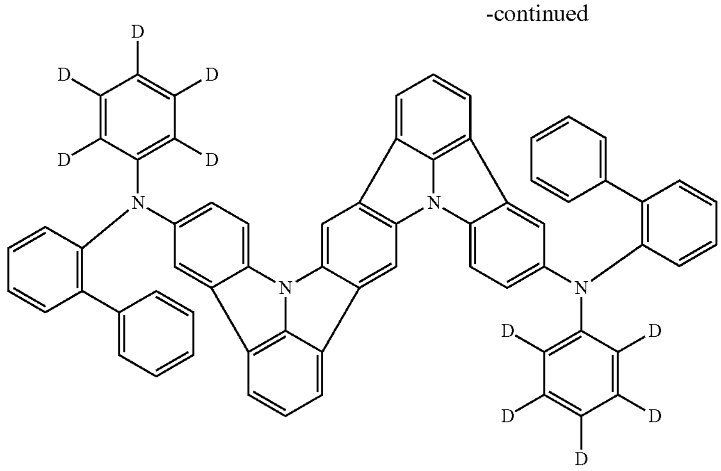
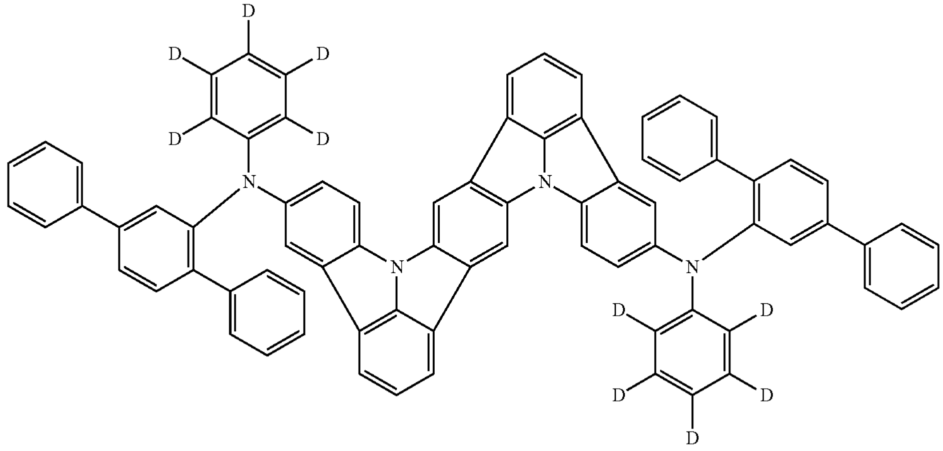 [SMILES: [2H]c1c([2H])c([2H])c(N(c2ccc3c(c2)c2cccc4c5cc6c(cc5n3c24)c2cccc3c4cc(N(c5cc(-c7ccccc7)ccc5-c5ccccc5)c5c([2H])c([2H])c([2H])c([2H])c5[2H])ccc4n6c32)c2cc(-c3ccccc3)ccc2-c2ccccc2)c([2H])c1[2H]]
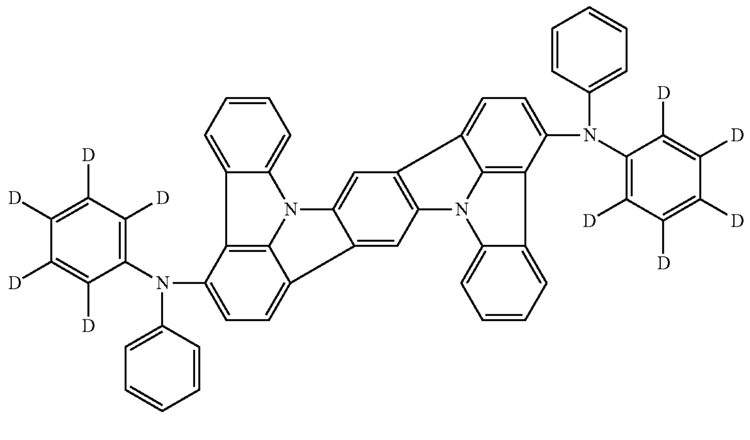

-continued
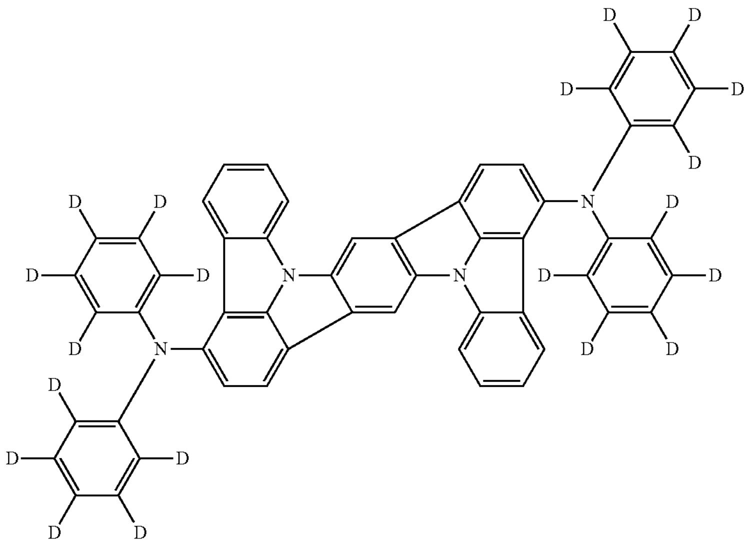
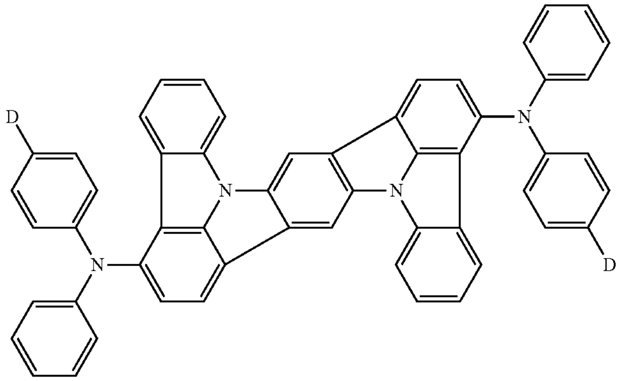
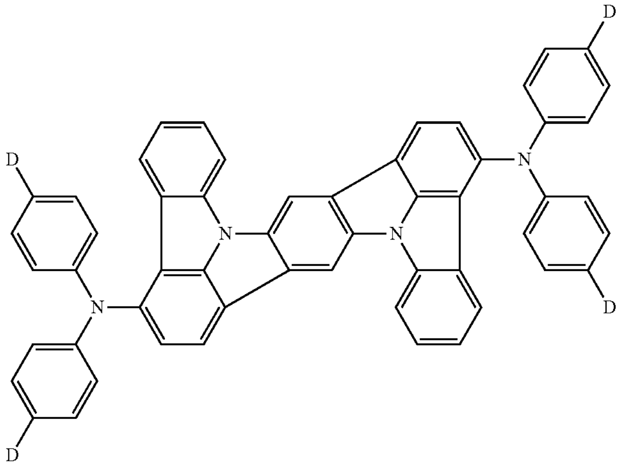

-continued
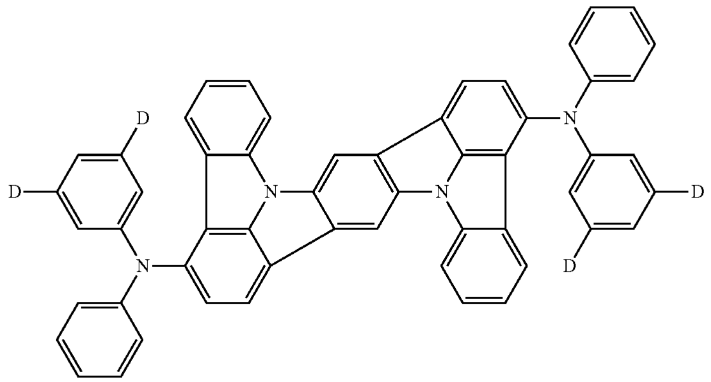
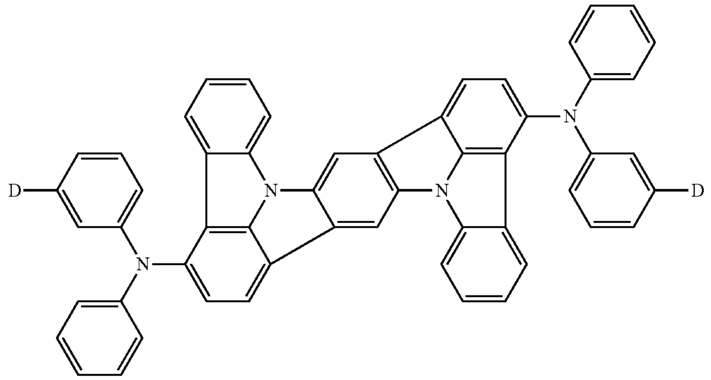
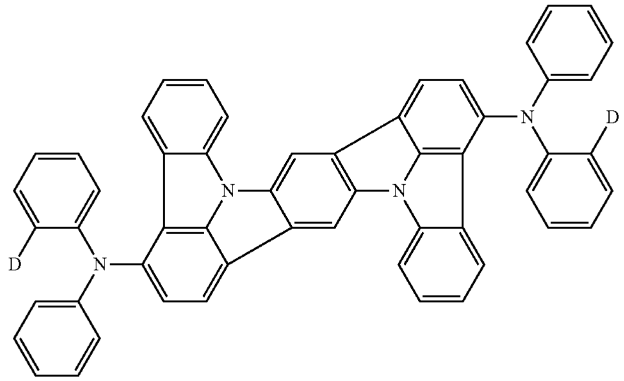
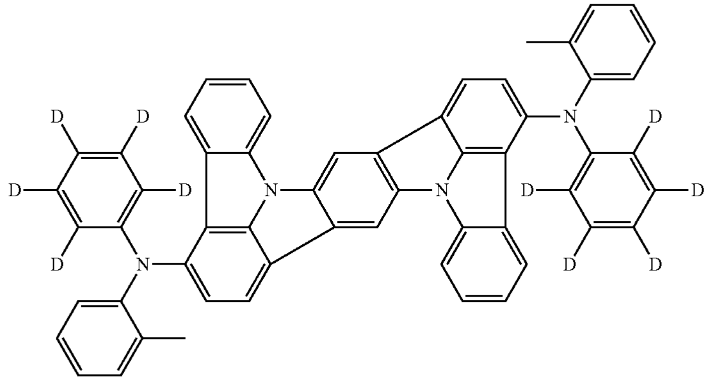

-continued
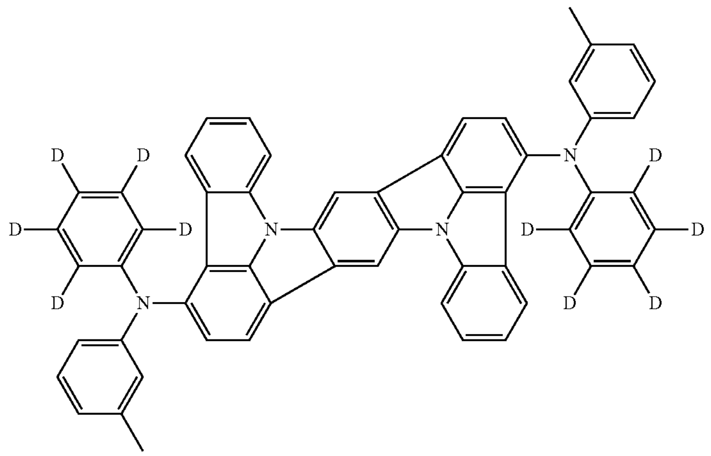
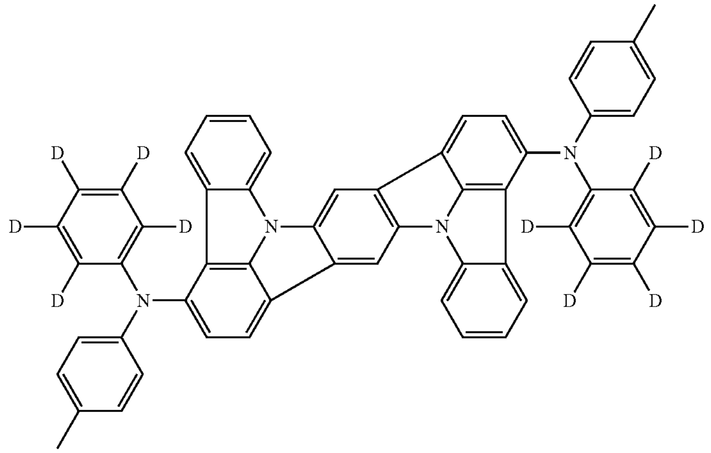
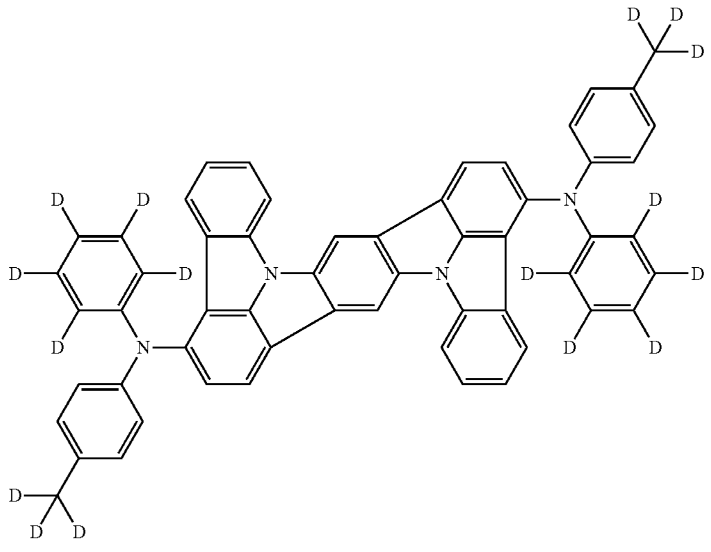

-continued
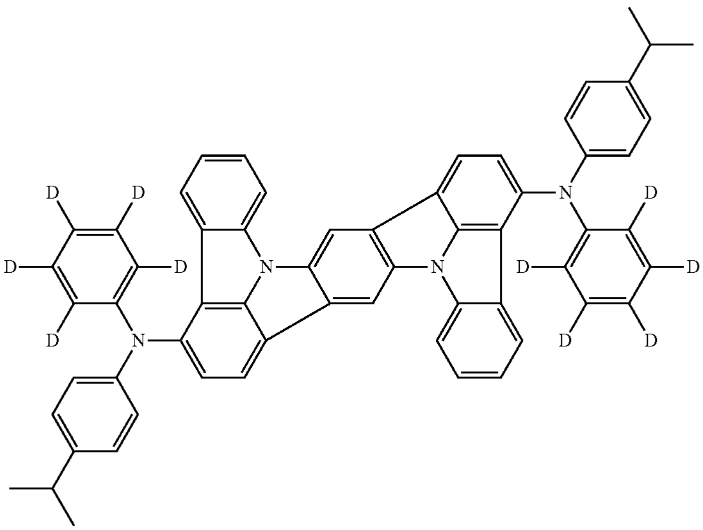
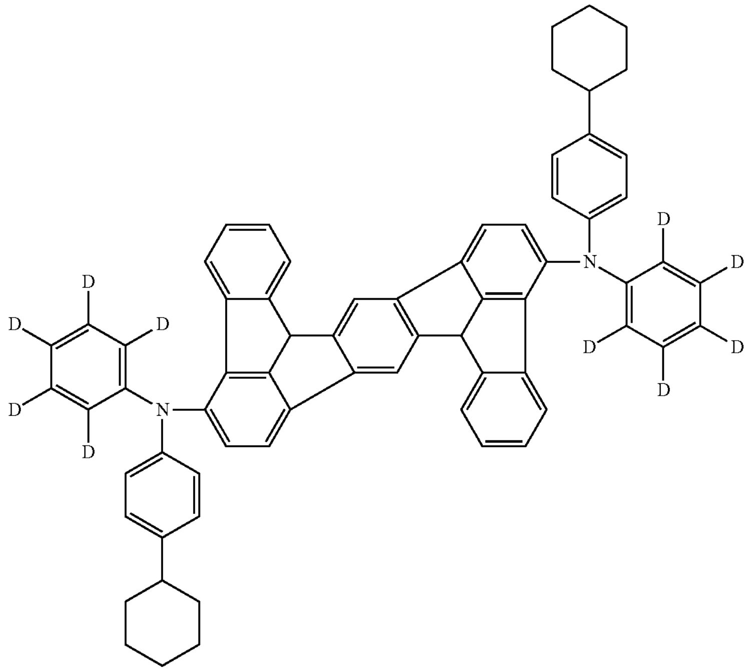

-continued
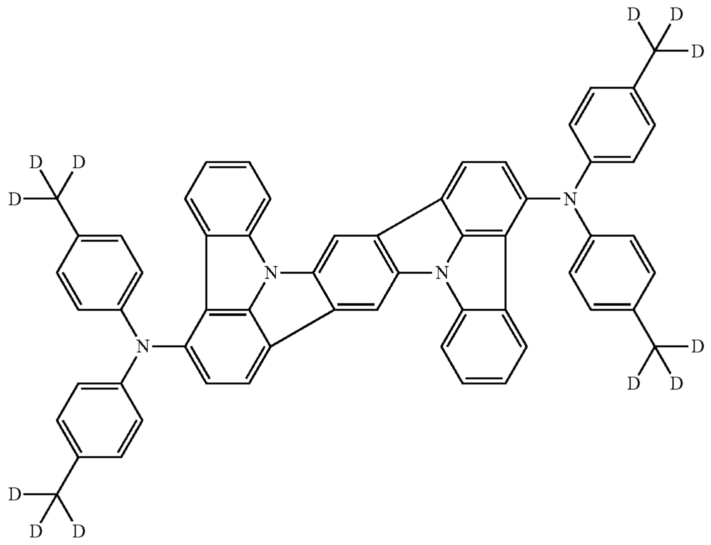
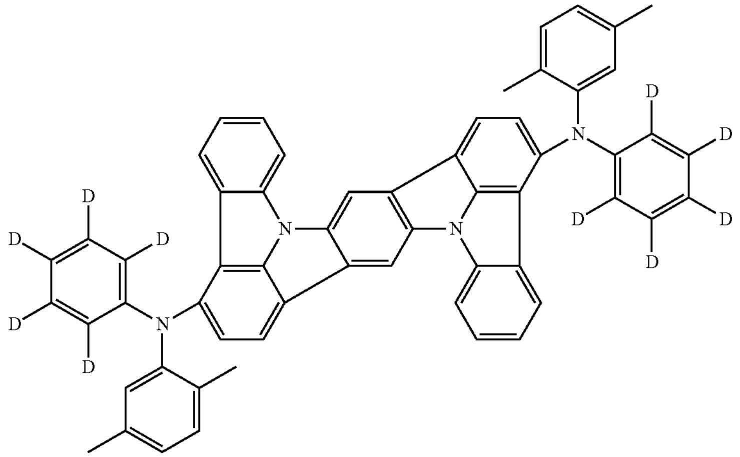
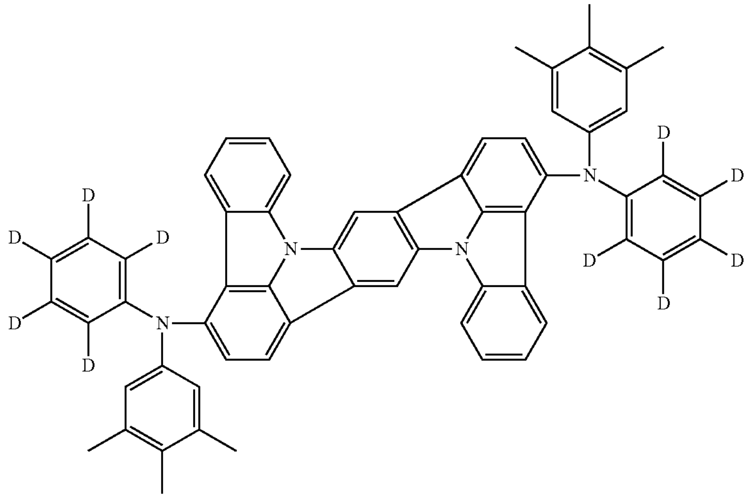

-continued
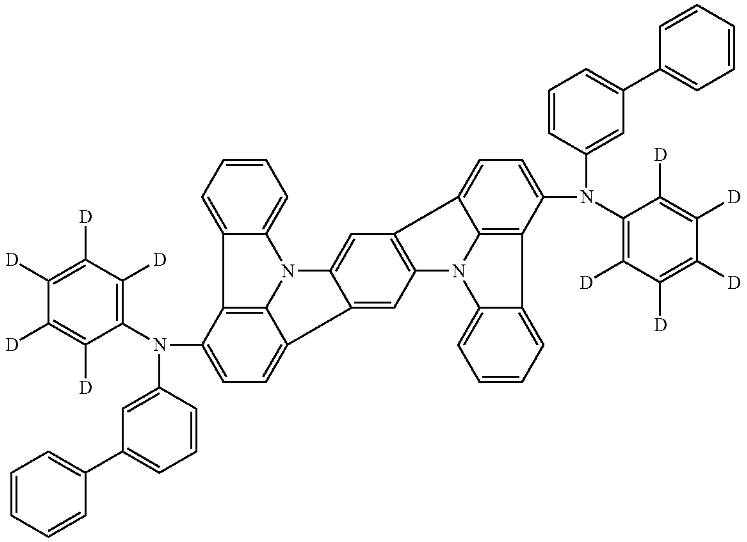
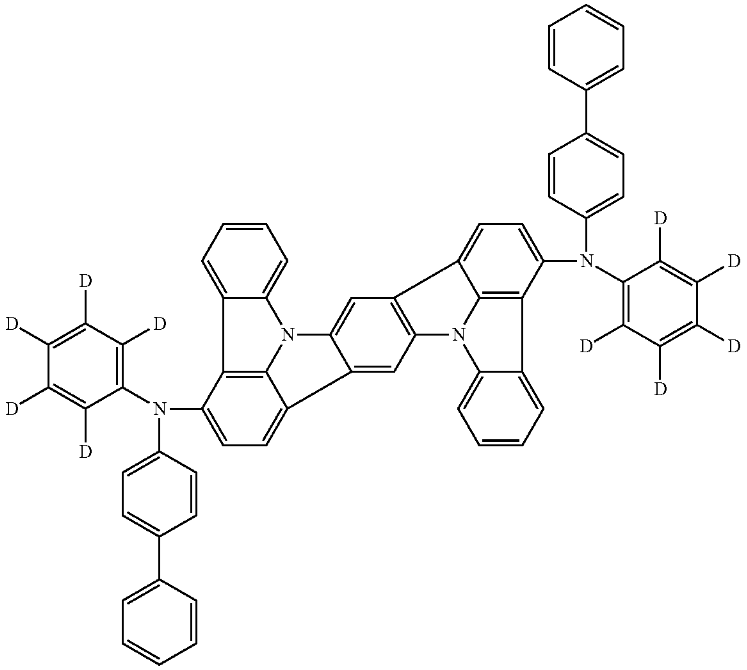
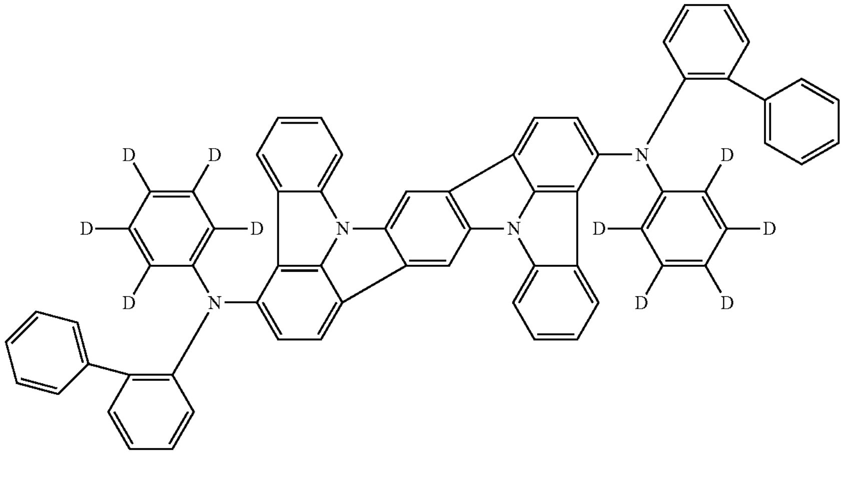

-continued
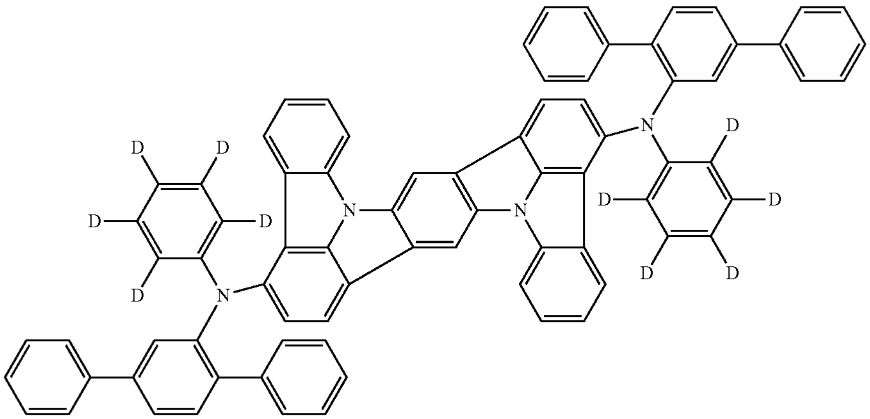
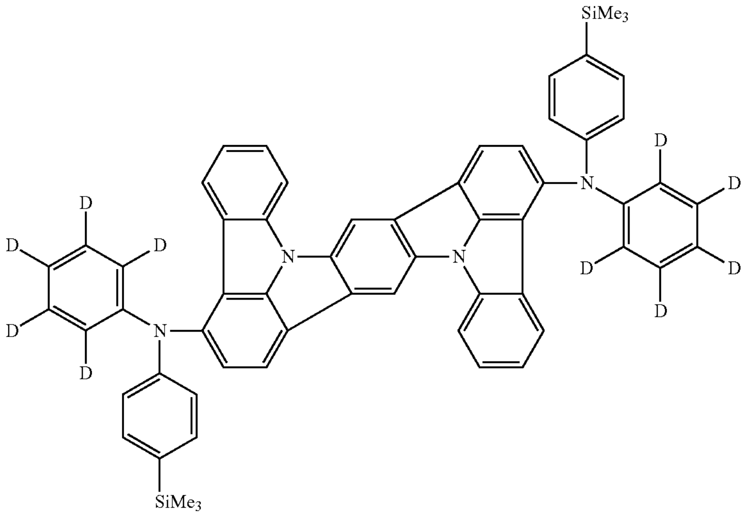
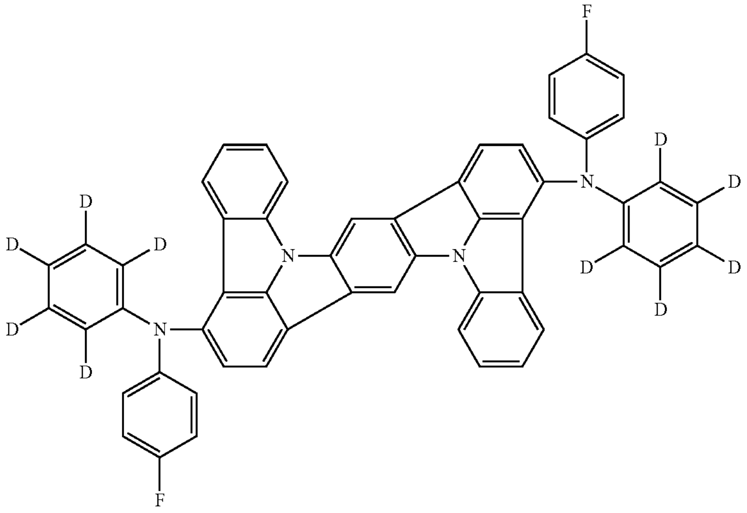

-continued
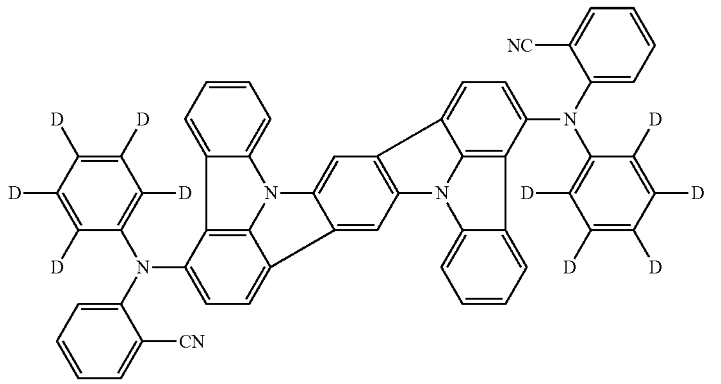
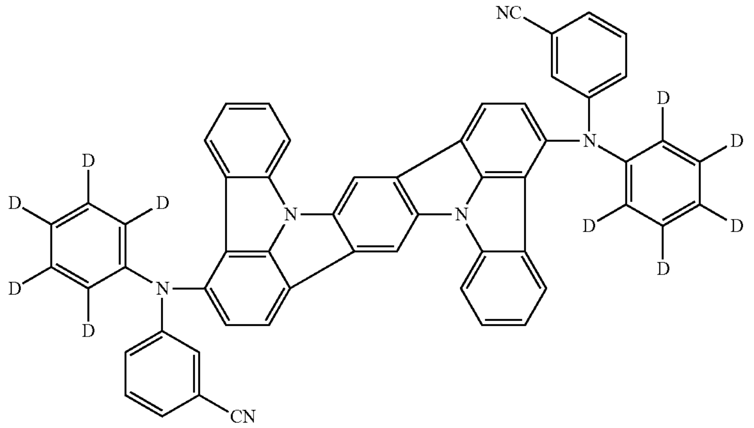
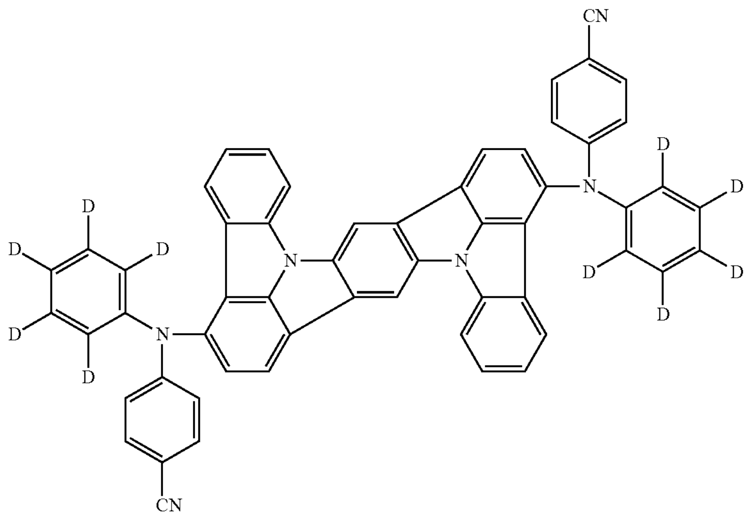

-continued
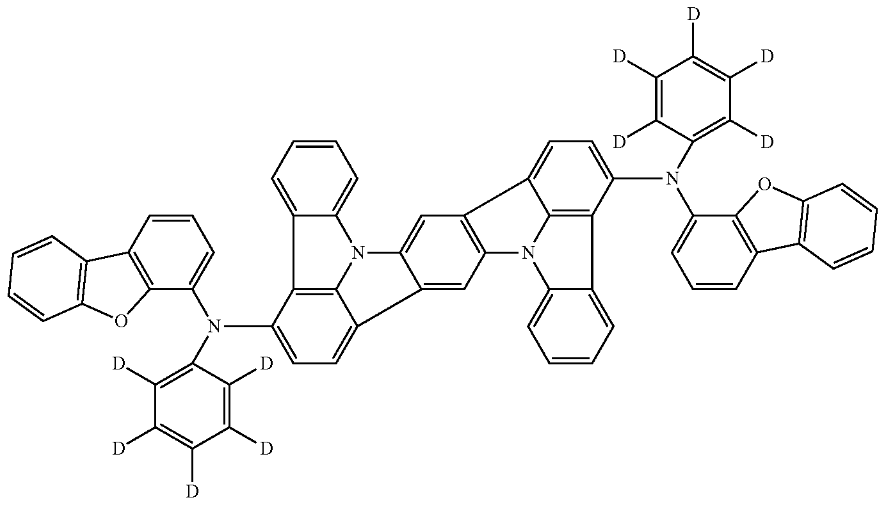
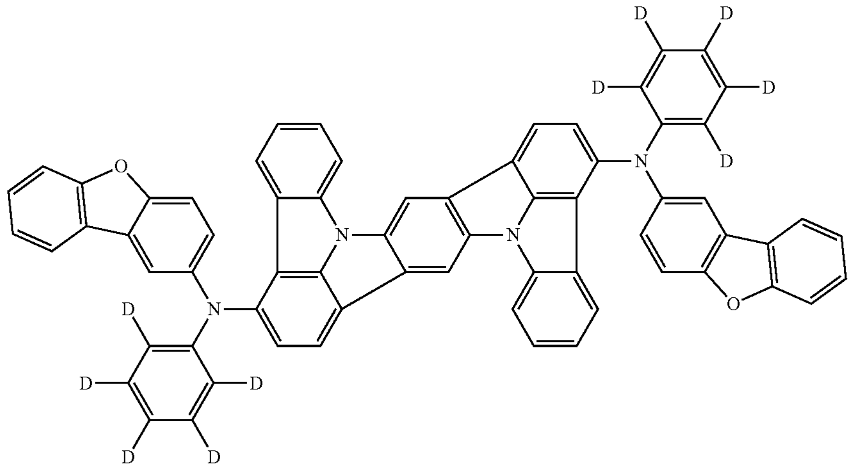
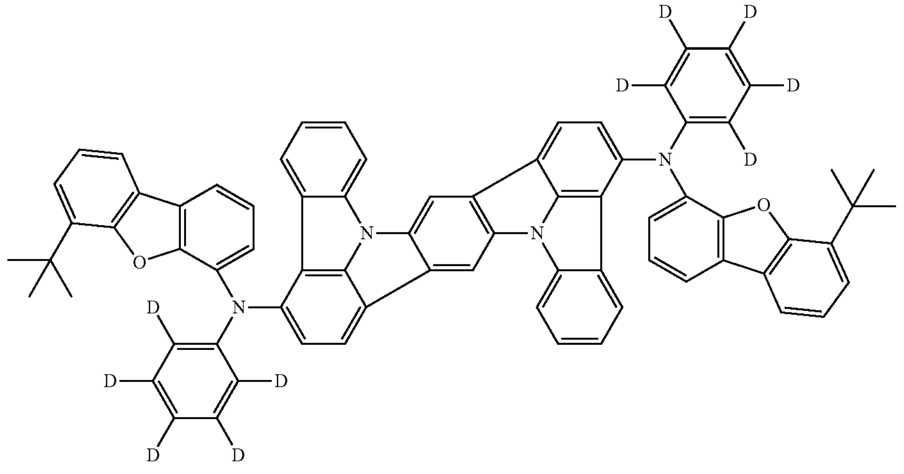

-continued
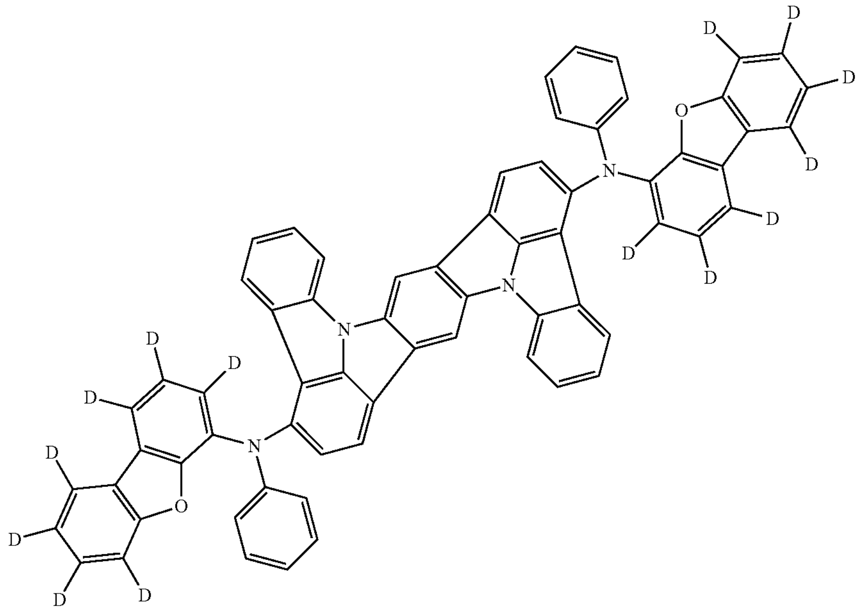
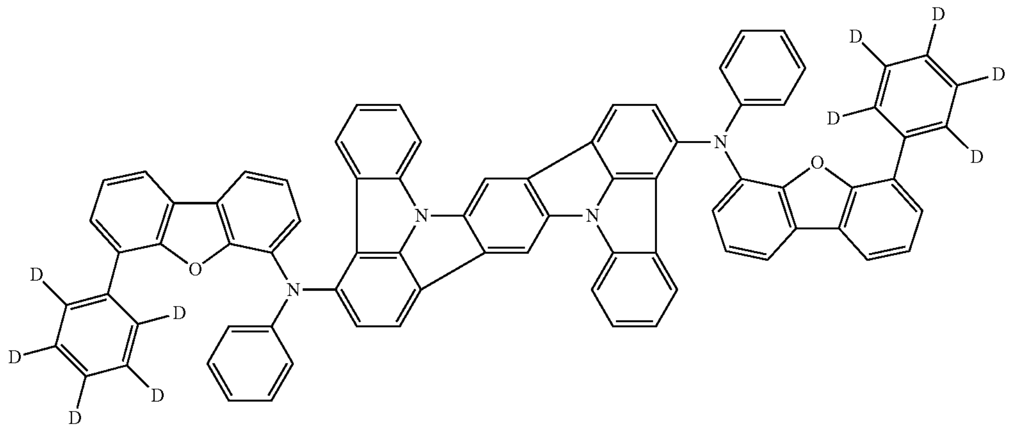

-continued
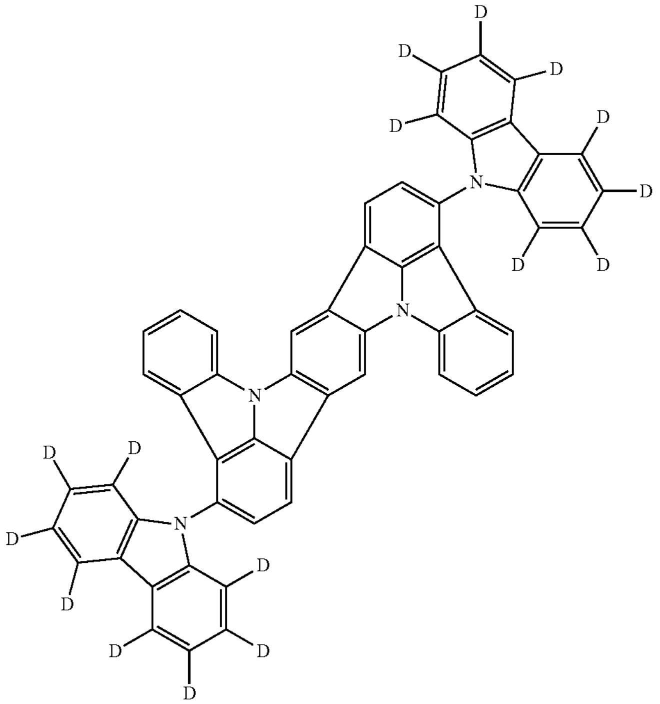
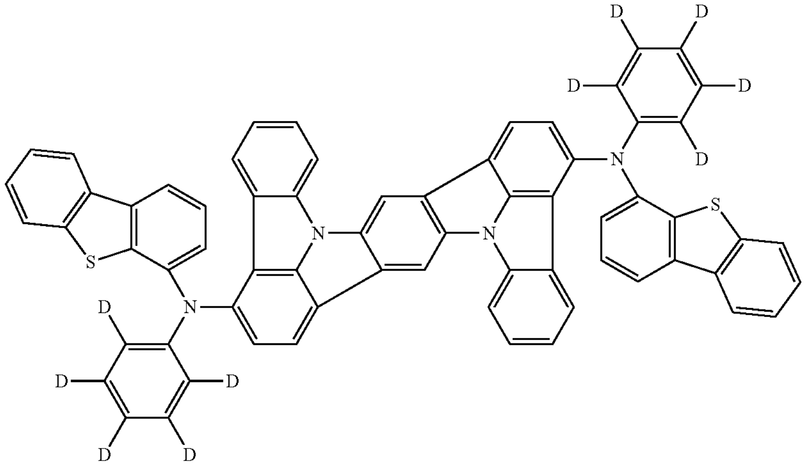
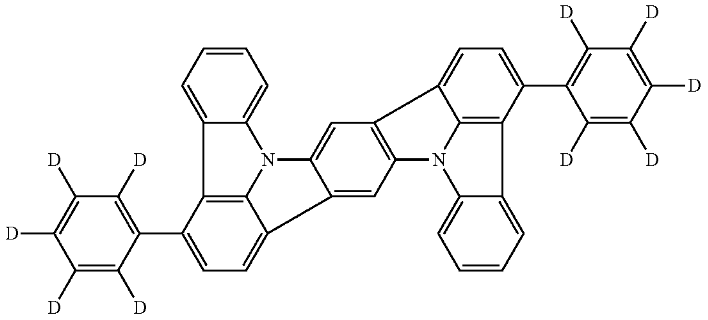

-continued
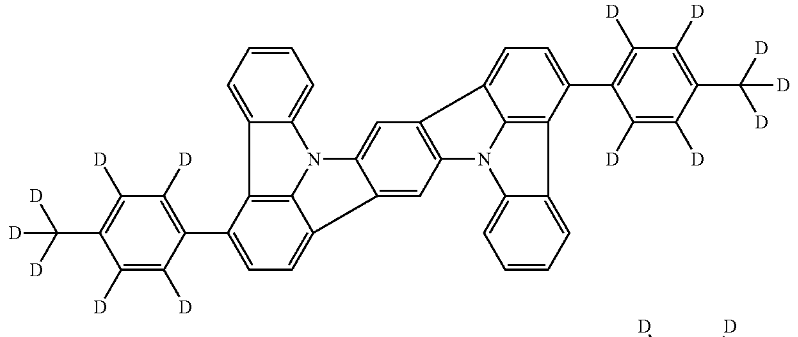
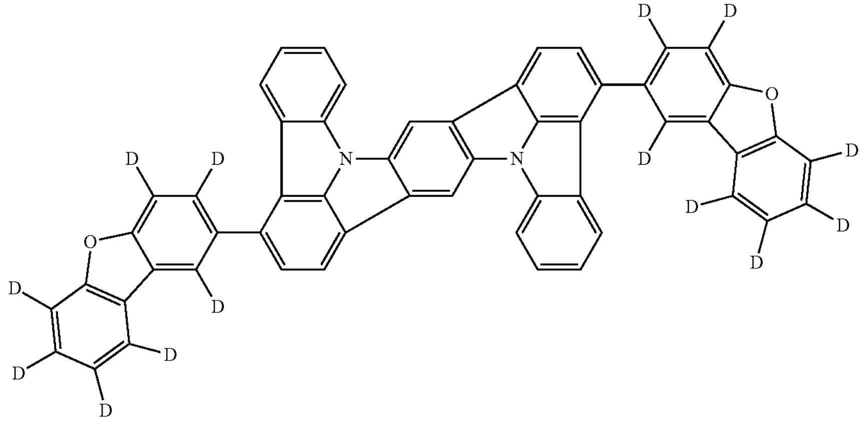
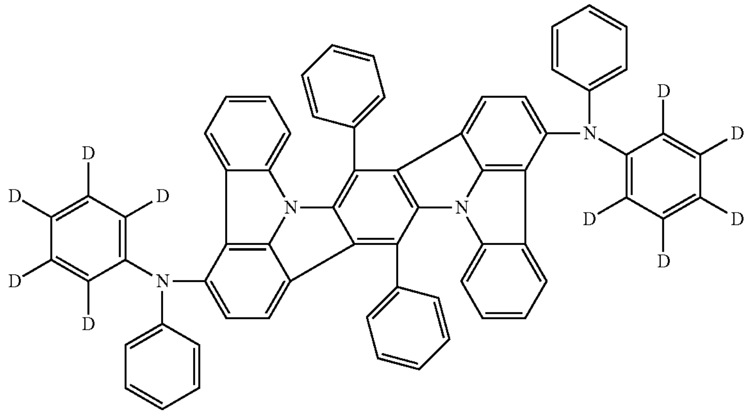
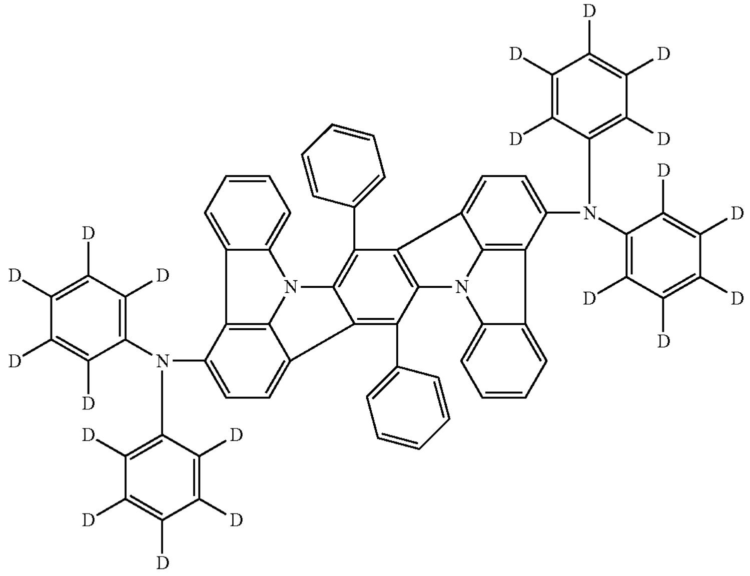

-continued
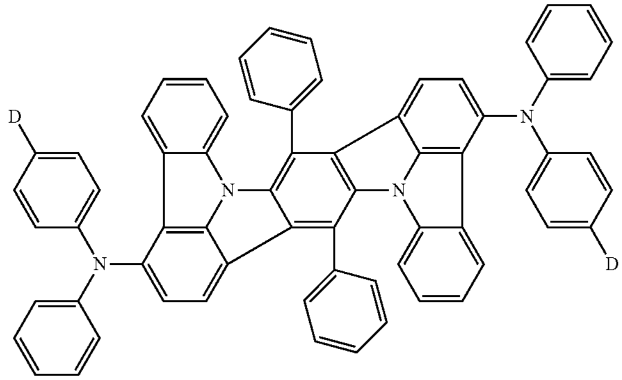
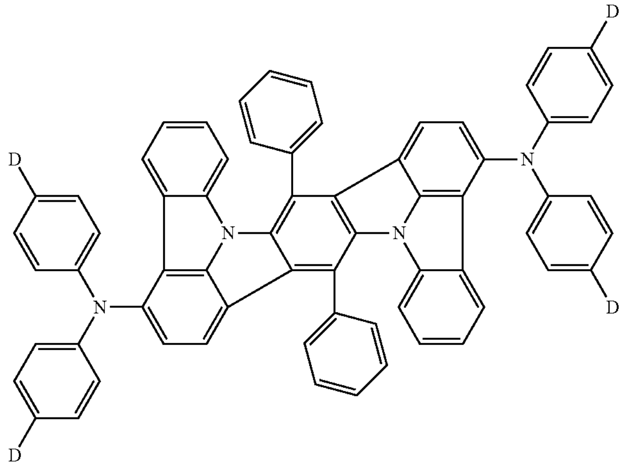
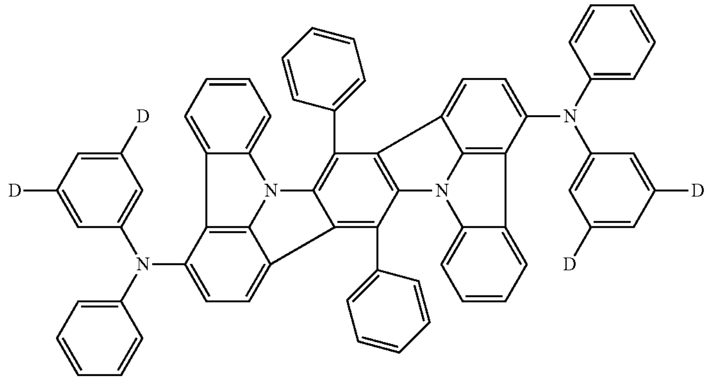
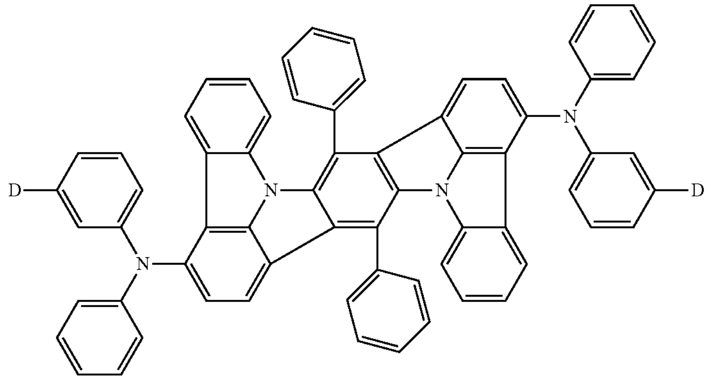

-continued
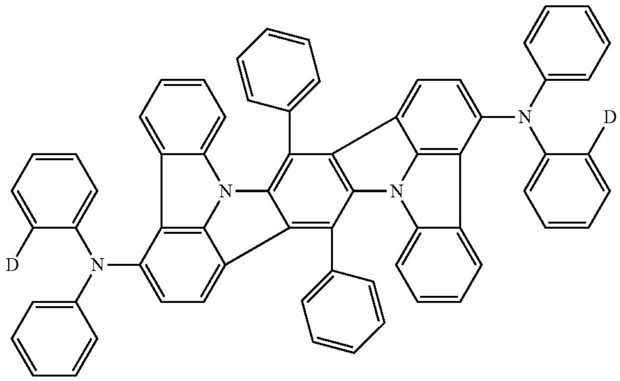
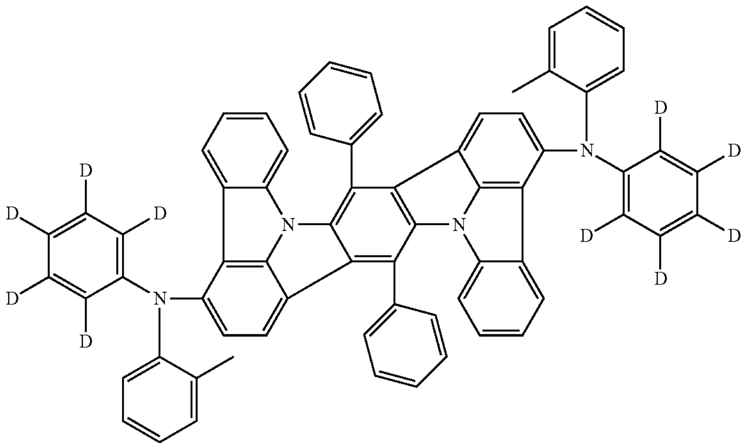
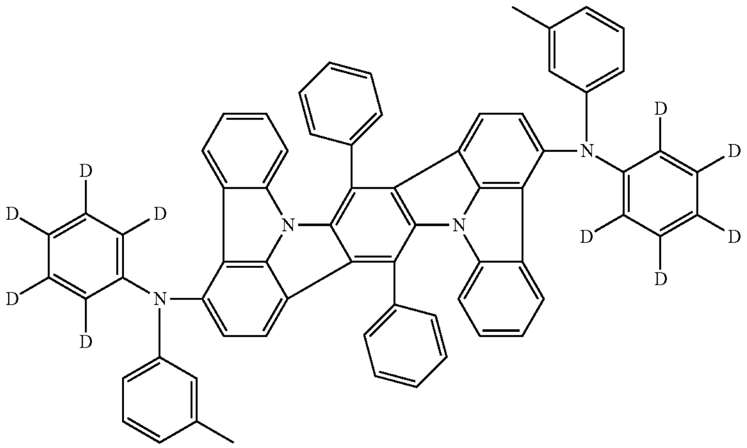

-continued
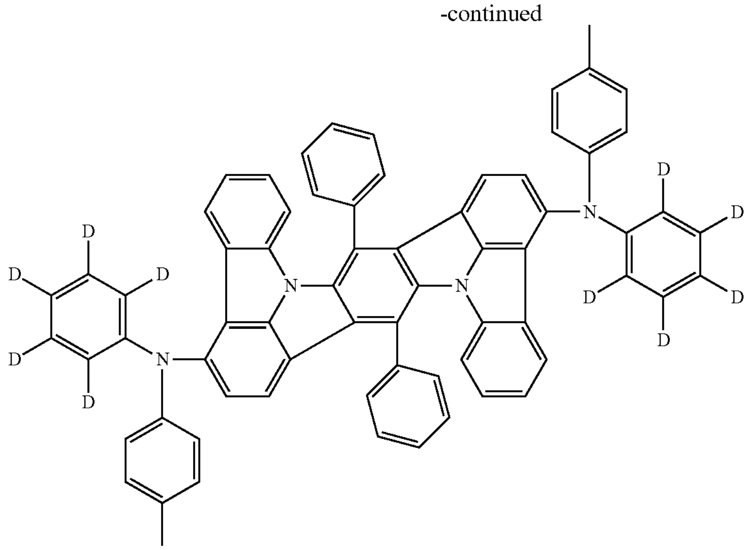
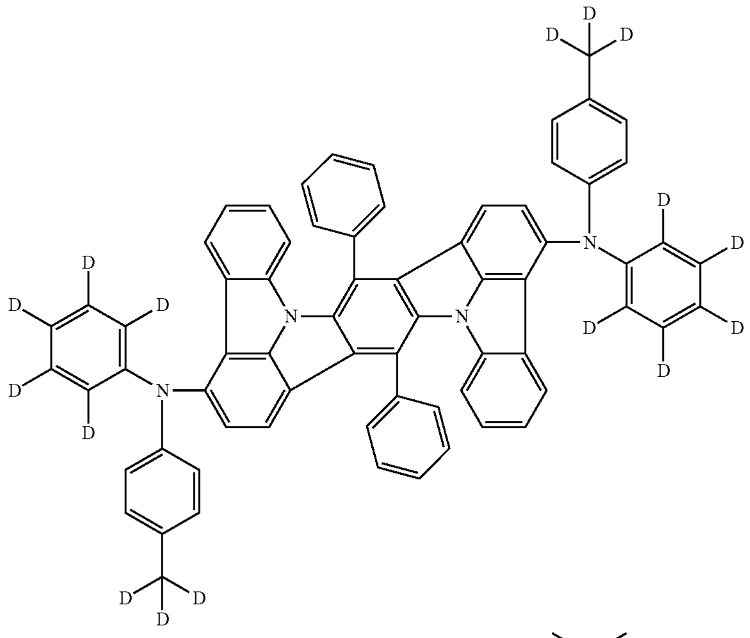
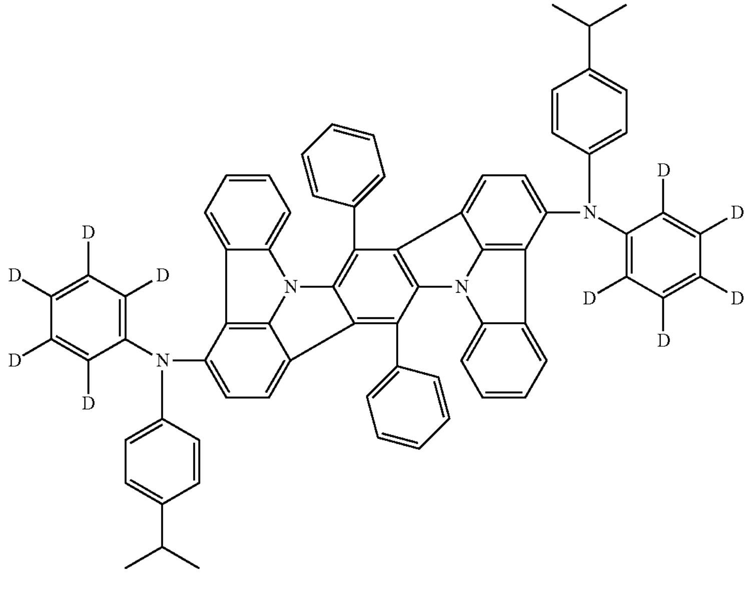

-continued
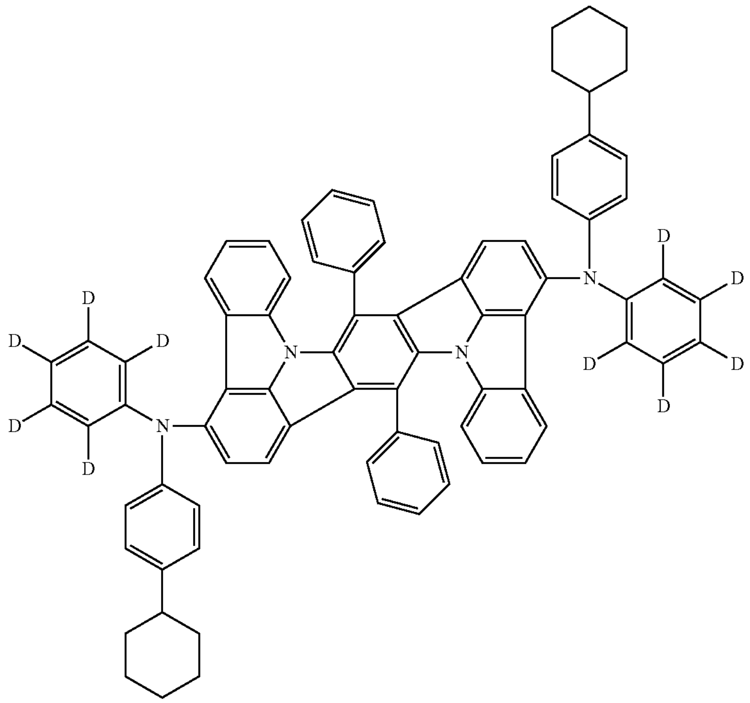
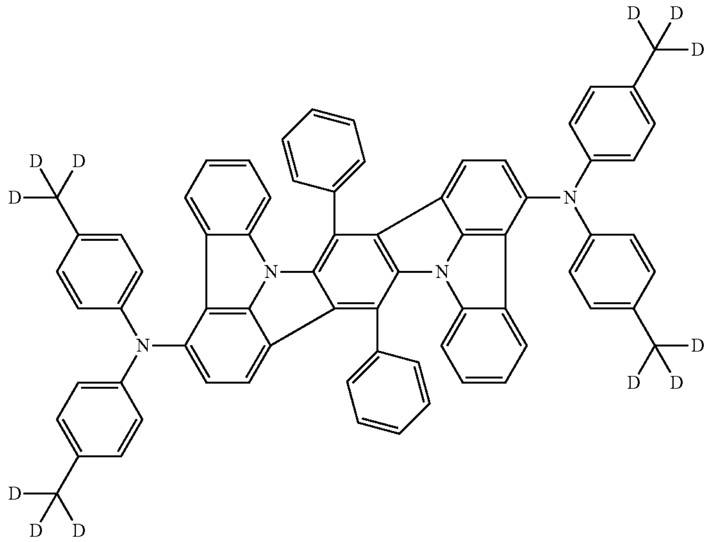
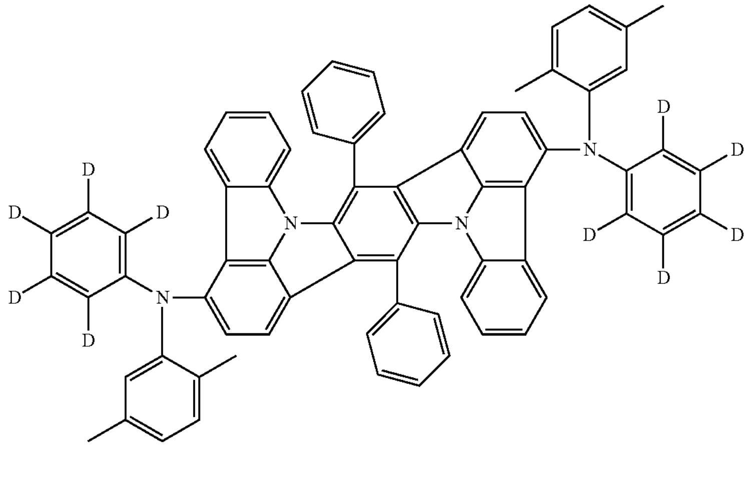

-continued
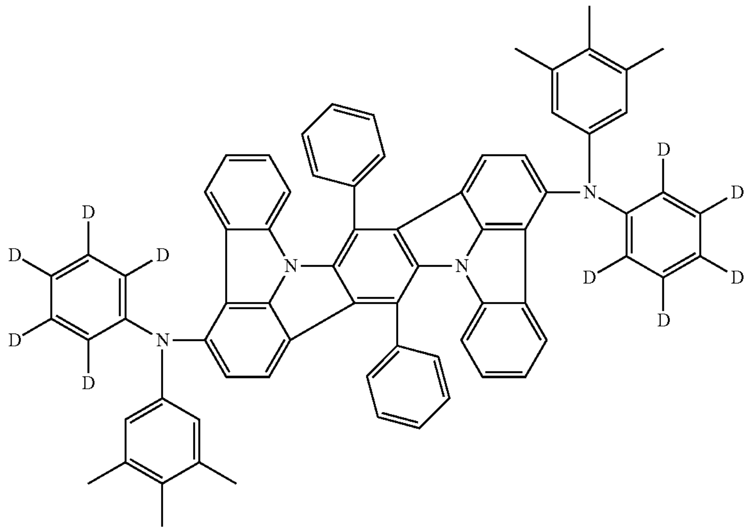
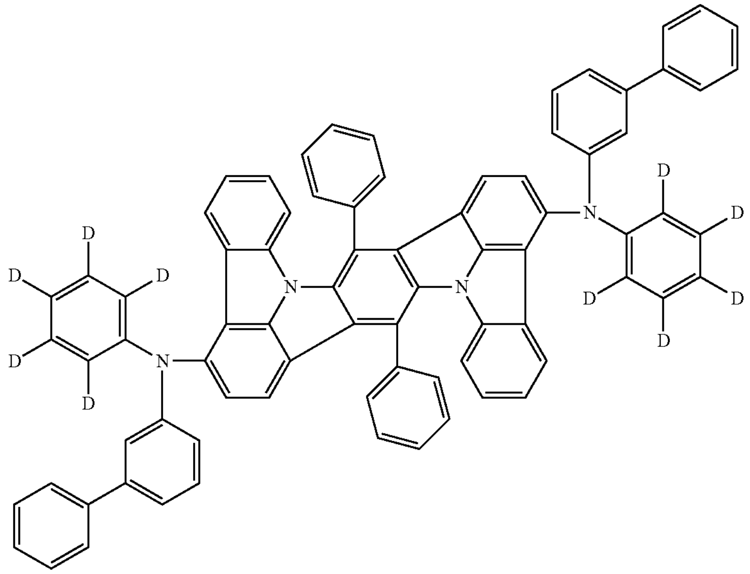

-continued
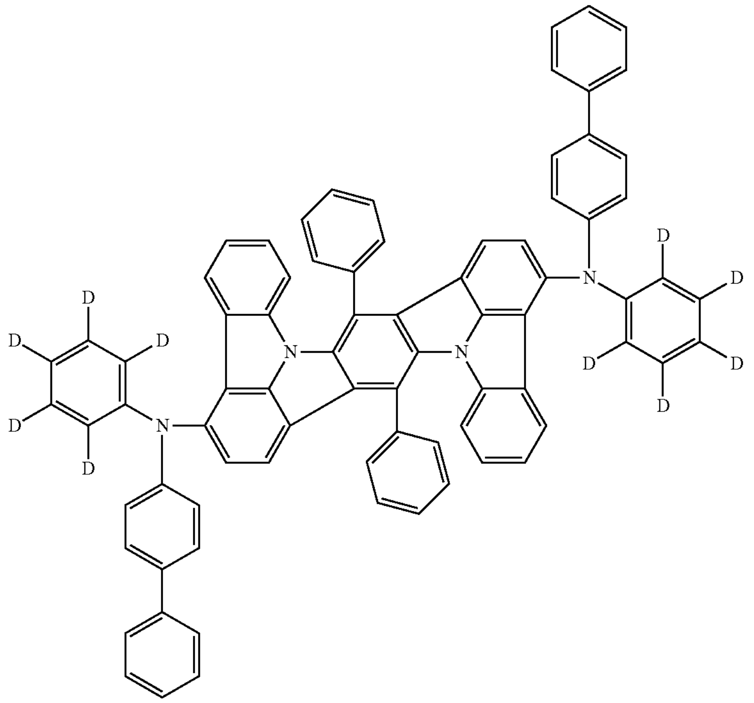
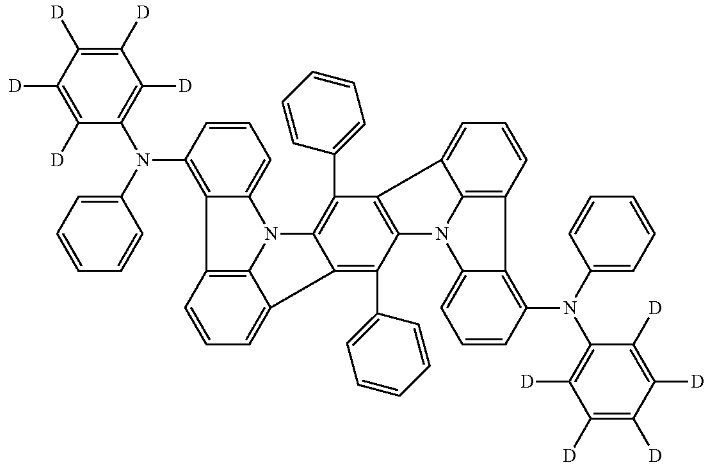
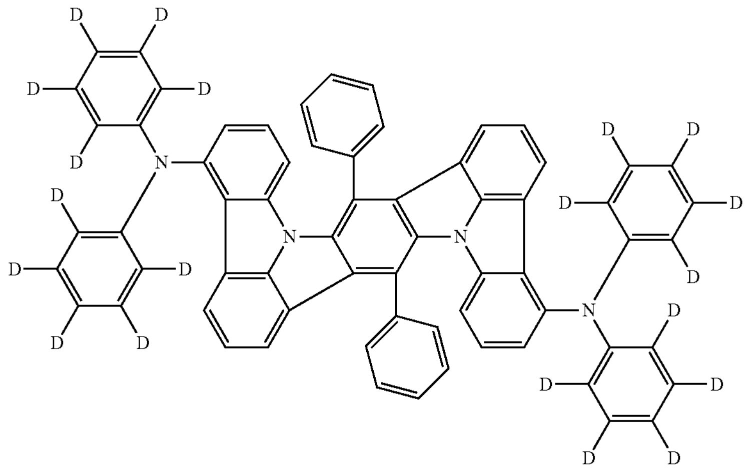

-continued
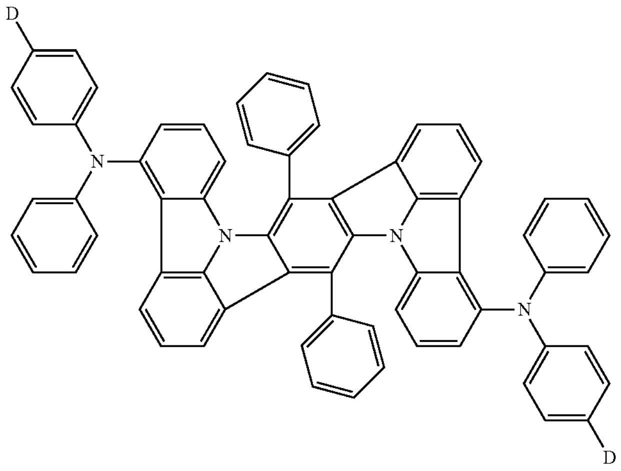
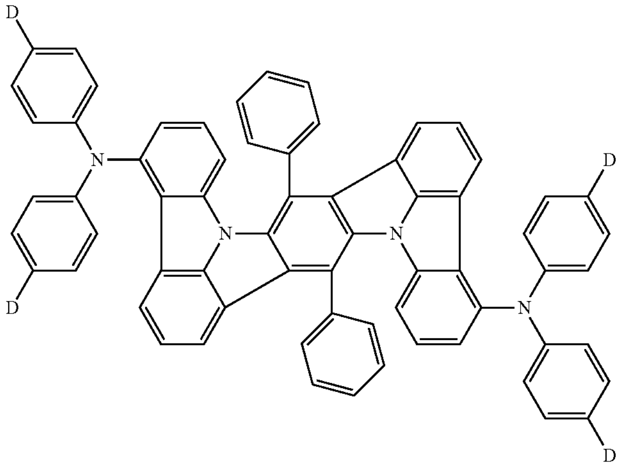
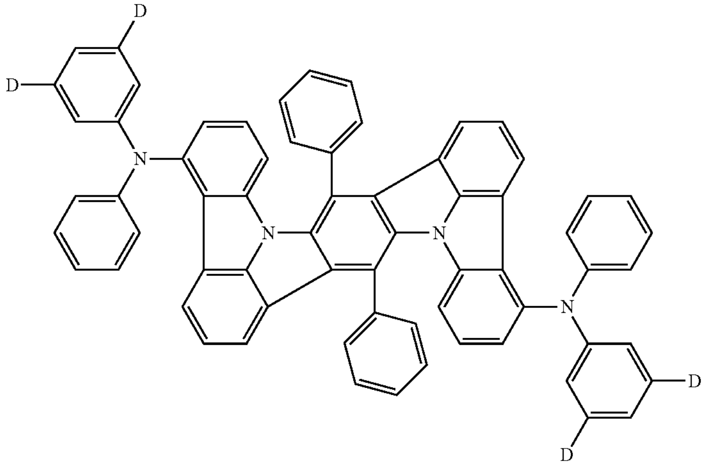

-continued
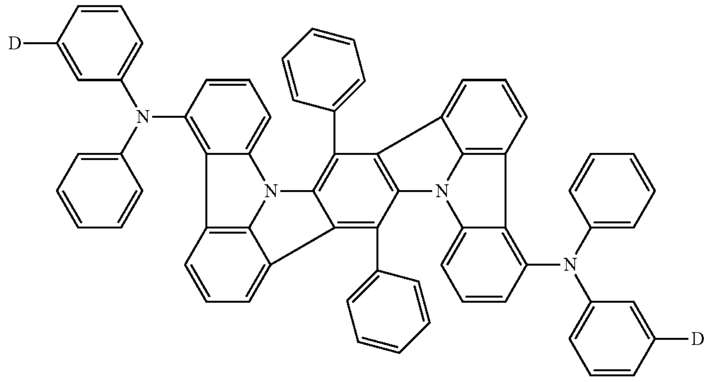
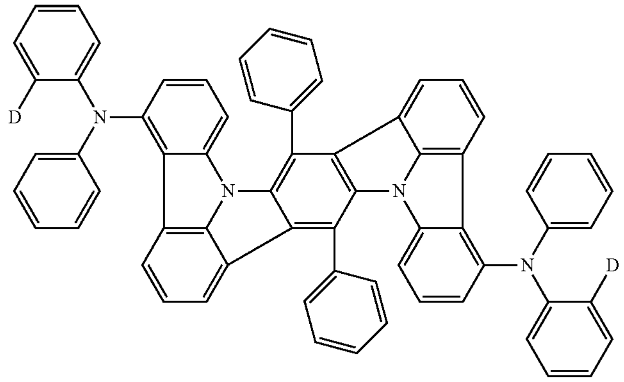
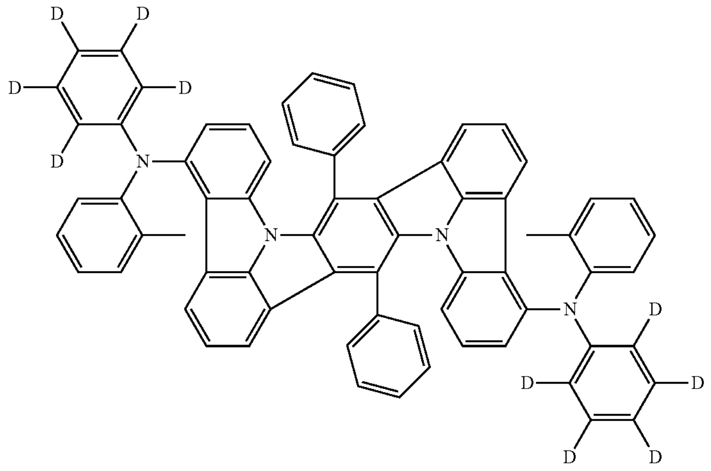
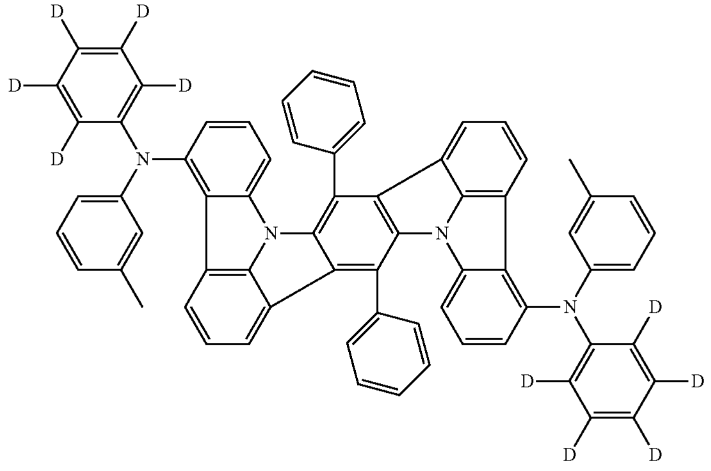

-continued
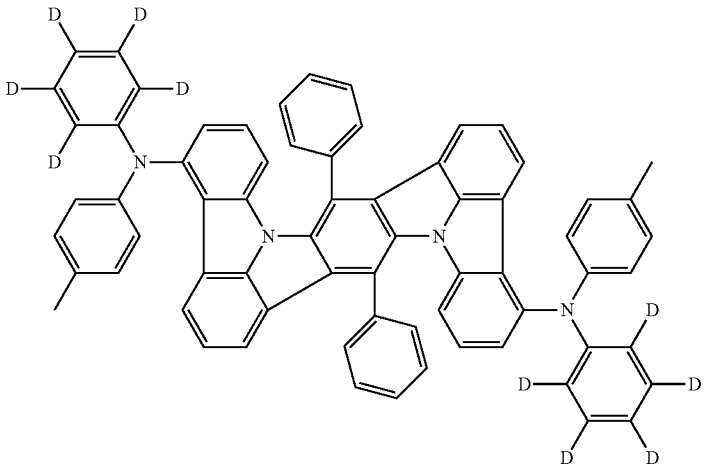
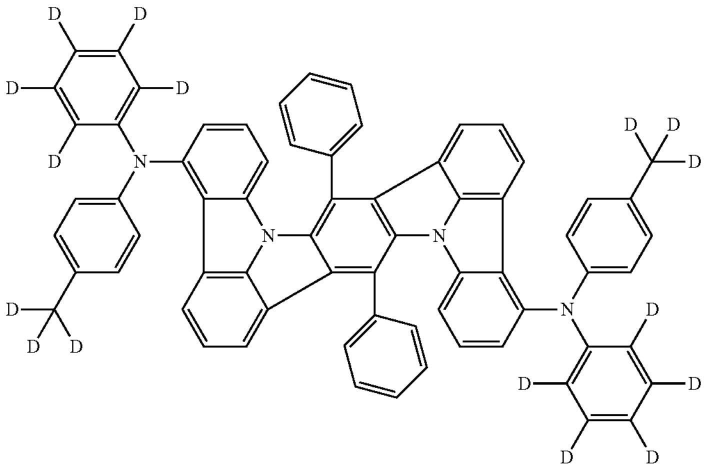
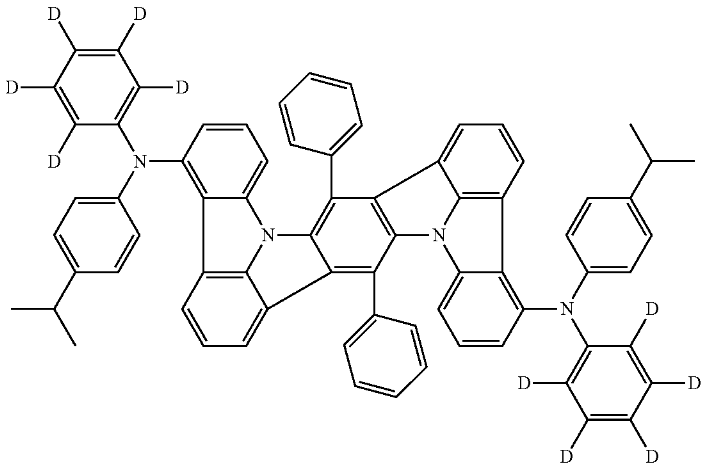

-continued
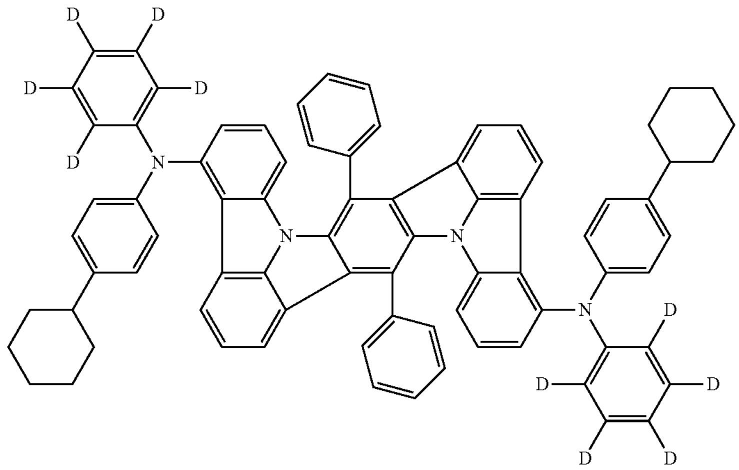
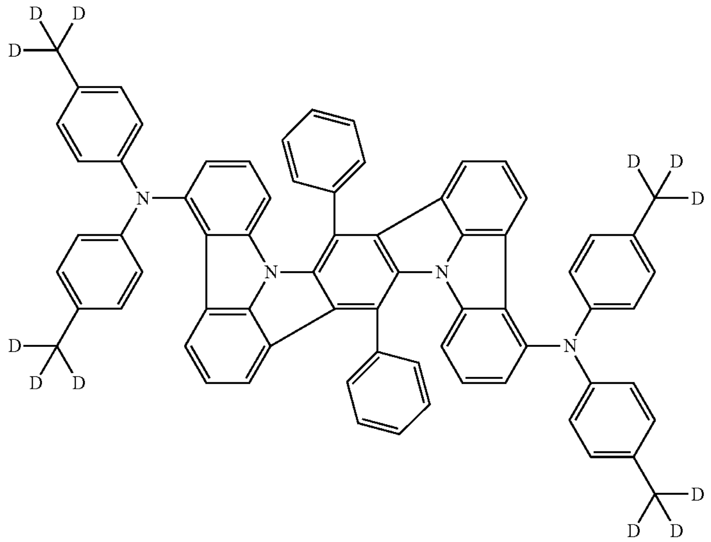
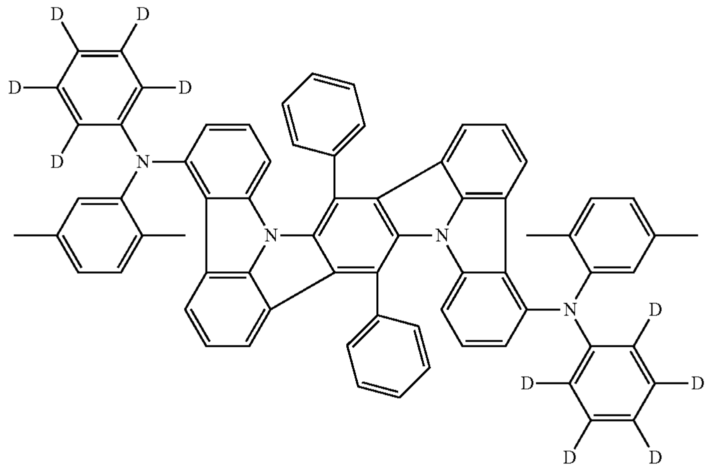

-continued
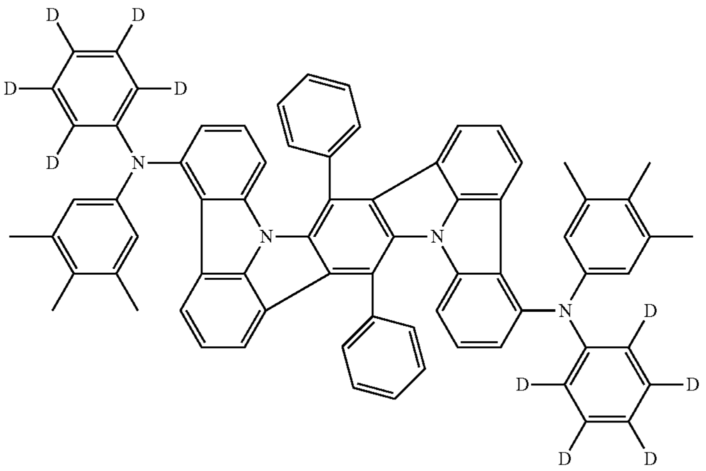
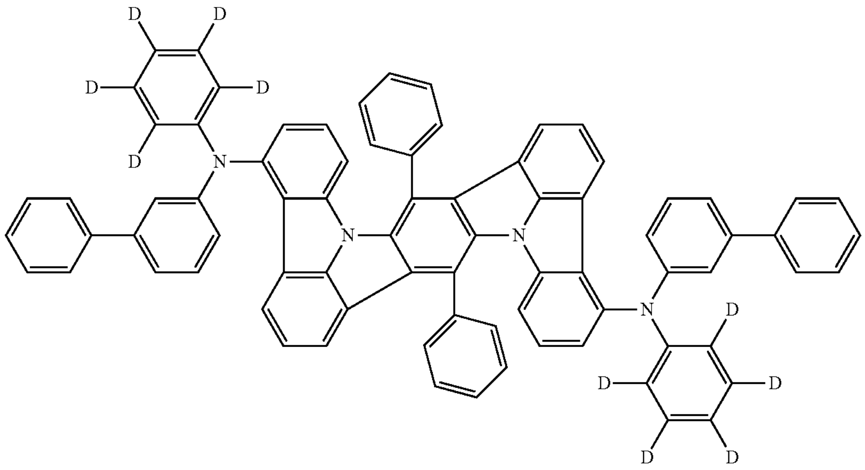
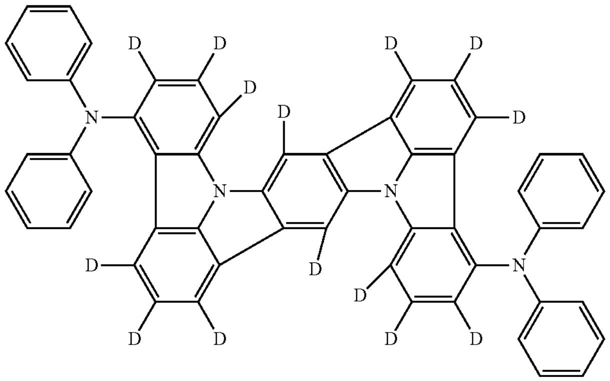
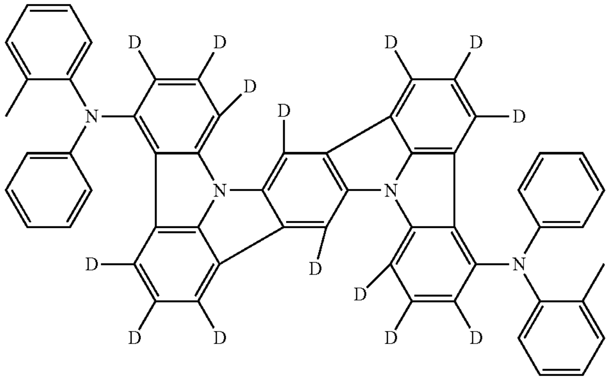

-continued
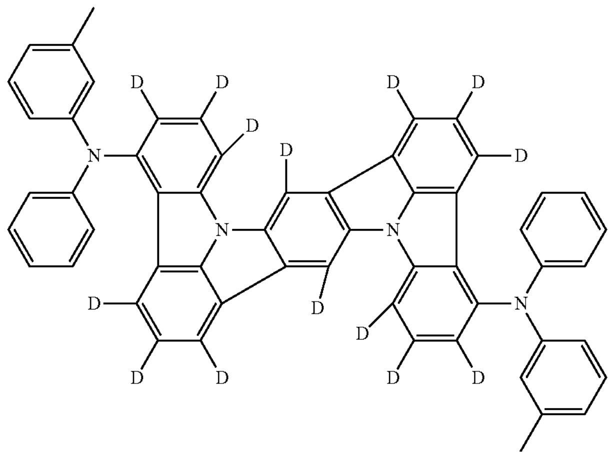
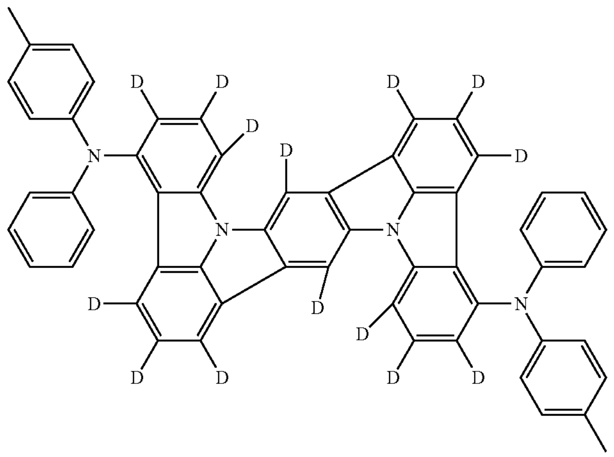
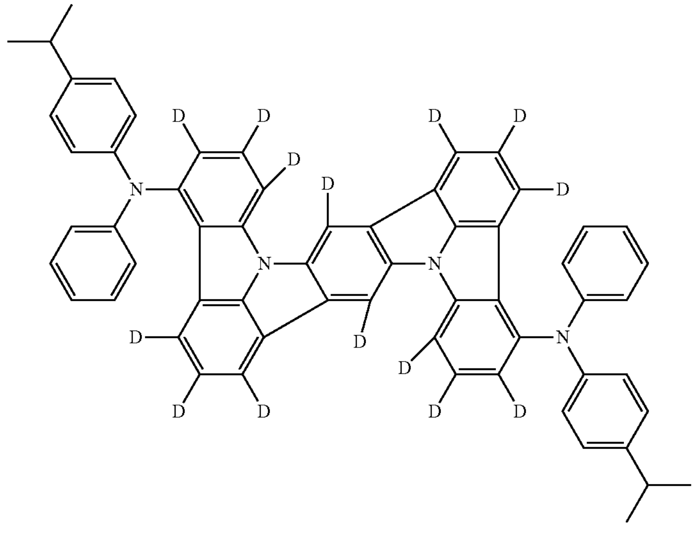

-continued
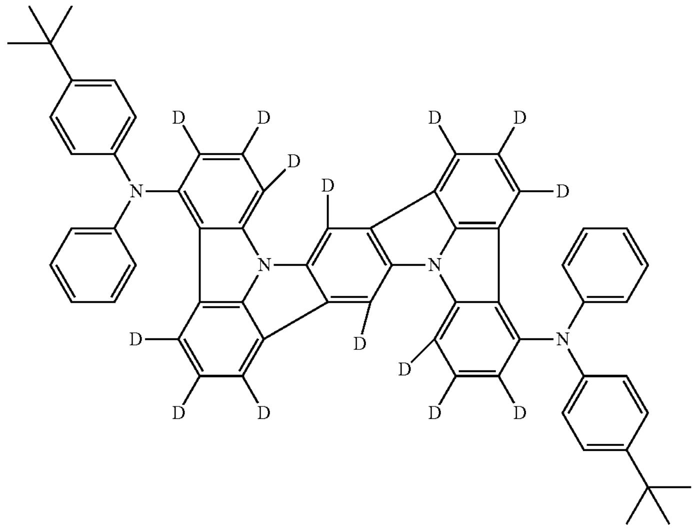
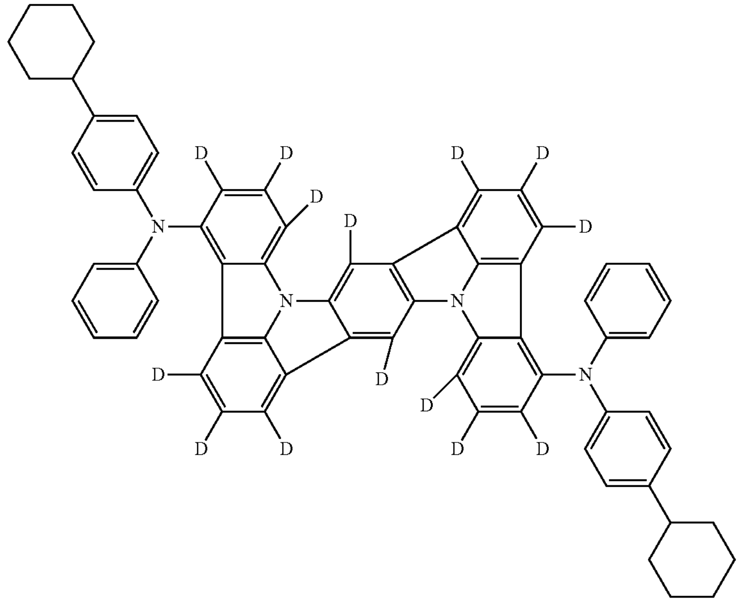
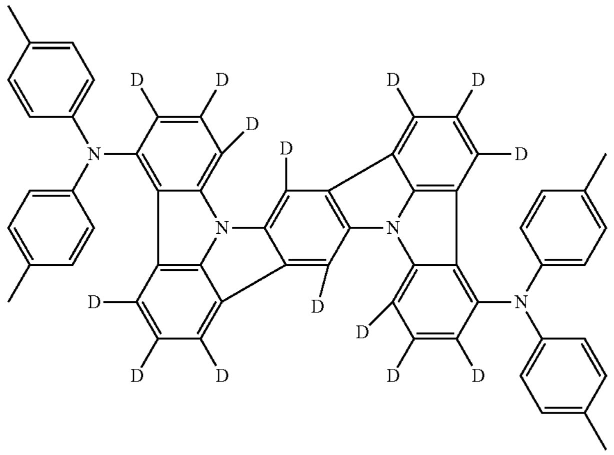

-continued
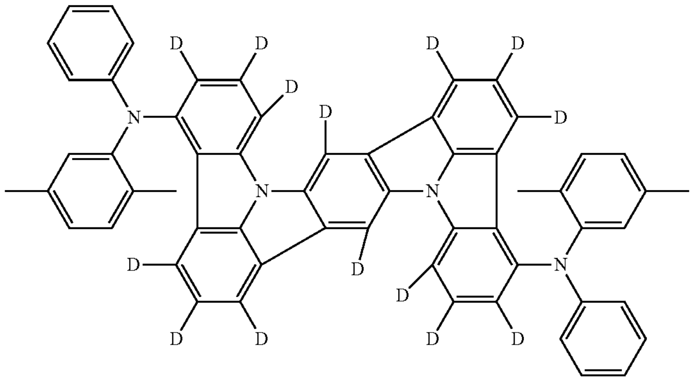
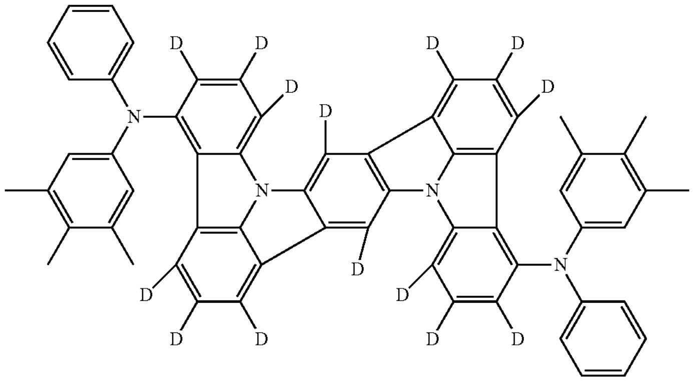
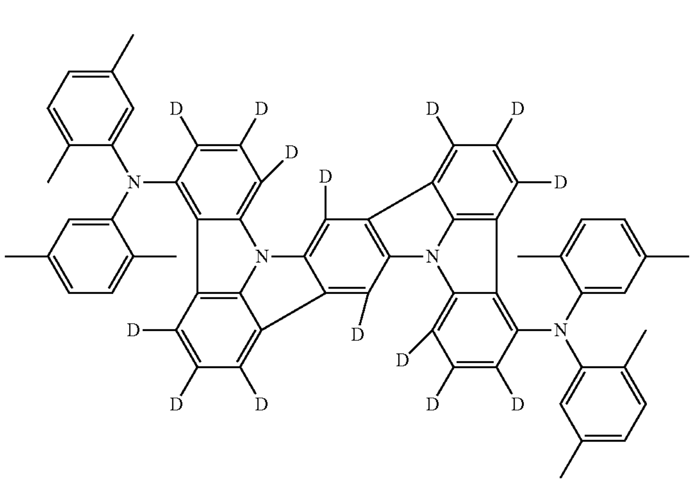

-continued
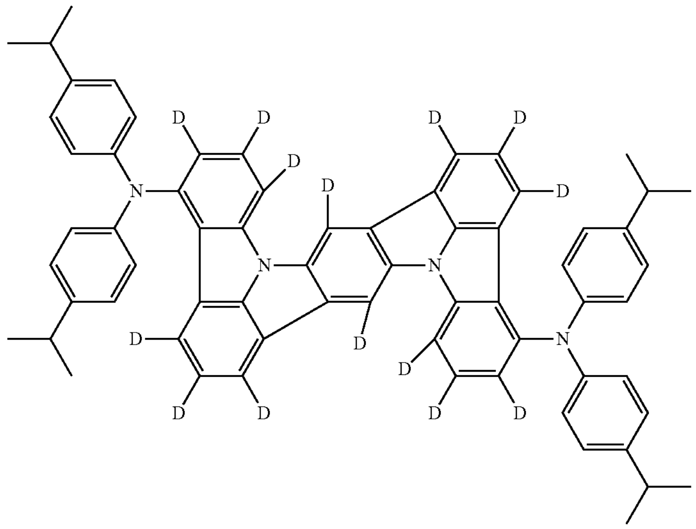
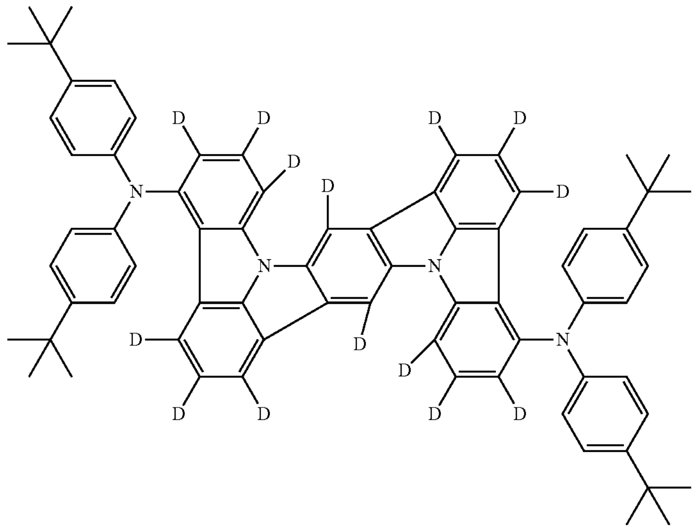
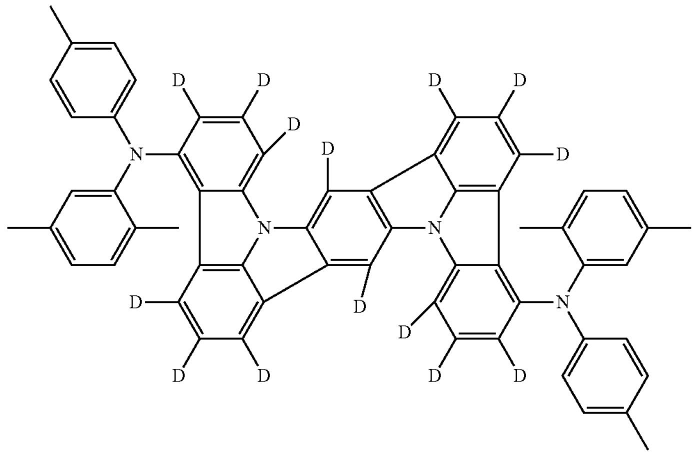

-continued
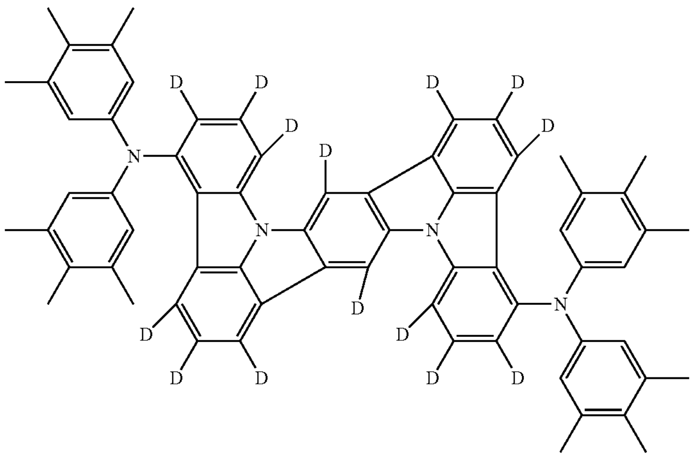
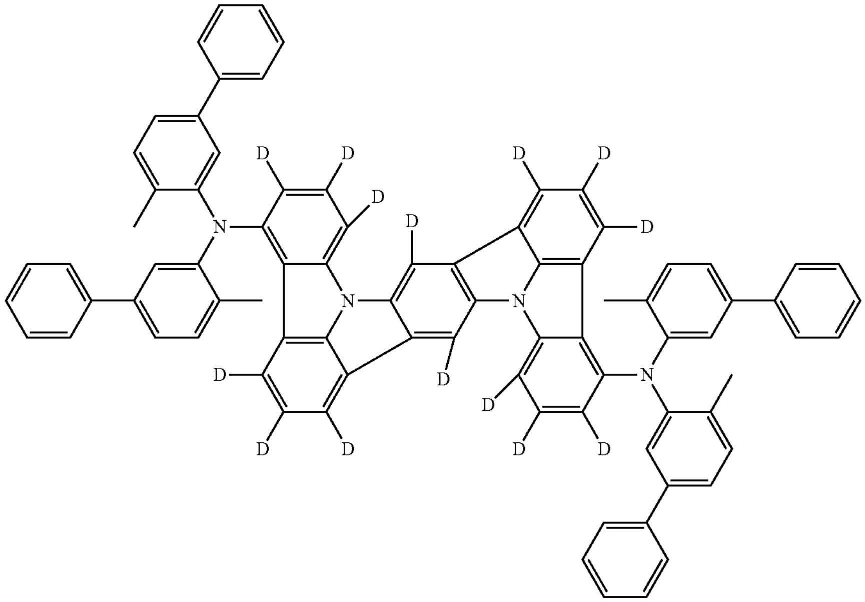
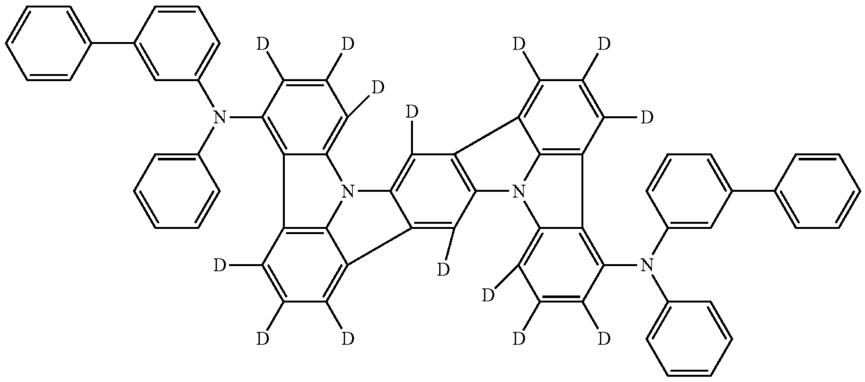

-continued
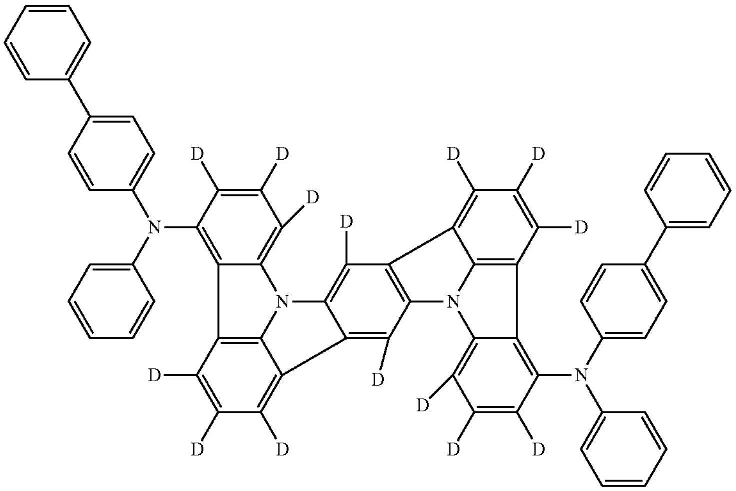
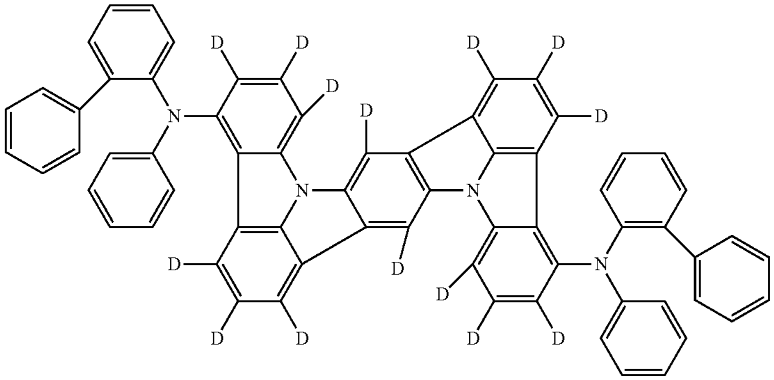
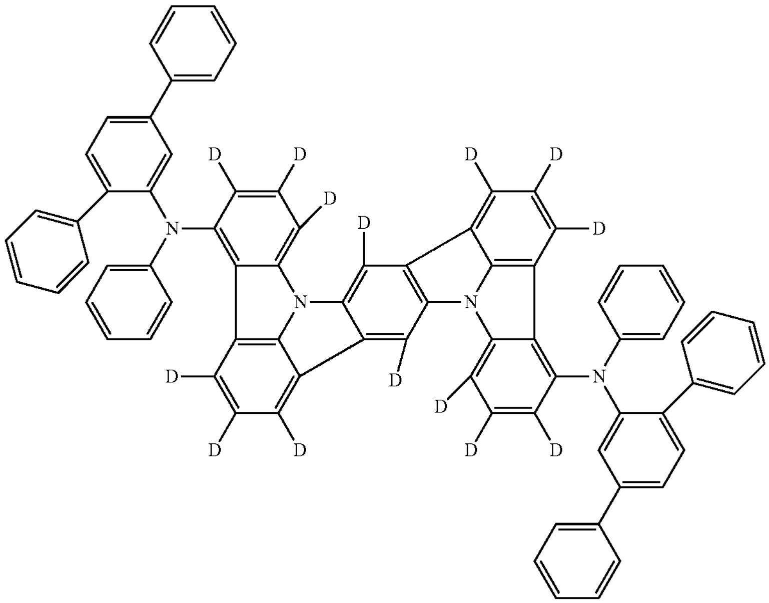

-continued
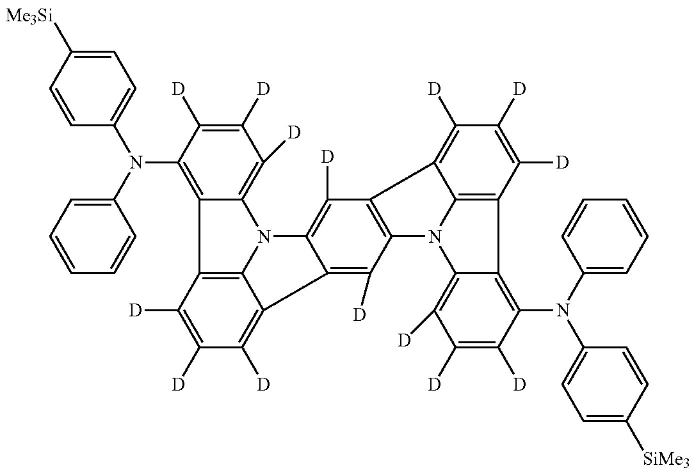
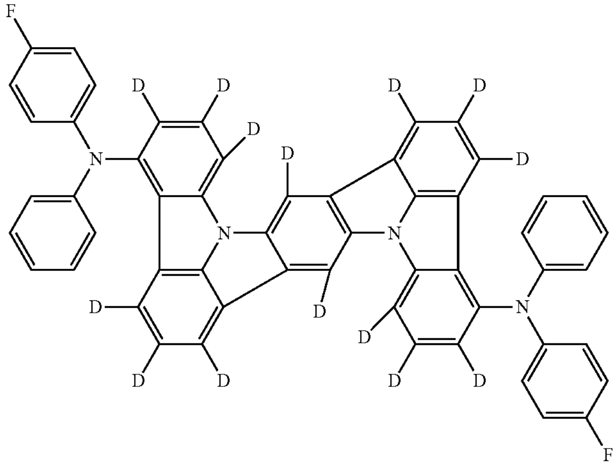
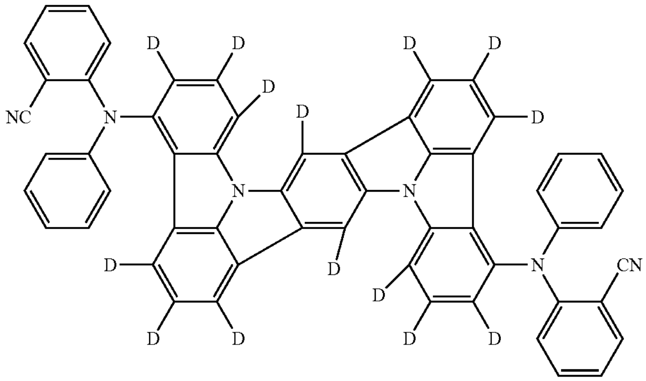

-continued
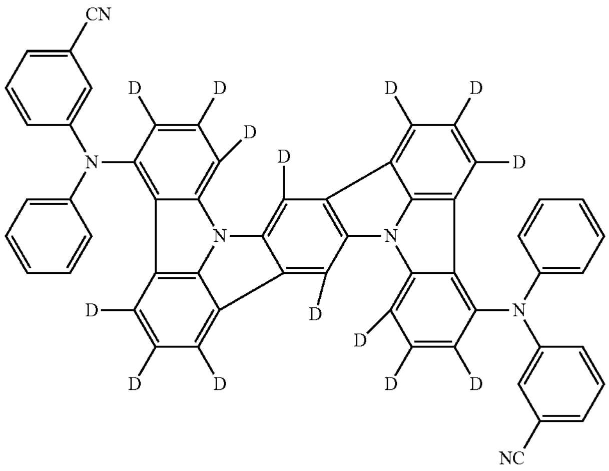
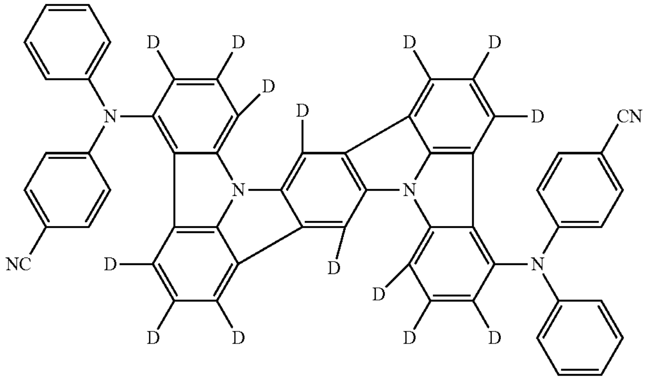
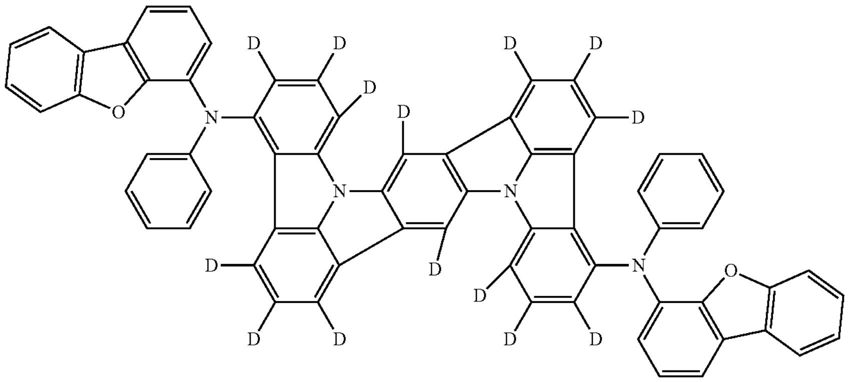
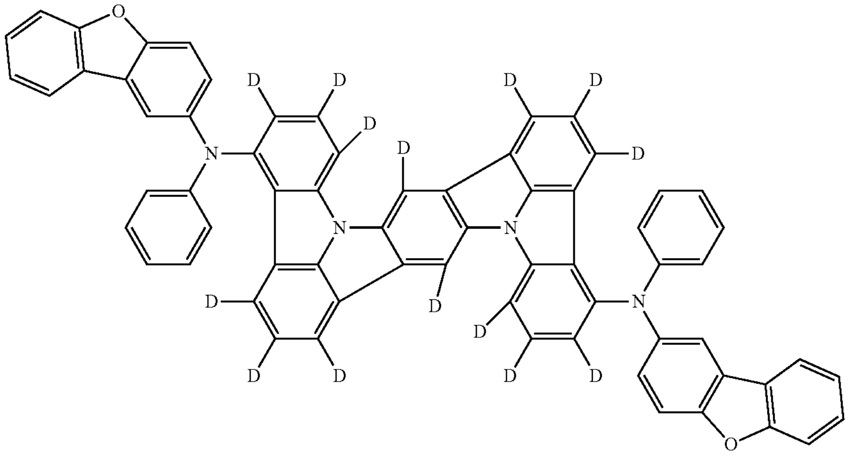

-continued
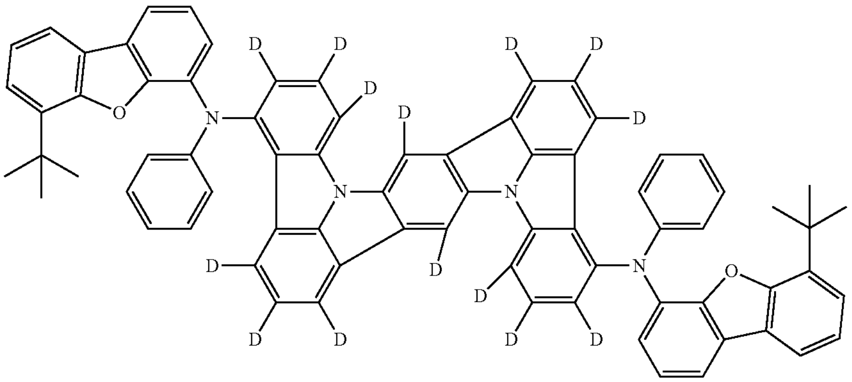
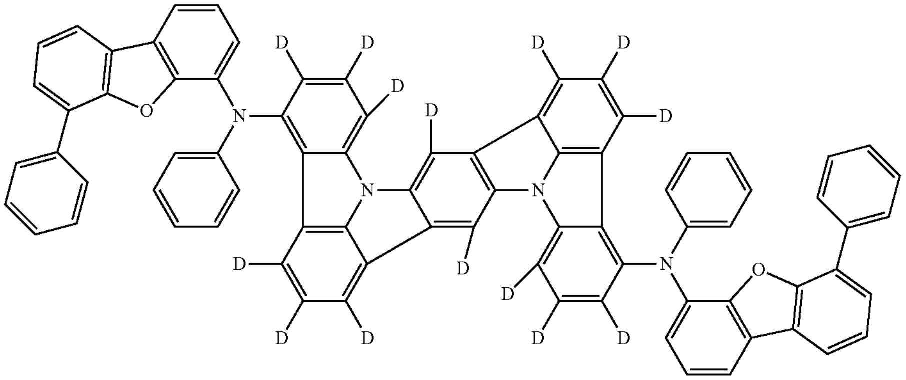
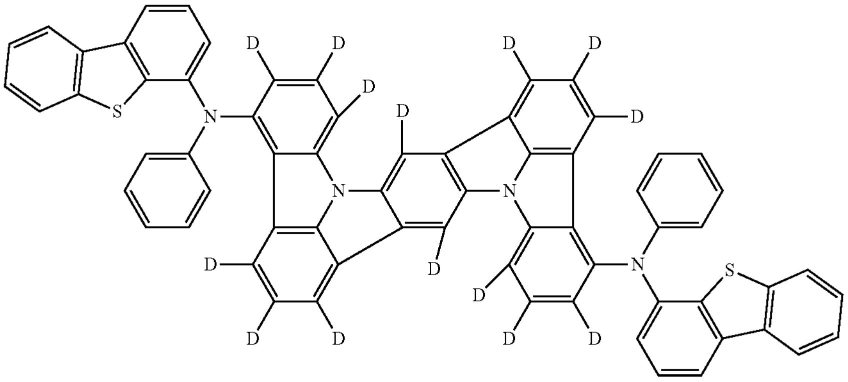
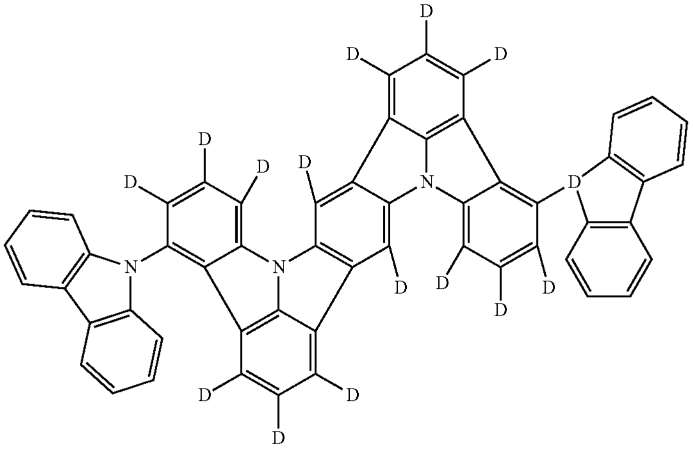

-continued
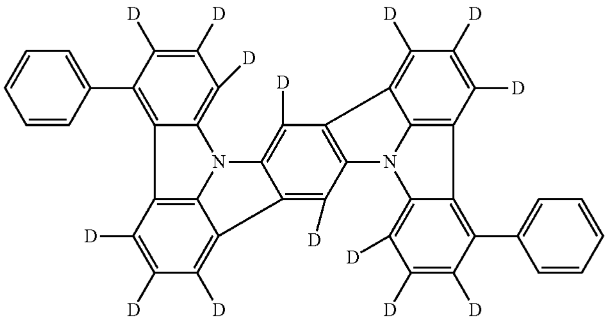
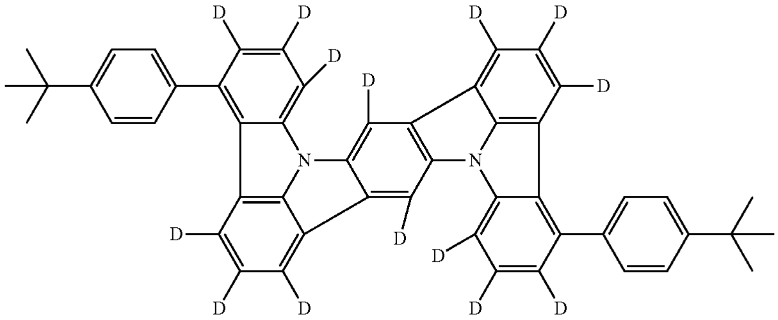
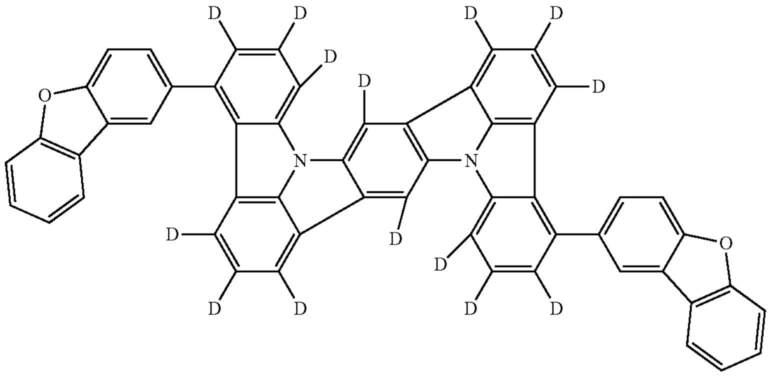
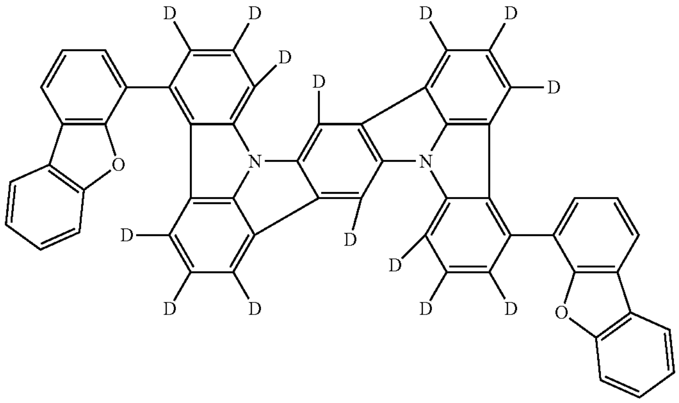

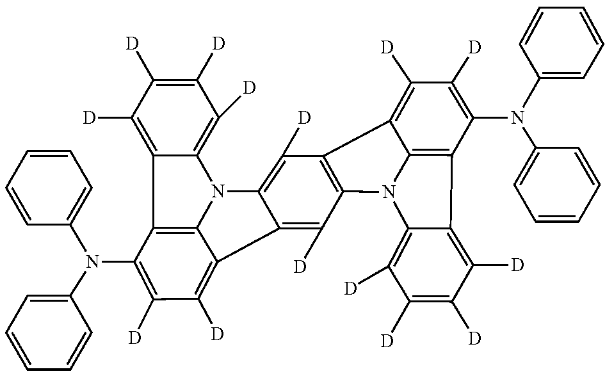
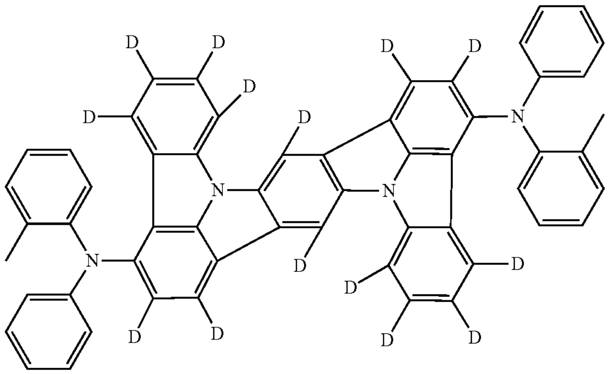
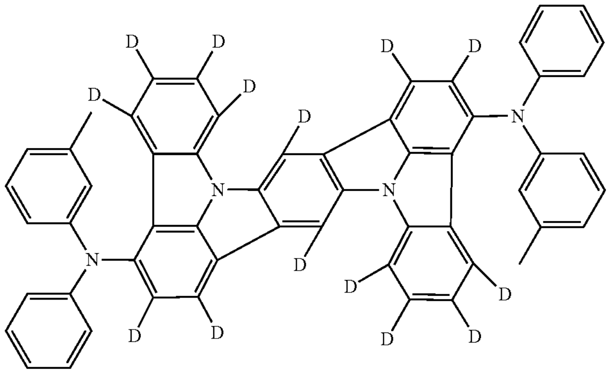
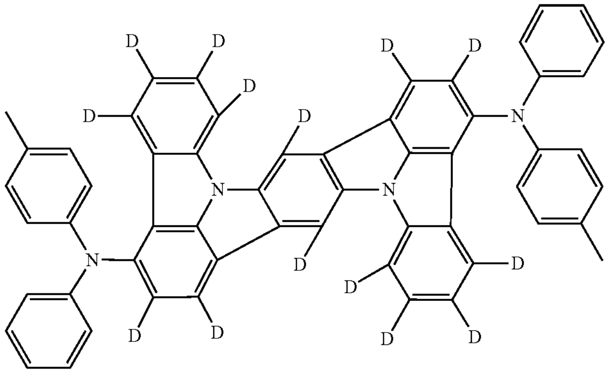

-continued
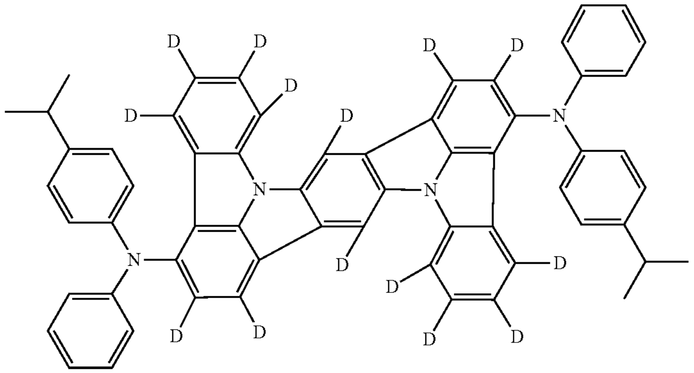
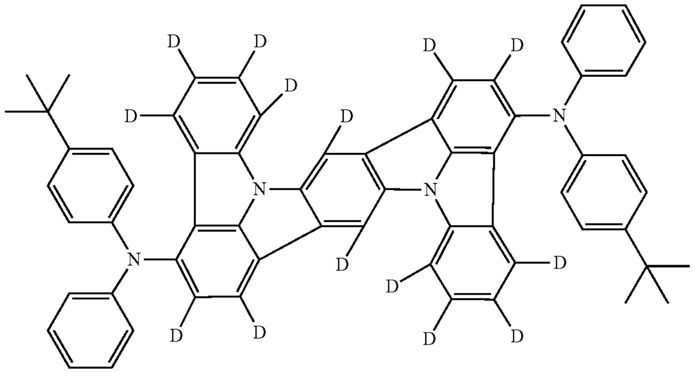
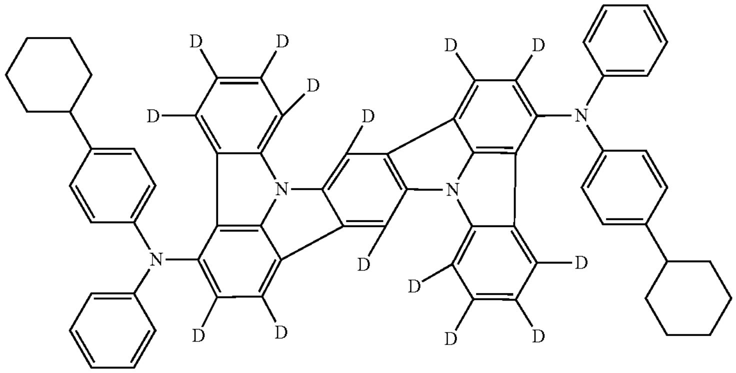
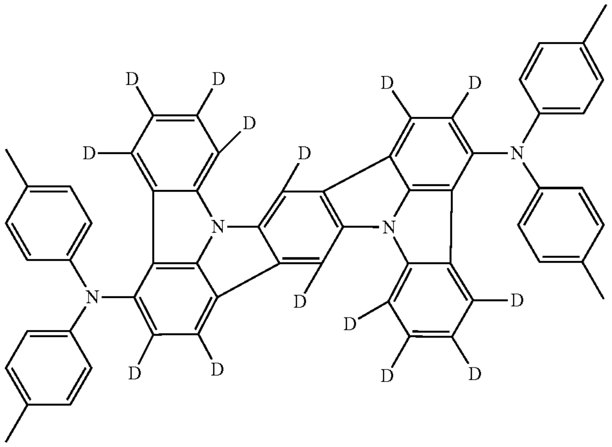

-continued
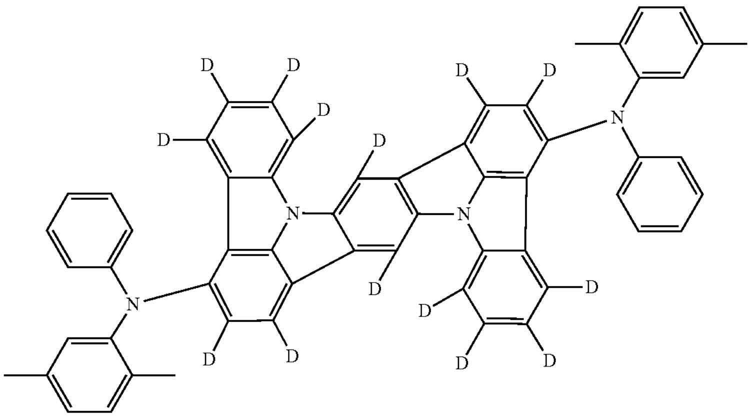
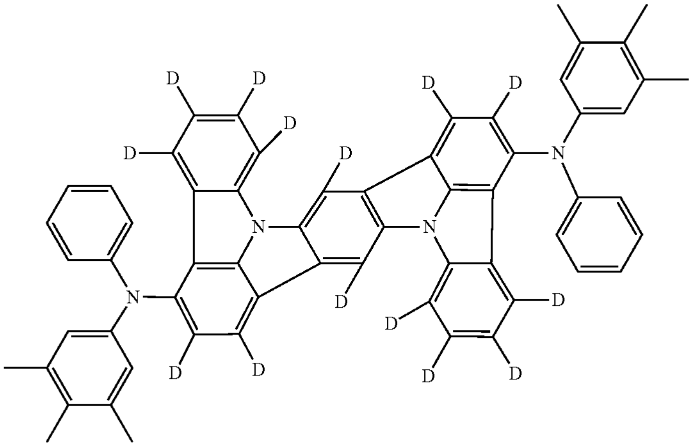
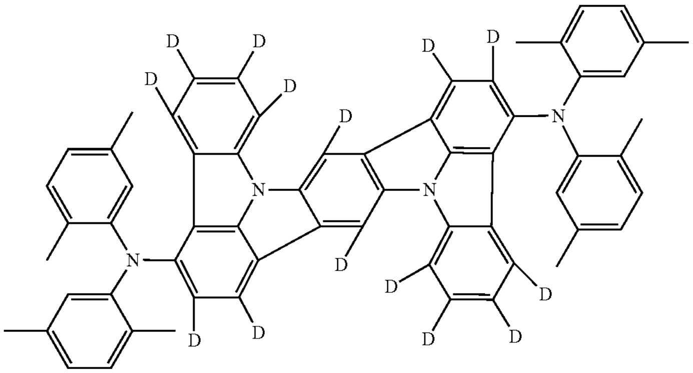

-continued
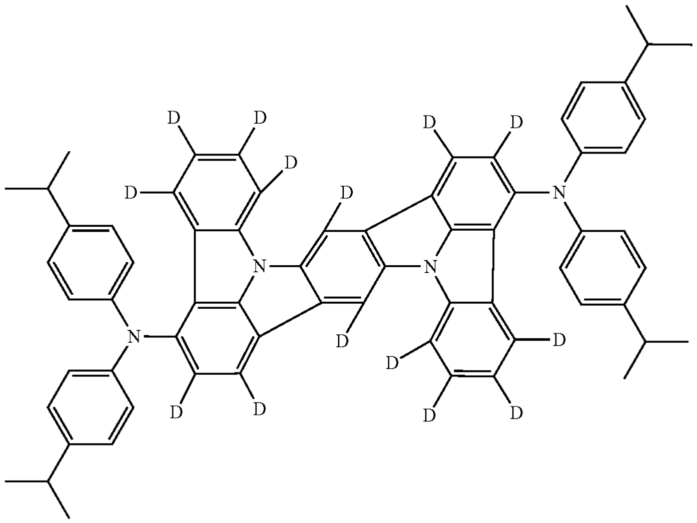
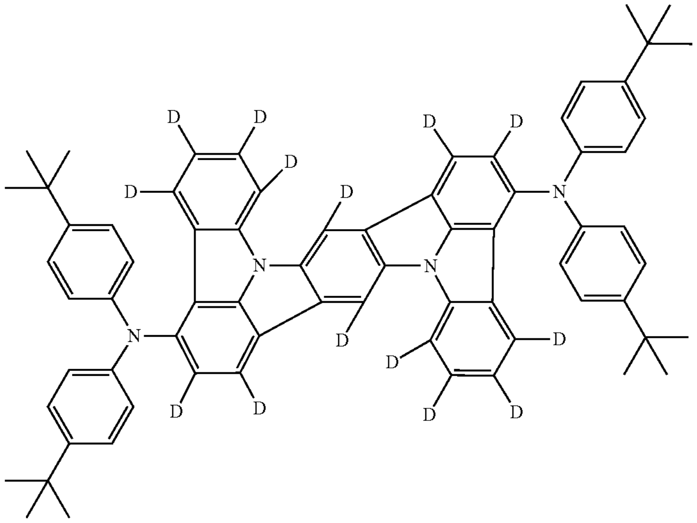
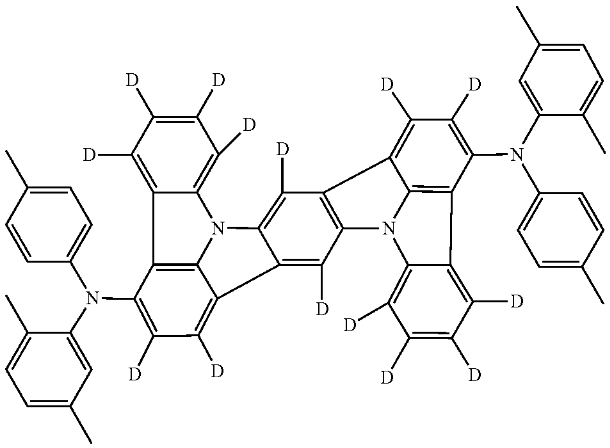

-continued
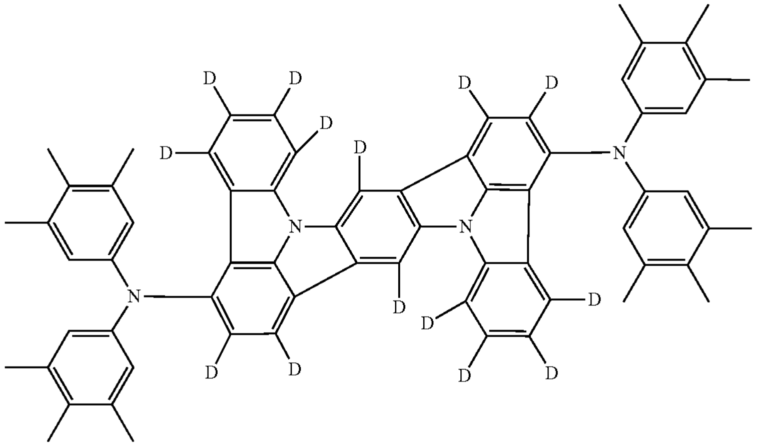
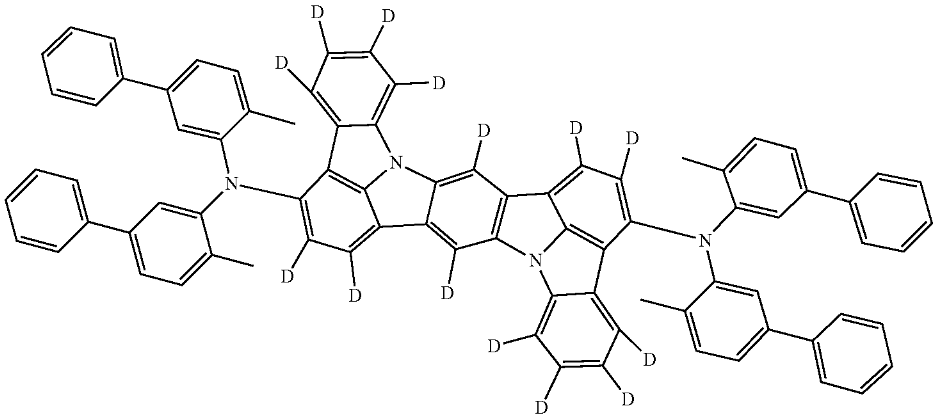
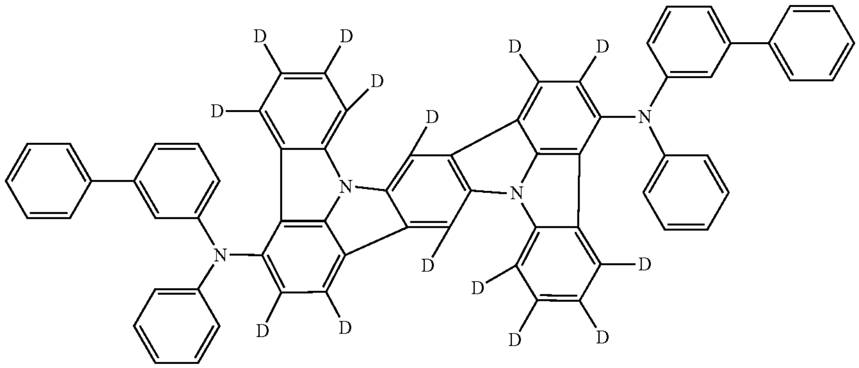
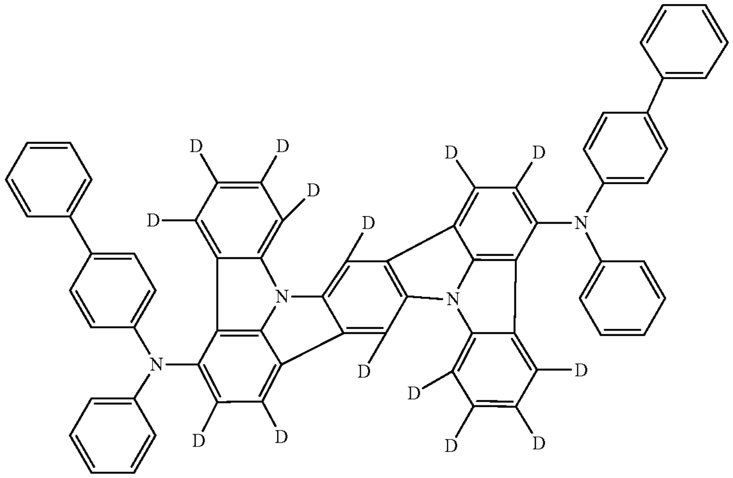

-continued
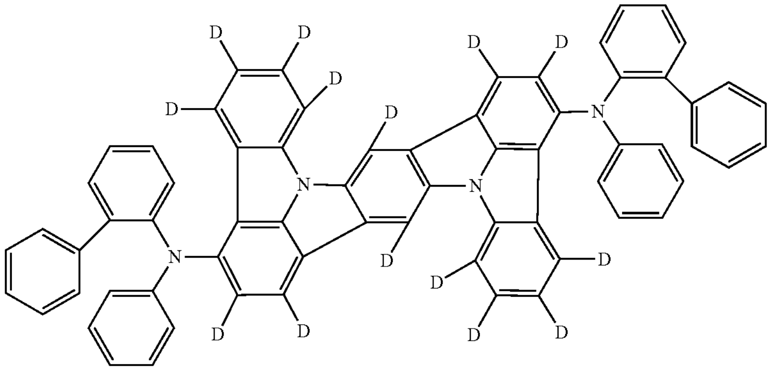
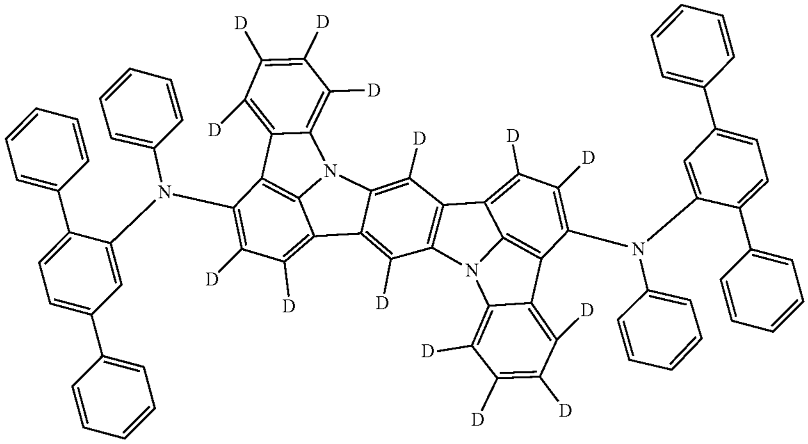
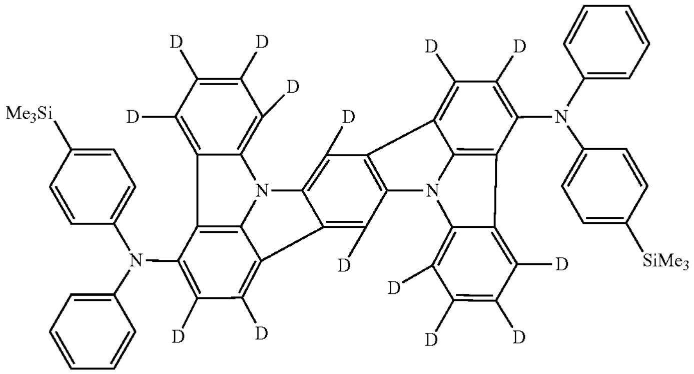
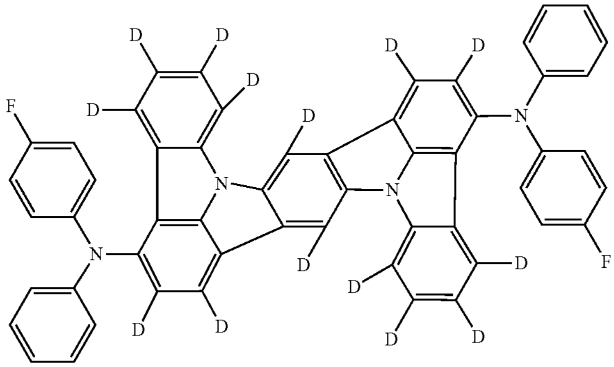

-continued
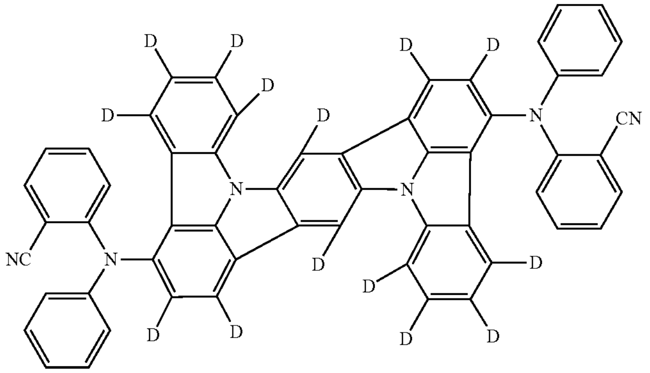
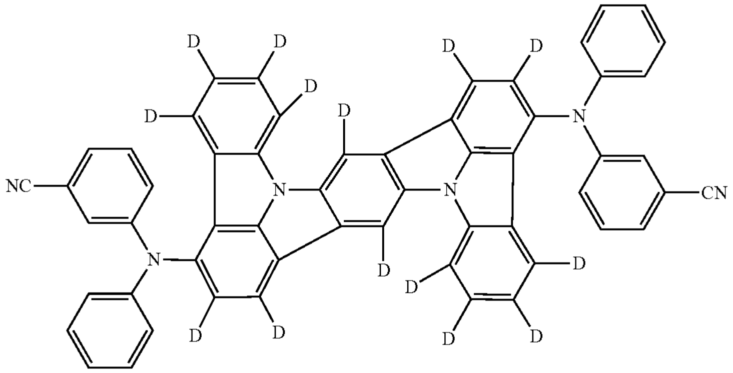
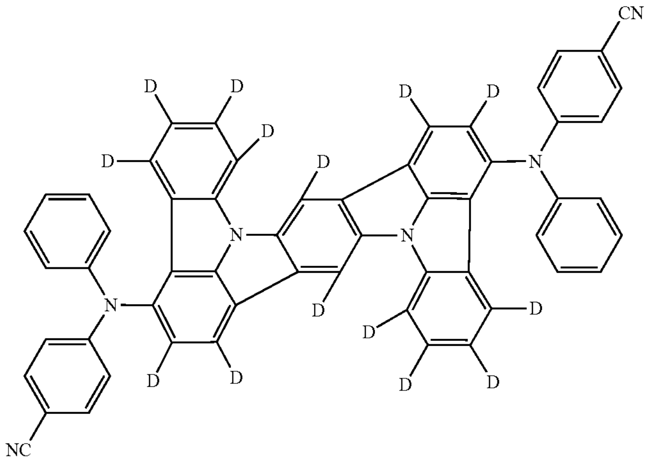
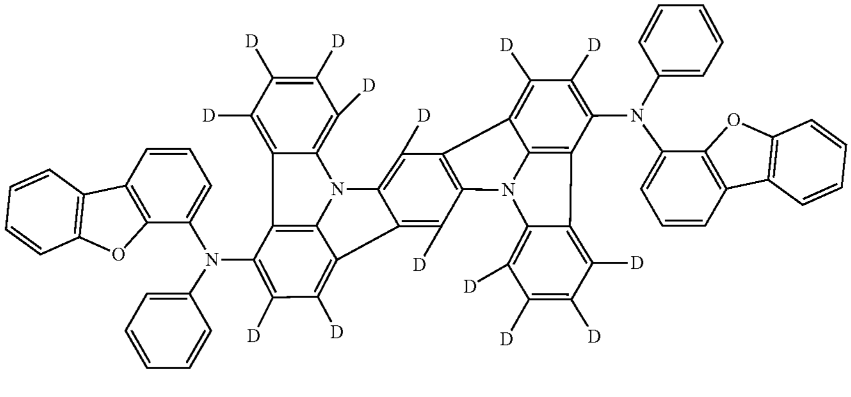

-continued
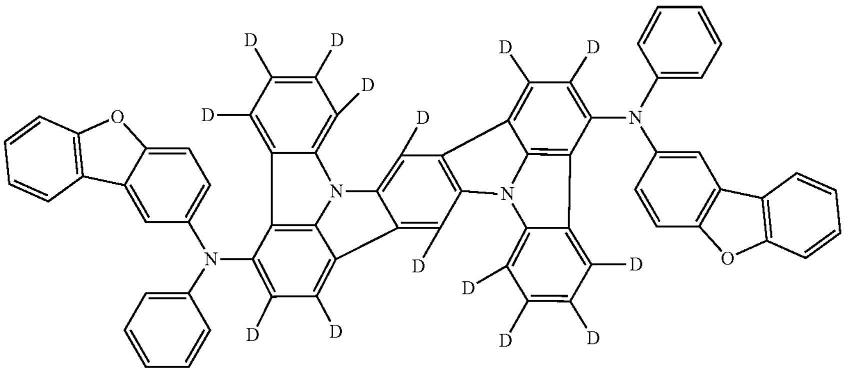
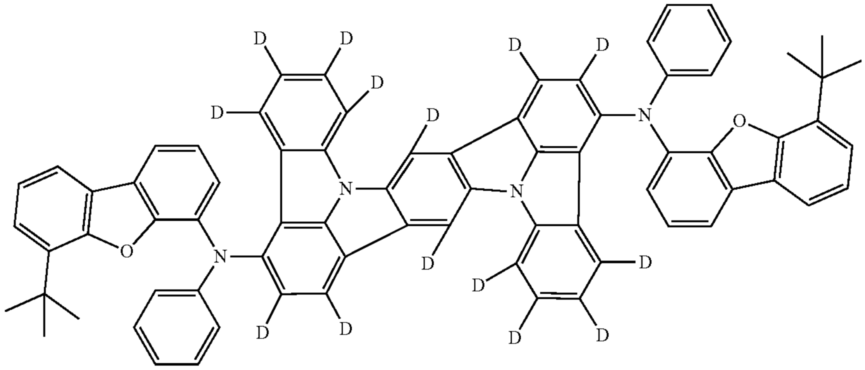
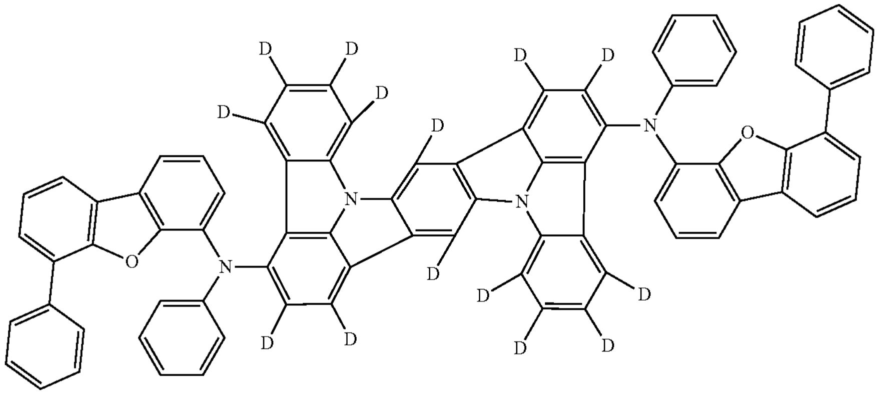
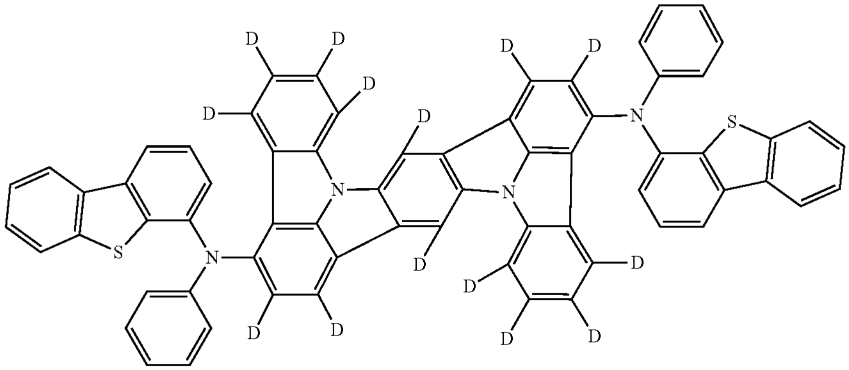

-continued
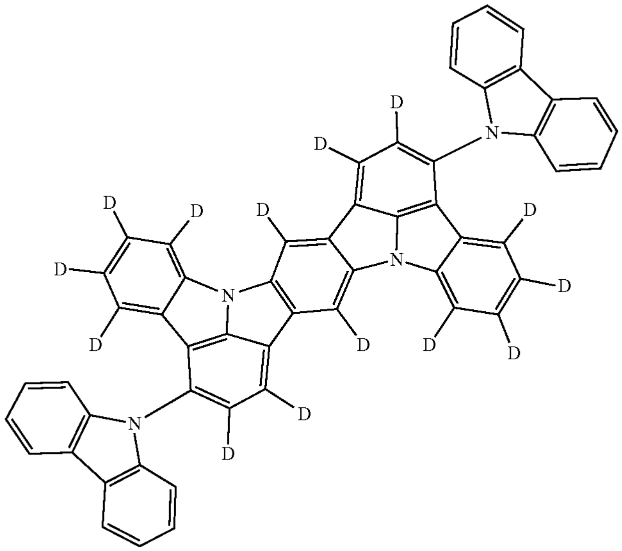
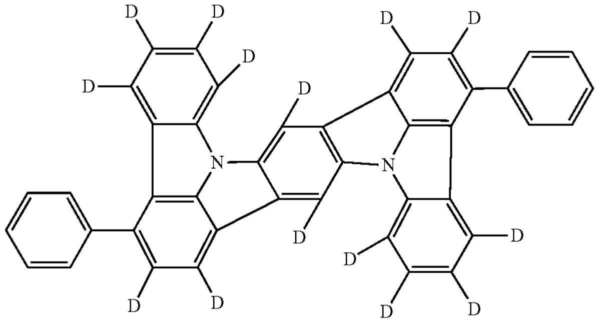
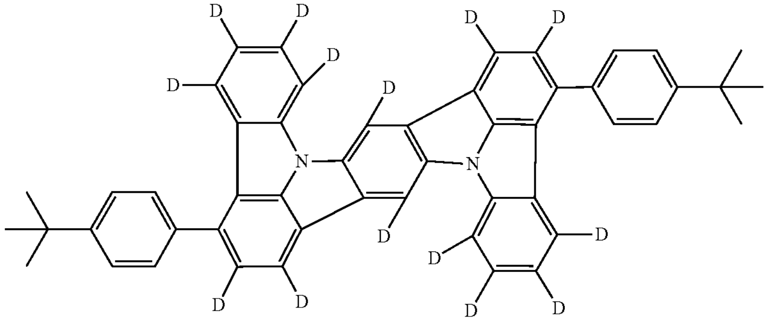
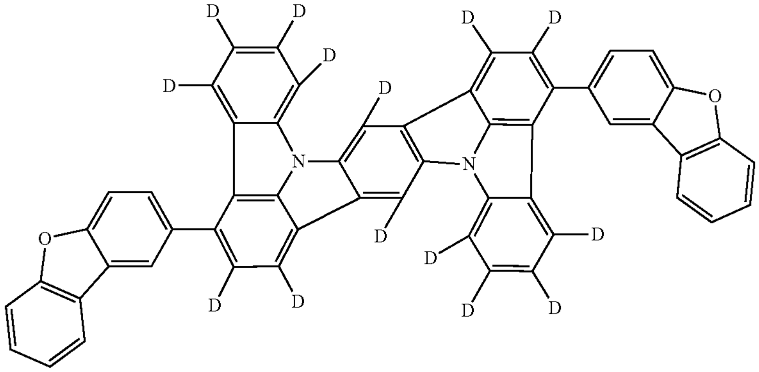

-continued
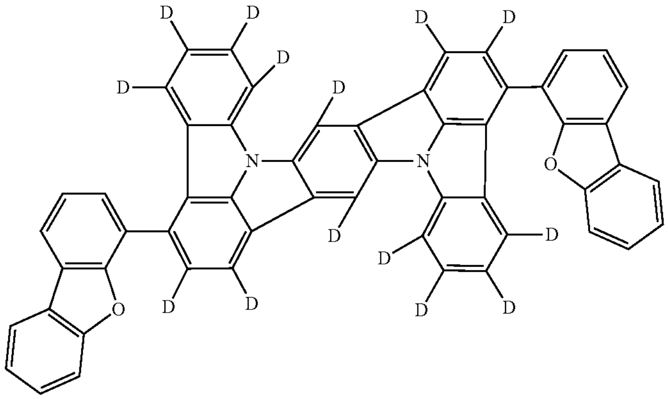
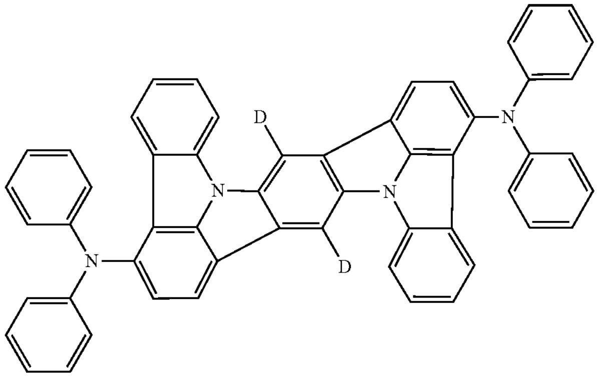
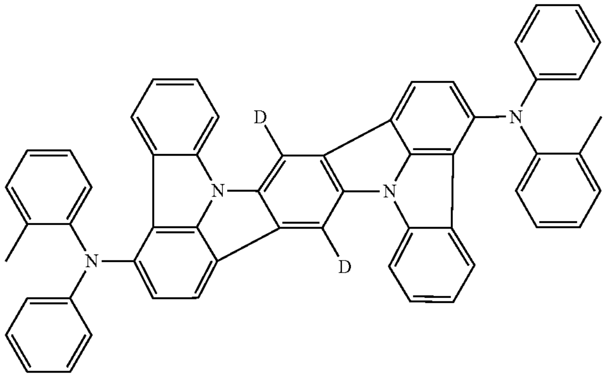
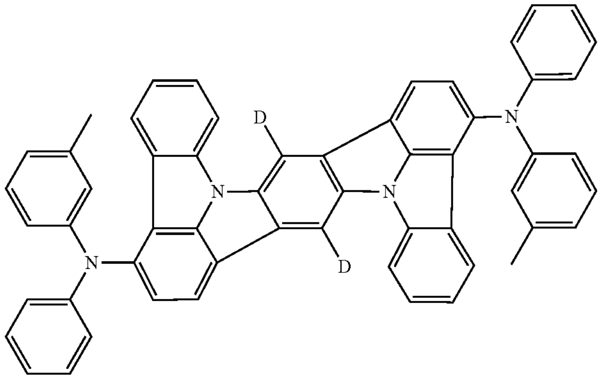

-continued
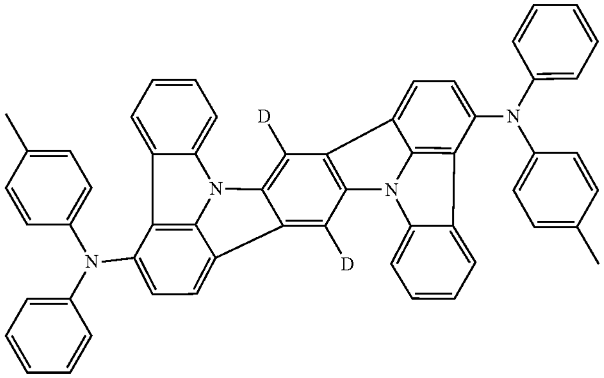
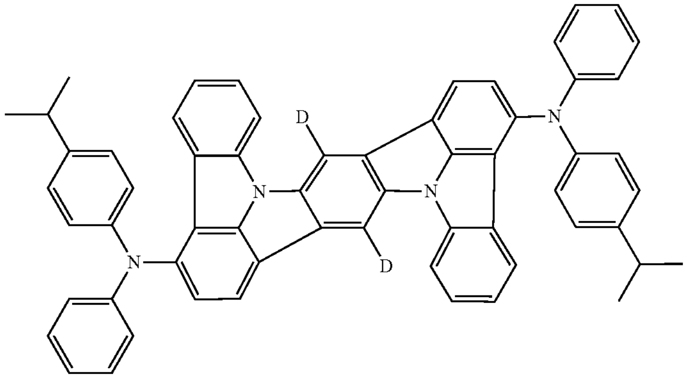
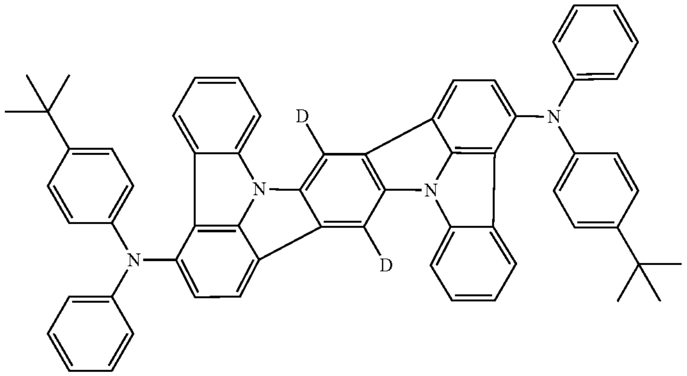
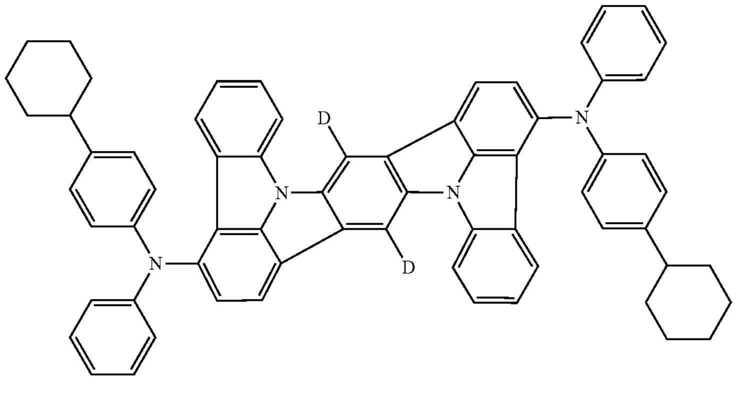

-continued
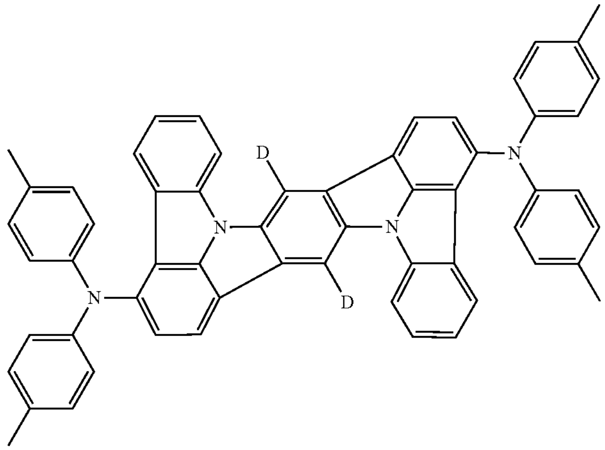
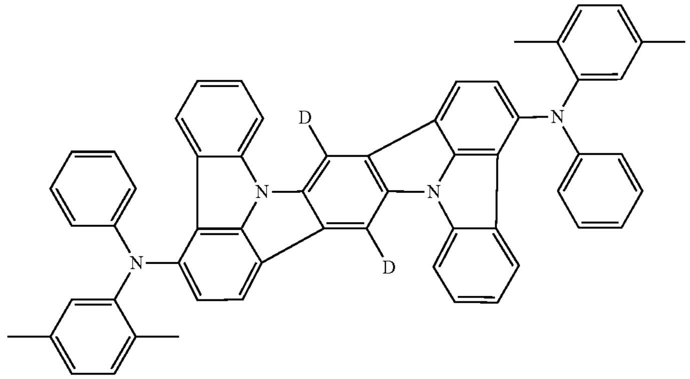
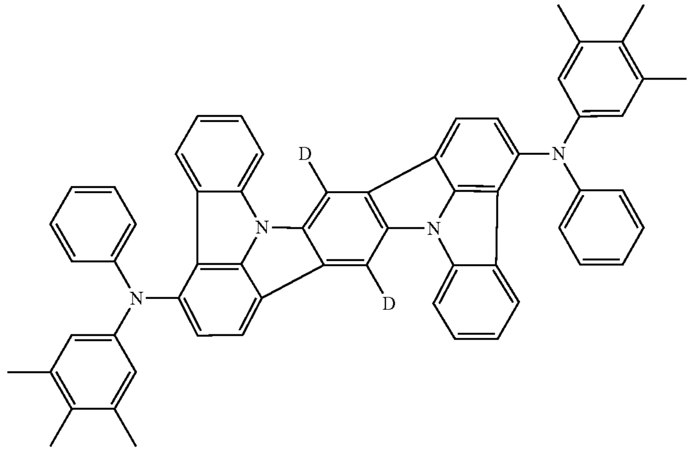
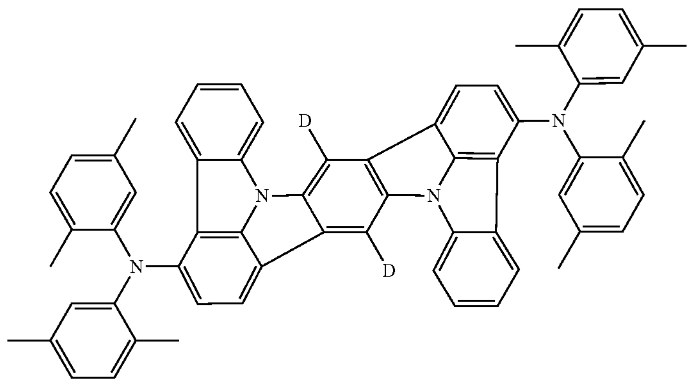

-continued
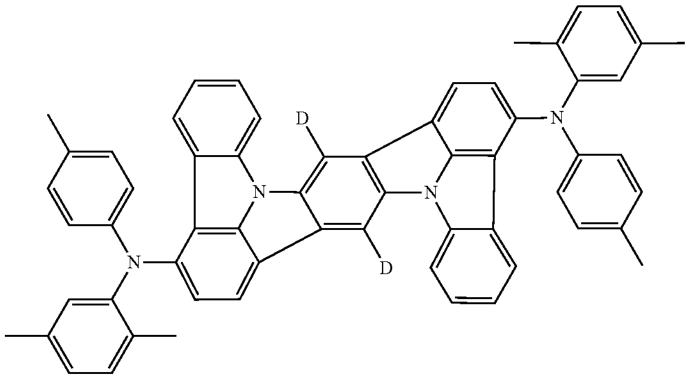
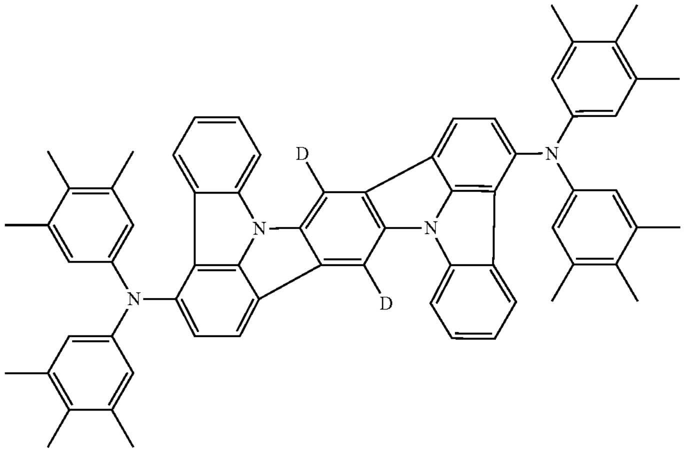
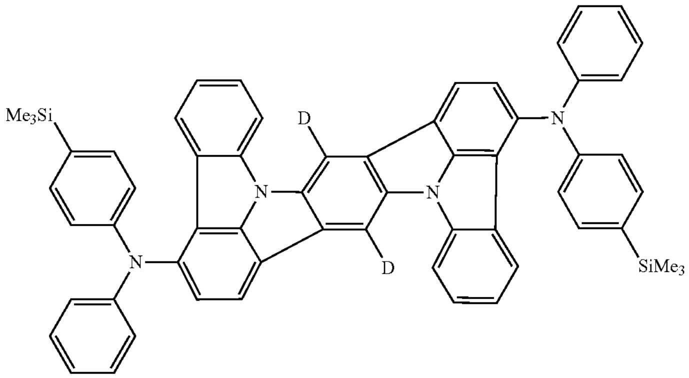
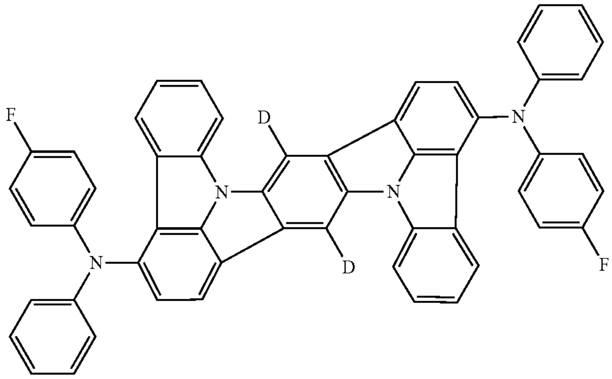

-continued
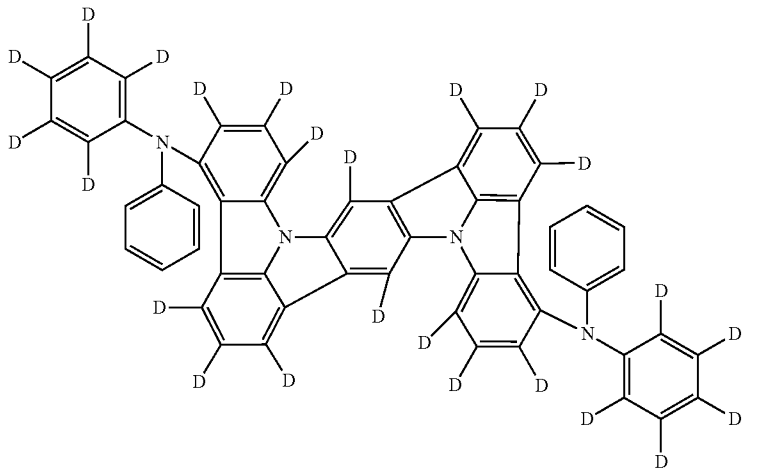
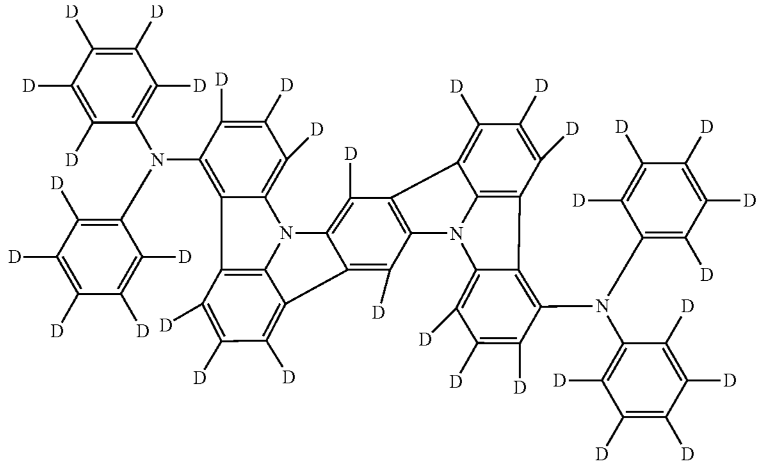
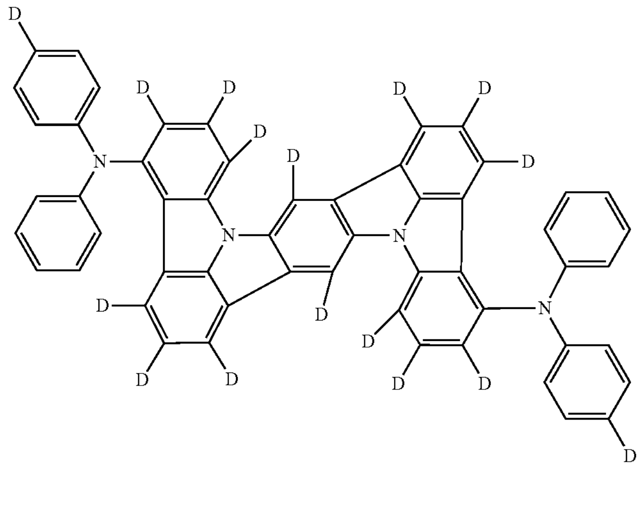

-continued
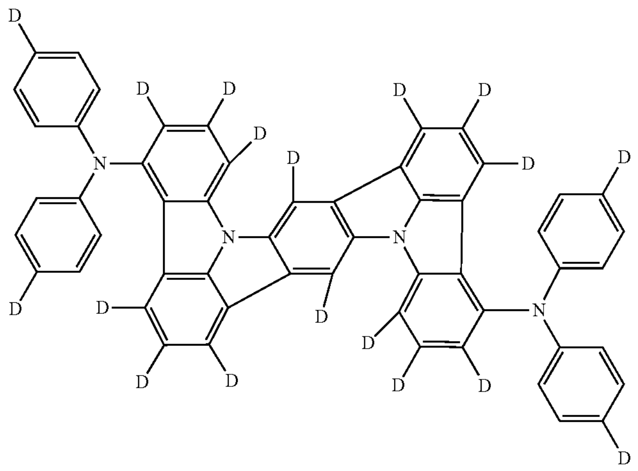
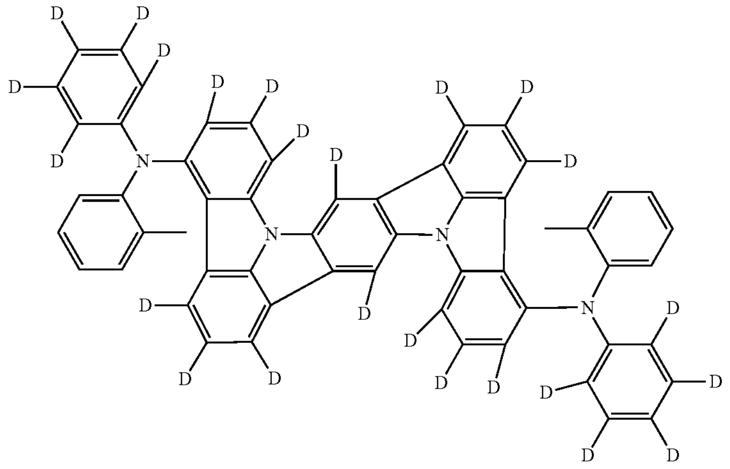
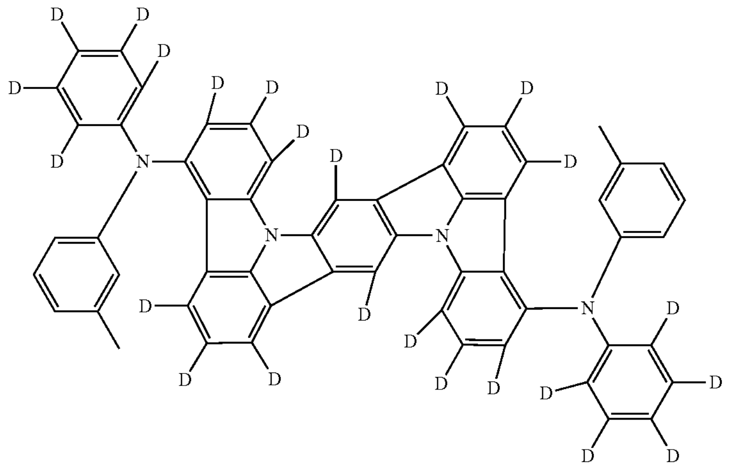

-continued
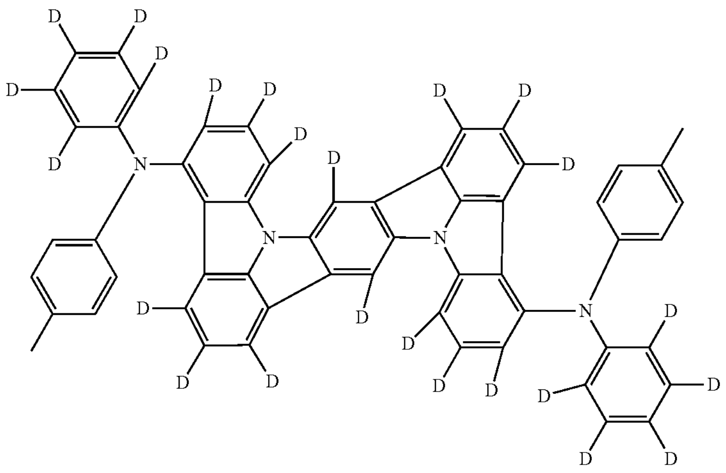
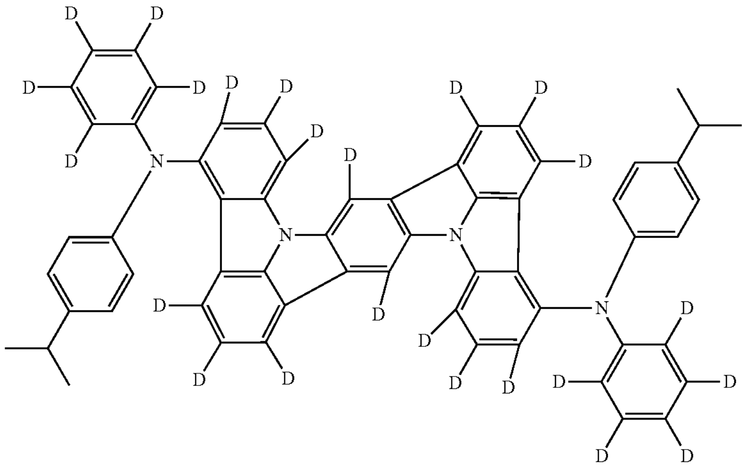
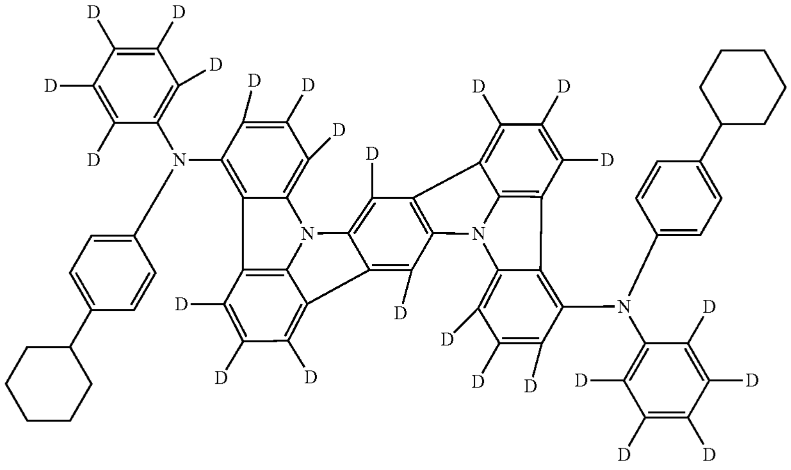

-continued
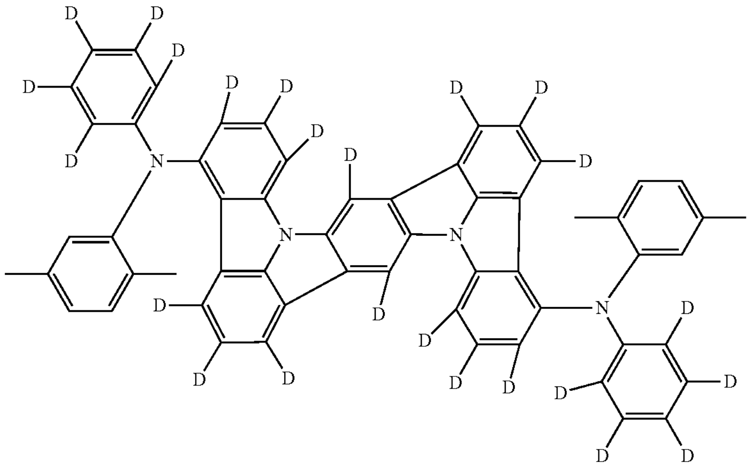
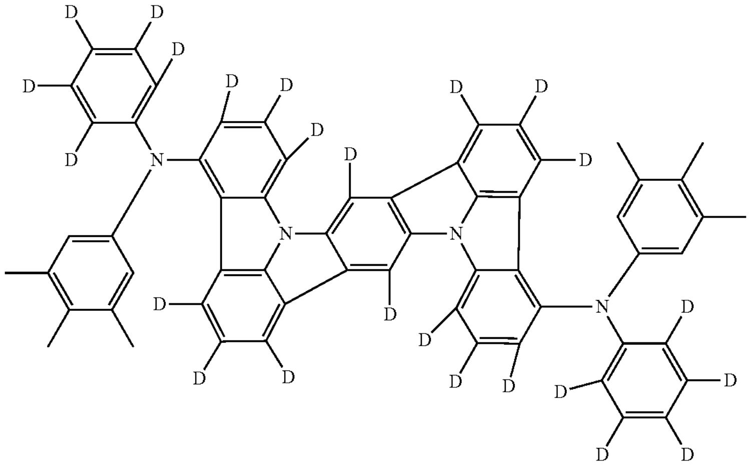
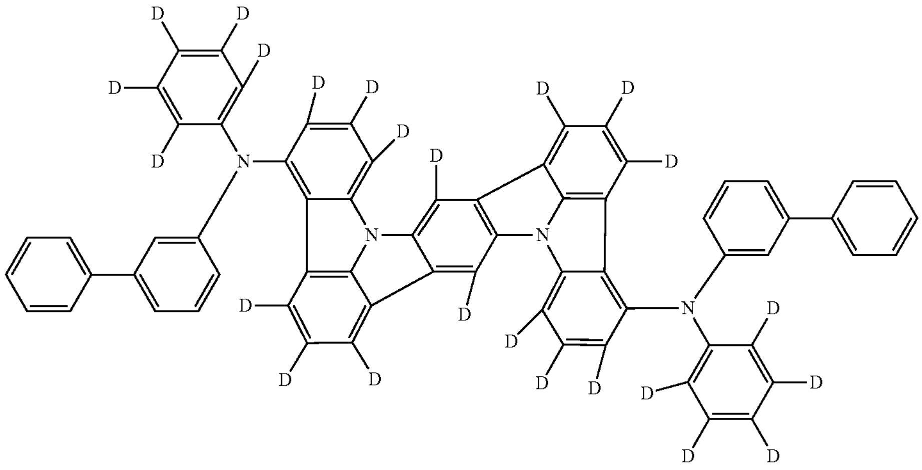

-continued
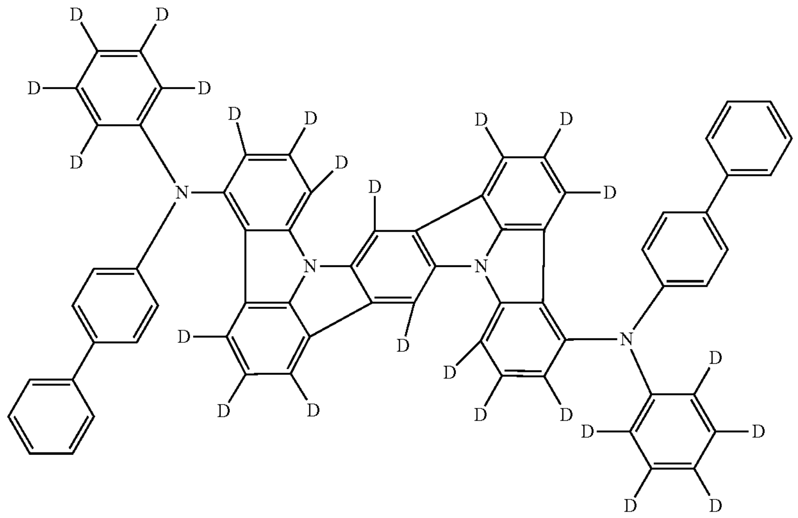
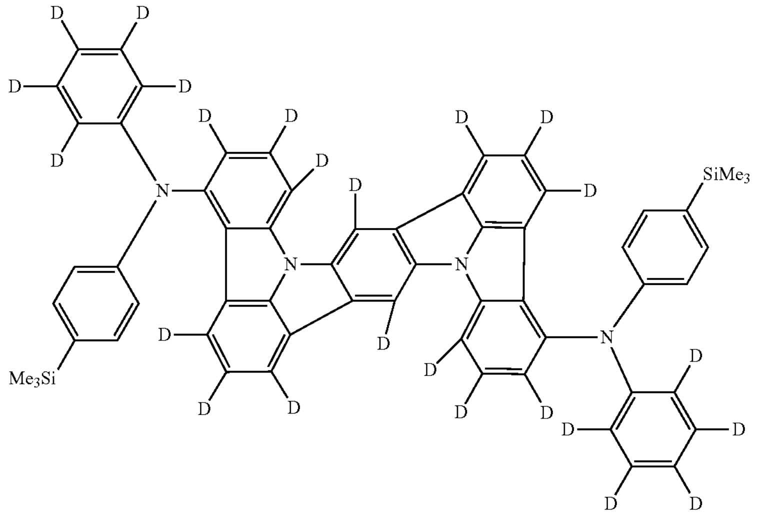
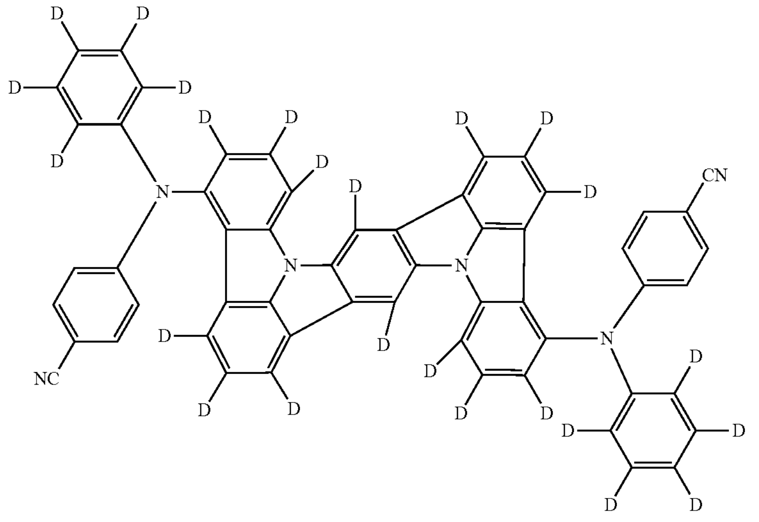

-continued
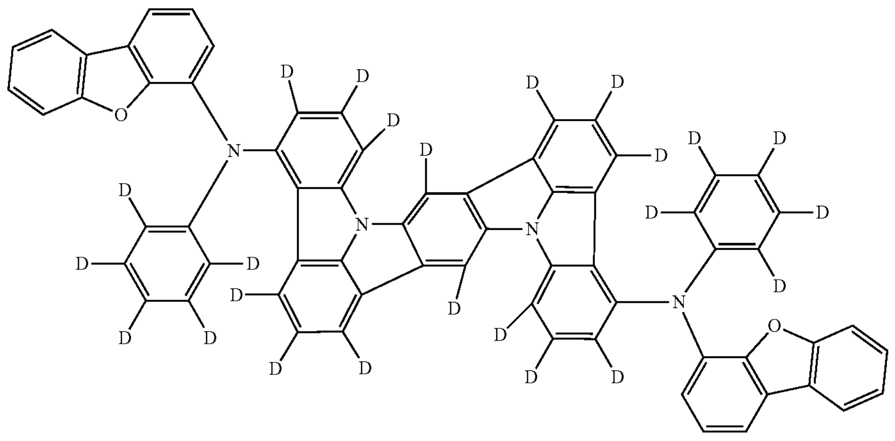
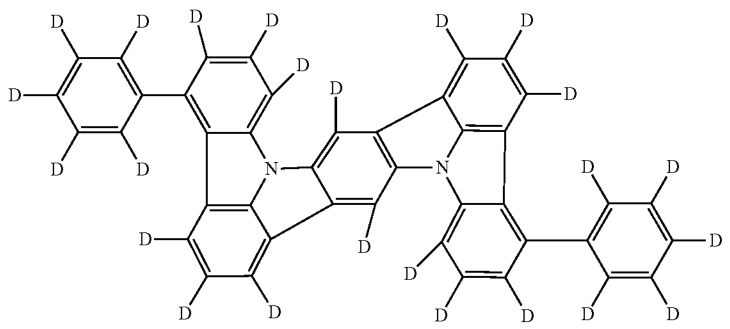
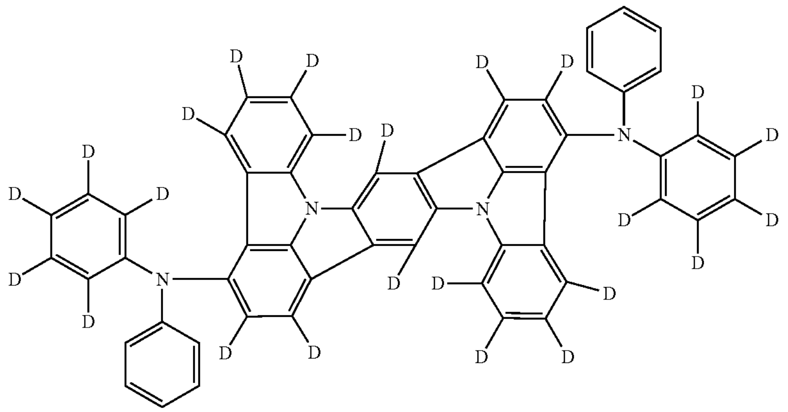

-continued
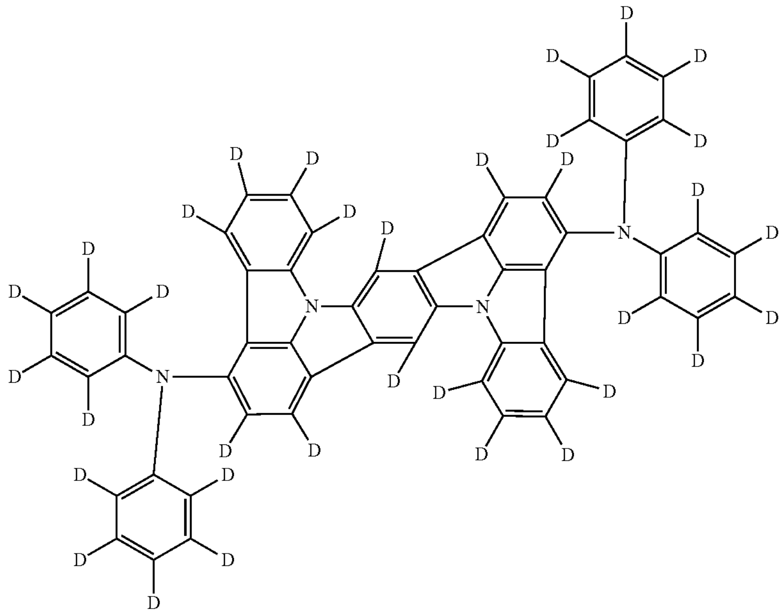
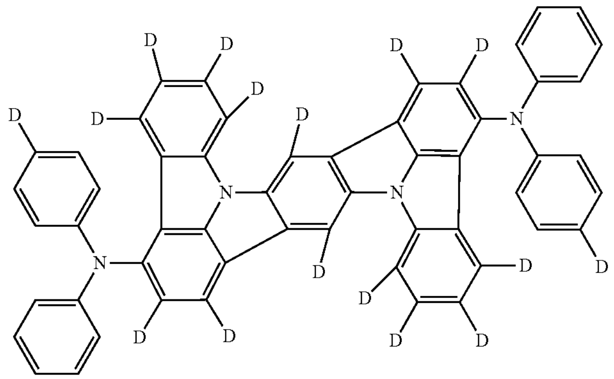
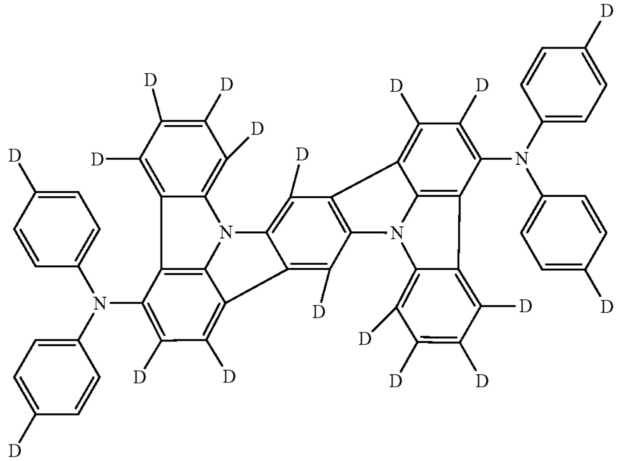

-continued
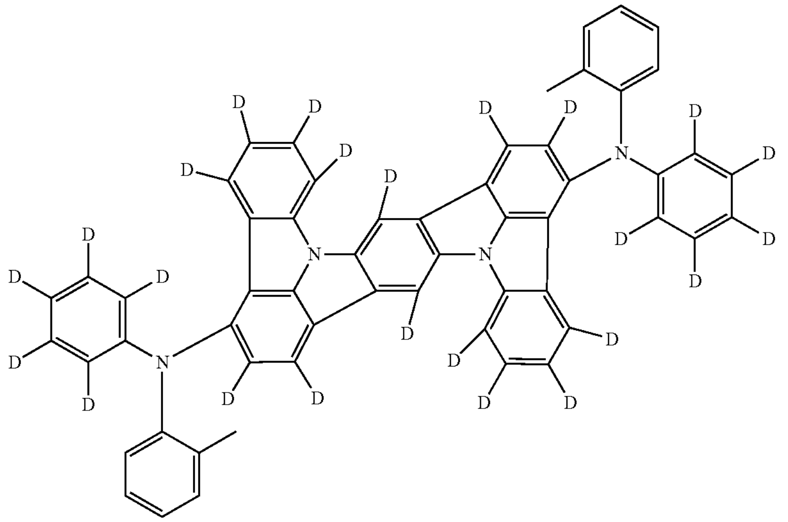
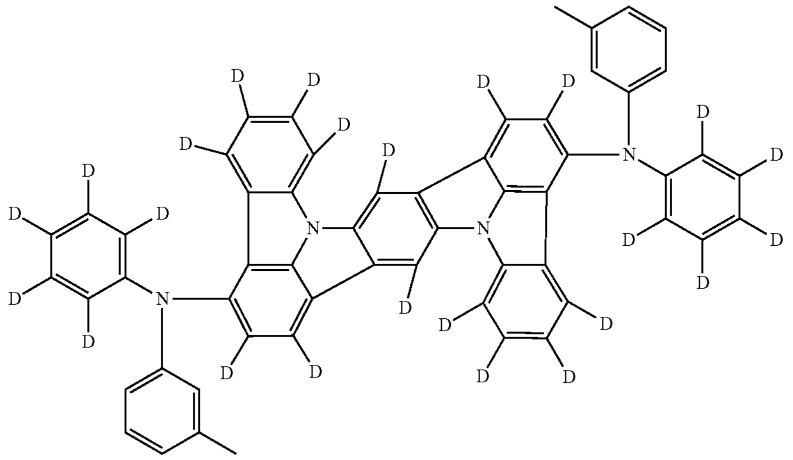
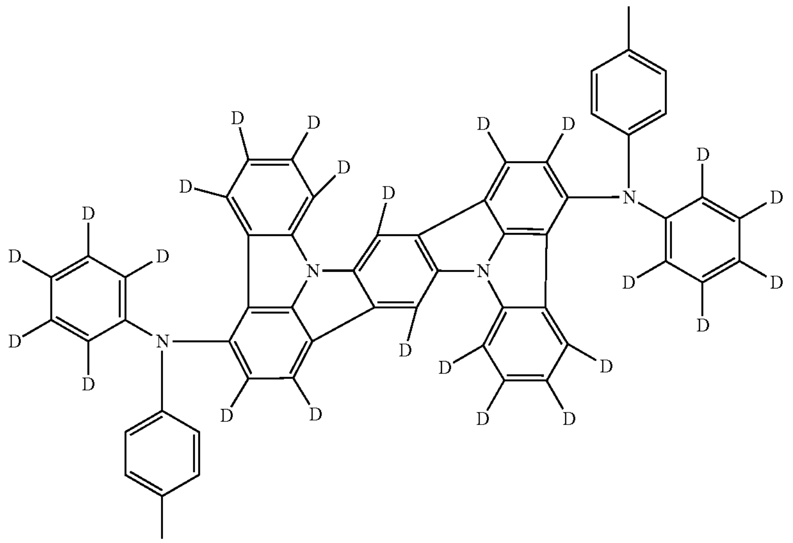

-continued
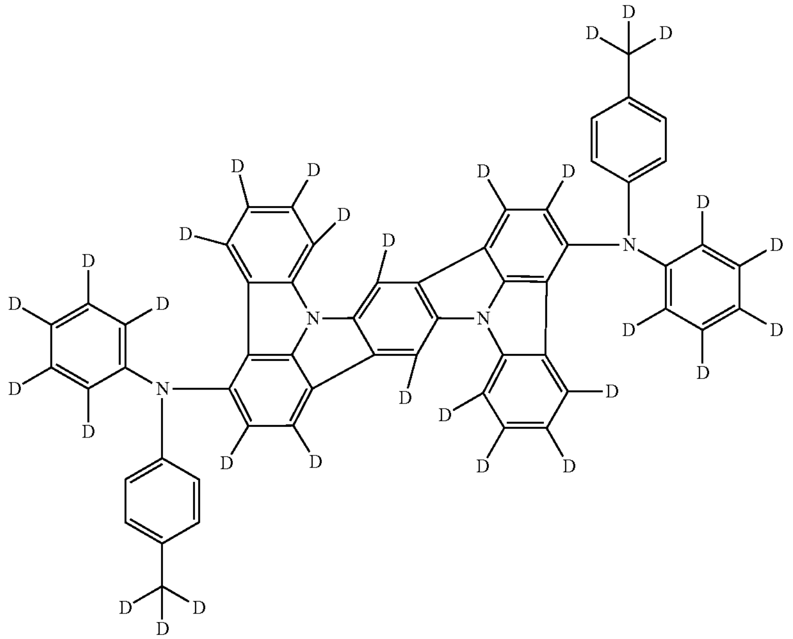
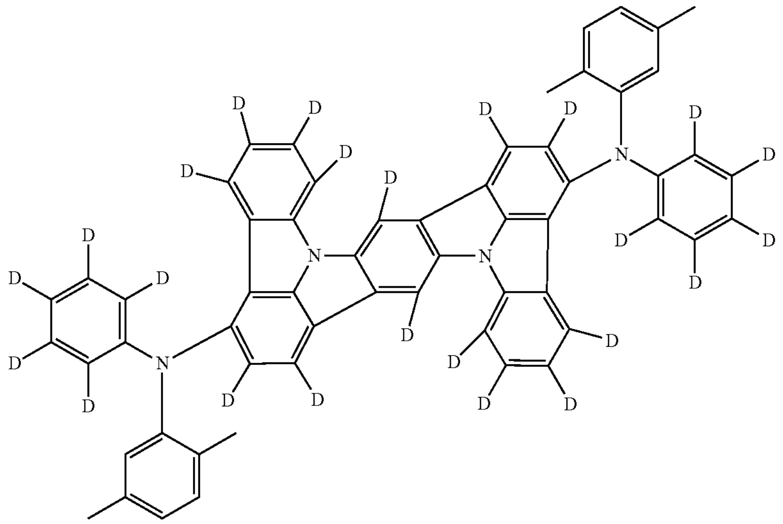
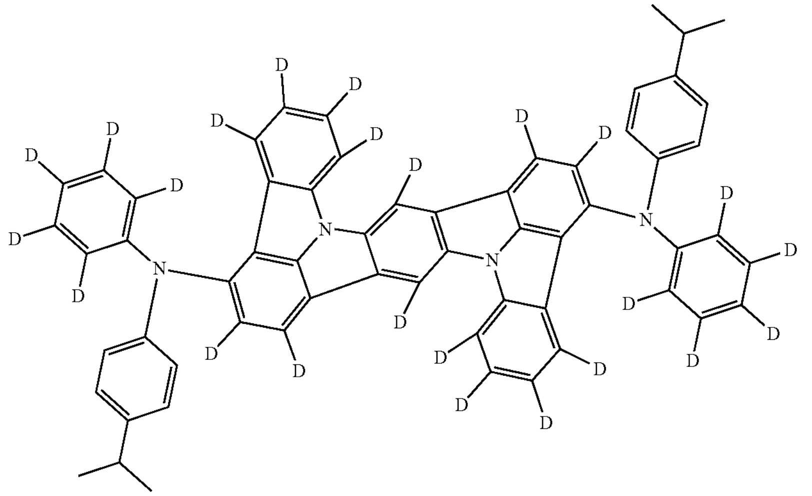

-continued
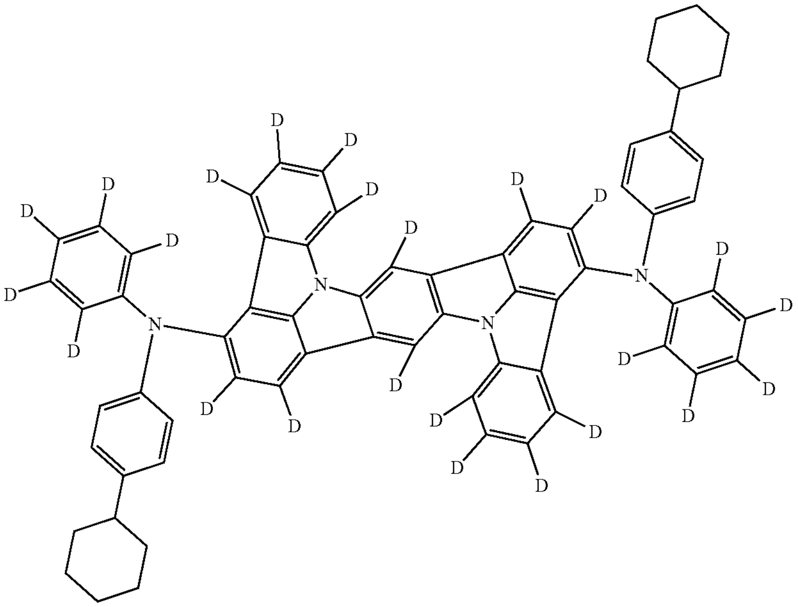
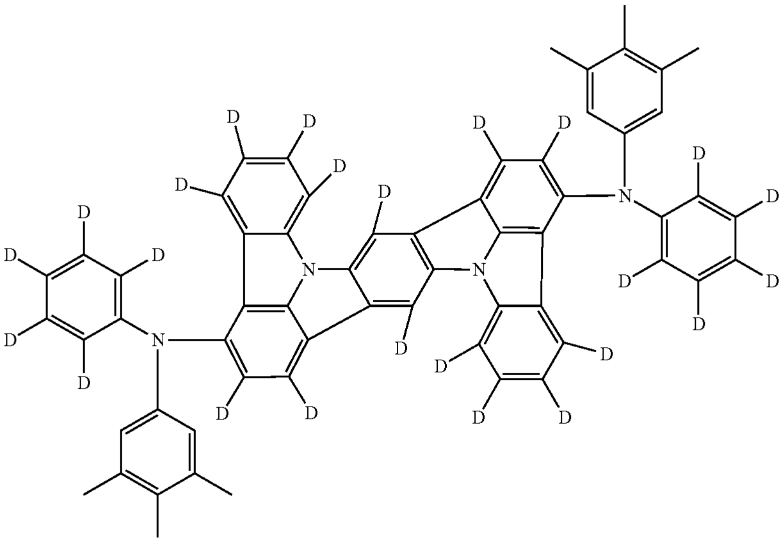

-continued
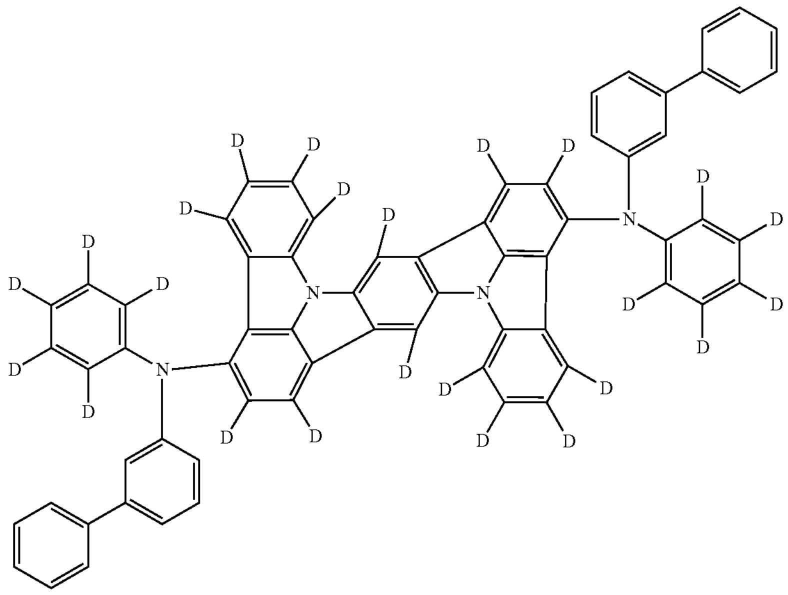
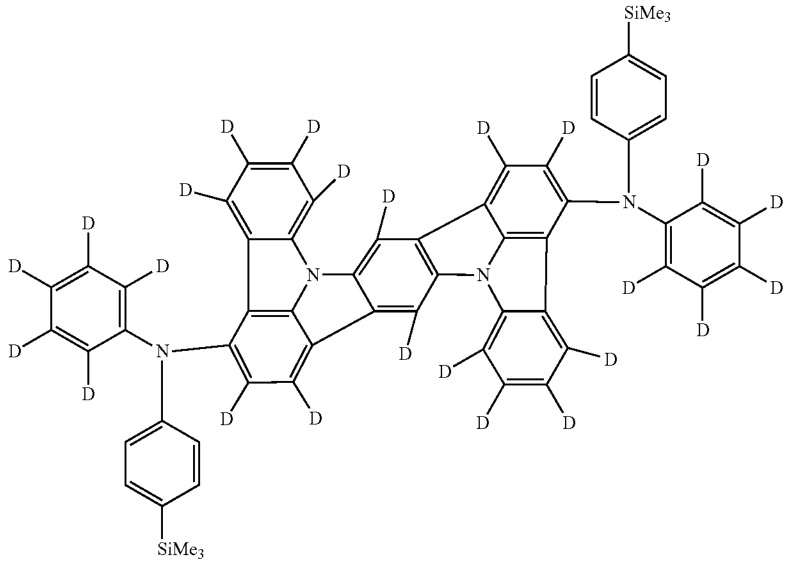
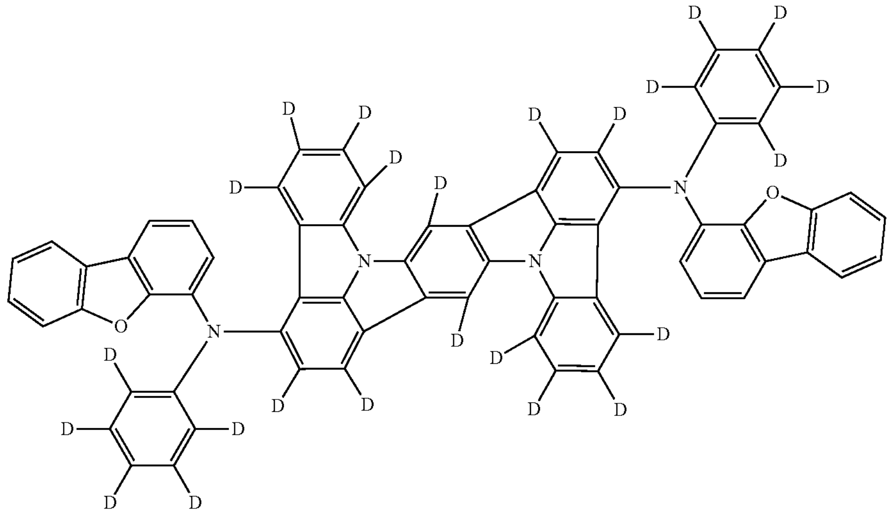

-continued
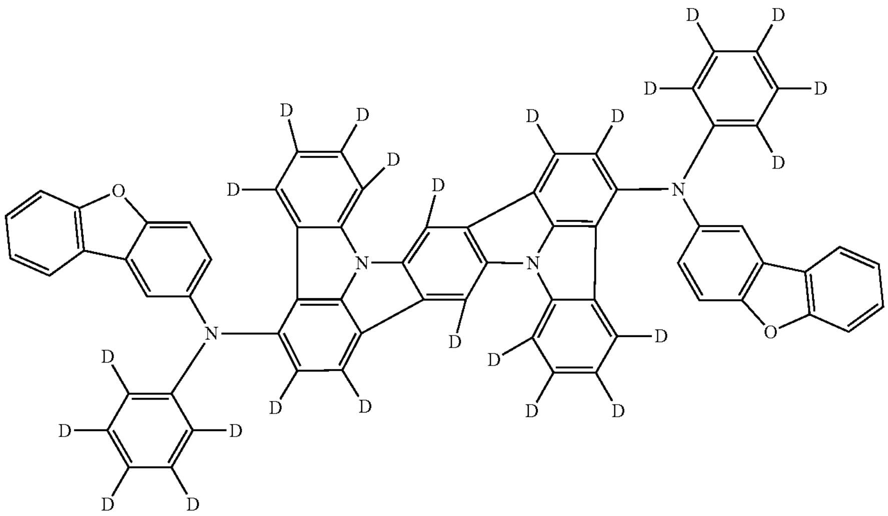
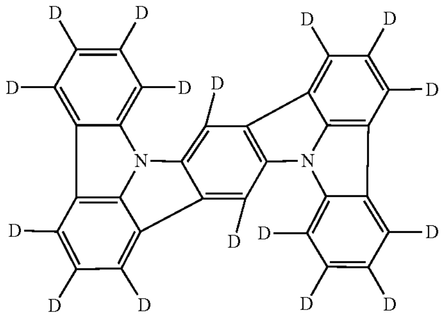
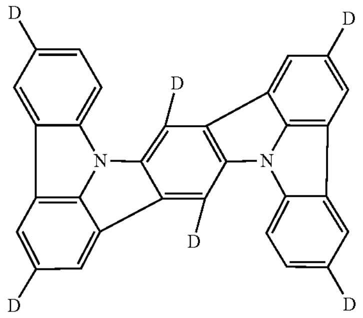
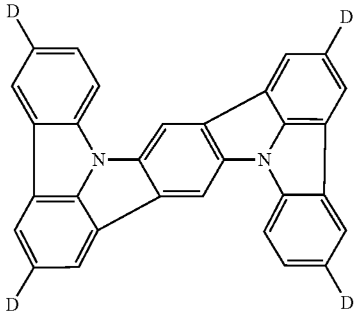
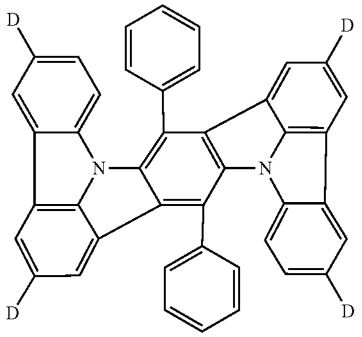
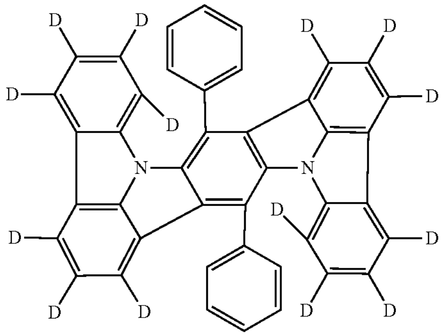
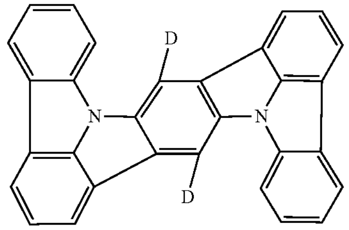

-continued
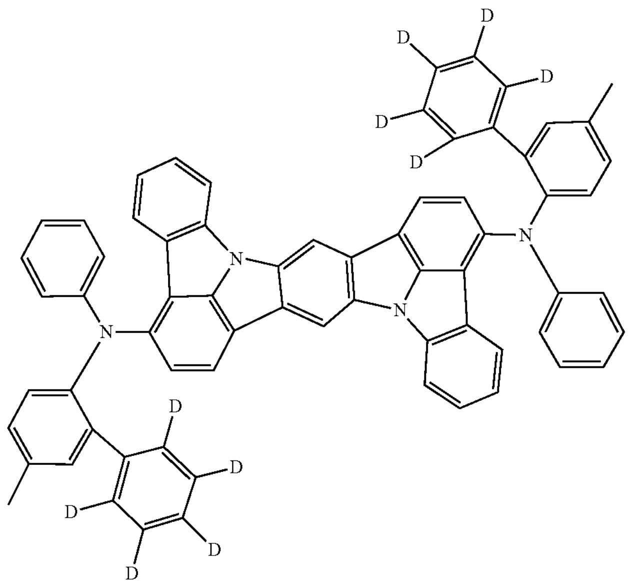
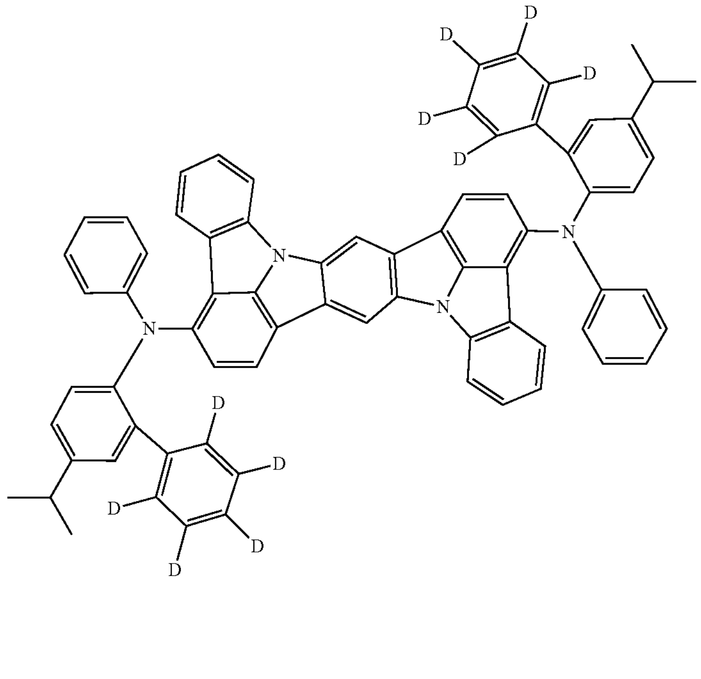

-continued
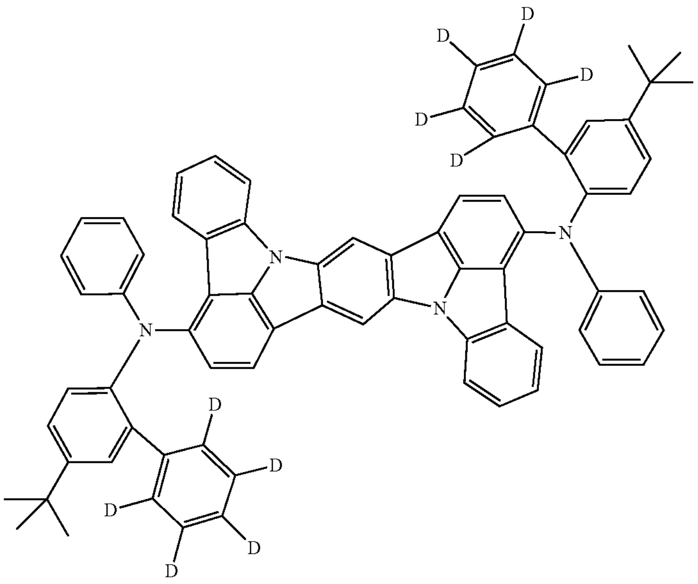
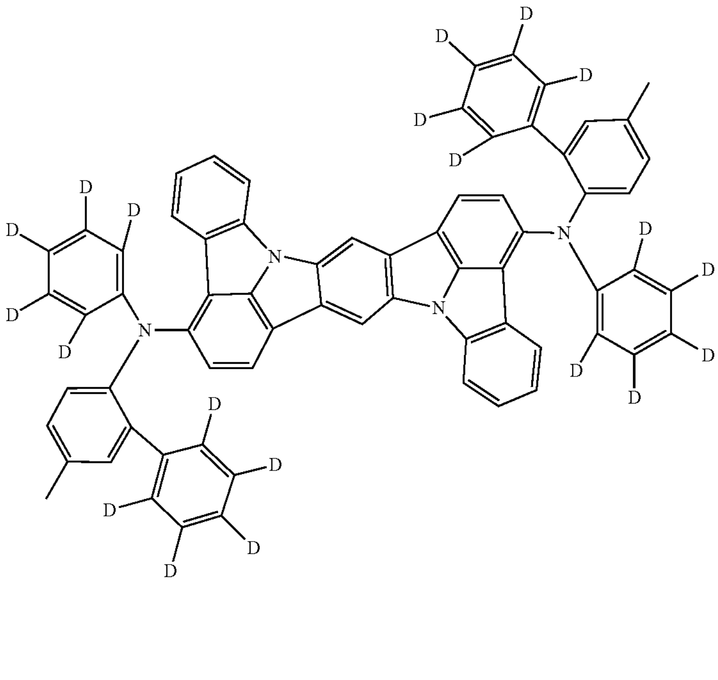

-continued
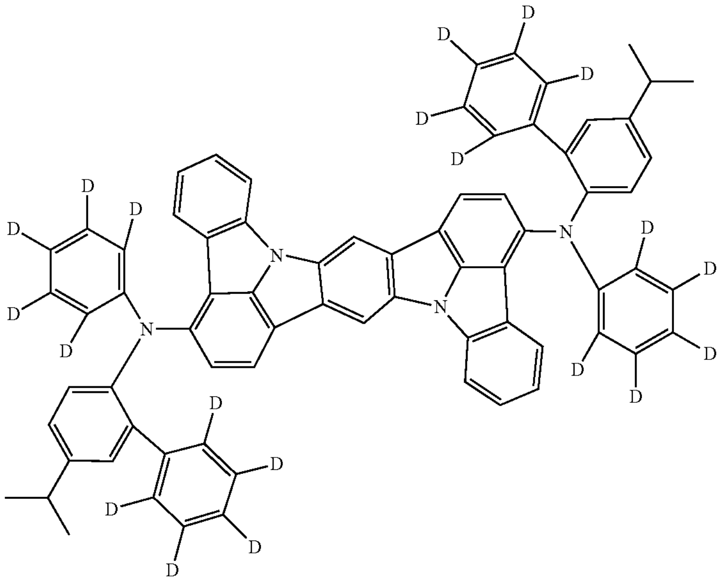
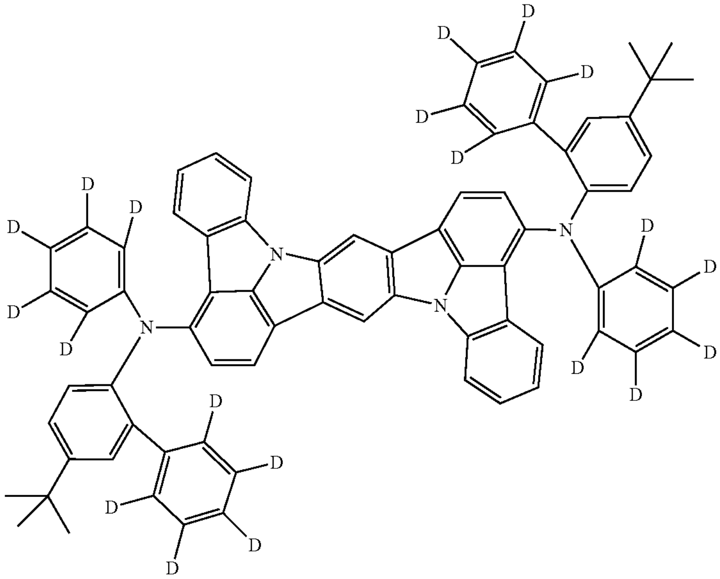
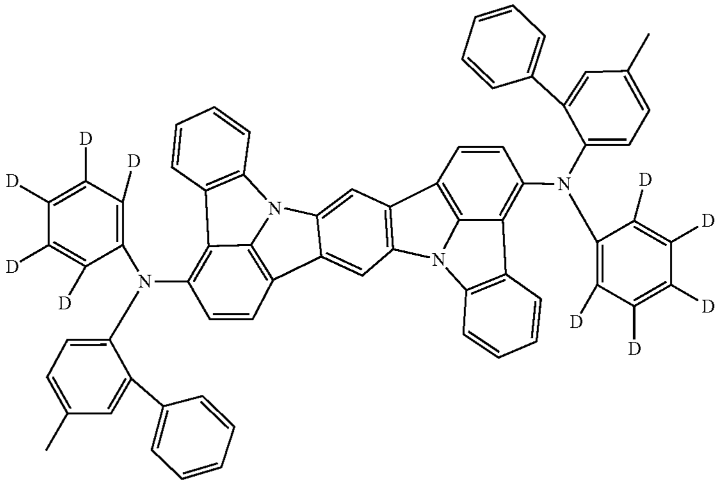

-continued
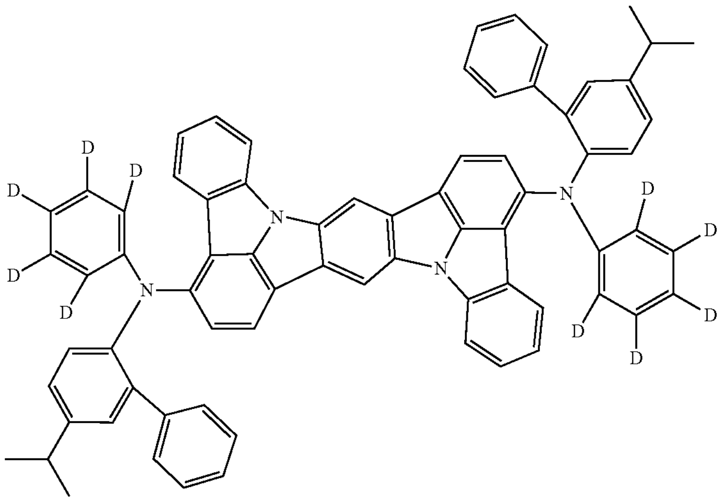
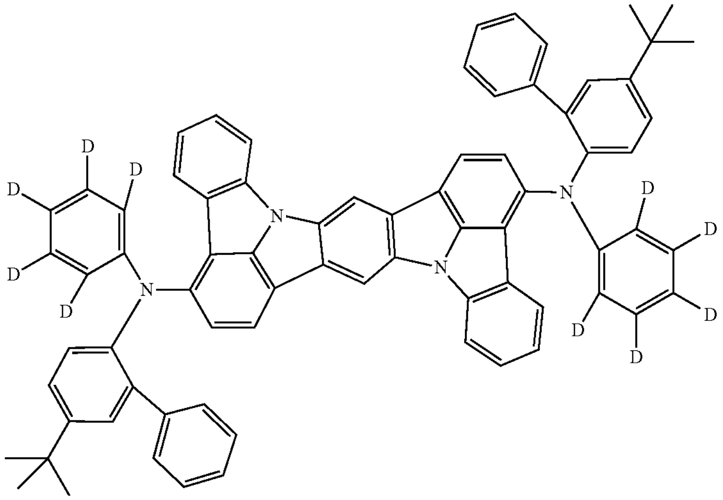
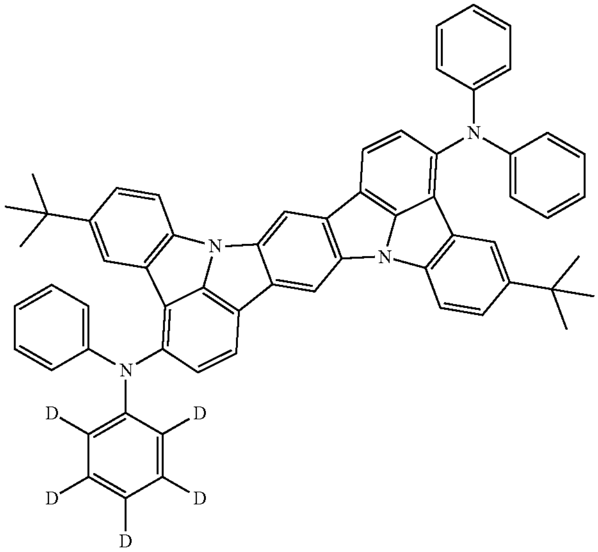

-continued
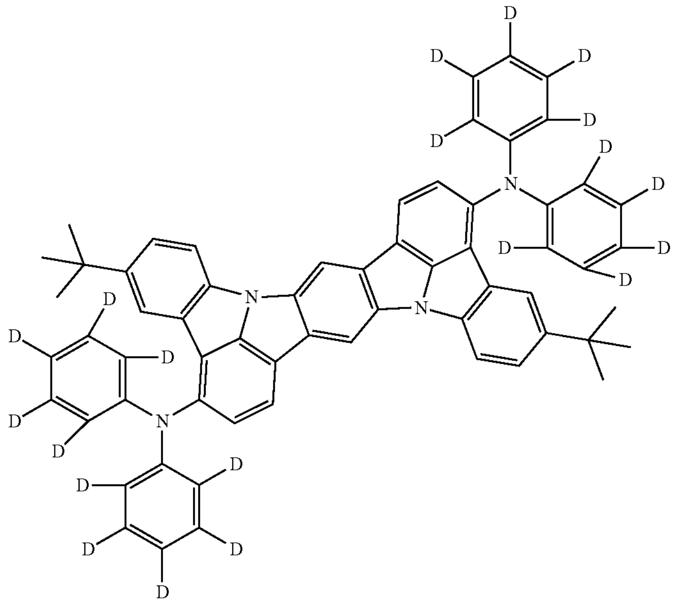
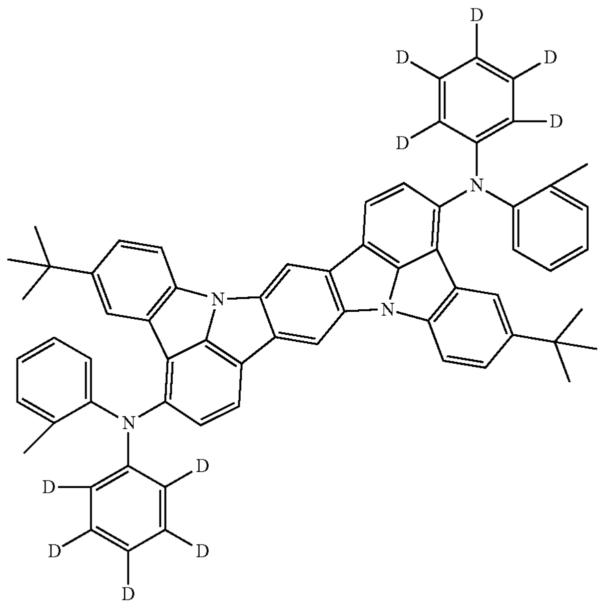

-continued
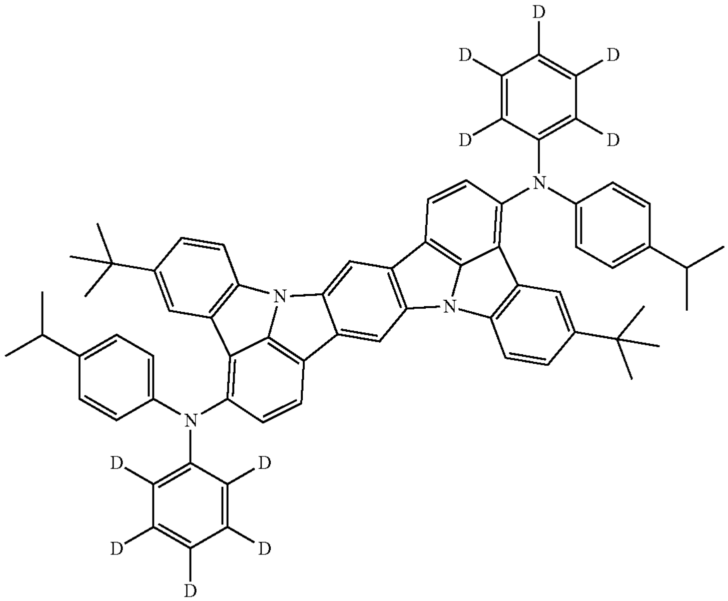
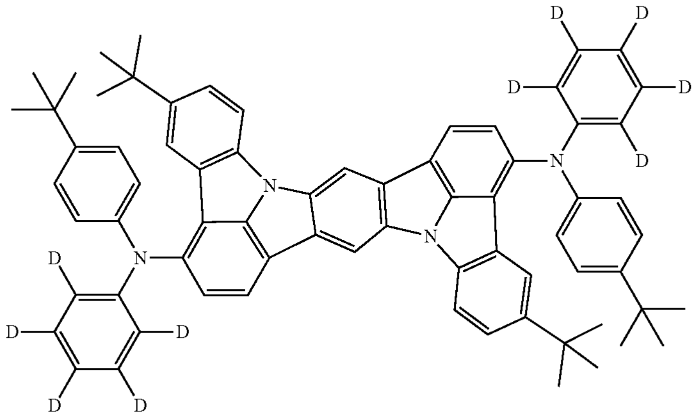
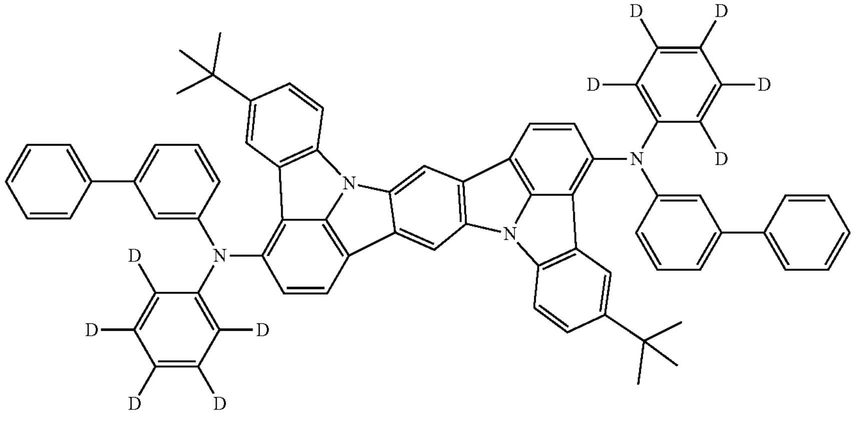

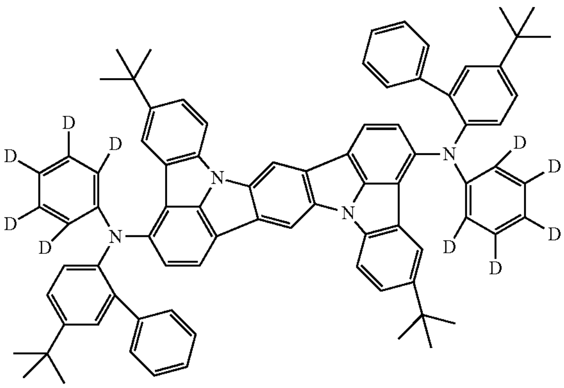
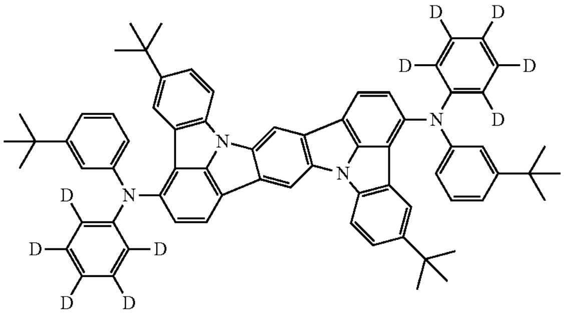
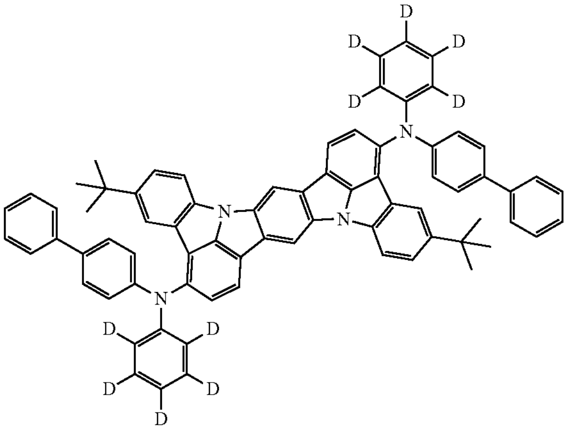
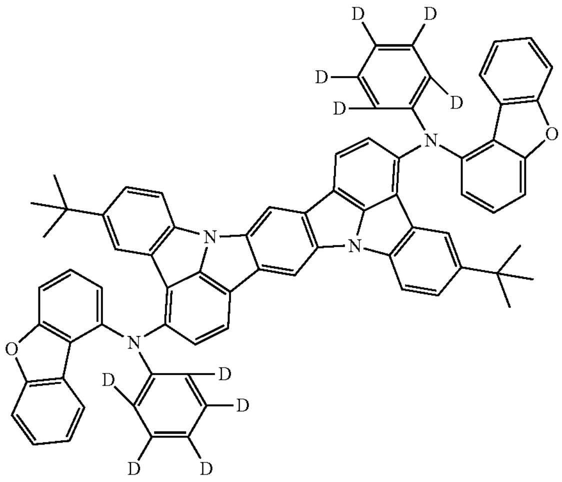
-continued
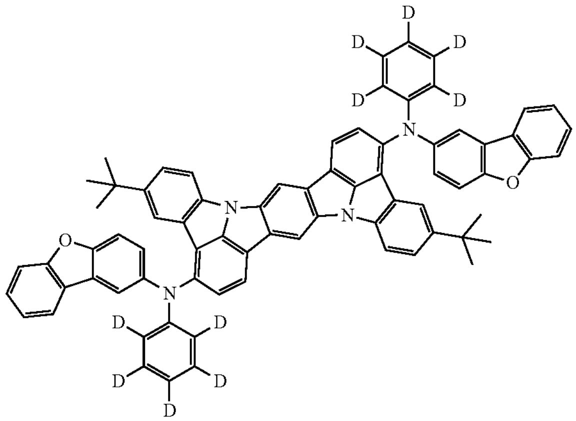
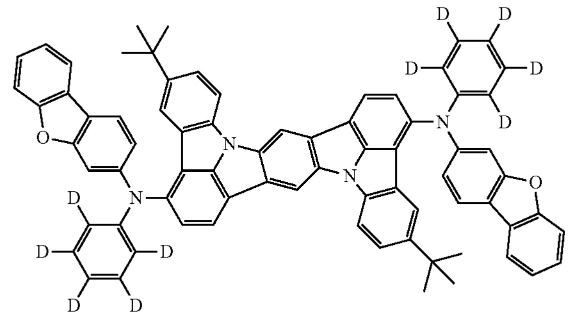
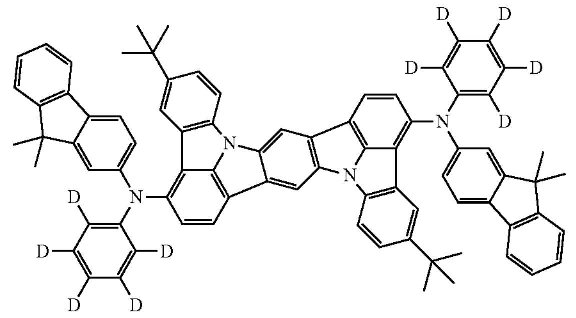
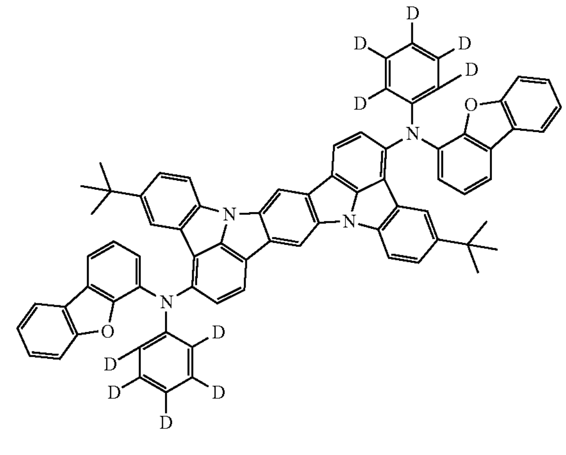

-continued
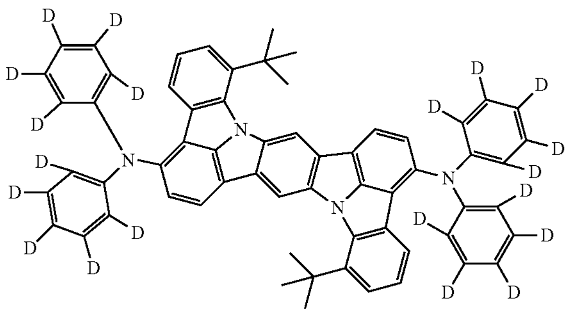
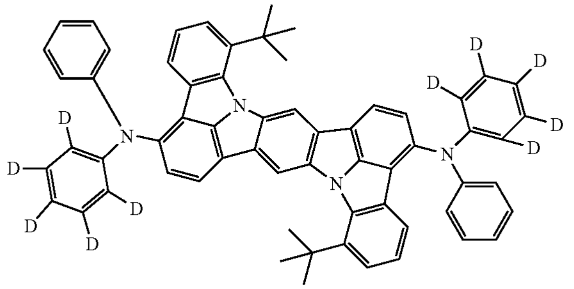
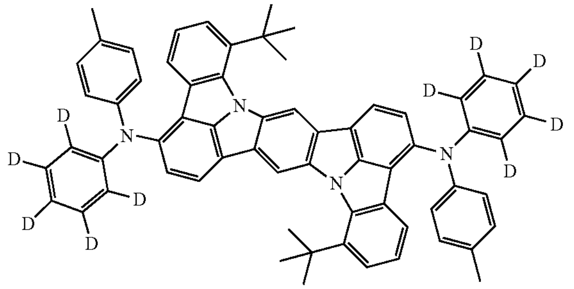
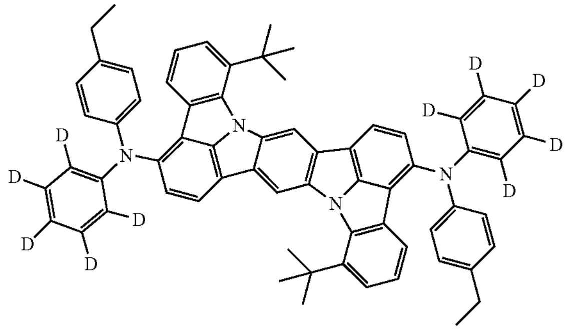
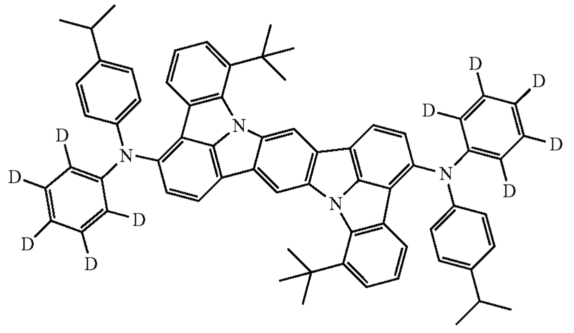
-continued
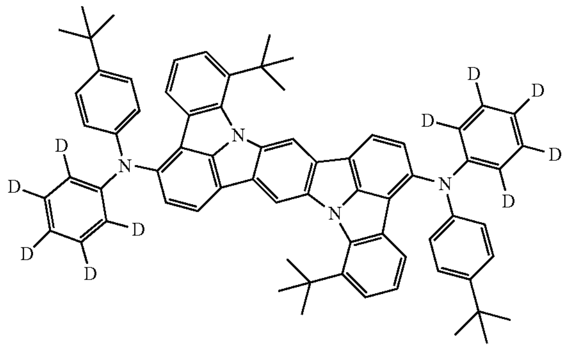
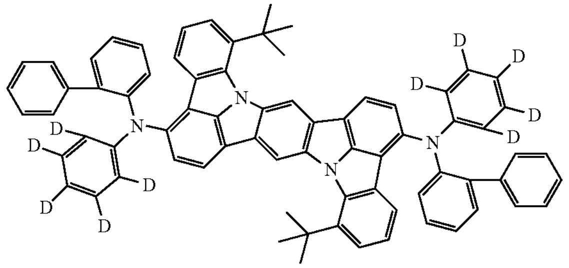
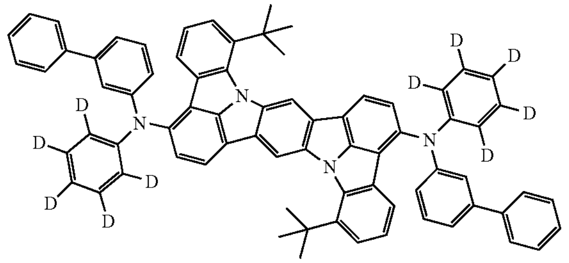
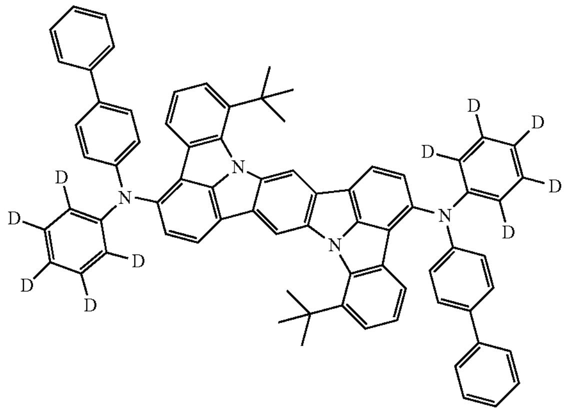
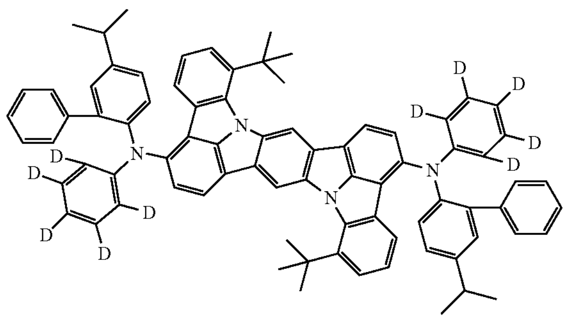

-continued
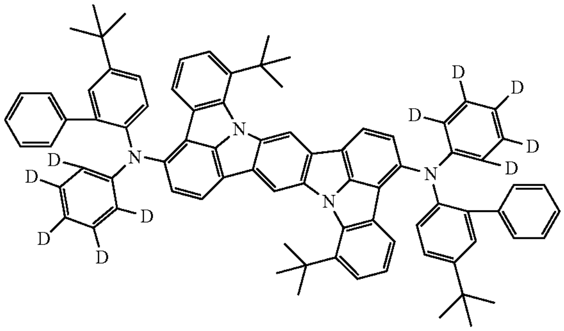
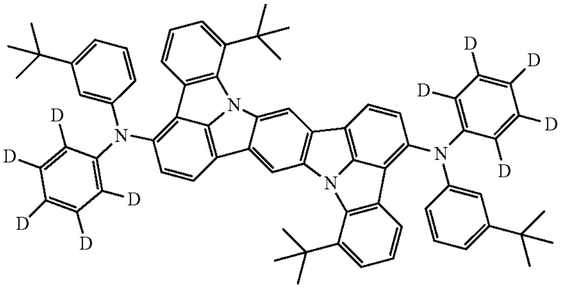
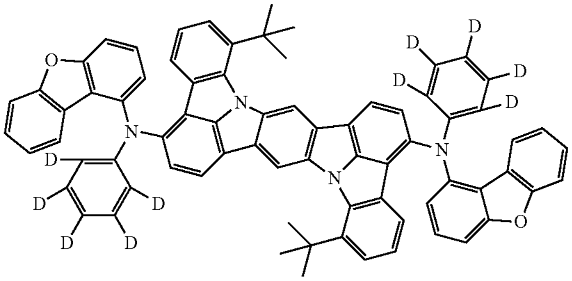
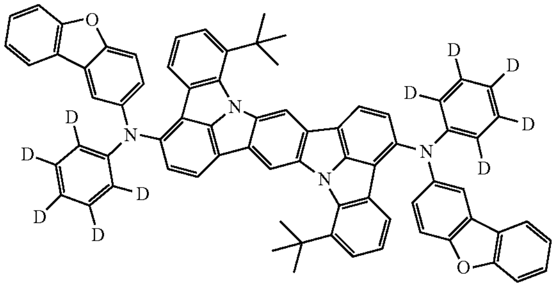
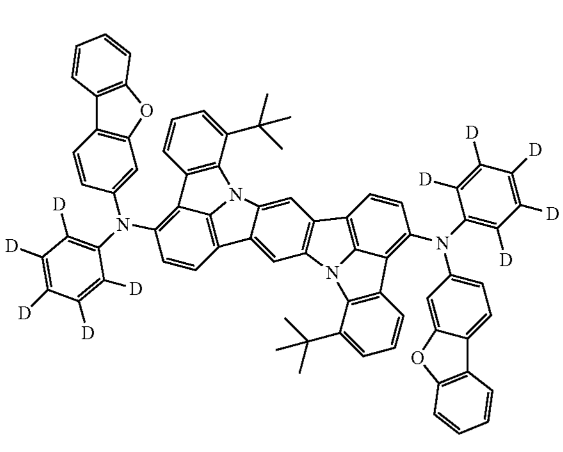
-continued
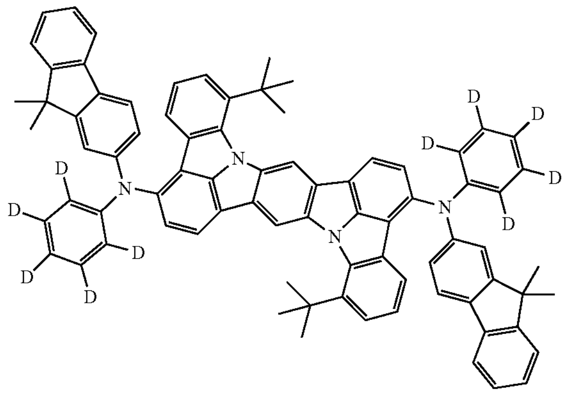
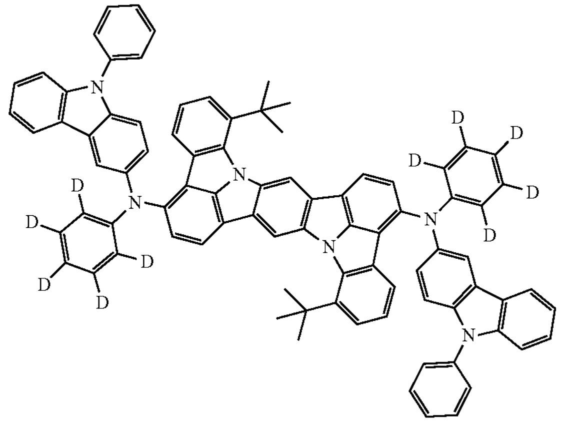
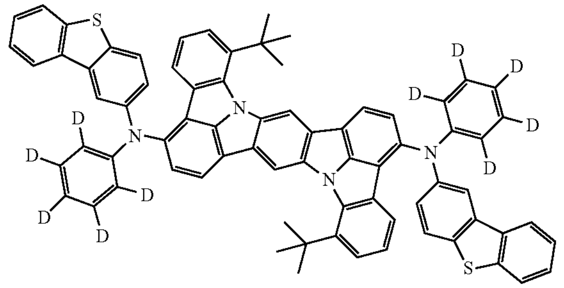
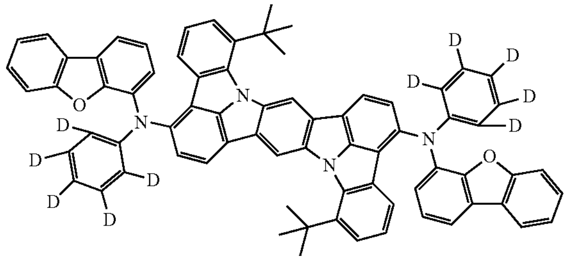
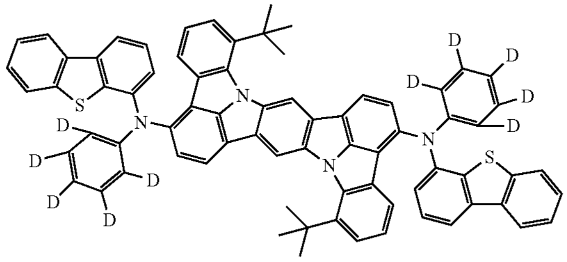

-continued
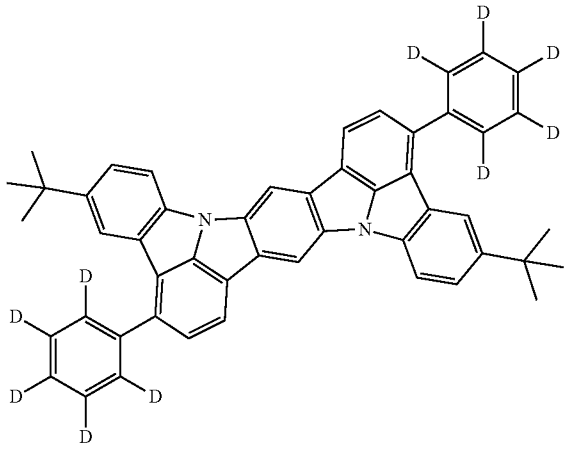
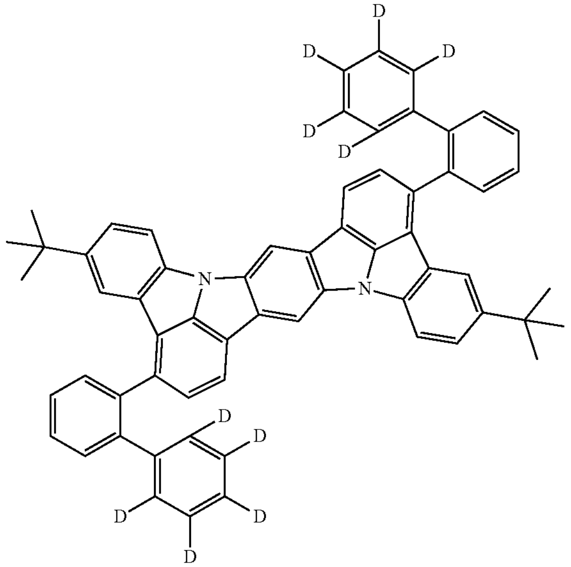
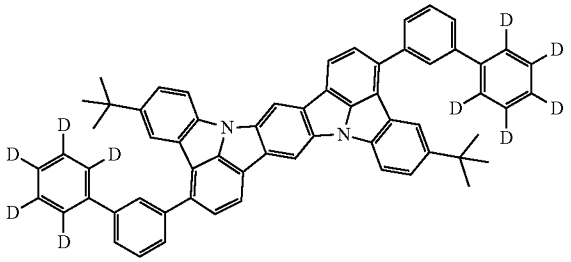
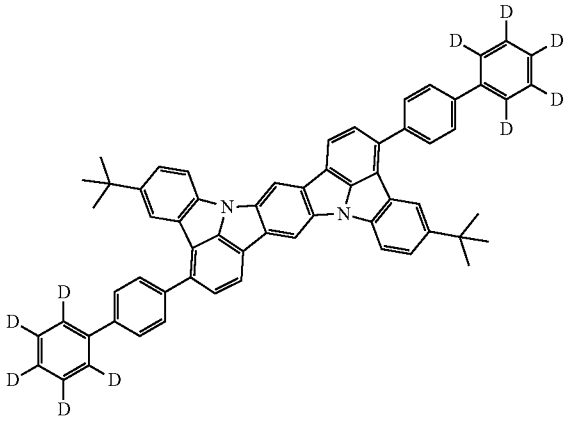
-continued
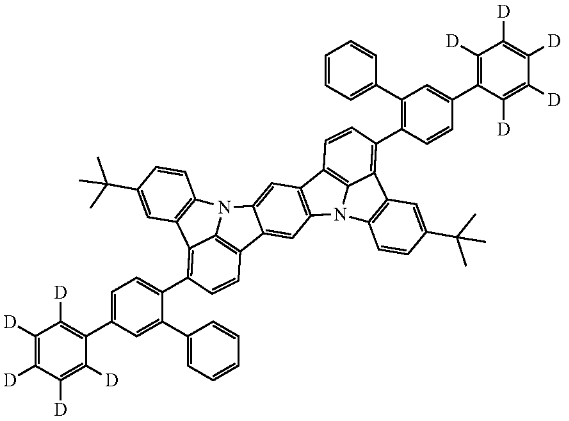
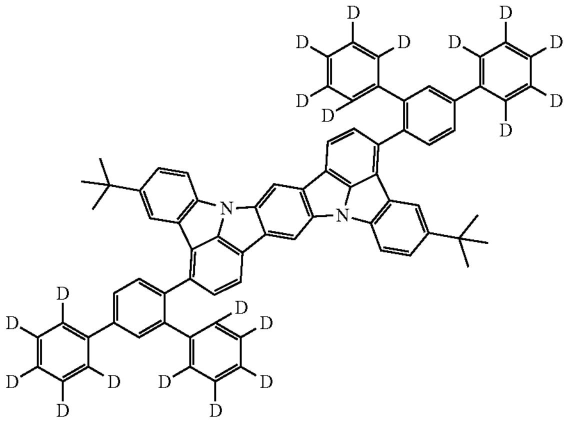
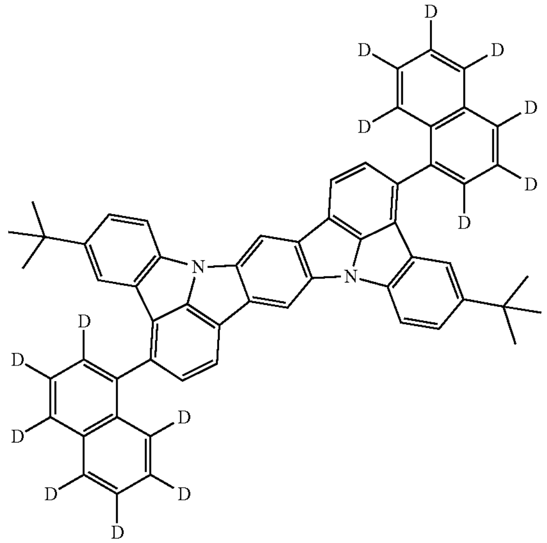

-continued
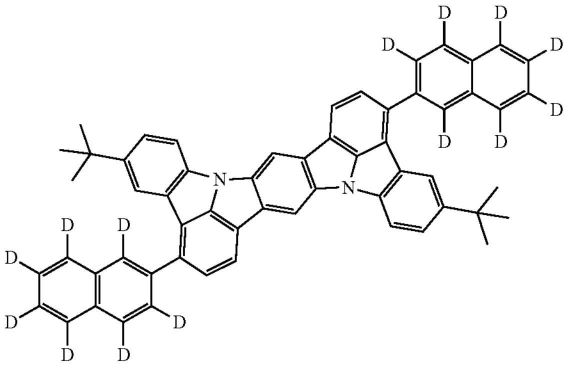
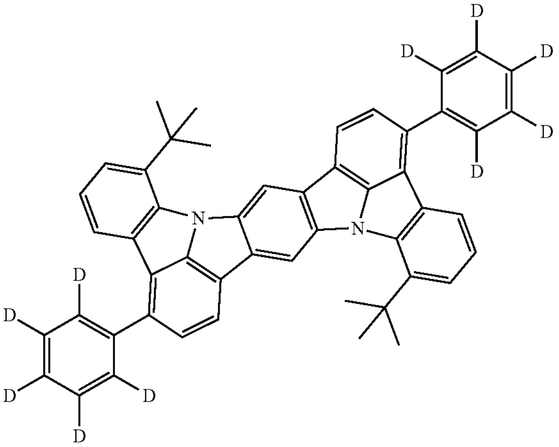
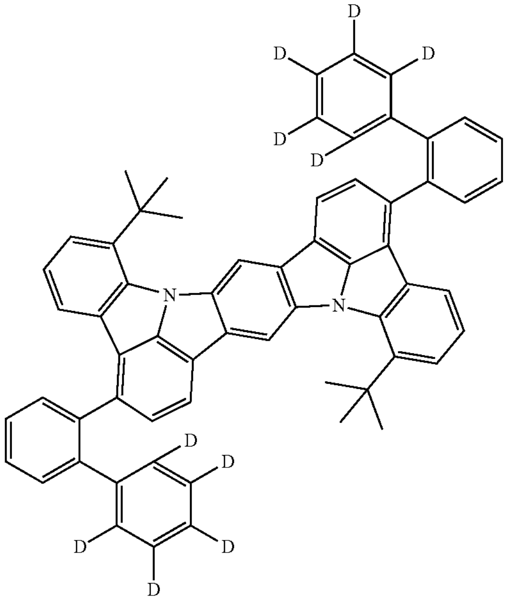
-continued
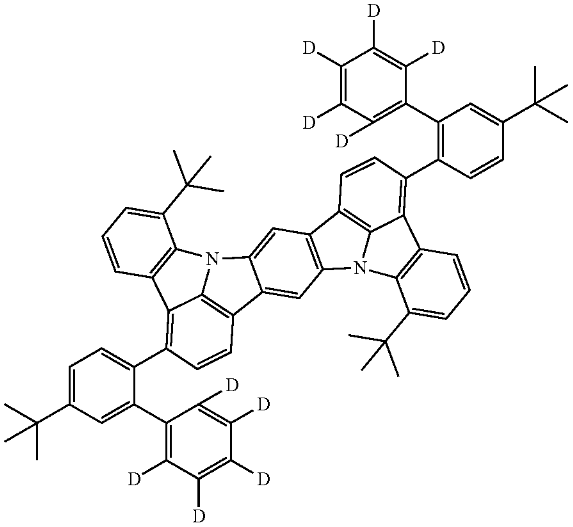
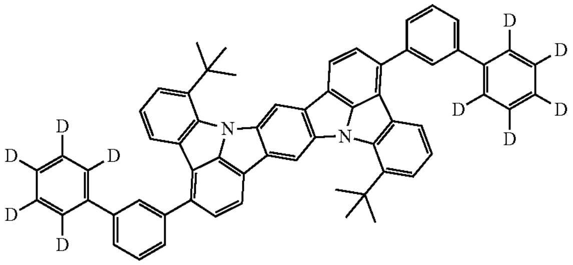
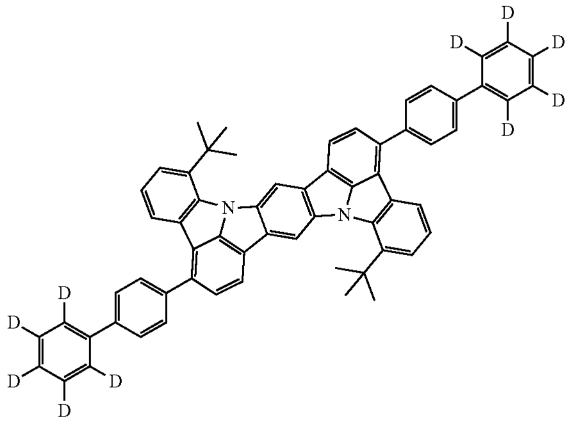
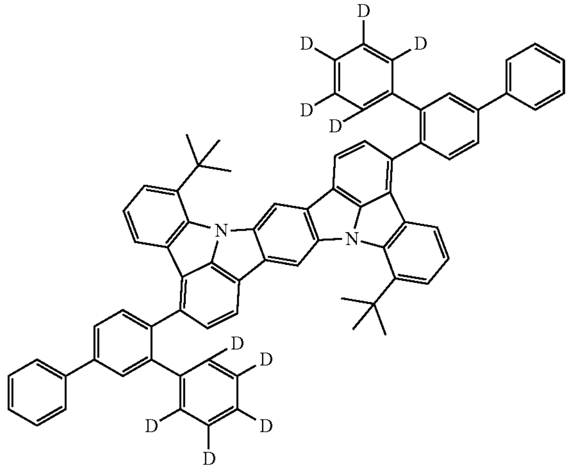

-continued
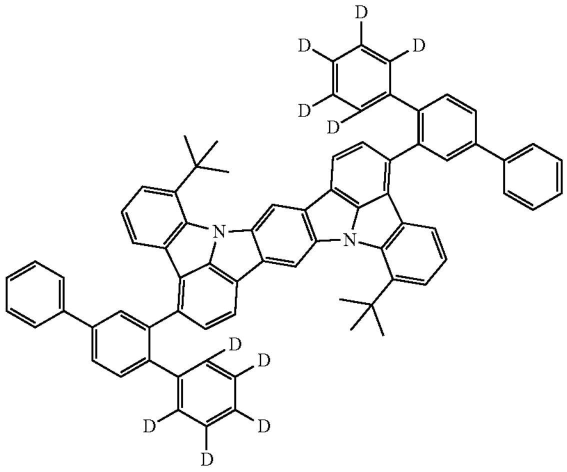
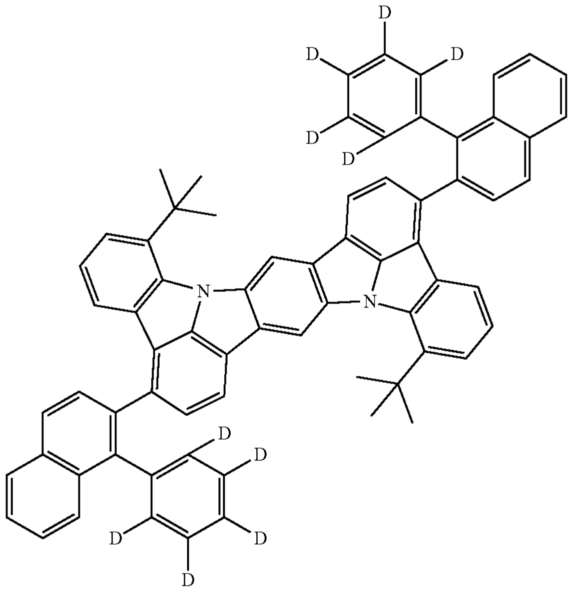
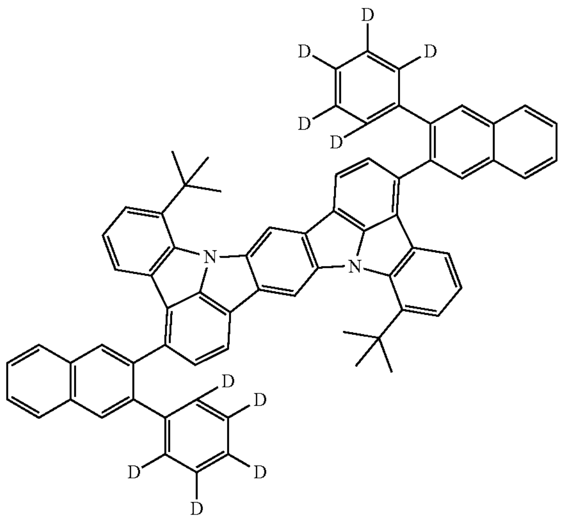
-continued
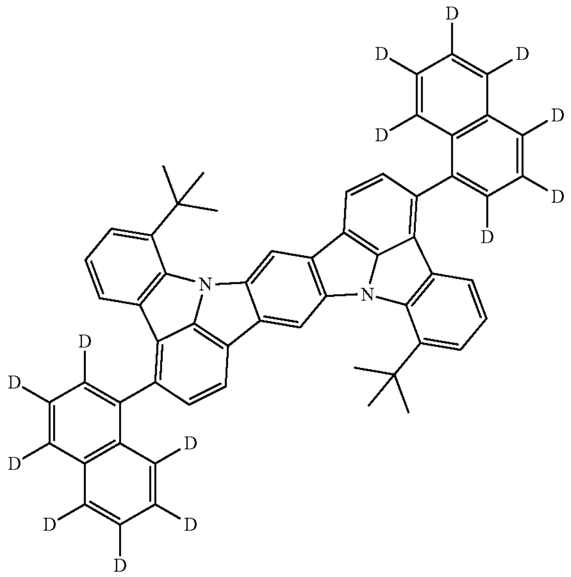
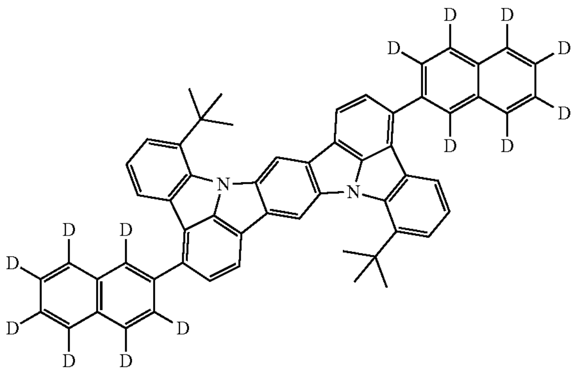
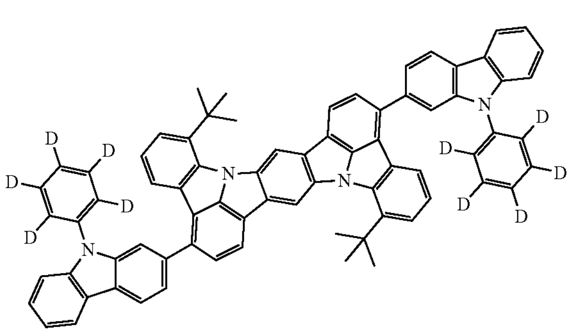

-continued
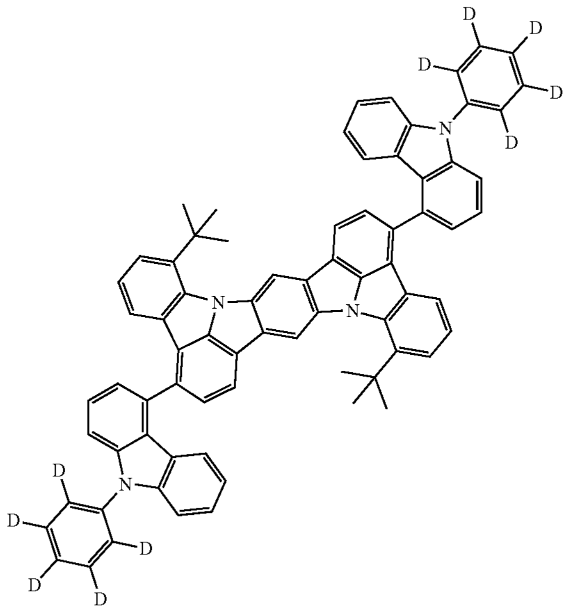
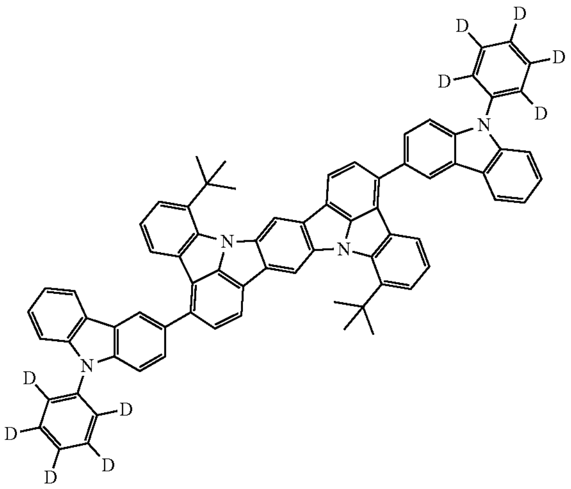
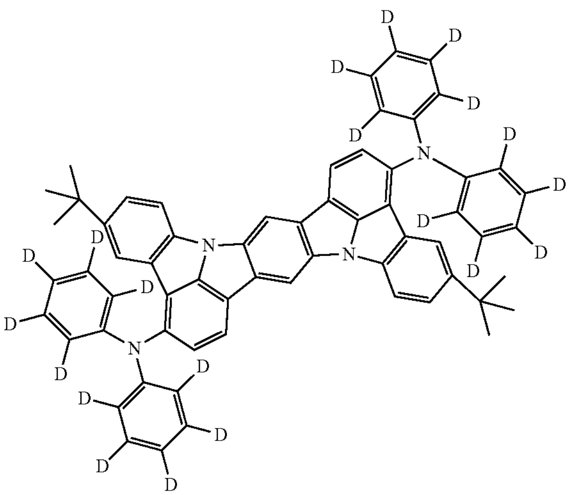
-continued
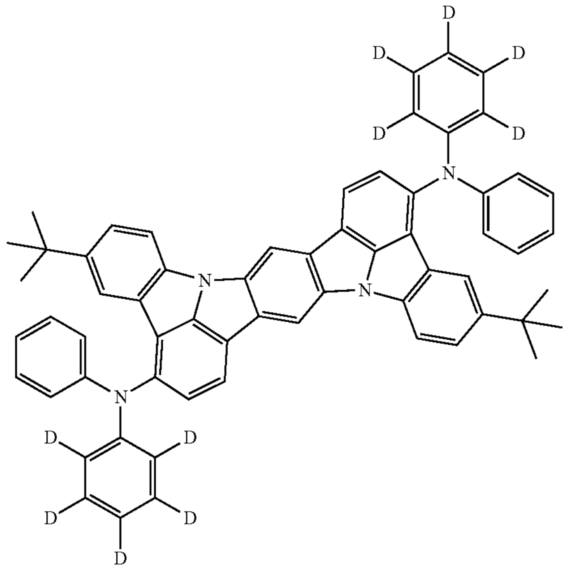
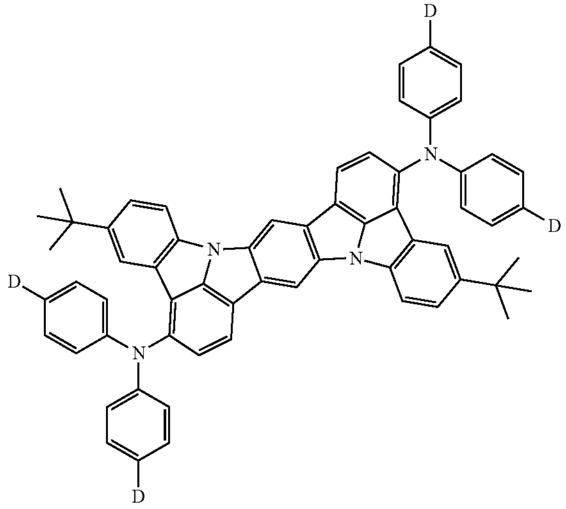
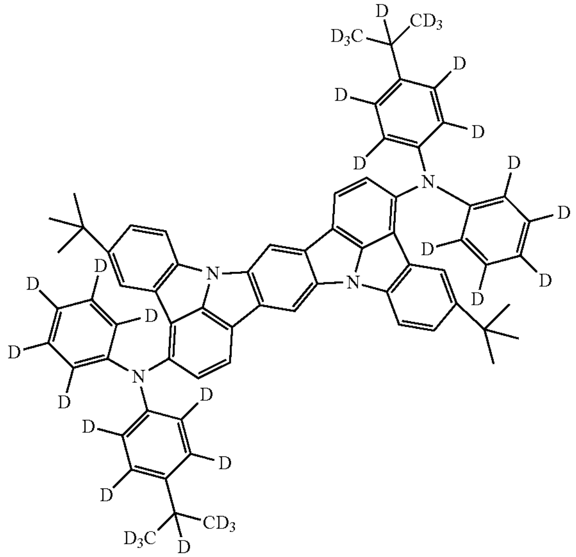

-continued
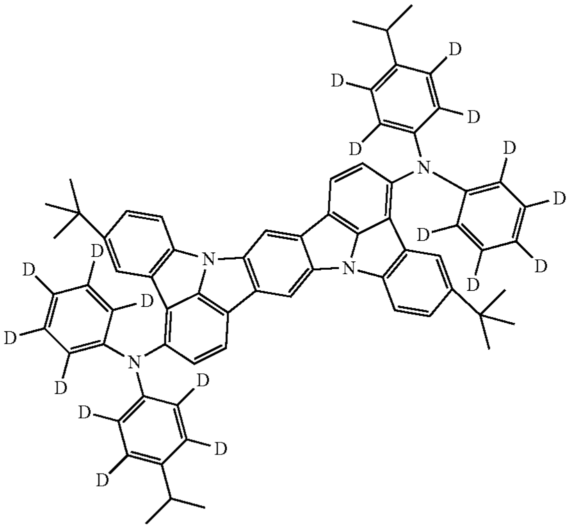
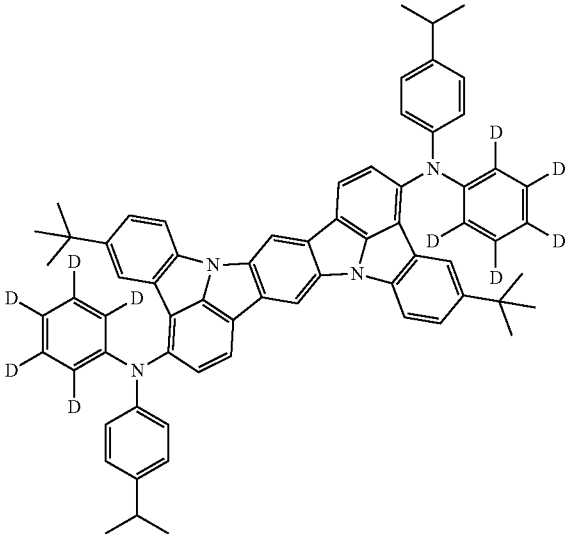
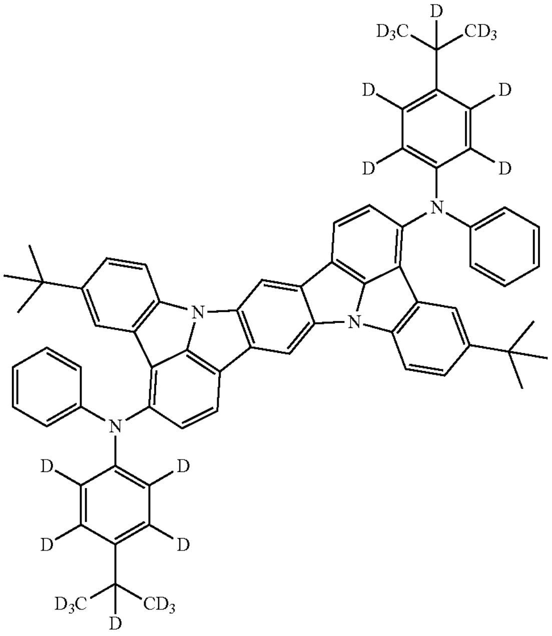
-continued
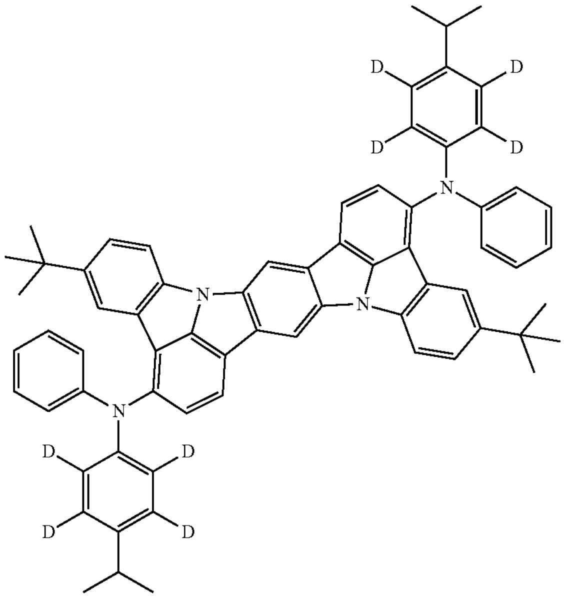
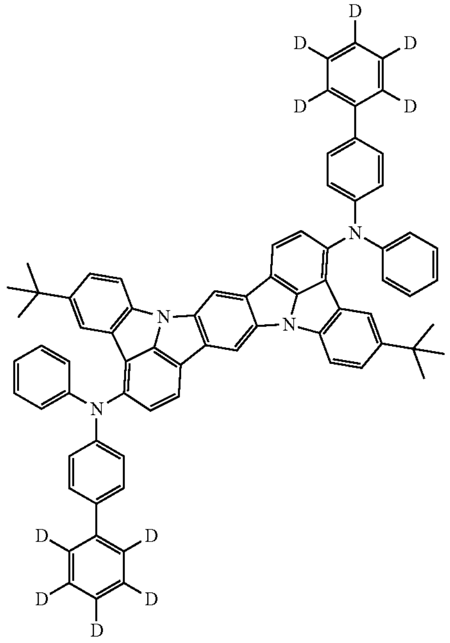
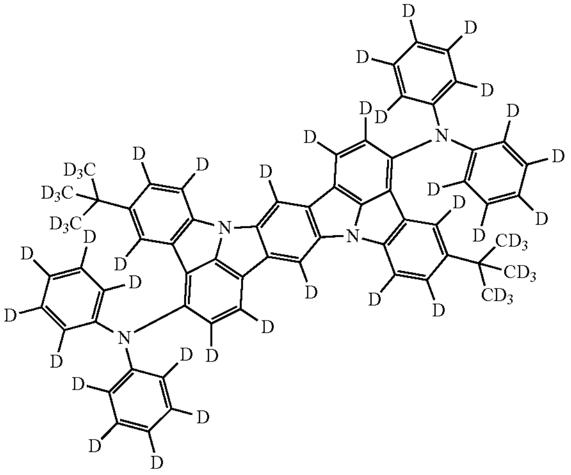

-continued
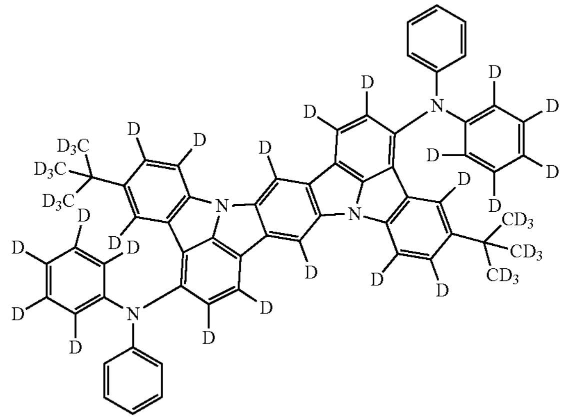
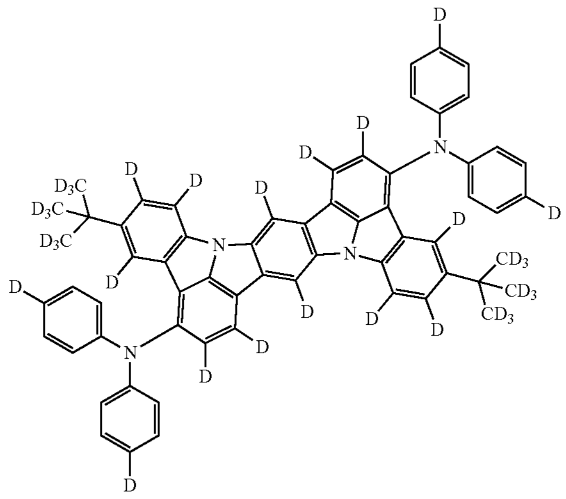
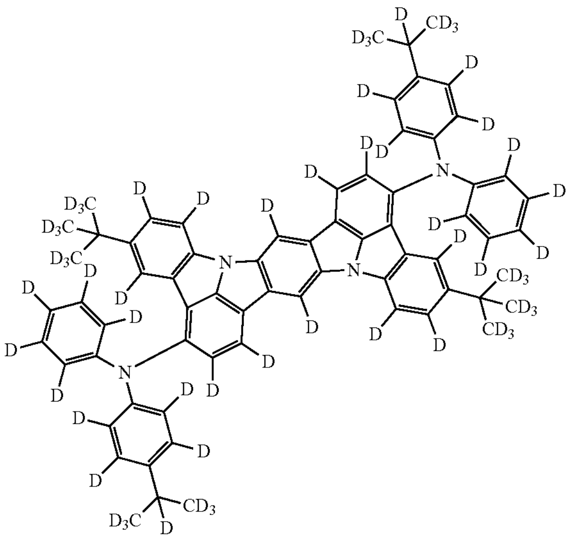
-continued
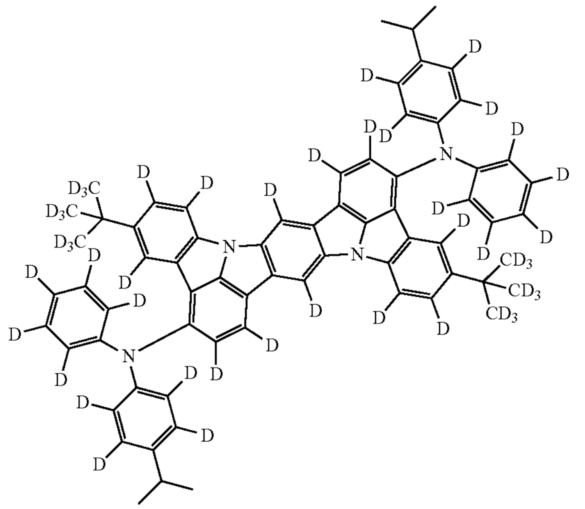
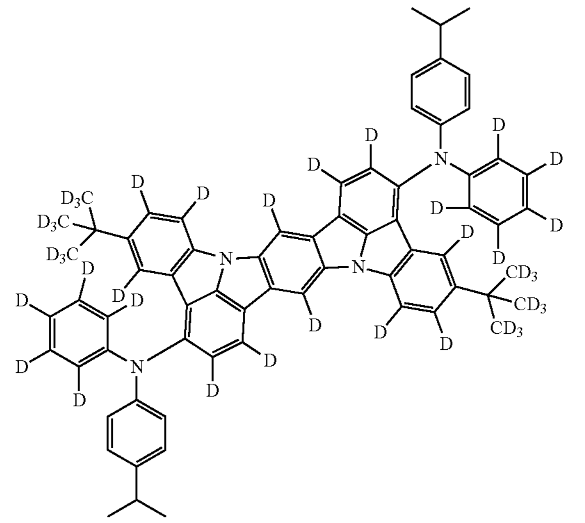
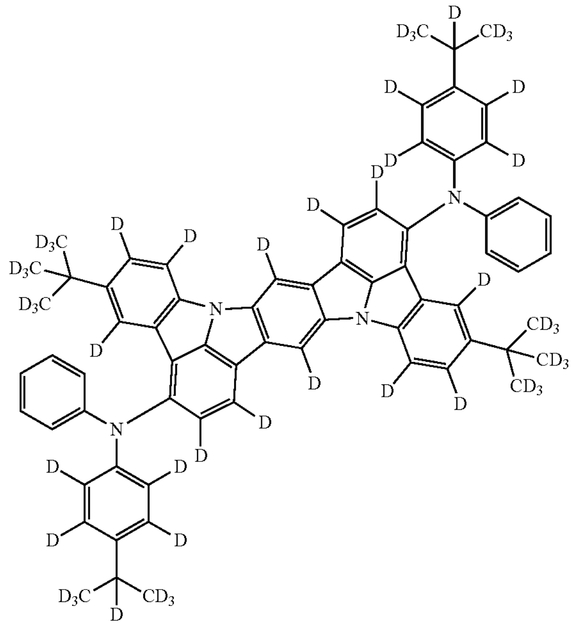

-continued
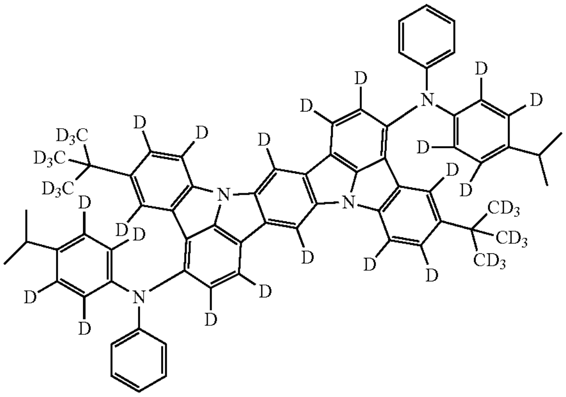
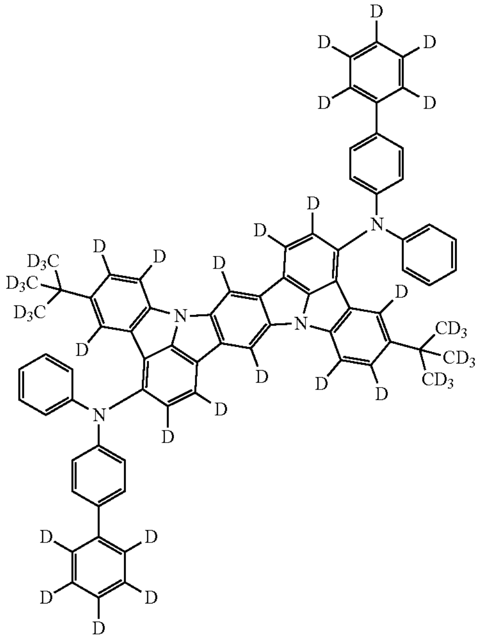
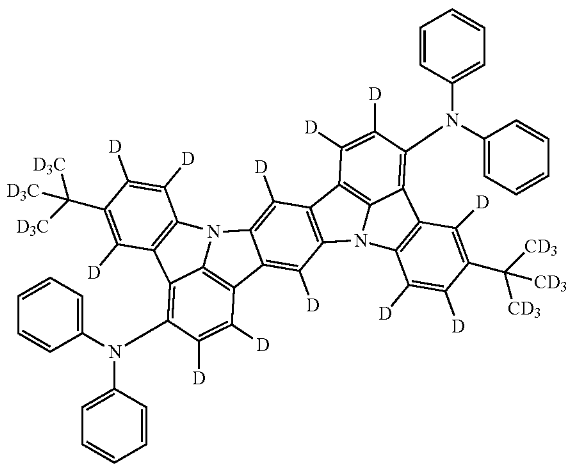
-continued
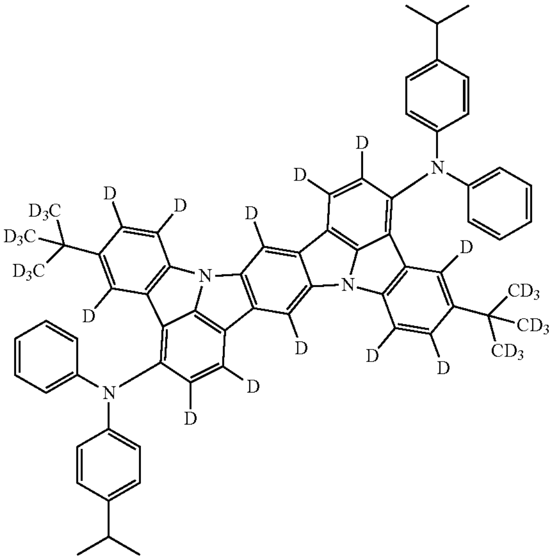
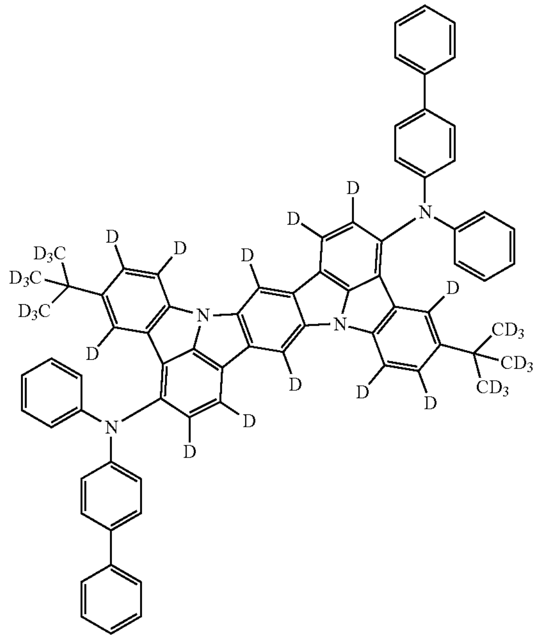
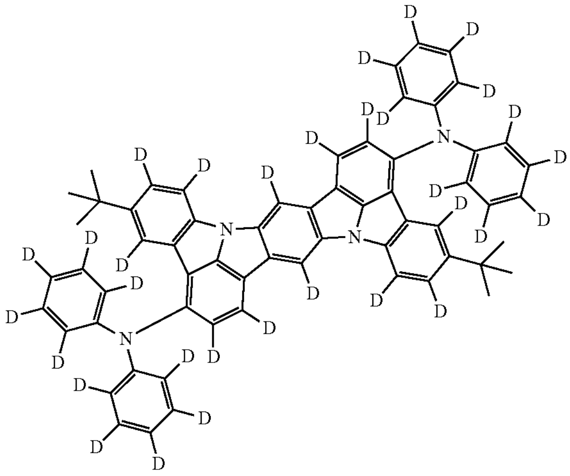

-continued
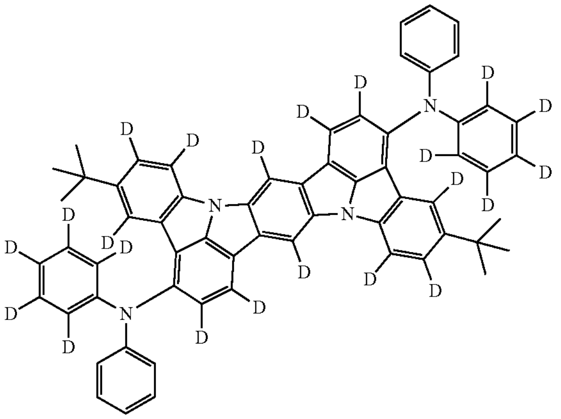
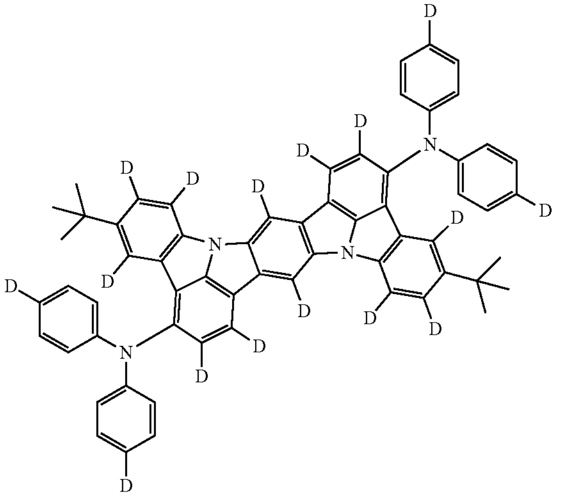
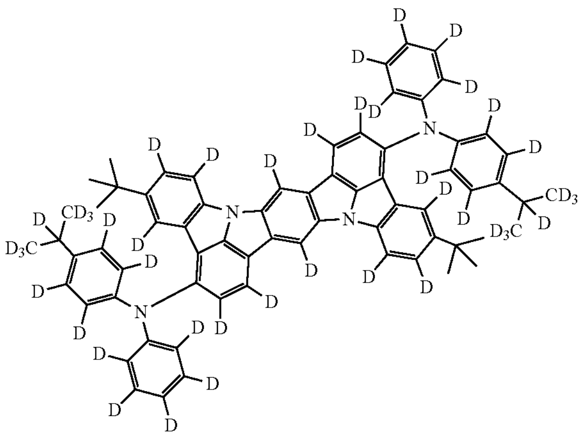
-continued
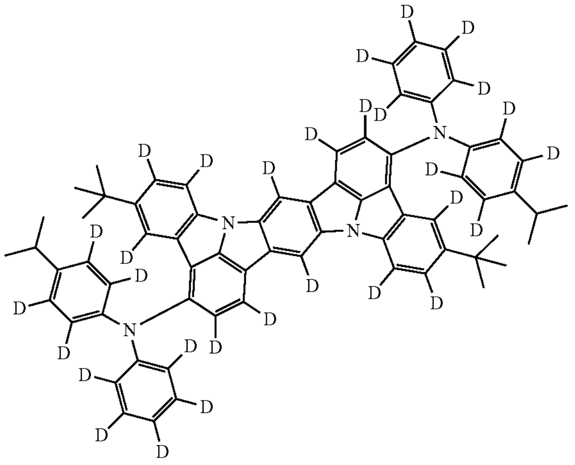
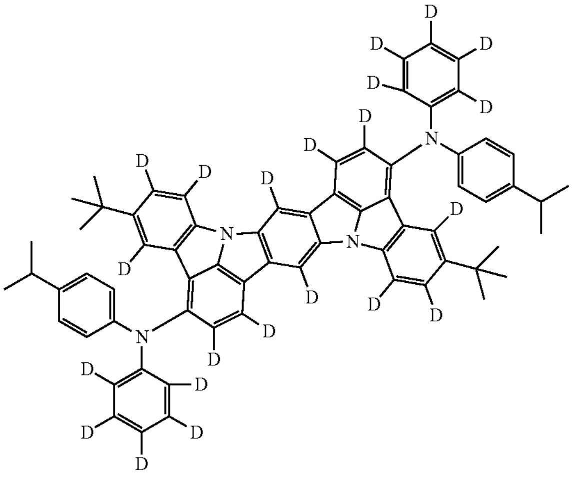
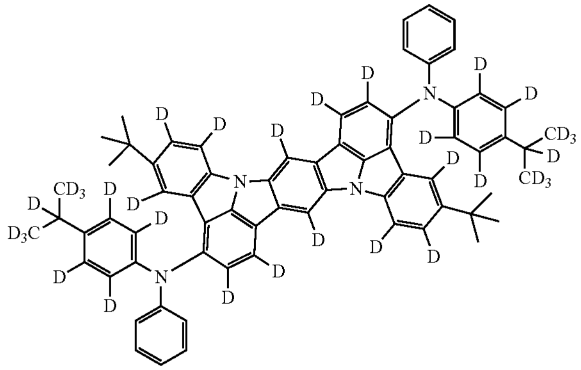
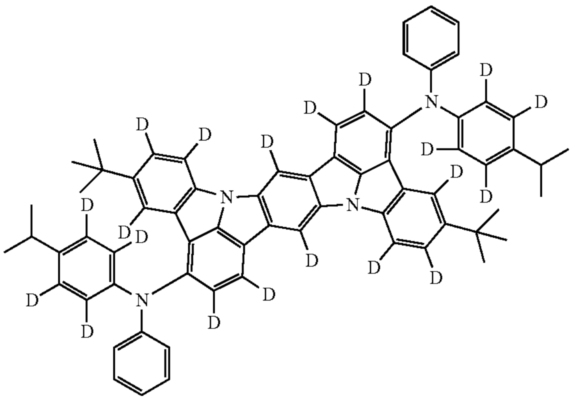

-continued
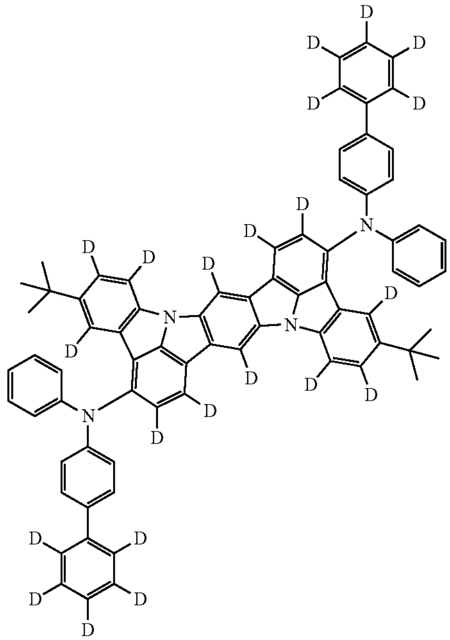
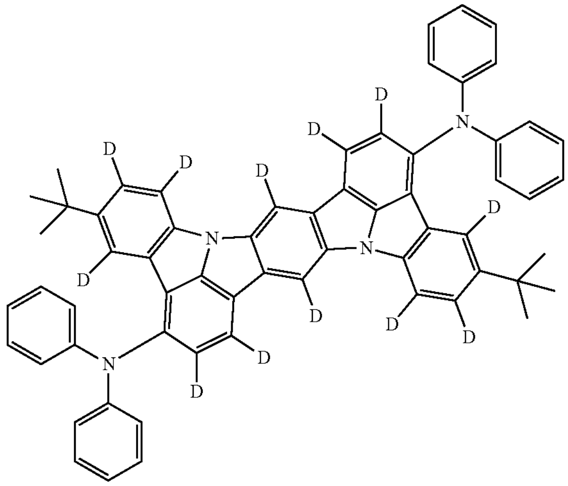
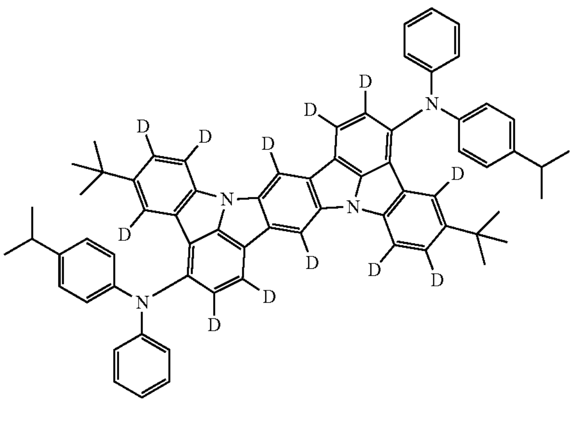
-continued
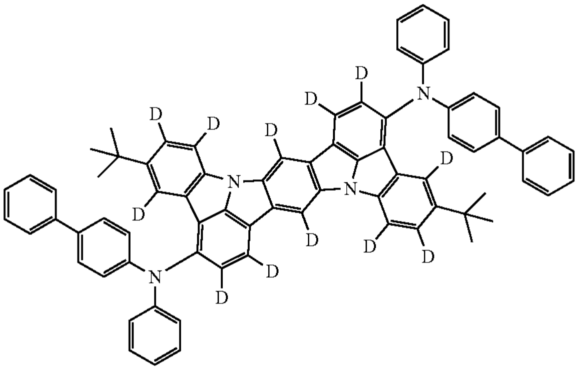
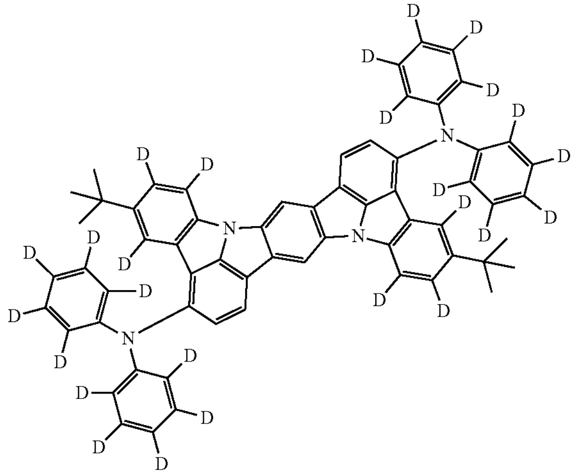
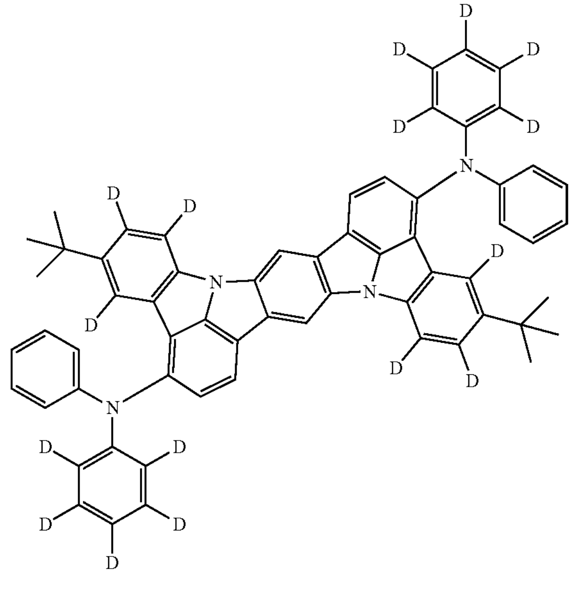

-continued
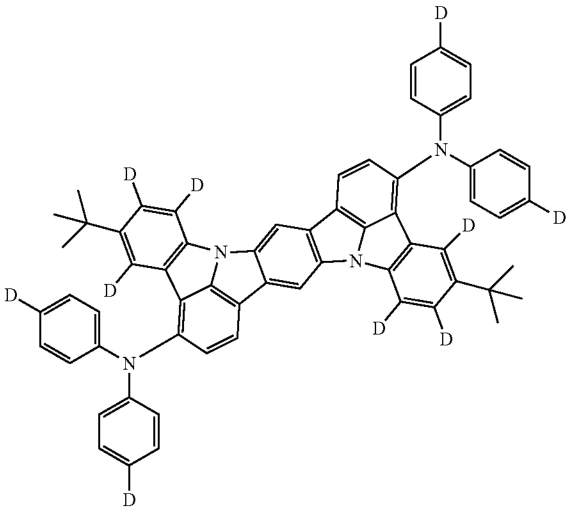
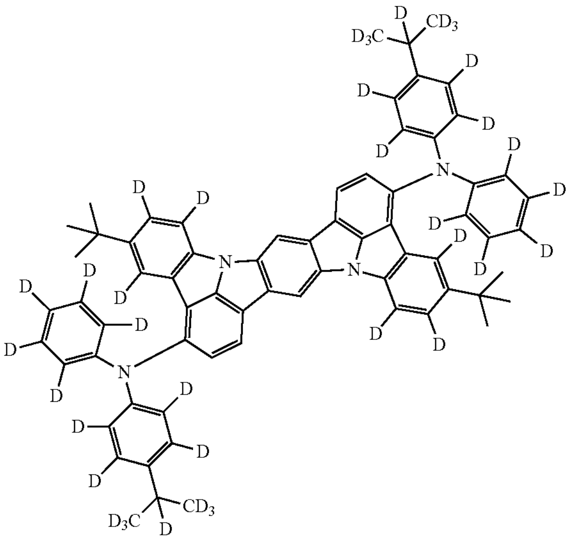
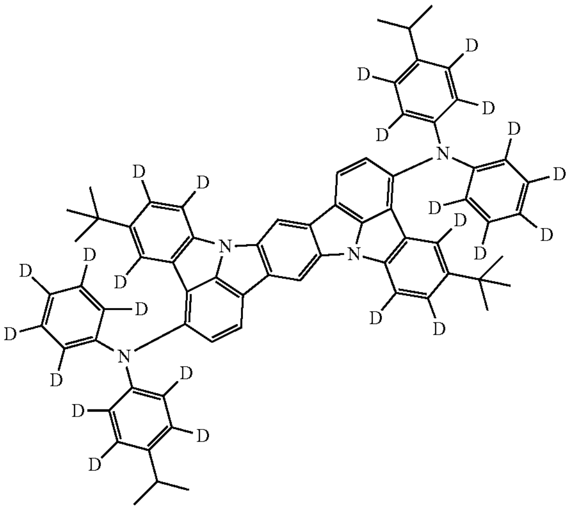
-continued
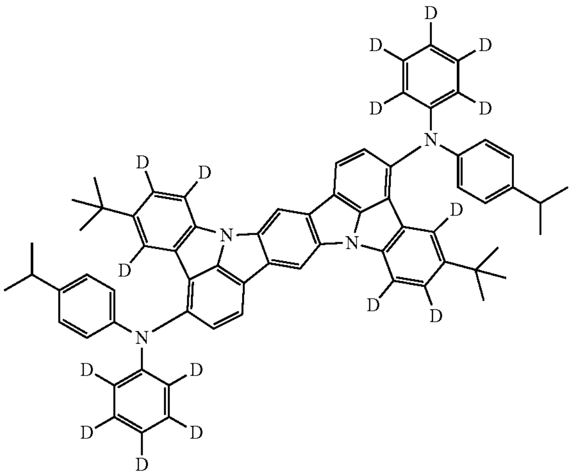
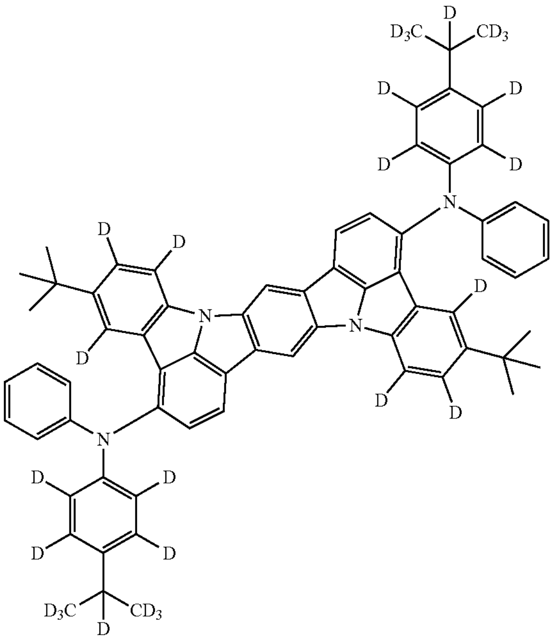
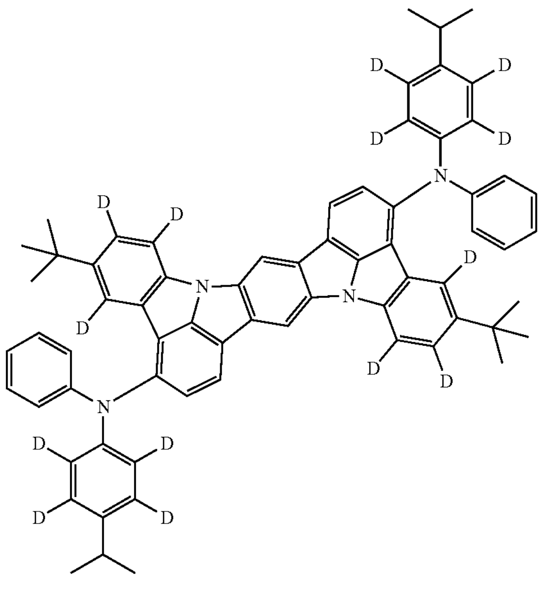

-continued
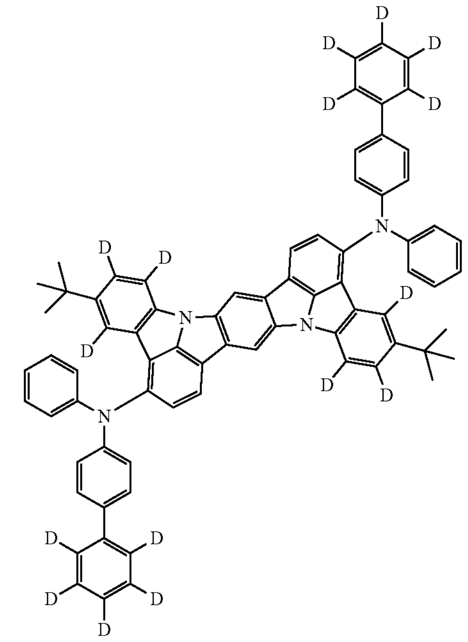
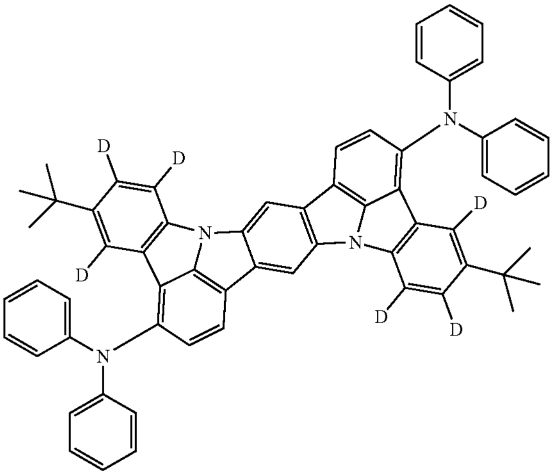
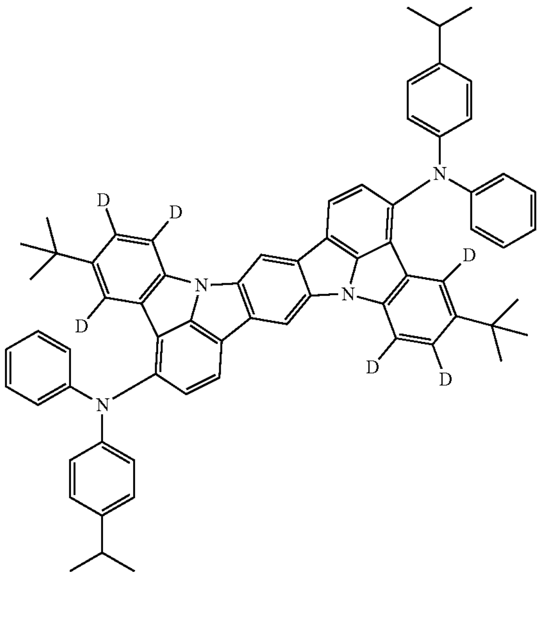
-continued
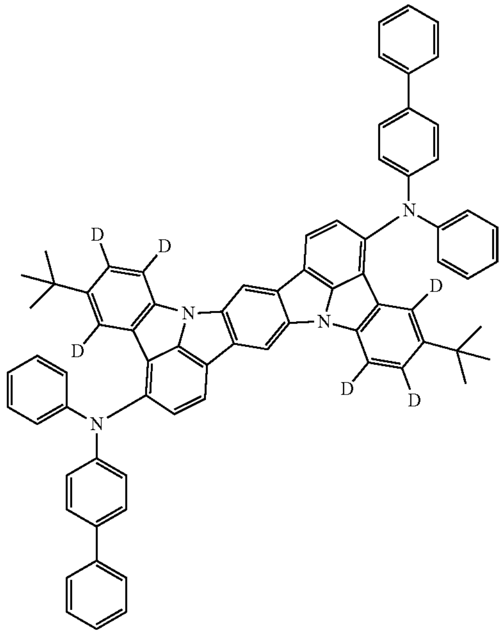
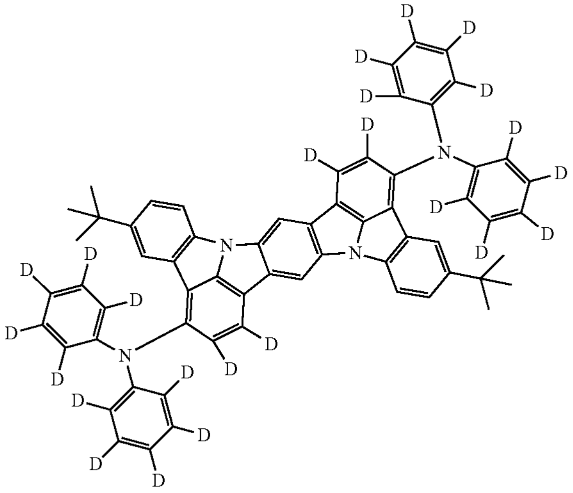
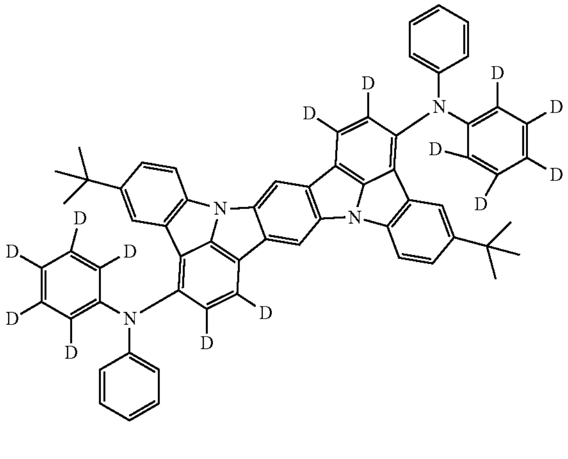

-continued
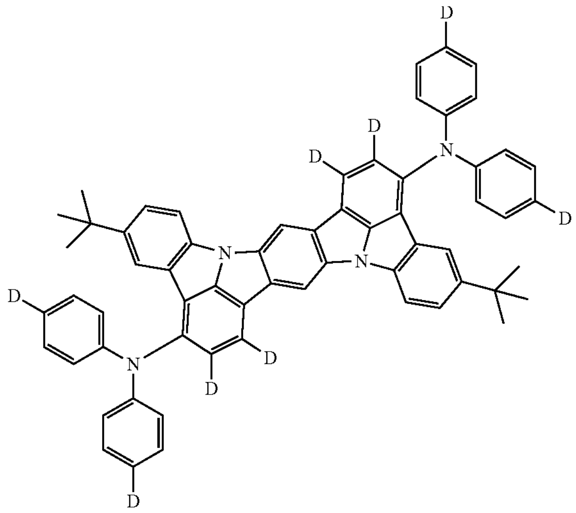
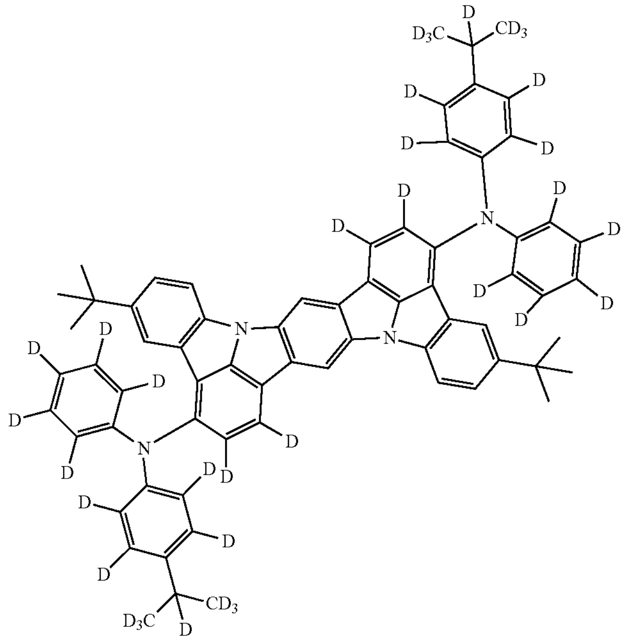

-continued
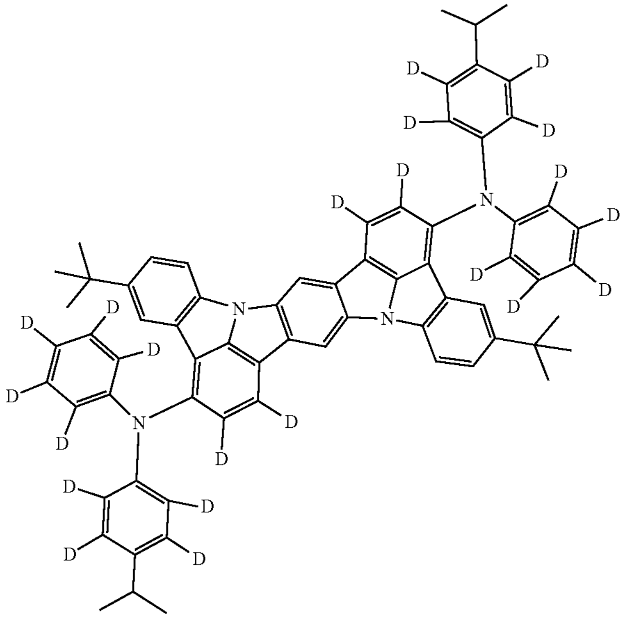
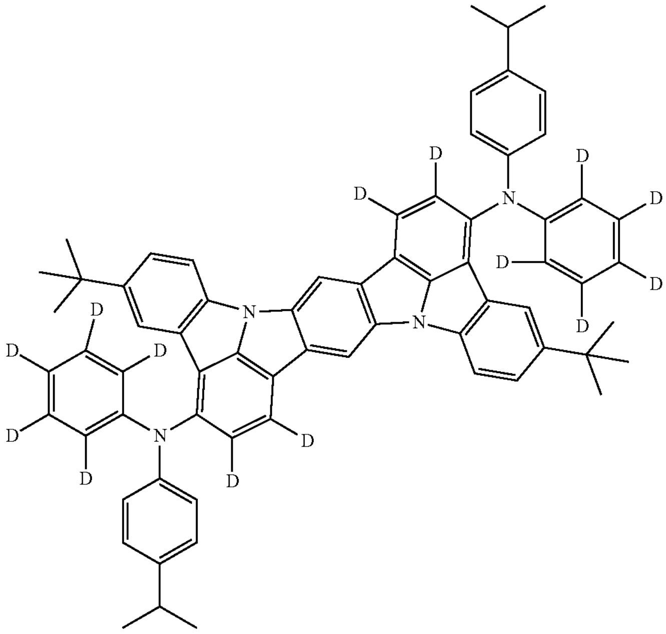

-continued
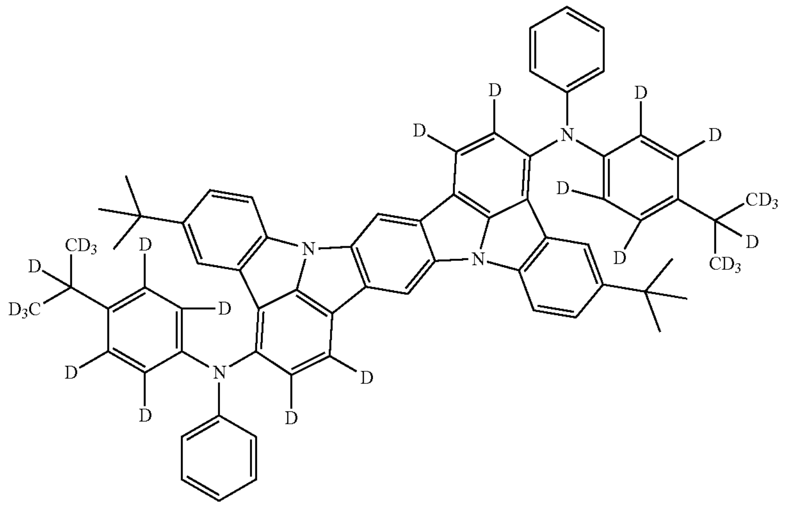
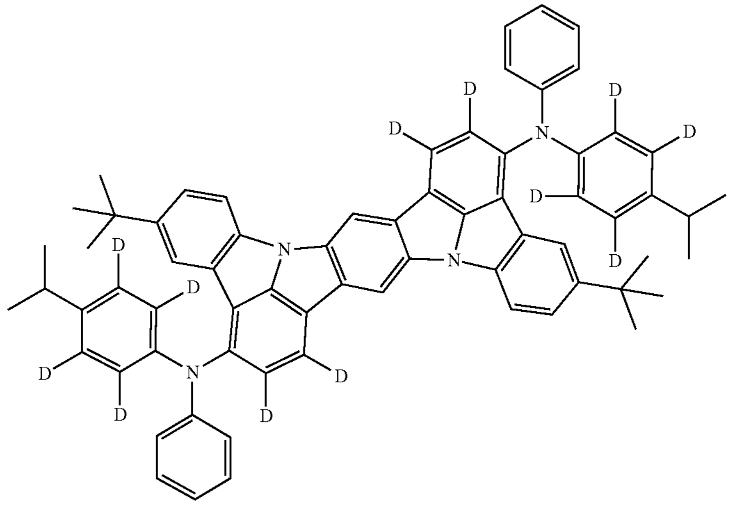
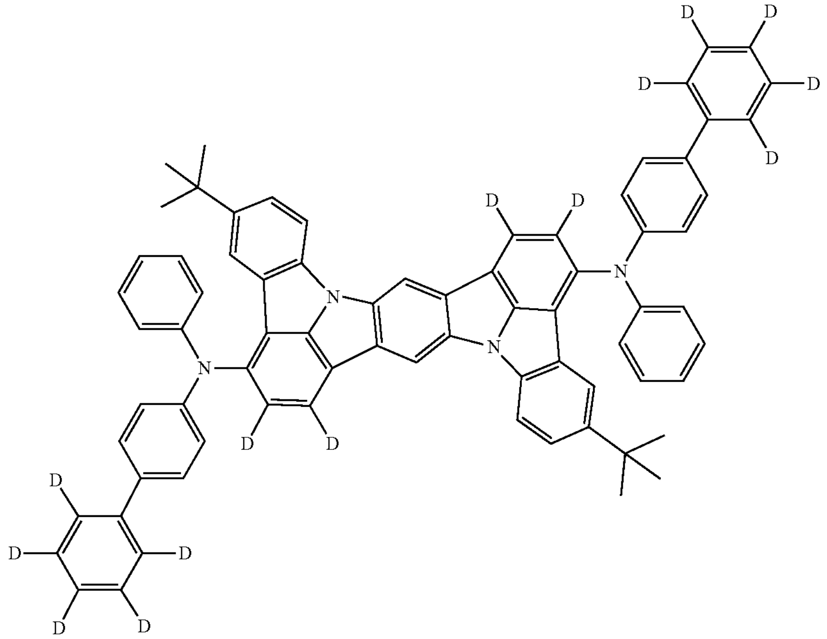

-continued
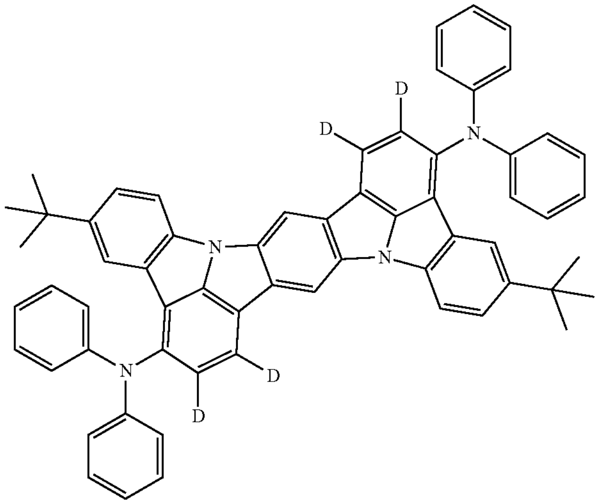
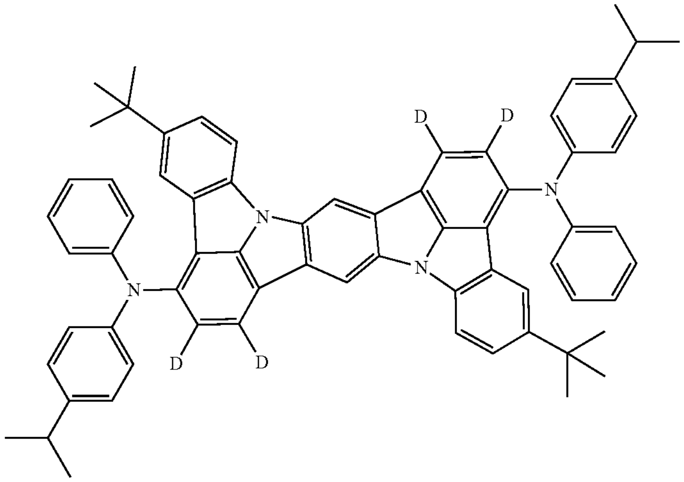
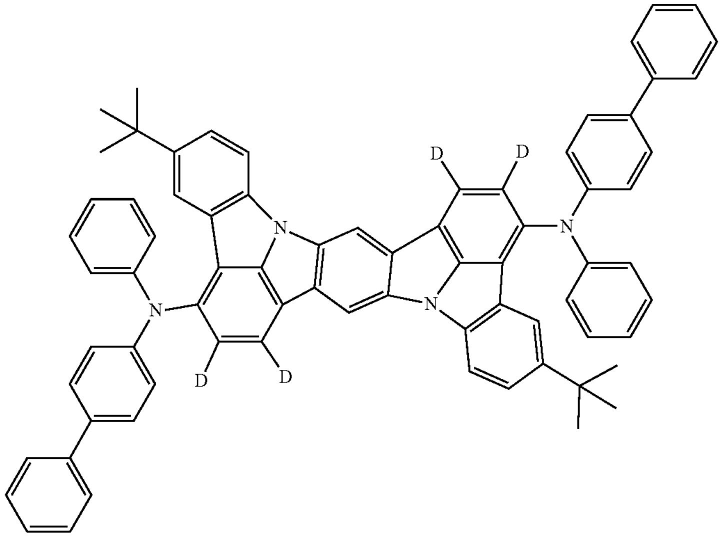

-continued
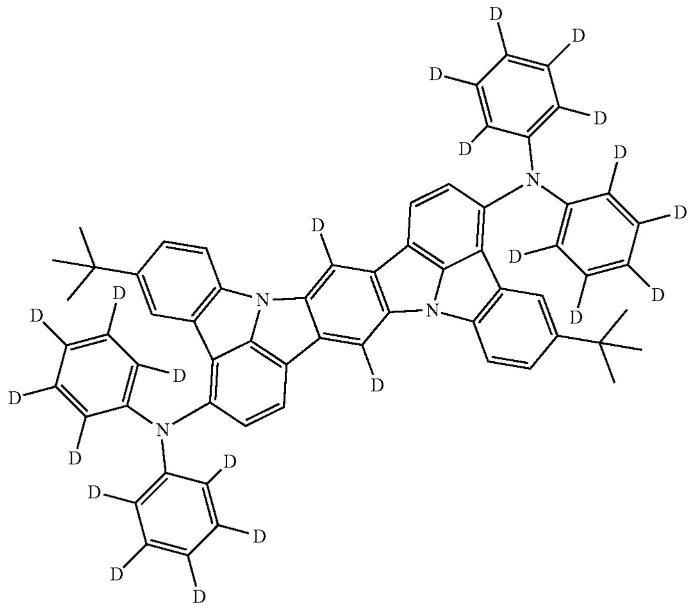
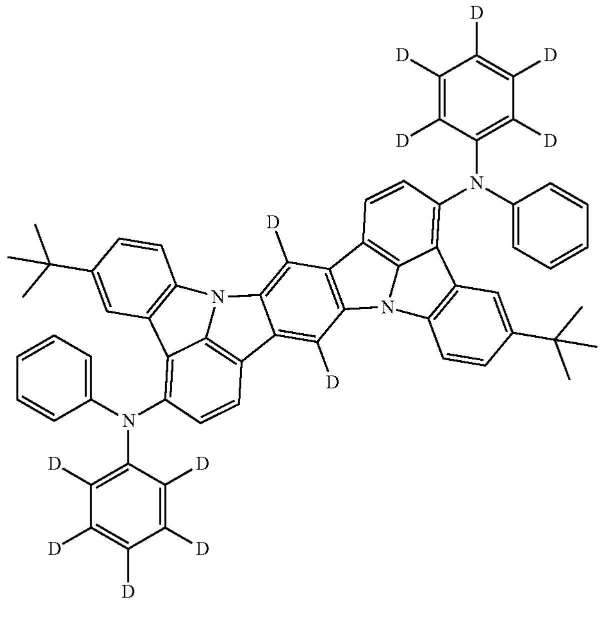

-continued
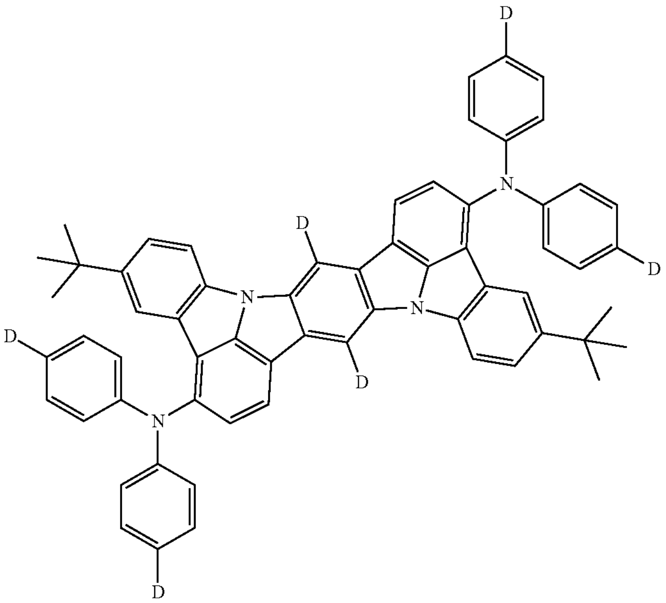
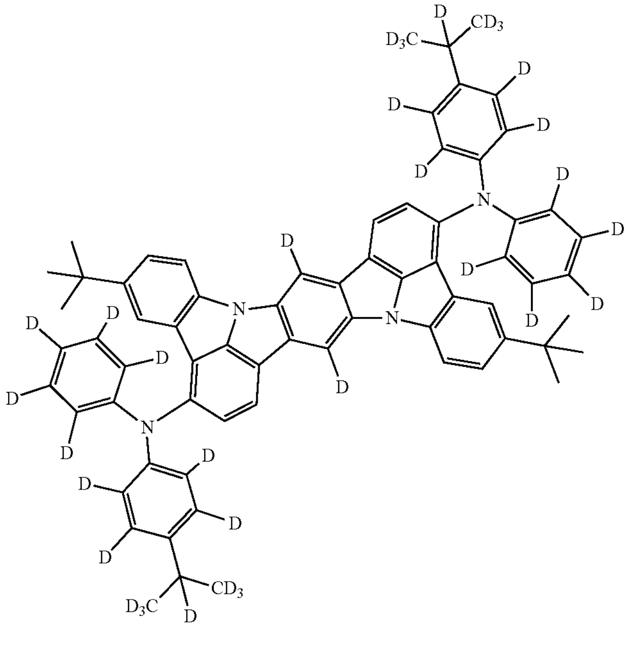

-continued
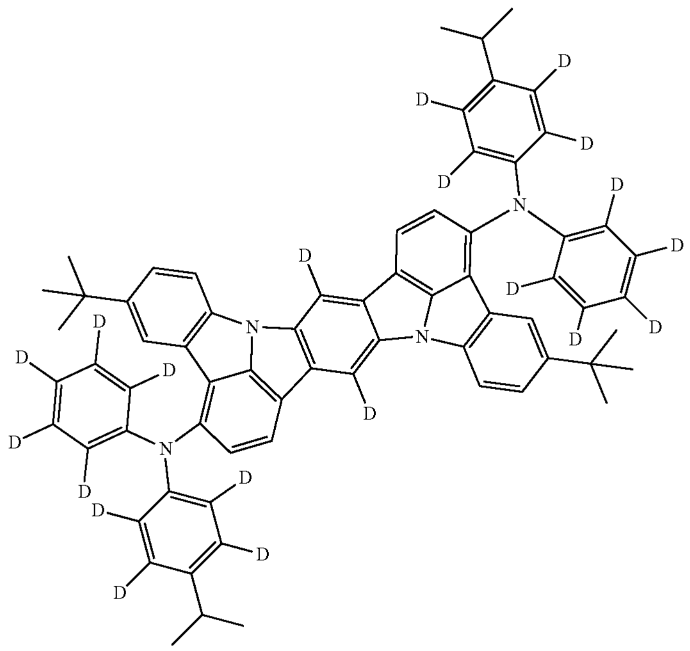
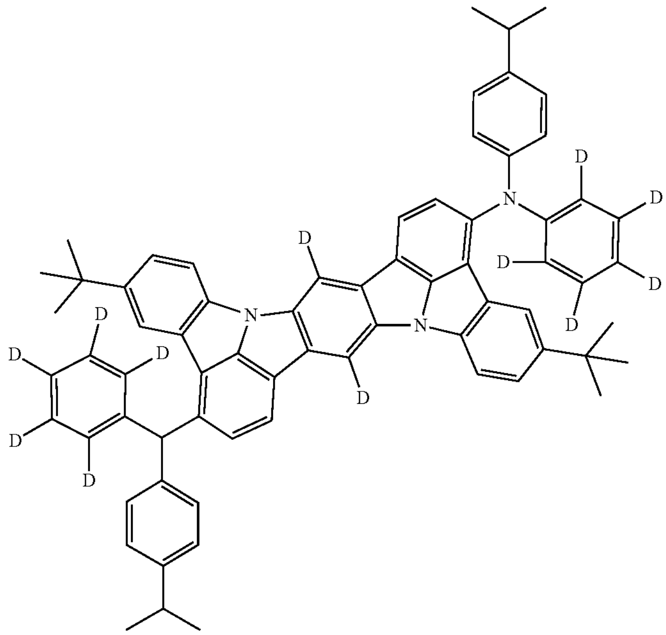

-continued
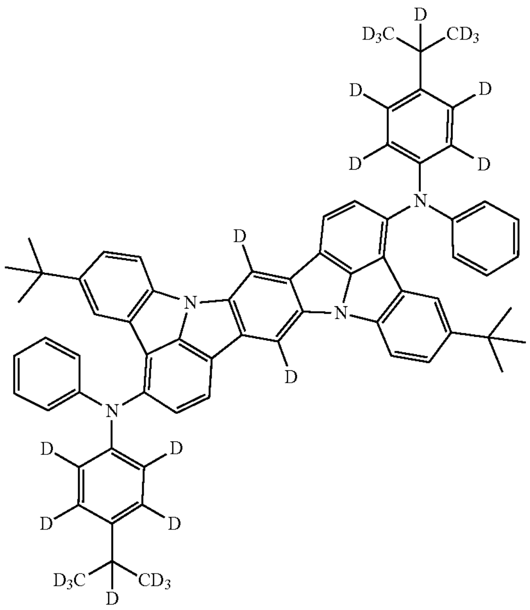
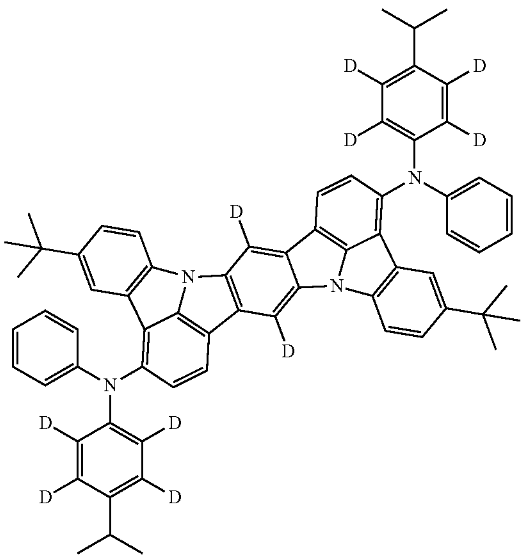
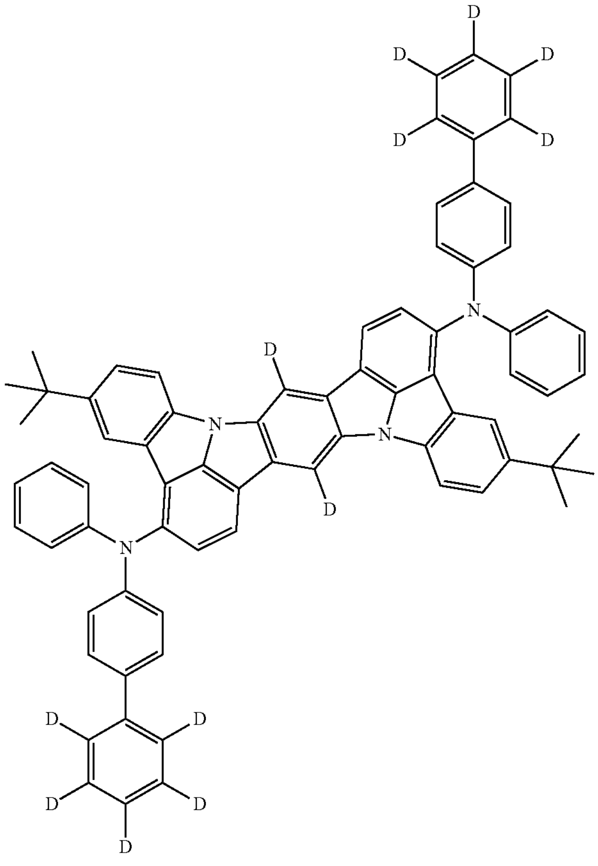

-continued
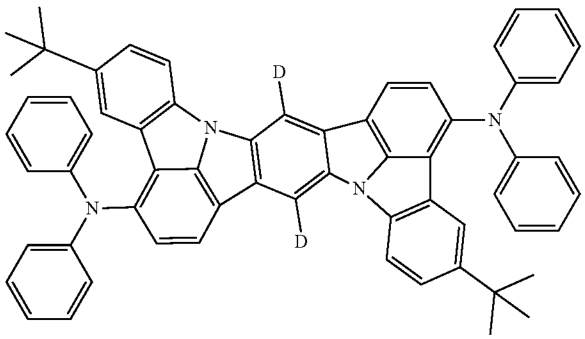
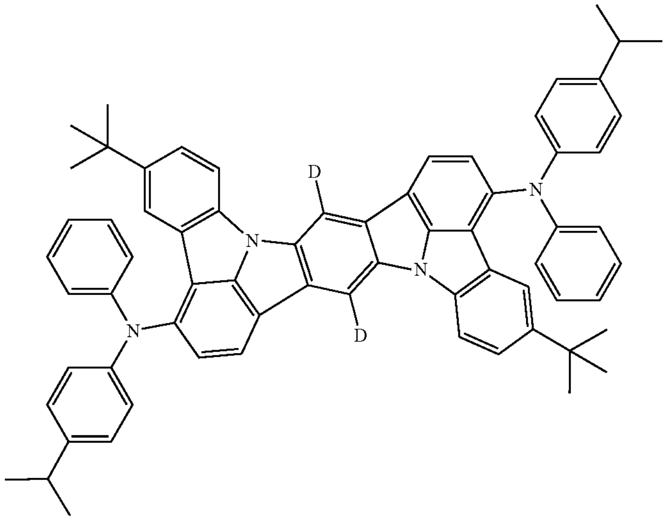
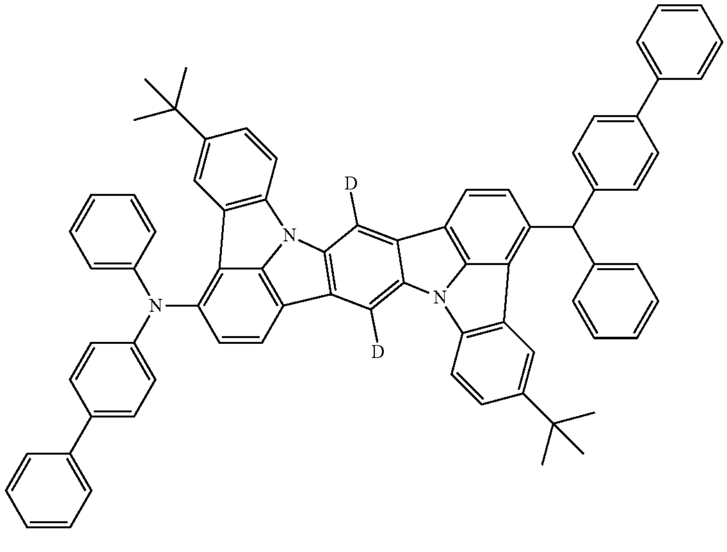

-continued
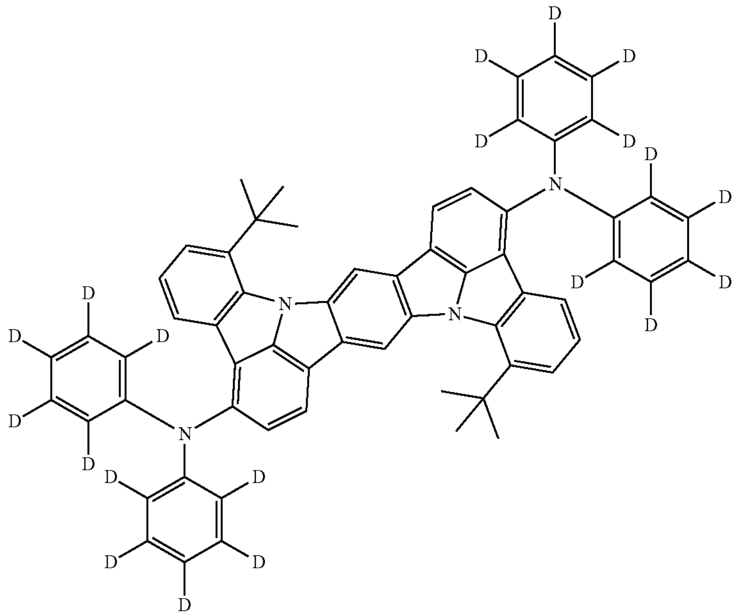
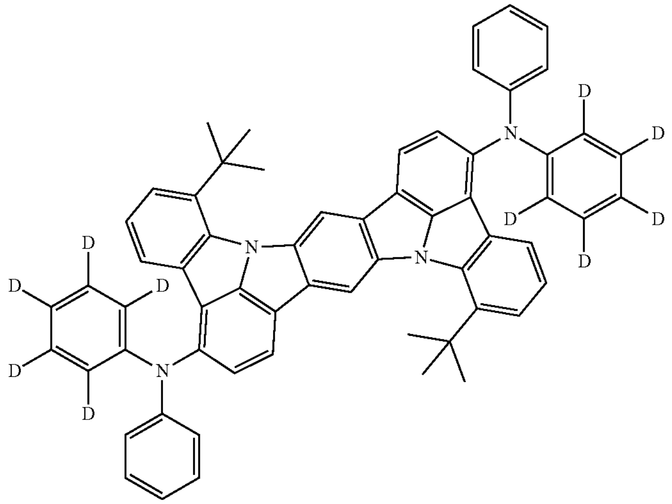
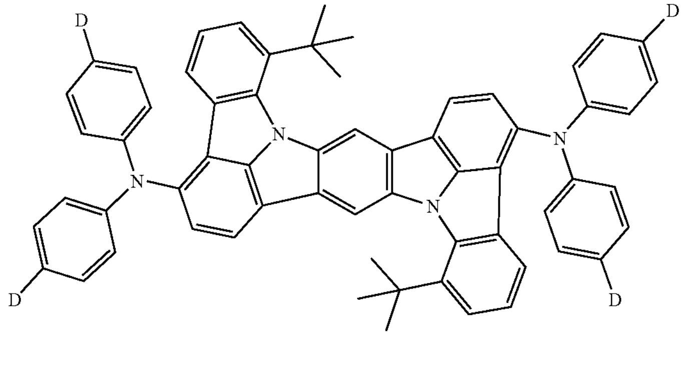

-continued
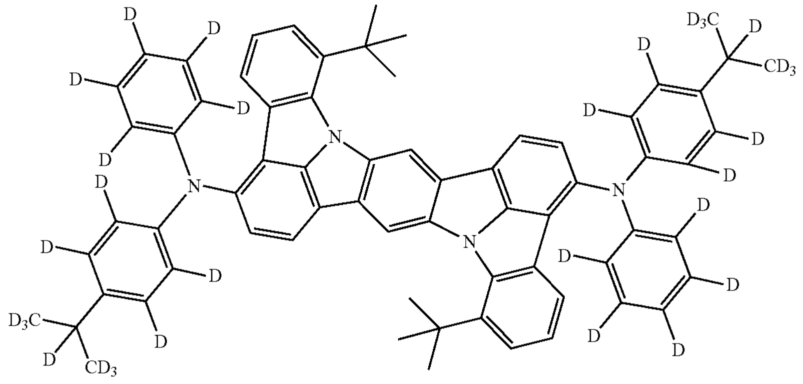
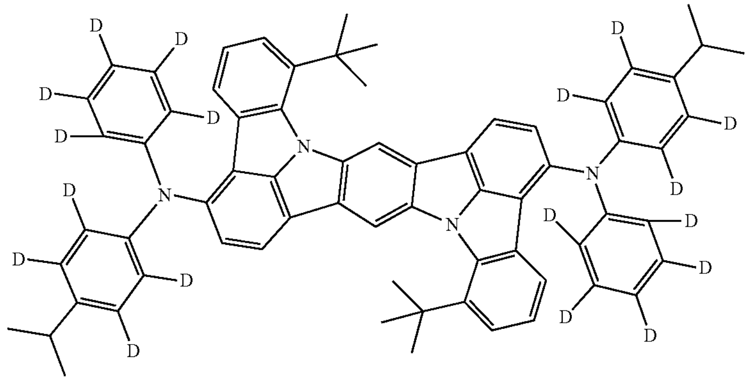
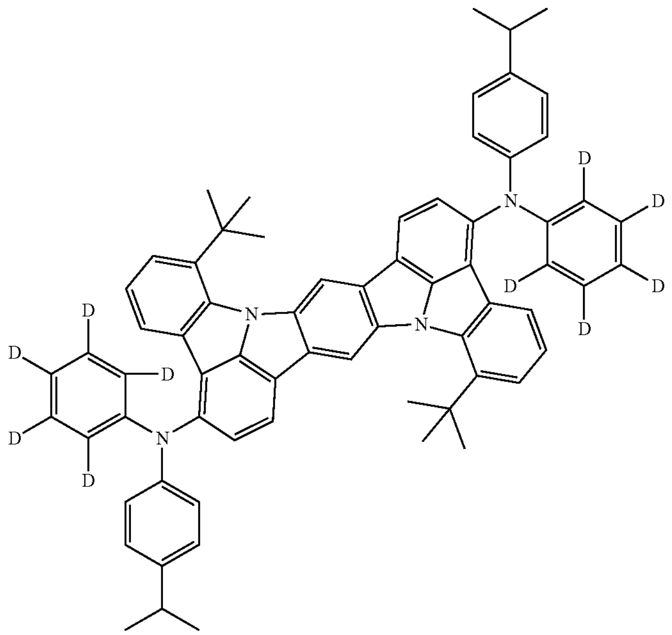

-continued
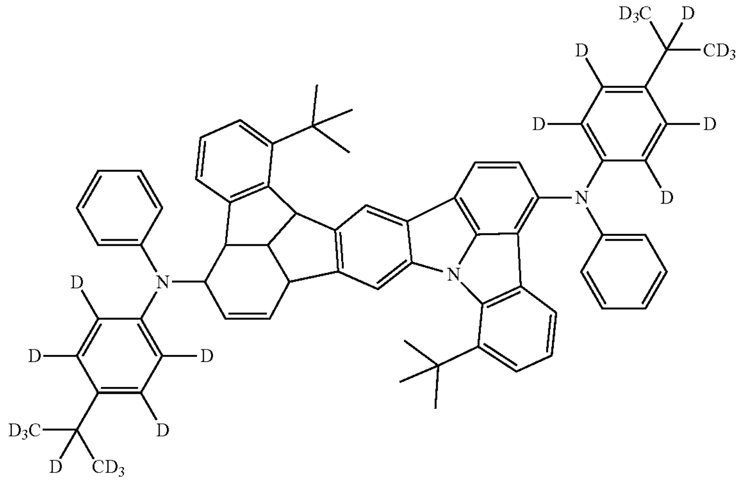
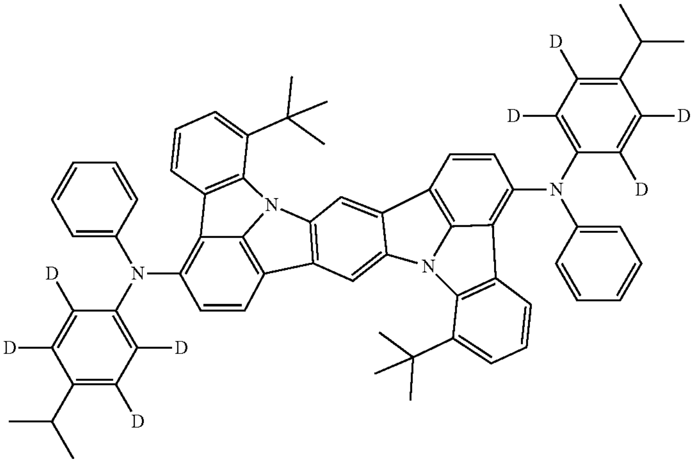
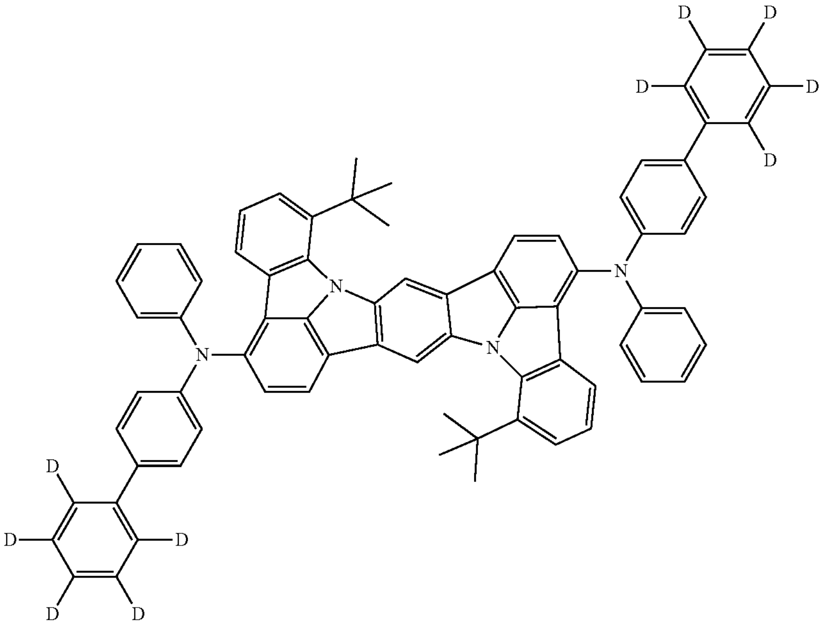

-continued
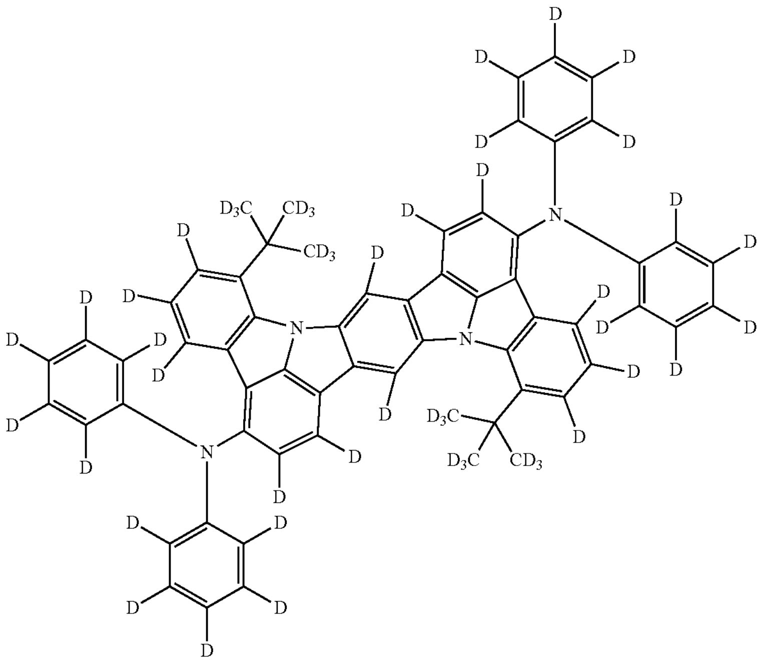
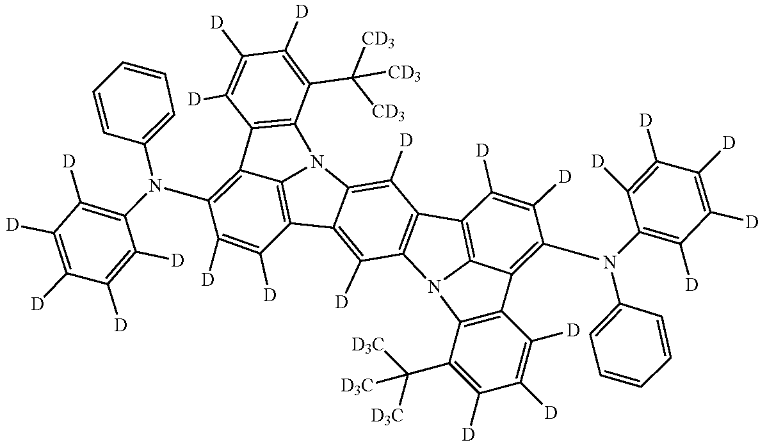
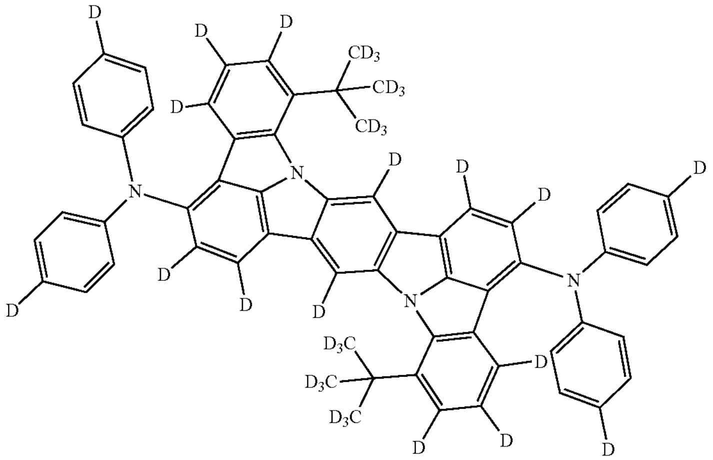

-continued
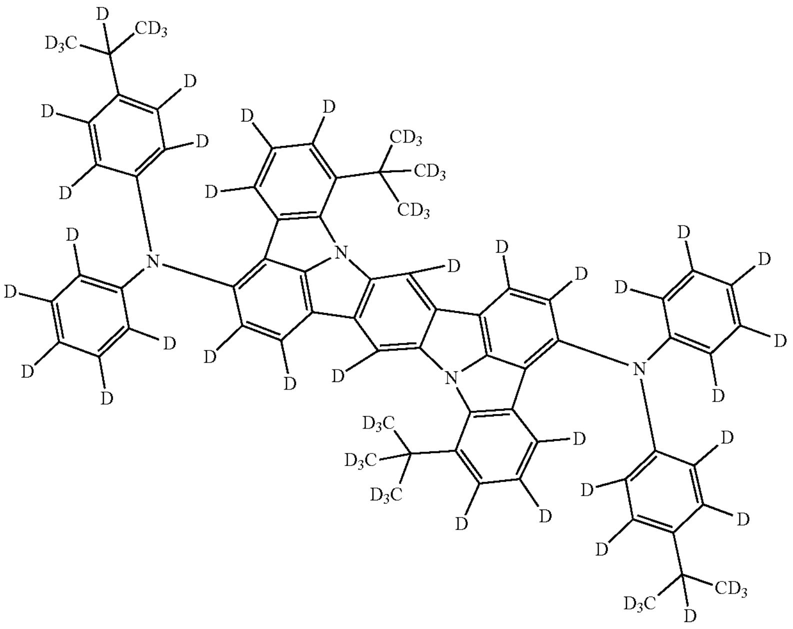
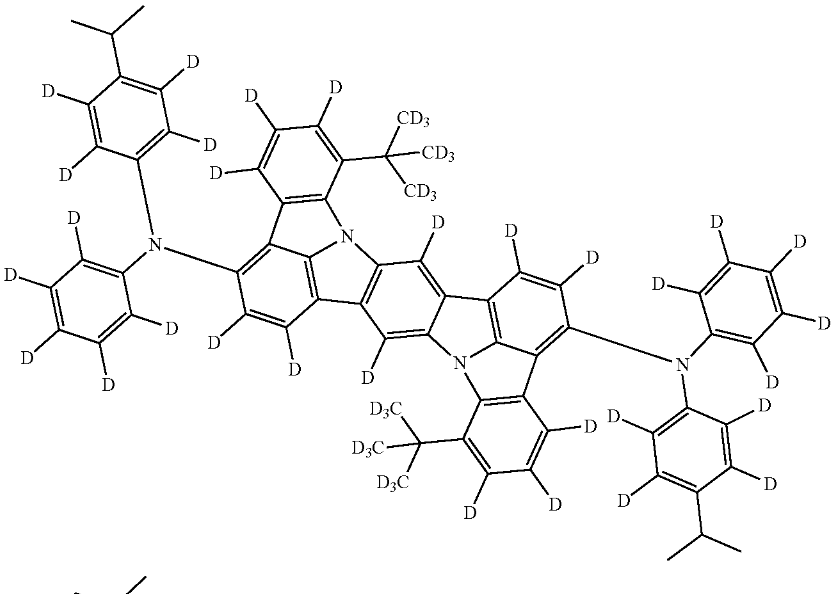
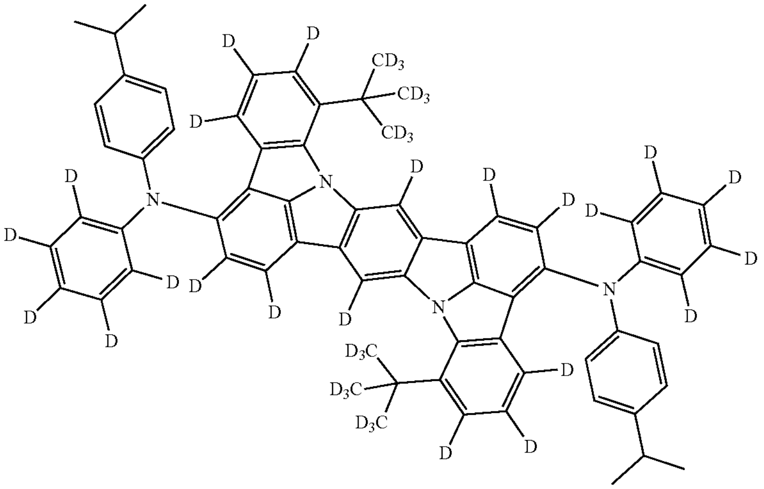

-continued
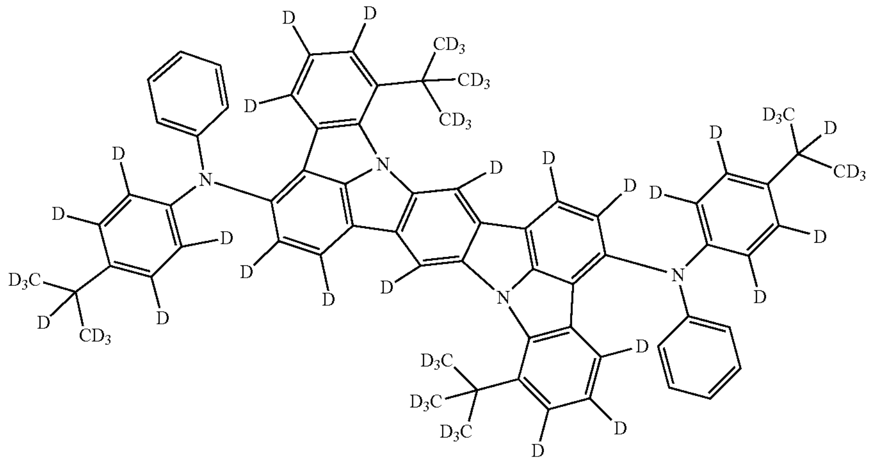
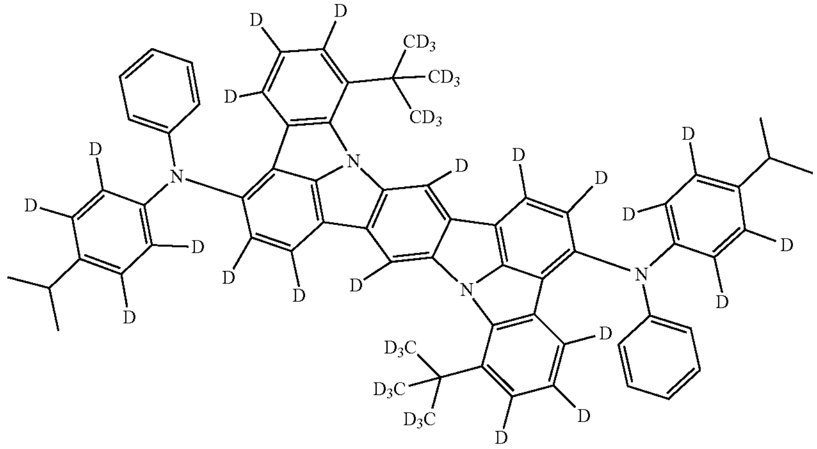
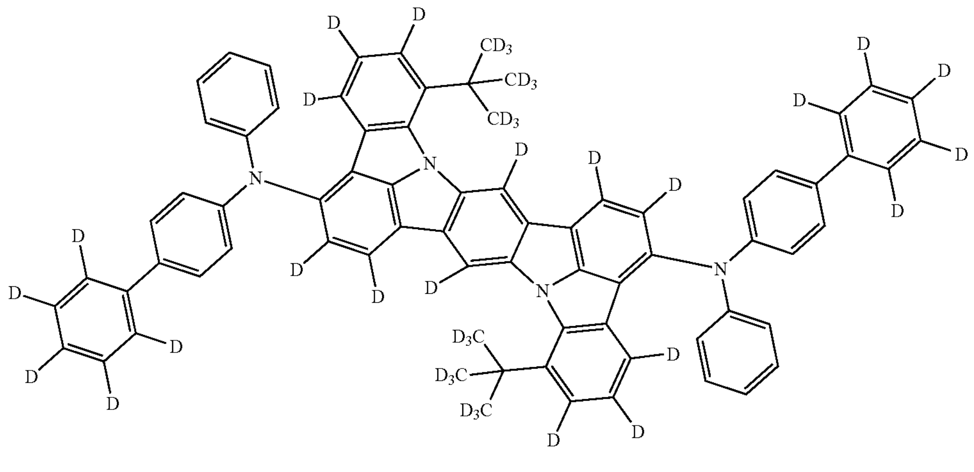

-continued
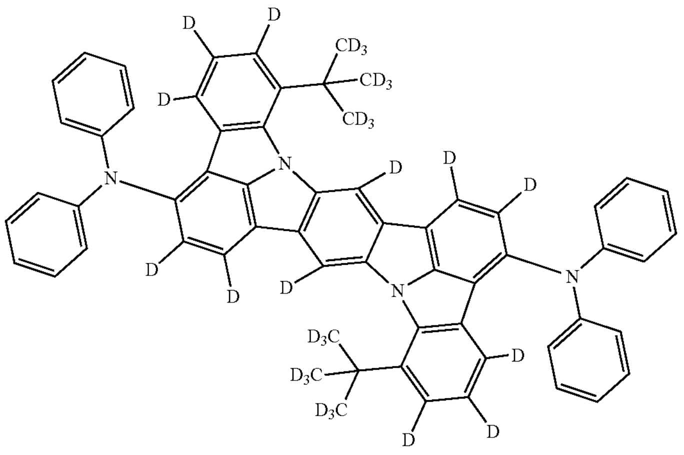
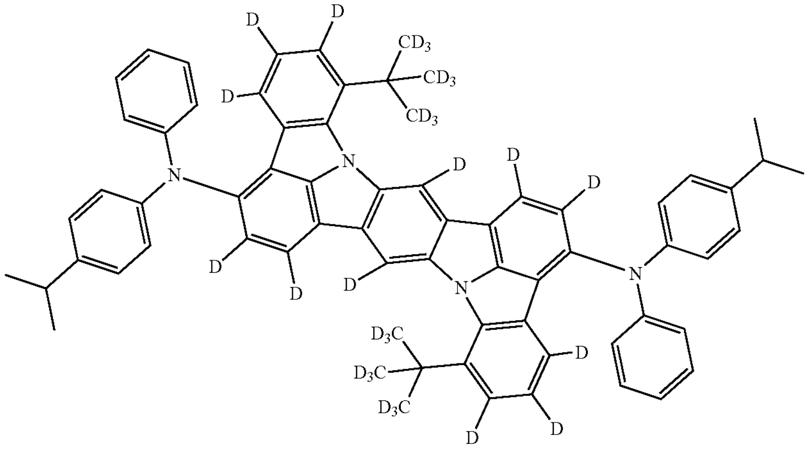
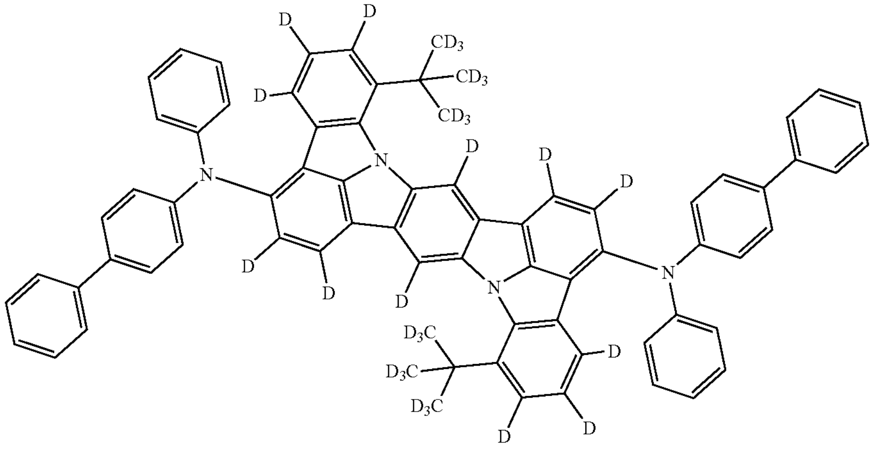

-continued
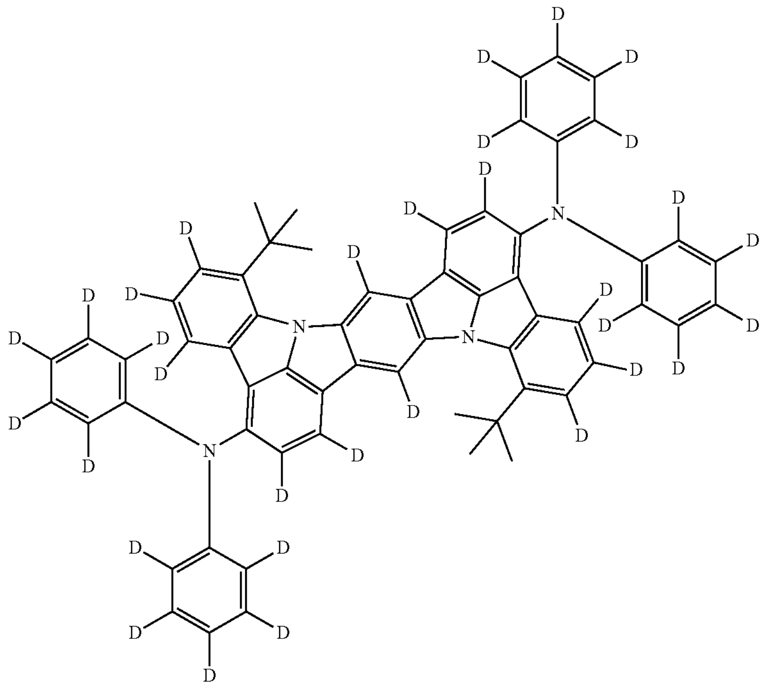
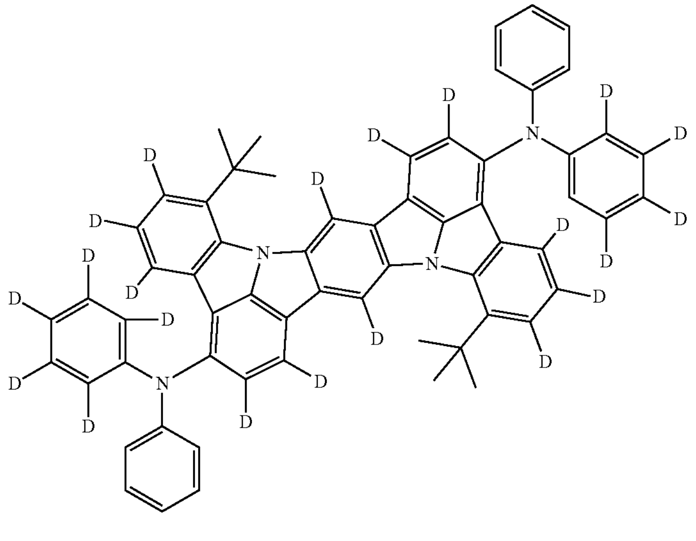
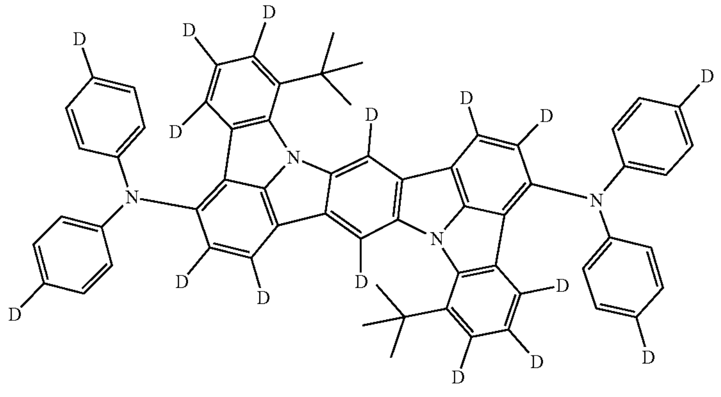

-continued
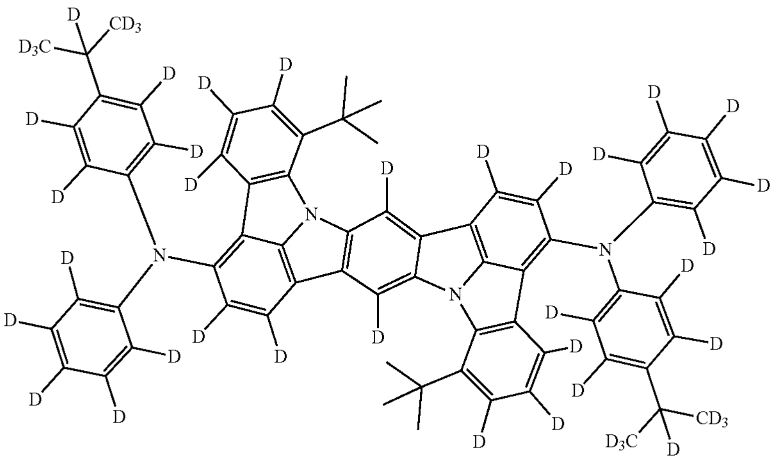
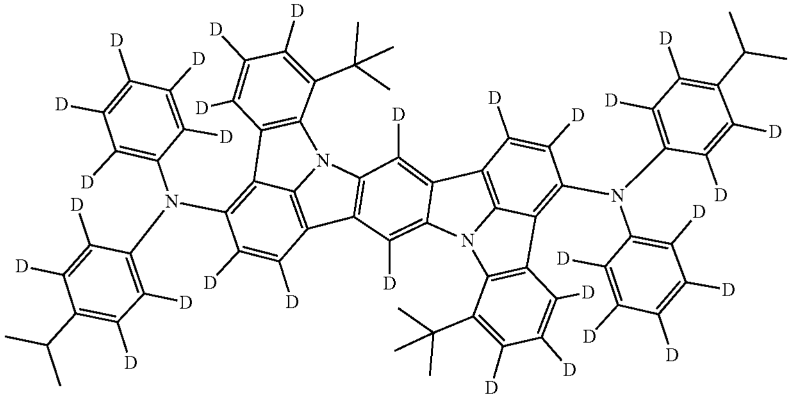
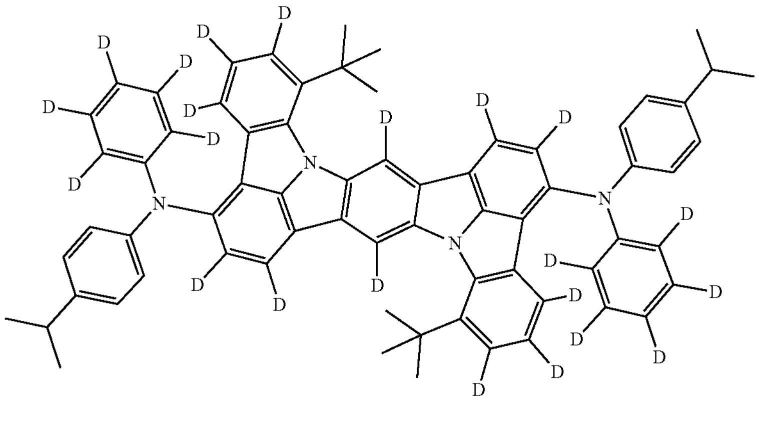

-continued
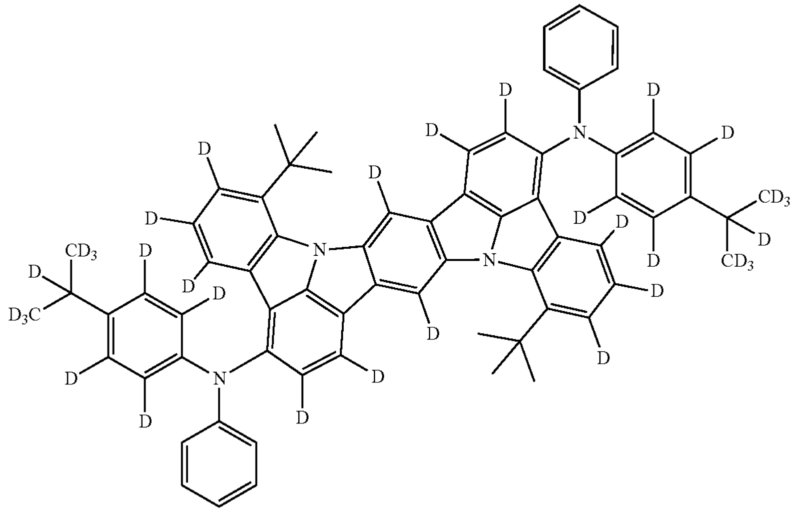
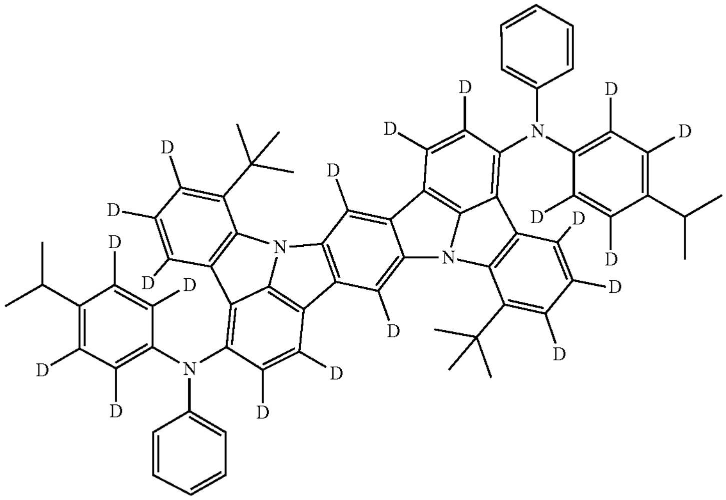
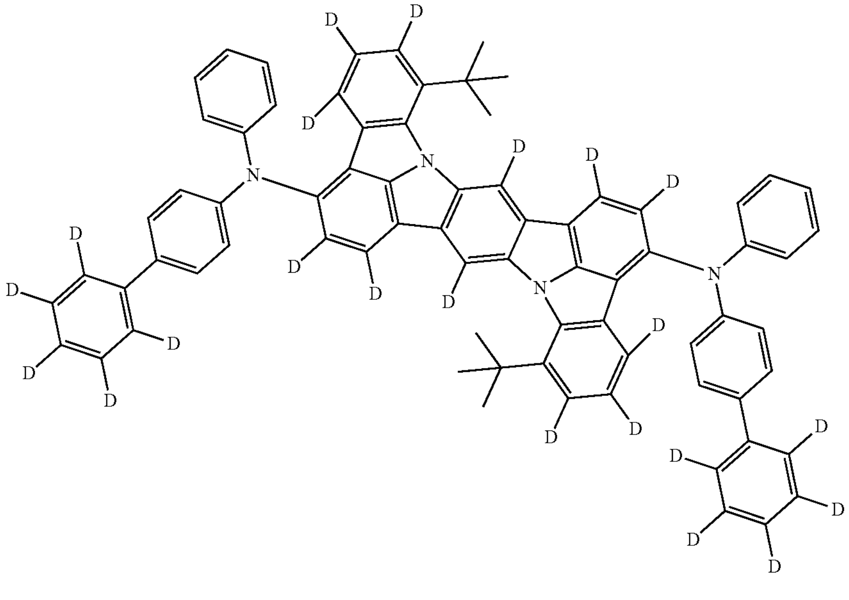

-continued
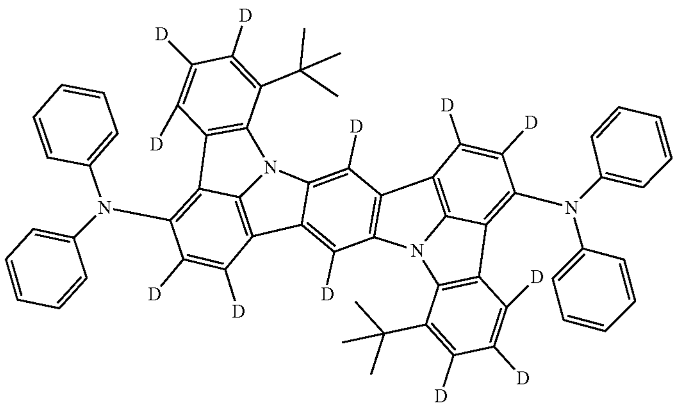
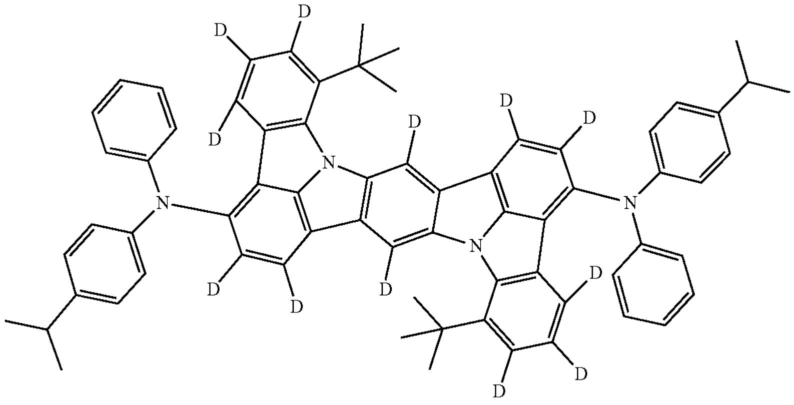
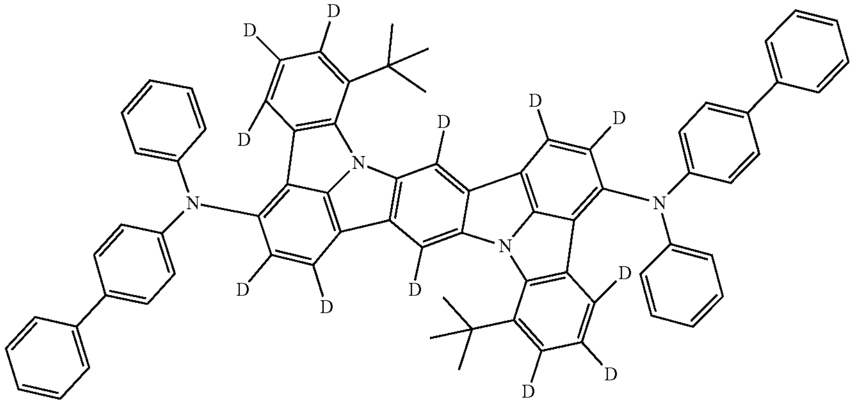

-continued
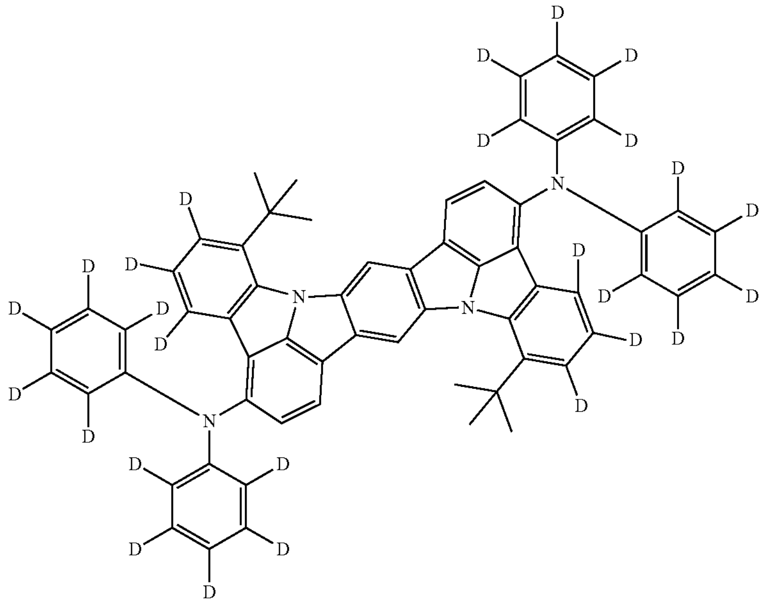
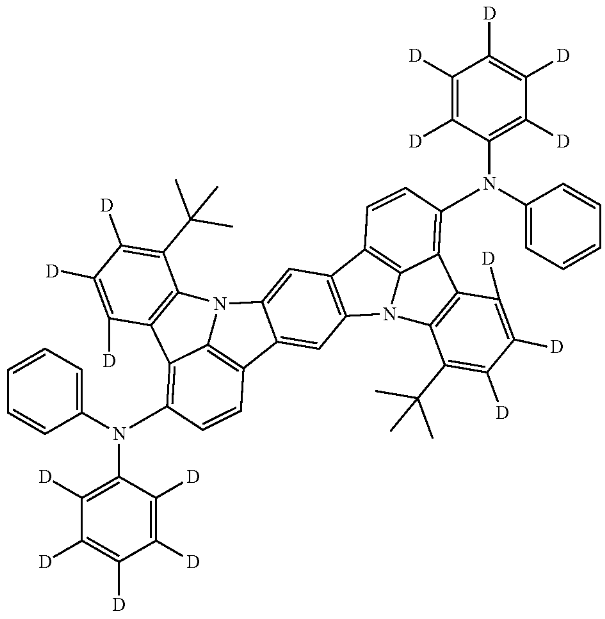

-continued
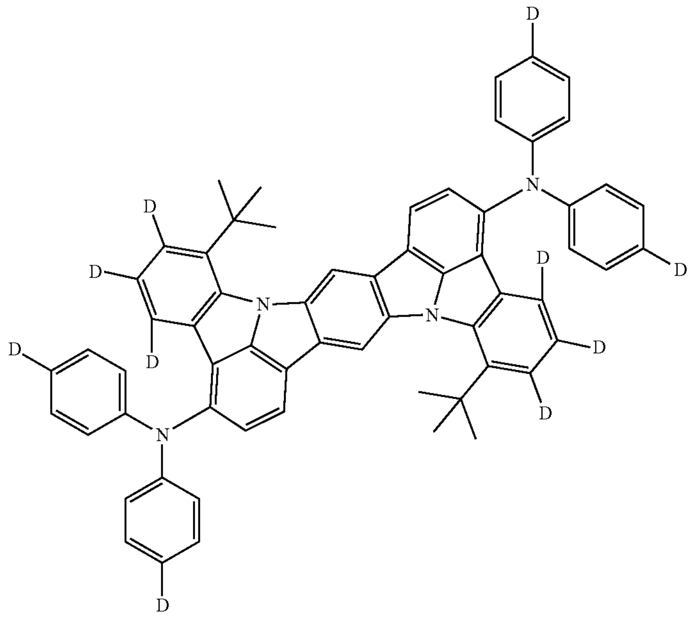
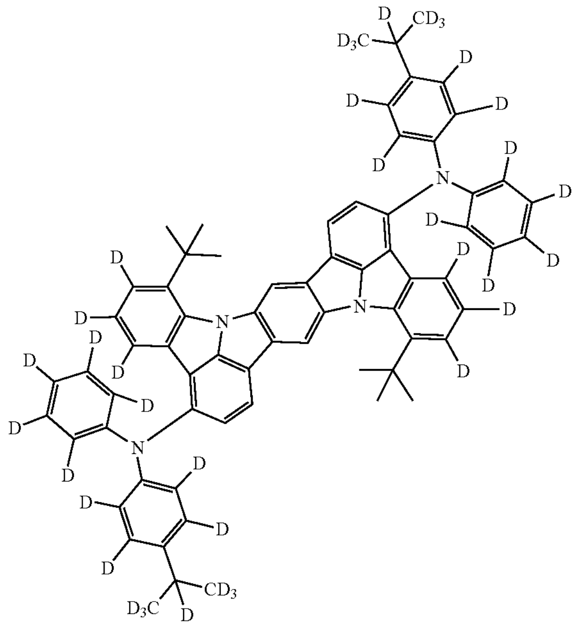

-continued
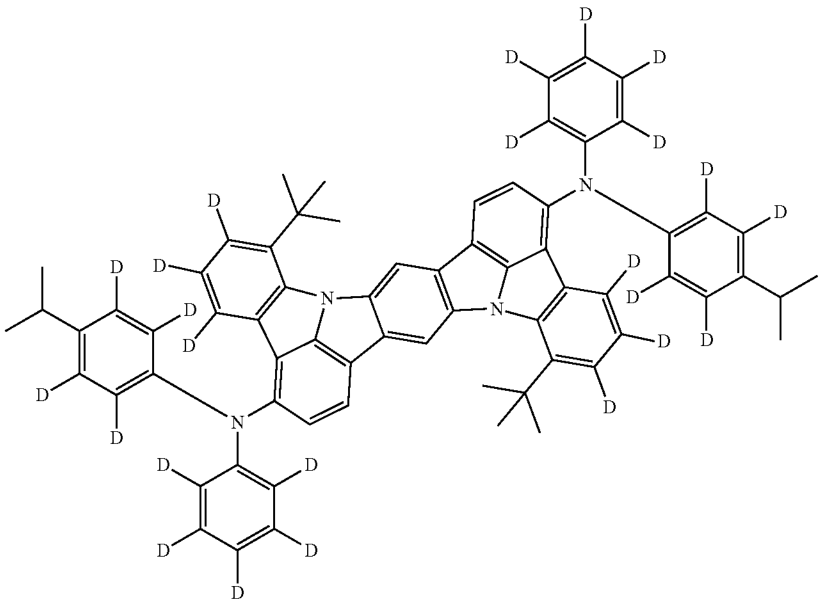
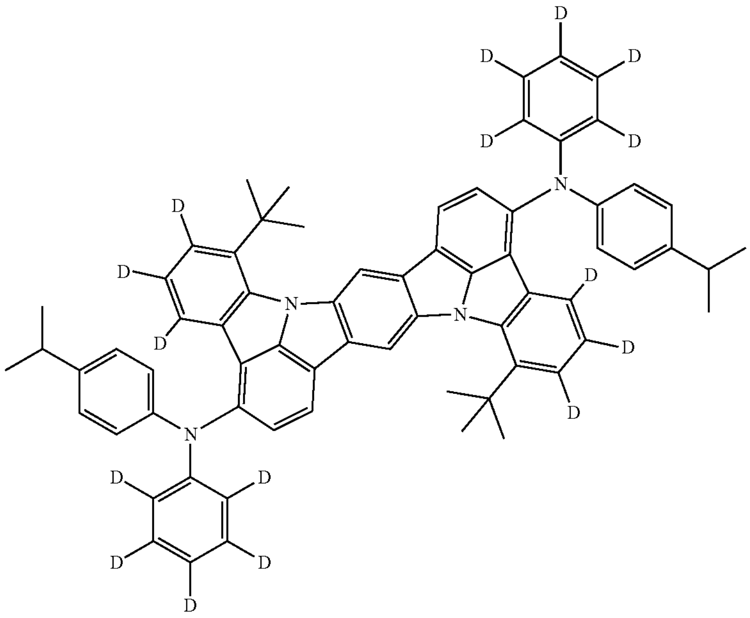

-continued
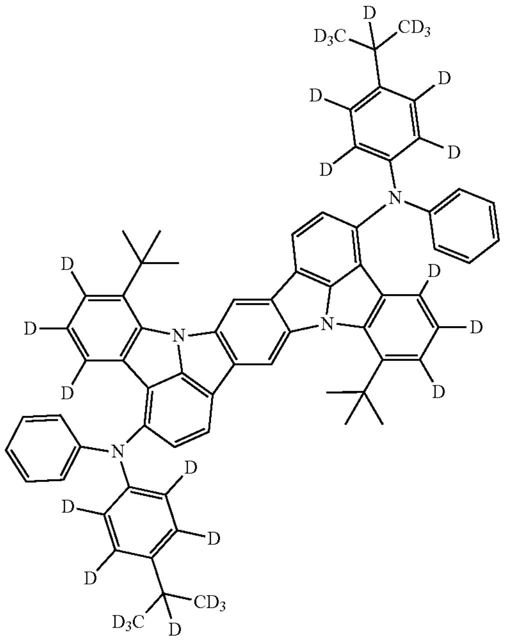
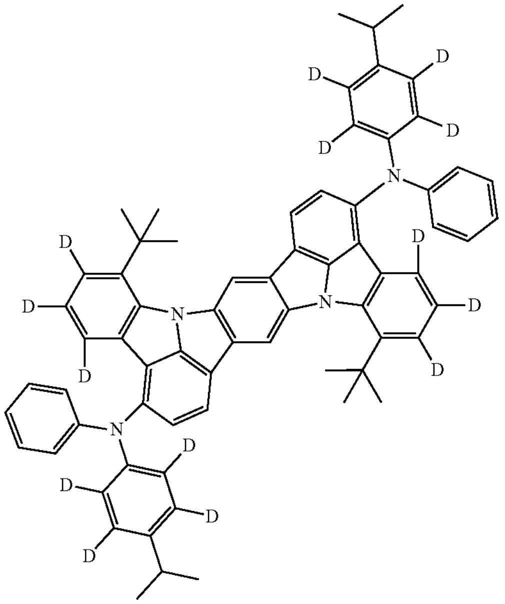
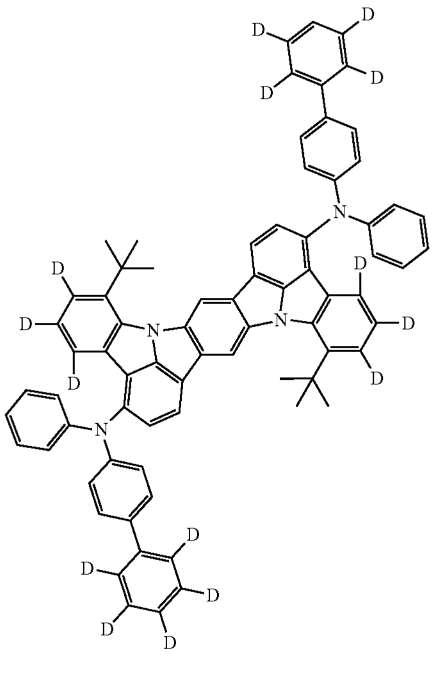
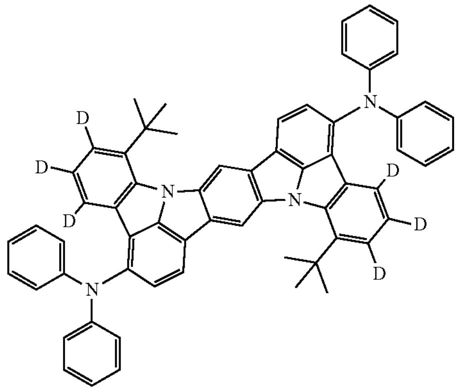

-continued
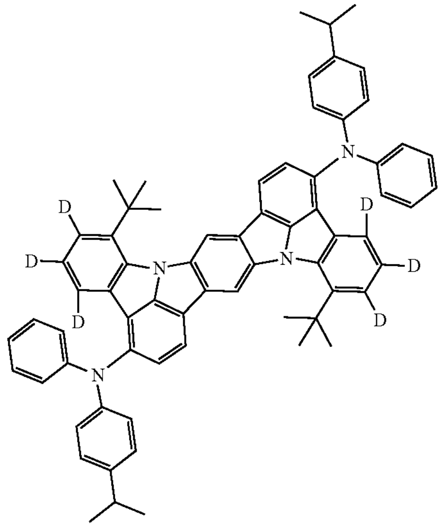
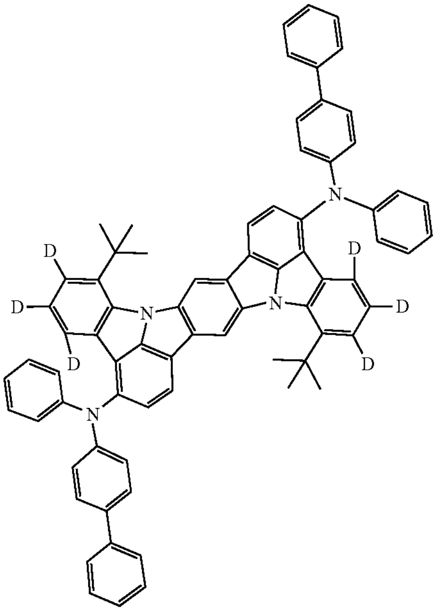
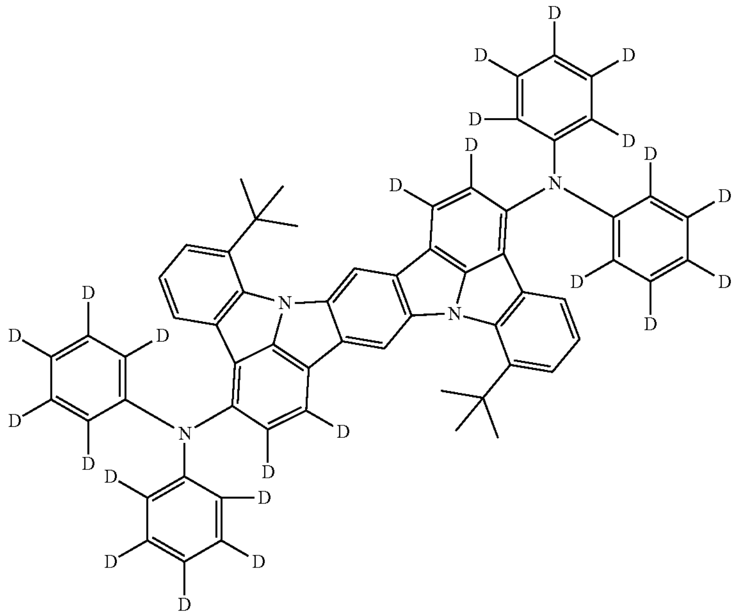
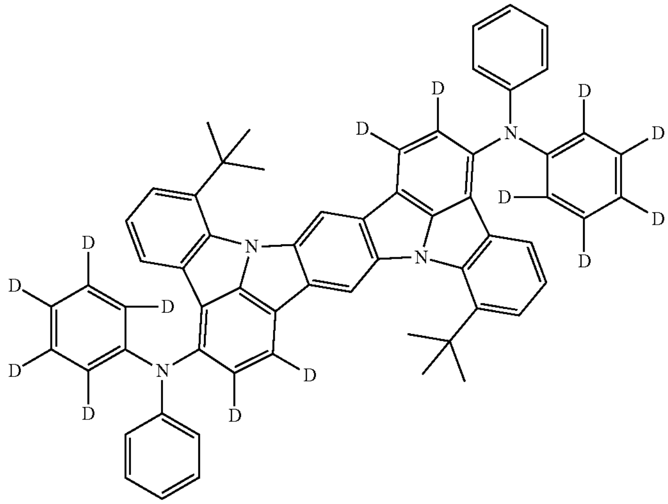

-continued
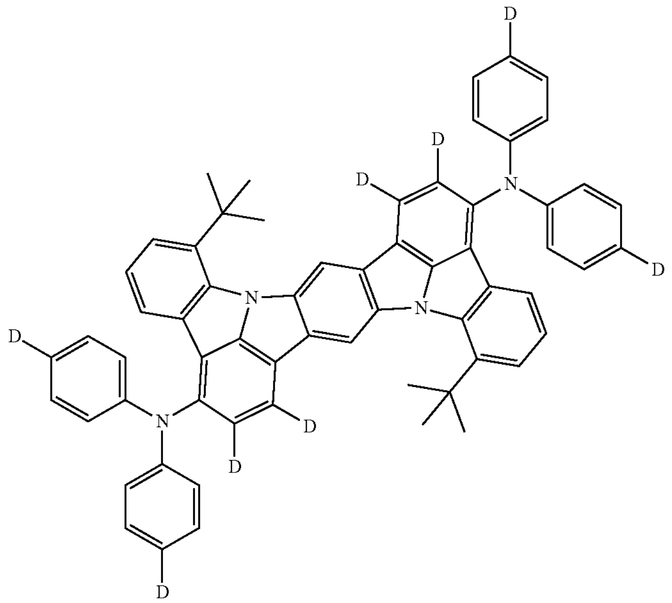
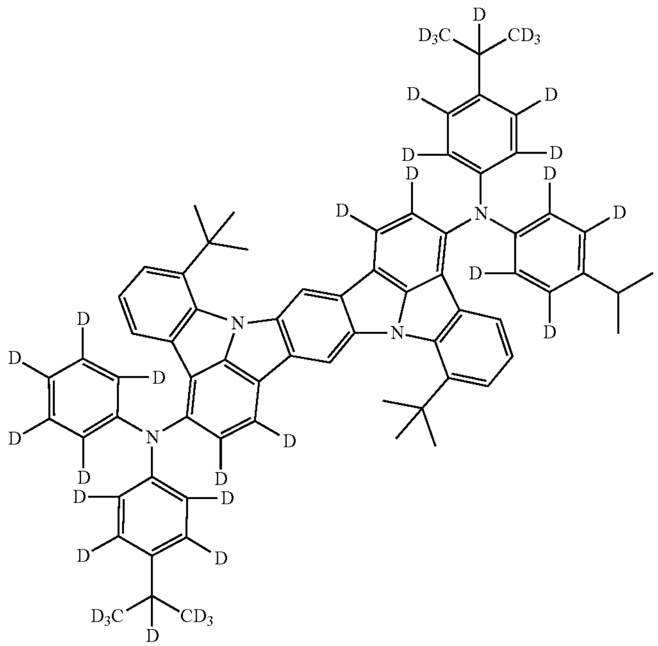

-continued
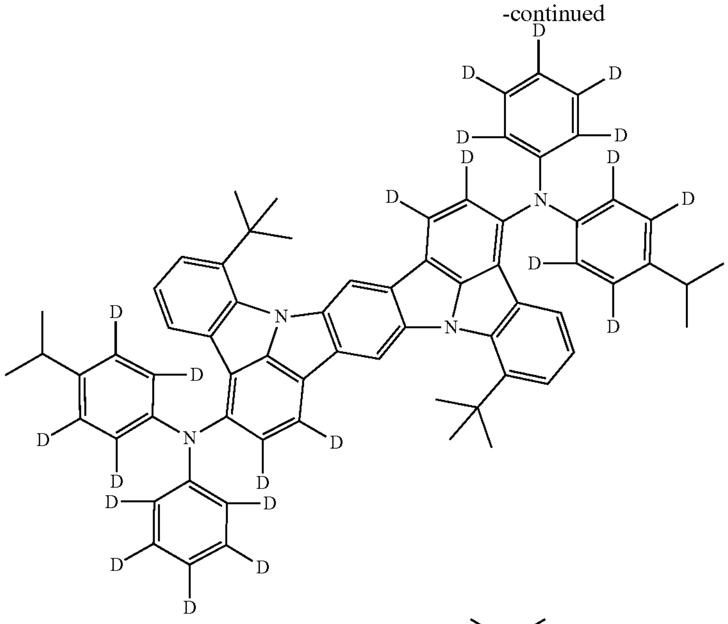
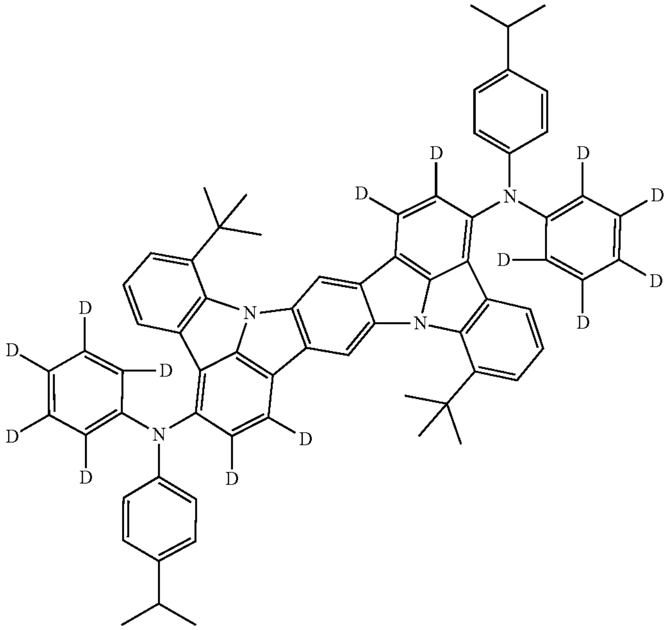
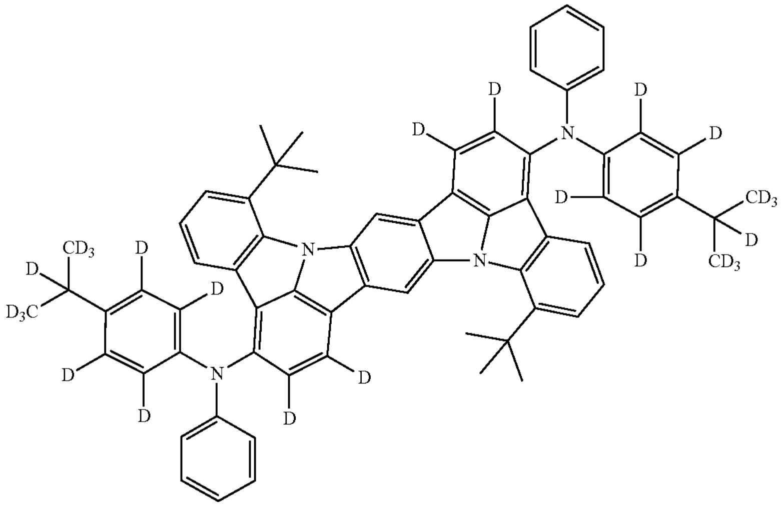

-continued
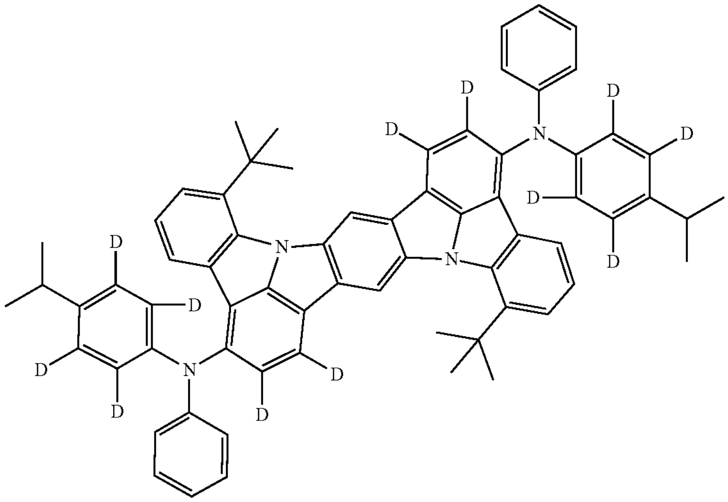
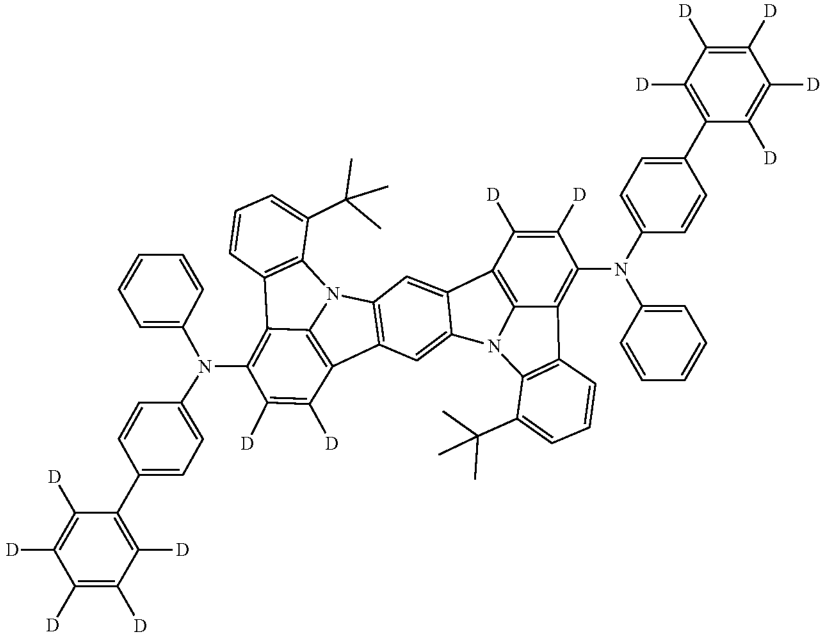
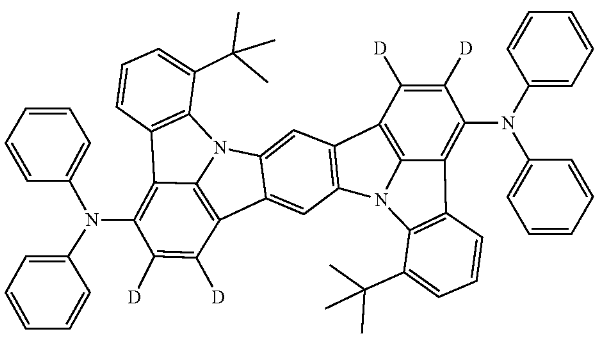

-continued
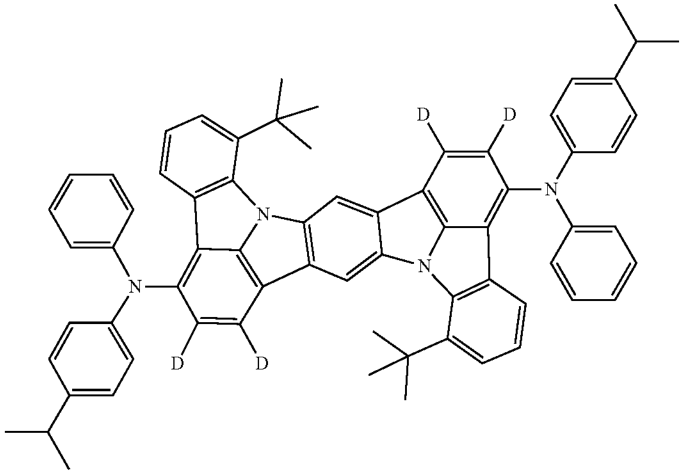
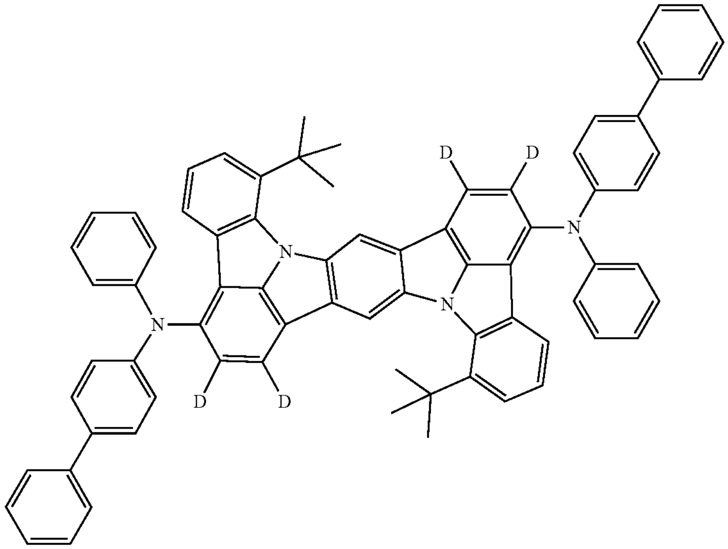
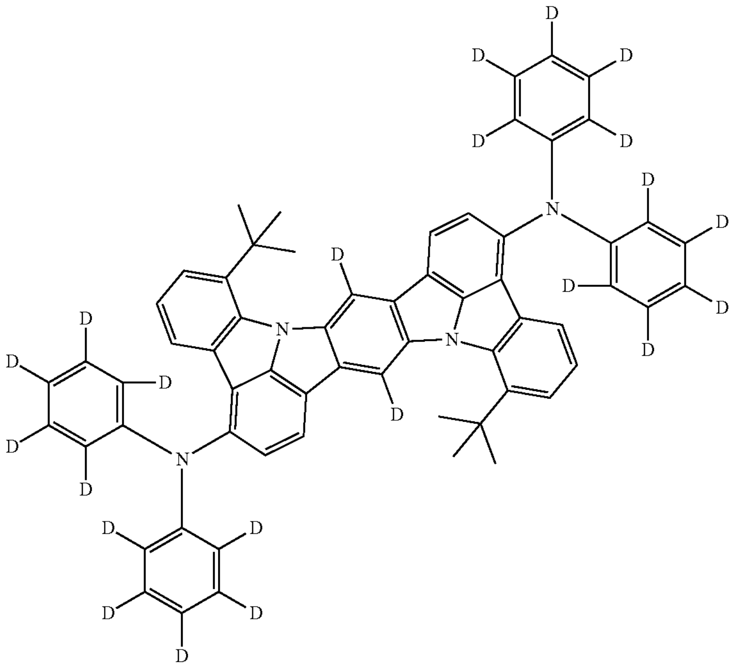

-continued
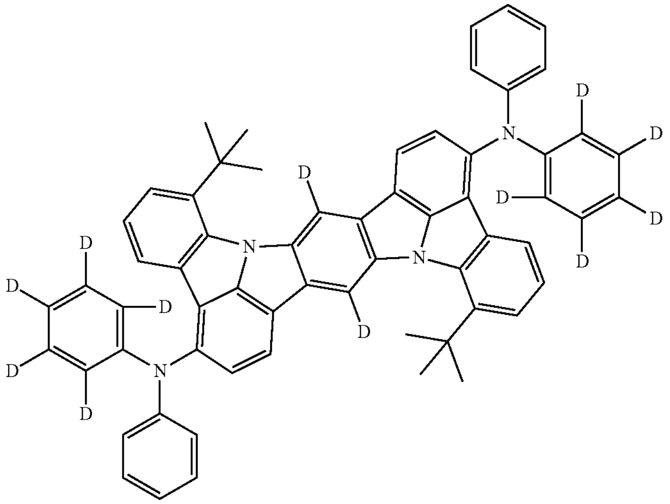
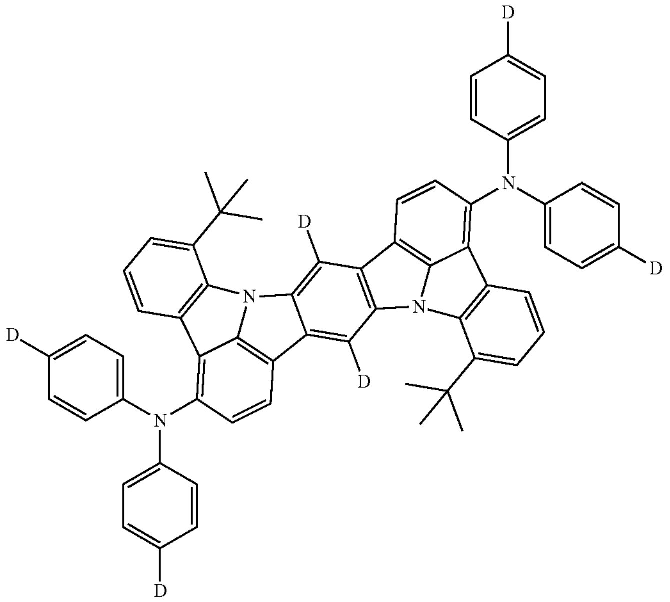
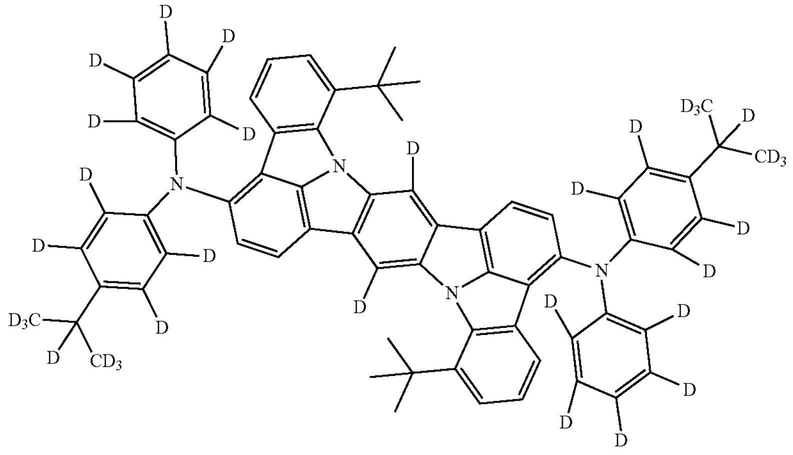

-continued
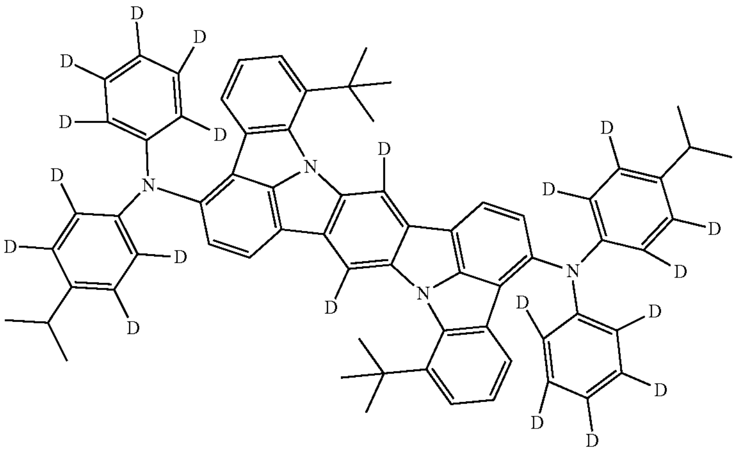
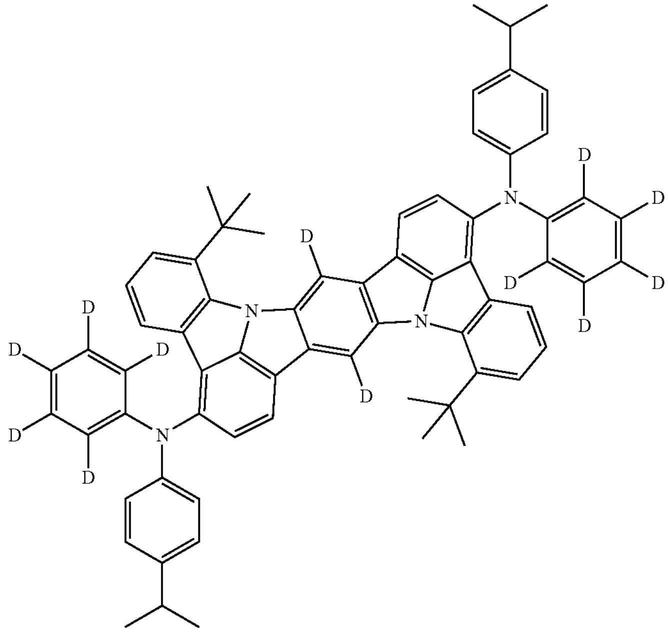
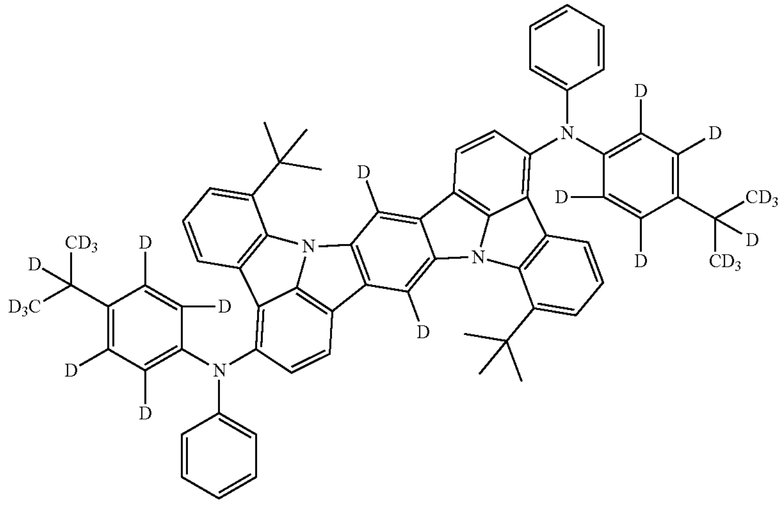

-continued
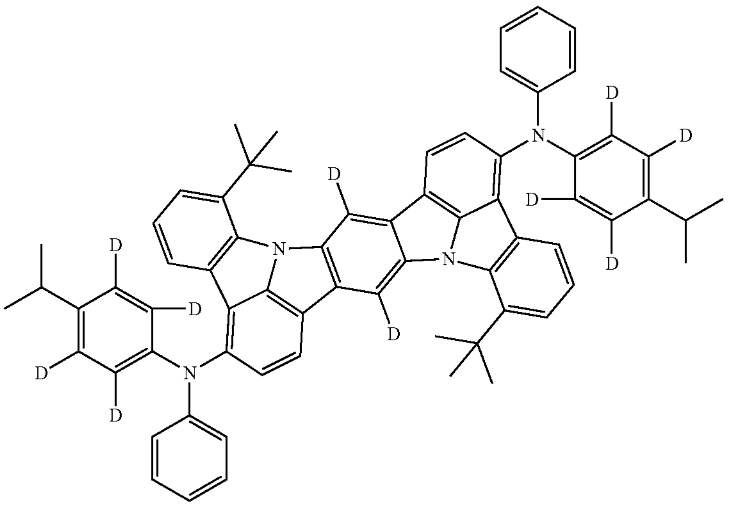
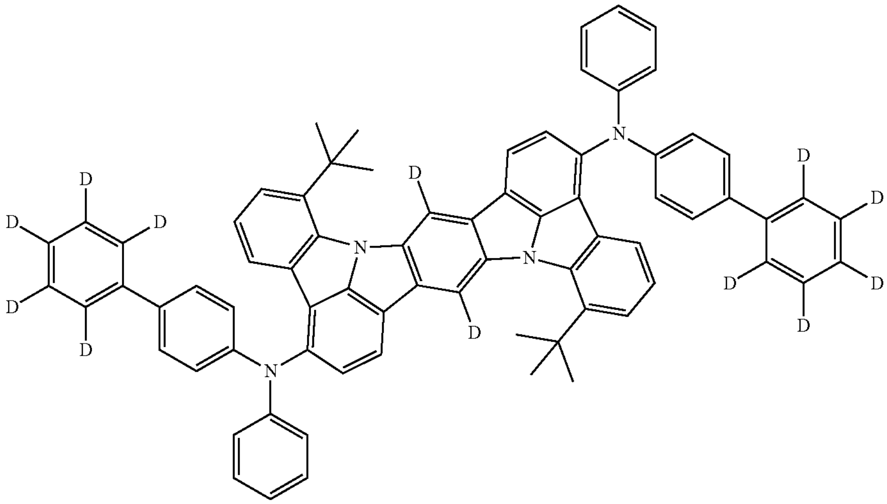
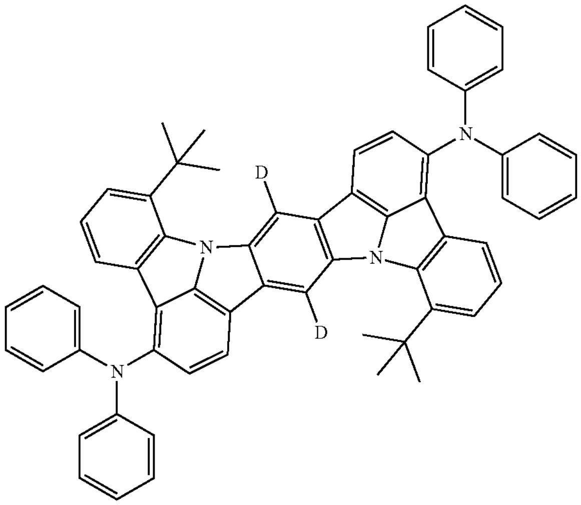

-continued

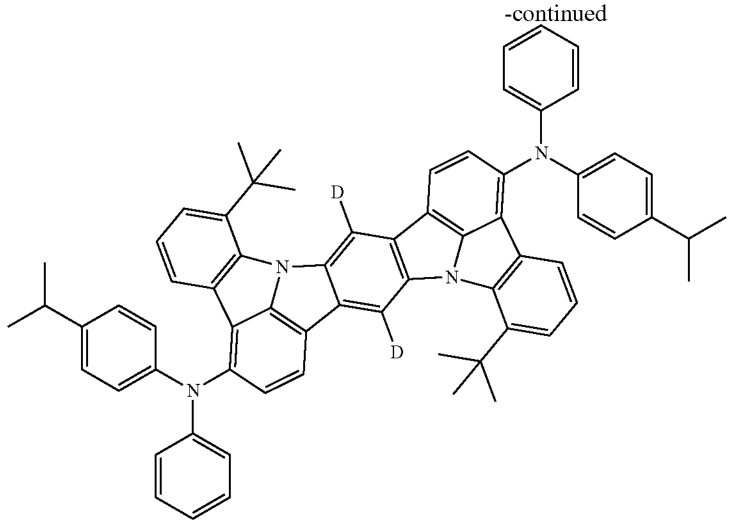

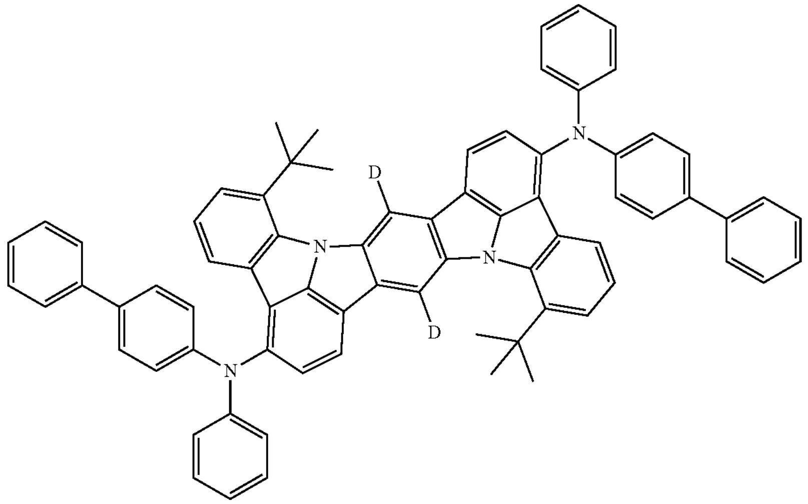

The compound represented by the formula (A1) can be synthesized, for example, with reference to the reactions described in Synthesis Examples later by using known alternative reactions or raw materials tailored to the target compound.

An intermediate F for synthesizing the compound represented by the formula (A10) can be synthesized, for example, according to the following synthetic scheme.

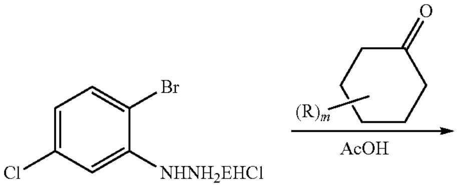

Intermediate A

-continued

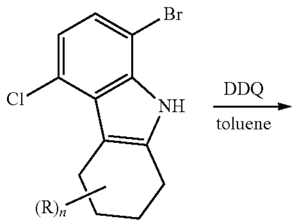

Intermediate B

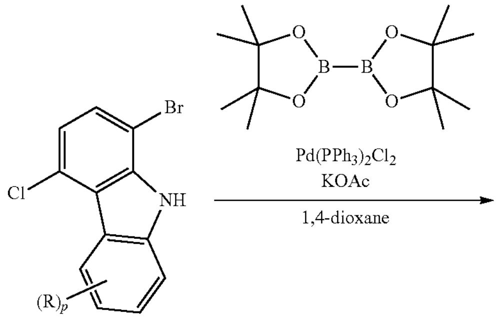

Intermediate C

-continued

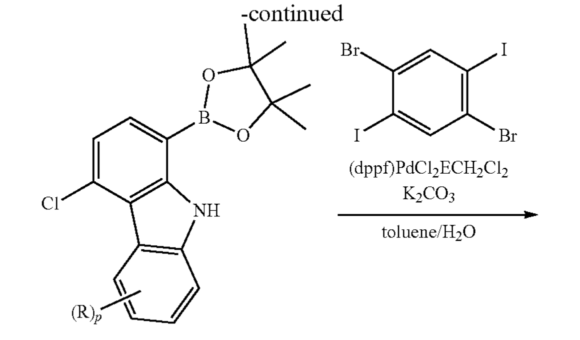

Intermediate D

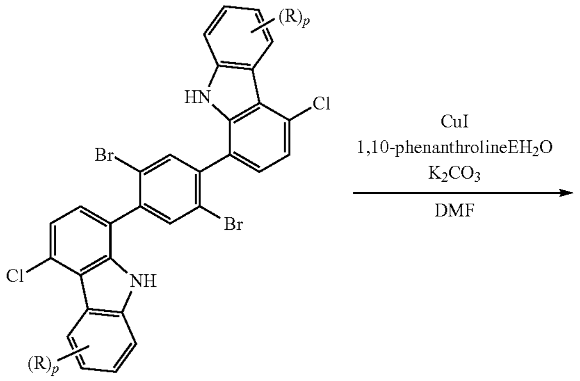

Intermediate E

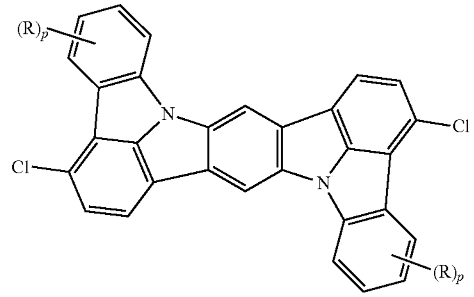

Intermediate F

In the above scheme, m is an integer of 0 to 10, n is an integer of 0 to 8, p is an integer of 0 to 4, and when p is an integer of 1 to 4, R is the same as the substituent R in the case where each of $R_1$ to $R_4$ and $R_1$ to $R_{13}$ in the formula (A10) is the substituent R.

DDQ is 2,3-dichloro-5,6-dicyano-p-benzoquinone.

$Pd(PPh)_2Cl_2$ is [1,1'-bis(diphenylphosphino)ferrocene]dichloropalladium(II).

$(dppf)PdCl_2$—$CH_2C_2$ is a [1,1'-bis(diphenylphosphino) ferrocene]dichloropalladium(II) dichloromethane complex.

DMF is dimethylformamide.

[Material for Organic EL Device]

A material for an organic EL device according to one aspect of the invention contains a compound represented by the formula (A1).

In one embodiment, the material for the organic EL device contains the compound represented by the formula (A1) (hereinafter also referred to as the "deuterium compound"), and a compound having the structures same as the compound represented by the formula (A1) except that the hydrogen atoms included therein are all protium atoms (hereinafter also referred to as the "protium compound"), and the former is contained in a content ratio of 1 mol % or more, relative to the sum thereof.

In one embodiment, the content ratio of the deuterium compound is 30 mol % or more, 60 mol % or more, 70 mol % or more, 90 mol % or more, 95% mol or more, 98 mol % or more, or 99 mol % or more.

[Organic EL Device]

The organic EL device of one aspect of the invention includes a cathode;

an anode; and at least one organic layer disposed between the cathode and the anode, wherein at least one layer of the at least one organic layer contains the compound represented by the formula (A1).

In one embodiment, the at least one organic layer includes an emitting layer, and the emitting layer contains the compound represented by the formula (A1).

In one embodiment, the compound represented by the formula (A1) is contained in the emitting layer as a dopant material.

A schematic configuration of an organic EL device according to one aspect of the invention will be described with reference to the FIGURE.

The organic EL device 1 according to one aspect of the invention includes a substrate 2, an anode 3, an emitting layer 5 as an organic layer, a cathode 10, an organic layer 4 between the anode 3 and the emitting layer 5, and an organic layer 6 between the emitting layer 5 and the cathode 10.

Each of the organic layer 4 and the organic layer 6 may be a single layer or may be composed of a plurality of layers.

Further, the organic layer 4 may include a hole-transporting region. The hole-transporting region may include a hole-injecting layer, a hole-transporting layer, an electron barrier layer, and the like. The organic layer 6 may include an electron-transporting region. The electron-transporting region may include an electron-injecting layer, an electron-transporting layer, a hole barrier layer, and the like.

The compound represented by the formula (A1) is contained in the organic layer 4, the emitting layer 5, or the organic layer 6. In one embodiment, the compound represented by the formula (A1) is contained in the emitting layer 5. The compound represented by the formula (A1) can function as a dopant material in the emitting layer 5.

The organic EL device according to one aspect of the invention exhibits high device performance by having the above-mentioned configuration. Specifically, an organic EL device having a long lifetime can be provided.

In addition, according to the organic EL device of one aspect, a method of improving the performance of the organic EL device can also be provided by using the compound represented by the formula (A1) in the emitting layer of the organic EL device. According to another aspect of the organic EL device, it is also possible to provide a method of improving the performance of the organic EL device by using the compound represented by the formula (A1) and a compound represented by the formula (10) described later in combination in the emitting layer of the organic EL device. Specifically, the method can improve the performance of the organic EL device as compared with the case where a compound having the structure same as the compound represented by the formula (A1) except that the hydrogen atoms included therein are all protium atoms (hereinafter, also referred to as the "protium compound") is used as the dopant material. Note that the case where "the protium compound is used" means the case where the compound substantially containing only protium is used as the dopant material in the emitting layer (e.g. the case where the protium compound is 90 mol % or more, 95 mol % or more, or 99 mol % or more, relative to the sum of the compound represented by the formula (A1) and the protium compound).

That is, the device performance can be improved by using a compound in which at least one of protium atoms of the protium compound is replaced with a deuterium atom (i.e. the compound represented by the formula (A1)) as the dopant material instead of the protium compound or in addition to the protium compound.

In one embodiment, the emitting layer contains the compound represented by the formula (A1) (deuterium compound), and a compound having the structures same as the compound represented by the formula (A1) except that the hydrogen atoms included therein are all protium atoms, and the former is contained in a content ratio of 1 mol % or more, relative to the sum thereof.

In one embodiment, the emitting layer contains the compound represented by the formula (A1), i.e., the deuterium compound and the protium compound, and the deuterium compound is contained in the emitting layer in a content ratio of 30 mass % or more, 60 mass % or more, 70 mass %, 90 mass % or more, 95 mass % or more, 98 mass % or more, or 99 mass % or more, relative to the sum thereof.

The organic EL device of one aspect of the invention includes a cathode;

an anode; and at least one organic layer disposed between the cathode and the anode, wherein the at least one organic layer includes an emitting layer, and the emitting layer contains the compound represented by the formula (A1), and a compound represented by the following formula (10).

The compound represented by the formula (A1) is as described above.

An effect of increasing the lifetime of the organic EL device is obtained by using the compound represented by the formula (A1) and the compound represented by the following formula (10) in the emitting layer.

<Compound Represented by Formula (10)>

The compound represented by the formula (10) will be described.

(10)

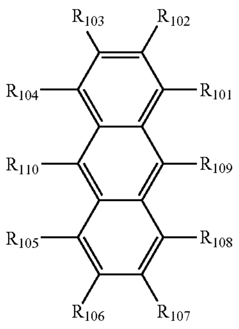

In the formula (10), one or more sets of adjacent two or more among $R_{101}$ to $R_{110}$ form a substituted or unsubstituted, saturated or unsaturated ring by bonding with each other, or do not form the substituted or unsubstituted, saturated or unsaturated ring.

$R_{101}$ to $R_{110}$ that do not form the substituted or unsubstituted, saturated or unsaturated ring are independently a hydrogen atom, a substituent R, or a group represented by the following formula (11):

$$-L_{101}-Ar_{101} \quad (11)$$

In the formula (11), $L_{101}$ is a single bond, a substituted or unsubstituted arylene group including 6 to 50 ring carbon atoms, or a substituted or unsubstituted divalent heterocyclic group including 5 to 50 ring atoms.

$Ar_{101}$ is a substituted or unsubstituted aryl group including 6 to 50 ring carbon atoms, or a substituted or unsubstituted monovalent heterocyclic group including 5 to 50 ring atoms.

the substituent R is a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms.

When two or more of the substituent R's are present, the two or more of the substituent R's may be the same as or different from each other.

$R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms.

When two or more of each of $R_{901}$ to $R_{907}$ are present, the two or more of each of $R_{901}$ to $R_{907}$ may be the same as or different from each other.

Provided that at least one of $R_{101}$ to $R_{110}$ that do not form the substituted or unsubstituted, saturated or unsaturated ring is a group represented by the formula (11). When two or more of the groups represented by the formula (11) are present, the two or more of the groups represented by the formula (11) may be the same as or different from each other.

The compound represented by the formula (10) may have a deuterium atom as a hydrogen atom.

In one embodiment, at least one $Ar_{101}$ in the formula (10) is a substituted or unsubstituted aryl group including 6 to 50 ring carbon atoms.

In one embodiment, at least one $Ar_{101}$ in the formula (10) is a substituted or unsubstituted monovalent heterocyclic group including 5 to 50 ring atoms.

In one embodiment, all $Ar_{101}$'s in the formula (10) are a substituted or unsubstituted aryl group including 6 to 50 ring carbon atoms. A plurality of $Ar_{101}$'s may be the same as or different from each other.

In one embodiment, one of $Ar_{101}$'s in the formula (10) is a substituted or unsubstituted monovalent heterocyclic group including 5 to 50 ring atoms, and the remaining $Ar_{101}$'s are a substituted or unsubstituted aryl group including 6 to 50 ring carbon atoms. A plurality of $Ar_{101}$'s may be the same as or different from each other.

In one embodiment, at least one $L_{101}$ in the formula (10) is a single bond.

In one embodiment, all of $L_{101}$'s in the formula (10) are single bonds.

In one embodiment, at least one $L_{101}$ in the formula (10) is a substituted or unsubstituted arylene group including 6 to 50 ring carbon atoms.

In one embodiment, at least one $L_{101}$ in the formula (10) is a substituted or unsubstituted phenylene group or a substituted or unsubstituted naphthyl group.

In one embodiment, the group represented by $-L_{101}-Ar_{101}$ in the formula (10) is selected from the group consisting of a substituted or unsubstituted phenyl group,
a substituted or unsubstituted naphthyl group,
a substituted or unsubstituted biphenyl group,
a substituted or unsubstituted phenanthrenyl group,
a substituted or unsubstituted benzophenanthrenyl group,
a substituted or unsubstituted fluorenyl group,
a substituted or unsubstituted benzofluorenyl group,
a substituted or unsubstituted dibenzofuranyl group,
a substituted or unsubstituted naphthobenzofuranyl group,
a substituted or unsubstituted dibenzothiophenyl group, and
a substituted or unsubstituted carbazolyl group.

In one embodiment, the substituent R in the formula (10) are independently a substituted or unsubstituted alkyl group including 1 to 50 carbon atoms,
a substituted or unsubstituted cycloalkyl group including 3 to 50 ring carbon atoms,
$—Si(R_{901})(R_{902})(R_{903})$,
$—O—(R_{904})$,
$—S—(R_{905})$,
$—N(R_{906})(R_{907})$,
a halogen atom, a cyano group, a nitro group, or
a substituted or unsubstituted aryl group including 6 to 50 ring carbon atoms.

$R_{901}$ to $R_{907}$ are as defined in the formula (10).

In one embodiment, the substituent in the case of the "substituted or unsubstituted" in the formula (10) are independently a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
$—Si(R_{901})(R_{902})(R_{903})$,
$—O—(R_{904})$,
$—S—(R_{905})$,
$—N(R_{906})(R_{907})$,
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms.

$R_{901}$ to $R_{907}$ are as defined in the formula (10).

In one embodiment, the substituent in the case of the "substituted or unsubstituted" in the formula (10) are independently a substituted or unsubstituted alkyl group including 1 to 50 carbon atoms,
a substituted or unsubstituted cycloalkyl group including 3 to 50 ring carbon atoms,
$—Si(R_{901})(R_{902})(R_{903})$,
$—O—(R_{904})$,
$—S—(R_{905})$,
$—N(R_{906})(R_{907})$,
a halogen atom, a cyano group, a nitro group, or
a substituted or unsubstituted aryl group including 6 to 50 ring carbon atoms.

$R_{901}$ to $R_{907}$ are as defined in the formula (10).

In one embodiment, the substituent in the case of the "substituted or unsubstituted" in the formula (10) is selected from the group consisting of an alkyl group including 1 to 18 carbon atoms,
an aryl group including 6 to 18 ring carbon atoms, and
a monovalent heterocyclic group including 5 to 18 ring atoms.

In one embodiment, the substituent in the case of the "substituted or unsubstituted" in the formula (10) is an alkyl group including 1 to 5 carbon atoms.

In one embodiment, the compound represented by the formula (10) is a compound represented by the following formula (20).

(20)

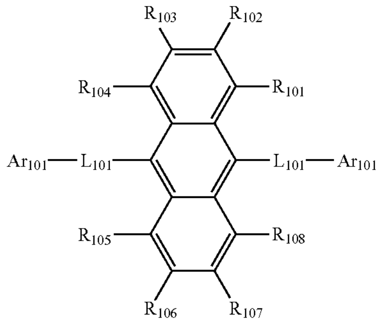

In the formula (20), $R_{101}$ to $R_{108}$, $L_{101}$, and $Ar_{101}$ are as defined in the formula (10).

The compound represented by the formula (20) may have a deuterium atom as a hydrogen atom.

In other words, in one embodiment, the compound represented by the formula (10) or formula (20) has at least two groups represented by the formula (11).

In one embodiment, the compound represented by the formula (10) or formula (20) has two or three groups represented by the formula (11).

In one embodiment, $R_{101}$ to $R_{110}$ in each of the formulas (10) and (20) do not form the substituted or unsubstituted, saturated or unsaturated ring.

In one embodiment, $R_{101}$ to $R_{110}$ in each of the formulas (10) and (20) are hydrogen atoms.

In one embodiment, the compound represented by the formula (20) is a compound represented by the following formula (30).

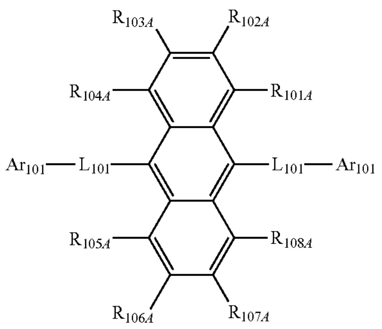

(30)

In the formula (30), $L_{101}$ and $Ar_{01}$ are as defined in the formula (10).

Adjacent two of $R_{101A}$ to $R_{108A}$ do not form a substituted or unsubstituted, saturated or unsaturated ring.

$R_{101A}$ to $R_{108A}$ are independently a hydrogen atom, or a substituent R.

The substituent R is as defined in the formula (10).

In other words, the compound represented by the formula (30) is a compound having two groups represented by the formula (11).

The compound represented by the formula (30) has substantially only protium atoms as hydrogen atoms.

Note that "having substantially only protium atoms" means the case where the content ratio of a compound having only protium atoms as hydrogen atoms (protium compound) is 90 mol % or more, 95 mol % or more, or 99 mol % or more, relative to the sum of the protium compound and a compound having the structure same as the protium compound but having at least one deuterium atoms as a hydrogen atom (deuterium compound).

In one embodiment, the compound represented by the formula (30) is a compound represented by the following formula (31).

In the formula (31), $L_{101}$ and $Ar_{101}$ are as defined in the formula (10).

$R_{101A}$ to $R_{108A}$ are as defined in the formula (30).

$X_b$ is O, S, $N(R_{131})$, or $C(R_{132})(R_{133})$.

One of $R_{121}$ to $R_{128}$ and $R_{131}$ to $R_{133}$ is a single bond which bonds with $L_{101}$.

One or more sets of adjacent two or more among $R_{121}$ to $R_{128}$ that are not a single bond which bonds with $L_{101}$ form a substituted or unsubstituted, saturated or unsaturated ring by bonding with each other, or do not form the substituted or unsubstituted, saturated or unsaturated ring.

$R_{121}$ to $R_{128}$ that are not a single bond which bonds with $L_{101}$ and do not form the substituted or unsubstituted, saturated or unsaturated ring are independently a hydrogen atom, or a substituent R.

The substituent R is as defined in the formula (10).

$R_{131}$ to $R_133$ that are not a single bond which bonds with $L_{101}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms.

When two or more of each of $R_{131}$ to $R_133$ are present, the two or more of each of $R_{131}$ to $R_{133}$ may be the same as or different from each other.

In one embodiment, the compound represented by the formula (31) is a compound represented by the following formula (32).

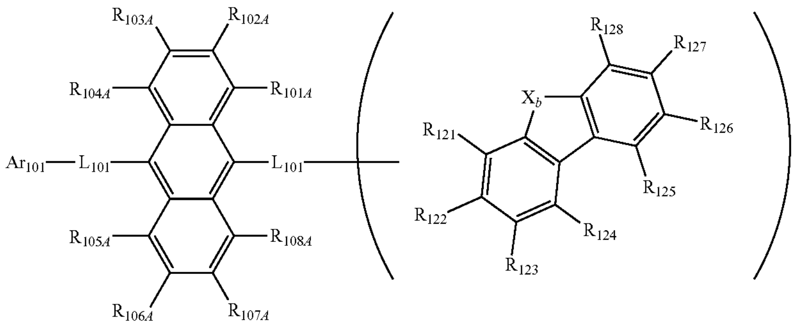

(31)

(32)

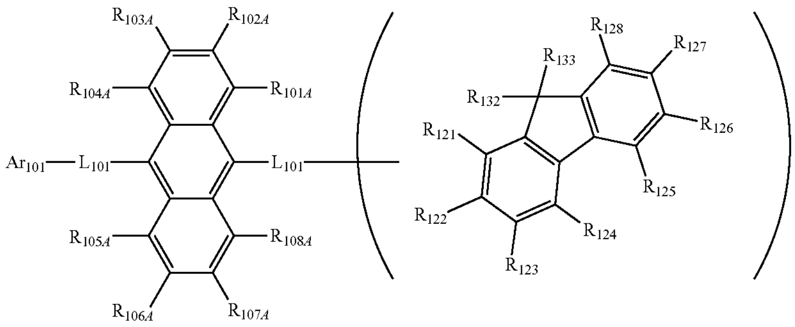

In the formula (32), $R_{101A}$ to $R_{108A}$, $L_{101}$, $Ar_{101}$, $R_{121}$ to $R_{128}$, $R_{132}$, and $R_{133}$ are as defined in the formula (31).

In one embodiment, the compound represented by the formula (31) is a compound represented by the following formula (33).

(33)

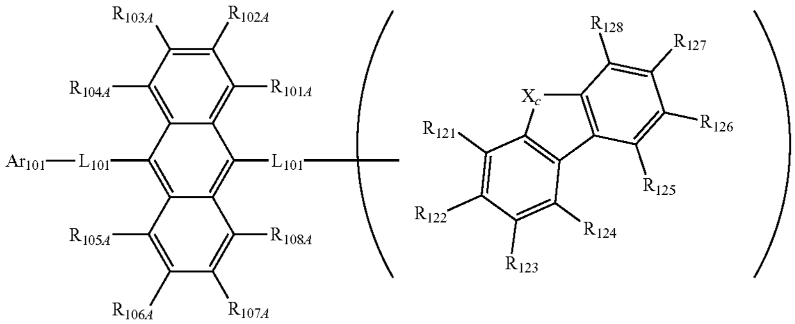

In the formula (33), $R_{101A}$ to $R_{108A}$, $L_{101}$, $Ar_{101}$, and $R_{121}$ to $R_{128}$ are as defined in the formula (31).

$X_c$ is O, S, or $NR_{131}$.

$R_{131}$ is as defined in the formula (31).

In one embodiment, the compound represented by the formula (31) is a compound represented by the following formula (34).

(34)

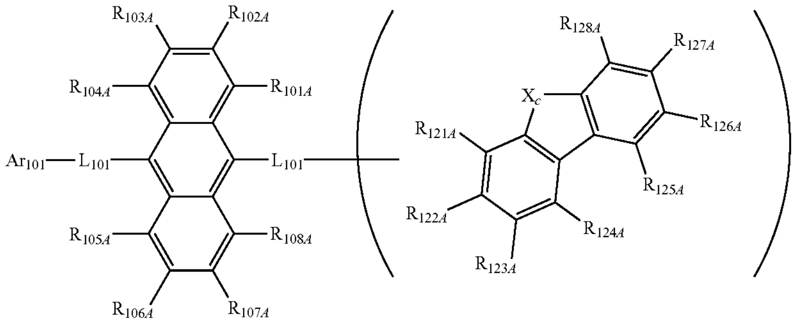

In the formula (34), $R_{101A}$ to $R_{108A}$, $L_{101}$, and $Ar_{101}$ are as defined in the formula (31).

$X_c$ is O, S, or $NR_{131}$.

$R_{131}$ is as defined in the formula (31).

One of $R_{121A}$ to $R_{128A}$ is a single bond which bonds with $L_{101}$.

One or more sets of adjacent two or more among $R_{121A}$ to $R_{128A}$ that are not a single bond which bonds with $L_{101}$ do not form a substituted or unsubstituted, saturated or unsaturated ring.

$R_{121A}$ to $R_{128A}$ that are not a single bond which bonds with $L_{101}$ are independently a hydrogen atom, or a substituent R.

The substituent R is as defined in the formula (10).

In one embodiment, the compound represented by the formula (31) is a compound represented by the following formula (35).

(35)

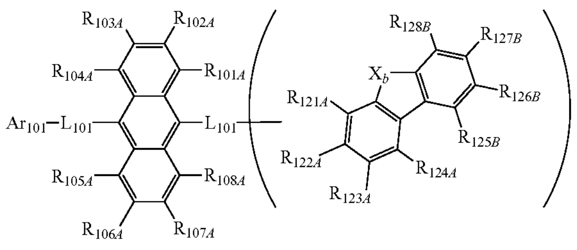

In the formula (35), $R_{101A}$ to $R_{108A}$, $L_{101}$, $Ar_{101}$, and $X_b$ are as defined in the formula (31).

One or more sets of adjacent two or more among $R_{121A}$ to $R_{124A}$ do not form a substituted or unsubstituted, saturated or unsaturated ring by bonding with each other.

Any one set of $R_{125B}$ and $R_{126B}$, $R_{126B}$ and $R_{127B}$, and $R_{127B}$ and $R_{128B}$ forms a ring represented by the following formula (35a) or (35b) by bonding with each other.

(35a)

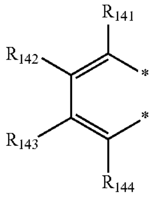

(35b)

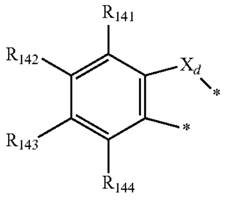

In the formulas (35a) and (35b), two *'s are respectively bonded with any one set of $R_{125B}$ and $R_{126B}$, $R_{126B}$ and $R_{127B}$, and $R_{127B}$ and $R_{128B}$.

$R_{141}$ to $R_{144}$ are independently a hydrogen atom, or a substituent R.

The substituent R is as defined in the formula (10).

$X_d$ is O or S.

One of $R_{121A}$ to $R_{124A}$, $R_{125B}$ to $R_{128B}$ that do not form the ring represented by the formula (35a) or (35b), and $R_{141}$ to $R_{144}$ is a single bond which bonds with $L_{101}$.

$R_{121A}$ to $R_{124A}$ which are not a single bond which bonds with $L_{101}$, and $R_{125B}$ to $R_{128B}$ which is not a single bond which bonds with $L_{101}$ and do not form the ring represented by the formula (35a) or (35b) are independently a hydrogen atom, or a substituent R.

The substituent R is as defined in the formula (10).

In one embodiment, the compound represented by the formula (35) is a compound represented by the following formula (36).

(36)

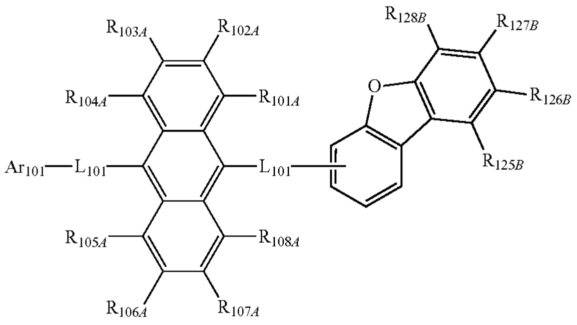

In the formula (36), $R_{101A}$ to $R_{108A}$, $L_{101}$, $Ar_{101}$, and $R_{125B}$ to $R_{128B}$ are as defined in the formula (35).

In one embodiment, the compound represented by the formula (34) is a compound represented by the following formula (37).

(37)

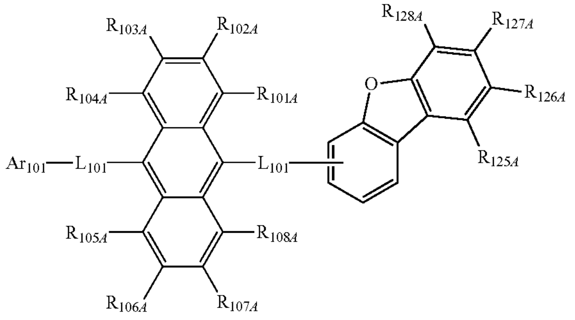

In the formula (37), $R_{101A}$ to $R_{108A}$, $R_{125A}$ to $R_{128A}$, $L_{101}$, and $Ar_{101}$ are as defined in the formula (34).

In one embodiment, $R_{101A}$ to $R_{108A}$ in each of the formulas (30) to (37) are hydrogen atoms.

In one embodiment, the compound represented by the formula (10) is a compound represented by the following formula (40).

(40)

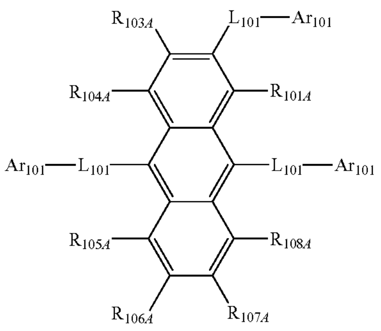

In the formula (40), $L_{101}$ and $Ar_{01}$ are as defined in the formula (10).

One or more sets of adjacent two or more among $R_{101A}$ and $R_{103A}$ to $R_{108A}$ form a substituted or unsubstituted, saturated or unsaturated ring by bonding with each other, or do not form a substituted or unsubstituted, saturated or unsaturated ring.

$R_{101A}$, and $R_{103A}$ to $R_{108A}$ that do not form the substituted or unsubstituted, saturated or unsaturated ring are independently a hydrogen atom, or a substituent R.

The substituent R is as defined in the formula (10).

In other words, the compound represented by the formula (40) is a compound having three groups represented by the formula (11). The compound represented by the formula (40) has substantially only protium atoms as hydrogen atoms.

In one embodiment, the compound represented by the formula (40) is a compound represented by the following formula (41).

(41)

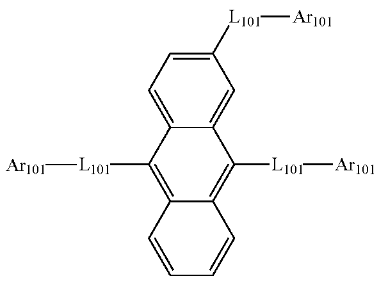

In the formula (41), $L_{101}$ and $Ar_{101}$ are as defined in the formula (40).

In one embodiment, the compound represented by the formula (40) is a compound represented by any one of the following formulas (42-1) to (42-3).

(42-1)

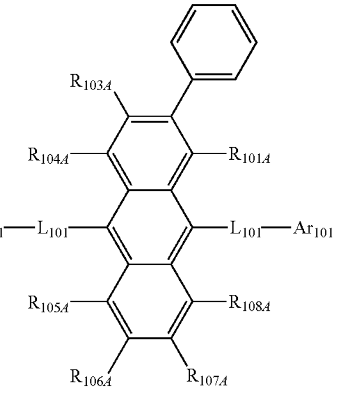

-continued (42-2)

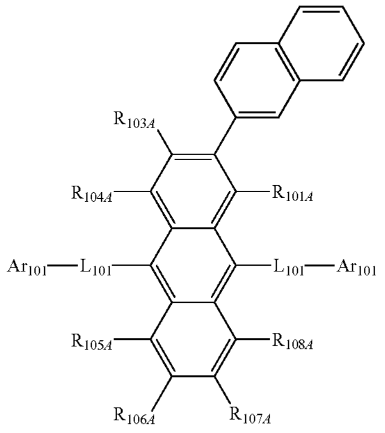

(42-3)

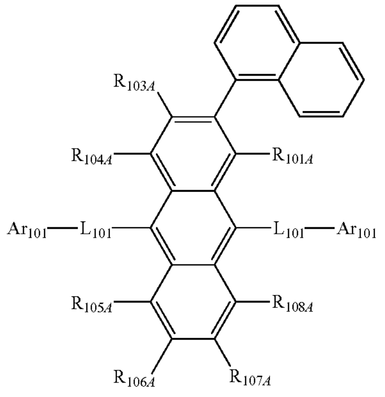

In the formulas (42-1) to (42-3), $R_{101A}$ to $R_{108A}$, $L_{101}$, and $Ar_{101}$ are as defined in the formula (40).

In one embodiment, the compounds represented by each of the formulas (42-1) to (42-3) are compounds represented by each of the following formulas (43-1) to (43-3), respectively.

(43-1)

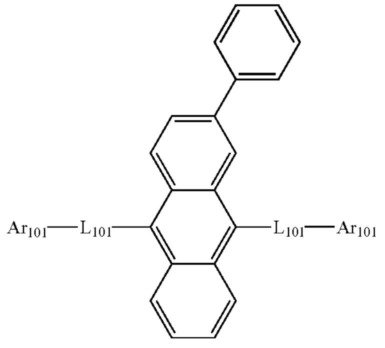

-continued (43-2)

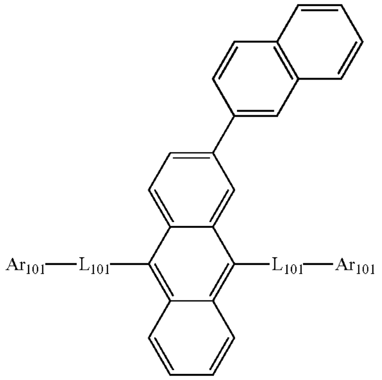

(43-3)

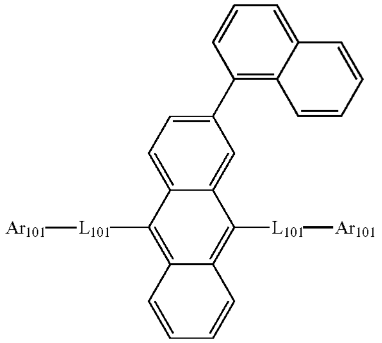

In the formulas (43-1) to (43-3), $L_{101}$ and $Ar_{101}$ are as defined in the formula (40).

In one embodiment, the group represented by $-L_{101}-Ar_{101}$ in each of the formulas (40), (41), (42-1) to (42-3), and (43-1) to (43-3) is selected from the group consisting of

- a substituted or unsubstituted phenyl group,
- a substituted or unsubstituted naphthyl group,
- a substituted or unsubstituted biphenyl group,
- a substituted or unsubstituted phenanthrenyl group,
- a substituted or unsubstituted benzophenanthrenyl group,
- a substituted or unsubstituted fluorenyl group,
- a substituted or unsubstituted benzofluorenyl group,
- a substituted or unsubstituted dibenzofuranyl group,
- a substituted or unsubstituted naphthobenzofuranyl group,
- a substituted or unsubstituted dibenzothiophenyl group, and
- a substituted or unsubstituted carbazolyl group.

In one embodiment, the compounds represented by each of the formula (10) and formula (20) respectively include a compound in which at least one hydrogen atom among the hydrogen atoms contained is a deuterium atom.

In one embodiment, in the formula (20), at least one hydrogen atom selected from the group consisting of the followings is a deuterium atom:

- hydrogen atoms when each of $R_{101}$ to $R_{108}$ is a hydrogen atom,
- hydrogen atoms possessed by $R_{101}$ to $R_{108}$ when each of $R_{101}$ to $R_{108}$ is the substituent R,
- hydrogen atoms possessed by $L_{101}$,
- hydrogen atoms possessed by a substituent that substitutes on $L_{101}$,
- hydrogen atoms possessed by $Ar_{101}$, and
- hydrogen atoms possessed by a substituent that substitutes on $Ar_{101}$.

In one embodiment, the compounds represented by each of the formulas (30) to (37) respectively include a compound in which at least one hydrogen atom among the hydrogen atoms contained is a deuterium atom.

In one embodiment, at least one hydrogen atom among the hydrogen atoms which bond with the carbon atoms constituting the anthracene skeleton in the compound represented by each of the formulas (30) to (37) is a deuterium atom.

In one embodiment, the compound represented by the formula (30) is a compound represented by the following formula (30D).

(30D)

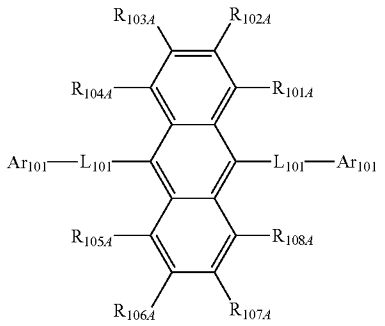

In the formula (30D), $R_{101A}$ to $R_{108A}$, $L_{101}$, and $Ar_{101}$ are as defined in the formula (30).

Provided that at least one hydrogen atom selected from the group consisting of the followings is a deuterium atom:

- hydrogen atoms when each of $R_{101A}$ to $R_{108A}$ is a hydrogen atom, hydrogen atoms possessed by $R_{101A}$ to $R_{108A}$ when each of $R_{101A}$ to $R_{108A}$ is the substituent R,
- hydrogen atoms possessed by $L_{101}$,
- hydrogen atoms possessed by a substituent that substitutes on $L_{101}$,
- hydrogen atoms possessed by $Ar_{101}$, and
- hydrogen atoms possessed by a substituent that substitutes on $Ar_{101}$.

In other words, the compound represented by the formula (30D) is a compound in which at least one hydrogen atom among the hydrogen atoms possessed by the compound represented by the formula (30) is a deuterium atom.

In one embodiment, at least one of the hydrogen atoms when each of $R_{101A}$ to $R_{108A}$ is a hydrogen atom in the formula (30D) is a deuterium atom.

In one embodiment, the compound represented by the formula (30D) is a compound represented by the following formula (31D).

(31D)

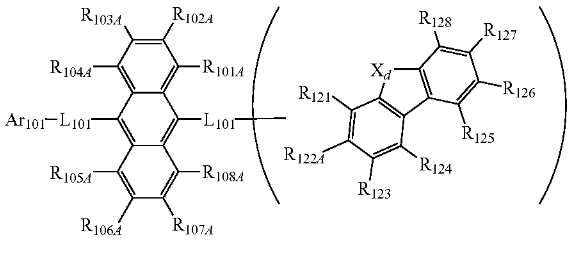

In the formula (31D), $R_{101A}$ to $R_{108A}$, $L_{101}$, and $Ar_{101}$ are as defined in the formula (30D).

$X_d$ is O or S.

One of $R_{121}$ to $R_{128}$ is a single bond which bonds with $L_{101}$.

One or more sets of adjacent two or more among $R_{121}$ to $R_{128}$ that are not a single bond which bonds with $L_{101}$ form a substituted or unsubstituted, saturated or unsaturated ring by bonding with each other, or do not form a substituted or unsubstituted, saturated or unsaturated ring.

$R_{121}$ to $R_{128}$ which are not a single bond which bonds with $L_{101}$ and do not form the substituted or unsubstituted, saturated or unsaturated ring are independently a hydrogen atom, or a substituent R.

The substituent R is as defined in the formula (10).

Provided that at least one hydrogen atom selected from the group consisting of the followings is a deuterium atom:

hydrogen atoms when each of $R_{101A}$ to $R_{108A}$ is a hydrogen atom, hydrogen atoms possessed by $R_{101A}$ to $R_{108A}$ when each of $R_{101A}$ to $R_{108A}$ is the substituent R, hydrogen atoms possessed by $L_{101}$, hydrogen atoms possessed by a substituent that substitutes on $L_{101}$, hydrogen atoms possessed by $Ar_{101}$, hydrogen atoms possessed by a substituent that substitutes on $Ar_{101}$ hydrogen atoms when each of $R_{121}$ to $R_{128}$ is a hydrogen atom, and hydrogen atoms possessed by $R_{121}$ to $R_{128}$ when each of $R_{121}$ to $R_{128}$ is the substituent R.

In one embodiment, the compound represented by the formula (31D) is a compound represented by the following formula (32D).

(32D)

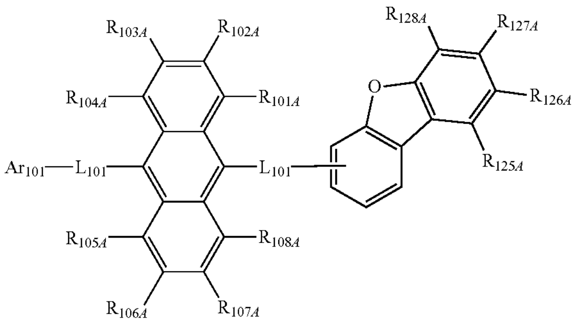

In the formula (32D), $R_{101A}$ to $R_{108A}$, $R_{125A}$ to $R_{128A}$, $L_{101}$, and $Ar_{101}$ are as defined in the formula (31D).

Provided that at least one hydrogen atom selected from the group consisting of the followings is a deuterium atom:

hydrogen atoms when each of $R_{101A}$ to $R_{108A}$ is a hydrogen atom, hydrogen atoms possessed by $R_{101A}$ to $R_{108A}$ when each of $R_{101A}$ to $R_{108A}$ is the substituent R, hydrogen atoms when each of $R_{125A}$ to $R_{128A}$ is a hydrogen atom, hydrogen atoms possessed by $R_{125A}$ to $R_{128A}$ when each of $R_{125A}$ to $R_{128A}$ is the substituent R, hydrogen atoms which bond to the carbon atoms constituting the dibenzofuran skeleton in the formula (32D), hydrogen atoms possessed by $L_{101}$, hydrogen atoms possessed by a substituent that substitutes on $L_{101}$, hydrogen atoms possessed by $Ar_{101}$, and hydrogen atoms possessed by a substituent that substitutes on $Ar_{101}$.

In one embodiment, the compound represented by the formula (32D) is a compound represented by the following formula (32D-1) or (32D-2).

(32D-1)

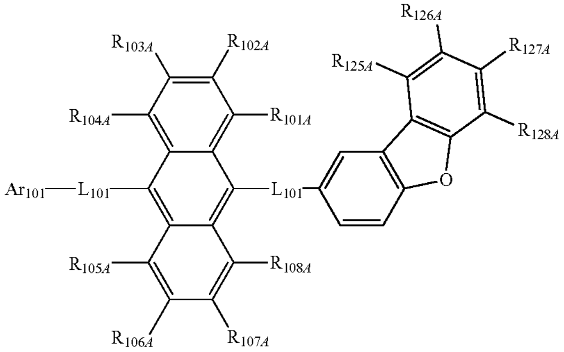

(32D-2)

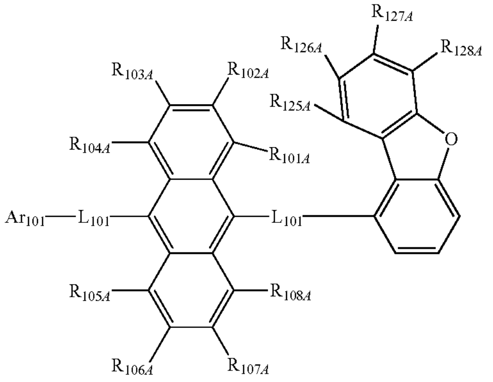

In the formulas (32D-1) and (32D-2), $R_{101A}$ to $R_{108A}$, $R_{125A}$ to $R_{128A}$, $L_{101}$, and $Ar_{01}$ are as defined in the formula (32D).

Provided that at least one hydrogen atom selected from the group consisting of the followings is a deuterium atom:

hydrogen atoms when each of $R_{101A}$ to $R_{108A}$ is a hydrogen atom, hydrogen atoms possessed by $R_{101A}$ to $R_{108A}$ when each of $R_{101A}$ to $R_{108A}$ is the substituent R, hydrogen atoms when each of $R_{125A}$ to $R_{128A}$ is a hydrogen atom, hydrogen atoms possessed by $R_{125A}$ to $R_{128A}$ when each of $R_{125A}$ to $R_{128A}$ is the substituent R, hydrogen atoms which bond to the carbon atoms constituting the dibenzofuran skeleton in each of the formulas (32D-1) and (32D-2), hydrogen atoms possessed by $L_{101}$, hydrogen atoms possessed by a substituent that substitutes on $L_{101}$, hydrogen atoms possessed by $Ar_{101}$, and hydrogen atoms possessed by a substituent that substitutes on $Ar_{101}$.

In one embodiment, at least one of the hydrogen atoms possessed by the compound represented by each of the formula (40), (41), (42-1) to (42-3), or (43-1) to (43-3) is a deuterium atom.

In one embodiment, at least one of the hydrogen atoms which bond with the carbon atoms constituting the anthracene skeleton in the compound represented by the formula (41) (i.e., hydrogen atoms when each of $R_{101A}$ to $R_{108A}$ is a hydrogen atom) is a deuterium atom.

In one embodiment, the compound represented by the formula (40) is a compound represented by the following formula (40D):

(40D)

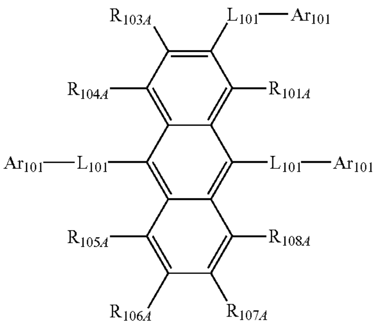

In the formula (40D), $L_{101}$ and $Ar_{101}$ are as defined in the formula (10).

One or more sets of adjacent two or more among $R_{101A}$ and $R_{103A}$ to $R_{108A}$ do not form a substituted or unsubstituted, saturated or unsaturated ring.

$R_{101A}$ and $R_{103A}$ to $R_{108A}$ are independently
- a hydrogen atom, or
- a substituent R.

The substituent R is as defined in the formula (10).

Provided that at least one hydrogen atom selected from the group consisting of the followings is a deuterium atom:
- hydrogen atoms when each of $R_{101A}$ and $R_{103A}$ to $R_{108A}$ is a hydrogen atom,
- hydrogen atoms possessed by $R_{101A}$ and $R_{103A}$ to $R_{108A}$ when each of $R_{101A}$ and $R_{103A}$ to $R_{108A}$ is the substituent R,
- hydrogen atoms possessed by $L_{101}$,
- hydrogen atoms possessed by a substituent that substitutes on $L_{101}$,
- hydrogen atoms possessed by $Ar_{101}$, and
- hydrogen atoms possessed by a substituent that substitutes on $Ar_{101}$.

In one embodiment, at least one of $R_{101A}$ and $R_{103A}$ to $R_{108A}$ in the formula (40D) is a deuterium atom.

In one embodiment, the compound represented by the formula (40D) is a compound represented by the following formula (41D).

(41D)

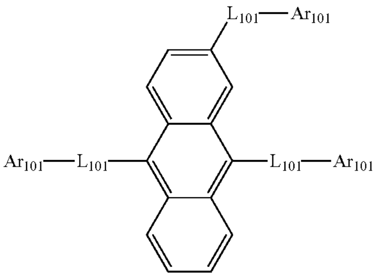

In the formula (41D), $L_{101}$ and $Ar_{101}$ are as defined in the formula (40D).

Provided that in the formula (41D), at least one hydrogen atom selected from the group consisting of the followings is a deuterium atom:
- hydrogen atoms which bond to the carbon atoms constituting the anthracene skeleton,
- hydrogen atoms possessed by $L_{101}$,
- hydrogen atoms possessed by a substituent that substitutes on $L_{101}$,
- hydrogen atoms possessed by $Ar_{101}$, and
- hydrogen atoms possessed by a substituent that substitutes on $Ar_{101}$.

In one embodiment, the compound represented by the formula (40D) is a compound represented by any one of the following formulas (42D-1) to (42D-3).

(42D-1)

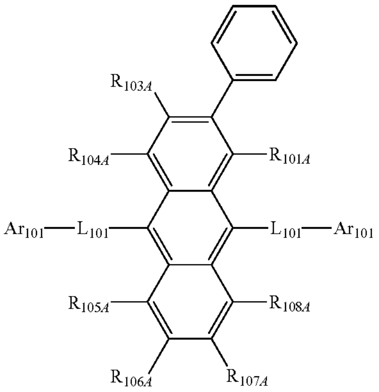

(42D-2)

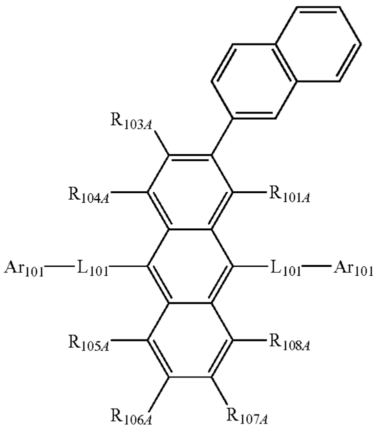

(42D-3)

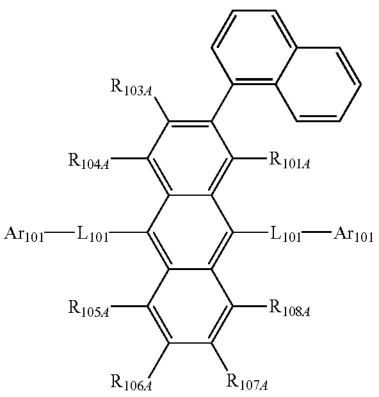

In the formulas (42D-1) to (42D-3), $R_{101A}$ to $R_{108A}$, $L_{101}$, and $Ar_{101}$ are as defined in the formula (40D).

Provided that in the formula (42D-1), at least one hydrogen atom selected from the group consisting of the followings is a deuterium atom:

hydrogen atoms when each of $R_{101A}$ and $R_{103A}$ to $R_{108A}$ is a hydrogen atom, hydrogen atoms possessed by $R_{101A}$ and $R_{103A}$ to $R_{108A}$ when each of $R_{101A}$ and $R_{103A}$ to $R_{108A}$ is the substituent R, hydrogen atoms possessed by $L_{101}$, hydrogen atoms possessed by a substituent that substitutes on $L_{101}$, hydrogen atoms possessed by $Ar_{101}$, hydrogen atoms possessed by a substituent that substitutes on $Ar_{101}$, and hydrogen atoms which bond to the carbon atoms constituting the phenyl group in the formula (42D-1).

In the formula (42D-2), at least one hydrogen atom selected from the group consisting of the followings is a deuterium atom:

hydrogen atoms when each of $R_{101A}$ and $R_{103A}$ to $R_{108A}$ is a hydrogen atom, hydrogen atoms possessed by $R_{101A}$ and $R_{103A}$ to $R_{108A}$ when each of $R_{101A}$ and $R_{103A}$ to $R_{108A}$ is the substituent R, hydrogen atoms possessed by $L_{101}$, hydrogen atoms possessed by a substituent that substitutes on $L_{101}$, hydrogen atoms possessed by $Ar_{101}$, hydrogen atoms possessed by a substituent that substitutes on $Ar_{101}$, and hydrogen atoms which bond to the carbon atoms constituting the naphthyl group in the formula (42D-2).

In the formula (42D-3), at least one hydrogen atom selected from the group consisting of the followings is a deuterium atom:

hydrogen atoms when each of $R_{101A}$ and $R_{103A}$ to $R_{108A}$ is a hydrogen atom, hydrogen atoms possessed by $R_{101A}$ and $R_{103A}$ to $R_{108A}$ when each of $R_{101A}$ and $R_{103A}$ to $R_{108A}$ is the substituent R, hydrogen atoms possessed by $L_{101}$, hydrogen atoms possessed by a substituent that substitutes on $L_{101}$, hydrogen atoms possessed by $Ar_{101}$, hydrogen atoms possessed by a substituent that substitutes on $Ar_{101}$, and hydrogen atoms which bond to the carbon atoms constituting the naphthyl group in the formula (42D-3).

In one embodiment, the compounds represented by each of the formulas (42D-1) to (42D-3) are compounds represented by each of the following formulas (43D-1) to (43D-3), respectively.

(43D-1)

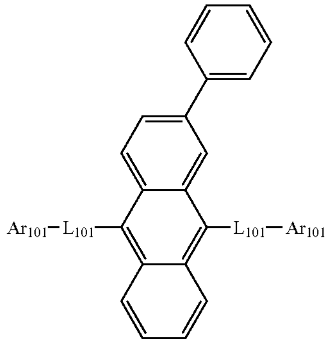

(43D-2)

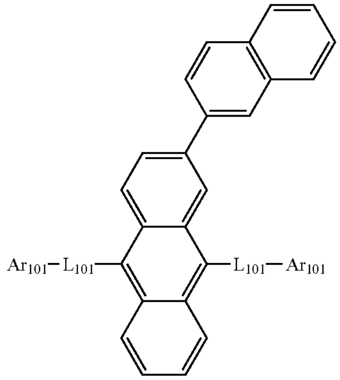

(43D-3)

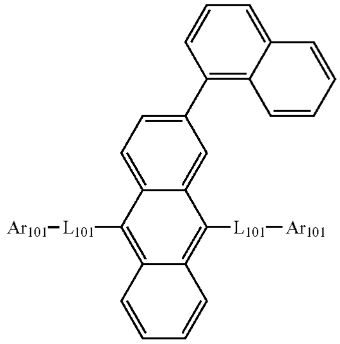

In the formulas (43D-1) to (43D-3), $L_{101}$ and $Ar_{101}$ are as defined in the formula (40D).

Provided that in the formula (43D-1), at least one hydrogen atom selected from the group consisting of the followings is a deuterium atom:

hydrogen atoms which bond to the carbon atoms constituting the anthracene skeleton in the formula (43D-1)

hydrogen atoms possessed by $L_{101}$, hydrogen atoms possessed by a substituent that substitutes on $L_{101}$, hydrogen atoms possessed by $Ar_{101}$, hydrogen atoms possessed by a substituent that substitutes on $Ar_{101}$, and hydrogen atoms which bond to the carbon atoms constituting the phenyl group in the formula (43D-1).

In the formula (43D-2), at least one hydrogen atom selected from the group consisting of the followings is a deuterium atom:

hydrogen atoms which bond to the carbon atoms constituting the anthracene skeleton in the formula (43D-2)

hydrogen atoms possessed by $L_{101}$, hydrogen atoms possessed by a substituent that substitutes on $L_{101}$, hydrogen atoms possessed by $Ar_{101}$, hydrogen atoms possessed by a substituent that substitutes on $Ar_{101}$, and hydrogen atoms which bond to the carbon atoms constituting the naphthyl group in the formula (43D-2).

In the formula (43D-3), at least one hydrogen atom selected from the group consisting of the followings is a deuterium atom:

hydrogen atoms which bond to the carbon atoms constituting the anthracene skeleton in the formula (43D-3)

hydrogen atoms possessed by $L_{101}$, hydrogen atoms possessed by a substituent that substitutes on $L_{101}$, hydrogen atoms possessed by $Ar_{101}$, hydrogen atoms possessed by a substituent that substitutes on $Ar_{101}$, and hydrogen atoms which bond to the carbon atoms constituting the naphthyl group in the formula (43D-3).

Specific examples of the compound represented by the formula (10) include the following compounds. The compound represented by the formula (10) is not limited to these specific examples. In the following specific examples, "Me" represents a methyl group, and "D" represents a deuterium atom.

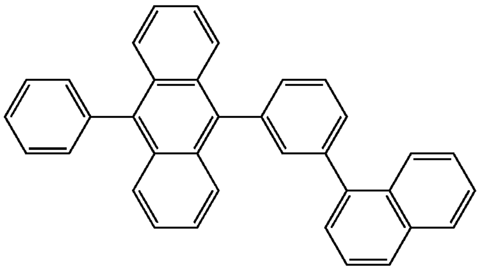

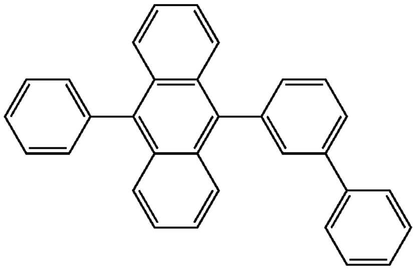

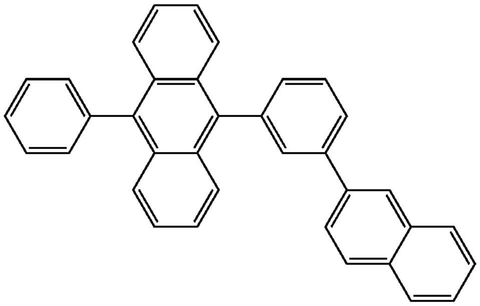

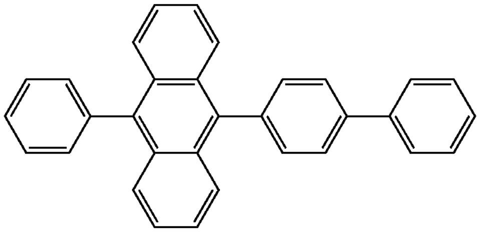

-continued

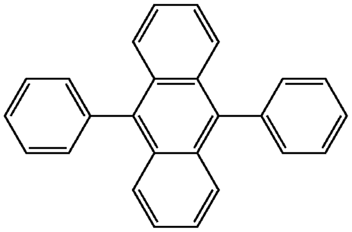

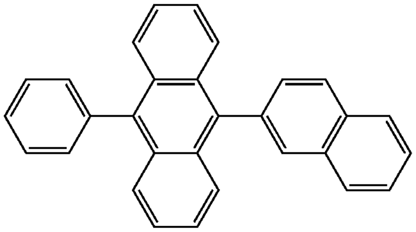

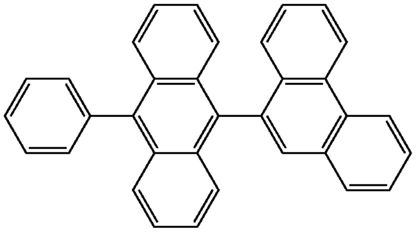

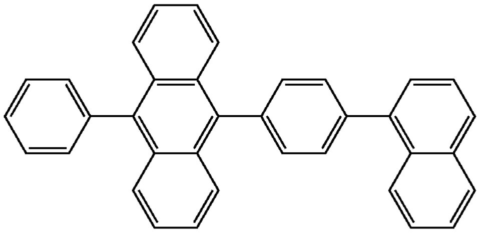

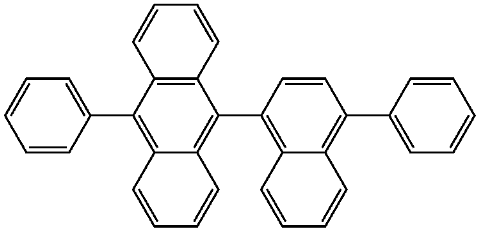

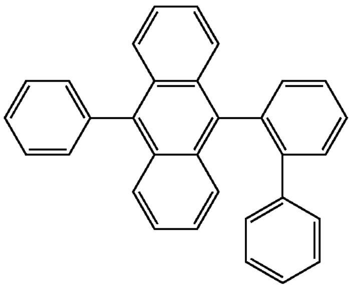

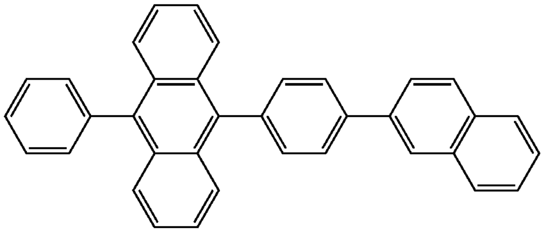

-continued
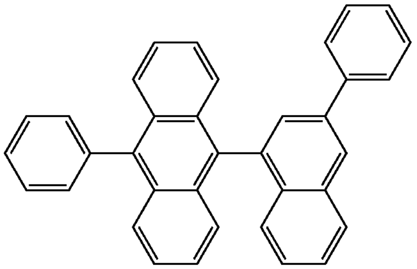
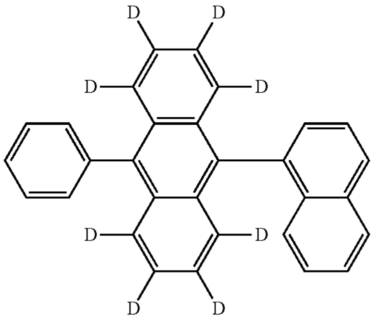
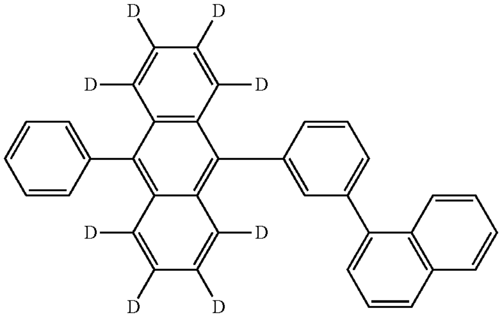
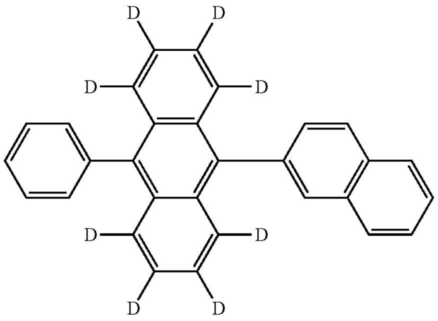
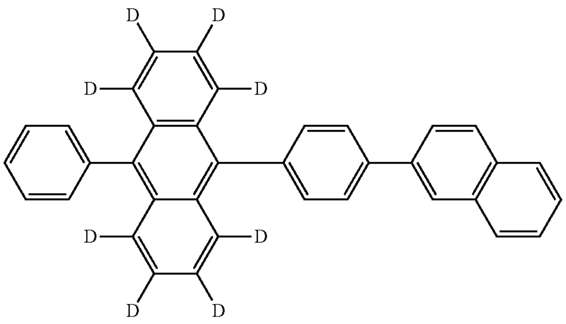
-continued
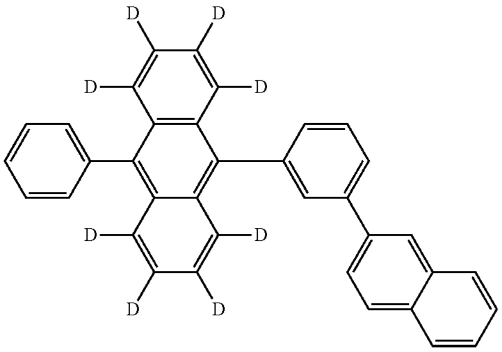
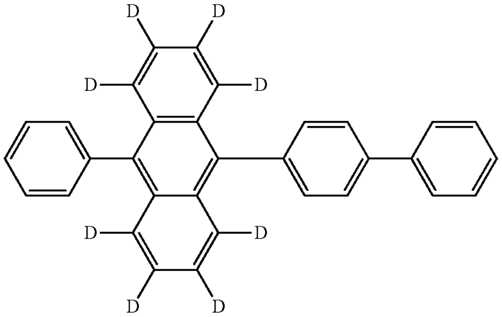
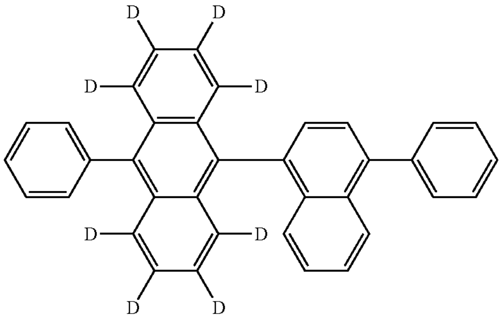
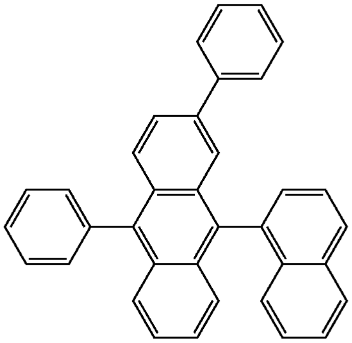

-continued
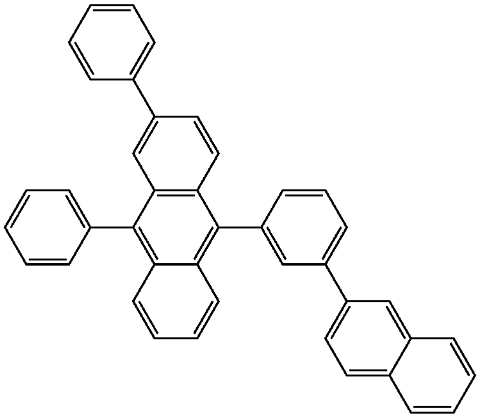
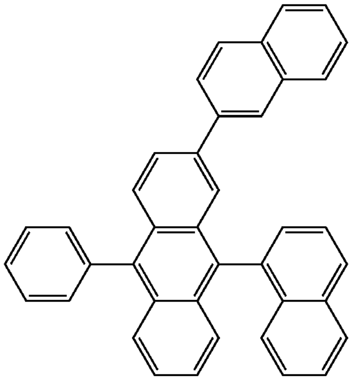
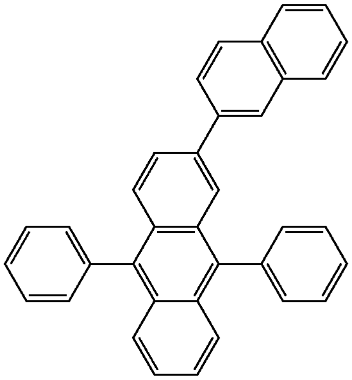
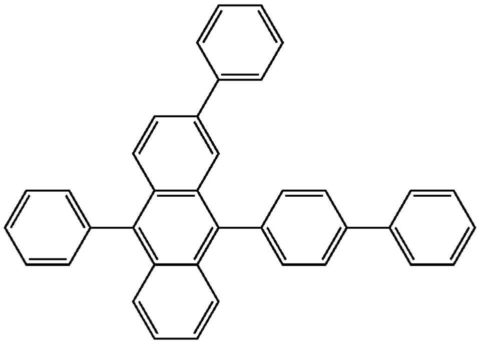
-continued
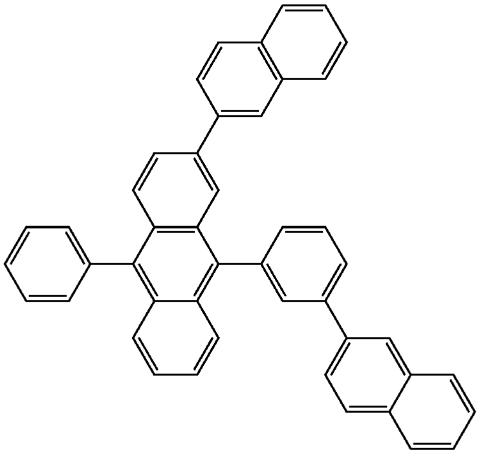
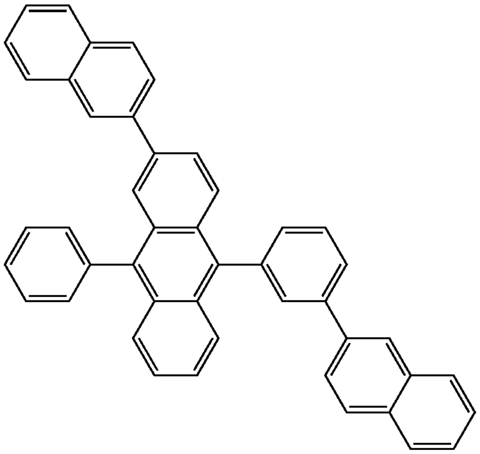
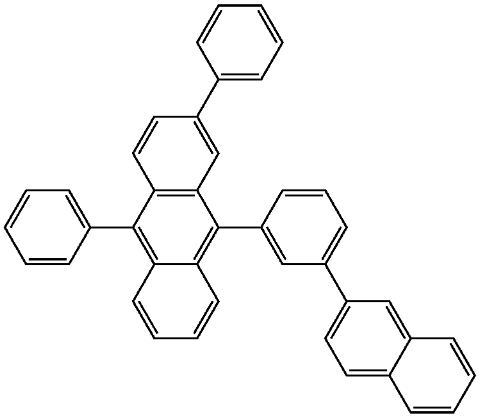
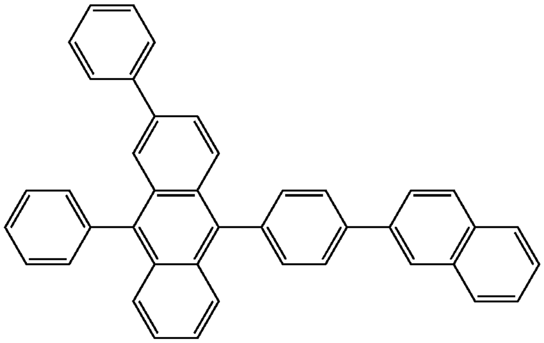

-continued
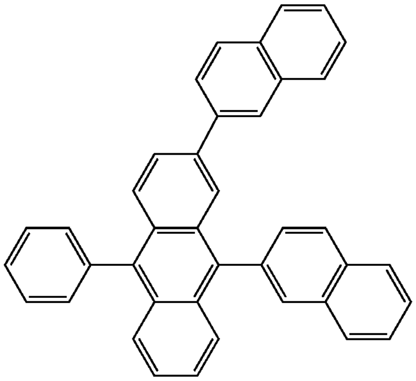
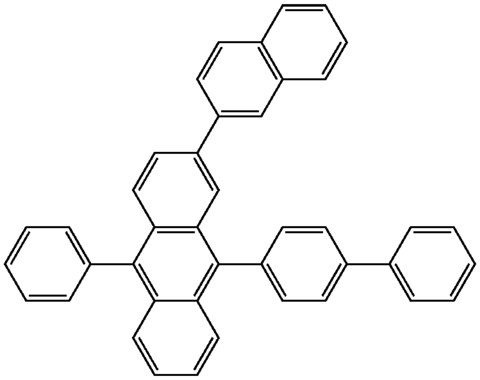
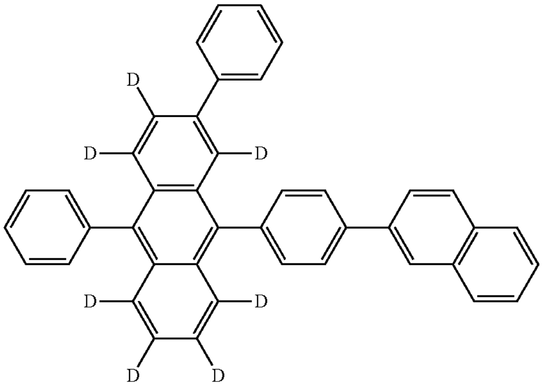
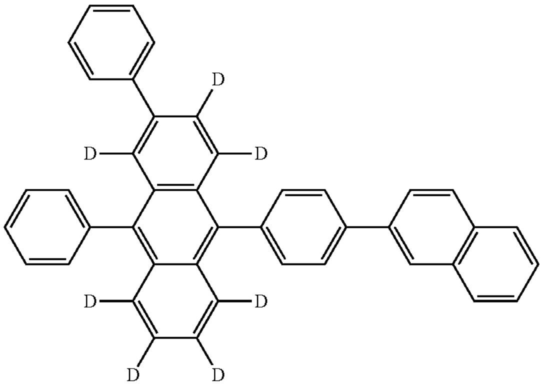
-continued
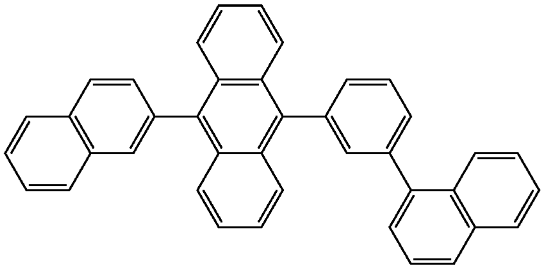
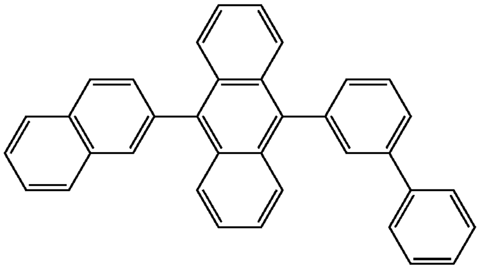
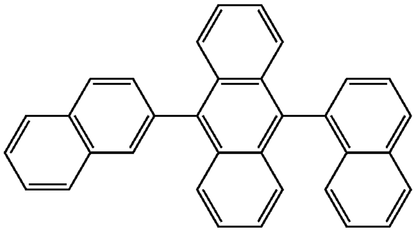
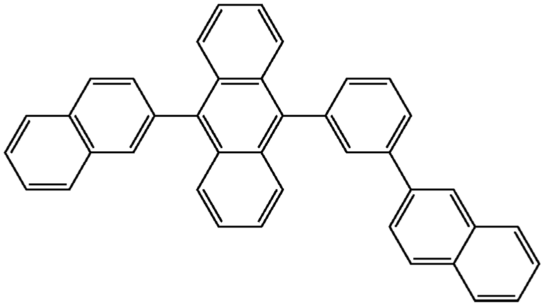
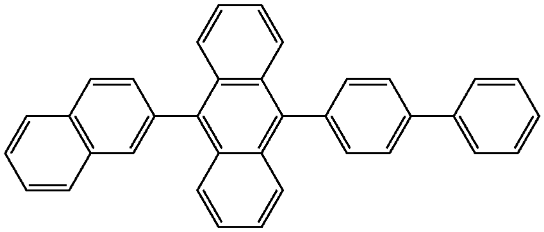
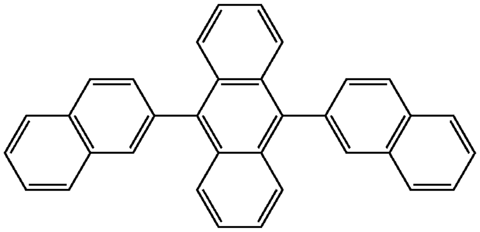

-continued
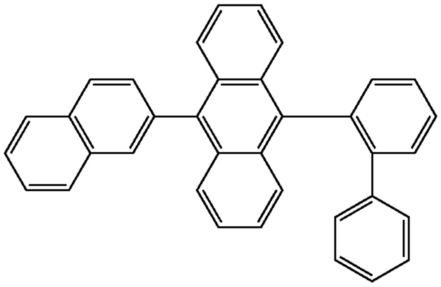
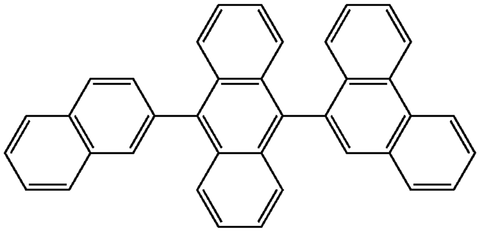
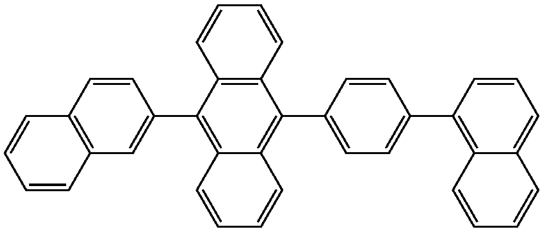
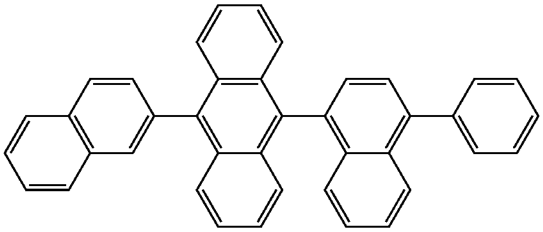
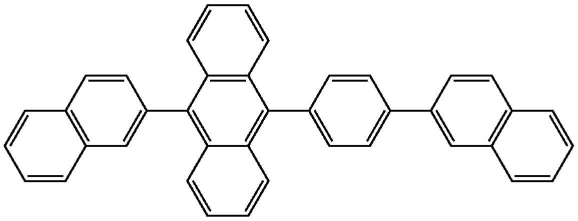
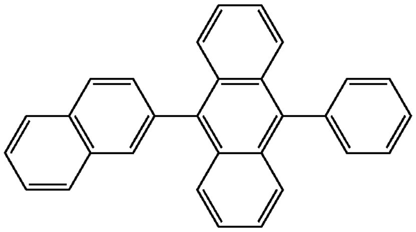
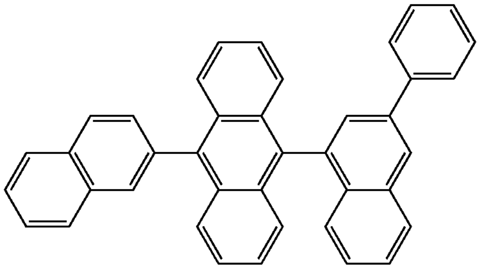
-continued
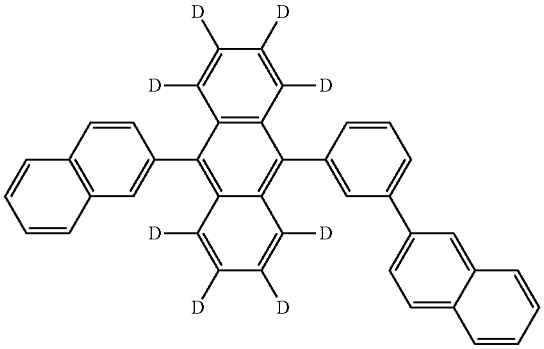
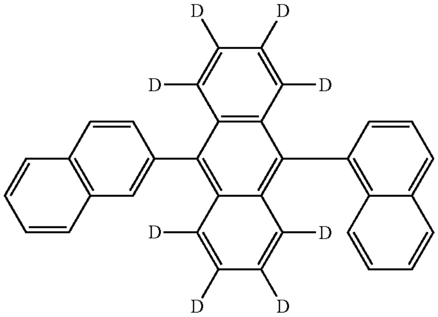
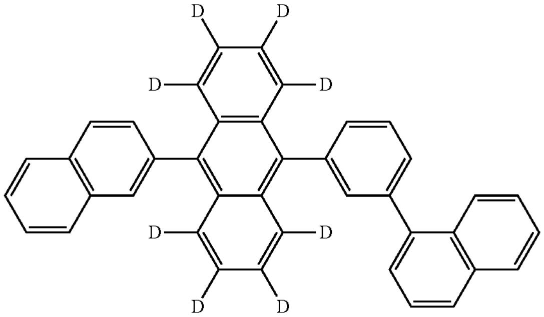
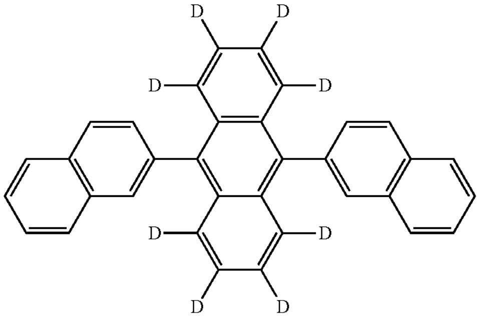
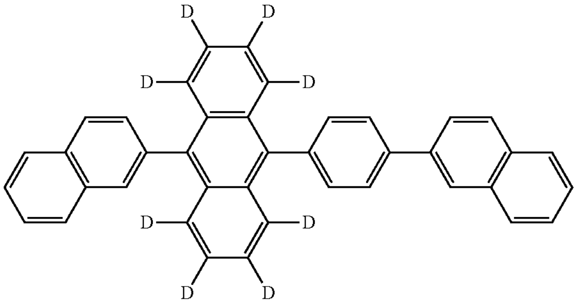

-continued
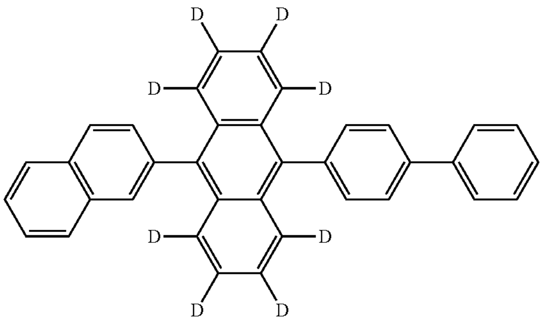
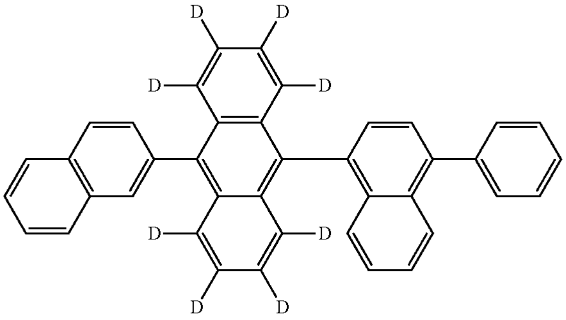
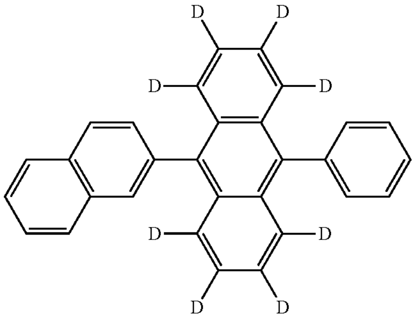
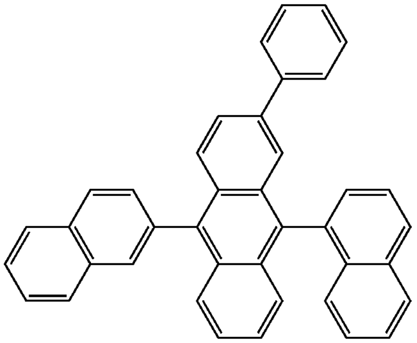
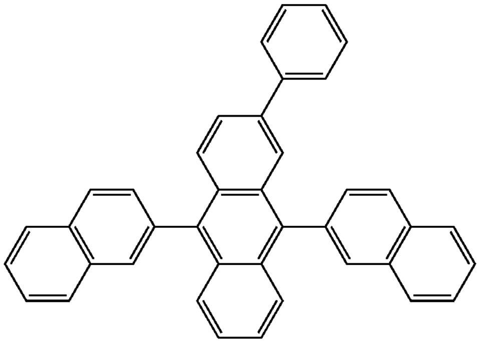
-continued
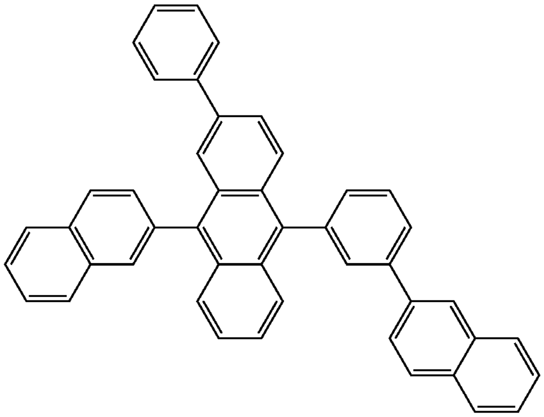
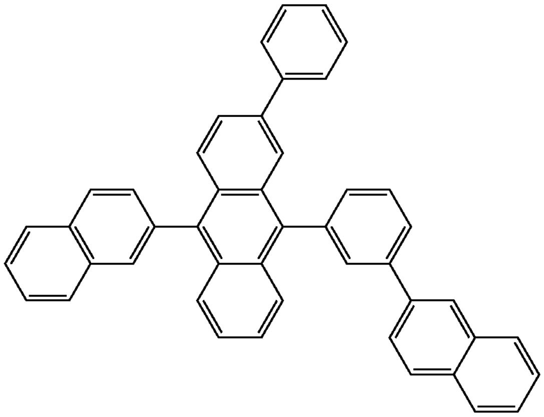
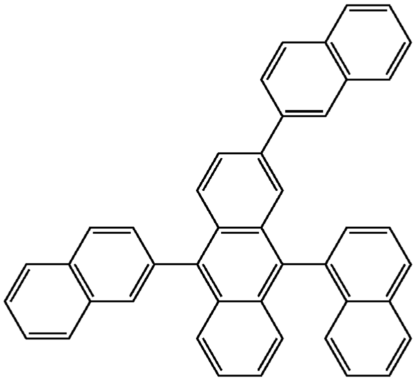
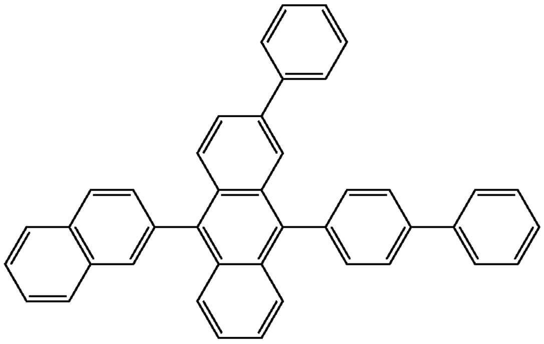

-continued
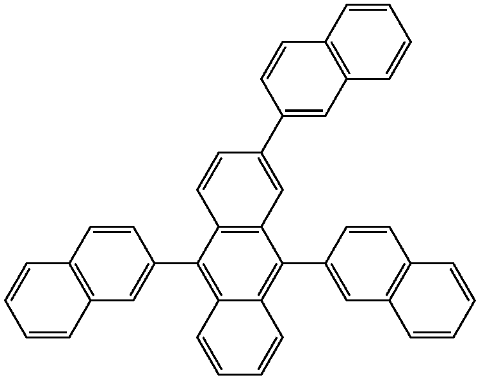
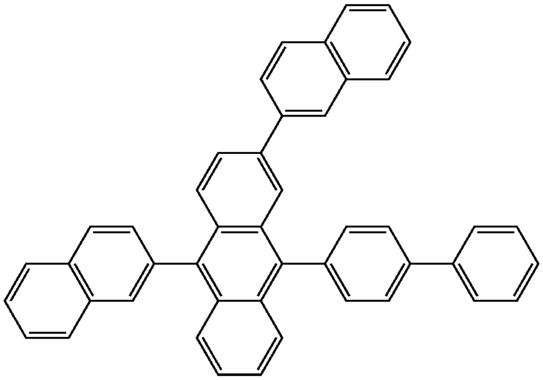
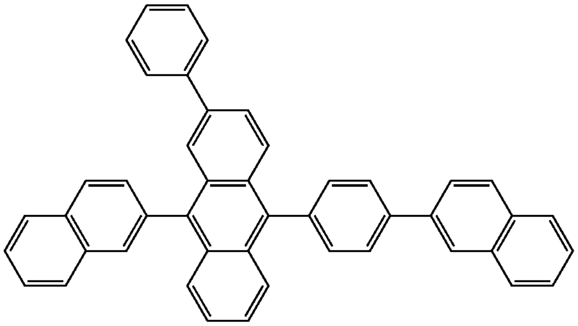
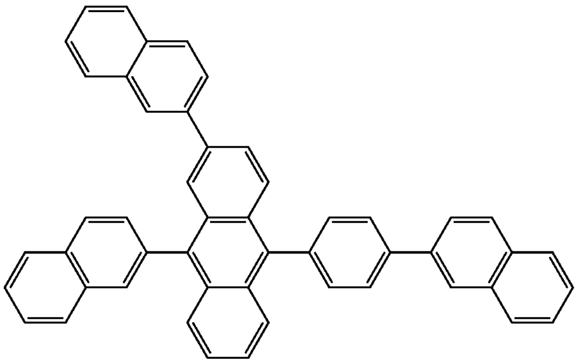
-continued
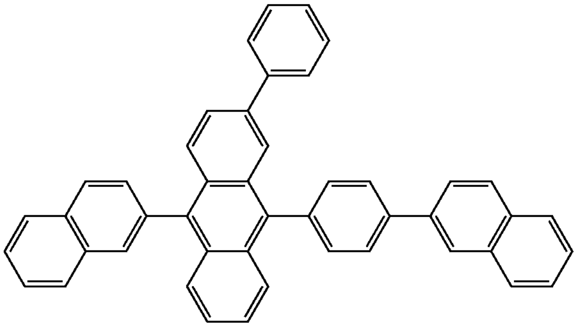
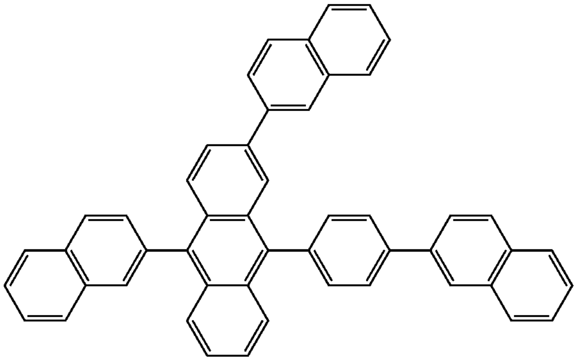
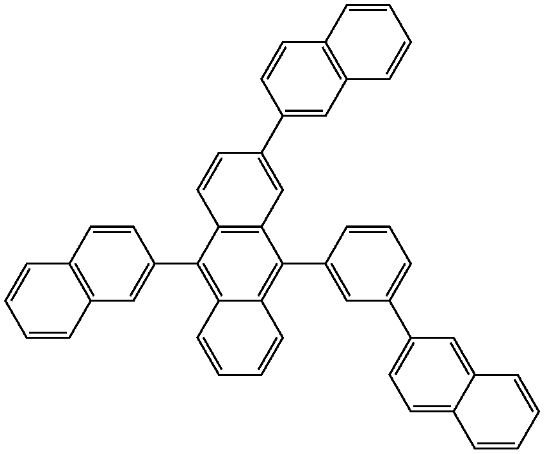
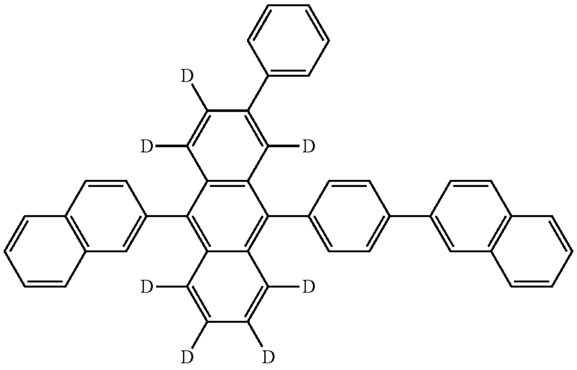

-continued
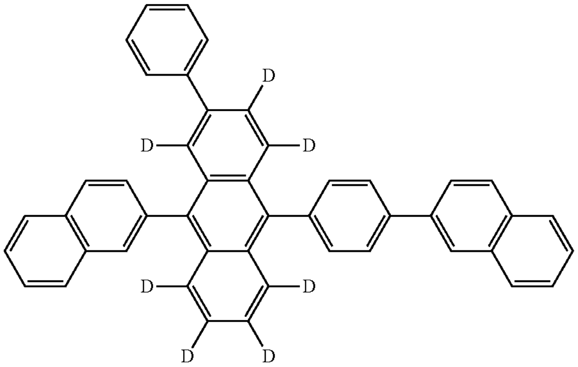
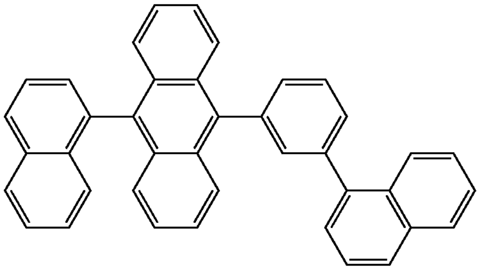
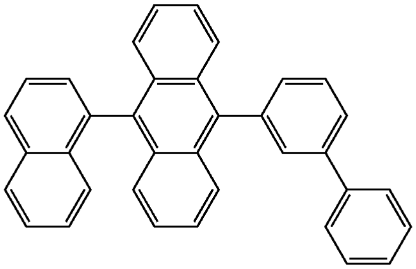
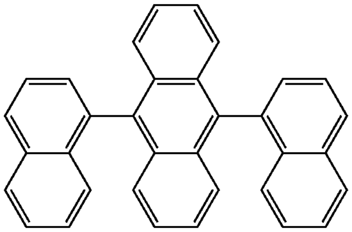
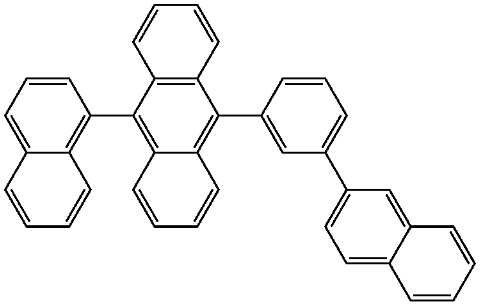
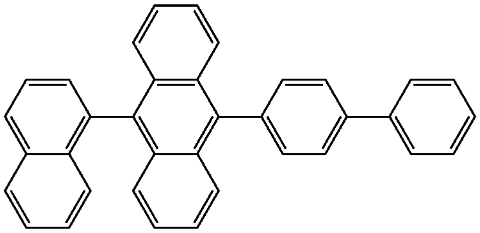
-continued
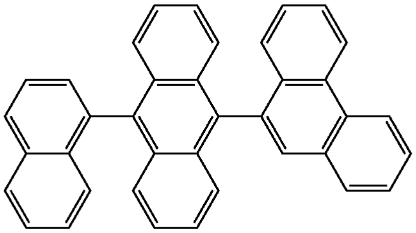
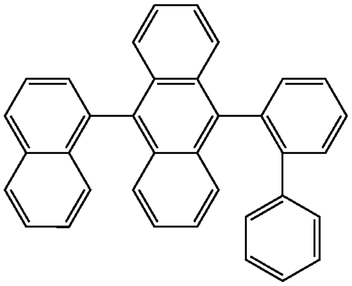
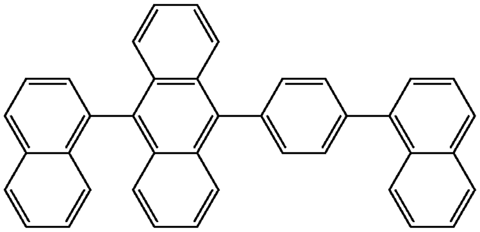
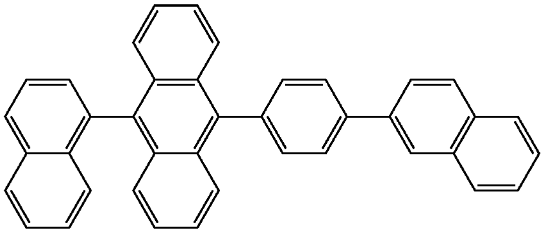
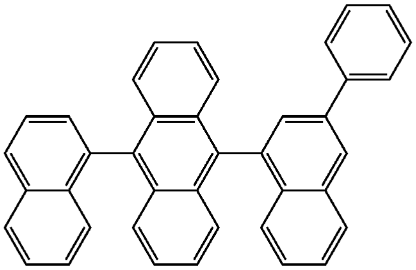
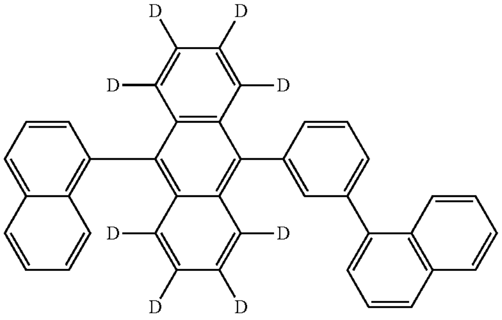

-continued
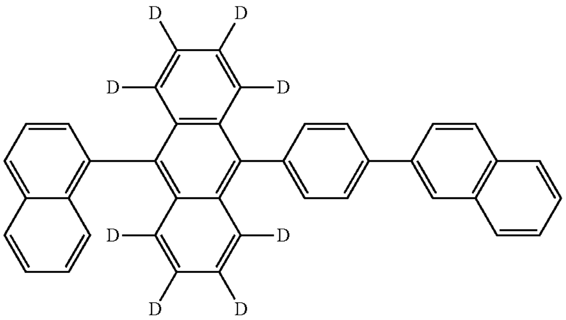
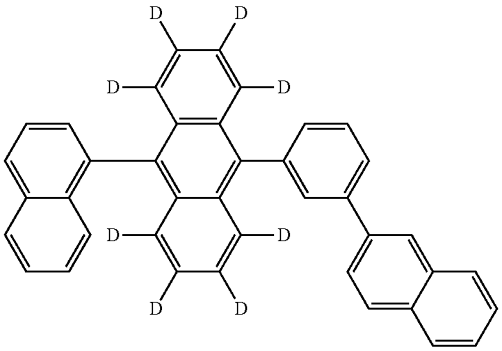
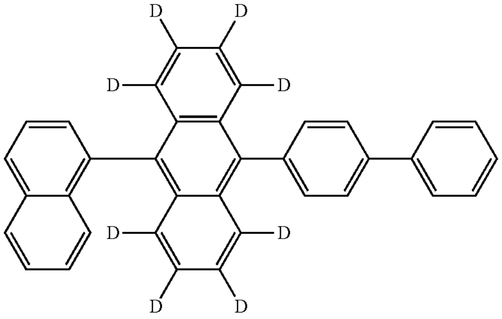
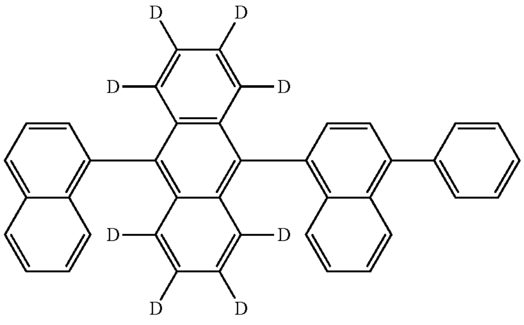
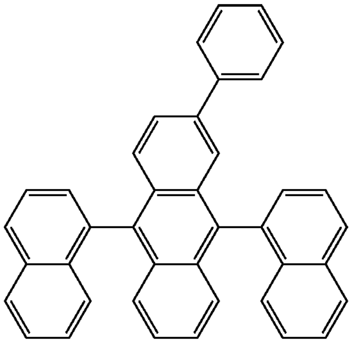
-continued
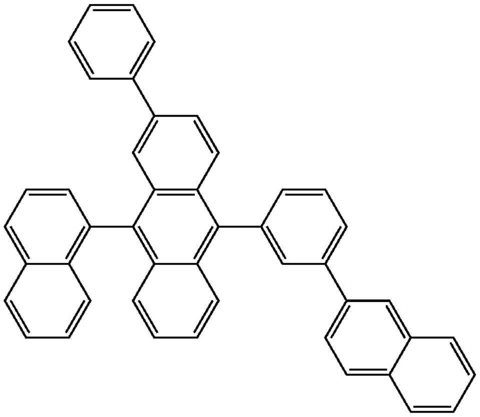
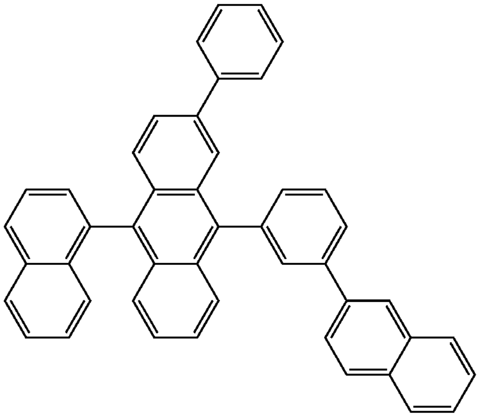
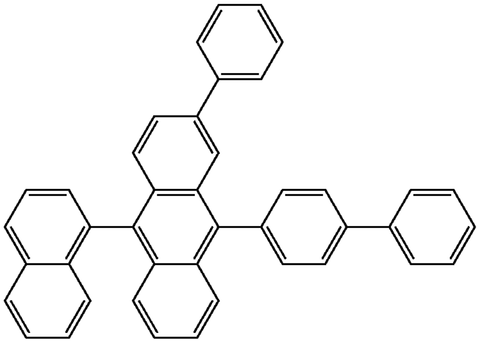
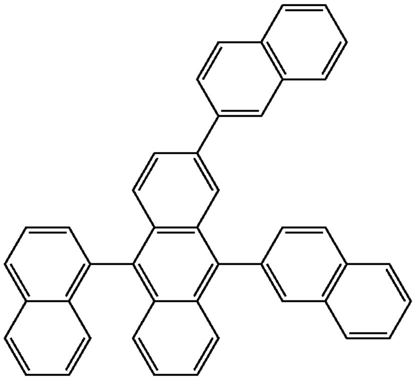

-continued
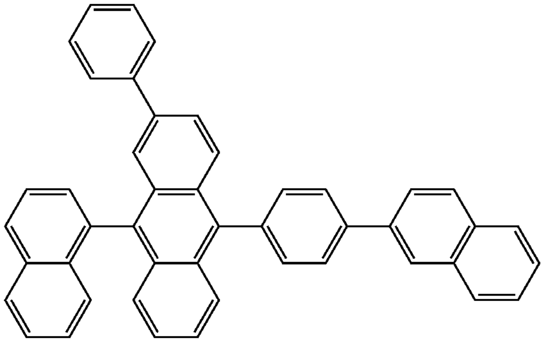
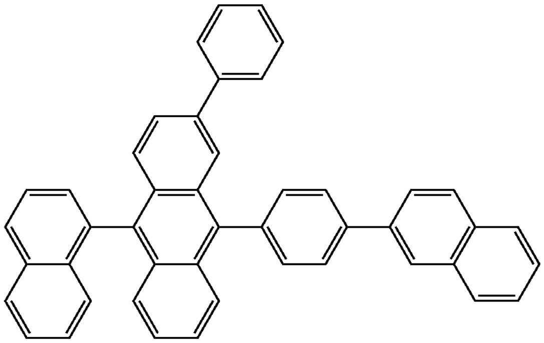
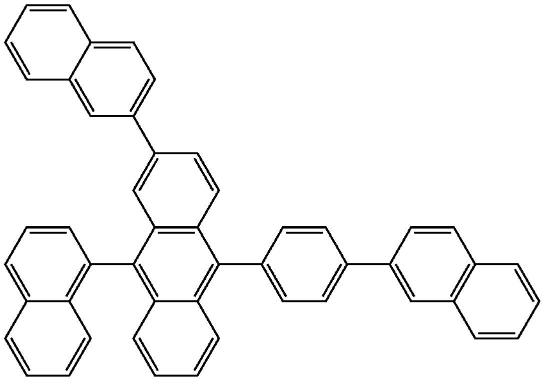
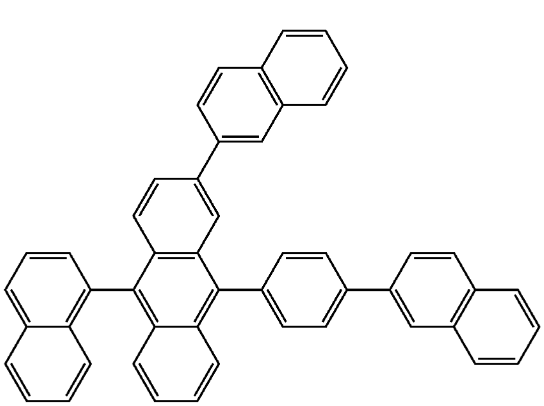
-continued
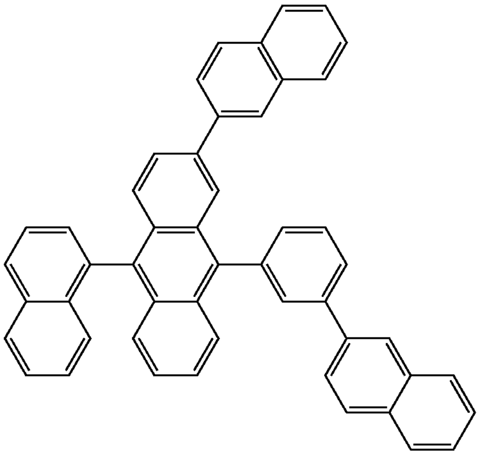
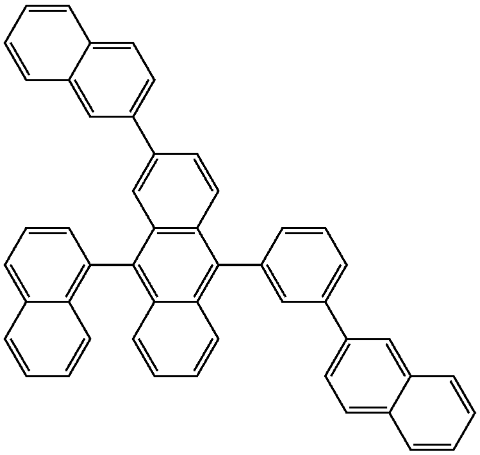
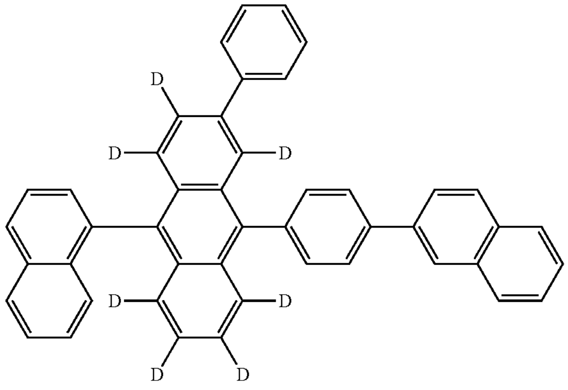
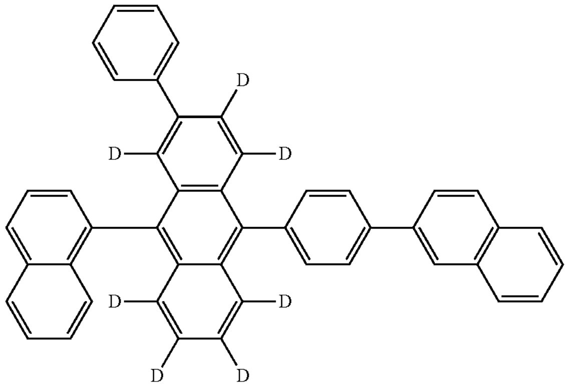

-continued
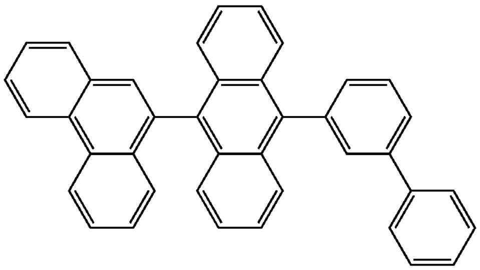
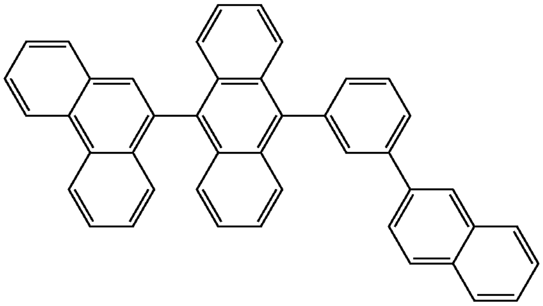
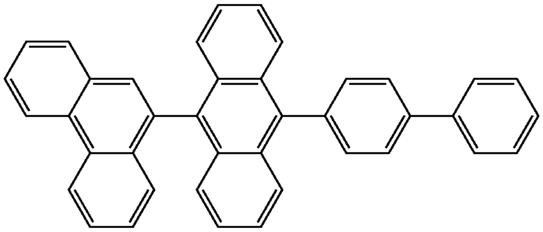
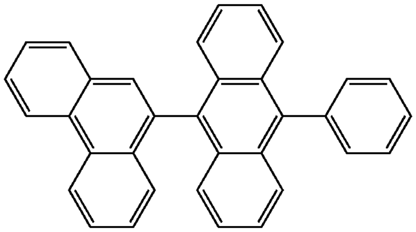
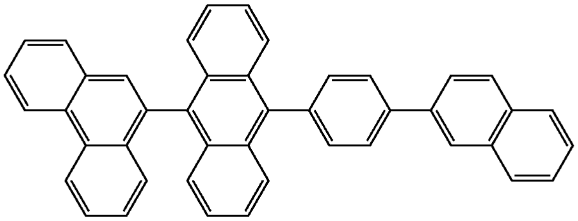
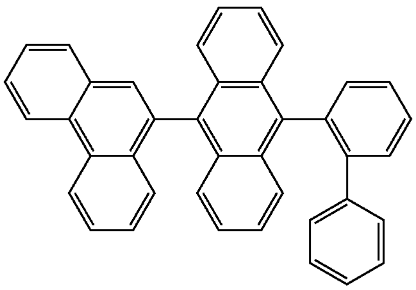
-continued
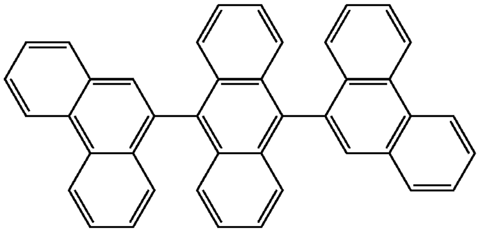
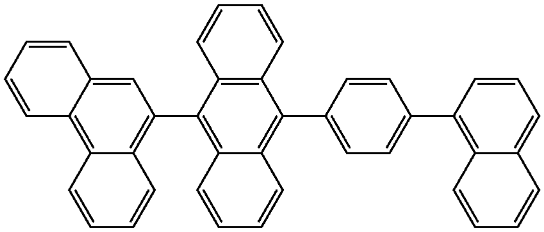
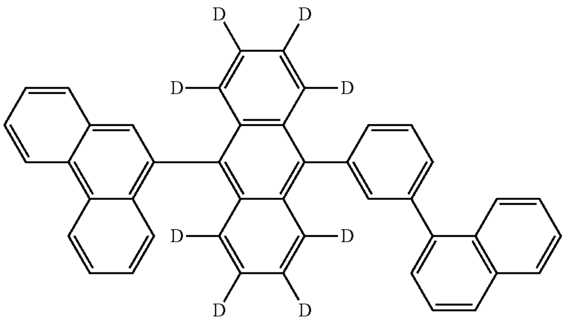
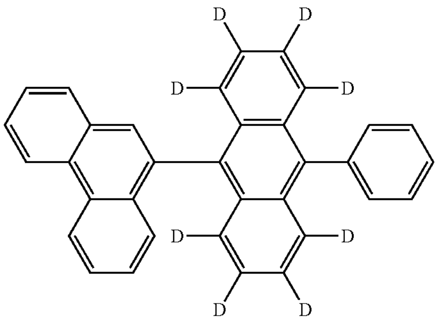
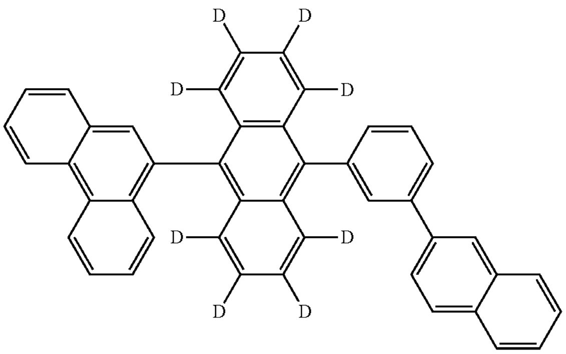

-continued
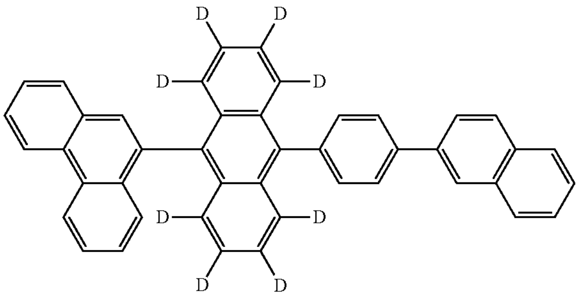
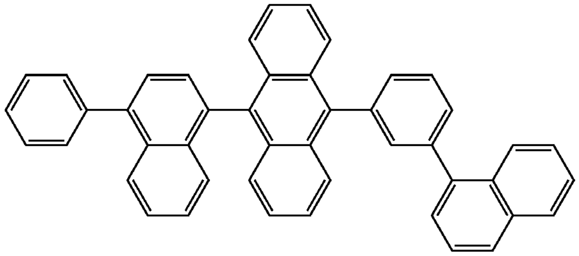
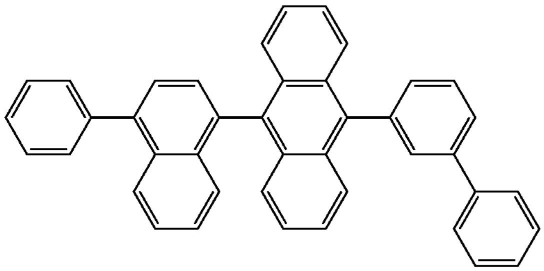
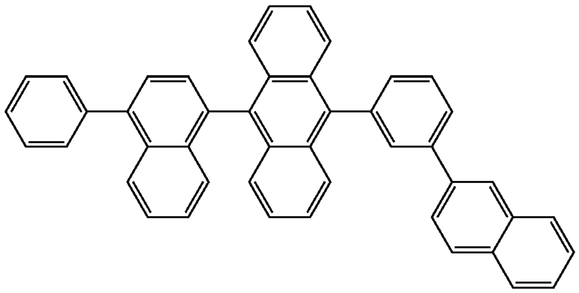
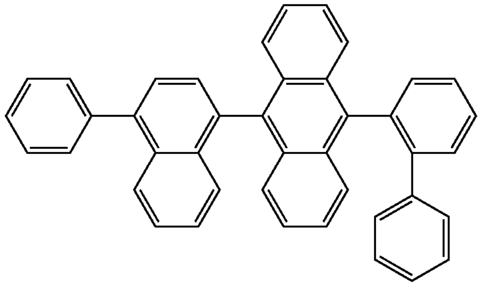
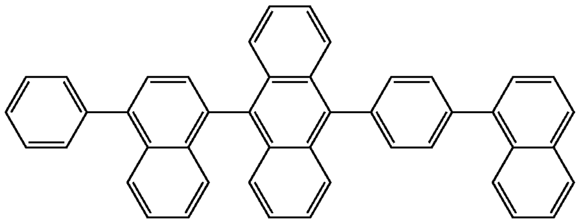
-continued
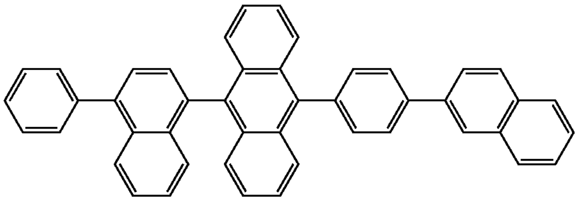
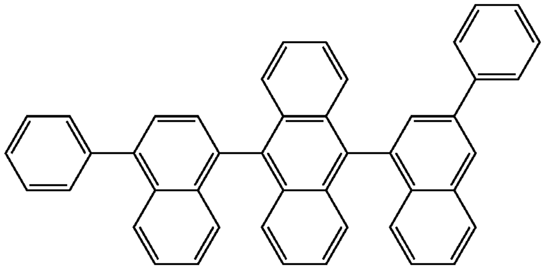
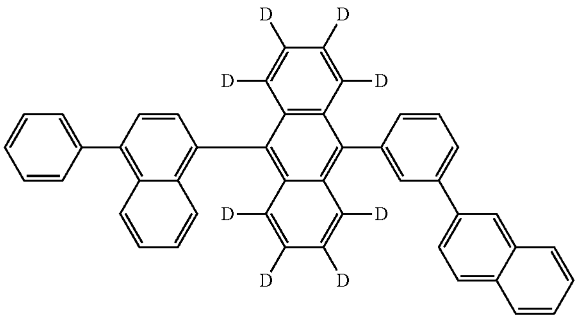
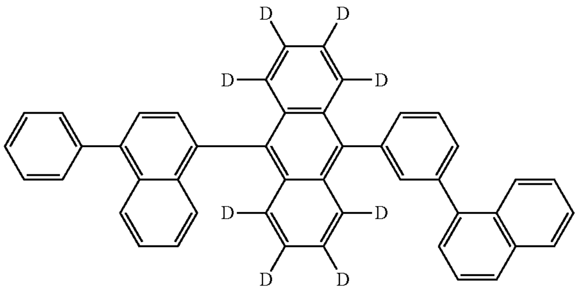
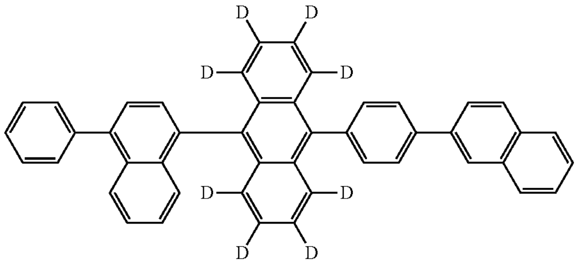
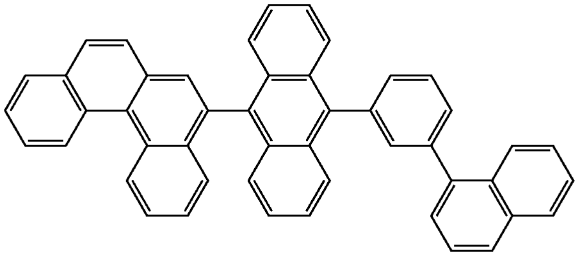

-continued
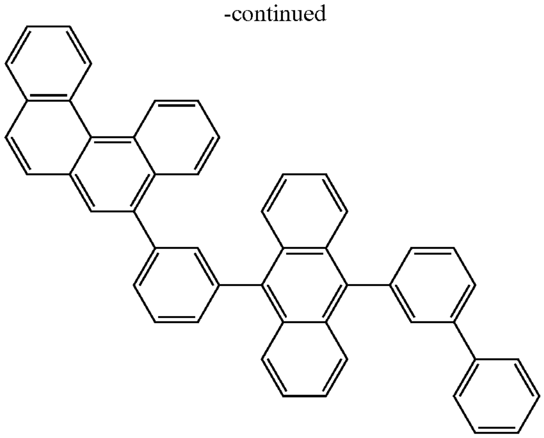
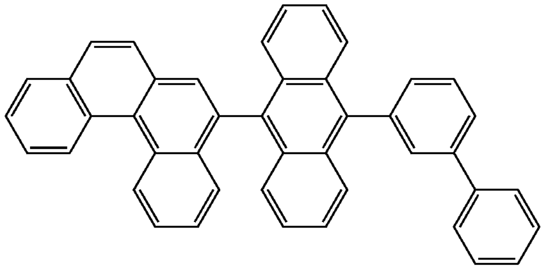
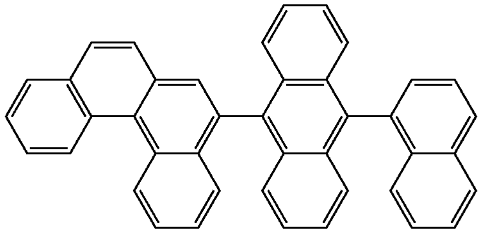
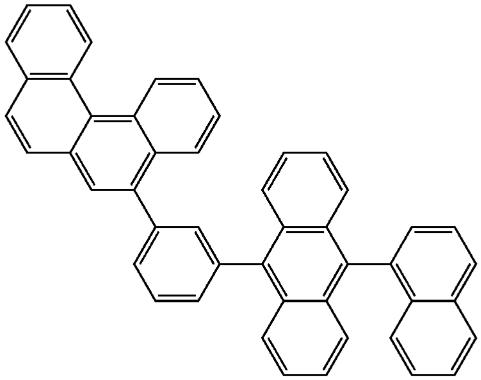
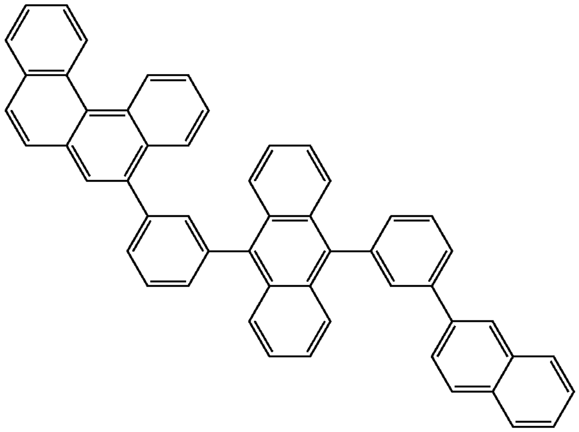
-continued
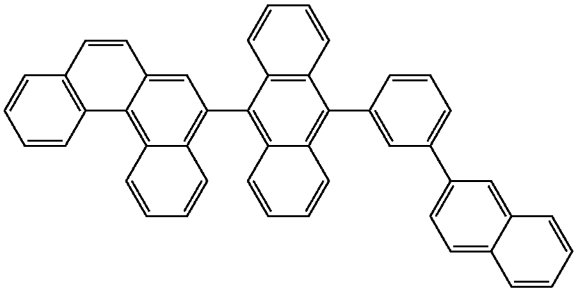
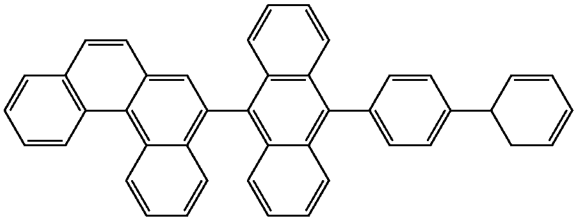
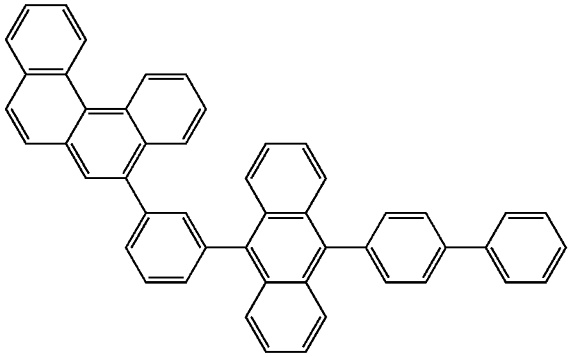
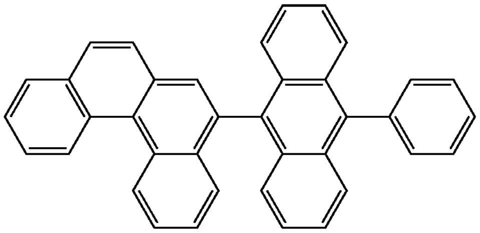
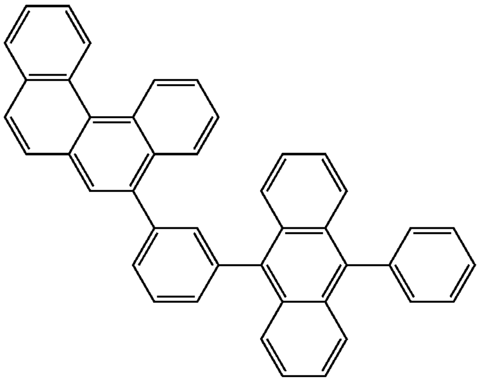

-continued
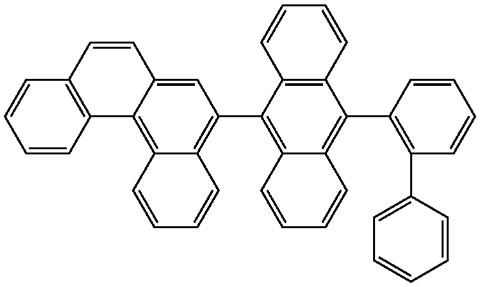
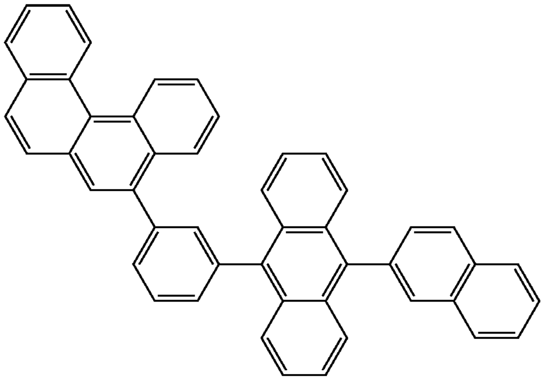
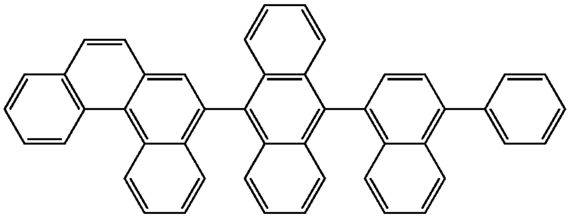
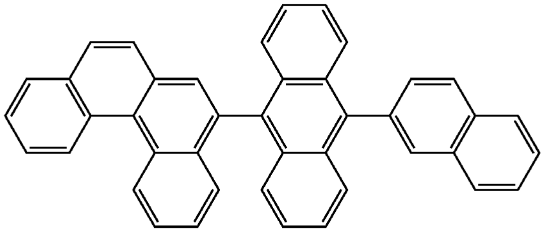
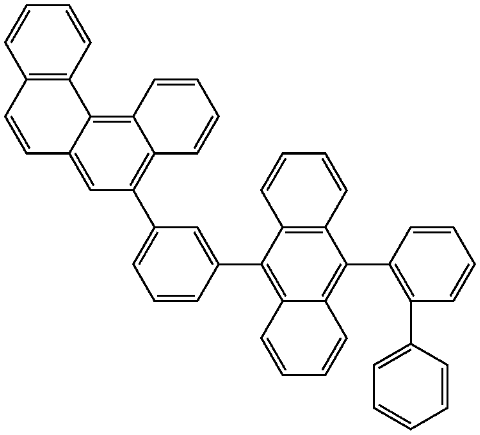
-continued
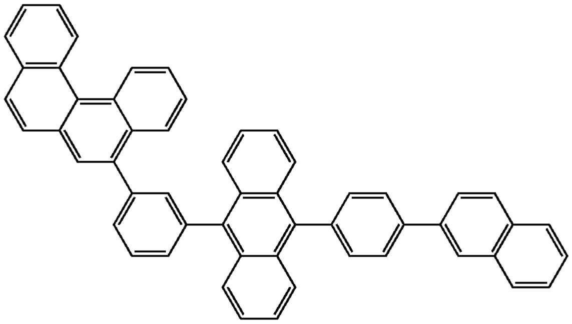
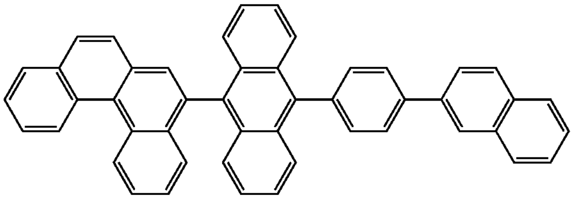
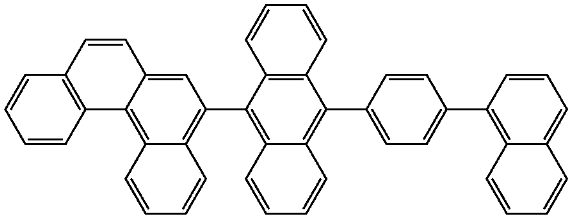
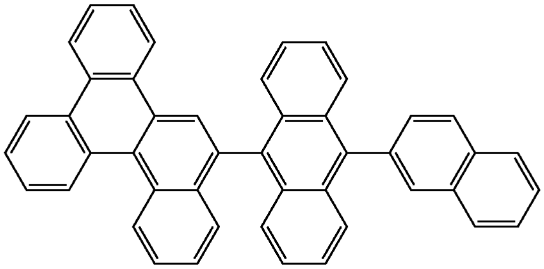
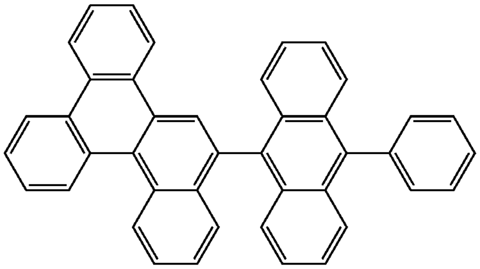
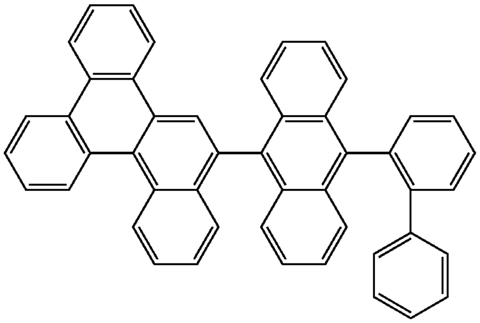

-continued
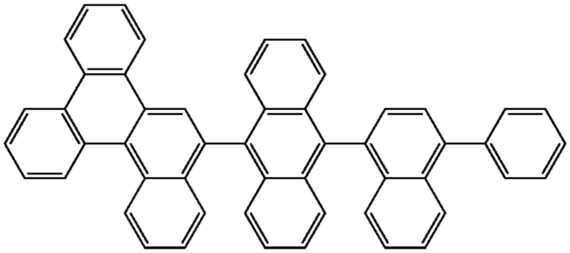
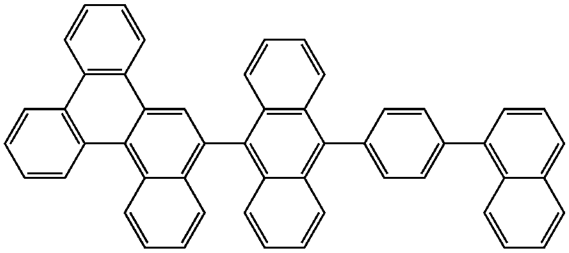
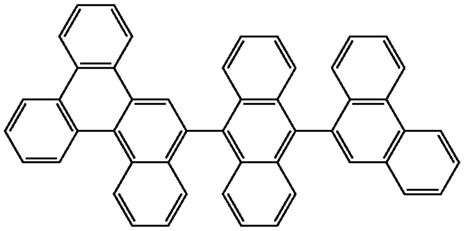
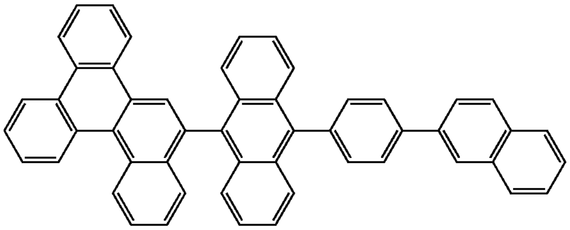
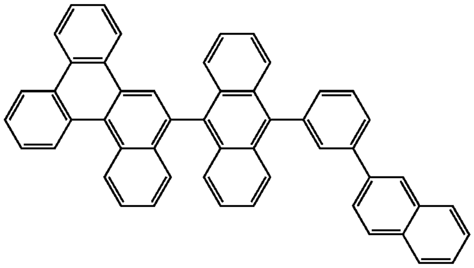
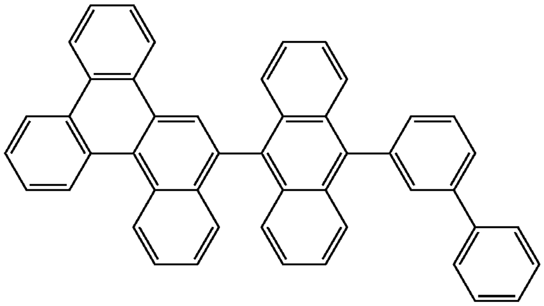
-continued
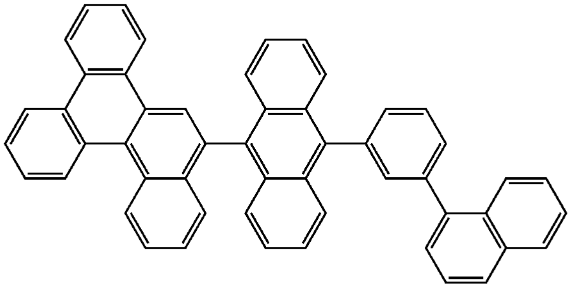
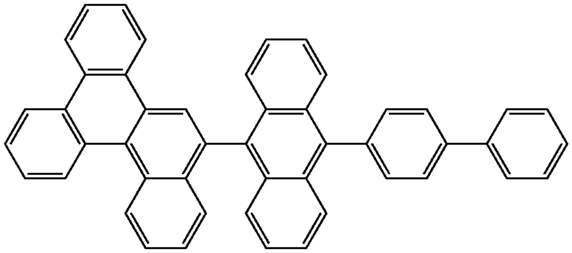
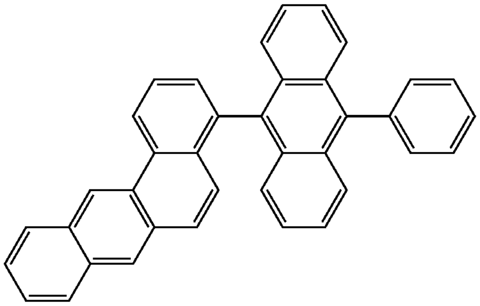
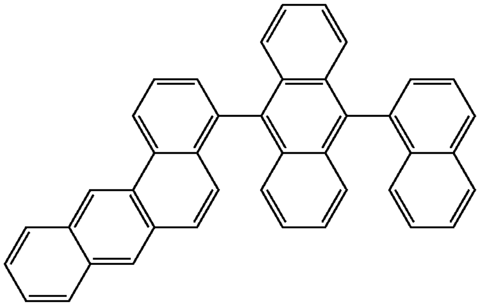
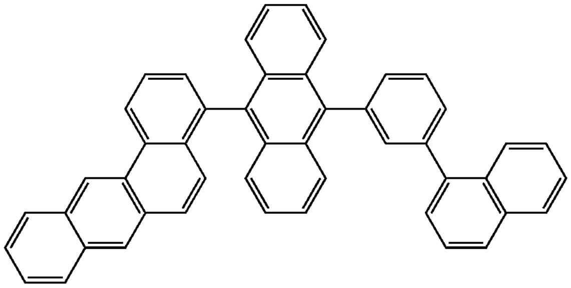

-continued
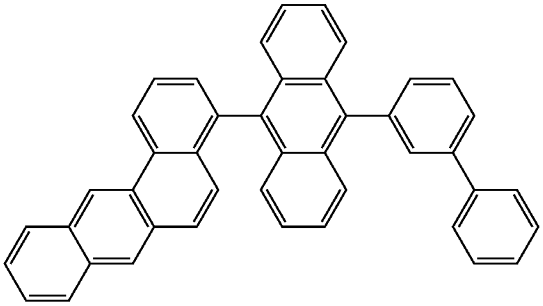
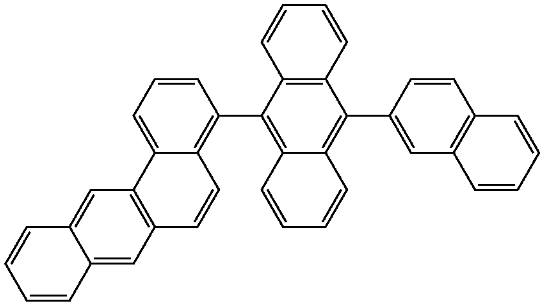
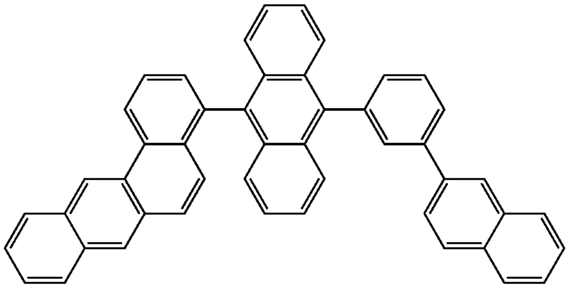
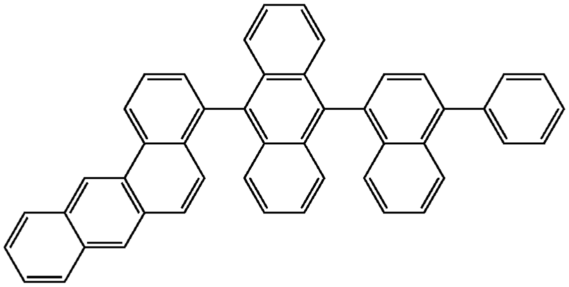
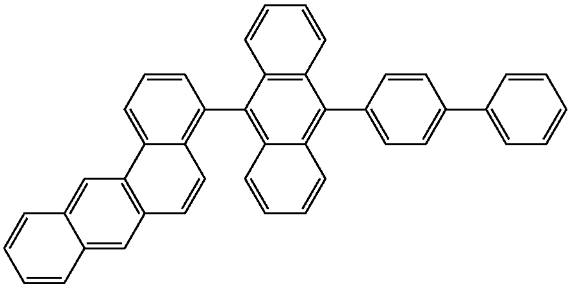
-continued
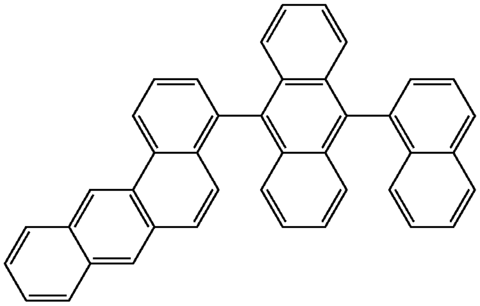
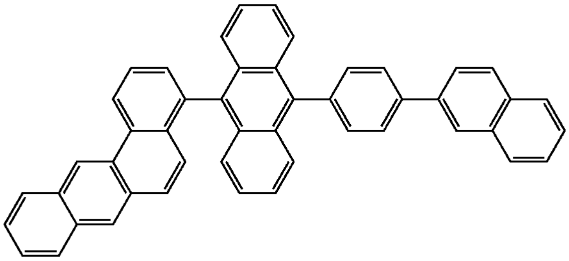
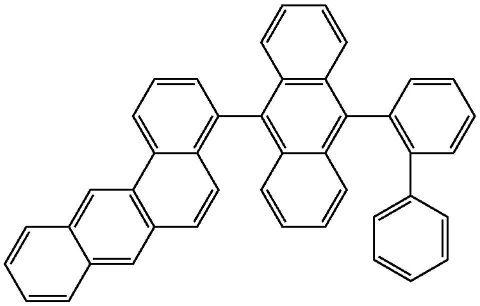
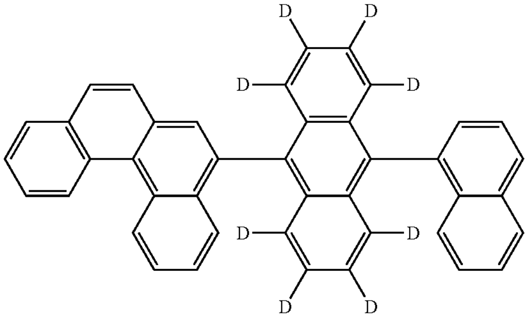
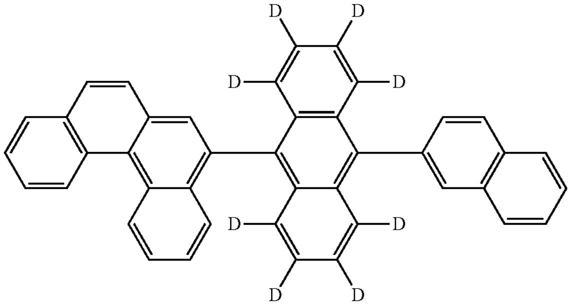

-continued
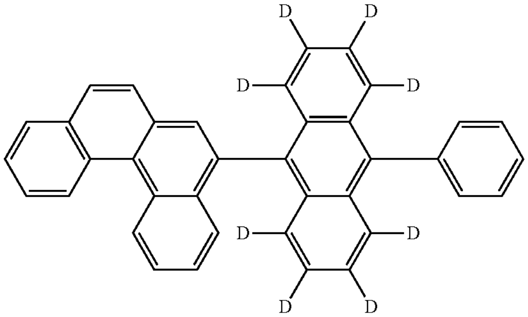
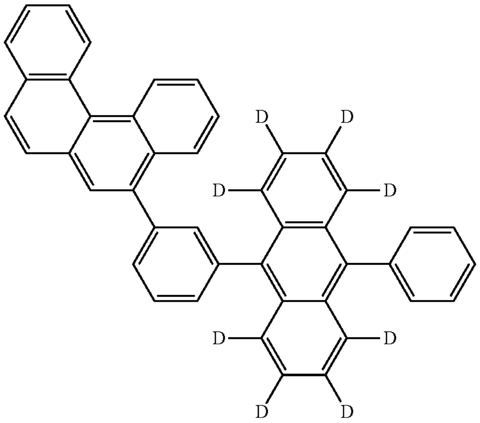
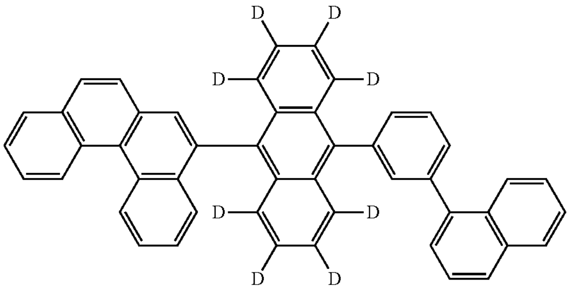
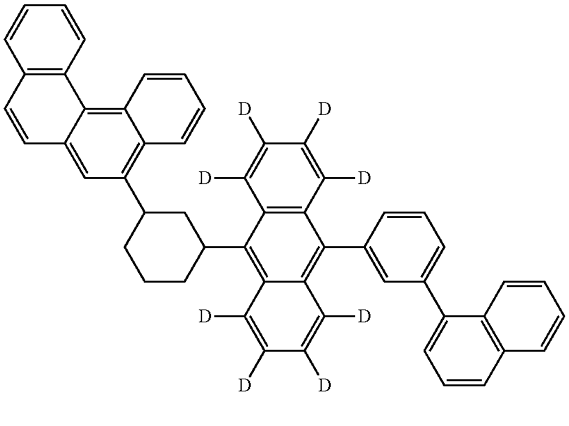
-continued
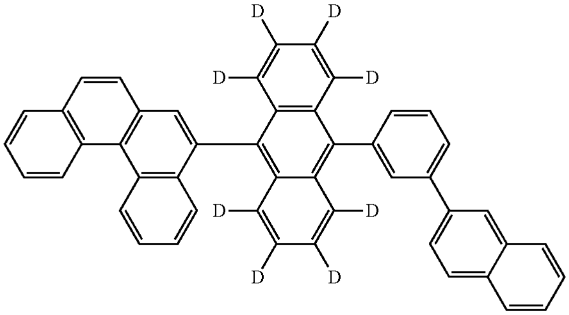
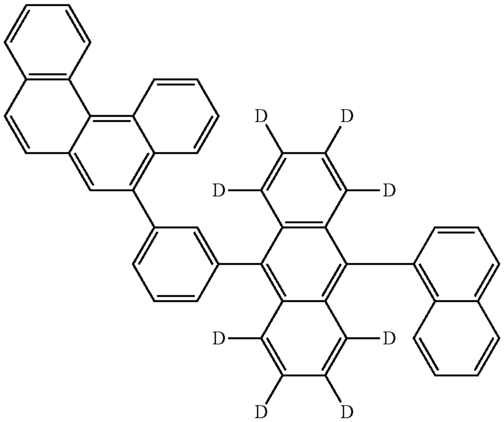
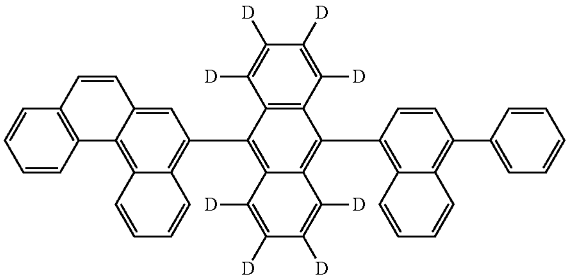
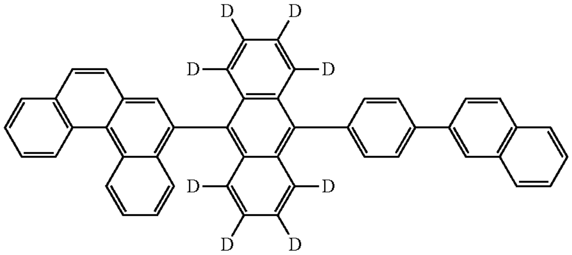
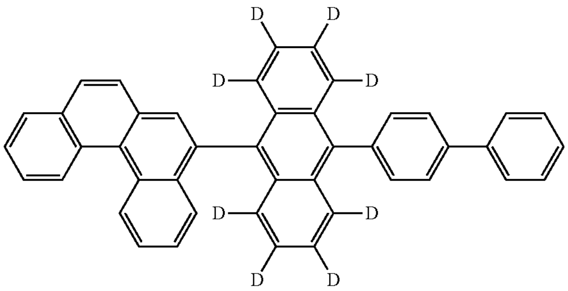

-continued
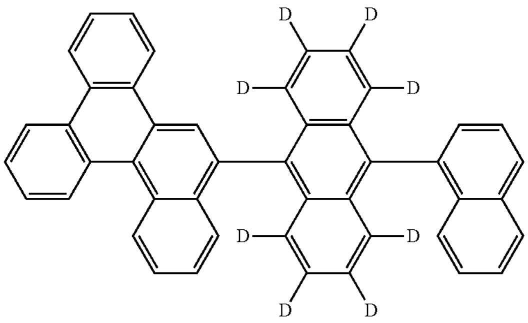
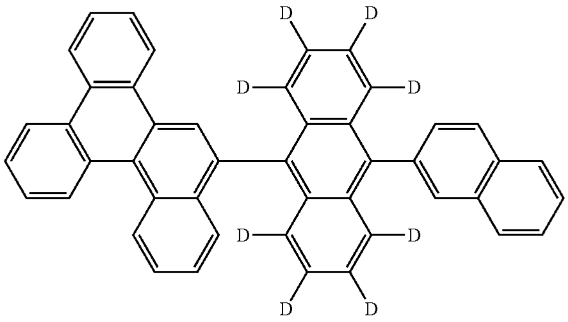
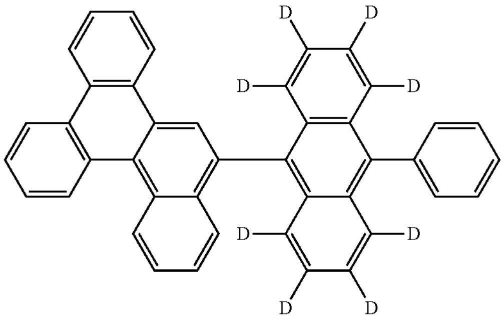
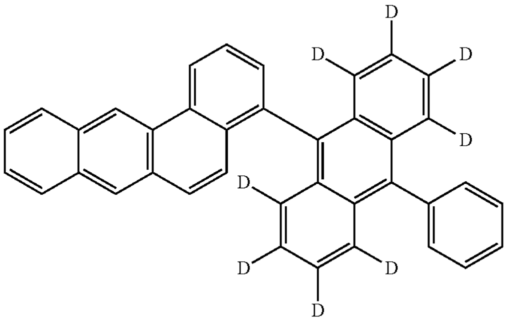
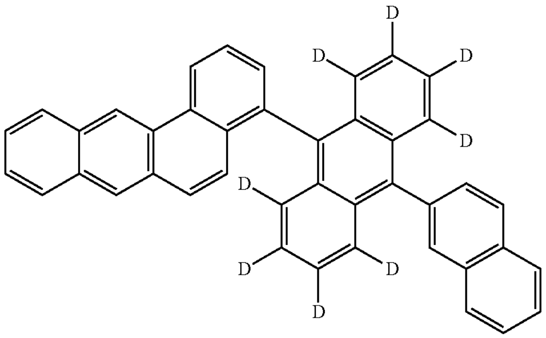
-continued
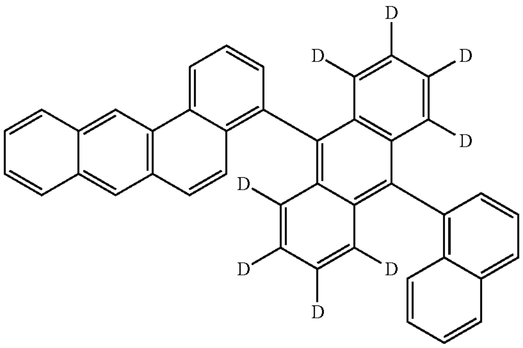
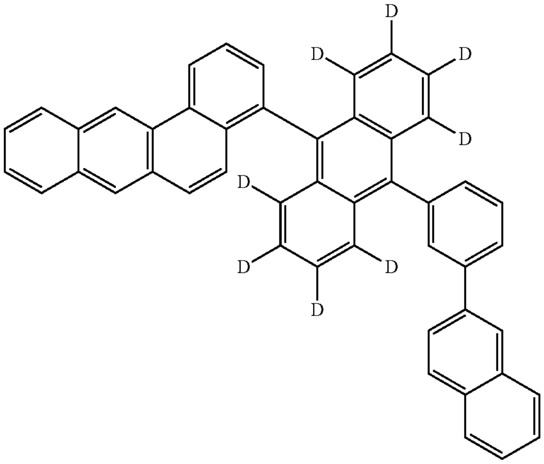
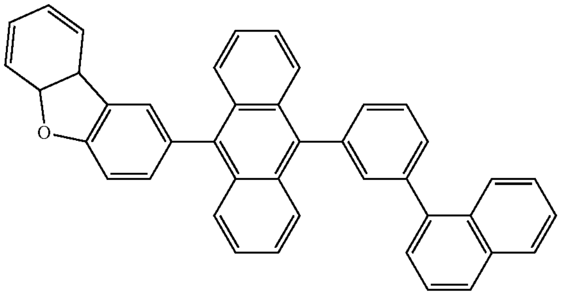
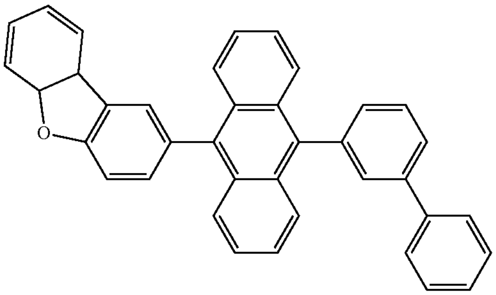
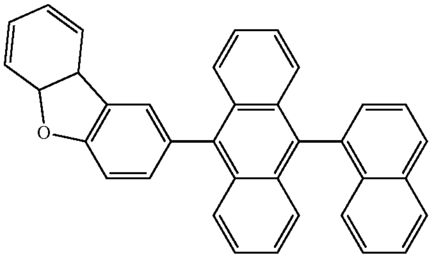

-continued
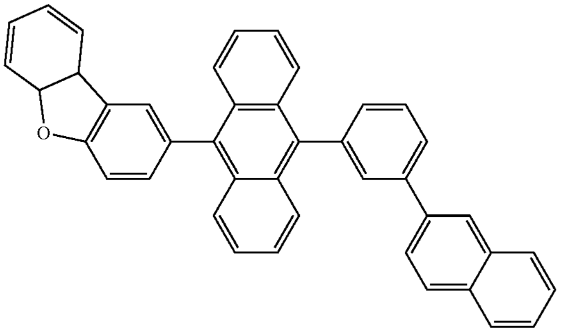
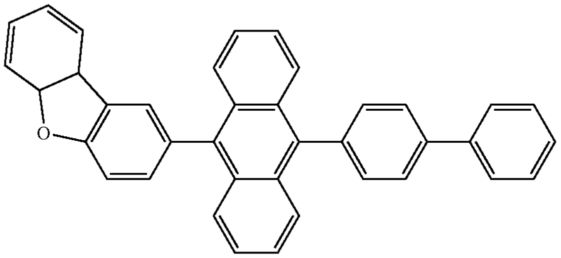
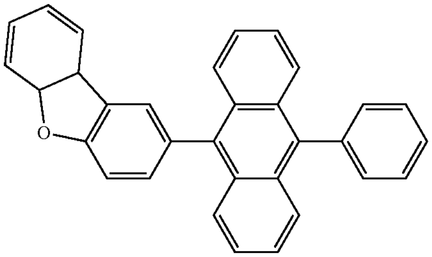
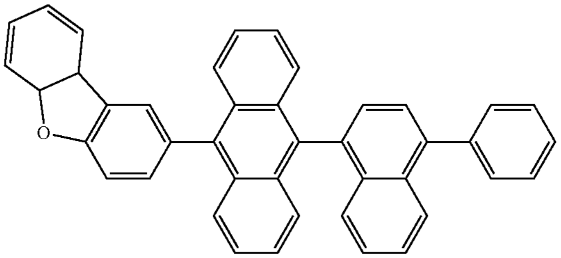
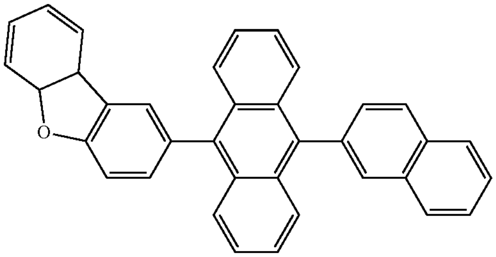
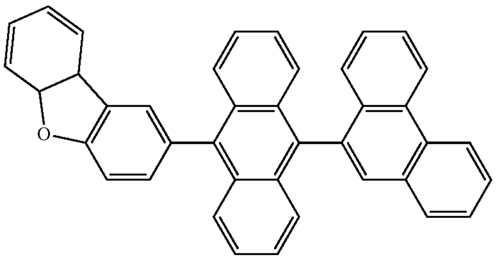
-continued
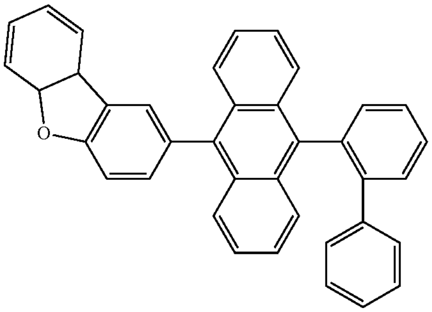
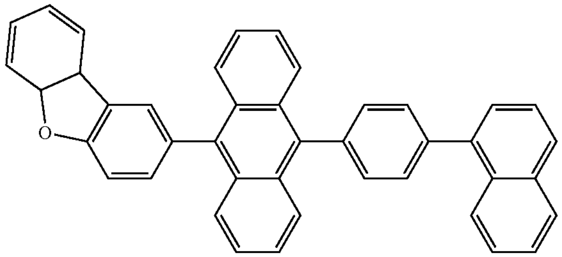
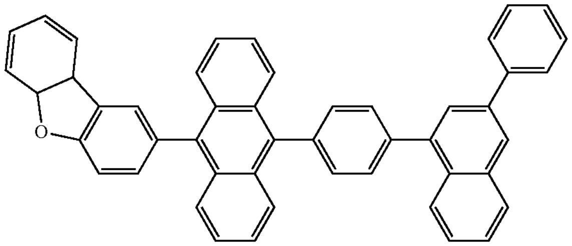
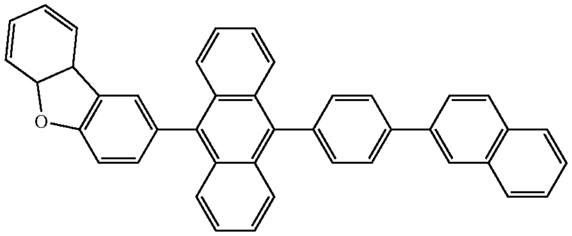
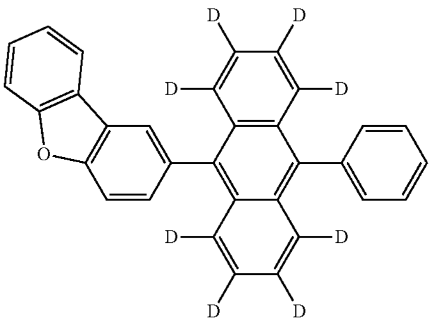
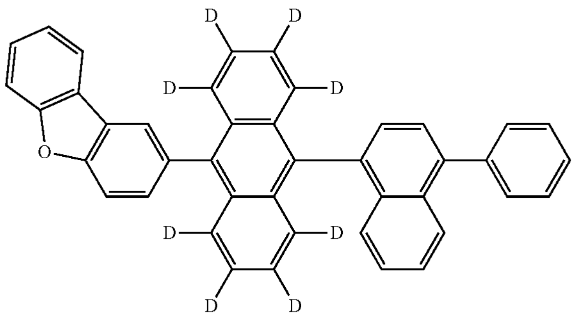

-continued
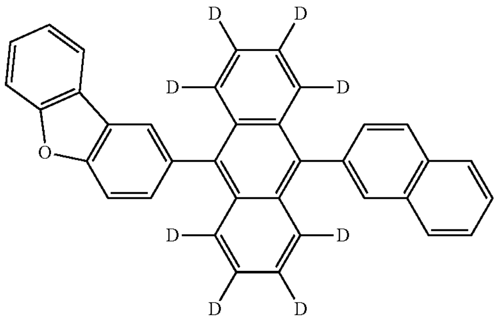
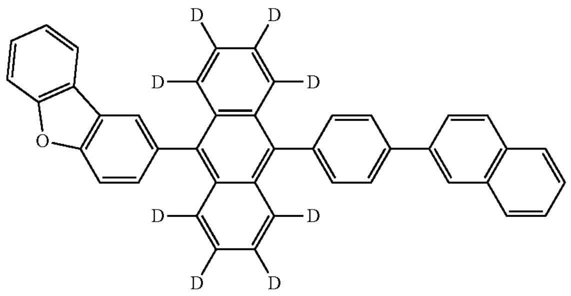
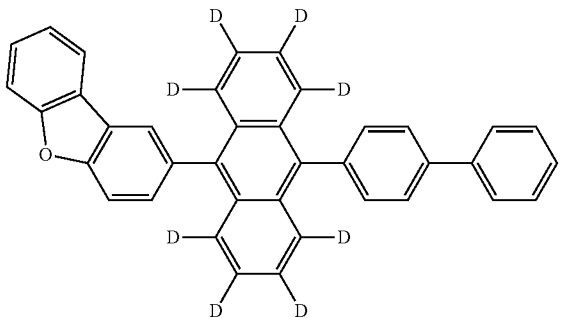
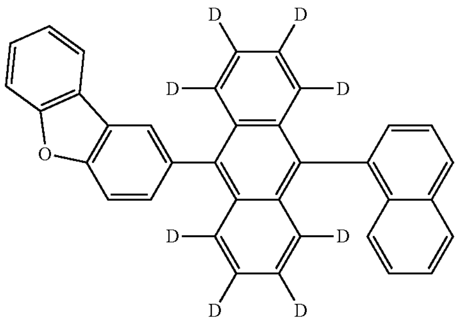
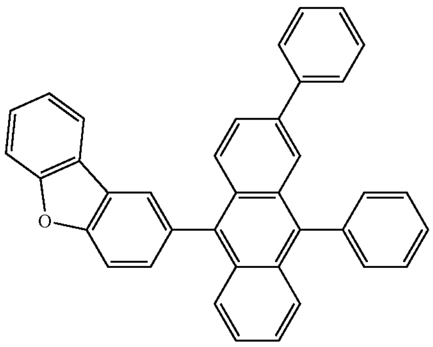
-continued
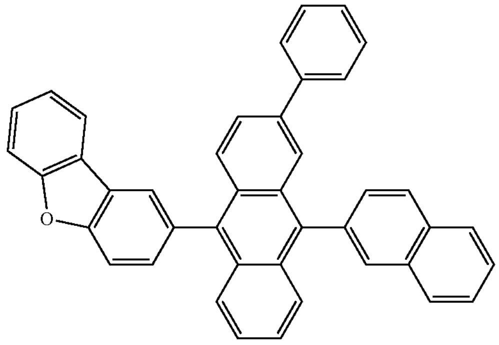
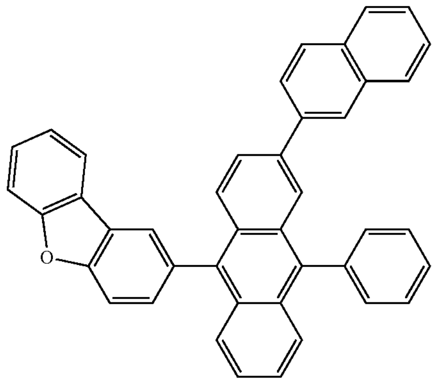
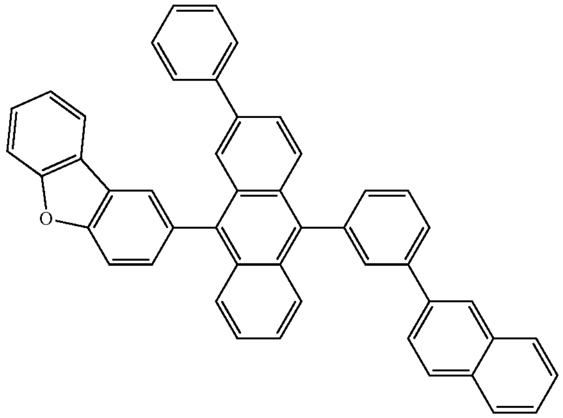
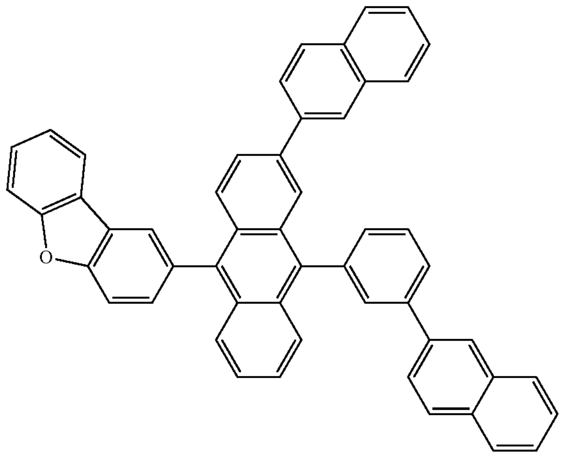

-continued
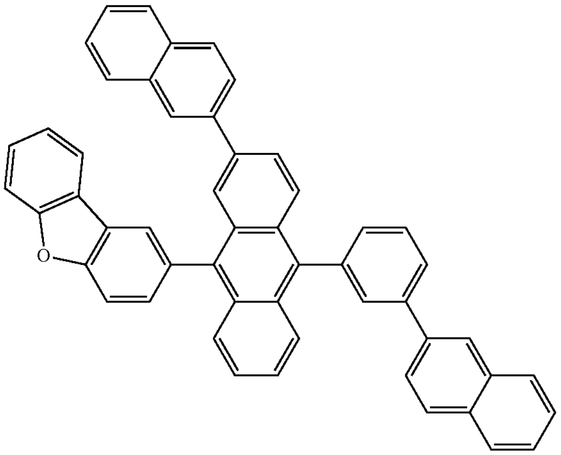
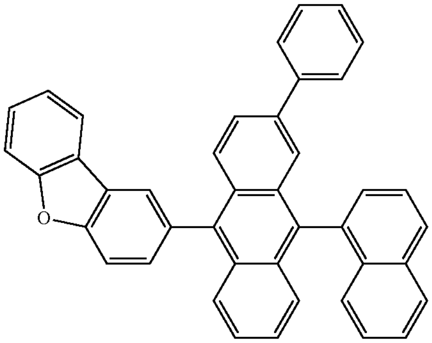
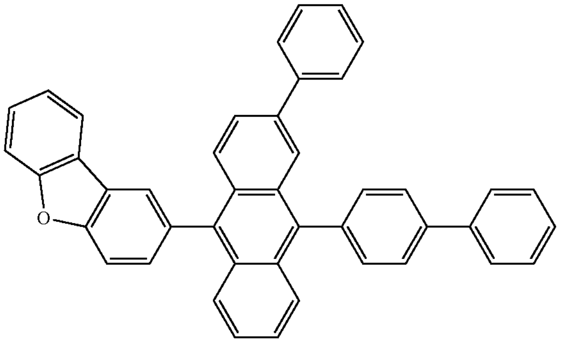
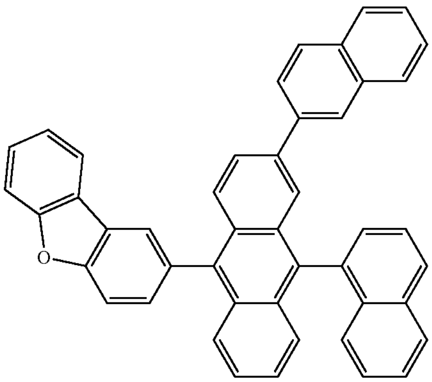
-continued
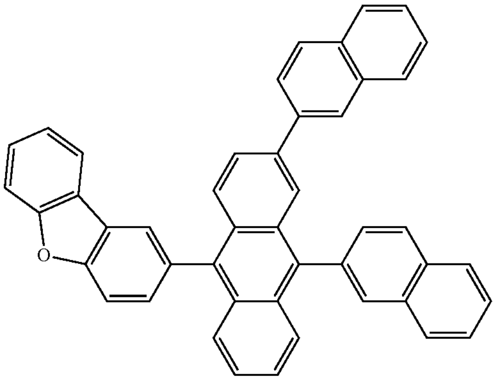
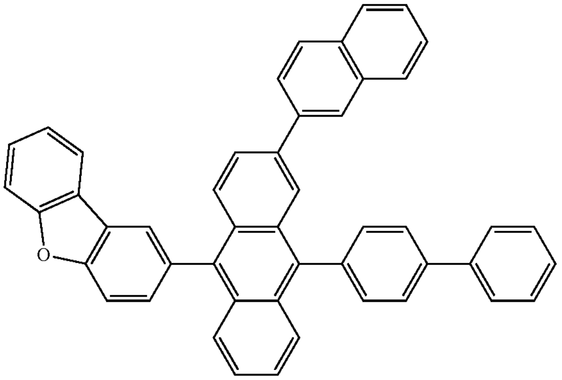
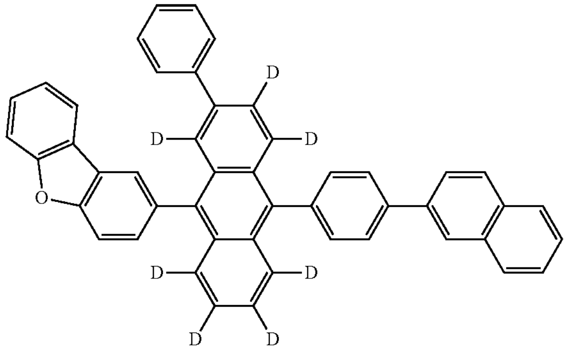
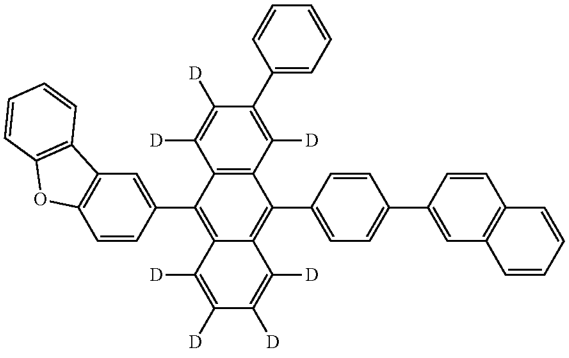

-continued
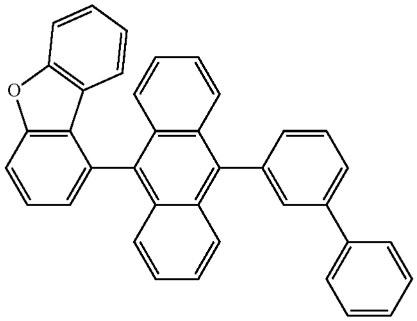
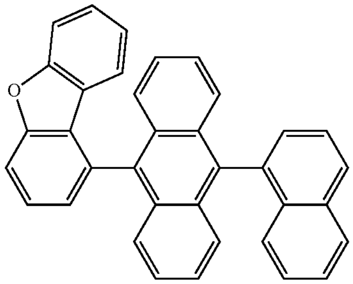
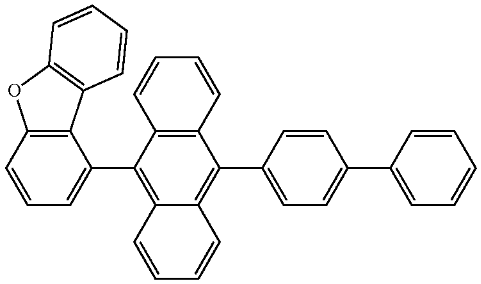
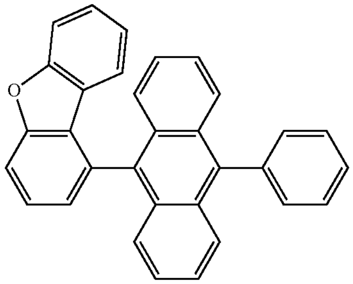
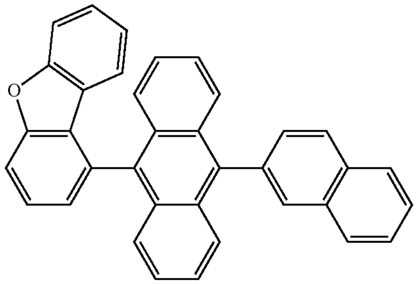
-continued
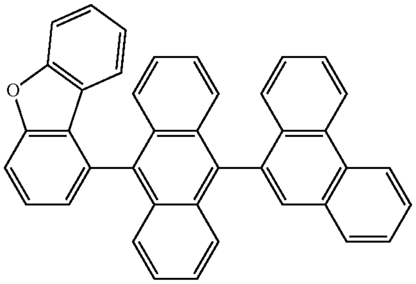
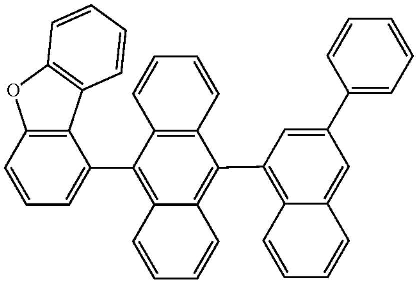
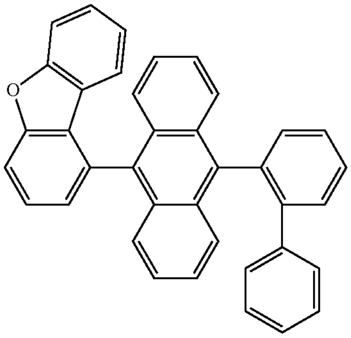
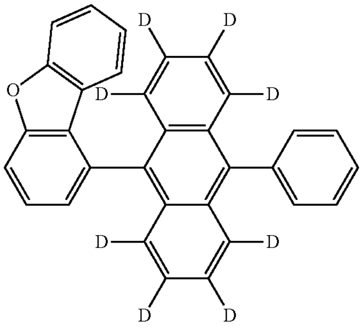
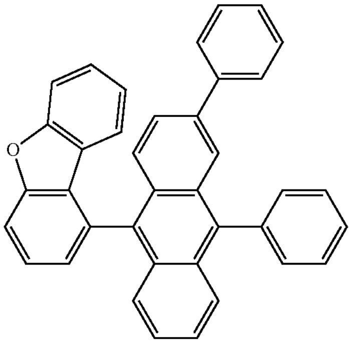

-continued
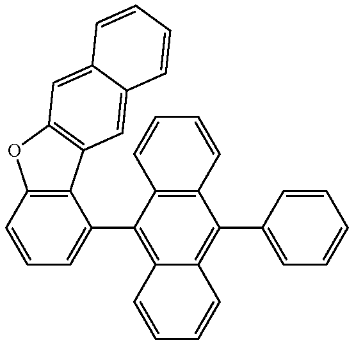
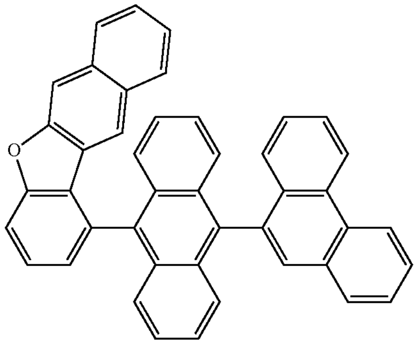
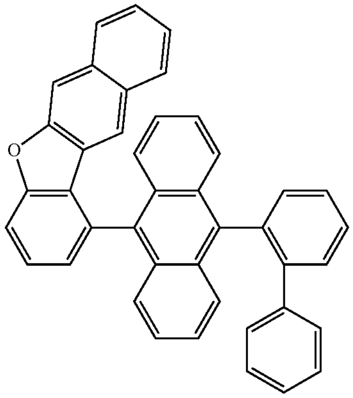
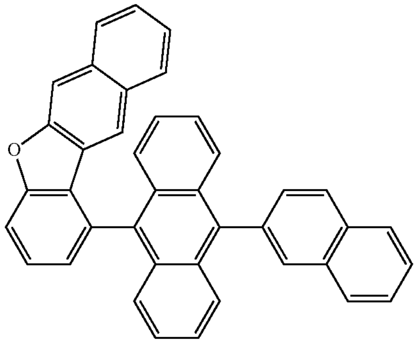
-continued
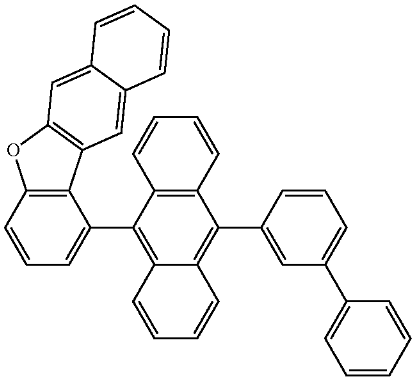
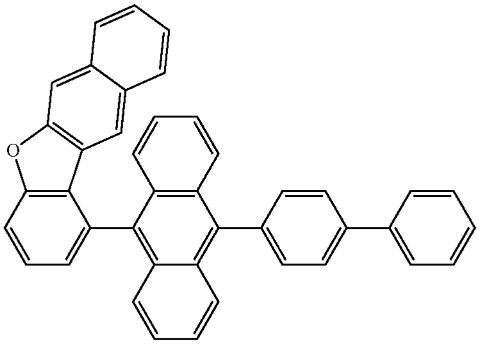
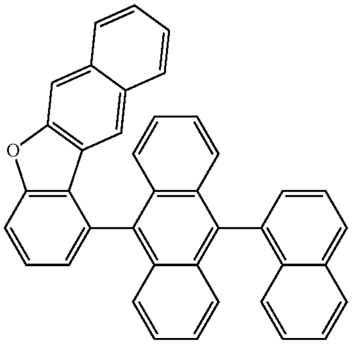
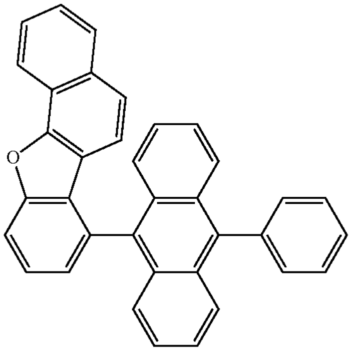

-continued
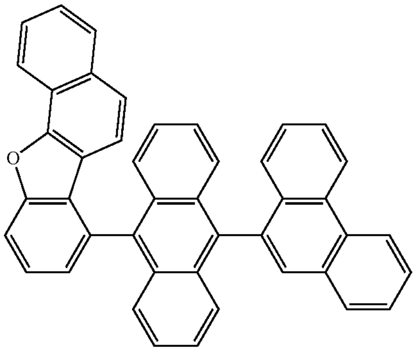
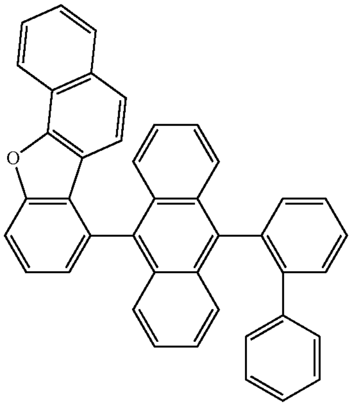
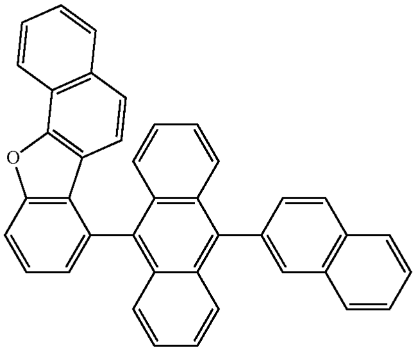
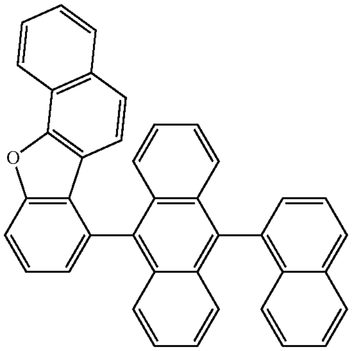
-continued
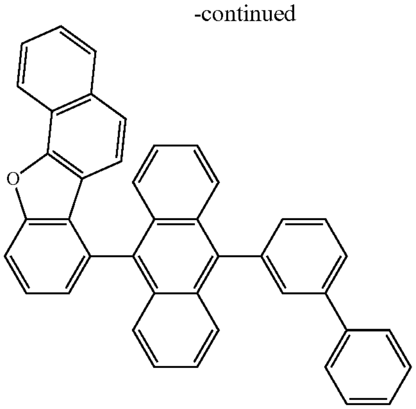
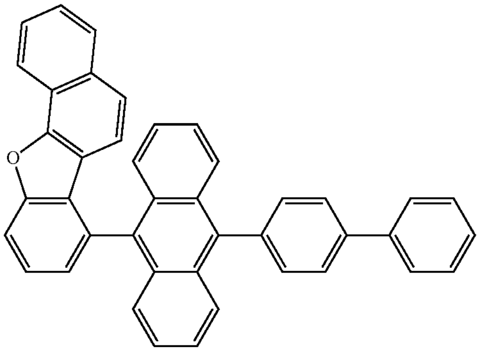
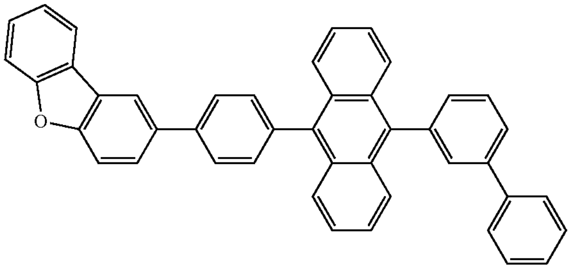
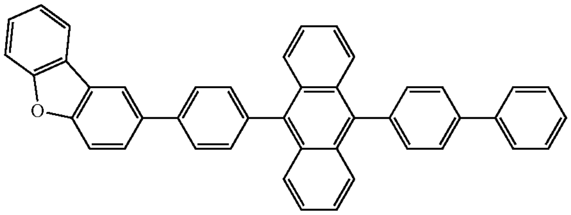
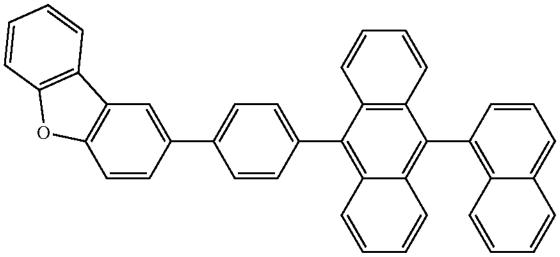
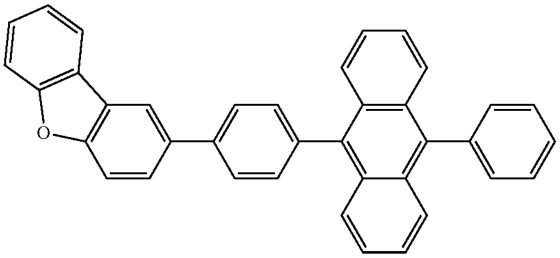

-continued
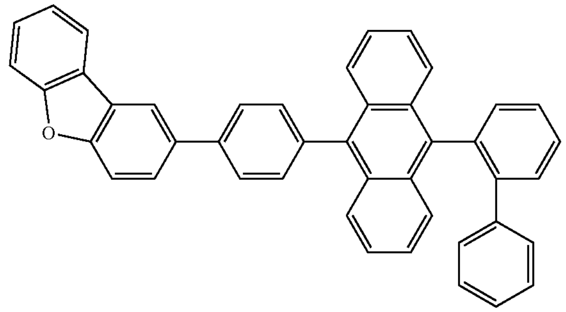
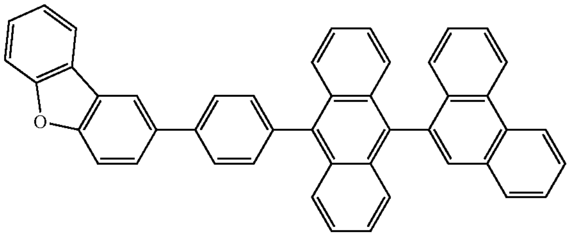
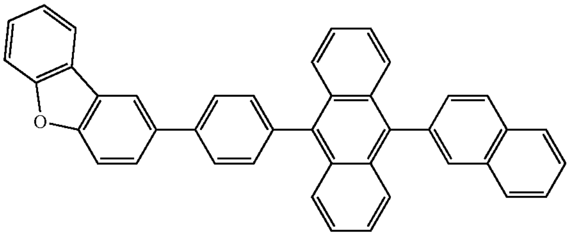
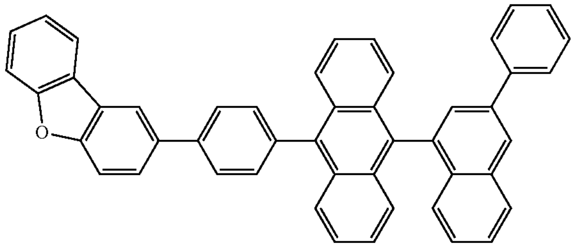
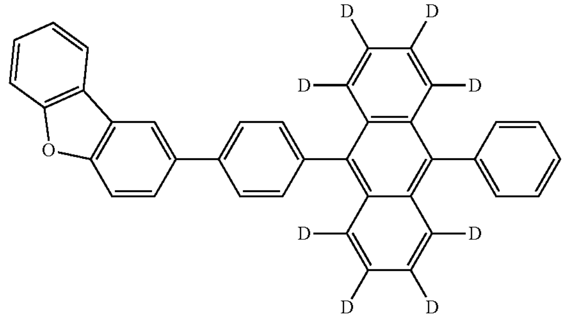
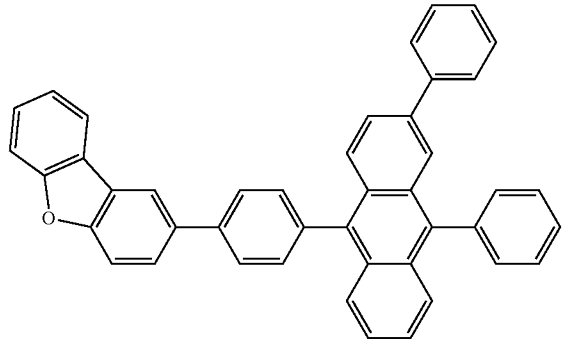
-continued
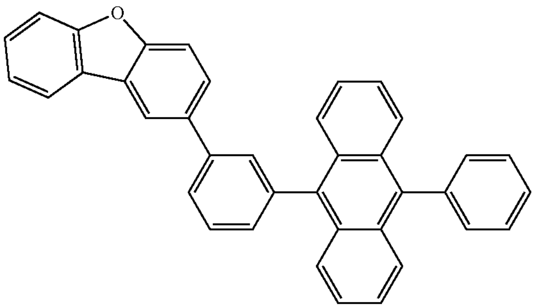
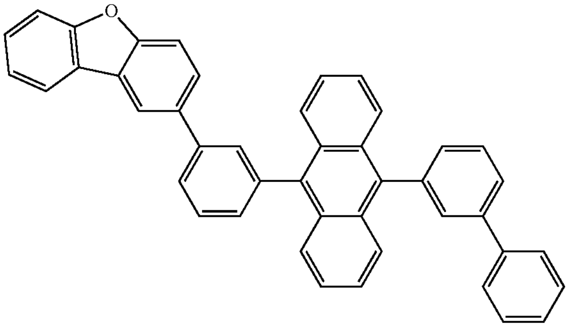
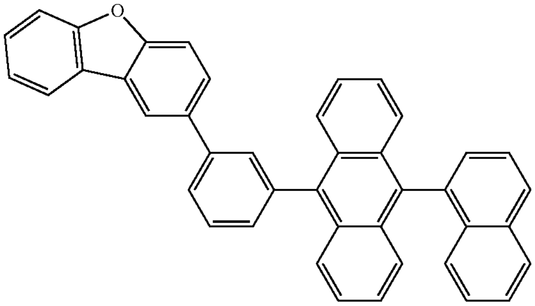
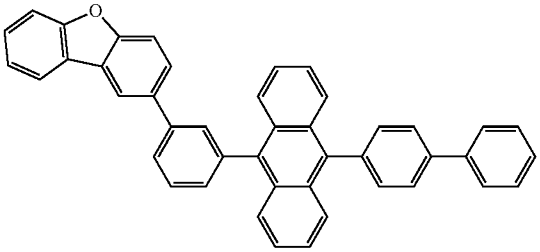
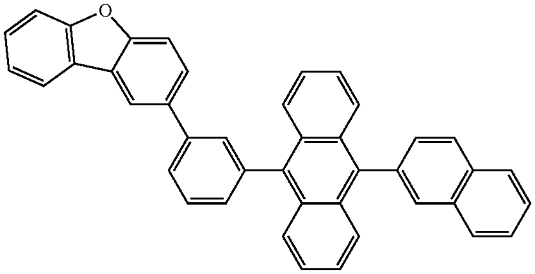

-continued
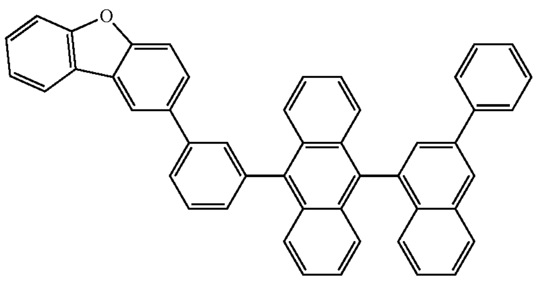
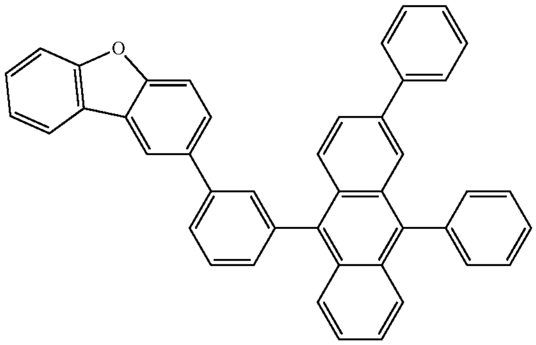
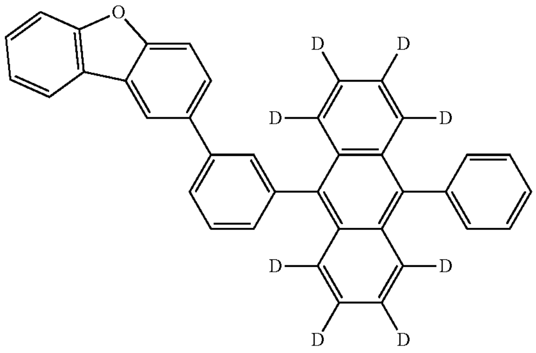
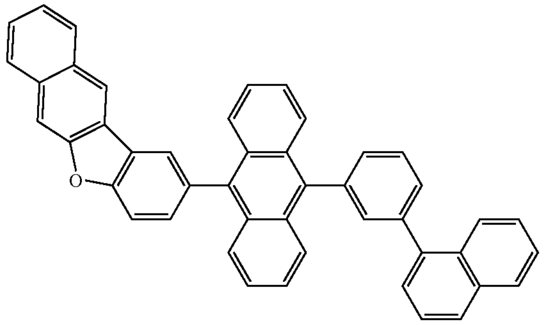
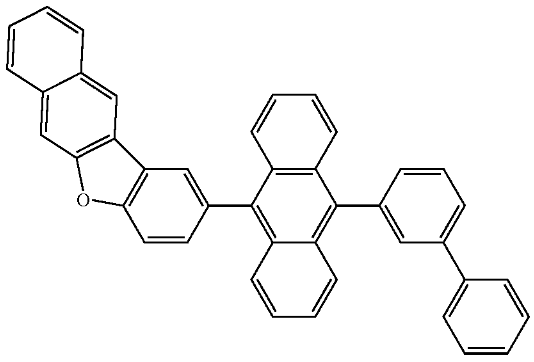
-continued
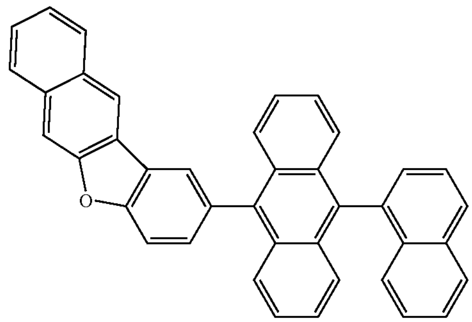
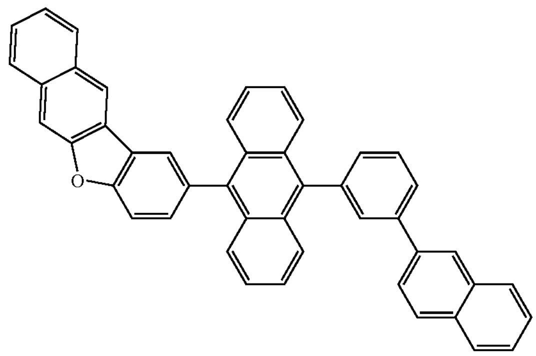
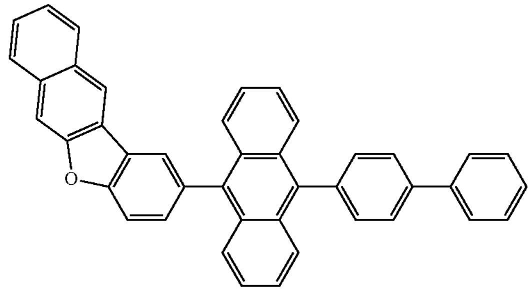
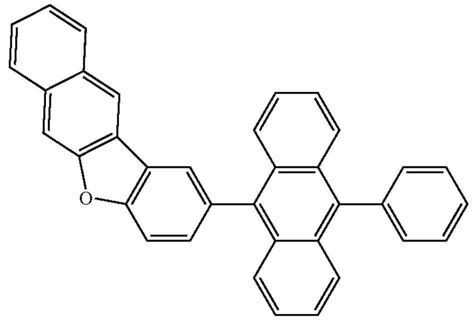
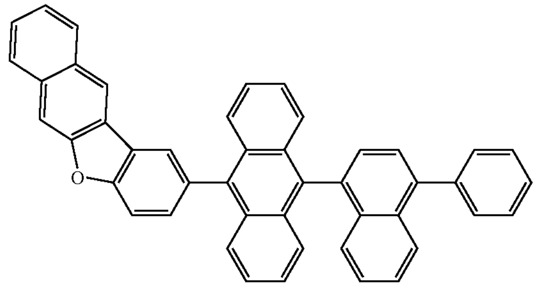

-continued
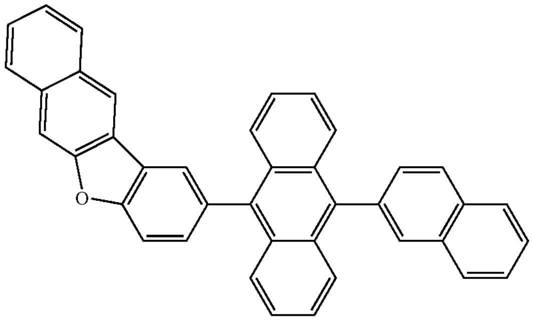
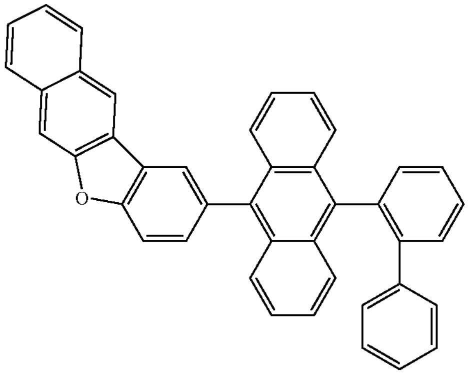
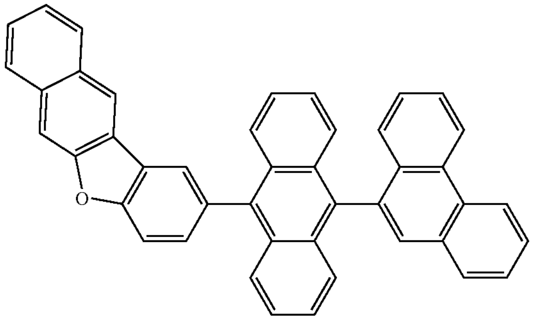
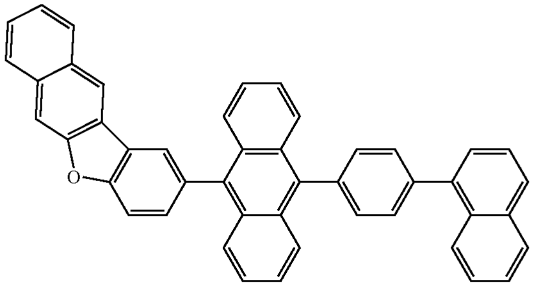
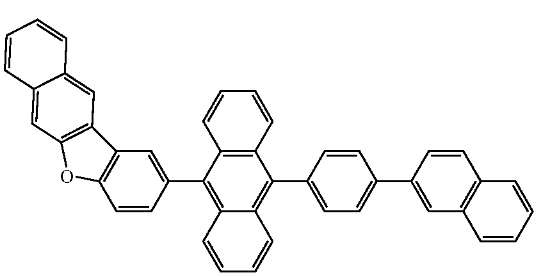
-continued
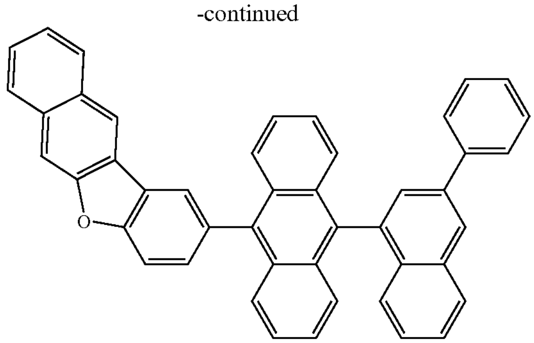
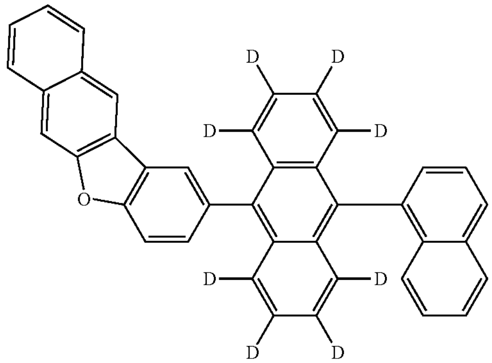
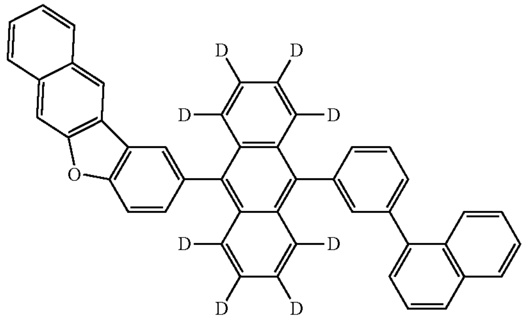
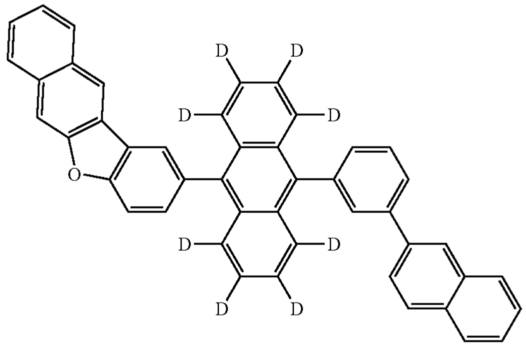
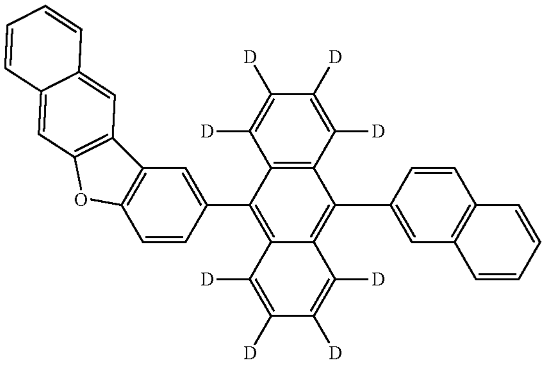

-continued
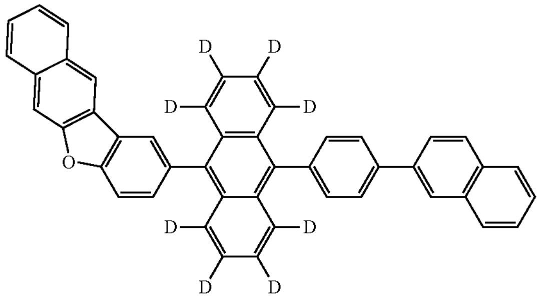
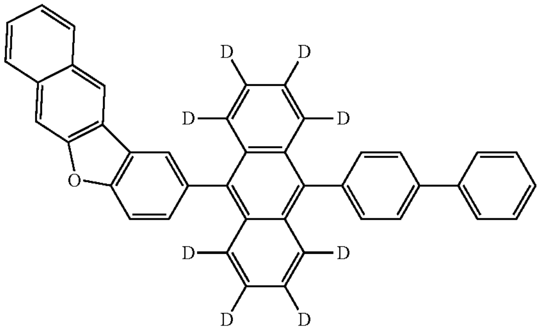
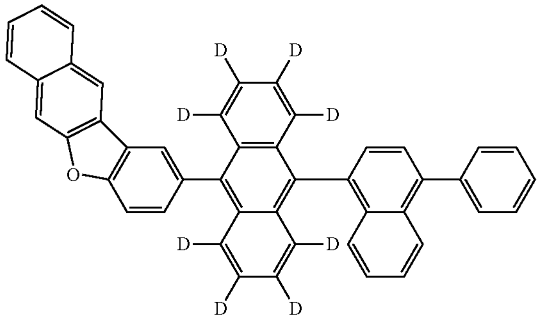
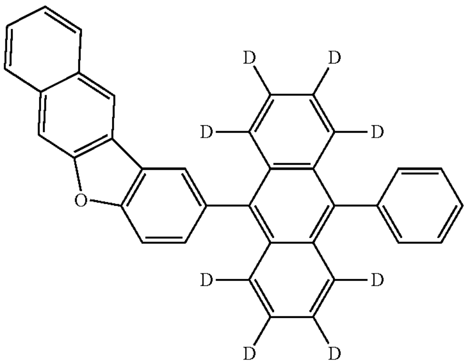
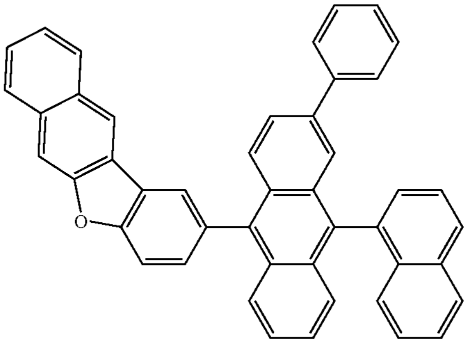
-continued
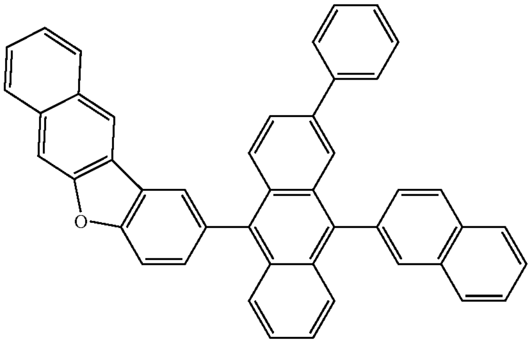
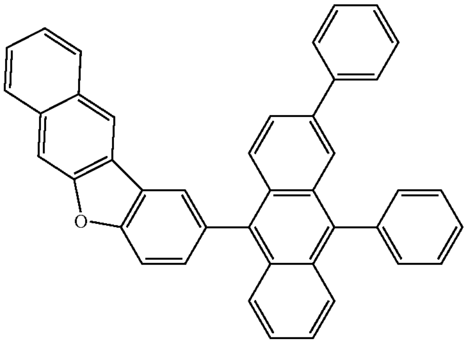
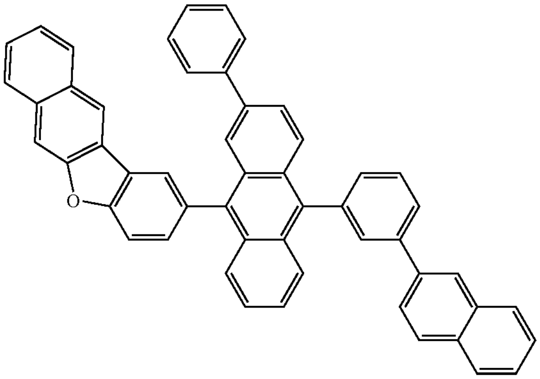
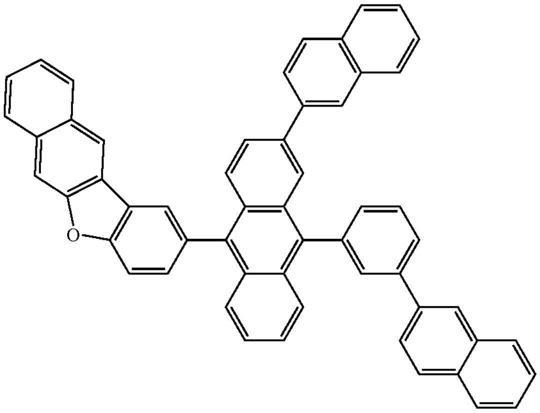

-continued
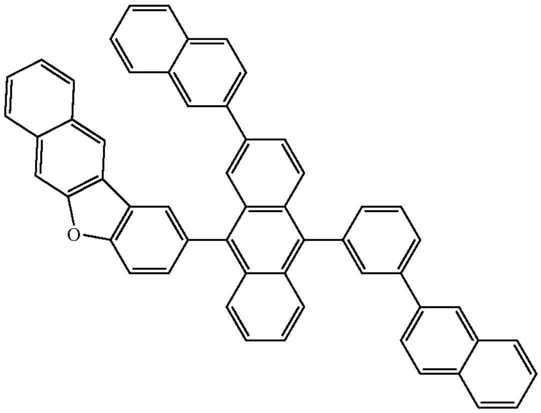
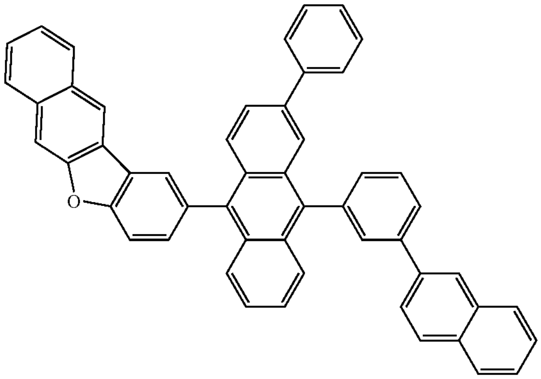
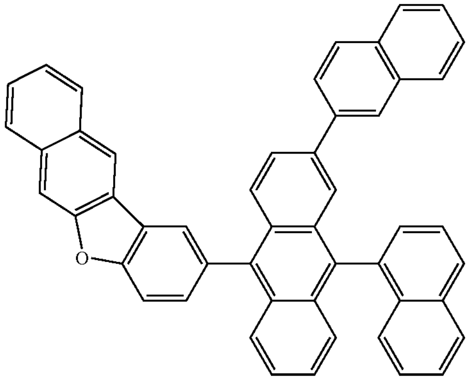
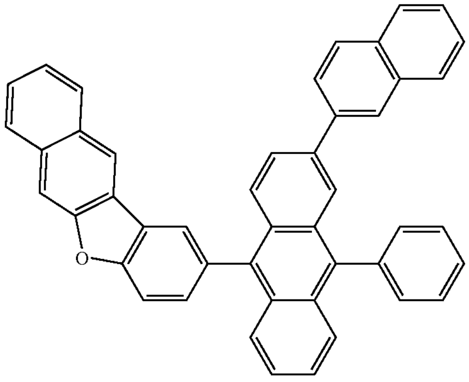
-continued
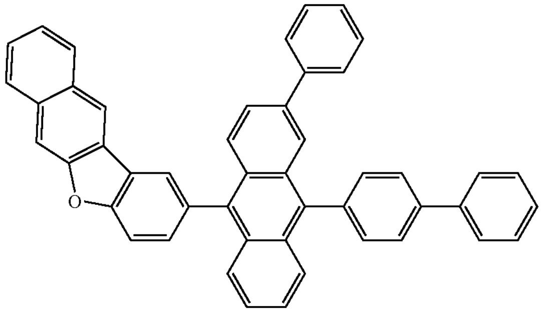
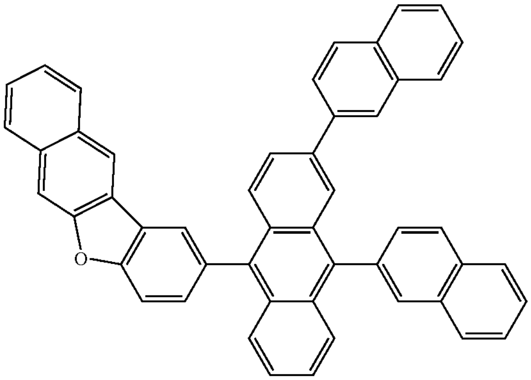
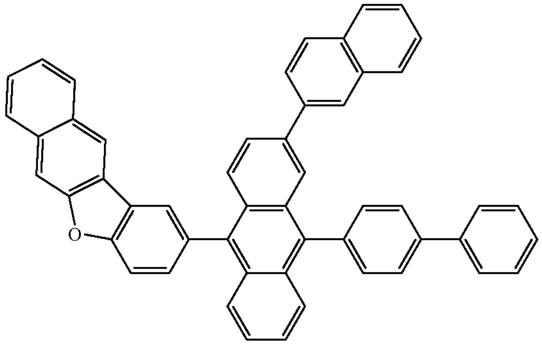
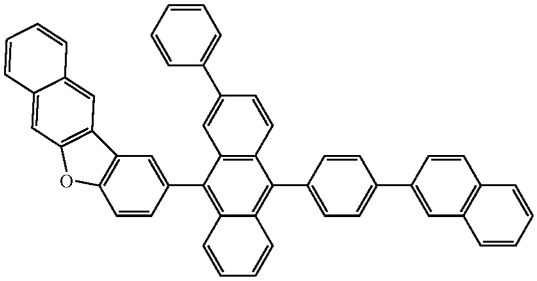
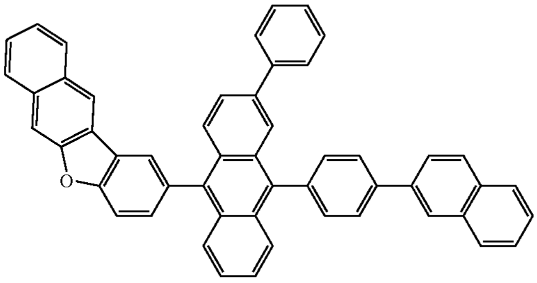

-continued
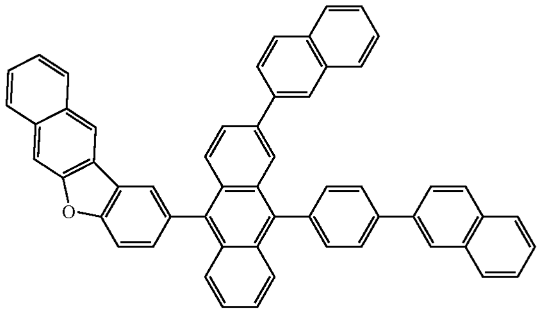
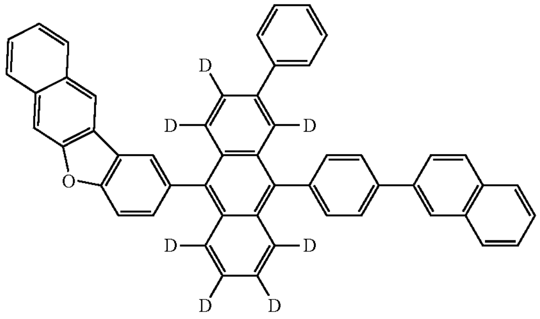
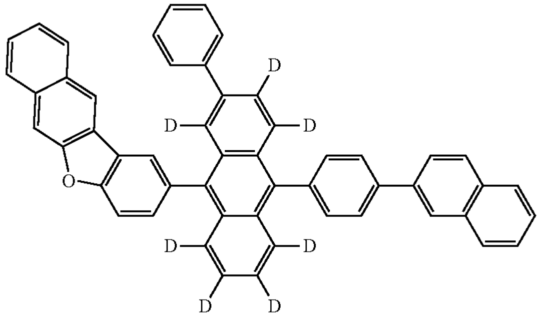
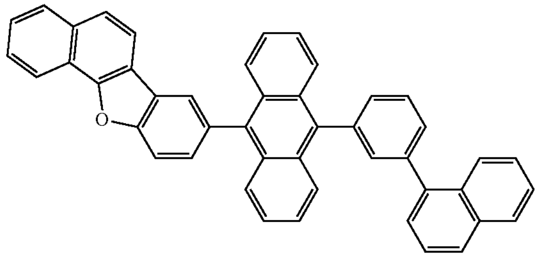
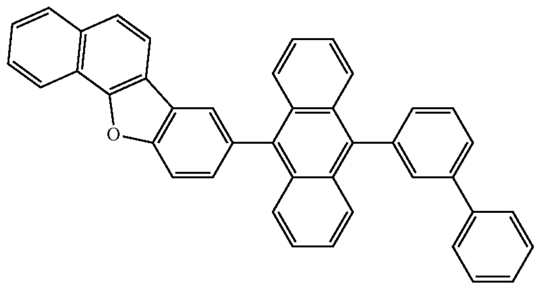
-continued
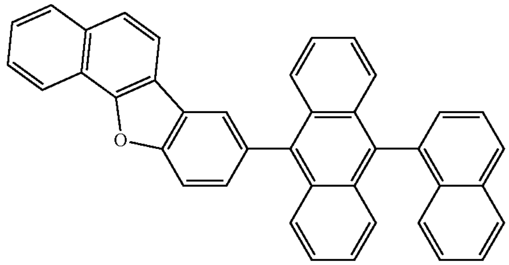
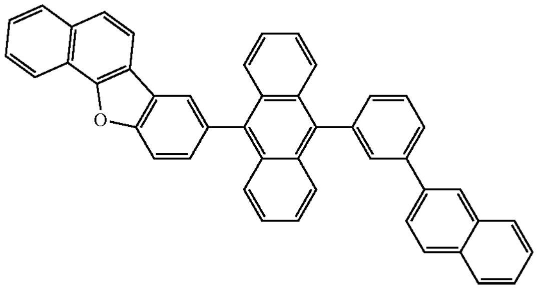
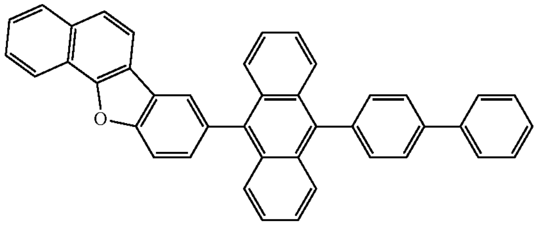
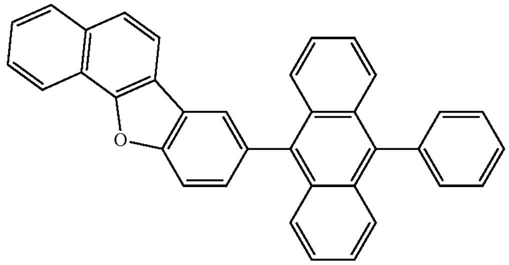
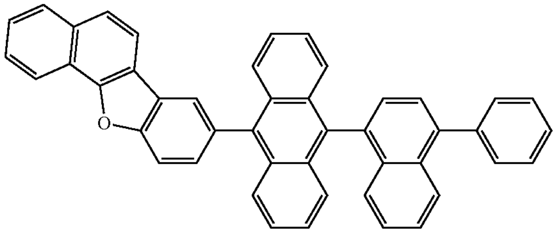
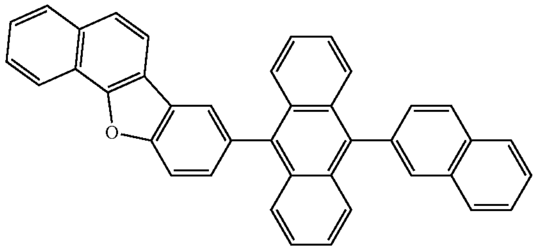

-continued
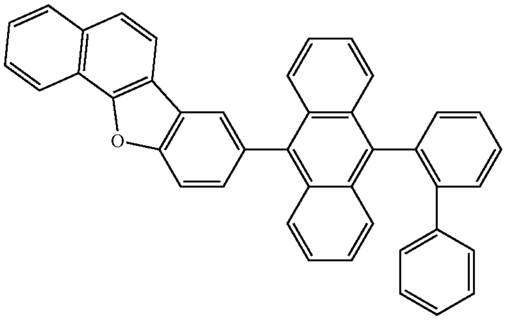
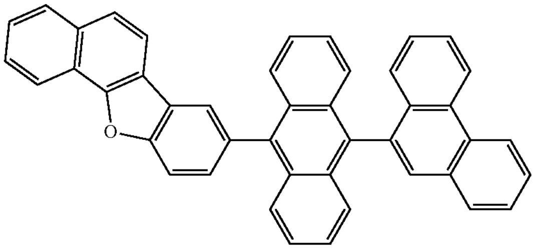
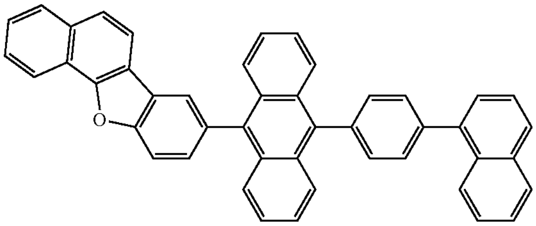
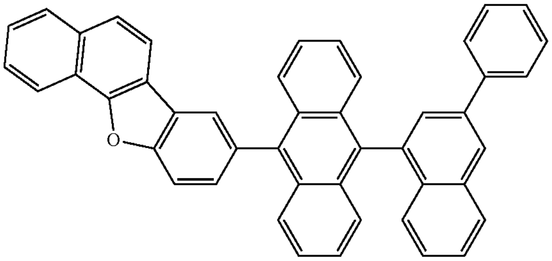
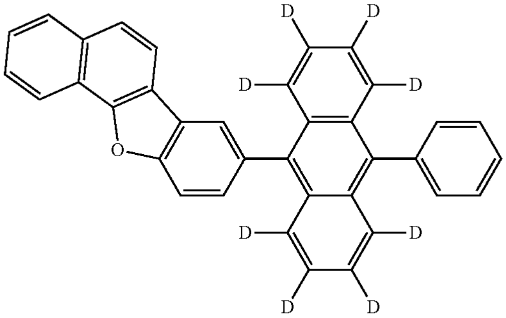
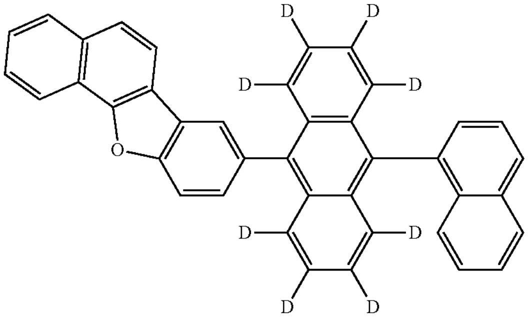
-continued
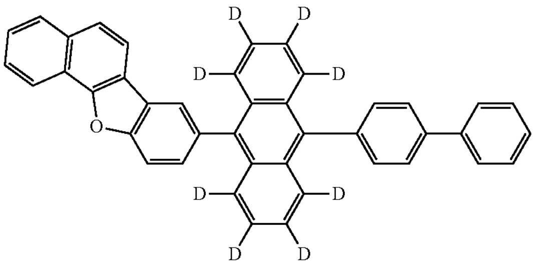
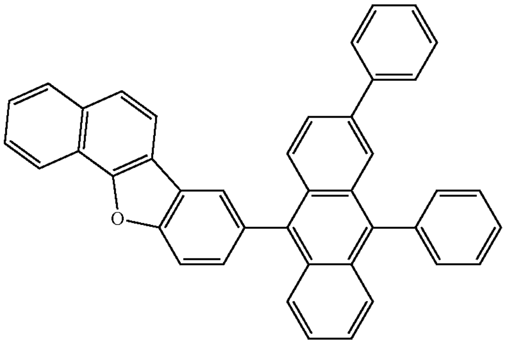
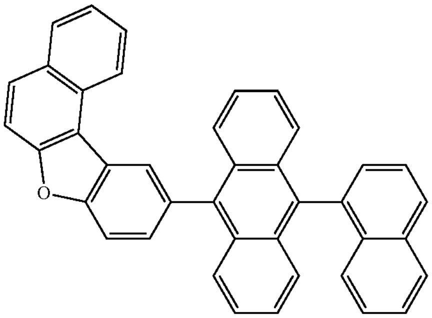
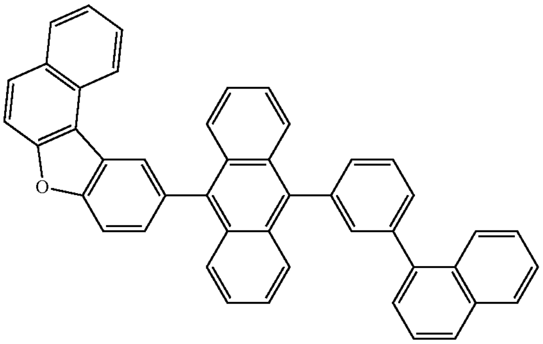
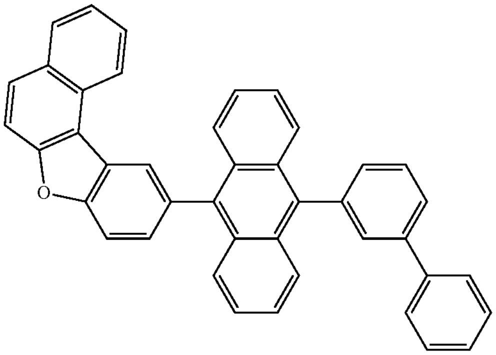

-continued
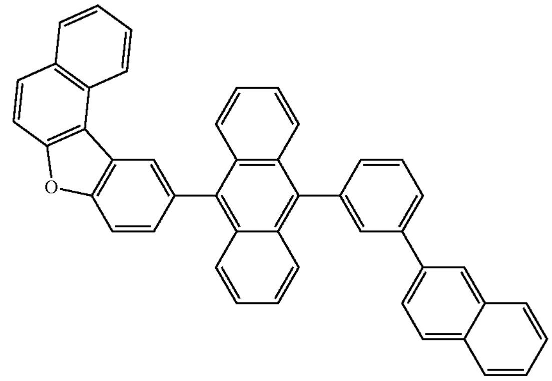
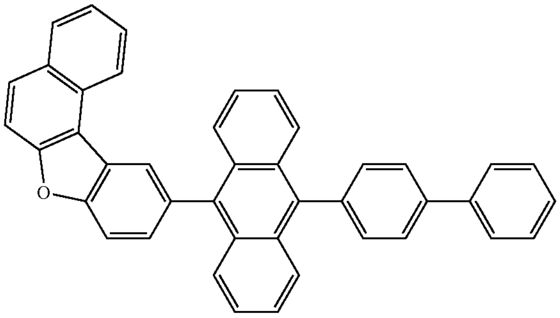
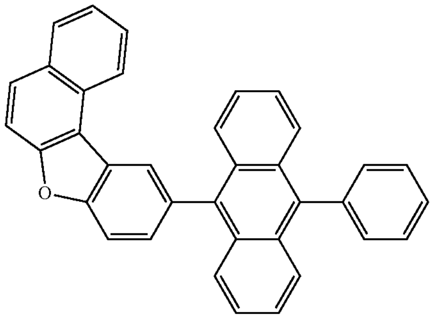
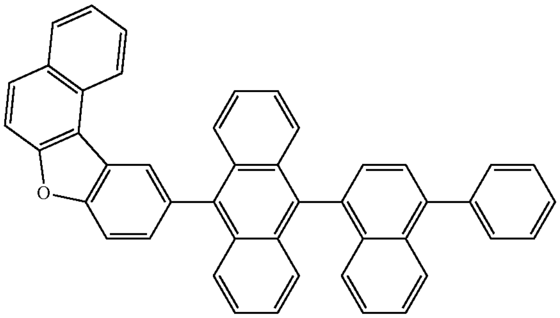
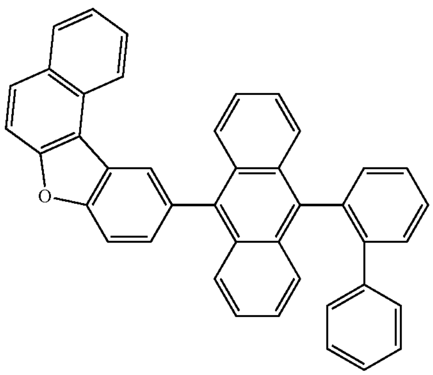
-continued
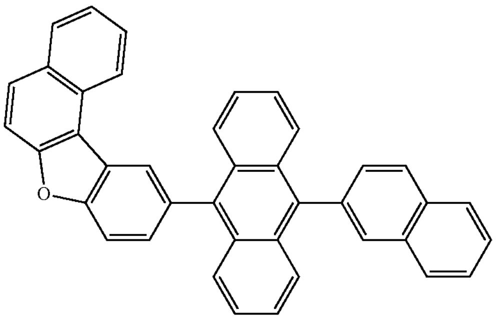
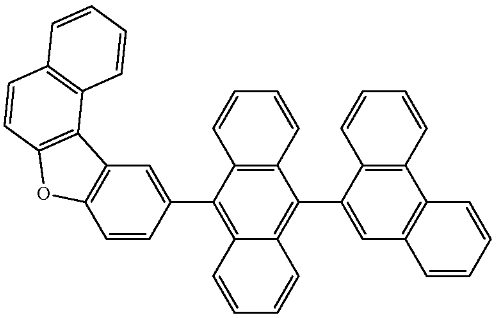
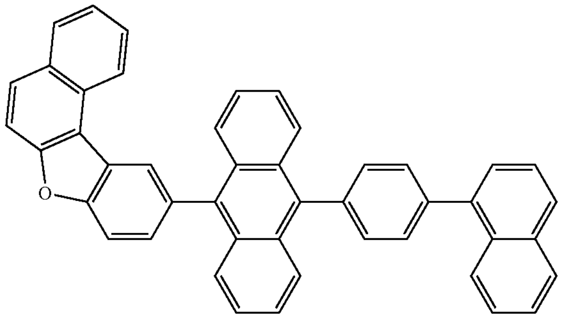
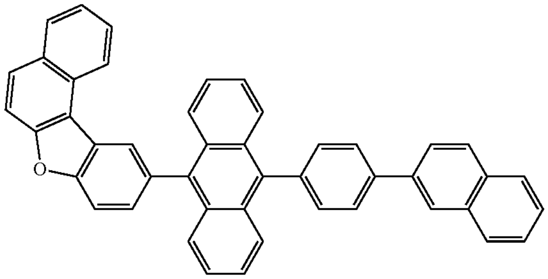
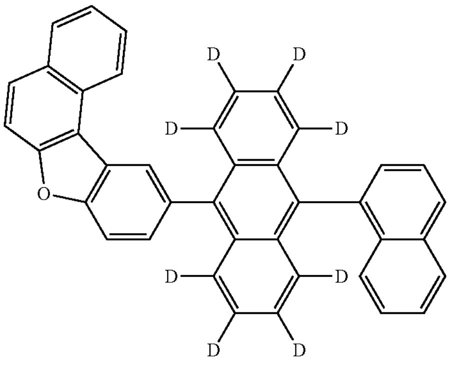

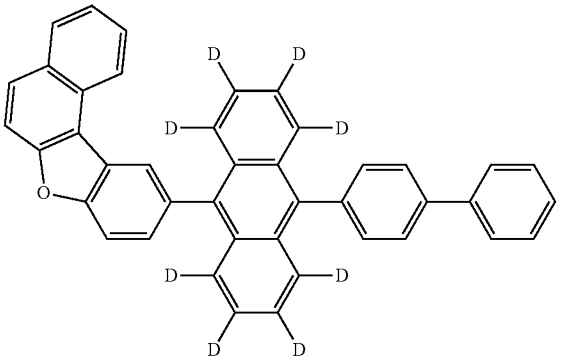
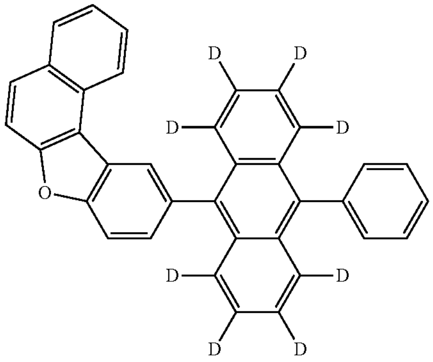
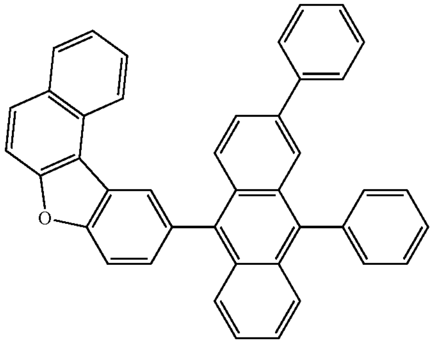
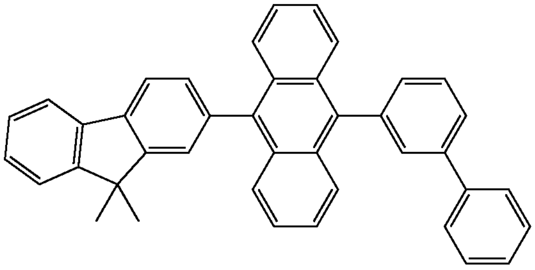
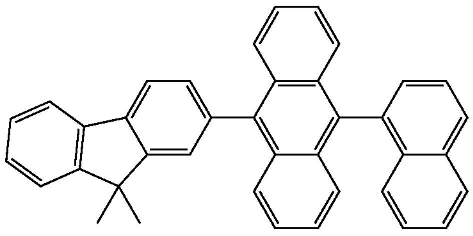
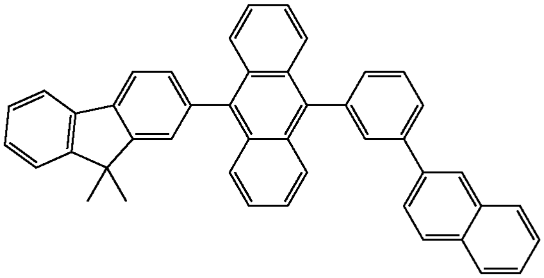
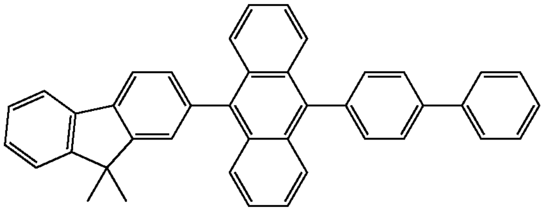
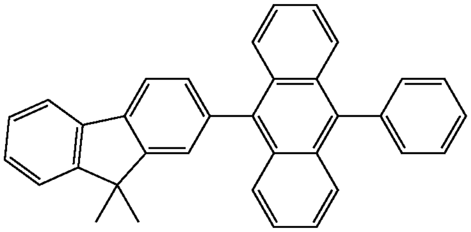
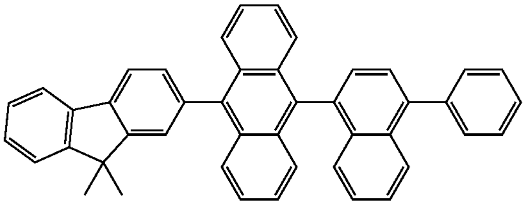
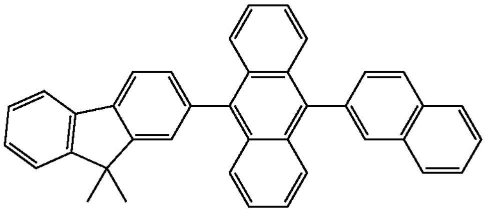
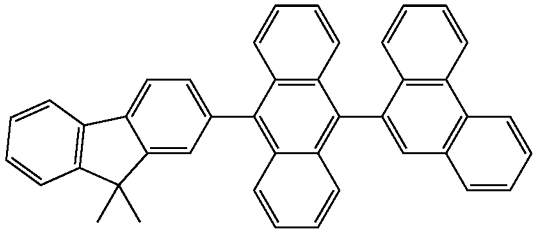
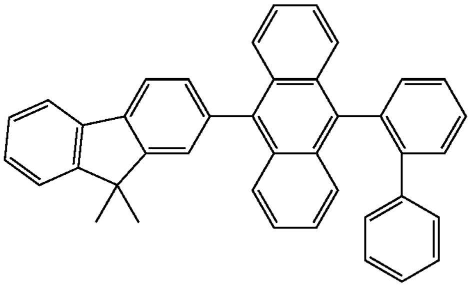

-continued
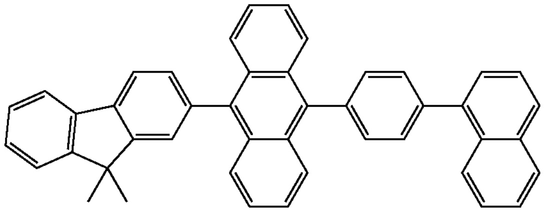
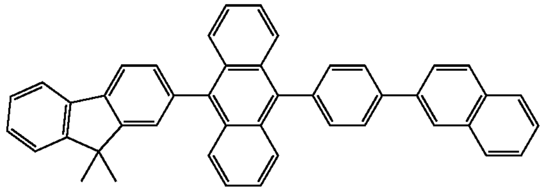
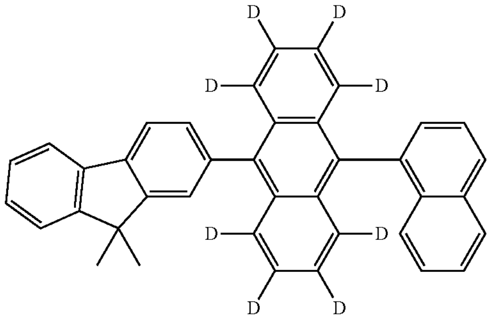
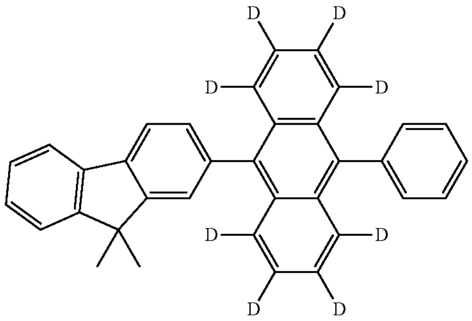
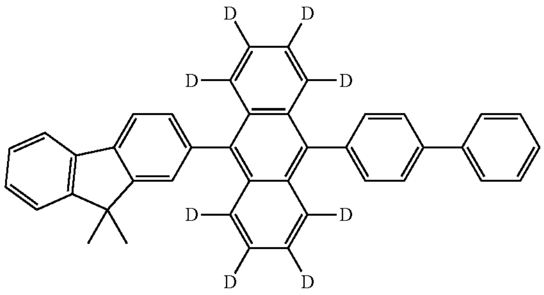
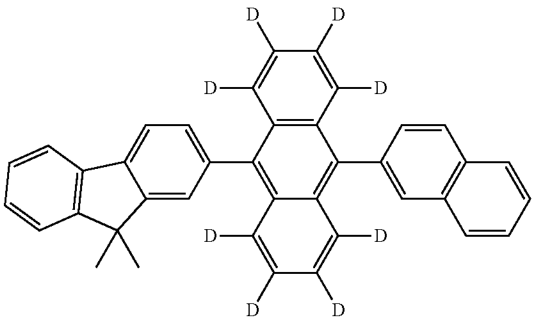
-continued
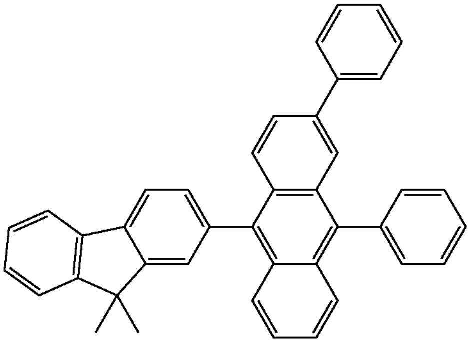
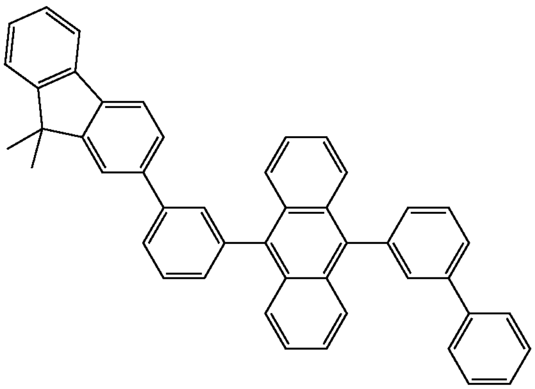
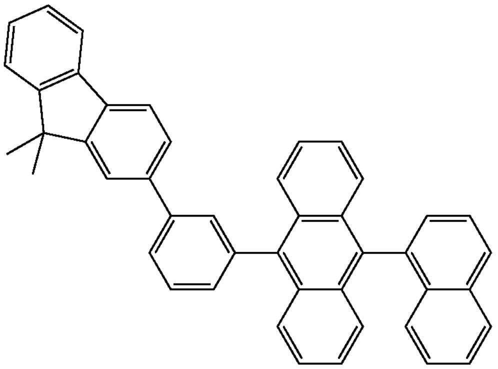
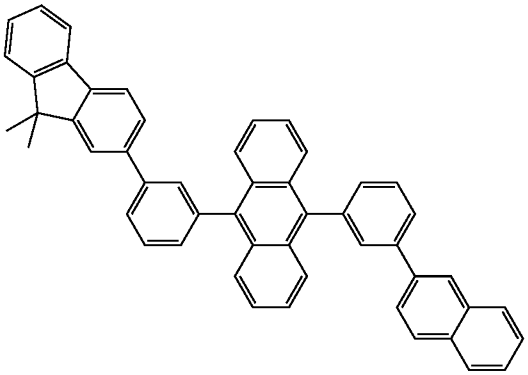

-continued
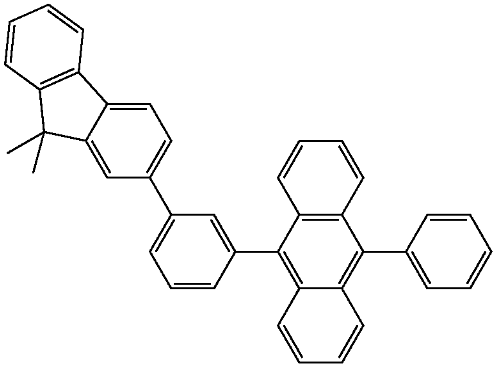
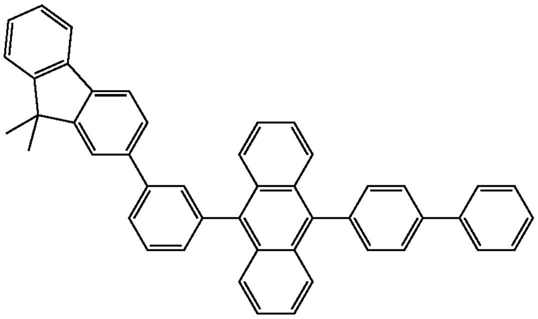
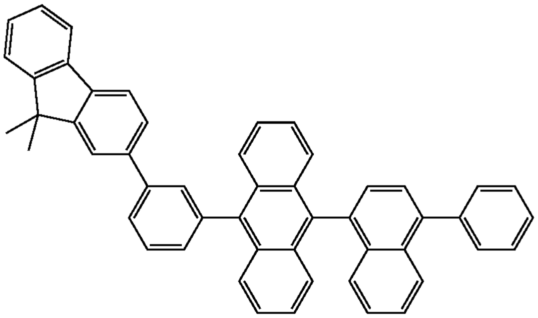
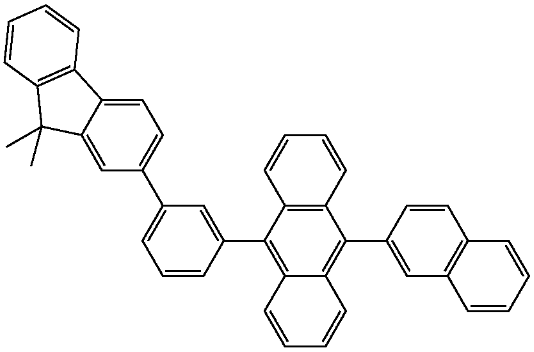
-continued
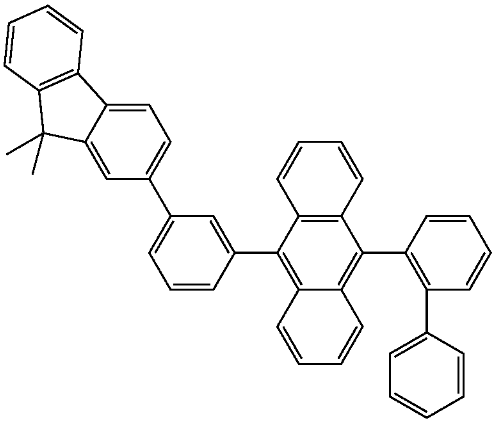
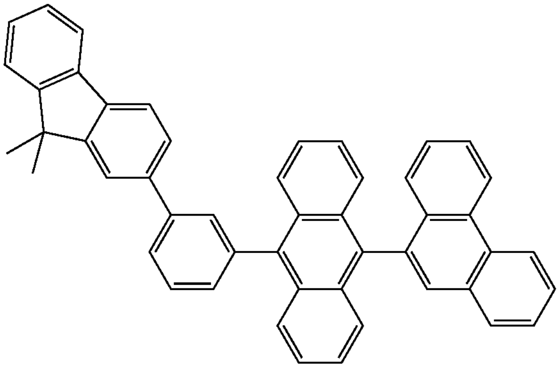
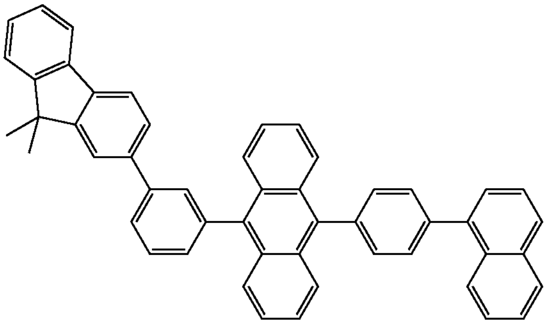
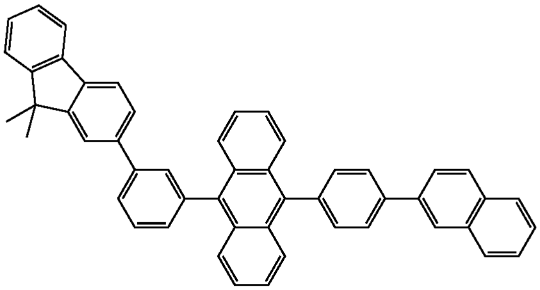

-continued
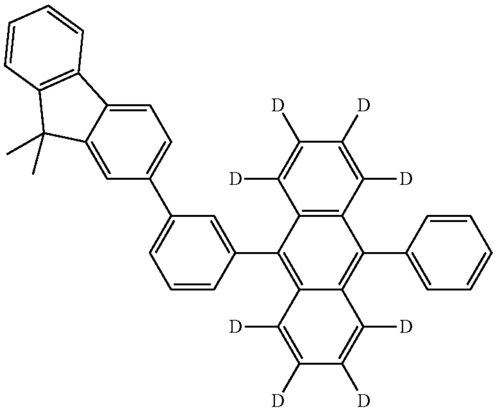
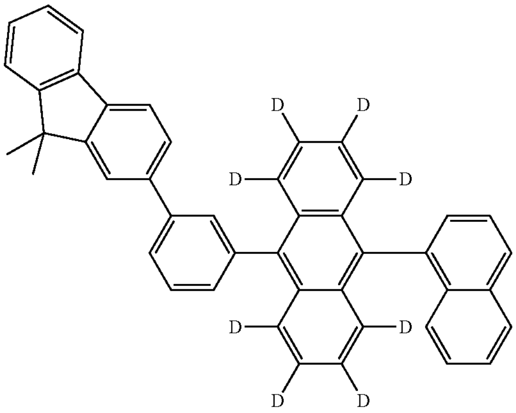
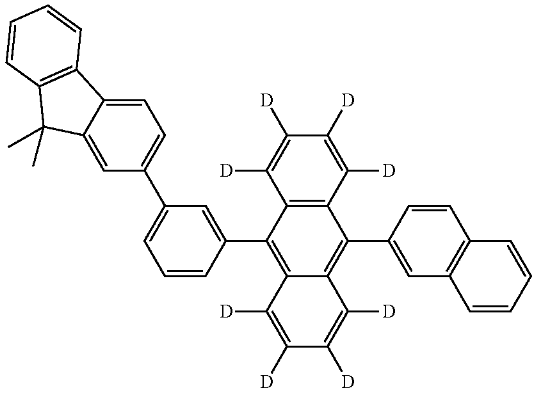
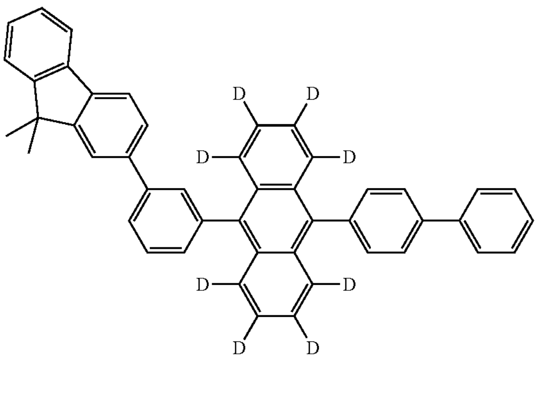
-continued
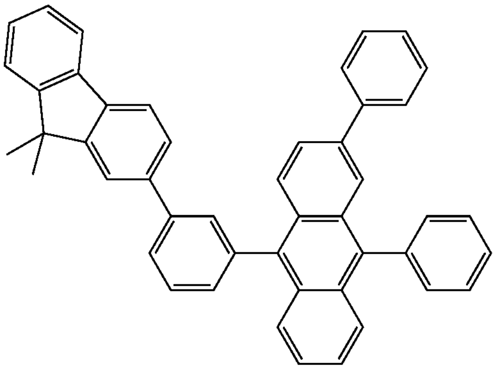
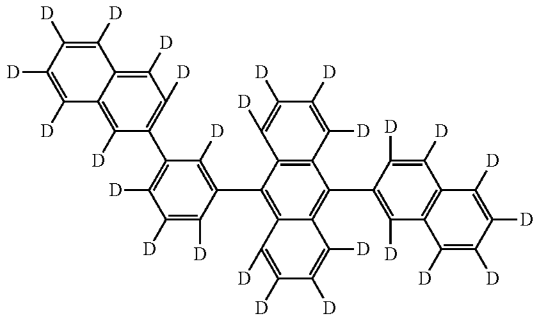
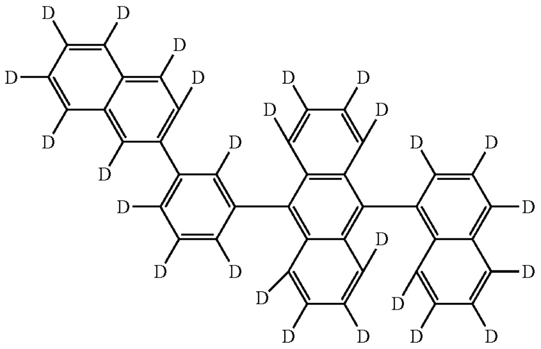
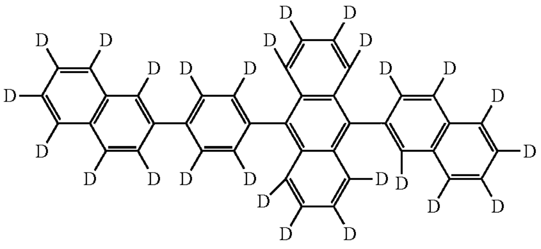
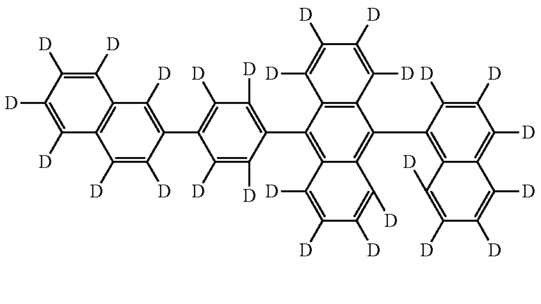

-continued

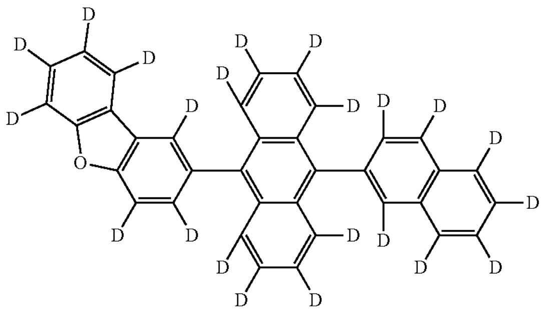

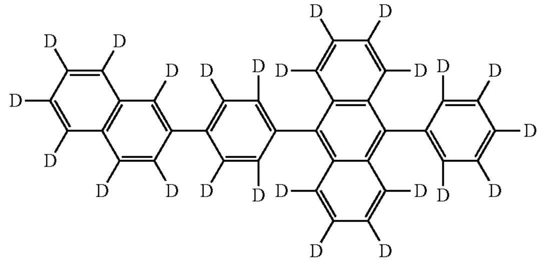

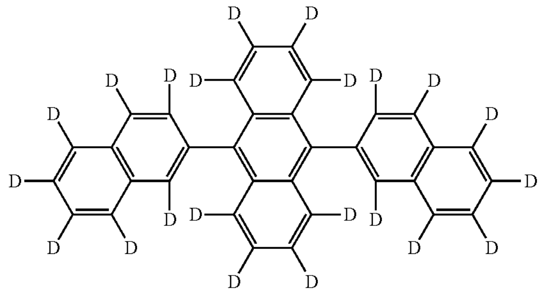

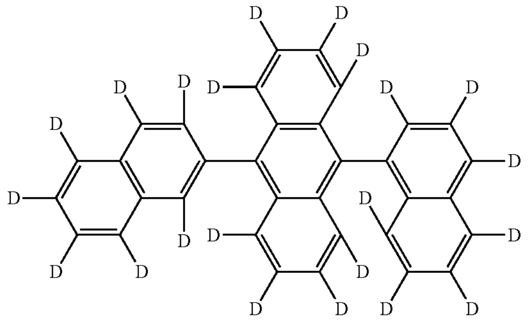

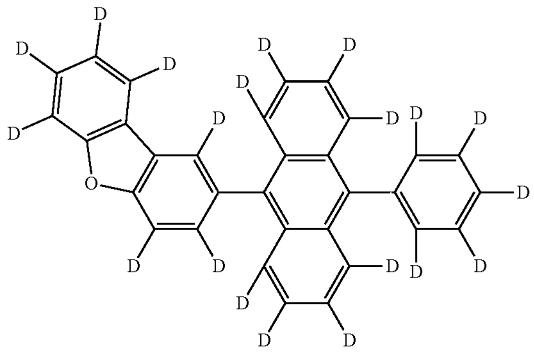 [SMILES: [2H]c1c([2H])c([2H])c(Cc2c3c([2H])c([2H])c([2H])c([2H])c3c(Cc3c([2H])c([2H])c4oc5c([2H])c([2H])c([2H])c([2H])c5c4c3[2H])c3c([2H])c([2H])c([2H])c([2H])c23)c([2H])c1[2H]]

Specific examples of each group in the formula (A1) and formula (10) and the like are as described in the section of [Definition] in this specification.

As described above, for the organic electroluminescenoe device according to one aspect of the invention, known materials and device configurations may be applied, as long as the device includes a cathode, an anode, and at least one organic layer disposed between the cathode and the anode, wherein at least one layer of the at least one organic layer contains a compound represented by the formula (A1), and the known materials and the device configurations do not impair the effect of the invention.

As described above, for the organic electroluminescence device according to one aspect of the invention, known materials and device configurations may be applied, as long as the device includes a cathode, an anode, and at least one organic layer disposed between the cathode and the anode, wherein at least one layer of the at least one organic layer contains compounds represented by each of the formula (A1) and (10), and the known materials and the device configurations do not impair the effect of the invention.

Parts, materials for forming respective layers other than the above-mentioned compounds, and the like which can be employed in the organic EL device according to one aspect of the invention, will be described below.

(Substrate)

A substrate is used as a support of an emitting device. As the substrate, glass, quartz, plastic, and the like can be used, for example. Further, a flexible substrate may be used. The "flexible substrate" means a bendable (flexible) substrate, and specific examples thereof include a plastic substrate formed of polycarbonate, polyvinyl chloride, or the like.

(Anode)

For the anode formed on the substrate, metals, alloys, electrically conductive compounds, mixtures thereof, and the like, which have a large work function (specifically 4.0 eV or larger) are preferably used. Specific examples thereof include indium oxide-tin oxide (ITO: Indium Tin Oxide), indium oxide-zinc oxide, tungsten oxide, graphene, and the like. The electrodes formed thereof may further contain other elements. For example, such other elements include silicon, iron, copper, chromium, nickel, and the like. In addition thereto, gold (Au), platinum (Pt), a nitride of a metallic material (for example, titanium nitride), and the like can be given.

(Hole-Injecting Layer)

The hole-injecting layer is a layer containing a substance having a high hole-injecting property. As such a substance having a high hole-injecting property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, or a polymer compound (oligomers, dendrimers, polymers, etc.) can be given.

(Hole-Transporting Layer)

The hole-transporting layer is a layer containing a substance having a high hole-transporting property. For the hole-transporting layer, an aromatic amine compound, a carbazole derivative, an anthracene derivative, and the like can be used. Polymer compounds such as poly(N-vinylcarbazole) (abbreviation: PVK) and poly(4-vinyltriphenylamine) (abbreviation: PVTPA) can also be used. However, a substance other than the above-described substances may be used as long as the substance has a higher hole-transporting property in comparison with an electron-transporting property. It should be noted that the layer containing the substance having a high hole-transporting property may be not only a single layer, but also a stacked layer of two or more layers each formed of the above-described substances.

(Guest Material for Emitting Layer)

The emitting layer is a layer containing a substance having a high emitting property, and can be formed by the use of various materials. For example, as the substances having a high emitting property, a fluorescent compound which emits fluorescence and a phosphorescent compound which emits phosphorescence can be used. The fluorescent compound is a compound which can emit from a singlet excited state, and the phosphorescent compound is a compound which can emit from a triplet excited state.

As a blue fluorescent emitting material which can be used for an emitting layer, a pyrene derivative, a styrylamine derivative, a chrysene derivative, a fluoranthene derivative, a fluorene derivative, a diamine derivative, a triarylamine derivative, and the like can be used. As a green fluorescent emitting material which can be used for an emitting layer, an aromatic amine derivative and the like can be used. As a red fluorescent emitting material which can be used for an emitting layer, a tetracene derivative, a diamine derivative, and the like can be used.

As a blue phosphorescent emitting material which can be used for an emitting layer, metal complexes such as an iridium complex, an osmium complex, and a platinum complex are used. As a green phosphorescent emitting material which can be used for an emitting layer, an iridium complex and the like are used. As a red phosphorescent emitting material which can be used for an emitting layer, metal complexes such as an iridium complex, a platinum complex, a terbium complex, and a europium complex are used.

(Host Material for Emitting Layer)

The emitting layer may have a constitution in which the above-mentioned substance having a high emitting property (guest material) is dispersed in another substance (host material). As a substance for dispersing the substance having a high emitting property, a variety of substances can be used, and it is preferable to use a substance having a higher lowest unoccupied orbital level (LUMO level) and a lower highest occupied orbital level (HOMO level) rather than the substance having a high emitting property.

As such a substance for dispersing the substance having a high emitting property (host material), 1) metal complexes such as an aluminum complex, a beryllium complex, and a zinc complex; 2) heterocyclic compounds such as an oxadiazole derivative, a benzimidazole derivative, and a phenanthroline derivative; 3) fused aromatic compounds such as a carbazole derivative, an anthracene derivative, a phenanthrene derivative, a pyrene derivative, and a chrysene derivative; and 4) 3) aromatic amine compounds such as a triarylamine derivative, and an aromatic amine derivative are used.

(Electron-Transporting Layer)

The electron-transporting layer is a layer which contains a substance having a high electron-transporting property. For the electron-transporting layer, 1) metal complexes such as an aluminum complex, a beryllium complex, and a zinc complex; 2) heteroaromatic compounds such as an imidazole derivative, a benzimidazole derivative, an azine derivative, a carbazole derivative, and a phenanthroline derivative; and 3) polymer compounds can be used.

(Electron-Injecting Layer)

The electron-injecting layer is a layer which contains a substance having a high electron-injecting property. For the electron-injecting layer, the compounds which can be used in the electron-transporting layer described above, lithium (Li), ytterbium (Yb), lithium fluoride (LiF), cesium fluoride (CsF), calcium fluoride ($CaF_2$), metal complex compounds such as 8-hydroxyquinolinolato-lithium (Liq); alkali metal oxides such as lithium oxide ($LiO_x$); alkaline earth metal oxides; compounds of an alkali metal; or compounds of an alkaline earth metal can be used.

(Cathode)

For the cathode, metals, alloys, electrically conductive compounds, mixtures thereof, and the like, which have a small work function (specifically, 3.8 eV or smaller) are preferably used. Specific examples of such cathode materials include elements belonging to Group 1 and Group 2 of the Periodic Table of the Elements, i.e., alkali metals such as lithium (Li) and cesium (Cs), alkaline earth metals such as magnesium (Mg), calcium (Ca) and strontium (Sr), and alloys containing these metals (e.g., MgAg and AlLi); rare earth metals such as europium (Eu) and ytterbium (Yb), and alloys containing these rare earth metals.

In the organic EL device according to one aspect of the invention, the methods for forming the respective layers are not particularly limited. A conventionally-known method for forming each layer according to a vacuum deposition process, a spin coating processor the like can be used. Each layer such as the emitting layer can be formed by a known method such as a vacuum deposition process, a molecular beam deposition process (MBE process), or an application process such as a dipping process, a spin coating process, a casting process, a bar coating process, or a roll coating process, which uses a solution prepared by dissolving the material in a solvent.

In the organic EL device according to one aspect of the invention, the thickness of each layer is not particularly limited, but is generally preferable that the thickness be in the range of several nm to 1 μm in order to suppress defects such as pinholes, to suppress applied voltages to be low, and to increase luminous efficiency.

[Electronic Apparatus]

The electronic apparatus according to one aspect of the invention is characterized in that the organic EL device according to one aspect of the invention is equipped with.

Specific examples of the electronic apparatuses include display components such as an organic EL panel module; display devices for a television, a cellular phone, and a personal computer; and emitting devices such as a light, and a vehicular lamp.

EXAMPLES

Next, the invention will be explained in more detail with reference to Examples and Comparative Examples, but the invention is not limited in any way by these Examples.

<Compounds>

The compounds represented by the formula (A1) used for fabricating organic EL devices of Examples are shown below.

BD-1
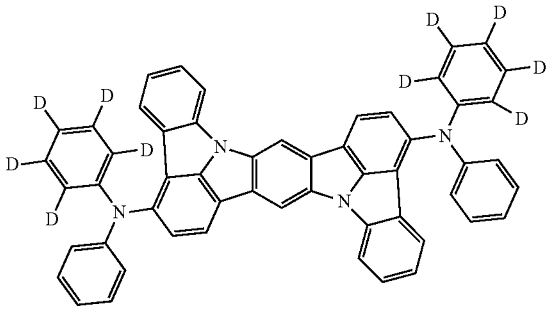
BD-2
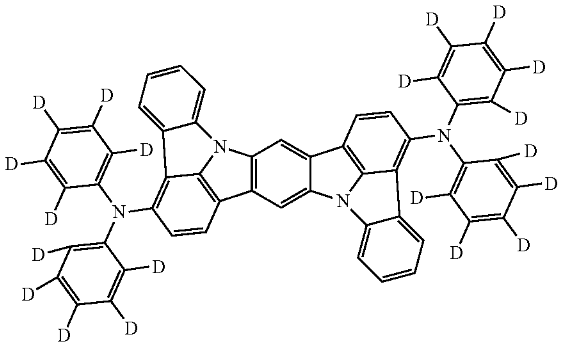
BD-3
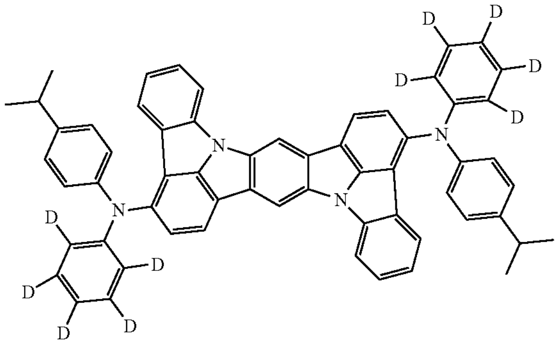
BD-4
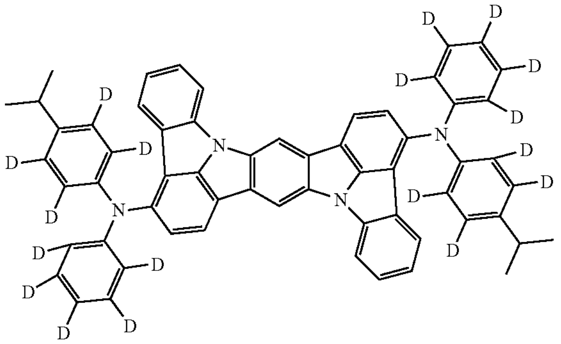
BD-5
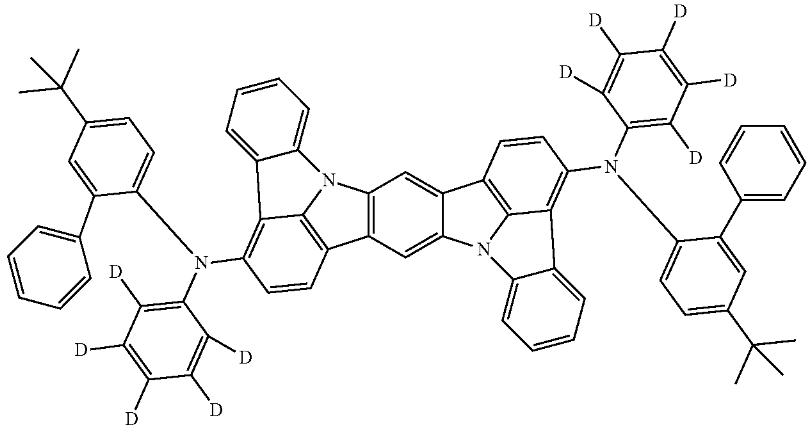
BD-6
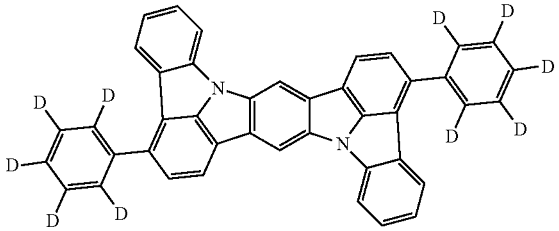
BD-7
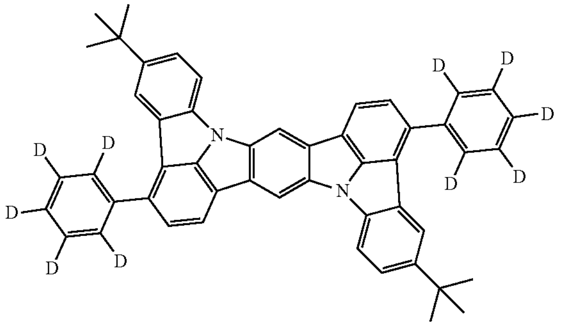

-continued
BD-8
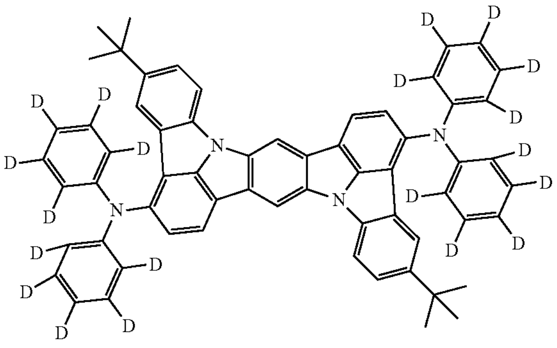
BD-9
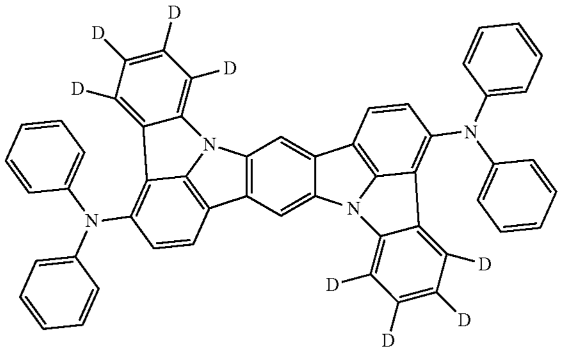
BD-10
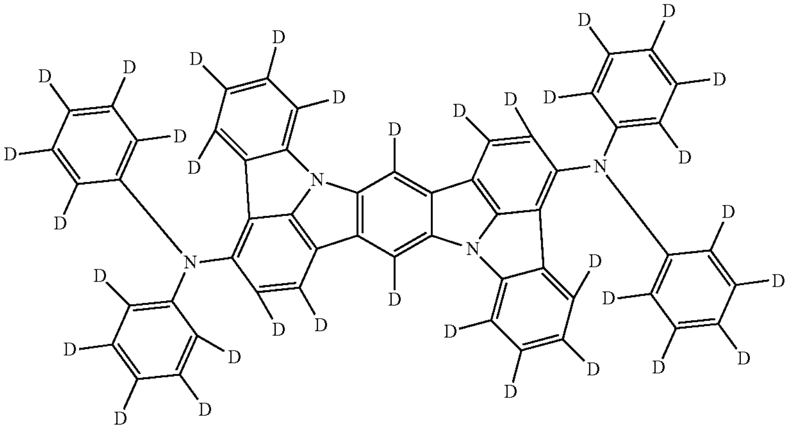
The comparative compounds used for fabricating organic EL devices of Comparative Examples are shown below.
Ref. BD-1
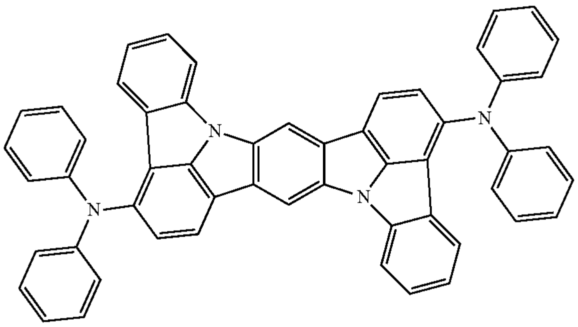
Ref. BD-3
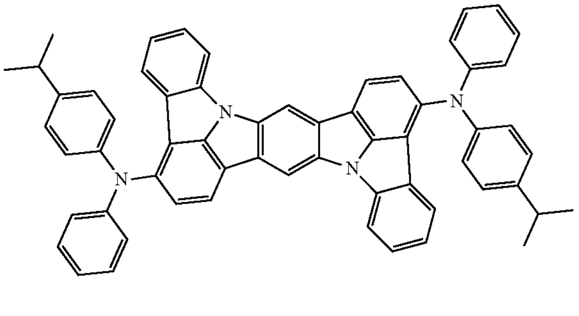
-continued
Ref. BD-5
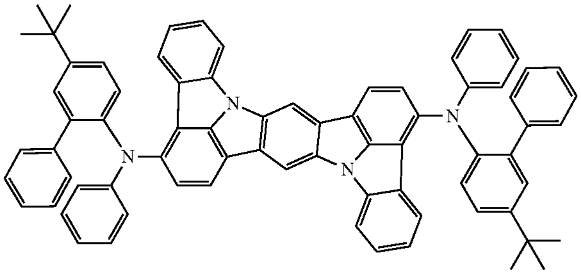
Ref. BD-6
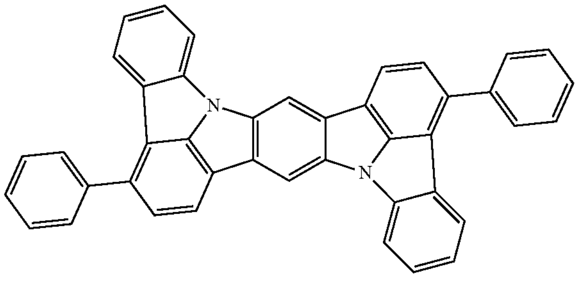

-continued
Ref. BD-7
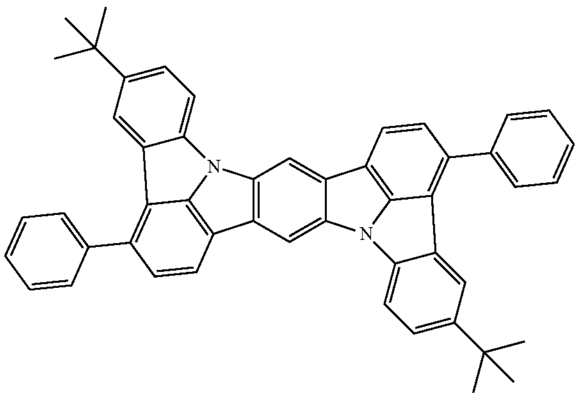
Ref. BD-8
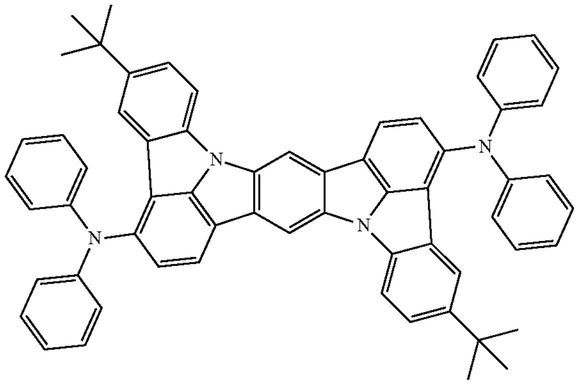
The compound represented by the formula (10) used for fabricating organic EL devices of Examples and Comparative examples are shown below.
BH-1
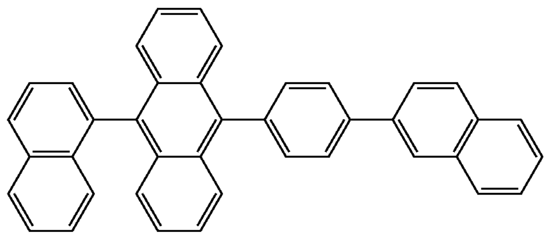
BH-1-D1
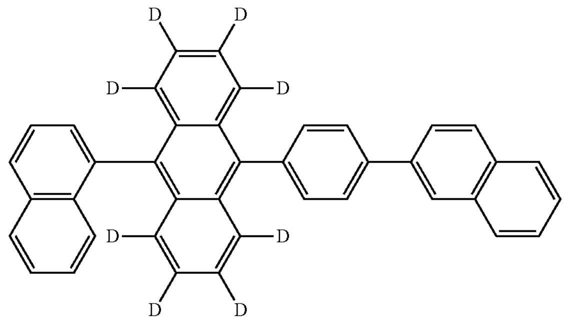
-continued
BH-1-D2
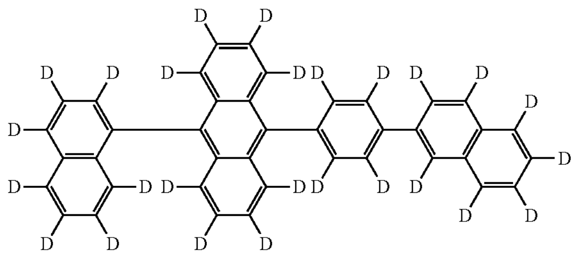
BH-2
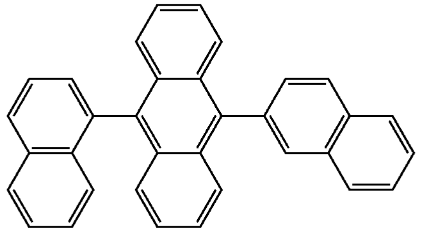
BH-2-D1
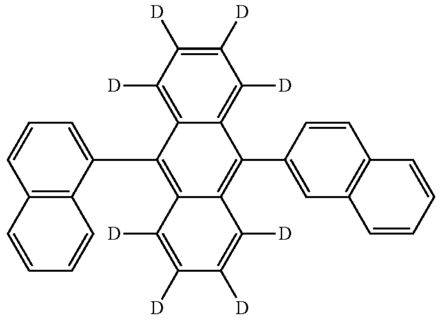
BH-2-D2
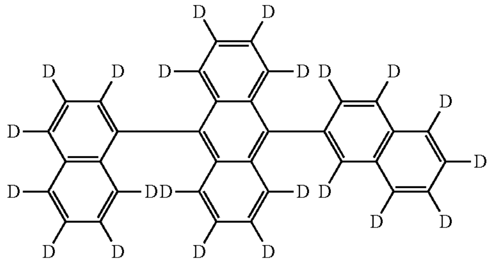
BH-3
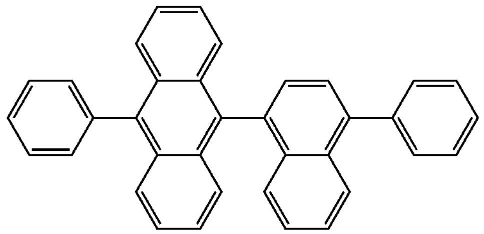

-continued
BH-4
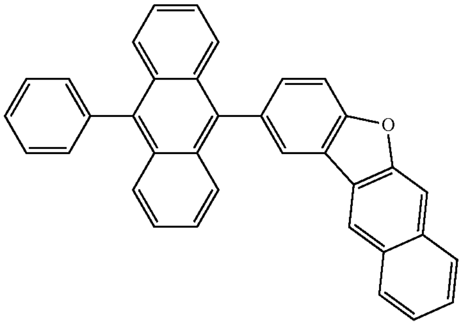
BH-4-D1
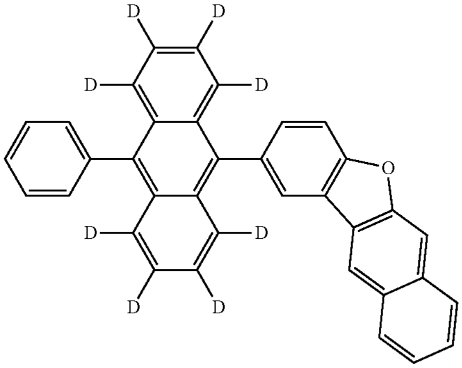
BH-4-D2
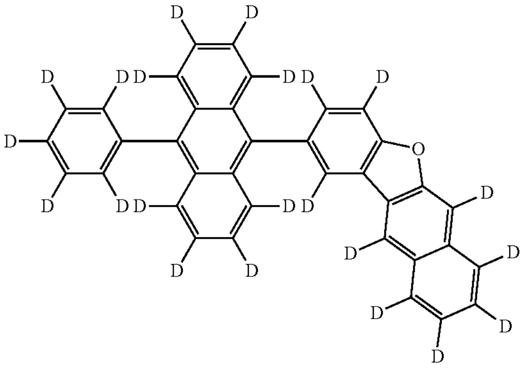
BH-5
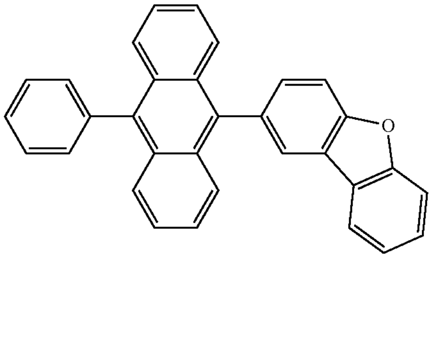
-continued
BH-5-D1
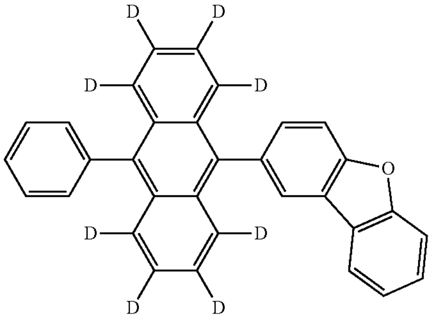
BH-5-D2
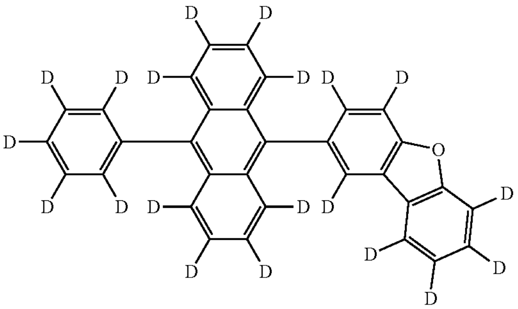
BH-6
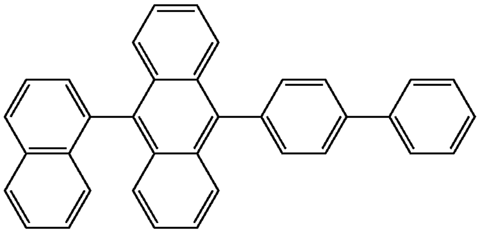
BH-7
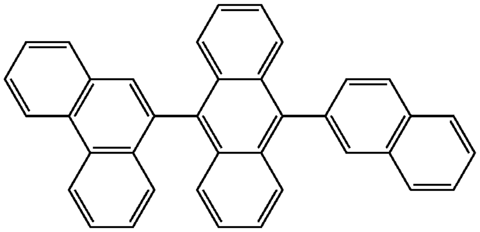
BH-8
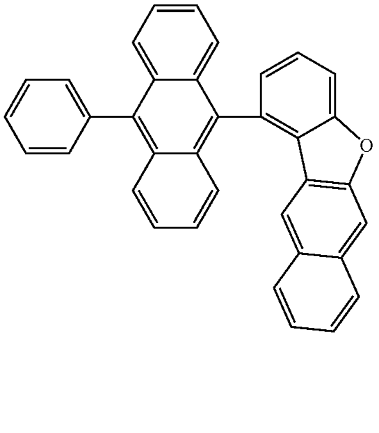

-continued
BH-8-D1
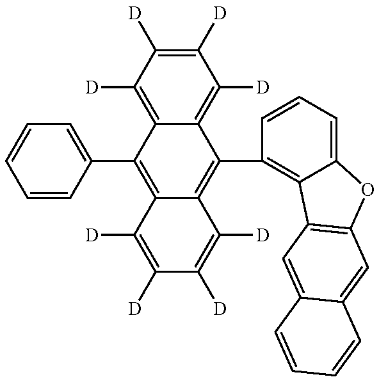
BH-8-D2
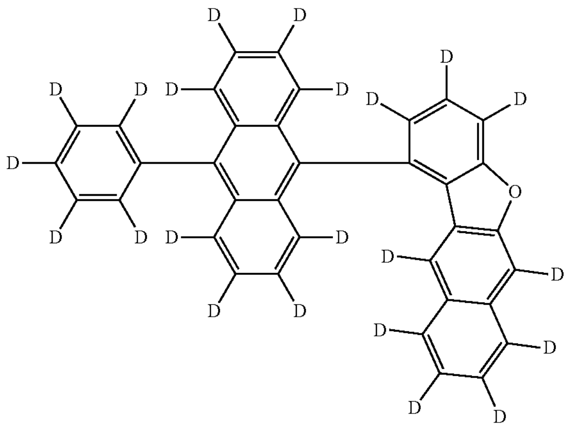
BH-9
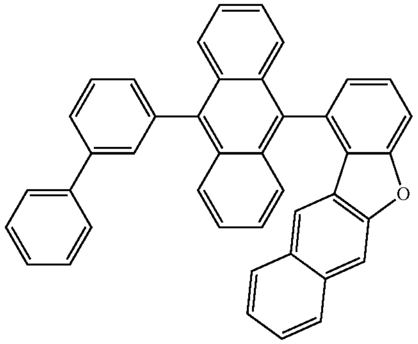
BH-10
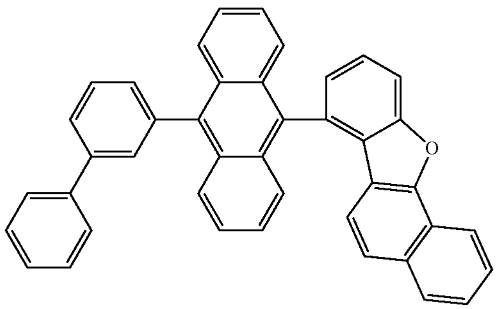
-continued
BH-10-D1
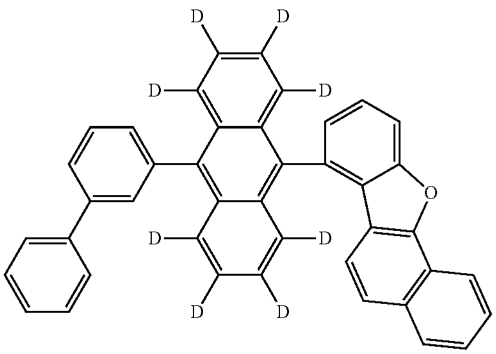
BH-10-D2
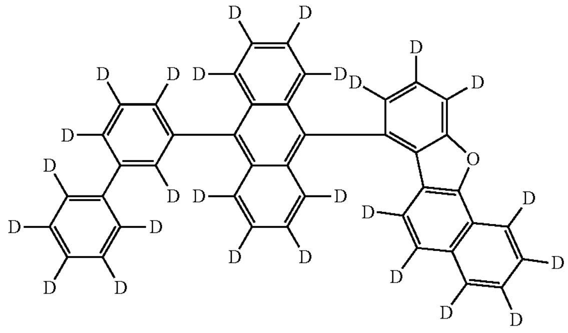
Other compounds used for fabricating organic EL devices of Examples and Comparative Examples are shown below.
HI
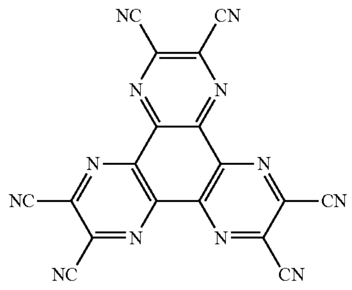
HT1
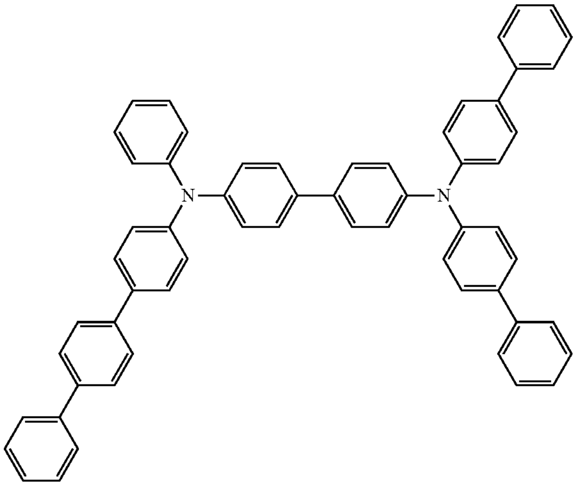

-continued

HT2

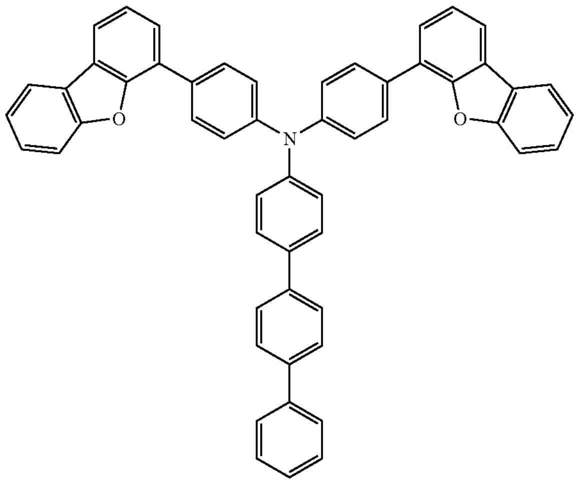

HBL

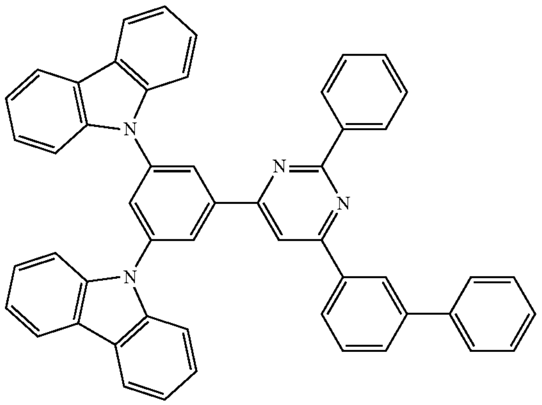

ET

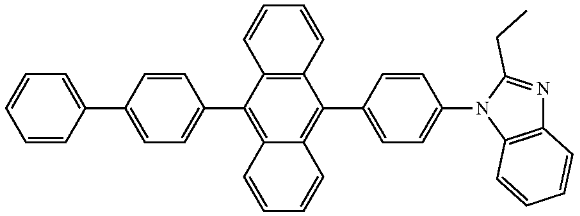

<Fabrication of Organic EL Device>

An organic EL device was fabricated and evaluated as follows.

Example 1-1

(Fabrication of Organic EL Device)

A 25 mm×75 mm×1.1 mm-thick glass substrate with an ITO transparent electrode (anode) (manufactured by GEOMATEC Co., Ltd.) was subjected to ultrasonic cleaning in isopropyl alcohol for 5 minutes, and then subjected to UV-ozone cleaning for 30 minutes. The thickness of the ITO film was 130 nm.

The glass substrate with the transparent electrode after being cleaned was mounted onto a substrate holder in a vacuum vapor deposition apparatus. First, a compound HI was deposited on a surface on the side on which the transparent electrode was formed so as to cover the transparent electrode to forma compound HI film having a thickness of 5 nm. This HI film functions as a hole-injecting layer.

Subsequent to the formation of the HI film, a compound HT1 was deposited thereon to form an HT1 film having a thickness of 80 nm on the HI film. The HT1 film functions as a first hole-transporting layer.

Subsequent to the formation of the HT1 film, a compound HT2 was deposited thereon to form an HT2 film having a thickness of 10 nm on the HT1 film. The HT2 film functions as a second hole-transporting layer.

A compound BH-1 (host material) and a compound BD-1 (dopant material) were co-deposited on the HT2 film to be 2% in a proportion (mass ratio) of the compound BD-1 to form an emitting layer having a thickness of 25 nm.

A compound HBL was vapor-deposited on the emitting layer to form an electron-transporting layer having a thickness of 10 nm. A compound ET of an electron-injecting material was deposited on the electron-transporting layer to form an electron-injecting layer having a thickness of 15 nm. LiF was deposited on the electron-injecting layer to form a LiF film having a thickness of 1 nm. Metal Al was deposited on the LiF film to form a metal cathode having a thickness of 80 nm.

The device configuration of the organic EL device of Example 1 is schematically shown as follows. ITO(130)/HI (5)/HT1(80)/HT2(10)/BH-1:BD-1 (25; 2%)/HBL(10)/ET (15)/LiF(1)/Al(80)

Numerical values in parentheses indicate a film thickness (unit: nm).

(Evaluation of Organic EL Device)

The lifetime characteristics of the obtained organic EL device was measured by driving under DC (direct current)-constant current 50 mA/cm$^2$ at room temperature.

Voltage was applied to the obtained organic EL device to be 50 mA/cm$^2$ in current density, and the time until the luminance becomes 95% of the initial luminance was measured. The result is shown in Table 1. Numerical values of LT95 (hr) in the tables are each expressed as a relative value when the numerical value of LT95 (hr) of the organic EL device fabricated in the corresponding Comparative Example is set to 100.

Comparative Example 1-1

An organic EL device was fabricated and evaluated in the same manner as in Example 1-1, except that a compound Ref. BD-1 was used as the dopant material. Results are shown in Table 1-1.

Hereinafter, organic EL devices were fabricated and evaluated in the same manner as in Example 1-1, except that a compound BD-1 or a compound Ref. BD-1 was used as the dopant material, and a compound shown in the respective tables below was used as the host material. The results are shown in the respective tables below.

TABLE 1-1

| | Host material | Dopant material | LT95(hr) (relative value) |
|---|---|---|---|
| Ex. 1-1 | BH-1 | BD-1 | 120 |
| Comp. Ex. 1-1 | | Ref. BD-1 | 100 |

TABLE 1-2

| | Host material | Dopant material | LT95(hr) (relative value) |
|---|---|---|---|
| Ex. 1-1-D1 | BH-1-D1 | BD-1 | 116 |
| Comp. Ex. 1-1-D1 | | Ref. BD-1 | 100 |

TABLE 1-3

| | Host material | Dopant material | LT95(hr) (relative value) |
|---|---|---|---|
| Ex. 1-1-D2 | BH-1-D2 | BD-1 | 121 |
| Comp. Ex. 1-1-D2 | | Ref. BD-1 | 100 |

TABLE 2-1

| | Host material | Dopant material | LT95(hr) (relative value) |
|---|---|---|---|
| Ex. 1-2 | BH-2 | BD-1 | 118 |
| Comp. Ex. 1-2 | | Ref. BD-1 | 100 |

TABLE 2-2

| | Host material | Dopant material | LT95(hr) (relative value) |
|---|---|---|---|
| Ex. 1-2-D1 | BH-2-D1 | BD-1 | 111 |
| Comp. Ex. 1-2-D1 | | Ref. BD-1 | 100 |

TABLE 2-3

| | Host material | Dopant material | LT95(hr) (relative value) |
|---|---|---|---|
| Ex. 1-2-D2 | BH-2-D2 | BD-1 | 120 |
| Comp. Ex. 1-2-D2 | | Ref.BD-1 | 100 |

TABLE 3

| | Host material | Dopant material | LT95(hr) (relative value) |
|---|---|---|---|
| Ex. 1-3 | BH-3 | BD-1 | 117 |
| Comp. Ex. 1-3 | | Ref.BD-1 | 100 |

TABLE 4-1

| | Host material | Dopant material | LT95(hr) (relative value) |
|---|---|---|---|
| Ex. 1-4 | BH-4 | BD-1 | 118 |
| Comp. Ex. 1-4 | | Ref.BD-1 | 100 |

TABLE 4-2

| | Host material | Dopant material | LT95(hr) (relative value) |
|---|---|---|---|
| Ex. 1-4-D1 | BH-4-D1 | BD-1 | 109 |
| Comp. Ex. 1-4-D1 | | Ref.BD-1 | 100 |

TABLE 4-3

| | Host material | Dopant material | LT95(hr) (relative value) |
|---|---|---|---|
| Ex. 1-4-D2 | BH-4-D2 | BD-1 | 116 |
| Comp. Ex. 1-4-D2 | | Ref.BD-1 | 100 |

TABLE 5-1

| | Host material | Dopant material | LT95(hr) (relative value) |
|---|---|---|---|
| Ex. 1-5 | BH-5 | BD-1 | 116 |
| Comp. Ex. 1-5 | | Ref.BD-1 | 100 |

TABLE 5-2

| | Host material | Dopant material | LT95(hr) (relative value) |
|---|---|---|---|
| Ex. 1-5-D1 | BH-5-D1 | BD-1 | 113 |
| Comp. Ex. 1-5-D1 | | Ref.BD-1 | 100 |

TABLE 5-3

| | Host material | Dopant material | LT95(hr) (relative value) |
|---|---|---|---|
| Ex. 1-5-D2 | BH-5-D2 | BD-1 | 113 |
| Comp. Ex. 1-5-D2 | | Ref.BD-1 | 100 |

TABLE 6

| | Host material | Dopant material | LT95(hr) (relative value) |
|---|---|---|---|
| Ex. 1-6 | BH-6 | BD-1 | 115 |
| Comp. Ex. 1-6 | | Ref.BD-1 | 100 |

TABLE 7

| | Host material | Dopant material | LT95(hr) (relative value) |
|---|---|---|---|
| Ex. 1-7 | BH-7 | BD-1 | 107 |
| Comp. Ex. 1-7 | | Ref.BD-1 | 100 |

TABLE 8-1

| | Host material | Dopant material | LT95(hr) (relative value) |
|---|---|---|---|
| Ex. 1-8 | BH-8 | BD-1 | 108 |
| Comp. Ex. 1-8 | | Ref.BD-1 | 100 |

TABLE 8-2

| | Host material | Dopant material | LT95(hr) (relative value) |
|---|---|---|---|
| Ex. 1-8-D1 | BH-8-D1 | BD-1 | 108 |
| Comp. Ex. 1-8-D1 | | Ref.BD-1 | 100 |

TABLE 8-3

| | Host material | Dopant material | LT95(hr) (relative value) |
|---|---|---|---|
| Ex. 1-8-D2 | BH-8-D2 | BD-1 | 127 |
| Comp. Ex. 1-8-D2 | | Ref.BD-1 | 100 |

TABLE 9

| | Host material | Dopant material | LT95(hr) (relative value) |
|---|---|---|---|
| Ex. 1-9 | BH-9 | BD-1 | 121 |
| Comp. Ex. 1-9 | | Ref.BD-1 | 100 |

TABLE 10

| | Host material | Dopant material | LT95(hr) (relative value) |
|---|---|---|---|
| Ex. 1-10 | BH-10 | BD-1 | 113 |
| Comp. Ex. 1-10 | | Ref.BD-1 | 100 |

TABLE 11-1

| | Host material | Dopant material | LT95(hr) (relative value) |
|---|---|---|---|
| Ex. 1-11 | BH-11 | BD-1 | 123 |
| Comp. Ex. 1-11 | | Ref.BD-1 | 100 |

TABLE 11-2

| | Host material | Dopant material | LT95(hr) (relative value) |
|---|---|---|---|
| Ex. 1-11-D1 | BH-11-D1 | BD-1 | 114 |
| Comp. Ex. 1-11-D1 | | Ref.BD-1 | 100 |

TABLE 11-3

| | Host material | Dopant material | LT95(hr) (relative value) |
|---|---|---|---|
| Ex. 1-11-D2 | BH-11-D2 | BD-1 | 122 |
| Comp. Ex. 1-11-D2 | | Ref.BD-1 | 100 |

Example 2-1 and Comparative Example 1-1

Organic EL devices were fabricated and evaluated in the same manner as in Example 1-1, except that a compound BD-2 or a compound Ref. BD-1 was used as the dopant material and a compound BH-1 was used as the host material. Results are shown in Table 12-1.

Hereinafter, organic EL devices were fabricated and evaluated in the same manner as in Example 1-1, except that a compound BD-2 or a compound Ref. BD-1 was used as the dopant material and a compound shown in the respective tables below was used as the host material. The results are shown in the respective tables below.

TABLE 12-1

| | Host material | Dopant material | LT95(hr) (relative value) |
|---|---|---|---|
| Ex. 2-1 | BH-1 | BD-2 | 122 |
| Comp. Ex. 1-1 | | Ref.BD-1 | 100 |

TABLE 12-2

| | Host material | Dopant material | LT95(hr) (relative value) |
|---|---|---|---|
| Ex. 2-1-D1 | BH-1-D1 | BD-2 | 128 |
| Comp. Ex. 1-1-D1 | | Ref.BD-1 | 100 |

TABLE 12-3

| | Host material | Dopant material | LT95(hr) (relative value) |
|---|---|---|---|
| Ex. 2-1-D2 | BH-1-D2 | BD-2 | 124 |
| Comp. Ex. 1-1-D2 | | Ref.BD-1 | 100 |

TABLE 13-1

| | Host material | Dopant material | LT95(hr) (relative value) |
|---|---|---|---|
| Ex. 2-2 | BH-2 | BD-2 | 125 |
| Comp. Ex. 1-2 | | Ref.BD-1 | 100 |

TABLE 13-2

| | Host material | Dopant material | LT95(hr) (relative value) |
|---|---|---|---|
| Ex. 2-2-D1 | BH-2-D1 | BD-2 | 125 |
| Comp. Ex. 1-2-D1 | | Ref.BD-1 | 100 |

TABLE 13-3

| | Host material | Dopant material | LT95(hr) (relative value) |
|---|---|---|---|
| Ex. 2-2-D2 | BH-2-D2 | BD-2 | 125 |
| Comp. Ex. 1-2-D2 | | Ref.BD-1 | 100 |

TABLE 14

| | Host material | Dopant material | LT95(hr) (relative value) |
|---|---|---|---|
| Ex. 2-3 | BH-3 | BD-2 | 126 |
| Comp. Ex. 1-3 | | Ref.BD-1 | 100 |

TABLE 15-1

| | Host material | Dopant material | LT95(hr) (relative value) |
|---|---|---|---|
| Ex. 24 | BH-4 | BD-2 | 126 |
| Comp. Ex. 1-4 | | Ref.BD-1 | 100 |

TABLE 15-2

| | Host material | Dopant material | LT95(hr) (relative value) |
|---|---|---|---|
| Ex. 2-4-D1 | BH-4-D1 | BD-2 | 123 |
| Comp. Ex. 1-4-D1 | | Ref.BD-1 | 100 |

TABLE 15-3

| | Host material | Dopant material | LT95(hr) (relative value) |
|---|---|---|---|
| Ex. 2-4-D2 | BH-4-D2 | BD-2 | 128 |
| Comp. Ex. 1-4-D2 | | Ref.BD-1 | 100 |

TABLE 16-1

| | Host material | Dopant material | LT95(hr) (relative value) |
|---|---|---|---|
| Ex. 2-5 | BH-5 | BD-2 | 126 |
| Comp. Ex. 1-5 | | Ref.BD-1 | 100 |

TABLE 16-2

| | Host material | Dopant material | LT95(hr) (relative value) |
|---|---|---|---|
| Ex. 2-5-D1 | BH-5-D1 | BD-2 | 120 |
| Comp. Ex. 1-5-D1 | | Ref.BD-1 | 100 |

TABLE 16-3

| | Host material | Dopant material | LT95(hr) (relative value) |
|---|---|---|---|
| Ex. 2-5-D2 | BH-5-D2 | BD-2 | 122 |
| Comp. Ex. 1-5-D2 | | Ref. BD-1 | 100 |

TABLE 17

| | Host material | Dopant material | LT95(hr) (relative value) |
|---|---|---|---|
| Ex. 2-6 | BH-6 | BD-2 | 128 |
| Comp. Ex. 1-6 | | Ref. BD-1 | 100 |

TABLE 18

| | Host material | Dopant material | LT95(hr) (relative value) |
|---|---|---|---|
| Ex. 2-7 | BH-7 | BD-2 | 127 |
| Comp. Ex. 1-7 | | Ref. BD-1 | 100 |

TABLE 19-1

| | Host material | Dopant material | LT95(hr) (relative value) |
|---|---|---|---|
| Ex. 2-8 | BH-8 | BD-2 | 121 |
| Comp. Ex. 1-8 | | Ref. BD-1 | 100 |

TABLE 19-2

| | Host material | Dopant material | LT95(hr) (relative value) |
|---|---|---|---|
| Ex. 2-8-D1 | BH-8-D1 | BD-2 | 129 |
| Comp. Ex. 1-8-D1 | | Ref. BD-1 | 100 |

TABLE 19-3

| | Host material | Dopant material | LT95(hr) (relative value) |
|---|---|---|---|
| Ex. 2-8-D2 | BH-8-D2 | BD-2 | 128 |
| Comp. Ex. 1-8-D2 | | Ref. BD-1 | 100 |

TABLE 20

| | Host material | Dopant material | LT95(hr) (relative value) |
|---|---|---|---|
| Ex. 2-9 | BH-9 | BD-2 | 122 |
| Comp. Ex. 1-9 | | Ref. BD-1 | 100 |

TABLE 21

| | Host material | Dopant material | LT95(hr) (relative value) |
|---|---|---|---|
| Ex. 2-10 | BH-10 | BD-2 | 129 |
| Comp. Ex. 1-10 | | Ref. BD-1 | 100 |

TABLE 22-1

| | Host material | Dopant material | LT95(hr) (relative value) |
|---|---|---|---|
| Ex. 2-11 | BH-11 | BD-2 | 126 |
| Comp. Ex. 1-11 | | Ref. BD-1 | 100 |

TABLE 22-2

| | Host material | Dopant material | LT95(hr) (relative value) |
|---|---|---|---|
| Ex. 2-11-D1 | BH-11-D1 | BD-2 | 120 |
| Comp. Ex. 1-11-D1 | | Ref. BD-1 | 100 |

TABLE 22-3

| | Host material | Dopant material | LT95(hr) (relative value) |
|---|---|---|---|
| Ex. 2-11-D2 | BH-11-D2 | BD-2 | 125 |
| Comp. Ex. 1-11-D2 | | Ref. BD-1 | 100 |

Organic EL devices were fabricated and evaluated in the same manner as in Example 1-1, except that a compound BD-3 or a compound Ref. BD-3 was used as the dopant material and a compound BH-1 was used as the host material. Results are shown in Table 23-1.

Hereinafter, organic EL devices were fabricated and evaluated in the same manner as in Example 1-1, except that a compound BD-3 or a compound Ref. BD-3 was used as the dopant material and a compound shown in the respective tables below was used as the host material. The results are shown in the respective tables below.

TABLE 23-1

| | Host material | Dopant material | LT95(hr) (relative value) |
|---|---|---|---|
| Ex. 3-1 | BH-1 | BD-3 | 107 |
| Comp. Ex. 3-1 | | Ref. BD-3 | 100 |

TABLE 23-2

| | Host material | Dopant material | LT95(hr) (relative value) |
|---|---|---|---|
| Ex. 3-1-D1 | BH-1-D1 | BD-3 | 107 |
| Comp. Ex. 3-1-D1 | | Ref. BD-3 | 100 |

TABLE 23-3

| | Host material | Dopant material | LT95(hr) (relative value) |
|---|---|---|---|
| Ex. 3-1-D2 | BH-1-D2 | BD-3 | 112 |
| Comp. Ex. 3-1-D2 | | Ref. BD-3 | 100 |

TABLE 24-1

| | Host material | Dopant material | LT95(hr) (relative value) |
|---|---|---|---|
| Ex. 3-2 | BH-2 | BD-3 | 114 |
| Comp. Ex. 3-2 | | Ref. BD-3 | 100 |

TABLE 24-2

| | Host material | Dopant material | LT95(hr) (relative value) |
|---|---|---|---|
| Ex. 3-2-D1 | BH-2-D1 | BD-3 | 107 |
| Comp. Ex. 3-2-D1 | | Ref. BD-3 | 100 |

TABLE 24-3

| | Host material | Dopant material | LT95(hr) (relative value) |
|---|---|---|---|
| Ex. 3-2-D2 | BH-2-D2 | BD-3 | 110 |
| Comp. Ex. 3-2-D2 | | Ref. BD-3 | 100 |

TABLE 25

| | Host material | Dopant material | LT95(hr) (relative value) |
|---|---|---|---|
| Ex. 3-3 | BH-3 | BD-3 | 109 |
| Comp. Ex. 3-3 | | Ref. BD-3 | 100 |

TABLE 26-1

| | Host material | Dopant material | LT95(hr) (relative value) |
|---|---|---|---|
| Ex. 3-4 | BH-4 | BD-3 | 109 |
| Comp. Ex. 3-4 | | Ref. BD-3 | 100 |

TABLE 26-2

| | Host material | Dopant material | LT95(hr) (relative value) |
|---|---|---|---|
| Ex. 3-4-D1 | BH-4-D1 | BD-3 | 113 |
| Comp. Ex. 3-4-D1 | | Ref.BD-3 | 100 |

TABLE 26-3

| | Host material | Dopant material | LT95(hr) (relative value) |
|---|---|---|---|
| Ex. 3-4-D2 | BH-4-D2 | BD-3 | 115 |
| Comp. Ex. 3-4-D2 | | Ref. BD-3 | 100 |

TABLE 27-1

| | Host material | Dopant material | LT95(hr) (relative value) |
|---|---|---|---|
| Ex. 3-5 | BH-5 | BD-3 | 108 |
| Comp. Ex. 3-5 | | Ref. BD-3 | 100 |

TABLE 27-2

| | Host material | Dopant material | LT95(hr) (relative value) |
|---|---|---|---|
| Ex. 3-5-D1 | BH-5-D1 | BD-3 | 113 |
| Comp. Ex. 3-5-D1 | | Ref. BD-3 | 100 |

TABLE 27-3

| | Host material | Dopant material | LT95(hr) (relative value) |
|---|---|---|---|
| Ex. 3-5-D2 | BH-5-D2 | BD-3 | 115 |
| Comp. Ex. 3-5-D2 | | Ref. BD-3 | 100 |

TABLE 28

| | Host material | Dopant material | LT95(hr) (relative value) |
|---|---|---|---|
| Ex. 3-6 | BH-6 | BD-3 | 112 |
| Comp. Ex. 3-6 | | Ref. BD-3 | 100 |

TABLE 29

| | Host material | Dopant material | LT95(hr) (relative value) |
|---|---|---|---|
| Ex. 3-7 | BH-7 | BD-3 | 108 |
| Comp. Ex. 3-7 | | Ref. BD-3 | 100 |

TABLE 30-1

| | Host material | Dopant material | LT95(hr) (relative value) |
|---|---|---|---|
| Ex. 3-8 | BH-8 | BD-3 | 114 |
| Comp. Ex. 3-8 | | Ref. BD-3 | 100 |

TABLE 30-2

| | Host material | Dopant material | LT95(hr) (relative value) |
|---|---|---|---|
| Ex. 3-8-D1 | BH-8-D1 | BD-3 | 111 |
| Comp. Ex. 3-8-D1 | | Ref. BD-3 | 100 |

TABLE 30-3

| | Host material | Dopant material | LT95(hr) (relative value) |
|---|---|---|---|
| Ex. 3-8-D2 | BH-8-D2 | BD-3 | 115 |
| Comp. Ex. 3-8-D2 | | Ref. BD-3 | 100 |

TABLE 31

| | Host material | Dopant material | LT95(hr) (relative value) |
|---|---|---|---|
| Ex. 3-9 | BH-9 | BD-3 | 113 |
| Comp. Ex. 3-9 | | Ref. BD-3 | 100 |

TABLE 32

| | Host material | Dopant material | LT95(hr) (relative value) |
|---|---|---|---|
| Ex. 3-10 | BH-10 | BD-3 | 112 |
| Comp. Ex. 3-10 | | Ref. BD-3 | 100 |

TABLE 33-1

| | Host material | Dopant material | LT95(hr) relative value) |
|---|---|---|---|
| Ex. 3-11 | BH-11 | BD-3 | 111 |
| Comp. Ex. 3-11 | | Ref. BD-3 | 100 |

TABLE 33-2

| | Host material | Dopant material | LT95(hr) (relative value) |
|---|---|---|---|
| Ex. 3-11-D1 | BH-11-D1 | BD-3 | 115 |
| Comp. Ex. 3-11-D1 | | Ref. BD-3 | 100 |

TABLE 33-3

| | Host material | Dopant material | LT95(hr) (relative value) |
|---|---|---|---|
| Ex. 3-11-D2 | BH-11-D2 | BD-3 | 113 |
| Comp. Ex. 3-11-D2 | | Ref. BD-3 | 100 |

Example 4-1 and Comparative Example 3-1

Organic EL devices were fabricated and evaluated in the same manner as in Example 1-1, except that a compound BD-4 or a compound Ref. BD-3 was used as the dopant material and a compound BH-1 was used as the host material. Results are shown in Table 34-1.

Hereinafter, organic EL devices were fabricated and evaluated in the same manner as in Example 1-1, except that a compound BD-4 or a compound Ref. BD-3 was used as the dopant material and a compound shown in the respective tables below was used as the host material. The results are shown in the respective tables below.

TABLE 34-1

| | Host material | Dopant material | LT95(hr) (relative value) |
|---|---|---|---|
| Ex. 4-1 | BH-1 | BD-4 | 110 |
| Comp. Ex. 3-1 | | Ref. BD-3 | 100 |

TABLE 34-2

| | Host material | Dopant material | LT95(hr) (relative value) |
|---|---|---|---|
| Ex. 4-1-D1 | BH-1-D1 | BD-4 | 119 |
| Comp. Ex. 3-1-D1 | | Ref. BD-3 | 100 |

TABLE 34-3

| | Host material | Dopant material | LT95(hr) (relative value) |
|---|---|---|---|
| Ex. 4-1-D2 | BH-1-D2 | BD-4 | 119 |
| Comp. Ex. 3-1-D2 | | Ref. BD-3 | 100 |

TABLE 35-1

| | Host material | Dopant material | LT95(hr) (relative value) |
|---|---|---|---|
| Ex. 4-2 | BH-2 | BD-4 | 121 |
| Comp. Ex. 3-2 | | Ref. BD-3 | 100 |

TABLE 35-2

| | Host material | Dopant material | LT95(hr) (relative value) |
|---|---|---|---|
| Ex. 4-2-D1 | BH-2-D1 | BD-4 | 113 |
| Comp. Ex. 3-2-D1 | | Ref. BD-3 | 100 |

TABLE 35-3

| | Host material | Dopant material | LT95(hr) (relative value) |
|---|---|---|---|
| Ex. 4-2-D2 | BH-2-D2 | BD-4 | 122 |
| Comp. Ex. 3-2-D2 | | Ref. BD-3 | 100 |

TABLE 36

| | Host material | Dopant material | LT95(hr) (relative value) |
|---|---|---|---|
| Ex. 4-3 | BH-3 | BD-4 | 115 |
| Comp. Ex. 3-3 | | Ref. BD-3 | 100 |

TABLE 37-1

| | Host material | Dopant material | LT95(hr) (relative value) |
|---|---|---|---|
| Ex. 4-4 | BH-4 | BD-4 | 130 |
| Comp. Ex. 3-4 | | Ref. BD-3 | 100 |

TABLE 37-2

| | Host material | Dopant material | LT95(hr) (relative value) |
|---|---|---|---|
| Ex. 4-4-D1 | BH-4-D1 | BD-4 | 118 |
| Comp. Ex. 3-4-D1 | | Ref. BD-3 | 100 |

TABLE 37-3

| | Host material | Dopant material | LT95(hr) (relative value) |
|---|---|---|---|
| Ex. 4-4-D2 | BH-4-D2 | BD-4 | 122 |
| Comp. Ex. 3-4-D2 | | Ref. BD-3 | 100 |

TABLE 38-1

| | Host material | Dopant material | LT95(hr) (relative value) |
|---|---|---|---|
| Ex. 4-5 | BH-5 | BD-4 | 130 |
| Comp. Ex. 3-5 | | Ref. BD-3 | 100 |

TABLE 38-2

| | Host material | Dopant material | LT95(hr) (relative value) |
|---|---|---|---|
| Ex. 4-5-D1 | BH-5-D1 | BD-4 | 116 |
| Comp. Ex. 3-5-D1 | | Ref. BD-3 | 100 |

TABLE 38-3

| | Host material | Dopant material | LT95(hr) (relative value) |
|---|---|---|---|
| Ex. 4-5-D2 | BH-5-D2 | BD-4 | 120 |
| Comp. Ex. 3-5-D2 | | Ref. BD-3 | 100 |

TABLE 39

| | Host material | Dopant material | LT95(hr) (relative value) |
|---|---|---|---|
| Ex. 4-6 | BH-6 | BD-4 | 116 |
| Comp. Ex. 3-6 | | Ref. BD-3 | 100 |

TABLE 40

| | Host material | Dopant material | LT95(hr) (relative value) |
|---|---|---|---|
| Ex. 4-7 | BH-7 | BD-4 | 114 |
| Comp. Ex. 3-7 | | Ref. BD-3 | 100 |

TABLE 41-1

| | Host material | Dopant material | LT95(hr) (relative value) |
|---|---|---|---|
| Ex. 4-8 | BH-8 | BD-4 | 128 |
| Comp. Ex. 3-8 | | Ref. BD-3 | 100 |

TABLE 41-2

| | Host material | Dopant material | LT95(hr) (relative value) |
|---|---|---|---|
| Ex. 4-8-D1 | BH-8-D1 | BD-4 | 115 |
| Comp. Ex. 3-8-D1 | | Ref. BD-3 | 100 |

TABLE 41-3

| | Host material | Dopant material | LT95(hr) (relative value) |
|---|---|---|---|
| Ex. 4-8-D2 | BH-8-D2 | BD-4 | 122 |
| Comp. Ex. 3-8-D2 | | Ref. BD-3 | 100 |

TABLE 42

| | Host material | Dopant material | LT95(hr) (relative value) |
|---|---|---|---|
| Ex. 4-9 | BH-9 | BD-4 | 130 |
| Comp. Ex. 3-9 | | Ref. BD-3 | 100 |

TABLE 43

| | Host material | Dopant material | LT95(hr) (relative value) |
|---|---|---|---|
| Ex. 4-10 | BH-10 | BD-4 | 117 |
| Comp. Ex. 3-10 | | Ref. BD-3 | 100 |

TABLE 44-1

| | Host material | Dopant material | LT95(hr) (relative value) |
|---|---|---|---|
| Ex. 4-11 | BH-11 | BD-4 | 119 |
| Comp. Ex. 3-11 | | Ref. BD-3 | 100 |

TABLE 44-2

| | Host material | Dopant material | LT95(hr) (relative value) |
|---|---|---|---|
| Ex. 4-11-D1 | BH-11-D1 | BD-4 | 120 |
| Comp. Ex. 3-11-D1 | | Ref. BD-3 | 100 |

TABLE 44-3

| | Host material | Dopant material | LT95(hr) (relative value) |
|---|---|---|---|
| Ex. 4-11-D2 | BH-11-D2 | BD-4 | 121 |
| Comp. Ex. 3-11-D2 | | Ref. BD-3 | 100 |

Example 5-1 and Comparative Example 5-1

Organic EL devices were fabricated and evaluated in the same manner as in Example 1-1, except that a compound BD-5 or a compound Ref. BD-5 was used as the dopant material and a compound BH-1 was used as the host material. Results are shown in Table 45-1.

Hereinafter, organic EL devices were fabricated and evaluated in the same manner as in Example 1-1, except that a compound BD-5 or a compound Ref. BD-5 was used as the dopant material and a compound shown in the respective tables below was used as the host material. The results are shown in the respective tables below.

TABLE 45-1

| | Host material | Dopant material | LT95(hr) (relative value) |
|---|---|---|---|
| Ex. 5-1 | BH-1 | BD-5 | 126 |
| Comp. Ex. 5-1 | | Ref. BD-5 | 100 |

TABLE 45-2

| | Host material | Dopant material | LT95(hr) (relative value) |
|---|---|---|---|
| Ex. 5-1-D1 | BH-1-D1 | BD-5 | 123 |
| Comp. Ex. 5-1-D1 | | Ref. BD-5 | 100 |

TABLE 45-3

| | Host material | Dopant material | LT95(hr) (relative value) |
|---|---|---|---|
| Ex. 5-1-D2 | BH-1-D2 | BD-5 | 131 |
| Comp. Ex. 5-1-D2 | | Ref. BD-5 | 100 |

TABLE 46-1

| | Host material | Dopant material | LT95(hr) (relative value) |
|---|---|---|---|
| Ex. 5-2 | BH-2 | BD-5 | 137 |
| Comp. Ex. 5-2 | | Ref. BD-5 | 100 |

TABLE 46-2

| | Host material | Dopant material | LT95(hr) (relative value) |
|---|---|---|---|
| Ex. 5-2-D1 | BH-2-D1 | BD-5 | 139 |
| Comp. Ex. 5-2-D1 | | Ref. BD-5 | 100 |

TABLE 46-3

| | Host material | Dopant material | LT95(hr) (relative value) |
|---|---|---|---|
| Ex. 5-2-D2 | BH-2-D2 | BD-5 | 120 |
| Comp. Ex. 5-2-D2 | | Ref. BD-5 | 100 |

TABLE 47

| | Host material | Dopant material | LT95(hr) (relative value) |
|---|---|---|---|
| Ex. 5-3 | BH-3 | BD-5 | 110 |
| Comp. Ex. 5-3 | | Ref. BD-5 | 100 |

TABLE 48-1

| | Host material | Dopant material | LT95(hr) (relative value) |
|---|---|---|---|
| Ex. 5-4 | BH-4 | BD-5 | 117 |
| Comp. Ex. 5-4 | | Ref. BD-5 | 100 |

TABLE 48-2

| | Host material | Dopant material | LT95(hr) (relative value) |
|---|---|---|---|
| Ex. 5-4-D1 | BH-4-D1 | BD-5 | 122 |
| Comp. Ex. 5-4-D1 | | Ref. BD-5 | 100 |

TABLE 48-3

| | Host material | Dopant material | LT95(hr) (relative value) |
|---|---|---|---|
| Ex. 5-4-D2 | BH-4-D2 | BD-5 | 121 |
| Comp. Ex. 5-4-D2 | | Ref. BD-5 | 100 |

TABLE 49-1

| | Host material | Dopant material | LT95(hr) (relative value) |
|---|---|---|---|
| Ex. 5-5 | BH-5 | BD-5 | 124 |
| Comp. Ex. 5-5 | | Ref. BD-5 | 100 |

TABLE 49-2

| | Host material | Dopant material | LT95(hr) (relative value) |
|---|---|---|---|
| Ex. 5-5-D1 | BH-5-D1 | BD-5 | 134 |
| Comp. Ex. 5-5-D1 | | Ref. BD-5 | 100 |

TABLE 49-3

| | Host material | Dopant material | LT95(hr) (relative value) |
|---|---|---|---|
| Ex. 5-5-D2 | BH-5-D2 | BD-5 | 125 |
| Comp. Ex. 5-5-D2 | | Ref. BD-5 | 100 |

TABLE 50

| | Host material | Dopant material | LT95(hr) (relative value) |
|---|---|---|---|
| Ex. 5-6 | BH-6 | BD-5 | 137 |
| Comp. Ex. 5-6 | | Ref. BD-5 | 100 |

TABLE 51

| | Host material | Dopant material | LT95(hr) (relative value) |
|---|---|---|---|
| Ex. 5-7 | BH-7 | BD-5 | 113 |
| Comp. Ex. 5-7 | | Ref. BD-5 | 100 |

TABLE 52-1

| | Host material | Dopant material | LT95(hr) (relative value) |
|---|---|---|---|
| Ex. 5-8 | BH-8 | BD-5 | 131 |
| Comp. Ex. 5-8 | | Ref. BD-5 | 100 |

TABLE 52-2

| | Host material | Dopant material | LT95(hr) (relative value) |
|---|---|---|---|
| Ex. 5-8-D1 | BH-8-D1 | BD-5 | 129 |
| Comp. Ex. 5-8-D1 | | Ref. BD-5 | 100 |

TABLE 52-3

| | Host material | Dopant material | LT95(hr) (relative value) |
|---|---|---|---|
| Ex. 5-8-D2 | BH-8-D2 | BD-5 | 139 |
| Comp. Ex. 5-8-D2 | | Ref. BD-5 | 100 |

TABLE 53

| | Host material | Dopant material | LT95(hr) (relative value) |
|---|---|---|---|
| Ex. 5-9 | BH-9 | BD-5 | 139 |
| Comp. Ex. 5-9 | | Ref. BD-5 | 100 |

TABLE 54

| | Host material | Dopant material | LT95(hr) (relative value) |
|---|---|---|---|
| Ex. 5-10 | BH-10 | BD-5 | 119 |
| Comp. Ex. 5-10 | | Ref. BD-5 | 100 |

TABLE 55-1

| | Host material | Dopant material | LT95(hr) (relative value) |
|---|---|---|---|
| Ex. 5-11 | BH-11 | BD-5 | 121 |
| Comp. Ex. 5-11 | | Ref. BD-5 | 100 |

TABLE 55-2

| | Host material | Dopant material | LT95(hr) (relative value) |
|---|---|---|---|
| Ex. 5-11-D1 | BH-11-D1 | BD-5 | 110 |
| Comp. Ex. 5-11-D1 | | Ref. BD-5 | 100 |

TABLE 55-3

| | Host material | Dopant material | LT95(hr) (relative value) |
|---|---|---|---|
| Ex. 5-11-D2 | BH-11-D2 | BD-5 | 111 |
| Comp. Ex. 5-11-D2 | | Ref. BD-5 | 100 |

Example 6-1 and Comparative Example 6-1

Organic EL devices were fabricated and evaluated in the same manner as in Example 1-1, except that a compound BD-6 or a compound Ref. BD-6 was used as the dopant material and a compound BH-1 was used as the host material. Results are shown in Table 56-1.

Hereinafter, organic EL devices were fabricated and evaluated in the same manner as in Example 1-1, except that a compound BD-6 or a compound Ref. BD-6 was used as the dopant material and a compound shown in the respective tables below was used as the host material. The results are shown in the respective tables below.

TABLE 56-1

| | Host material | Dopant material | LT95(hr) (relative value) |
|---|---|---|---|
| Ex. 6-1 | BH-1 | BD-6 | 125 |
| Comp. Ex. 6-1 | | Ref. BD-6 | 100 |

TABLE 56-2

| | Host material | Dopant material | LT95(hr) (relative value) |
|---|---|---|---|
| Ex. 6-1-D1 | BH-1-D1 | BD-6 | 126 |
| Comp. Ex. 6-1-D1 | | Ref. BD-6 | 100 |

TABLE 56-3

| | Host material | Dopant material | LT95(hr) (relative value) |
|---|---|---|---|
| Ex. 6-1-D2 | BH-1-D2 | BD-6 | 106 |
| Comp. Ex. 6-1-D2 | | Ref. BD-6 | 100 |

TABLE 57-1

| | Host material | Dopant material | LT95(hr) (relative value) |
|---|---|---|---|
| Ex. 6-2 | BH-2 | BD-6 | 127 |
| Comp. Ex. 6-2 | | Ref. BD-6 | 100 |

TABLE 57-2

| | Host material | Dopant material | LT95(hr) (relative value) |
|---|---|---|---|
| Ex. 6-2-D1 | BH-2-D1 | BD-6 | 113 |
| Comp. Ex. 6-2-D1 | | Ref. BD-6 | 100 |

TABLE 57-3

| | Host material | Dopant material | LT95(hr) (relative value) |
|---|---|---|---|
| Ex. 6-2-D2 | BH-2-D2 | BD-6 | 109 |
| Comp. Ex. 6-2-D2 | | Ref. BD-6 | 100 |

TABLE 58

| | Host material | Dopant material | LT95(hr) (relative value) |
|---|---|---|---|
| Ex. 6-3 | BH-3 | BD-6 | 117 |
| Comp. Ex. 6-3 | | Ref. BD-6 | 100 |

TABLE 59-1

| | Host material | Dopant material | LT95(hr) (relative value) |
|---|---|---|---|
| Ex. 6-4 | BH-4 | BD-6 | 123 |
| Comp. Ex. 6-4 | | Ref. BD-6 | 100 |

TABLE 59-2

| | Host material | Dopant material | LT95(hr) (relative value) |
|---|---|---|---|
| Ex. 6-4-D1 | BH-4-D1 | BD-6 | 122 |
| Comp. Ex. 6-4-D1 | | Ref. BD-6 | 100 |

TABLE 59-3

| | Host material | Dopant material | LT95(hr) (relative value) |
|---|---|---|---|
| Ex. 6-4-D2 | BH-4-D2 | BD-6 | 113 |
| Comp. Ex. 6-4-D2 | | Ref. BD-6 | 100 |

TABLE 60-1

| | Host material | Dopant material | LT95(hr) (relative value) |
|---|---|---|---|
| Ex. 6-5 | BH-5 | BD-6 | 114 |
| Comp. Ex. 6-5 | | Ref. BD-6 | 100 |

TABLE 60-2

| | Host material | Dopant material | LT95(hr) (relative value) |
|---|---|---|---|
| Ex. 6-5-D1 | BH-5-D1 | BD-6 | 129 |
| Comp. Ex. 6-5-D1 | | Ref. BD-6 | 100 |

TABLE 60-3

| | Host material | Dopant material | LT95(hr) (relative value) |
|---|---|---|---|
| Ex. 6-5-D2 | BH-5-D2 | BD-6 | 126 |
| Comp. Ex. 6-5-D2 | | Ref. BD-6 | 100 |

TABLE 61

| | Host material | Dopant material | LT95(hr) (relative value) |
|---|---|---|---|
| Ex. 6-6 | BH-6 | BD-6 | 110 |
| Comp. Ex. 6-6 | | Ref. BD-6 | 100 |

TABLE 62

| | Host material | Dopant material | LT95(hr) (relative value) |
|---|---|---|---|
| Ex. 6-7 | BH-7 | BD-6 | 127 |
| Comp. Ex. 6-7 | | Ref. BD-6 | 100 |

TABLE 63-1

| | Host material | Dopant material | LT95(hr) (relative value) |
|---|---|---|---|
| Ex. 6-8 | BH-8 | BD-6 | 124 |
| Comp. Ex. 6-8 | | Ref. BD-6 | 100 |

TABLE 63-2

| | Host material | Dopant material | LT95(hr) (relative value) |
|---|---|---|---|
| Ex. 6-8-D1 | BH-8-D1 | BD-6 | 107 |
| Comp. Ex. 6-8-D1 | | Ref. BD-6 | 100 |

TABLE 63-3

| | Host material | Dopant material | LT95(hr) (relative value) |
|---|---|---|---|
| Ex. 6-8-D2 | BH-8-D2 | BD-6 | 121 |
| Comp. Ex. 6-8-D2 | | Ref. BD-6 | 100 |

TABLE 64

| | Host material | Dopant material | LT95(hr) (relative value) |
|---|---|---|---|
| Ex. 6-9 | BH-9 | BD-6 | 123 |
| Comp. Ex. 6-9 | | Ref. BD-6 | 100 |

TABLE 65

| | Host material | Dopant material | LT95(hr) (relative value) |
|---|---|---|---|
| Ex. 6-10 | BH-10 | BD-6 | 113 |
| Comp. Ex. 6-10 | | Ref. BD-6 | 100 |

TABLE 66-1

| | Host material | Dopant material | LT95(hr) (relative value) |
|---|---|---|---|
| Ex. 6-11 | BH-11 | BD-6 | 121 |
| Comp. Ex. 6-11 | | Ref. BD-6 | 100 |

TABLE 66-2

| | Host material | Dopant material | LT95(hr) (relative value) |
|---|---|---|---|
| Ex. 6-11-D1 | BH-11-D1 | BD-6 | 118 |
| Comp. Ex. 6-11-D1 | | Ref. BD-6 | 100 |

TABLE 66-3

| | Host material | Dopant material | LT95(hr) (relative value) |
|---|---|---|---|
| Ex. 6-11-D2 | BH-11-D2 | BD-6 | 118 |
| Comp. Ex. 6-11-D2 | | Ref. BD-6 | 100 |

Example 7-1 and Comparative Example 7-1

Organic EL devices were fabricated and evaluated in the same manner as in Example 1-1, except that a compound BD-7 or a compound Ref. BD-7 was used as the dopant material and a compound BH-1 was used as the host material. Results are shown in Table 67-1.

Hereinafter, organic EL devices were fabricated and evaluated in the same manner as in Example 1-1, except that a compound BD-7 or a compound Ref. BD-7 was used as the dopant material and a compound shown in the respective tables below was used as the host material. The results are shown in the respective tables below.

TABLE 67-1

| | Host material | Dopant material | LT95(hr) (relative value) |
|---|---|---|---|
| Ex. 7-1 | BH-1 | BD-7 | 119 |
| Comp. Ex. 7-1 | | Ref. BD-7 | 100 |

TABLE 67-2

| | Host material | Dopant material | LT95(hr) (relative value) |
|---|---|---|---|
| Ex. 7-1-D1 | BH-1-D1 | BD-7 | 121 |
| Comp. Ex. 7-1-D1 | | Ref. BD-7 | 100 |

TABLE 67-3

| | Host material | Dopant material | LT95(hr) (relative value) |
|---|---|---|---|
| Ex. 7-1-D2 | BH-1-D2 | BD-7 | 115 |
| Comp. Ex. 7-1-D2 | | Ref. BD-7 | 100 |

TABLE 68-1

| | Host material | Dopant material | LT95(hr) (relative value) |
|---|---|---|---|
| Ex. 7-2 | BH-2 | BD-7 | 118 |
| Comp. Ex. 7-2 | | Ref. BD-7 | 100 |

TABLE 68-2

| | Host material | Dopant material | LT95(hr) (relative value) |
|---|---|---|---|
| Ex. 7-2-D1 | BH-2-D1 | BD-7 | 113 |
| Comp. Ex. 7-2-D1 | | Ref. BD-7 | 100 |

TABLE 68-3

| | Host material | Dopant material | LT95(hr) (relative value) |
|---|---|---|---|
| Ex. 7-2-D2 | BH-2-D2 | BD-7 | 130 |
| Comp. Ex. 7-2-D2 | | Ref. BD-7 | 100 |

TABLE 69

| | Host material | Dopant material | LT95(hr) (relative value) |
|---|---|---|---|
| Ex. 7-3 | BH-3 | BD-7 | 117 |
| Comp. Ex. 7-3 | | Ref. BD-7 | 100 |

TABLE 70-1

| | Host material | Dopant material | LT95(hr) (relative value) |
|---|---|---|---|
| Ex. 7-4 | BH-4 | BD-7 | 118 |
| Comp. Ex. 7-4 | | Ref. BD-7 | 100 |

TABLE 70-2

| | Host material | Dopant material | LT95(hr) (relative value) |
|---|---|---|---|
| Ex. 7-4-D1 | BH-4-D1 | BD-7 | 129 |
| Comp. Ex. 7-4-D1 | | Ref. BD-7 | 100 |

TABLE 70-3

| | Host material | Dopant material | LT95(hr) (relative value) |
|---|---|---|---|
| Ex. 7-4-D2 | BH-4-D2 | BD-7 | 128 |
| Comp. Ex. 7-4-D2 | | Ref. BD-7 | 100 |

TABLE 71-1

| | Host material | Dopant material | LT95(hr) (relative value) |
|---|---|---|---|
| Ex. 7-5 | BH-5 | BD-7 | 116 |
| Comp. Ex. 7-5 | | Ref. BD-7 | 100 |

TABLE 71-2

| | Host material | Dopant material | LT95(hr) (relative value) |
|---|---|---|---|
| Ex. 7-5-D1 | BH-5-D1 | BD-7 | 112 |
| Comp. Ex. 7-5-D1 | | Ref. BD-7 | 100 |

TABLE 71-3

| | Host material | Dopant material | LT95(hr) (relative value) |
|---|---|---|---|
| Ex. 7-5-D2 | BH-5-D2 | BD-7 | 130 |
| Comp. Ex. 7-5-D2 | | Ref. BD-7 | 100 |

TABLE 72

| | Host material | Dopant material | LT95(hr) (relative value) |
|---|---|---|---|
| Ex. 7-6 | BH-6 | BD-7 | 108 |
| Comp. Ex. 7-6 | | Ref. BD-7 | 100 |

TABLE 73

| | Host material | Dopant material | LT95(hr) (relative value) |
|---|---|---|---|
| Ex. 7-7 | BH-7 | BD-7 | 123 |
| Comp. Ex. 7-7 | | Ref. BD-7 | 100 |

TABLE 74-1

| | Host material | Dopant material | LT95(hr) (relative value) |
|---|---|---|---|
| Ex. 7-8 | BH-8 | BD-7 | 126 |
| Comp. Ex. 7-8 | | Ref. BD-7 | 100 |

TABLE 74-2

| | Host material | Dopant material | LT95(hr) (relative value) |
|---|---|---|---|
| Ex. 7-8-D1 | BH-8-D1 | BD-7 | 125 |
| Comp. Ex. 7-8-D1 | | Ref. BD-7 | 100 |

TABLE 74-3

| | Host material | Dopant material | LT95(hr) (relative value) |
|---|---|---|---|
| Ex. 7-8-D2 | BH-8-D2 | BD-7 | 110 |
| Comp. Ex. 7-8-D2 | | Ref. BD-7 | 100 |

TABLE 75

| | Host material | Dopant material | LT95(hr) (relative value) |
|---|---|---|---|
| Ex. 7-9 | BH-9 | BD-7 | 127 |
| Comp. Ex. 7-9 | | Ref. BD-7 | 100 |

TABLE 76

| | Host material | Dopant material | LT95(hr) (relative value) |
|---|---|---|---|
| Ex. 7-10 | BH-10 | BD-7 | 110 |
| Comp. Ex. 7-10 | | Ref. BD-7 | 100 |

TABLE 77-1

| | Host material | Dopant material | LT95(hr) (relative value) |
|---|---|---|---|
| Ex. 7-11 | BH-11 | BD-7 | 127 |
| Comp. Ex. 7-11 | | Ref. BD-7 | 100 |

TABLE 77-2

| | Host material | Dopant material | LT95(hr) (relative value) |
|---|---|---|---|
| Ex. 7-11-D1 | BH-11-D1 | BD-7 | 125 |
| Comp. Ex. 7-11-D1 | | Ref. BD-7 | 100 |

TABLE 77-3

| | Host material | Dopant material | LT95(hr) (relative value) |
|---|---|---|---|
| Ex. 7-11-D2 | BH-11-D2 | BD-7 | 115 |
| Comp. Ex. 7-11-D2 | | Ref. BD-7 | 100 |

Example 8-1 and Comparative Example 8-1

Organic EL devices were fabricated and evaluated in the same manner as in Example 1-1, except that a compound BD-8 or a compound Ref. BD-8 was used as the dopant material and a compound BH-1 was used as the host material. Results are shown in Table 78-1.

Hereinafter, organic EL devices were fabricated and evaluated in the same manner as in Example 1-1, except that a compound BD-8 or a compound Ref. BD-8 was used as the dopant material and a compound shown in the respective tables below was used as the host material. The results are shown in the respective tables below.

TABLE 78-1

| | Host material | Dopant material | LT95(hr) (relative value) |
|---|---|---|---|
| Ex. 8-1 | BH-1 | BD-8 | 115 |
| Comp. Ex. 8-1 | | Ref. BD-8 | 100 |

TABLE 78-2

| | Host material | Dopant material | LT95(hr) (relative value) |
|---|---|---|---|
| Ex. 8-1-D1 | BH-1-D1 | BD-8 | 112 |
| Comp. Ex. 8-1-D1 | | Ref. BD-8 | 100 |

TABLE 78-3

| | Host material | Dopant material | LT95(hr) (relative value) |
|---|---|---|---|
| Ex. 8-1-D2 | BH-1-D2 | BD-8 | 109 |
| Comp. Ex. 8-1-D2 | | Ref. BD-8 | 100 |

TABLE 79-1

| | Host material | Dopant material | LT95(hr) (relative value) |
|---|---|---|---|
| Ex. 8-2 | BH-2 | BD-8 | 105 |
| Comp. Ex. 8-2 | | Ref. BD-8 | 100 |

TABLE 79-2

| | Host material | Dopant material | LT95(hr) (relative value) |
|---|---|---|---|
| Ex. 8-2-D1 | BH-2-D1 | BD-8 | 115 |
| Comp. Ex. 8-2-D1 | | Ref. BD-8 | 100 |

TABLE 79-3

| | Host material | Dopant material | LT95(hr) (relative value) |
|---|---|---|---|
| Ex. 8-2-D2 | BH-2-D2 | BD-8 | 105 |
| Comp. Ex. 8-2-D2 | | Ref. BD-8 | 100 |

TABLE 80

| | Host material | Dopant material | LT95(hr) (relative value) |
|---|---|---|---|
| Ex. 8-3 | BH-3 | BD-8 | 114 |
| Comp. Ex. 8-3 | | Ref. BD-8 | 100 |

TABLE 81-1

| | Host material | Dopant material | LT95(hr) (relative value) |
|---|---|---|---|
| Ex. 8-4 | BH-4 | BD-8 | 106 |
| Comp. Ex. 8-4 | | Ref. BD-8 | 100 |

TABLE 81-2

| | Host material | Dopant material | LT95(hr) (relative value) |
|---|---|---|---|
| Ex. 8-4-D1 | BH-4-D1 | BD-8 | 108 |
| Comp. Ex. 8-4-D1 | | Ref. BD-8 | 100 |

TABLE 81-3

| | Host material | Dopant material | LT95(hr) (relative value) |
|---|---|---|---|
| Ex. 8-4-D2 | BH-4-D2 | BD-8 | 118 |
| Comp. Ex. 8-4-D2 | | Ref. BD-8 | 100 |

TABLE 82-1

| | Host material | Dopant material | LT95(hr) (relative value) |
|---|---|---|---|
| Ex. 8-5 | BH-5 | BD-8 | 110 |
| Comp. Ex. 8-5 | | Ref. BD-8 | 100 |

TABLE 82-2

| | Host material | Dopant material | LT95(hr) (relative value) |
|---|---|---|---|
| Ex. 8-5-D1 | BH-5-D1 | BD-8 | 108 |
| Comp. Ex. 8-5-D1 | | Ref. BD-8 | 100 |

TABLE 82-3

| | Host material | Dopant material | LT95(hr) (relative value) |
|---|---|---|---|
| Ex. 8-5-D2 | BH-5-D2 | BD-8 | 110 |
| Comp. Ex. 8-5-D2 | | Ref. BD-8 | 100 |

TABLE 83

| | Host material | Dopant material | LT95(hr) (relative value) |
|---|---|---|---|
| Ex. 8-6 | BH-6 | BD-8 | 111 |
| Comp. Ex. 8-6 | | Ref. BD-8 | 100 |

TABLE 84

| | Host material | Dopant material | LT95(hr) (relative value) |
|---|---|---|---|
| Ex. 8-7 | BH-7 | BD-8 | 115 |
| Comp. Ex. 8-7 | | Ref. BD-8 | 100 |

TABLE 85-1

| | Host material | Dopant material | LT95(hr) (relative value) |
|---|---|---|---|
| Ex. 8-8 | BH-8 | BD-8 | 105 |
| Comp. Ex. 8-8 | | Ref. BD-8 | 100 |

TABLE 85-2

| | Host material | Dopant material | LT95(hr) (relative value) |
|---|---|---|---|
| Ex. 8-8-D1 | BH-8-D1 | BD-8 | 115 |
| Comp. Ex. 8-8-D1 | | Ref. BD-8 | 100 |

TABLE 85-3

| | Host material | Dopant material | LT95(hr) (relative value) |
|---|---|---|---|
| Ex. 8-8-D2 | BH-8-D2 | BD-8 | 117 |
| Comp. Ex. 8-8-D2 | | Ref. BD-8 | 100 |

TABLE 86

| | Host material | Dopant material | LT95(hr) (relative value) |
|---|---|---|---|
| Ex. 8-9 | BH-9 | BD-8 | 120 |
| Comp. Ex. 8-9 | | Ref. BD-8 | 100 |

TABLE 87

| | Host material | Dopant material | LT95(hr) (relative value) |
|---|---|---|---|
| Ex. 8-10 | BH-10 | BD-8 | 116 |
| Comp. Ex. 8-10 | | Ref. BD-8 | 100 |

TABLE 88-1

| | Host material | Dopant material | LT95(hr) (relative value) |
|---|---|---|---|
| Ex. 8-11 | BH-11 | BD-8 | 113 |
| Comp. Ex. 8-11 | | Ref. BD-8 | 100 |

TABLE 88-2

| | Host material | Dopant material | LT95(hr) (relative value) |
|---|---|---|---|
| Ex. 8-11-D1 | BH-11-D1 | BD-8 | 113 |
| Comp. Ex. 8-11-D1 | | Ref. BD-8 | 100 |

TABLE 88-3

| | Host material | Dopant material | LT95(hr) (relative value) |
|---|---|---|---|
| Ex. 8-11-D2 | BH-11-D2 | BD-8 | 106 |
| Comp. Ex. 8-11-D2 | | Ref. BD-8 | 100 |

Example 9-1 and Comparative Example 1-1

Organic EL devices were fabricated and evaluated in the same manner as in Example 1-1, except that a compound BD-9 or a compound Ref. BD-1 was used as the dopant material and a compound BH-1 was used as the host material. Results are shown in Table 89-1.

Hereinafter, organic EL devices were fabricated and evaluated in the same manner as in Example 1-1, except that a compound BD-9 or a compound Ref. BD-1 was used as the dopant material and a compound shown in the respective tables below was used as the host material. The results are shown in the respective tables below.

TABLE 89-1

| | Host material | Dopant material | LT95(hr) (relative value) |
|---|---|---|---|
| Ex. 9-1 | BH-1 | BD-9 | 109 |
| Comp. Ex. 1-1 | | Ref. BD-1 | 100 |

TABLE 89-2

| | Host material | Dopant material | LT95(hr) (relative value) |
|---|---|---|---|
| Ex. 9-1-D1 | BH-1-D1 | BD-9 | 109 |
| Comp. Ex. 1-1-D1 | | Ref. BD-1 | 100 |

TABLE 89-3

| | Host material | Dopant material | LT95(hr) (relative value) |
|---|---|---|---|
| Ex. 9-1-D2 | BH-1-D2 | BD-9 | 112 |
| Comp. Ex. 1-1-D2 | | Ref. BD-1 | 100 |

TABLE 90-1

| | Host material | Dopant material | LT95(hr) (relative value) |
|---|---|---|---|
| Ex. 9-2 | BH-2 | BD-9 | 109 |
| Comp. Ex. 1-2 | | Ref. BD-1 | 100 |

TABLE 90-2

| | Host material | Dopant material | LT95(hr) (relative value) |
|---|---|---|---|
| Ex. 9-2-D1 | BH-2-D1 | BD-9 | 108 |
| Comp. Ex. 1-2-D1 | | Ref. BD-1 | 100 |

TABLE 90-3

| | Host material | Dopant material | LT95(hr) (relative value) |
|---|---|---|---|
| Ex. 9-2-D2 | BH-2-D2 | BD-9 | 109 |
| Comp. Ex. 1-2-D2 | | Ref. BD-1 | 100 |

TABLE 91

| | Host material | Dopant material | LT95(hr) (relative value) |
|---|---|---|---|
| Ex. 9-3 | BH-3 | BD-9 | 108 |
| Comp. Ex. 1-3 | | Ref. BD-1 | 100 |

TABLE 92-1

| | Host material | Dopant material | LT95(hr) (relative value) |
|---|---|---|---|
| Ex. 9-4 | BH-4 | BD-9 | 112 |
| Comp. Ex. 1-4 | | Ref. BD-1 | 100 |

TABLE 92-2

| | Host material | Dopant material | LT95(hr) (relative value) |
|---|---|---|---|
| Ex. 9-4-D1 | BH-4-D1 | BD-9 | 113 |
| Comp. Ex. 1-4-D1 | | Ref. BD-1 | 100 |

TABLE 92-3

| | Host material | Dopant material | LT95(hr) (relative value) |
|---|---|---|---|
| Ex. 9-4-D2 | BH-4-D2 | BD-9 | 113 |
| Comp. Ex. 1-4-D2 | | Ref. BD-1 | 100 |

TABLE 93-1

| | Host material | Dopant material | LT95(hr) (relative value) |
|---|---|---|---|
| Ex. 9-5 | BH-5 | BD-9 | 111 |
| Comp. Ex. 1-5 | | Ref. BD-1 | 100 |

TABLE 93-2

| | Host material | Dopant material | LT95(hr) (relative value) |
|---|---|---|---|
| Ex. 9-5-D1 | BH-5-D1 | BD-9 | 114 |
| Comp. Ex. 1-5-D1 | | Ref. BD-1 | 100 |

TABLE 93-3

| | Host material | Dopant material | LT95(hr) (relative value) |
|---|---|---|---|
| Ex. 9-5-D2 | BH-5-D2 | BD-9 | 112 |
| Comp. Ex. 1-5-D2 | | Ref. BD-1 | 100 |

TABLE 94

| | Host material | Dopant material | LT95(hr) (relative value) |
|---|---|---|---|
| Ex. 9-6 | BH-6 | BD-9 | 114 |
| Comp. Ex. 1-6 | | Ref. BD-1 | 100 |

TABLE 95

| | Host material | Dopant material | LT95(hr) (relative value) |
|---|---|---|---|
| Ex. 9-7 | BH-7 | BD-9 | 110 |
| Comp. Ex. 1-7 | | Ref. BD-1 | 100 |

TABLE 96-1

| | Host material | Dopant material | LT95(hr) (relative value) |
|---|---|---|---|
| Ex. 9-8 | BH-8 | BD-9 | 112 |
| Comp. Ex. 1-8 | | Ref. BD-1 | 100 |

TABLE 96-2

| | Host material | Dopant material | LT95(hr) (relative value) |
|---|---|---|---|
| Ex. 9-8-D1 | BH-8-D1 | BD-9 | 113 |
| Comp. Ex. 1-8-D1 | | Ref. BD-1 | 100 |

TABLE 96-3

| | Host material | Dopant material | LT95(hr) (relative value) |
|---|---|---|---|
| Ex. 9-8-D2 | BH-8-D2 | BD-9 | 109 |
| Comp. Ex. 1-8-D2 | | Ref. BD-1 | 100 |

TABLE 97

| | Host material | Dopant material | LT95(hr) (relative value) |
|---|---|---|---|
| Ex. 9-9 | BH-9 | BD-9 | 112 |
| Comp. Ex. 1-9 | | Ref. BD-1 | 100 |

TABLE 98

| | Host material | Dopant material | LT95(hr) (relative value) |
|---|---|---|---|
| Ex. 9-10 | BH-10 | BD-9 | 111 |
| Comp. Ex. 1-10 | | Ref. BD-1 | 100 |

TABLE 99-1

| | Host material | Dopant material | LT95(hr) (relative value) |
|---|---|---|---|
| Ex. 9-11 | BH-11 | BD-9 | 112 |
| Comp. Ex. 1-11 | | Ref. BD-1 | 100 |

TABLE 99-2

| | Host material | Dopant material | LT95(hr) (relative value) |
|---|---|---|---|
| Ex. 9-11-D1 | BH-11-D1 | BD-9 | 114 |
| Comp. Ex. 1-11-D1 | | Ref. BD-1 | 100 |

TABLE 99-3

| | Host material | Dopant material | LT95(hr) (relative value) |
|---|---|---|---|
| Ex. 9-11-D2 | BH-11-D2 | BD-9 | 118 |
| Comp. Ex. 1-11-D2 | | Ref. BD-1 | 100 |

Organic EL devices were fabricated and evaluated in the same manner as in Example 1-1, except that a compound BD-10 or a compound Ref. BD-1 was used as the dopant material and a compound BH-1 was used as the host material. Results are shown in Table 100-1.

Hereinafter, organic EL devices were fabricated and evaluated in the same manner as in Example 1-1, except that a compound BD-10 or a compound Ref. BD-1 was used as the dopant material and a compound shown in the respective tables below was used as the host material. The results are shown in the respective tables below.

TABLE 100-1

| | Host material | Dopant material | LT95(hr) (relative value) |
|---|---|---|---|
| Ex. 10-1 | BH-1 | BD-10 | 125 |
| Comp. Ex. 1-1 | | Ref. BD-1 | 100 |

TABLE 100-2

| | Host material | Dopant material | LT95(hr) (relative value) |
|---|---|---|---|
| Ex. 10-1-D1 | BH-1-D1 | BD-10 | 117 |
| Comp. Ex. 1-1-D1 | | Ref. BD-1 | 100 |

TABLE 100-3

| | Host material | Dopant material | LT95(hr) (relative value) |
|---|---|---|---|
| Ex. 10-1-D2 | BH-1-D2 | BD-10 | 117 |
| Comp. Ex. 1-1-D2 | | Ref. BD-1 | 100 |

TABLE 101-1

| | Host material | Dopant material | LT95(hr) (relative value) |
|---|---|---|---|
| Ex. 10-2 | BH-2 | BD-10 | 113 |
| Comp. Ex. 1-2 | | Ref. BD-1 | 100 |

TABLE 101-2

| | Host material | Dopant material | LT95(hr) (relative value) |
|---|---|---|---|
| Ex. 10-2-D1 | BH-2-D1 | BD-10 | 124 |
| Comp. Ex. 1-2-D1 | | Ref. BD-1 | 100 |

TABLE 101-3

| | Host material | Dopant material | LT95(hr) (relative value) |
|---|---|---|---|
| Ex. 10-2-D2 | BH-2-D2 | BD-10 | 120 |
| Comp. Ex. 1-2-D2 | | Ref. BD-1 | 100 |

TABLE 102

| | Host material | Dopant material | LT95(hr) (relative value) |
|---|---|---|---|
| Ex. 10-3 | BH-3 | BD-10 | 135 |
| Comp. Ex. 1-3 | | Ref. BD-1 | 100 |

TABLE 103-1

| | Host material | Dopant material | LT95(hr) (relative value) |
|---|---|---|---|
| Ex. 10-4 | BH-4 | BD-10 | 121 |
| Comp. Ex. 1-4 | | Ref. BD-1 | 100 |

TABLE 103-2

| | Host material | Dopant material | LT95(hr) (relative value) |
|---|---|---|---|
| Ex. 10-4-D1 | BH-4-D1 | BD-10 | 128 |
| Comp. Ex. 1-4-D1 | | Ref. BD-1 | 100 |

TABLE 103-3

| | Host material | Dopant material | LT95(hr) (relative value) |
|---|---|---|---|
| Ex. 10-4-D2 | BH-4-D2 | BD-10 | 126 |
| Comp. Ex. 1-4-D2 | | Ref. BD-1 | 100 |

TABLE 104-1

| | Host material | Dopant material | LT95(hr) (relative value) |
|---|---|---|---|
| Ex. 10-5 | BH-5 | BD-10 | 123 |
| Comp. Ex. 1-5 | | Ref. BD-1 | 100 |

TABLE 104-2

| | Host material | Dopant material | LT95(hr) (relative value) |
|---|---|---|---|
| Ex. 10-5-D1 | BH-5-D1 | BD-10 | 126 |
| Comp. Ex. 1-5-D1 | | Ref. BD-1 | 100 |

TABLE 104-3

| | Host material | Dopant material | LT95(hr) (relative value) |
|---|---|---|---|
| Ex. 10-5-D2 | BH-5-D2 | BD-10 | 119 |
| Comp. Ex. 1-5-D2 | | Ref. BD-1 | 100 |

TABLE 105

| | Host material | Dopant material | LT95(hr) (relative value) |
|---|---|---|---|
| Ex. 10-6 | BH-6 | BD-10 | 126 |
| Comp. Ex. 1-6 | | Ref. BD-1 | 100 |

TABLE 106

| | Host material | Dopant material | LT95(hr) (relative value) |
|---|---|---|---|
| Ex. 10-7 | BH-7 | BD-10 | 126 |
| Comp. Ex. 1-7 | | Ref. BD-1 | 100 |

TABLE 107-1

| | Host material | Dopant material | LT95(hr) (relative value) |
|---|---|---|---|
| Ex. 10-8 | BH-8 | BD-10 | 119 |
| Comp. Ex. 1-8 | | Ref. BD-1 | 100 |

TABLE 107-2

| | Host material | Dopant material | LT95(hr) (relative value) |
|---|---|---|---|
| Ex. 10-8-D1 | BH-8-D1 | BD-10 | 125 |
| Comp. Ex. 1-8-D1 | | Ref. BD-1 | 100 |

TABLE 107-3

| | Host material | Dopant material | LT95(hr) (relative value) |
|---|---|---|---|
| Ex. 10-8-D2 | BH-8-D2 | BD-10 | 122 |
| Comp. Ex. 1-8-D2 | | Ref. BD-1 | 100 |

TABLE 108

| | Host material | Dopant material | LT95(hr) (relative value) |
|---|---|---|---|
| Ex. 10-9 | BH-9 | BD-10 | 121 |
| Comp. Ex. 1-9 | | Ref. BD-1 | 100 |

TABLE 109

| | Host material | Dopant material | LT95(hr) (relative value) |
|---|---|---|---|
| Ex. 10-10 | BH-10 | BD-10 | 125 |
| Comp. Ex. 1-10 | | Ref. BD-1 | 100 |

TABLE 110-1

| | Host material | Dopant material | LT95(hr) (relative value) |
|---|---|---|---|
| Ex. 10-11 | BH-11 | BD-10 | 118 |
| Comp. Ex. 1-11 | | Ref. BD-1 | 100 |

TABLE 110-2

| | Host material | Dopant material | LT95(hr) (relative value) |
|---|---|---|---|
| Ex. 10-11-D1 | BH-11-D1 | BD-10 | 123 |
| Comp. Ex. 1-11-D1 | | Ref. BD-1 | 100 |

TABLE 110-3

| | Host material | Dopant material | LT95(hr) (relative value) |
|---|---|---|---|
| Ex. 10-11-D2 | BH-11-D2 | BD-10 | 132 |
| Comp. Ex. 1-11-D2 | | Ref. BD-1 | 100 |

From the results of each of the above tables, it can be seen that, by using the respective compounds BD-1 to BD-10 represented by the formula (A1) which have a deuterium atom, the devices have a lifetime longer than that of the devices using the comparative compounds Ref. BD-1, Ref. BD-3, Ref. BD-5, Ref. BD-6, Ref. BD-7, and Ref. BD-8 which are the corresponding protium compounds, respectively. It is presumed that this is because the stability of the compound was increased by having a deuterium atom.

<Synthesis of Compounds>

Synthesis Example 1: Synthesis of Compound BD-1

The compound BD-1 was synthesized in accordance with the following synthetic scheme.

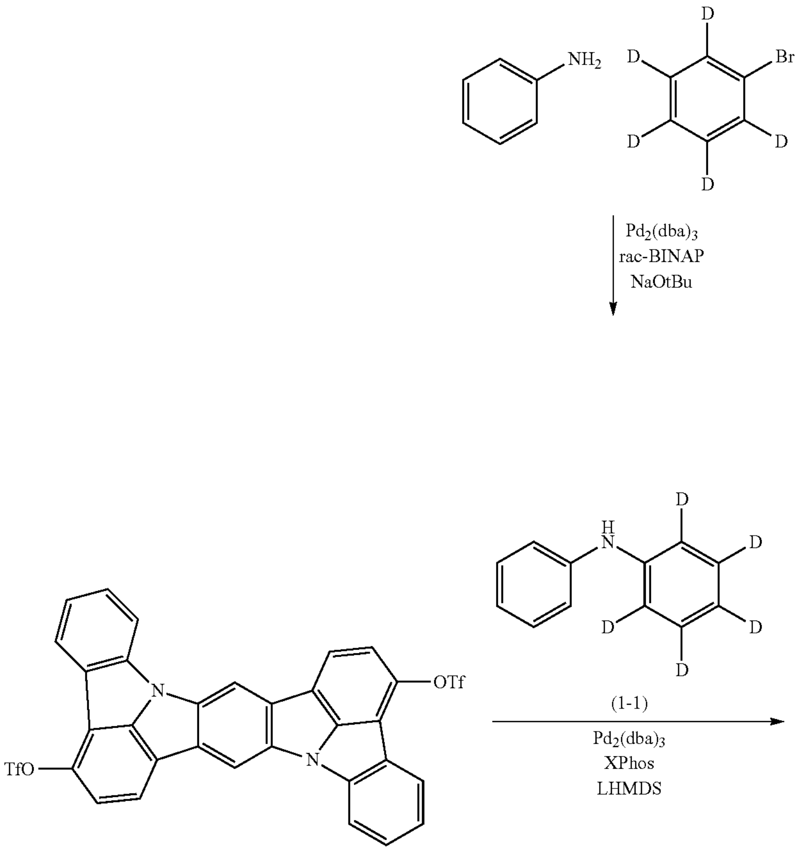

(1-2)

-continued

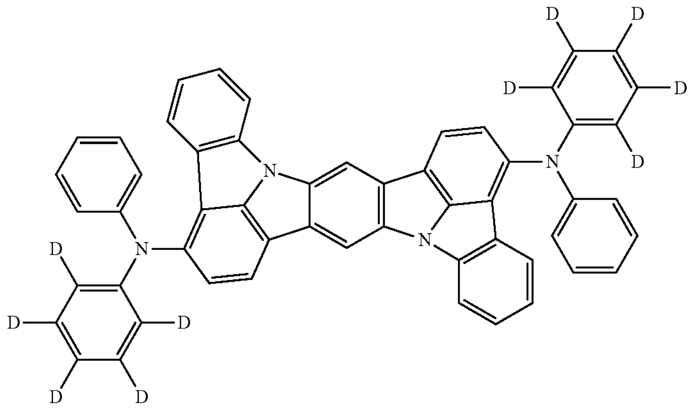

(BD-1)

Synthesis of Intermediate 1-1

Under an argon atmosphere, 1-bromobenzene-2,3,4,5,6-d5 (15.0 g, 92.5 mmol), aniline (12.9 g, 138 mmol), tris(dibenzylideneacetone)palladium (0) ($Pd_2(dba)_3$, 1.27 g, 1.39 mmol), rac-2,2'-bis(diphenylphosphino)-1,1'-binaphthyl (rac-BINAP, 1.73 g, 2.78 mmol), and NaOt-Bu (17.8 g, 185 mmol) were dissolved in xylene (280 mL), and the reaction mixture was stirred at 100° C. for 5 hours. After completion of the reaction, toluene was added to the reaction solution, followed by filtration through celite. The solvent was distilled off to obtain a solid, and the solid obtained was purified by column chromatography to obtain a white solid (7.40 g, yield: 46%). The obtained solid was identified as the intermediate 1-1, which was an intended product, based on the fact that the result of mass spectrometric analysis was: m/e=174 for the molecular weight of 174.

Synthesis of Compound BD-1

Under an argon-atmosphere, a known intermediate 1-2 (synthesized by the method described in U.S. Pat. No. 10,249,832, 739 mg, 1.06 mmol), the intermediate 1-1 (387 mg, 2.22 mmol), tris(dibenzylideneacetone)dipalladium(0) ($Pd_2(dba)_3$, 48 mg, 0.053 mmol), and 2-dicyclohexylphosphino-2',4',6'-triisopropylbiphenyl (XPhos, 101 mg, 0.211 mmol) were dissolved in xylene (60 mL), and a 1 M solution of lithium bis(trimethylsilyl)amide (LHMDS) in tetrahydrofuran (2.6 mL, 2.6 mmol) was added thereto. The reaction solution was refluxed for 5 hours. After completion of the reaction, methanol was added to the reaction solution, followed by subjecting filtration. The obtained solid was purified by column chromatography to obtain a yellow solid (681 mg, yield: 86%). The obtained solid was identified as the compound BD-1, which was an intended product, based on the fact that the result of mass spectrometric analysis was: m/e=748 for the molecular weight of 748.

Synthesis Example 2: Synthesis of Compound BD-2

The compound BD-2 was synthesized in accordance with the following synthetic scheme.

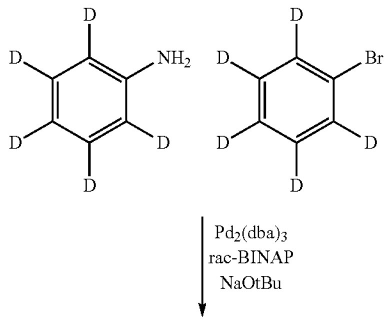

-continued

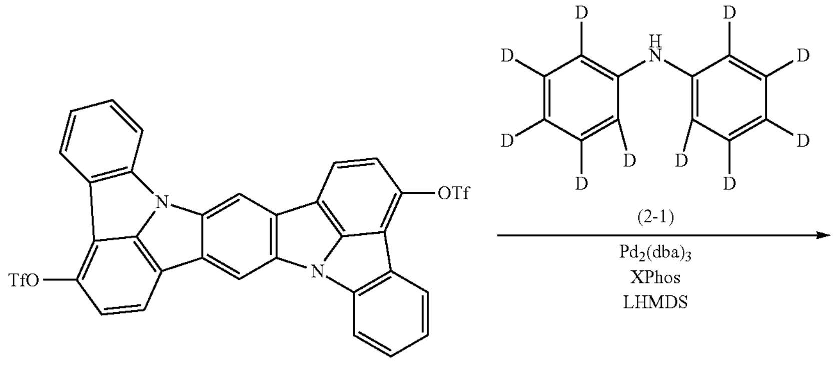

(1-2)

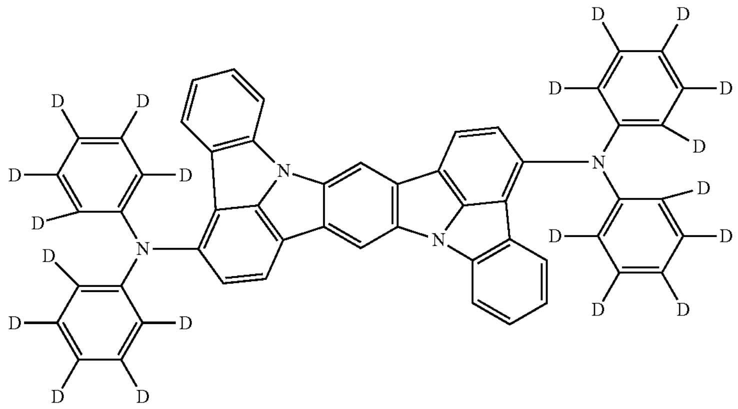

(BD-2)

Synthesis of Intermediate 2-1

Under an argon atmosphere, 1-bromobenzene-2,3,4,5,6-d5 (20.8 g, 128 mmol), benzene-d5-amine (18.9 g, 193 mmol), tris(dibenzylideneacetone)dipalladium(0) ($Pd_2$(dba) $_3$, 1.76 g, 1.93 mmol), rac-2,2'-bis(diphenylphosphino)-1,1'-binaphthyl (rac-BINAP, 2.40 g, 3.85 mmol), and NaOt-Bu (24.7 g, 257 mmol) were dissolved in xylene (386 mL) and the reaction solution was heated with stirring at 100° C. for 18 hours. After completion of the reaction, toluene was added to the reaction solution, followed by filtration through celite. The solvent was distilled off to obtain a solid, and the solid was purified by column chromatography to obtain a white solid (9.50 g, yield: 41%). The obtained solid was identified as the intermediate 2-1, which was an intended product, based on the fact that the result of mass spectrometric analysis was: m/e=179 for the molecular weight of 179.

Synthesis of Compound BD-2

Under an argon atmosphere, the intermediate 1-2 (739 mg, 1.06 mmol), the intermediate 2-1 (398 mg, 2.22 mmol), tris(dibenzylideneacetone)dipalladium(0) ($Pd_2(dba)_3$, 48 mg, 0.053 mmol), and 2-dicyclohexylphosphino-2',4',6'-triisopropylbiphenyl (XPhos, 101 mg, 0.211 mmol) were dissolved in xylene (60 mL), and a 1 M solution of lithium bis(trimethylsilyl)amide (LHMDS) in tetrahydrofuran (2.6 mL, 2.6 mmol) was added to the reaction solution, followed by reflux for 4 hours. After completion of the reaction, methanol was added to the reaction solution, followed by filtration. The obtained solid was purified by column chromatography to obtain a yellow solid (405 mg, yield: 51%). The obtained solid was identified as the compound BD-2, which was an intended product, based on the fact that the result of mass spectrometric analysis was: m/e=758 for the molecular weight of 758.

Synthesis Example 3: Synthesis of Compound BD-3

The compound BD-3 was synthesized in accordance with the following synthetic scheme.

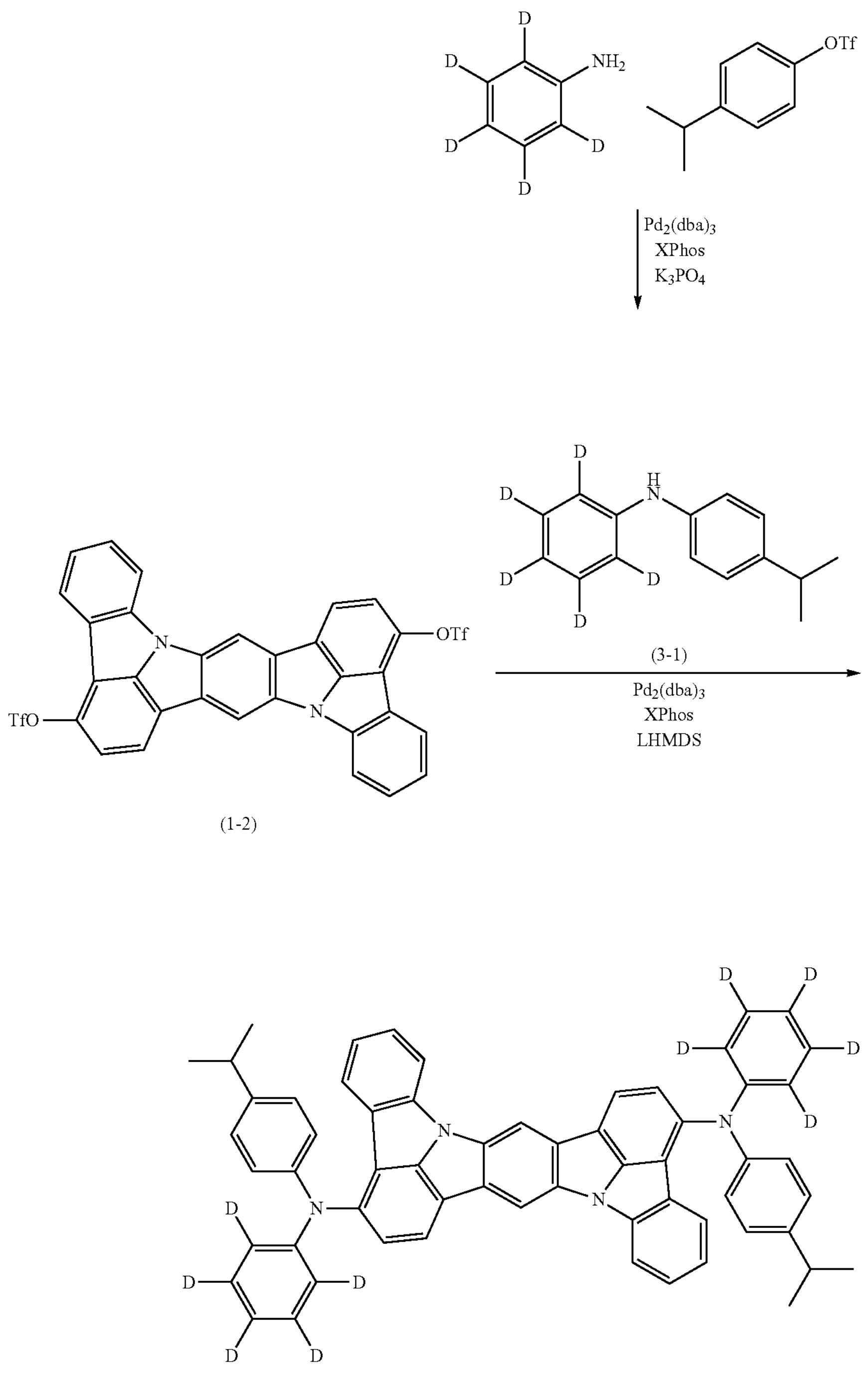

(3-1)

(1-2)

(BD-3)

Synthesis of Intermediate 3-1

Under an argon-atmosphere, 4-isopropylphenyltifluoromethanesulfonic acid (28.7 g, 107 mmol), benzene-d5-amine (21.0 g, 214 mmol), tris(dibenzylideneacetone)dipalladium(0) ($Pd_2(dba)_3$, 1.47 g, 1.60 mmol), 2-dicyclohexylphosphino-2',4',6'-triisopropylbiphenyl (XPhos, 1.53 g, 3.21 mmol), and tripotassium phosphate (45.4 g, 214 mmol) were dissolved in xylene (500 ml), and the reaction mixture was heated under stirring at 100° C. for 20 hours. After completion of the reaction, toluene was added to the reaction solution, followed by filtration through celite. The solvent was distilled off to obtain a solid, and the solid was purified by column chromatography to obtain a white solid (9.50 g, yield: 41%). The obtained solid was identified as the intermediate 3-1, which was an intended product, based on the fact that the result of mass spectrometric analysis was: m/e=216 for the molecular weight of 216.

Synthesis of Compound BD-3

Under an argon-atmosphere, the intermediate 1-2 (1.60 g, 2.28 mmol), the intermediate 3-1 (1.04 g, 4.79 mmol), tris(dibenzylideneacetone)dipalladium(0) ($Pd_2(dba)_3$, 104 mg, 0.114 mmol), and 2-dicyclohexylphosphino-2',4',6'-triisopropylbiphenyl (XPhos, 218 mg, 0.456 mmol) were dissolved in xylene (120 mL), and a 1 M solution of lithium bis(trimethylsilyl)amide (LHMDS) in tetrahydrofuran (5.7 mL, 5.7 mmol) were added to the reaction mixture, followed by reflux for 5 hours. After completion of the reaction, methanol was added to the reaction solution, followed by filtration. The obtained solid was purified by column chromatography to obtain a yellow solid (1.31 g, yield: 69%). The obtained solid was identified as the compound BD-3, which was an intended product, based on the fact that the result of mass spectrometric analysis was: m/e=833 for the molecular weight of 833.

Synthesis Example 4: Synthesis of Compound BD-4

The compound BD-4 was synthesized in accordance with the following synthetic scheme.

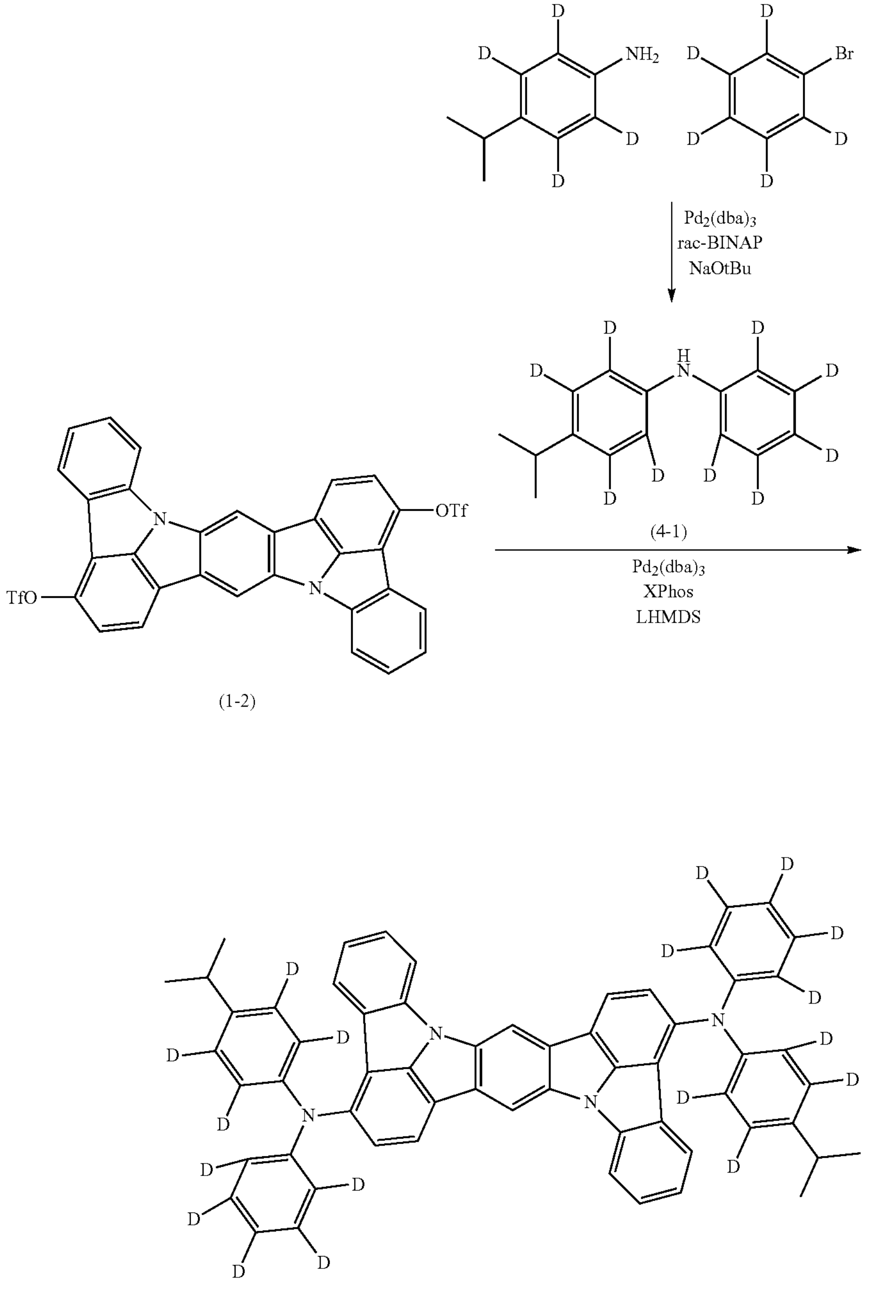

(4-1)

(1-2)

(BD-4)

The compound BD-4 was synthesized in the same manner as in the synthesis of the compound BD-3, except that bromobenzene-d5 was used in place of 4-isopropylphenyl-trifluoromethanesulfonic acid, and 4-isopropylaniline-2,3,5,6-d4 was used in place of benzen-d5-amine as reaction raw materials.

Synthesis Example 5: Synthesis of Compound BD-5

The compound BD-5 was synthesized in accordance with the following synthetic scheme.

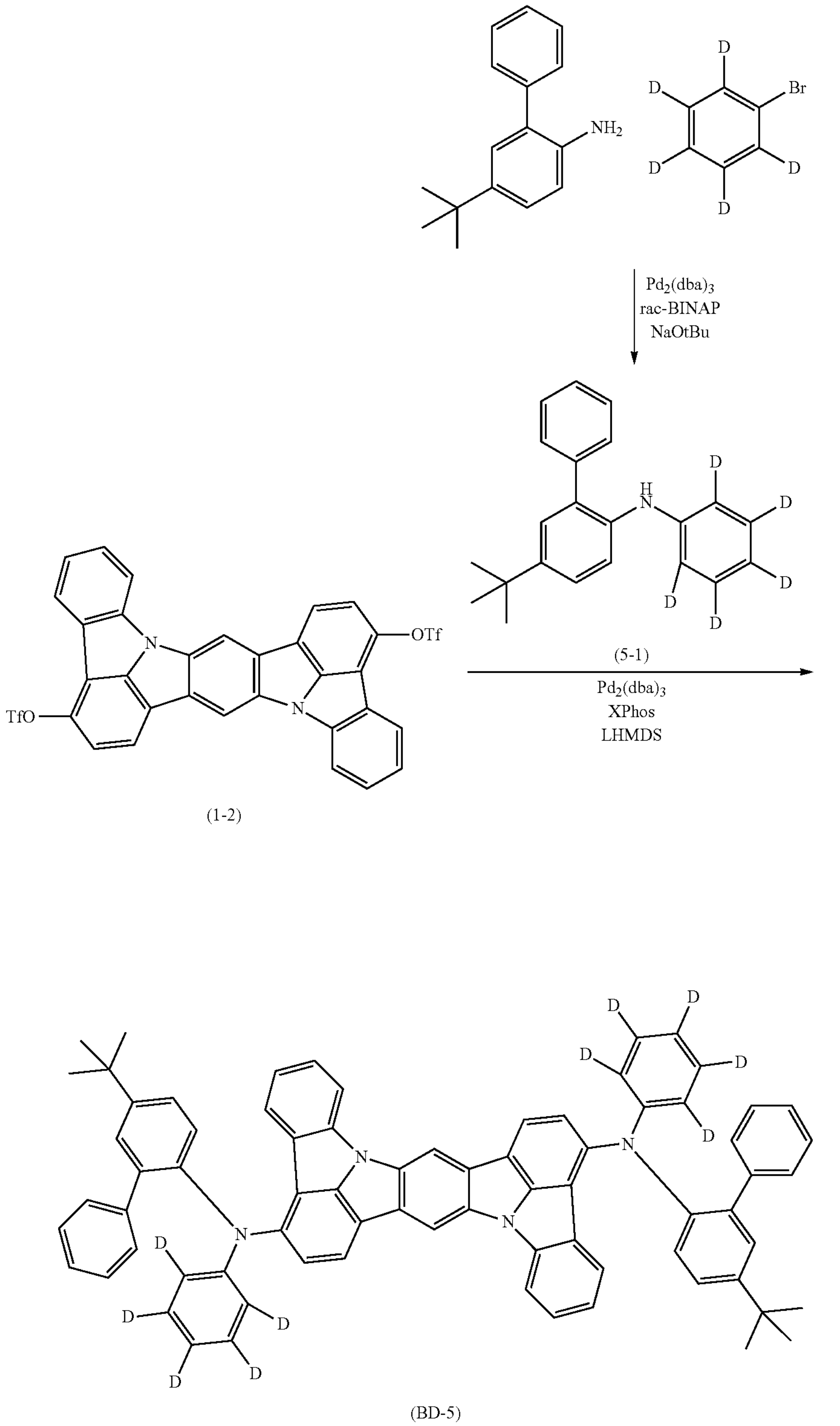

(5-1)

(1-2)

(BD-5)

The compound BD-5 was synthesized in the same manner as in the synthesis of the compound BD-3, except that bromobenzene-d5 was used in place of 4-isopropylphenyl-trifluoromethanesulfonic acid, and 5-(t-butyl)-(1,1'-biphenyl)-2-amine was used in place of benzen-d5-amine as reaction raw materials.

Synthesis Example 6: Synthesis of Compound BD-6

The compound BD-6 was synthesized in accordance with the following synthetic scheme.

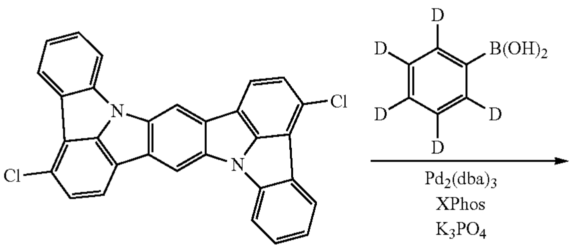

(1-3)

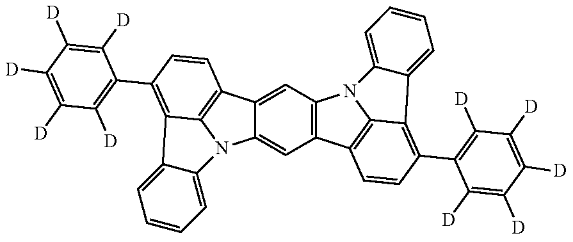

(BD-6)

Under an argon atmosphere, a known intermediate 1-3 (1.00 g, 2.11 mmol), phenyl-d5-boronic acid (1.34 g, 10.6 mmol), tris(dibenzylideneacetone)dipalladium(0) (Pd$_2$(dba)$_3$, 97 mg, 0.106 mmol), 2-dicyclohexylphosphino-2',4',6'-triisopropylbiphenyl (XPhos, 403 mg, 0.845 mmol), and tripotassium phosphate (K3PO$_4$, 2.69 g, 12.7 mmol) were dissolved in xylene (100 mL) and the reaction solution was refluxed for 10 hours. After completion of the reaction, methanol was added to the reaction solution, followed by filtration. The obtained solid was purified by column chromatography to obtain a yellow solid (0.45 g, yield: 38%). The obtained solid was identified as the compound BD-6, which was an intended product, based on the fact that the result of mass spectrometric analysis was: m/e=566 for the molecular weight of 566.

Synthesis Example 7: Synthesis of Compound BD-7

The compound BD-7 was synthesized in accordance with the following synthetic scheme.

(1) Synthesis of Intermediate B-1

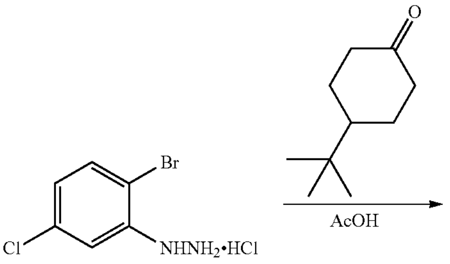

Intermedfiate A

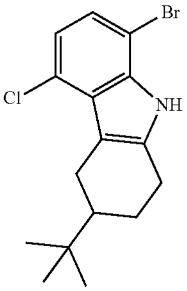

Intermedfiate B-1

A known intermediate A (9.00 g), and 4-t-butylcyclohexan-1-one (5.38 g) were added to acetic acid (35 mL), and the reaction solution was heated at 100° C. for 6 hours with stirring under an argon atmosphere. Dichloromethane and water were added to the reaction solution, and the organic phase was separated, followed by washing with an aqueous solution of sodium hydrogen carbonate. The reaction solution was concentrated under reduced pressure and then purified by column chromatography to obtain an intermediate B-1 (5.94 g, yield: 50%).

(2) Synthesis of Intermediate C-1

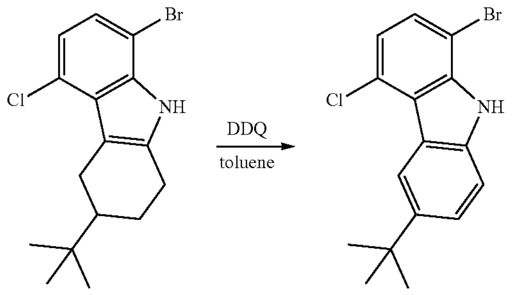

Intermedfiate B-1 Intermedfiate C-1

The intermediate B-1 (6.32 g), and 2,3-dichloro-5,6-dicyano-p-benzoquinone (DDQ; 8.42 g) were added to toluene (90 mL), and the reaction solution was heated at 100° C. for 3 hours with stirring under an argon atmosphere. The reaction solution was filtered through celite and then purified by column chromatography to obtain an intermediate C-1 (5.50 g, yield: 88%).

(3) Synthesis of Intermediate D-1

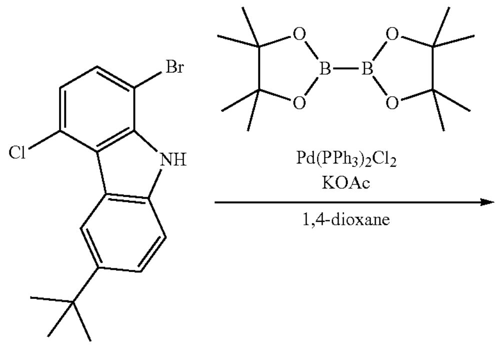

Intermedfiate C-1

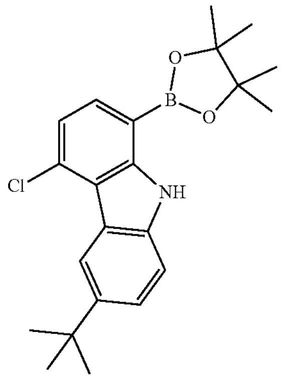

Intermedfiate D-1

The intermediate C-1 (5.80 g), bis(pinacolato)diboron (13.12 g), bis(triphenylphosphine)palladium(II) dichloride ($Pd(PPh_3)_2Cl_2$; 0.25 g), and potassium acetate (3.38 g) were added to 1,4-dioxane (120 ml) and the reaction solution was heated at 100° C. for 4 hours with stirring under an argon atmosphere. After filtering the reaction solution through celite, the solvent was distilled off. The solid obtained was purified by column chromatography and recrystallization to obtain an intermediate D-1 (3.65 g, yield: 55%).

(4) Synthesis of Intermediate E-1

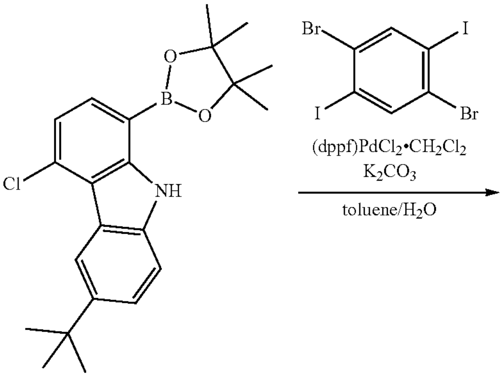

Intermedfiate D-1

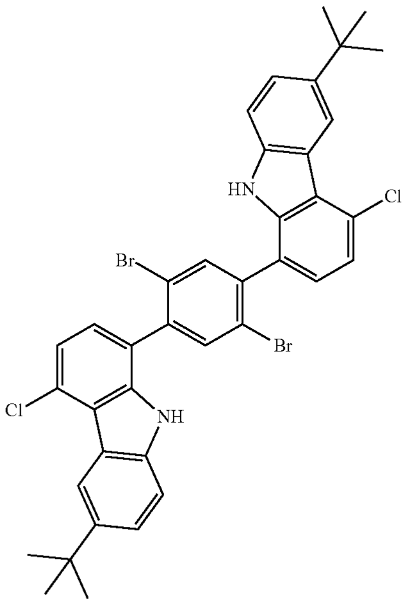

Intermedfiate E-1

The intermediate D-1 (8.37 g), 1,4-dibromo-2,5-diiodo-benzene (4.30 g), [1,1'-bis(diphenylphosphino)ferrocene]di-chloropalladium(II) dichloromethane complex ((dppf) $PdCl_2$—$CH_2CH_2$; 0.29 g), and potassium carbonate (3.66 g) were added to a mixed solvent of toluene (129 mL) and water (65 mL), and the reaction solution was heated at 90° C. for 7 hours with stirring under an argon atmosphere. Toluene and water were added to the reaction solution, followed by stirring at room temperature. The organic phase was separated and subjected to column chromatography, followed by washing with toluene to obtain an intermediate E-1 (4.42 g, yield: 67%).

(5) Synthesis of Intermediate F-1

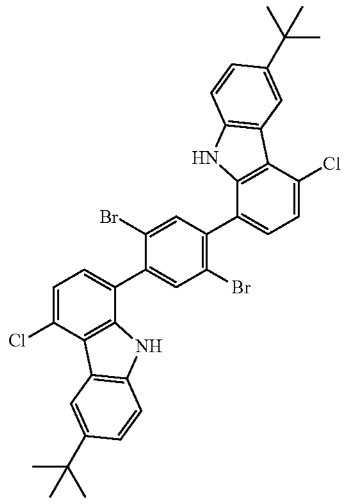

Intermediate E-1

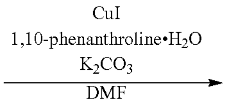

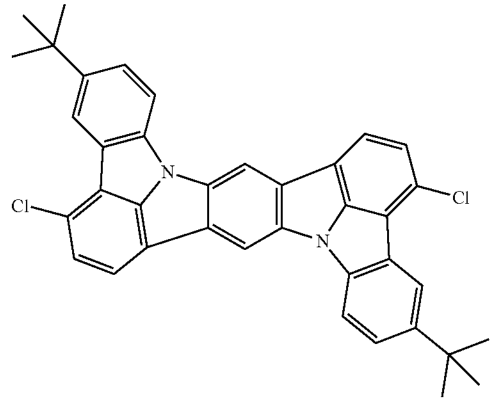

Intermediate F-1

The intermediate E-1 (5.04 g), copper(I) iodide (0.13 g), 1,10-phenanthroline monohydrate (0.24 g), and potassium carbonate (2.33 g) were added to dimethylformamide (DMF; 135 mL), and the reaction solution was heated at 100° C. for 3 hours with stirring under an argon atmosphere. Water (150 mL) was added to the reaction solution, and the solid was collected by filtration, followed by purification by column chromatography to obtain an intermediate F-1 (3.54 g, yield: 90%).

(6) Synthesis of Compound BD-7

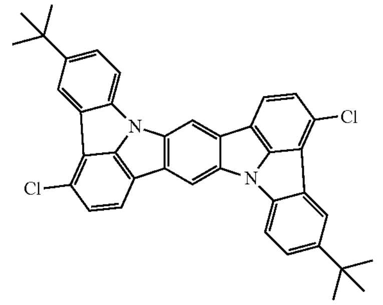

(F-1)

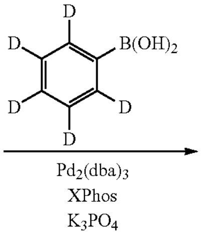

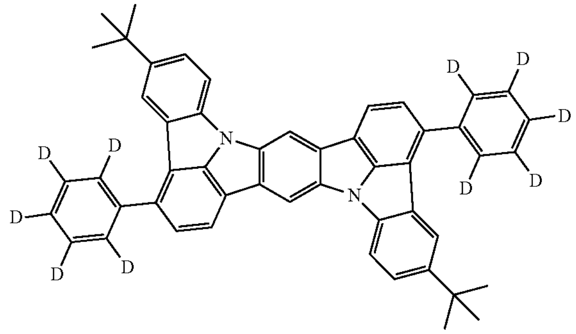

(BD-7)

The compound BD-7 was synthesized in the same manner as in the synthesis of the compound BD-6, except that the intermediate (F-1) was used in place of the intermediate (1-3) as a reaction raw material.

Synthesis Example 8: Synthesis of Compound BD-8

The compound BD-8 was synthesized by the following synthetic scheme.

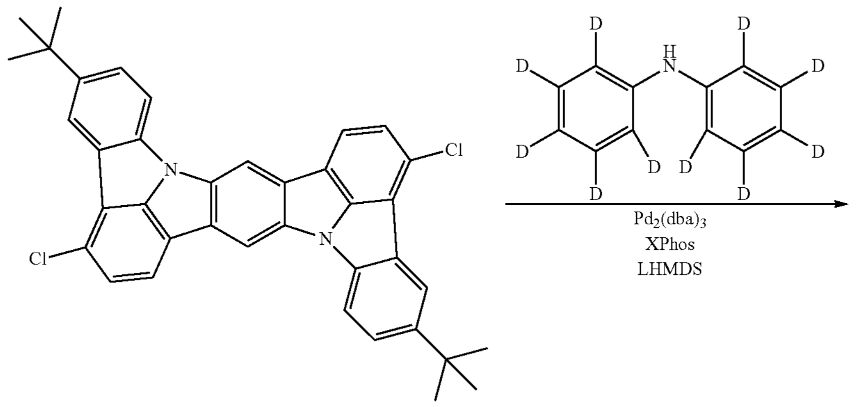

(F-1)

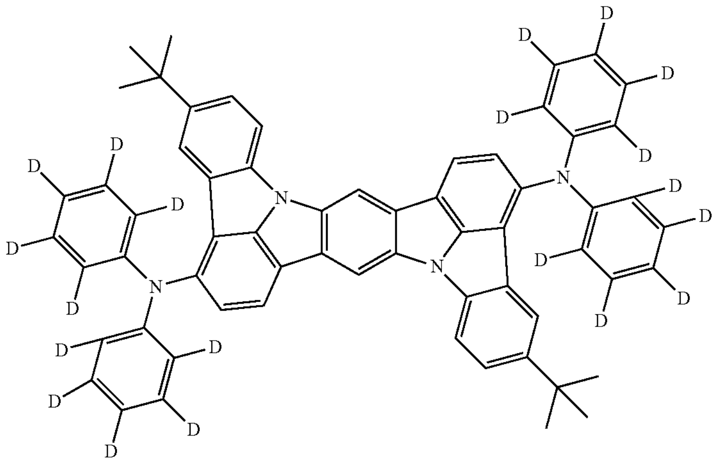

(BD-8)

To a suspension (80 mL) of the intermediate F-1 (1.00 g), bis(phenyl-d5)amine (643 mg), tris(dibenzylideneacetone) dipalladium(0) ($Pd_2(dba)_3$; 78 mg), and 2-dicydohexylphosphino-2',4',6'-triisopropylbiphenyl (XPhos) (163 mg) in toluene, a solution of lithium bis(trimethylsilyl)amide (LHMDS) (1 M, 3.5 mL) in toluene, and the reaction solution was heated at 100° C. for 3 hours with stirring under an argon atmosphere. After the reaction solution was allowed to cool to room temperature, the reaction solution was purified by column chromatography to obtain the compound BD-8 (1.10 g, yield: 74%). The molecular weight of the compound BD-8 was 871, and the analytical result of the mass spectrum of the obtained compound was m/e=871.

Synthesis Example 9: Synthesis of Compound BD-9

The compound BD-9 was synthesized in accordance with the following synthetic scheme.

(1) Synthesis of intermediate F-2

(F-2)

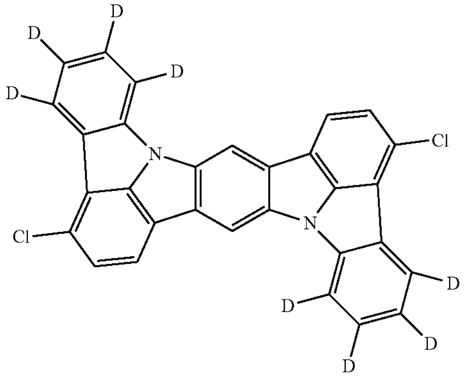

The intermediate (F-2) was synthesized in the same manner as in "(1) Synthesis of intermediate B-1 to (5) Synthesis of intermediate F-1 of Synthesis Example 7", except that cyclohexanone-d10 was used in place of 4-t-butylcyclohexan-1-one as a reaction raw material.

(2) Synthesis of Compound BD-9

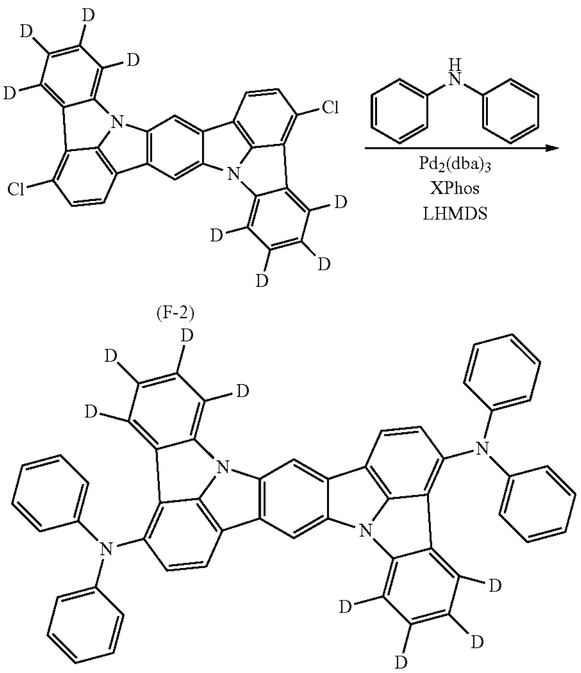

(F-2)

(BD-9)

The compound BD-9 was synthesized in the same manner as in the "Synthesis of the compound BD-1", except that the intermediate (F-2) was used in place of the intermediate (1-2) and diphenylamine was used in place of the intermediate (1-1) as reaction raw materials.

Synthesis Example 10: Synthesis of Compound BD-10

The compound BD-10 was synthesized in accordance with the following synthetic scheme.

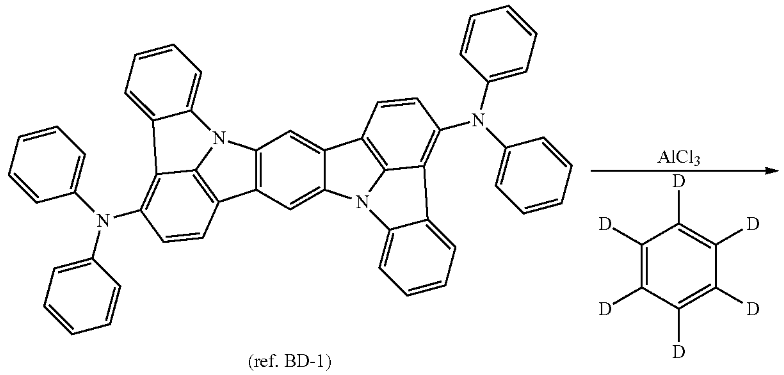

(ref. BD-1)

-continued

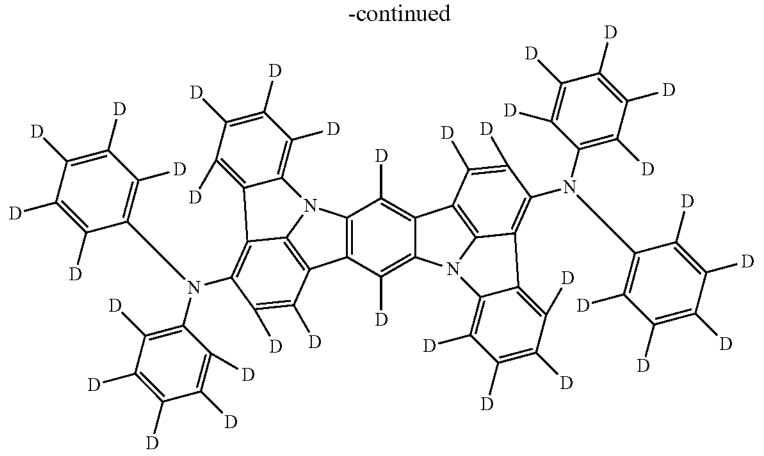

(BD-10)

To a known compound Ref. BD-1 (1.00 g) and aluminum chloride (36 mg), benzene-d6 (20 mL) was added, and the reaction mixture was heated at 80° C. for 30 hours with stirring under an argon atmosphere. After the reaction solution was filtered through celite, the solvent was distilled off to obtain a solid. The solid obtained was purified by column chromatography to obtain the compound BD-10 (0.34 g, yield: 33%).

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The invention claimed is:

1. A compound represented by the following formula (A1):

(A1)

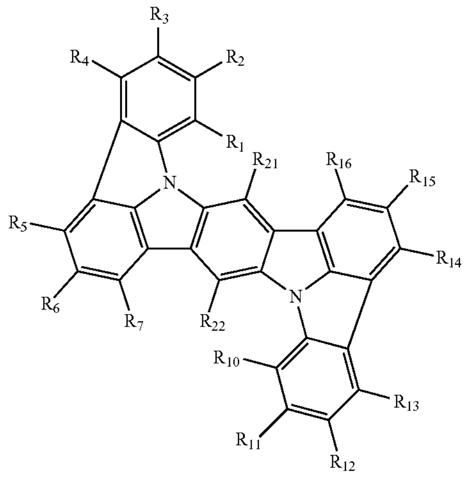

wherein in the formula (A1), one or more sets of adjacent two or more among $R_1$ to $R_7$ and $R_{10}$ to $R_{16}$ form a substituted or unsubstituted, saturated or unsaturated ring by bonding with each other, or do not form a substituted or unsubstituted, saturated or unsaturated ring;

$R_{21}$ and $R_{22}$, $R_1$ to $R_7$ that do not form the substituted or unsubstituted, saturated or unsaturated ring, and $R_{10}$ to $R_{16}$ that do not form the substituted or unsubstituted, saturated or unsaturated ring are independently a hydrogen atom, or a substituent R;

the substituent R is a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms;

when two or more of the substituent R's are present, the two or more of the substituent R's may be the same as or different from each other;

$R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms;

when two or more of each of $R_{901}$ to $R_{907}$ are present, the two or more of each of $R_{901}$ to $R_{907}$ may be the same as or different from each other; and one or more hydrogen atoms selected from the group consisting of the followings are deuterium atoms:

hydrogen atoms possessed by the formed substituted or unsubstituted, saturated or unsaturated ring, hydrogen atoms possessed by a substituent that substitutes on the formed substituted or unsubstituted, saturated or unsaturated ring, hydrogen atoms when each of $R_{21}$ and $R_{22}$ is a hydrogen atom, hydrogen atoms when each of $R_1$ to $R_7$ and $R_{10}$ to $R_{16}$ is a hydrogen atom, and hydrogen atoms possessed by $R_{21}$, $R_{22}$, $R_1$ to $R_7$, and $R_{10}$ to $R_{16}$ when each of $R_{21}$, $R_{22}$, $R_1$ to $R_7$, and $R_{10}$ to $R_{16}$ is the substituent R.

2. The compound according to claim 1, wherein at least one of $R_{21}$ and $R_{22}$, $R_1$ to $R_7$ that do not form the substituted or unsubstituted, saturated or unsaturated ring, and $R_{10}$ to $R_{16}$ that do not form the substituted or unsubstituted, saturated or unsaturated ring is the substituent R and the rest are hydrogen atoms.

3. The compound according to claim 1, wherein at least one of $R_1$ to $R_7$ and $R_{10}$ to $R_{16}$ in the formula (A1) is —$N(R_{906})(R_{907})$.

4. The compound according to claim 1, wherein at least two of $R_1$ to $R_7$ and $R_{10}$ to $R_{16}$ in the formula (A1) are —$N(R_{906})(R_{907})$.

5. The compound according to claim 1, wherein the compound represented by the formula (A1) is a compound represented by the following formula (A10):

(A10)

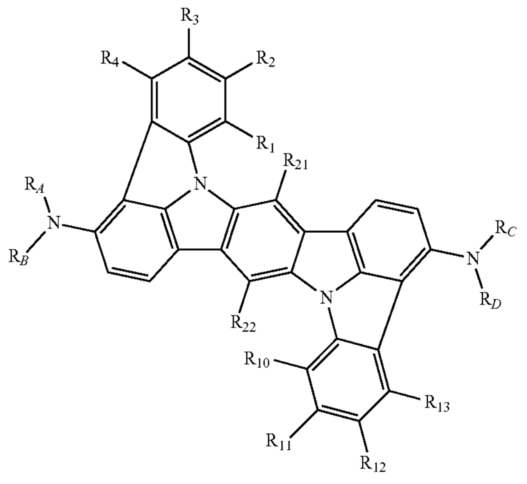

wherein in the formula (A10), $R_1$ to $R_4$, $R_{10}$ to $R_{13}$, $R_{21}$, and $R_{22}$ are as defined in the formula (A1);

$R_A$, $R_B$, $R_C$, and $R_D$ are independently a substituted or unsubstituted aryl group including 6 to 18 ring carbon atoms, or a substituted or unsubstituted monovalent heterocyclic group including 5 to 18 ring atoms.

6. The compound according to claim 5, wherein the compound represented by the formula (A10) is a compound represented by the following formula (A11):

(A11)

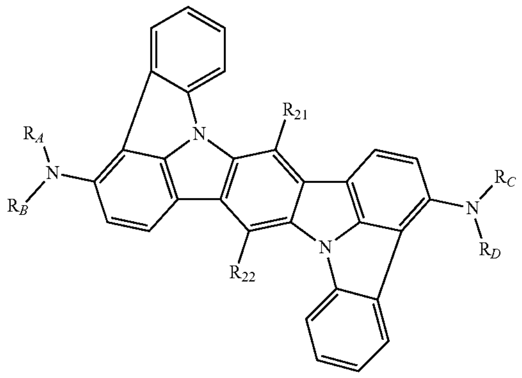

wherein in the formula (A11), $R_{21}$, $R_{22}$, $R_A$, $R_B$, $R_C$, and $R_D$ are as defined in the formula (A10).

7. The compound according to claim 5, wherein $R_A$, $R_B$, $R_C$, and $R_D$ are independently a substituted or unsubstituted aryl group including 6 to 18 ring carbon atoms.

8. The compound according to claim 5, wherein $R_A$, $R_B$, $R_C$, and $R_D$ are independently a substituted or unsubstituted phenyl group.

9. The compound according to claim 1, wherein $R_{21}$ and $R_{22}$ in the formula (A1) are independently a protium atom, a deuterium atom, or a substituted or unsubstituted phenyl group.

10. A material for an organic electroluminescence device, comprising the compound represented by the formula (A1) according to claim 1.

11. The material for an organic electroluminescence device according to claim 10, comprising a compound represented by the formula (A1), and a compound having the same structures as the compound represented by the formula (A1) except that the hydrogen atoms included therein are all protium atoms, and the former being contained in a content ratio of 1 mol % or more, relative to the sum thereof.

12. An organic electroluminescence device comprising:

a cathode;

an anode; and at least one organic layer disposed between the cathode and the anode; wherein at least one layer of the at least one organic layer comprises the compound represented by formula (A1) according to claim 1.

13. The organic electroluminescence device according to claim 12, wherein the at least one organic layer comprises an emitting layer, and the emitting layer comprises the compound represented by the formula (A1).

14. The organic electroluminescence device according to claim 13, wherein the emitting layer comprises the compound represented by the formula (A1) and a compound having the same structure as the compound represented by the formula (A1) except that the hydrogen atoms included therein are all protium atoms, and the former being contained in a content ratio of 1 mol % or more, relative to the sum thereof.

15. An organic electroluminescence device comprising:

a cathode;

an anode; and at least one organic layer disposed between the cathode and the anode; wherein the at least one organic layer comprises an emitting layer, and the emitting layer comprises the compound represented by the formula (A1) according to claim 1, and a compound represented by the following formula (10):

(10)

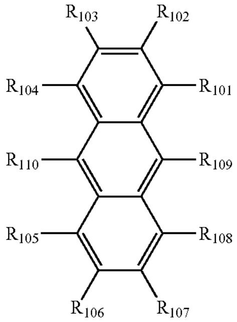

wherein in the formula (10), one or more sets of adjacent two or more among $R_{101}$ to $R_{110}$ form a substituted or unsubstituted, saturated or unsaturated ring, or do not form a substituted or unsubstituted, saturated or unsaturated ring;

$R_{101}$ to $R_{110}$ that do not form the substituted or unsubstituted, saturated or unsaturated ring are independently a hydrogen atom, a substituent R, or a group represented by the following formula (11):

$$-L_{101}-Ar_{101} \quad (11)$$

wherein in the formula (11), $L_{101}$ is a single bond, a substituted or unsubstituted arylene group including 6 to 50 ring carbon atoms, or a substituted or unsubstituted divalent heterocyclic group including 5 to 50 ring atoms;

$Ar_{101}$ is a substituted or unsubstituted aryl group including 6 to 50 ring carbon atoms, or a substituted or unsubstituted monovalent heterocyclic group including 5 to 50 ring atoms;

the substituent R is a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms;

when two or more of the substituent R's are present, the two or more of the substituent R's may be the same as or different from each other;

$R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms;

when two or more of each of $R_{901}$ to $R_{907}$ are present, the two or more of each of $R_{901}$ to $R_{907}$ may be the same as or different from each other;

provided that at least one $R_{101}$ to $R_{110}$ which does not form the substituted or unsubstituted, saturated or unsaturated ring is a group represented by the formula (11);

when two or more groups represented by the formula (11) are present, the two or more of each of the groups represented by the formula (11) may be the same as or different from each other.

16. The organic electroluminescence device according to claim 15, wherein the compound represented by the formula (10) is a compound represented by the following formula (20):

(20)

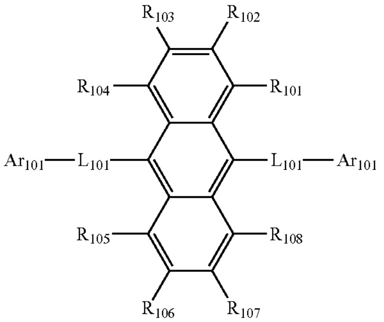

wherein in the formula (20), $R_{101}$ to $R_{108}$, $L_{101}$, and $Ar_{101}$ are as defined in the formula (10).

17. The organic electroluminescence device according to claim 16, wherein in the formula (20), at least one hydrogen atom selected from the group consisting of the followings is a deuterium atom:

hydrogen atoms when each of $R_{101}$ to $R_{108}$ is a hydrogen atom, hydrogen atoms possessed by $R_{101}$ to $R_{108}$ when each of $R_{101}$ to $R_{108}$ is the substituent R, hydrogen atoms possessed by $L_{101}$, hydrogen atoms possessed by a substituent that substitutes on $L_{101}$, hydrogen atoms possessed by $Ar_{101}$, and hydrogen atoms possessed by a substituent that substitutes on $Ar_{101}$.

18. The organic electroluminescence device according to claim 12, comprising a hole-transporting region disposed between the anode and the emitting layer.

19. The organic electroluminescence device according to claim 12, comprising an electron-transporting region disposed between the cathode and the emitting layer.

20. An electronic apparatus, equipped with the organic electroluminescence device according to claim 12.

* * * * *